(12) United States Patent
Kim et al.

(10) Patent No.: US 7,662,832 B2
(45) Date of Patent: Feb. 16, 2010

(54) PYRROLO[2,3-C]PYRIDINE DERIVATIVES AND PROCESSES FOR THE PREPARATION THEREOF

(75) Inventors: Jae-Gyu Kim, Seoul (KR); Byung-Nak Ahn, Seoul (KR); Hyouk-Woo Lee, Yongin-si (KR); Suk-Won Yoon, Seoul (KR); Young-Ae Yoon, Seoul (KR); Dong-Hoon Kim, Gunpo-si (KR); Chan-Sun Park, Yongin-si (KR); Seok-Hee Han, Seoul (KR); Myung-Hun Cha, Anyang-si (KR); Heui-Il Kang, Gunpo-si (KR); Sun-Young Jang, Suwon-si (KR)

(73) Assignee: Yuhan Corporation, Seoul (KR)

( * ) Notice: Subject to any disclaimer, the term of this patent is extended or adjusted under 35 U.S.C. 154(b) by 63 days.

(21) Appl. No.: 11/574,408

(22) PCT Filed: Sep. 3, 2005

(86) PCT No.: PCT/KR2005/002927

§ 371 (c)(1),
(2), (4) Date: Feb. 27, 2007

(87) PCT Pub. No.: WO2006/025716

PCT Pub. Date: Mar. 9, 2006

(65) Prior Publication Data

US 2007/0219230 A1    Sep. 20, 2007

(30) Foreign Application Priority Data

Sep. 3, 2004    (KR) .................... 10-2004-0070533

(51) Int. Cl.
*A01N 43/42* (2006.01)
*A61K 31/44* (2006.01)
*C07D 471/02* (2006.01)
*C07D 491/02* (2006.01)

(52) U.S. Cl. ...................................... 514/300; 546/113

(58) Field of Classification Search .................. 546/113; 514/300; 544/127
See application file for complete search history.

(56) References Cited

U.S. PATENT DOCUMENTS

| 4,450,164 | A | 5/1984 | Bristol et al. |
| 5,681,959 | A | 10/1997 | Bishop et al. |
| 5,714,495 | A | 2/1998 | Viaud et al. |
| 2004/0110785 | A1 | 6/2004 | Wang et al. |

FOREIGN PATENT DOCUMENTS

| EP | 775120 | | 2/1996 |
| JP | 06247967 | | 9/1994 |
| WO | 9837080 | | 8/1998 |
| WO | 9928322 | A1 | 6/1999 |
| WO | 0017200 | | 3/2000 |
| WO | 03044015 | | 5/2003 |
| WO | 03053970 | | 7/2003 |
| WO | 2005/121140 | * | 12/2005 |
| WO | 2006/011670 | * | 2/2006 |

OTHER PUBLICATIONS

James J. Kaminshi et al., Antiulcer agents. 6. Analysis of the in vitro biochemical and vivo gastric antisecretory activity of substituted imidazo [1,2-a] pyridines and related analogues using comparative molecular field analysis and hypothetical active site lattice methodologies. Journal of Medicinal Chemistry, Feb. 14, 1997, vol. 40, No. 4, pp. 427-436, XP00253837.
Supplemental European Search Report dated, Jul. 23, 2009.

* cited by examiner

*Primary Examiner*—D. Margaret Seaman
*Assistant Examiner*—Niloofar Rahmani
(74) *Attorney, Agent, or Firm*—Sughrue Mion, PLLC

(57) ABSTRACT

The present invention provides novel pyrrolo[2,3-c]pyridine derivatives or pharmaceutically acceptable salts thereof, processes for the preparation thereof, and compositions comprising the same. The pyrrolo[2,3-c]pyridine derivatives or pharmaceutically acceptable salts thereof of the present invention have excellent proton pump inhibition effects and possess the ability to attain a reversible proton pump inhibitory effect.

6 Claims, No Drawings

PYRROLO[2,3-C]PYRIDINE DERIVATIVES AND PROCESSES FOR THE PREPARATION THEREOF

FIELD OF THE INVENTION

The present invention relates to novel pyrrolo[2,3-c]pyridine derivatives or pharmaceutically acceptable salts thereof which have an excellent inhibitory activity against gastric acid secretion, processes for the preparation thereof, and pharmaceutical compositions comprising the same.

BACKGROUND OF THE INVENTION

Peptic ulcer disease occurs when offensive factors involving gastric acid secretion are strong or defensive factors of gastric mucous are weak. For the treatment of peptic ulcer disease, various drugs such as antacid, anticholinergic agent, $H_2$-receptor antagonist, and proton pump inhibitor have been used. The advent of omeprazole as a proton pump inhibitor has rekindled research activities in this field.

However, it has been pointed out that proton pump inhibition by omeprazole is irreversible, thereby incurring long-term inhibition of gastric acid secretion, which may induce side effects. Accordingly, various attempts to develop a reversible proton pump inhibitor are being made. For example, imidazopyridine derivatives are disclosed in WO 98/37,080 (AstraZeneca AB), WO 00/17,200 (Byk Gulden Lomberg Chem.), and U.S. Pat. No. 4,450,164 (Schering Corporation) as a reversible proton pump inhibitor. Further, pyrimidine derivatives are also disclosed in European Patent No. 775,120 (Yuhan Corp.).

DISCLOSURE OF THE INVENTION

The present invention provides novel pyrrolo[2,3-c]pyridine derivatives or pharmaceutically acceptable salts thereof, which have excellent proton pump inhibition effects and possess the ability to attain a reversible proton pump inhibitory effect.

According to an aspect of the present invention, there is provided a pyrrolo[2,3-c]pyridine derivative or a pharmaceutically acceptable salt thereof.

Further, according to another aspect of the present invention, there is provided a process for the preparation of the pyrrolo[2,3-c]pyridine derivative or a pharmaceutically acceptable salt thereof.

Further, according to another aspect of the present invention, there is provided a pharmaceutical composition comprising the pyrrolo[2,3-c]pyridine derivative or a pharmaceutically acceptable salt thereof as an active ingredient and a pharmaceutically acceptable carrier.

BEST MODE FOR CARRYING OUT THE INVENTION

In accordance with an aspect of the present invention, there is provided a compound of the formula (I) or a pharmaceutically acceptable salt thereof:

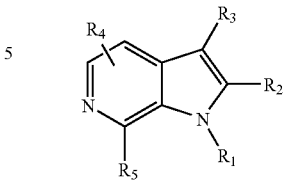

(I)

wherein:

$R_1$ is hydrogen; a straight or branched $C_1$-$C_7$ alkyl group, optionally substituted with one or more substituents selected from the group consisting of hydroxy, halogen, cyano, $C_3$-$C_7$ cycloalkyl, $C_1$-$C_5$ alkoxy, $C_1$-$C_5$ alkoxycarbonyl, a straight or branched $C_1$-$C_5$ alkylcarbonyloxy, $C_1$-$C_3$ alkoxy-$C_1$-$C_3$ alkoxy, $C_1$-$C_3$ alkylsulfanyl, $C_2$-$C_5$ alkenyloxy, formyl, pyridyl, naphthyl, thiazolyl (the thizole ring is optionally substituted with one or more $C_1$-$C_3$ alkyl), thiophenyl (the thiophene ring is optionally substituted with one or more halogen), isoxazolyl (the isoxazole ring is optionally substituted with one or more $C_1$-$C_3$ alkyl), 1,3-dioxolanyl (the 1,3-dioxolane ring is optionally substituted with one or more $C_1$-$C_3$ alkyl), 1,3-dioxanyl, oxiranyl, and tetrahydropyranyl; a straight or branched $C_2$-$C_6$ alkenyl group optionally substituted with phenyl; a straight or branched $C_2$-$C_6$ alkynyl group; a $C_3$-$C_6$ dienyl group; or a —$(CH_2)_p$-phenyl group (p is 0, 1, 2, or 3 and the phenyl ring is optionally substituted with one or more substituents selected from the group consisting of halogen, cyano, a straight or branched $C_1$-$C_5$ alkyl, $C_1$-$C_3$ alkoxy, $C_1$-$C_3$ alkoxycarbonyl, trifluoro-$C_1$-$C_3$ alkyl, trifluoro-$C_1$-$C_3$ alkoxy, and $C_1$-$C_3$ alkylsulfonyl), $R_2$ is a straight or branched $C_1$-$C_6$ alkyl group, $R_3$ is hydrogen; a straight or branched $C_1$-$C_6$ alkyl group, optionally substituted with one or more substituents selected from the group consisting of hydroxy, $C_1$-$C_5$ alkoxy, $C_1$-$C_3$ alkylcarbonyloxy, cyano, morpholinyl, and mono-, di-, or tri-$C_1$-$C_3$ alkylamino; a halogen group; a cyano group; a formyl group; a $C_1$-$C_3$ alkylsulfanyl group; a $C_1$-$C_3$ alkylsulfonyl group; or a $C_1$-$C_3$ alkylsulfinyl group, $R_4$ is hydrogen; a straight or branched $C_1$-$C_6$ alkyl group, optionally substituted with one or more substituents selected from the group consisting of halogen, hydroxy, cyano, amino, $C_1$-$C_5$ alkylamino, $C_3$-$C_6$ cycloalkylamino, phenylamino (the phenyl ring is optionally substituted with one or more halogen), benzylamino (the benzyl ring is optionally substituted with one or more substituents selected from the group consisting of halogen and $C_1$-$C_3$ alkyl), morpholinyl, and piperazinyl (the piperazinyl ring is optionally substituted with $C_1$-$C_3$ alkyl); a straight or branched $C_2$-$C_6$ alkynyl group; a halogen group; a cyano group; a hydroxy group; an amino group; a morpholinyl group; a mercapto group; an aminosulfonyl group; a tetrazolyl group optionally substituted with one or more $C_1$-$C_3$ alkyl; a group of the formula (A)

(A)

wherein, $R_4'$ is hydrogen, a hydroxy group, a $C_1$-$C_5$ alkyl group, a $C_1$-$C_3$ alkoxy group, a $C_3$-$C_6$ cycloalkyl group, an imidazolyl group, a morpholinyl group, a thiomorpholinyl group, a pyrrolidyl group, a tetrahydropyridyl group, a piperazinyl group (the piperazinyl ring is optionally substituted with $C_1$-$C_3$ alkyl or phenyl), or a piperidinyl group (the piperidinyl ring is optionally substituted with $C_1$-$C_3$ alkyl, hydroxy, or hydroxy-$C_1$-$C_3$ alkyl); or a group of formula (B)

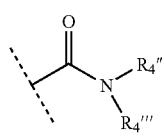

(B)

wherein, $R_4''$ is hydrogen or a $C_1$-$C_3$ alkyl group and $R_4'''$ is hydrogen, a straight or branched $C_1$-$C_5$ alkyl group, a $C_2$-$C_5$ alkenyl group, a $C_3$-$C_6$ cycloalkyl group, a hydroxy-$C_1$-$C_3$ alkyl group, a trifluoro-$C_1$-$C_3$ alkyl group, a benzyl group (the benzyl ring is optionally one or more substituted with $C_1$-$C_3$ alkyl or halogen), or a piperonyl group, and $R_5$ is a 1,2,3,4-tetrahydroisoquinolinyl group, optionally substituted with one or more substituents selected from the group consisting of $C_1$-$C_5$ alkyl, $C_1$-$C_3$ alkoxy, halogen, and $C_3$-$C_6$ cycloalkyl; a naphthyl group; a phenyl-$C_2$-$C_5$ alkenyl group; an oxo-1,2,3,4-tetrahydroisoquinolinyl group; a phenoxymethyl group (the phenyl ring is optionally substituted with one or more substituents selected from the group consisting of halogen and $C_1$-$C_3$ alkyl); a —$(CH_2)_q$-phenyl group (q is 0, 1, 2, or 3 and the phenyl ring is optionally substituted with one or more substituents selected from the group consisting of halogen, $C_1$-$C_3$ alkyl, $C_1$-$C_3$ alkoxy, $C_2$-$C_5$ alkenyl, and $C_1$-$C_5$ alkylsulfanyl); a group of formula (C)

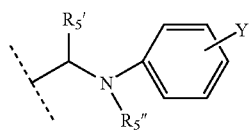

(C)

wherein, Y is hydrogen or a halogen group, $R_5'$ is hydrogen, a $C_1$-$C_3$ alkyl group, a benzyl group, or a cyano group, and $R_5''$ is hydrogen, or $C_1$-$C_5$ alkyl group; or a group of formula (D)

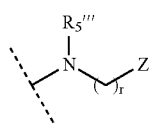

(D)

wherein, r is 0, 1, 2, or 3, $R_5'''$ is hydrogen or a $C_1$-$C_3$ alkyl group, and Z is a 1,3-benzodioxolyl group or a phenyl group (the phenyl ring is optionally substituted with one or more substituents selected from the group consisting of halogen, $C_1$-$C_5$ alkyl, trifluoro-$C_1$-$C_3$ alkoxy, and formyl).

Among the compounds of the formula (I) or its pharmaceutically acceptable salt of the present invention, preferred are those wherein:

$R_1$ is hydrogen; a straight or branched $C_1$-$C_7$ alkyl group; a $C_1$-$C_3$ alkyl group substituted with one or more substituents selected from the group consisting of hydroxy, halogen, cyano, cyclopropyl, cyclobutyl, cyclohexyl, methoxy, ethoxy, methoxycarbonyl, methylcarbonyloxy, tert-butylcarbonyloxy, methoxyethoxy, methylsulfanyl, allyloxy, formyl, pyridyl, naphthyl, methylthiazolyl, chlorothiophenyl, dimethylisoxazolyl, 1,3-dioxolanyl, 1,3-dioxanyl, oxiranyl, and tetrahydropyranyl; a chlorobutyl group; a (methyl-1,3-dioxolanyl)propyl group; a straight or branched $C_2$-$C_6$ alkenyl group; a phenylallyl group; a straight or branched $C_2$-$C_6$ alkynyl group; a propa-1,2-dienyl group; or a —$(CH_2)_n$-phenyl group (n is 1, 2, or 3 and the phenyl ring is optionally substituted with one or more substituents selected from the group consisting of halogen, cyano, $C_1$-$C_5$ alkyl, $C_1$-$C_3$ alkoxy, $C_1$-$C_3$ alkoxycarbonyl, trifluoromethyl, trifluoromethoxy, and methylsulfonyl), $R_2$ is a methyl group, $R_3$ is hydrogen; a straight or branched $C_1$-$C_6$ alkyl group; a $C_1$-$C_3$ alkyl group substituted with one or more substituents selected from the group consisting of hydroxy, ethoxy, methylcarbonyloxy, cyano, morpholinyl, dimethylamino, and trimethylamino; a bromo group; a cyano group; a formyl group; a methylsulfanyl group; a methylsulfonyl group; or a methylsulfinyl group, $R_4$ is hydrogen; a $C_1$-$C_3$ alkyl group substituted with one or more substituents selected from the group consisting of halogen, hydroxy, cyano, amino, $C_1$-$C_5$ alkylamino, cyclopropylamino, cyclobutylamino, fluorophenylamino, chlorobenzylamino, methylbenzylamino, morpholinyl, and methylpiperazinyl; a ethynyl group; a halogen group; a cyano group; a hydroxy group; an amino group; a morpholinyl group; a mercapto group; an aminosulfonyl group; a tetrazolyl group; a methyltetrazolyl group; an ethyltetrazolyl group; a group of the formula (A)

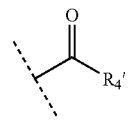

(A)

wherein, $R_4'$ is hydrogen, a hydroxy group, a $C_1$-$C_5$ alkyl group, a $C_1$-$C_3$ alkoxy group, a cyclohexyl group, an imidazolyl group, a morpholinyl group, a thiomorpholinyl group, a pyrrolidyl group, a dihydropyridyl group, a piperazinyl group, a methylpiperazinyl group, an ethylpiperazinyl group, a phenylpiperazinyl group, or a piperidinyl group (the piperidinyl ring is optionally substituted with $C_1$-$C_3$ alkyl, hydroxy, or hydroxy-$C_1$-$C_3$ alkyl); or a group of formula (B)

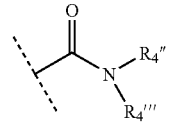

(B)

wherein, $R_4''$ is hydrogen or a $C_1$-$C_3$ alkyl group and $R_4'''$ is hydrogen, a $C_1$-$C_5$ alkyl group, a $C_2$-$C_5$ alkenyl group, a $C_3$-$C_6$ cycloalkyl group, a hydroxyethyl group, a trifluoro-$C_1$-$C_3$ alkyl group, a chlorobenzyl group, a methylbenzyl group, or a piperonyl group, and $R_5$ is a 1,2,3,4-tetrahydroisoquinolinyl group, optionally substituted with one or more substituents selected from the group consisting of $C_1$-$C_3$ alkyl, $C_1$-$C_3$ alkoxy, halogen, and $C_3$-$C_6$ cycloalkyl; a naphthyl group; a phenyl-ethenyl group; a 3,4-dihydro-2H-isoquinolin-1-one-2-yl group; a phenoxymethyl group substituted with one or more substituents selected from the group consisting of halogen and $C_1$-$C_3$ alkyl; a —$(CH_2)_m$-phenyl group (m is 0, 1, 2, or 3 and the phenyl ring is optionally substituted with one or more substituents selected from the group consisting of halogen, $C_1$-$C_3$ alkyl, $C_1$-$C_3$ alkoxy, $C_2$-$C_5$ alkenyl, and methylsulfanyl); a group of formula (C)

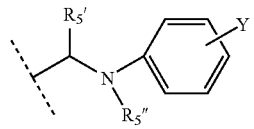

(C)

wherein, Y is hydrogen or a halogen group, $R_5'$ is hydrogen, a $C_1$-$C_3$ alkyl group, a benzyl group, or a cyano group, and $R_5''$ is hydrogen, or $C_1$-$C_5$ alkyl group; or a group of formula (D)

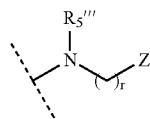

(D)

wherein, r is 0, 1, 2, or 3, $R_5'''$ is hydrogen or a $C_1$-$C_3$ alkyl group, and Z is a 1,3-benzodioxolyl group or a phenyl group (the phenyl ring is optionally substituted with one or more substituents selected from the group consisting of halogen, $C_1$-$C_5$ alkyl, trifluoromethoxy, and formyl).

The compounds of the present invention may be pharmaceutically acceptable non-toxic salt forms. The non-toxic salts may include conventional acid addition salts used in the field of anti-ulcer agents, e.g., salts originated from inorganic acid such as hydrochloric acid, hydrobromic acid, sulfuric acid, sulfamic acid, phosphoric acid, or nitric acid, and organic acid such as acetic acid, propionic acid, succinic acid, glycolic acid, stearic acid, citric acid, maleic acid, malonic acid, methanesulfonic acid, tartaric acid, malic acid, phenylacetic acid, glutamic acid, benzoic acid, salicylic acid, 2-acetoxybenzoic acid, fumaric acid, toluenesulfonic acid, oxalic acid, or trifluoroacetic acid. Further, the non-toxic salts include conventional metal salt forms, e.g., salts originated from metal such as lithium, sodium, potassium, magnesium, or calcium. Such acid addition salts or metal salts may be prepared in accordance with any of the conventional methods.

The present invention includes, within its scope, a process for preparing a compound of formula (I) or a pharmaceutically acceptable salt thereof, in accordance with the following Scheme 1:

Scheme 1.

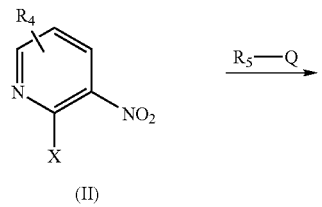

(II)

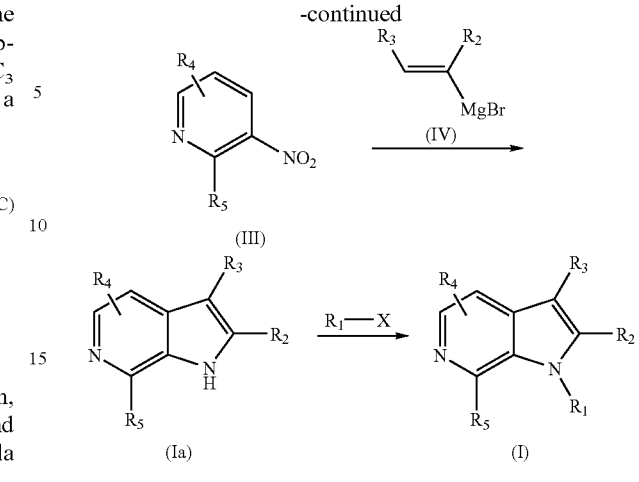

wherein, $R_1$, $R_2$, $R_3$, $R_4$, and $R_5$ are the same as defined in the above; X is halogen; and Q is hydrogen or $B(OH)_2$.

Specifically, the compound of formula (I) or its pharmaceutically acceptable salt may be prepared using a process which comprises: reacting a compound of formula (II) with $R_5$-Q to obtain a compound of formula (III), reacting the compound of formula (III) with a compound of formula (IV) to obtain a compound of formula (Ia), and reacting the compound of formula (Ia) with $R_1$—X to obtain a compound of formula (I).

In the processes of Scheme 1, the compounds of formula (II) and (IV) are commercially available. The reaction of the compound of formula (II) and $R_5$-Q may be performed in the presence of a base, such as sodium hydride, potassium tert-butoxide, sodium carbonate, or potassium hydroxide. Further, the reaction may be carried out in an organic solvent, such as anhydrous tetrahydrofuran and N,N-dimethylformamide, and at room temperature or under heating, e.g., at a temperature of 40° C.~140° C. In case that Q is $B(OH)_2$, the reaction may be carried out in the presence of potassium carbonate as a base and ligand-coupled palladium as a metallic catalyst. Further, in case that Q is $B(OH)_2$, the reaction may be carried out in an organic solvent, e.g., 1,4-dioxane, under heating.

The compound of formula (III) is reacted with a compound of formula (IV) to obtain a compound of formula (Ia). The reaction of the compound of formula (III) and the compound of formula (IV) may be performed in an anhydrous aprotic polar organic solvent, e.g., anhydrous tetrahydrofuran. Further, the reaction may be carried out at room temperature or at a temperature of −78° C.~0° C.

The compound of formula (Ia) is reacted with $R_1$—X to obtain a compound of formula (I). The reaction of the compound of formula (Ia) and $R_1$—X may be performed in the presence of a base, such as sodium hydride or potassium tert-butoxide. Further, the reaction may be carried out in an organic solvent, such as tetrahydrofuran or N,N-dimethylformamide, and at room temperature or at a temperature of 40° C.~100° C. In order to increase a reaction rate and/or a yield of the reaction, a catalytic amount of 18-crown-6 may be used.

In accordance with another aspect of the present invention, the compound of formula (I) or its pharmaceutically acceptable salt may be prepared in accordance with the following Scheme 2:

Scheme 2.

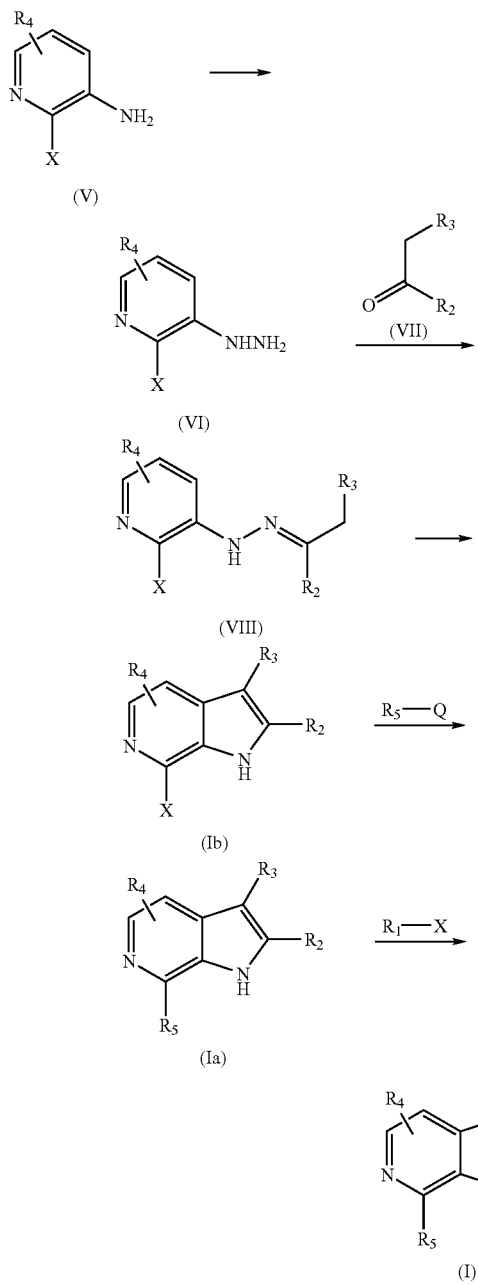

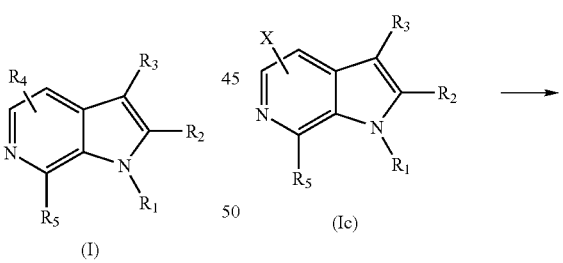

wherein, $R_1$, $R_2$, $R_3$, $R_4$, $R_5$, X and Q are the same as defined in the above.

Specifically, the compound of formula (I) or its pharmaceutically acceptable salt may be prepared using a process which comprises: (a) adding a sodium nitrite solution to a compound of formula (V), followed by reducing the resulting product with tin chloride, to obtain a compound of formula (VI); (b) reacting the compound of formula (VI) with a compound of formula (VII) to obtain a compound of formula (VIII); (c) cyclizing the compound of formula (VIII) to obtain a compound of formula (Ib); (d) reacting the compound of formula (Ib) with $R_5$-Q to obtain a compound of formula (Ia); and (e) reacting the compound of formula (Ia) with $R_1$—X to obtain a compound of formula (I).

In the processes of Scheme 2, the compounds of formula (V) and (VII) are commercially available. The step (a) may be performed by adding a sodium nitrite solution at a temperature of −20° C.~5° C. to a solution of the compound of formula (V) in an inorganic acid, followed by reducing the resulting product with tin chloride.

A compound of formula (VIII) may be prepared by reacting the compound of formula (VI) with a compound of formula (VII) under heating, in an organic solvent, e.g., ethanol.

The cyclization of the compound of formula (VIII) may be carried out by heating the compound of formula (VIII) in an organic solvent, e.g., diphenyl ether having a high melting point, at a temperature of 100° C.~300° C.

The reaction of the compound of formula (Ib) and $R_5$-Q may be performed in the presence of a base, such as sodium hydride, potassium tert-butoxide, sodium carbonate, or potassium hydroxide. Further, the reaction may be carried out in an organic solvent, such as anhydrous tetrahydrofuran and N,N-dimethylformamide, and at room temperature or at a temperature of 40° C.~140° C.

The compound of formula (Ia) is reacted with $R_1$—X to obtain a compound of formula (I). The reaction of the compound of formula (Ia) and $R_1$—X may be performed in the presence of a base, such as sodium hydride or potassium tert-butoxide. Further, the reaction may be carried out in an organic solvent, such as tetrahydrofuran or N,N-dimethylformamide, and at room temperature or at a temperature of 40° C.~100° C. In order to increase a reaction rate and/or a yield of the reaction, a catalytic amount of 18-crown-6 may be used.

In accordance with another aspect of the present invention, the compound of formulas (If) or (Ig); or its pharmaceutically acceptable salt may be prepared in accordance with the following Scheme 3:

Scheme 3.

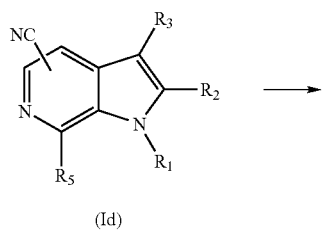

-continued

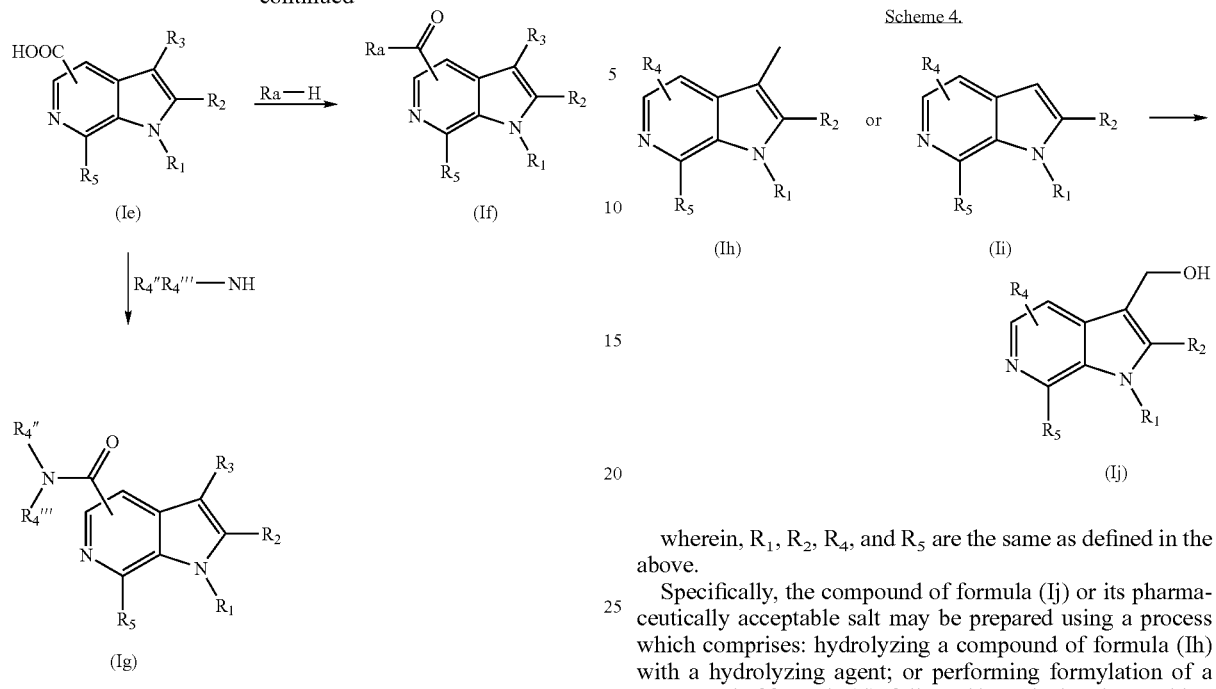

wherein, $R_1$, $R_2$, $R_3$, $R_4''$, $R_4'''$, $R_5$, and X are the same as defined in the above, and Ra is a $C_1$-$C_3$ alkoxy group; an imidazolyl group; a morpholinyl group; a thiomorpholinyl group; a pyrrolidyl group; a tetrahydropyridyl group; a piperazinyl group optionally substituted with $C_1$-$C_3$ alkyl or phenyl; or a piperidinyl group optionally substituted with $C_1$-$C_3$ alkyl, hydroxy, or hydroxy-$C_1$-$C_3$ alkyl.

Specifically, the compound of formula (If) or (Ig); or its pharmaceutically acceptable salt may be prepared using a process which comprises: reacting a compound of formula (Ic) with copper cyanide to obtain a compound of formula (Id), hydrolyzing the compound of formula (Id) to obtain a compound of formula (Ie), and reacting the compound of formula (Ie) with Ra—H or $R_4''R_4'''$—NH to obtain a compound of formulas (If) or (Ig).

In the processes of Scheme 3, a compound of formula (Id) may be prepared by refluxing a mixture of a compound of formula (Ic) and copper cyanide, in an organic solvent, e.g., N,N-dimethylformamide.

The compound of formula (Id) is hydrolyzed in an acidic or basic condition to produce a compound of formula (Ie). The hydrolysis reaction may be carried out with hydrochloric acid as an acid or a potassium hydroxide solution as a base at a temperature of 50° C.~100° C.

The reaction of the compound of formula (Ie) and Ra—H or $R_4''R_4'''$—NH may be performed in the presence of a coupling agent, e.g., N-(3-dimethylaminopropyl)-N'-ethyl-carbodiimide (EDC) or 1-hydroxy-7-azabenzotriazole (HOBT). The coupling reaction may be carried out in an organic solvent, e.g., dichloromethane or N,N-dimethylformamide.

In accordance with another aspect of the present invention, the compound of formula (Ij) or its pharmaceutically acceptable salt may be prepared in accordance with the following Scheme 4:

wherein, $R_1$, $R_2$, $R_4$, and $R_5$ are the same as defined in the above.

Specifically, the compound of formula (Ij) or its pharmaceutically acceptable salt may be prepared using a process which comprises: hydrolyzing a compound of formula (Ih) with a hydrolyzing agent; or performing formylation of a compound of formula (Ii), followed by reducing the resulting product, to obtain a compound of formula (Ij).

In the processes of Scheme 4, the hydrolysis reaction of a compound of formula (Ih) may be performed with a hydrolyzing agent, e.g., lithium hydroxide, in the presence of ammonium cerium (IV) nitrate and acetic acid. The formylation of a compound of formula (II) may be carried out using phosphorus oxychloride and N,N-dimethylformamide and the reduction of the resulting aldehyde group may be carried out with a reducing agent, e.g., sodium borohydride.

In accordance with another aspect of the present invention, the compound of formula (Ik) or its pharmaceutically acceptable salt may be prepared using a process which comprises: performing a Mannich reaction of a compound of formula (Ii), followed by reacting the resulting product with sodium cyanide or potassium cyanide, to obtain a compound of formula (Ik), as the following Scheme 5:

Scheme 5.

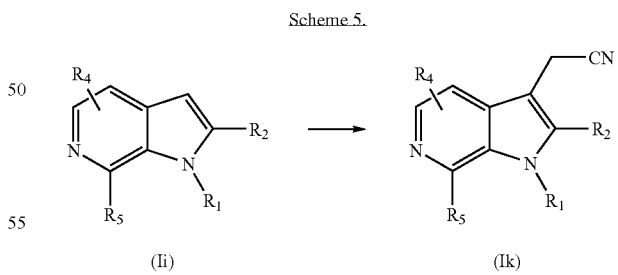

wherein, $R_1$, $R_2$, $R_4$, and $R_5$ are the same as defined in the above.

The present invention further includes, within its scope, a pharmaceutical composition comprising a therapeutically effective amount of any of the compound of formula (I), as defined above, or a pharmaceutically acceptable salt thereof and a pharmaceutically acceptable carrier. The compound of formula (I) or a pharmaceutically acceptable salt thereof may be used for prevention and treatment of gastrointestinal inflammatory diseases and gastric acid-related diseases in mammals including human, such as gastritis, gastric ulcer, duodenal ulcer, reflux esophagitis and Zollinger-Ellison syndrome. Furthermore, the compounds or their salts of the present invention may be used for treatment of other gastrointestinal disorders where gastric antisecretory effect is desirable, e.g. in patients with gastrinomas, and in patients with acute upper gastrointestinal bleeding. The compounds or their salts of the present invention may also be used in patients in intensive care situations, and pre- and postoperatively to prevent acid aspiration and stress ulceration.

The composition of the present invention may include additives such as lactose or corn starch, lubricants such as magnesium stearate, emulsifiers, suspending agents, stabilizers, and isotonic agents. If necessary, sweetening agents and/or flavoring agents may be added.

The composition of the present invention may be administered orally or parenterally, including intravenous, intraperitoneal, subcutaneous, rectal and topical routes of administration. Therefore, the composition of the present invention may be formulated into various forms such as tablets, capsules, aqueous solutions or suspensions. In the case of tablets for oral use, carriers such as lactose, corn starch, and lubricating agents, e.g. magnesium stearate, are commonly added. In the case of capsules for oral administration, lactose and/or dried corn starch can be used as a diluent. When an aqueous suspension is required for oral use, the active ingredient may be combined with emulsifying and/or suspending agents. If desired, certain sweetening and/or flavoring agents may be added. For intramuscular, intraperitoneal, subcutaneous and intravenous use, stertle solutions of the active ingredient are usually prepared, and the pH of the solutions should be suitably adjusted and buffered. For intravenous use, the total concentration of solutes should be controlled in order to render the preparation isotonic. The composition of the present invention may be in the form of an aqueous solution containing pharmaceutically acceptable carriers, e.g., saline, at a pH level of 7.4. The solutions may be introduced into a patient's intramuscular blood-stream by local bolus injection.

The compounds of the present invention may be administered in an effective amount ranging from about 0.1 mg/kg to about 500 mg/kg per day to a subject patient. Of course, the dosage may be changed according to the patient's age, weight, susceptibility, or symptom.

The following examples are provided for illustration purposes only, and are not intended to limit the scope of the invention.

Preparation 1.
2-(4-fluorophenoxymethyl)-3-nitropyridine

Step 1: 2-methyl-3-nitropyridine

A solution of 2-chloro-3-nitropyridine (20 g, 0.126 mol), methylboronic acid (8.3 g, 0.139 mol), tetrakis(triphenylphosphine)palladium (0) (14.58 g, 0.013 mol) and potassium carbonate (52,3 g, 0.378 mol) in anhydrous 1,4-dioxane (100 ml) was refluxed for 2 days. The reaction mixture was cooled to room temperature, filtered, and concentrated under reduced pressure. The resulting residue was purified with silica gel column chromatography (ethyl acetate/n-hexane=1/3, v/v) to give 14 g of the titled compound as brown oil.

1H-NMR(400 MHz, CDCl$_3$) δ 8.74 (d, 1H), 8.27 (d, 1H), 7.34 (t, 1H), 2.88 (s, 3H)

Step 2: 2-bromomethyl-3-nitropyridine 2,2'-azobis(isobutyronitrile) (2.7 g, 16.4 mmol) was added to a solution of 2-methyl-3-nitropyridine (12.97 g, 92.6 mmol) prepared in Step 1 and N-bromosuccinimide (23.06 g, 130 mmol) in carbon tetrachloride (100 ml) and then the reaction mixture was refluxed for 3 days. The reaction mixture was cooled to room temperature and then concentrated under reduced pressure. The resulting residue was diluted with ethyl acetate (100 ml) and then washed with a saturated sodium bicarbonate solution and a saturated sodium thiosulfate solution. The organic layer was dried on anhydrous magnesium sulfate and then purified with silica gel column chromatography (dichloromethane/n-hexane=2/1, v/v) to give 7.5 g of the titled compound as brown oil.

1H-NMR(400 MHz, CDCl$_3$) δ 8.82 (d, 1H), 8.39 (d, 1H), 7.56 (t, 1H), 5.07 (s, 2H)

Step 3: 2-(4-fluorophenoxymethyl)-3-nitropyridine

2-Bromomethyl-3-nitropyridine (100 mg, 0.456 mmol) prepared in Step 2 was added at room temperature to a solution of 4-fluorophenol (56 mg, 0.502 mmol) and potassium carbonate (189 mg, 1.37 mmol) in N,N-dimethylformamide (3 ml) and then stirred for 3 hours. The reaction mixture was diluted with ethyl acetate (10 ml), washed with a saturated sodium bicarbonate solution, dried on anhydrous magnesium sulfate, and then concentrated under reduced pressure. The resulting residue was purified with silica gel column chromatography (dichloromethane/n-hexane=2/1, v/v) to give 71 mg of the titled compound as yellow solid.

1H-NMR(400 MHz, CDCl$_3$) δ 8.85 (d, 1H), 8.34 (d, 1H), 7.52 (t, 1H), 6.97 (m, 4H), 5.53 (s, 2H)

Preparation 2. (4-fluorophenyl)-(3-nitropyridin-2-ylmethyl)-carbamic acid tert-butyl ester Step 1:
(4-fluorophenyl)-(3-nitropyridin-2-ylmethyl)-amine A solution of 2-bromomethyl-3-nitropyridine (2 g, 9.13 mmol) prepared in Step 2 of Preparation 1 and 4-fluoroaniline (0.87 ml, 9.13 mmol) in ethanol (15 ml) was stirred for 2 hours at 40° C. The reaction mixture was concentrated under reduced pressure to give 2.6 g of the titled compound as a brown solid. The product was used in the subsequent step without further purification.

Step 2: (4-fluorophenyl)-(3-nitropyridin-2-ylmethyl)-carbamic acid tert-butyl ester A solution of (4-fluorophenyl)-(3-nitropyridin-2-ylmethyl)-amine (2.28 g, 9.13 mmol) prepared in Step 1, di-tert-butyl dicarbonate (9.2 g, 23.7 mmol), and sodium bicarbonate (3.07 g, 36.6 mmol) in toluene (50 ml) was refluxed overnight. The reaction mixture was cooled to room temperature, diluted with ethyl ether, filtered, and then concentrated under reduced pressure. The resulting residue was purified with silica gel column chromatography (ethyl acetate/n-hexane=1/5, v/v) to give 1.4 g of the titled compound as yellow oil.

1H-NMR(400 MHz, CDCl$_3$) δ 8.87 (m, 1H), 8.37 (d, 1H), 7.26 (m, 3H), 6.96 (m, 2H), 5.28 (s, 3H), 1.35 (s, 9H)

Preparation 3. 1-allyl-2,3-dimethyl-1H-pyrrolo[2,3-c]pyridin-7-carbaldehyde

Step 1: 2-formyl-3-nitropyridine

A solution of 2-methyl-3-nitropyridine (10.155 g, 72.46 mmol) prepared in Step 1 of Preparation 1 and selenium dioxide (8.84 g, 79.71 mmol) in 1,4-dioxane (80 ml) was refluxed for 2 days. The reaction mixture was cooled to room temperature, filtered, and then concentrated under reduced pressure. The resulting residue was purified with silica gel column chromatography (ethyl acetate/n-hexane=1/2, v/v) to give 12.8 g of the titled compound as red oil.

1H-NMR(400 MHz, $CDCl_3$) δ 10.27 (s, 1H), 9.00 (d, 1H), 8.28 (t, 1H), 7.76 (d, 1H)

Step 2: 2-dibutoxymethyl-3-nitropyridine

A solution of 2-formyl-3-nitropyridine (12.8 g, 83 mmol) prepared in Step 1,1-butyl alcohol (53.1 ml, 883 mmol), and p-toluenesulfonic acid (0.32 g, 1.68 mmol) in toluene (15 ml) was refluxed for 3 days. The reaction mixture was cooled to room temperature, diluted with ethyl acetate (20 ml), washed with a saturated sodium bicarbonate solution (10 ml), dried on anhydrous magnesium sulfate, and then concentrated under reduced pressure. The resulting residue was purified with silica gel column chromatography (ethyl acetate/n-hexane=1/10, v/v) to give 11.53 g of the titled compound as reddish brown oil.

1H-NMR(400 MHz, $CDCl_3$) δ 8.82 (d, 1H), 8.08 (d, 1H), 7.45 (t, 1H), 5.98 (s, 1H), 3.70 (m, 2H), 3.59 (m, 2H), 1.60 (m, 4H), 1.39 (m, 4H), 0.90 (m, 6H)

Step 3: 7-dibutoxymethyl-2,3-dimethyl-1H-pyrrolo[2,3-c]pyridine

1-Methyl-1-propenyl magnesium bromide (0.5M in tetrahydrofuran solution, 243 ml, 121 mmol) was slowly added at −78° C. to a solution of 2-dibutoxymethyl-3-nitropyridine (11.53 g, 40 mmol) prepared in Step 2 in tetrahydrofuran (100 ml). The reaction mixture was stirred overnight and a saturated ammonium chloride solution (50 ml) was added thereto. The reaction mixture was diluted with ethyl acetate (100 ml), washed with water, dried on anhydrous magnesium sulfate, and then concentrated under reduced pressure to give 8 g of the titled compound as brown oil. The product was used in the subsequent step without further purification.

Step 4: 1-allyl-2,3-dimethyl-1H-pyrrolo[2,3-c]pyridin-7-carbaldehyde

Sodium hydride (60%, 23 mg, 0.562 mmol) and allyl bromide (36 μl, 0.413 mmol) were added at 0° C. to a solution of 7-dibutoxymethyl-2,3-dimethyl-1H-pyrrolo[2,3-c]pyridine (0.109 g, 0.375 mmol) prepared in Step 3 in anhydrous tetrahydrofuran (3 ml). The reaction mixture was stirred for 1 hour at room temperature and water (1 ml) was added thereto. The reaction mixture was extracted with ethyl acetate (10 ml), dried on anhydrous magnesium sulfate, and then concentrated under reduced pressure. Tetrahydrofuran (10 ml) was added to the resulting residue. 0.5N hydrochloric acid (3 ml, 1.5 mmol) was added to the reaction mixture, which was then refluxed overnight. The reaction mixture was cooled to room temperature, concentrated under reduced pressure, basified with a saturated sodium bicarbonate solution, extracted with ethyl acetate (20 ml), dried on anhydrous magnesium sulfate, and then concentrated under reduced pressure. The resulting residue was purified with silica gel column chromatography (ethyl acetate/n-hexane=1/5, v/v) to give 50 mg of the titled compound as yellow oil.

1H-NMR(400 MHz, $CDCl_3$) δ 10.17 (s, 1H), 8.41 (d, 1H), 7.62 (d, 1H), 5.89 (m, 1H), 5.30 (d, 2H), 4.98 (d, 1H), 4.48 (d, 1H), 2.38 (s, 3H), 2.25 (s, 3H)

Preparation 4. 2-[N-(4-fluorobenzyl)-N-methyl]amino-3-nitropyridine

Step 1: 2-(4-fluorobenzyl)amino-3-nitropyridine

4-Fluorobenzylamine (5.88 ml, 51.4 mmol) was added to a solution of 2-chloro-3-nitropyridine (8.16 g, 51.4 mmol) and sodium carbonate (8.72 g, 82,3 mmol) in anhydrous N,N-dimethylformamide (100 ml). The reaction mixture was stirred at 100° C. for 1 hour. The reaction mixture was cooled to room temperature, diluted with ethyl acetate, and then filtered to discard an insoluble solid. Water was added to the reaction mixture, which was then extracted with ethyl acetate. The organic layer washed with a saturated sodium chloride solution (100 ml) four times, dried on anhydrous magnesium sulfate, and then concentrated under reduced pressure. The resulting residue was purified with silica gel column chromatography (ethyl acetate/n-hexane=1/10, v/v) to give 11.5 g of the titled compound as yellow solid.

1H-NMR(400 MHz, $CDCl_3$) δ 8.48 (brs, 1H), 8.45 (m, 2H), 7.35 (m, 2H), 7.03 (m, 2H), 6.70 (m, 1H), 4.83 (d, 2H)

Step 2: 2-[N-(4-fluorobenzyl)-N-methyl]amino-3-nitropyridine 2-(4-fluorobenzyl)amino-3-nitropyridine (10.4 g, 41.9 mmol) prepared in Step 1, potassium tert-butoxide (4.71 g, 41.9 mmol), and 18-crown-6 (1.11 g, 4.19 mmol) were added to anhydrous tetrahydrofuran (100 ml). Iodomethane (3.92 ml, 62.9 mmol) was slowly added to the reaction mixture, which was then stirred overnight at room temperature. Water was added to the reaction mixture, which was then extracted with ethyl acetate. The separated organic layer was dried on anhydrous magnesium sulfate and then concentrated under reduced pressure. The resulting residue was purified with silica gel column chromatography (ethyl acetate/n-hexane=1/10, v/v) to give 8.26 g of the titled compound as yellow solid. (Yield: 75%).

1H-NMR(400 MHz, $CDCl_3$) δ 8.33 (m, 1H), 8.13 (m, 1H), 7.26 (m, 2H), 7.02 (t, 2H), 6.74 (m, 1H), 4.89 (s, 2H), 2.78 (s, 3H)

Preparation 5. 2-(N-benzyl-N-tert-butoxycarbonyl)amino-3-nitropyridine

Step 1: 2-benzylamino-3-nitropyridine

In accordance with the same procedures as in Step 1 of Preparation 4, except for using 2-chloro-3-nitropyridine and benzylamine, the titled compound was obtained as yellow solid. (Yield: 91%)

1H-NMR(400 MHz, $CDCl_3$) δ 8.52 (brs, 1H), 8.44 (m, 2H), 7.31 (m, 5H), 6.68 (m, 1H), 4.87 (d, 2H),

Step 2: 2-(N-benzyl-N-tert-butoxycarbonyl)amino-3-nitropyridine

Di-tert-butyl dicarbonate (36.68 ml, 160 mmol) was added to a solution of 2-benzylamino-3-nitropyridine (12.2 g, 53.2 mmol) prepared in Step 1 and 4-dimethylaminopyridine (9.75 g, 79.8 mmol) in tetrahydrofuran (100 ml). The reaction mixture was stirred overnight at room temperature and then concentrated under reduced pressure. The resulting residue was purified with silica gel column chromatography (ethyl acetate/n-hexane=1/10, v/v) to give 17.5 g of the titled compound as yellow oil.

1H-NMR(400 MHz, CDCl$_3$) δ 8.58 (m, 1H), 8.21 (m, 1H), 7.44 (m, 2H), 7.28 (m, 2H), 7.22 (m, 2H), 5.24 (s, 2H), 1.36 (s, 9H)

Preparation 6. 2-(5-fluoro-3-nitropyridin-2-yl)-1,2,3,4-tetrahydroisoquinoline

Step 1: 5-fluoro-2-methoxypyridine 5-amino-2-methoxypyridine (81.5 g, 0.657 mol) was dissolved in a mixture of concentrated hydrochloric acid (120 ml) and water (530 ml). A solution of sodium nitrate (56.5 g, 0.819 mol) in water (100 ml) was added at −5° C. to the solution. The reaction mixture was stirred for 45 minutes at room temperature and sodium nitrate (56.5 g, 0.819 mol) was further added thereto. Hexafluorophosphoric acid (132 ml) was added to the reaction mixture, which was then stirred for 20 minutes at room temperature. The reaction mixture was filtered to obtain a solid, which washed with water and ethyl ether and then dried under reduced pressure. The resulting compound was heated for 15 minutes at 150° C., dissolved in dichloromethane, and then washed with 3N sodium hydroxide solution. The organic layer was dried on anhydrous magnesium sulfate, concentrated under reduced pressure, and then fractionally distilled to give 22.6 g of the titled compound as colorless oil. (Yield: 27%).

1H-NMR(400 MHz, CDCl$_3$) δ 7.99 (d, 1H), 7.33 (m, 1H), 6.71 (dd, 1H), 3.91 (s, 3H)

Step 2: 5-fluoro-2-hydroxypyridine

A solution of 5-fluoro-2-methoxypyridine (16.6 g, 131 mmol) prepared in Step 1 in 48% hydrobromic acid solution (250 ml) was stirred for 3 hours at 150° C. The reaction mixture was cooled to room temperature to obtain a yellow solid. The solid was dissolved in methanol (50 ml), neutralized with a sodium carbonate solution, and then extracted with dichloromethane. The organic layer was dried on anhydrous magnesium sulfate and then concentrated under reduced pressure to give 13.1 g of the titled compound as a white solid. (Yield: 88%)

1H-NMR (400 MHz, CDCl$_3$) δ 13.34 (brs, 1H), 7.42 (m, 1H), 7.30 (m, 1H), 6.59 (dd, 1H)

Step 3: 5-fluoro-2-hydroxy-3-nitropyridine

A mixture of nitric acid (70%, 15 ml) and sulfuric acid (15 ml) was slowly added at 5° C.~10° C. to a solution of 5-fluoro-2-hydroxypyridine (13.0 g, 115 mmol) prepared in Step 2 in sulfuric acid (31 ml). The reaction mixture was heated for 2 hours at 85° C. and then cooled to room temperature. Water was added to the reaction mixture, which was then filtered. The resulting yellow solid was dried to give 11 g of the titled compound as yellow solid. (Yield: 60%).

1H-NMR(400 MHz, DMSO-d$_6$) δ 12.71 (brs, 1H), 8.37 (dd, 1H), 7.98 (m, 1H)

Step 4: 2-chloro-5-fluoro-3-nitropyridine 5-fluoro-2-hydroxy-3-nitropyridine (11.0 g, 69.4 mmol) prepared in Step 3 was added to a mixed solution of phosphorus oxychloride (38.8 ml, 416 mmol) and N,N-dimethylformamide (537 μl, 6.94 mmol). The reaction mixture was stirred for 5 hours at 110° C. Water (250 ml) was added to the reaction mixture, which was then extracted with ethyl acetate. The organic layer washed with a sodium chloride solution (250 ml) three times, dried on anhydrous magnesium sulfate, and then concentrated under reduced pressure. The resulting residue was purified with silica gel column chromatography (ethyl acetate) to give 9.02 g of the titled compound as yellow solid. (Yield: 74%).

1H-NMR(400 MHz, CDCl$_3$) δ 8.56 (d, 1H), 8.04 (dd, 1H)

Step 5: 2-(5-fluoro-3-nitropyridin-2-yl)-1,2,3,4-tetrahydroisoquinoline 2-chloro-5-fluoro-3-nitropyridine (1.00 g, 5.66 mmol) prepared in Step 4 and sodium carbonate (1.25 g, 9.06 mmol) were added to anhydrous N,N-dimethylformamide (50 ml). 1,2,3,4-tetrahydroisoquinoline (712 μl, 5.66 mmol) was added to the reaction mixture. The reaction mixture was stirred for 1 hour at 100° C. and then cooled to room temperature. Water was added to the reaction mixture, which was then extracted with ethyl acetate. The organic layer washed with a sodium chloride solution three times, dried on anhydrous magnesium sulfate, and then concentrated under reduced pressure. The resulting residue was purified with silica gel column chromatography (ethyl acetate/n-hexane=1/5, v/v) to give 1.34 g of the titled compound as yellow solid. (Yield: 86%).

1H-NMR(400 MHz, CDCl$_3$) δ 8.33 (d, 1H), 8.01 (dd, 1H), 7.20 (m, 3H), 7.12 (m, 1H), 4.45 (s, 2H), 3.72 (t, 2H), 3.02 (t, 2H)

Preparation 7. 2-(6-chloro-3-nitropyridin-2-yl)-1,2,3,4-tetrahydroisoquinoline 2,6-Dichloro-3-nitropyridine (10 g, 51.8 mmol) and sodium carbonate (8.8 g, 82.9 mmol) were added to anhydrous N,N-dimethylformamide (250 ml). 1,2,3,4-tetrahydroisoquinoline (7.14 ml, 82.9 mmol) was added at 0° C. to the reaction mixture, which was then stirred for 2 hours at 0° C. Water was added to the reaction mixture, which was then extracted with ethyl acetate. The organic layer was dried on anhydrous magnesium sulfate and then concentrated under reduced pressure. The resulting residue was purified with silica gel column chromatography (ethyl acetate/n-hexane=1/5, v/v) to give 10 g of the titled compound as yellow solid. (Yield: 81%).

1H-NMR(400 MHz, CDCl$_3$) δ 8.12 (d, 1H), 7.20 (m, 3H), 7.12 (m, 1H), 6.68 (d, 1H), 4.47 (s, 2H), 3.75 (t, 2H), 3.02 (t, 2H)

Preparation 8. (6-chloro-3-nitropyridin-2-yl)-(4-fluorobenzyl)-methylamine

Step 1: (6-chloro-3-nitropyridin-2-yl)-(4-fluorobenzyl)-amine

In accordance with the same procedures as in Preparation 7, except for using 2,6-dichloro-3-nitropyridine and 4-fluorobenzylamine, the titled compound was obtained as yellow solid. (Yield: 65%)

1H-NMR(400 MHz, CDCl$_3$) δ 8.56 (brs, 1H), 8.37 (d, 1H), 7.36 (m, 2H), 7.05 (m, 2H), 6.67 (d, 1H), 4.78 (d, 2H)

Step 2: (6-chloro-3-nitropyridin-2-yl)-(4-fluorobenzyl)-methylamine

In accordance with the same procedures as in Step 2 of Preparation 4, except for using (6-chloro-3-nitropyridin-2-yl)-(4-fluorobenzyl)-amine prepared in Step 1 and iodomethane, the titled compound was obtained as yellow solid. (Yield: 65%)

1H-NMR(400 MHz, CDCl$_3$) δ 8.07 (d, 1H), 7.30 (m, 2H), 7.04 (m, 2H), 6.70 (d, 1H), 4.85 (s, 2H), 2.79 (s, 3H)

Preparation 9. 3-nitro-2-(4-vinylphenyl)pyridine

2-Chloro-3-nitropyridine (4.37 g, 27.6 mmol), 4-vinylphenylboronic acid (4.5 g, 30.4 mmol), tetrakis(triphenylphosphine)palladium (0) (3.19 g, 2.8 mmol), and potassium carbonate (11.4 g, 82.8 mmol) were added to anhydrous 1,4-dioxane (60 ml). The reaction mixture was refluxed for 24 hours. The reaction mixture was cooled to room temperature, filtered with a Celite pad, and then concentrated under reduced pressure. The resulting residue was purified with silica gel column chromatography and then crystallized with ethyl ether to give 4.9 g of the titled compound as a white solid. (Yield: 79%) The product was used in the subsequent step without further purification.

Preparation 10. 3-nitro-2-(4-methylthiophenyl)pyridine

In accordance with the same procedures as in Preparation 9, except for using (4-methylthiophenyl)boronic acid, the titled compound was obtained as a white solid. (Yield: 77%) The product was used in the subsequent step without further purification.

Preparation 11. 3-nitro-2-(4-methylphenyl)pyridine

In accordance with the same procedures as in Preparation 9, except for using 4-methylphenylboronic acid, the titled compound was obtained as a white solid. (Yield: 75%) The product was used in the subsequent step without further purification.

Preparation 12. 3-nitro-2-(4-chlorophenyl)pyridine

In accordance with the same procedures as in Preparation 9, except for using 4-chlorophenylboronic acid, the titled compound was obtained as a white solid. (Yield: 80%) The product was used in the subsequent step without further purification.

Preparation 13. 3-nitro-2-(4-fluorophenyl)pyridine

In accordance with the same procedures as in Preparation 9, except for using 4-fluorophenylboronic acid, the titled compound was obtained as a white solid. (Yield: 74%) The product was used in the subsequent step without further purification.

Preparation 14. 3-nitro-2-(4-methoxyphenyl)pyridine

In accordance with the same procedures as in Preparation 9, except for using 4-methoxyphenylboronic acid, the titled compound was obtained as a white solid. (Yield: 77%) The product was used in the subsequent step without further purification.

Preparation 15. 3-nitro-2-phenylpyridine

In accordance with the same procedures as in Preparation 9, except for using phenylboronic acid, the titled compound was obtained as a white solid. (Yield: 71%)

1H-NMR(400 MHz, CDCl$_3$) δ 8.86 (d, 1H), 8.13 (d, 1H), 7.57 (m, 2H), 7.46 (m, 4H)

Preparation 16. 2-(naphthalen-2-yl)-3-nitropyridine

In accordance with the same procedures as in Preparation 9, except for using naphthalene-2-boronic acid, the titled compound was obtained as a white solid. (Yield: 72%) The product was used in the subsequent step without further purification.

Preparation 17. 3-nitro-2-styryl-pyridine

In accordance with the same procedures as in Preparation 9, except for using styrylboronic acid, the titled compound was obtained as a white solid. (Yield: 65%)

1H-NMR(400 MHz, CDCl$_3$) δ 8.80 (d, 1H), 8.24 (d, 1H), 8.09 (d, 1H), 7.78 (d, 1H), 7.65 (m, 2H), 7.37 (m, 4H)

Preparation 18. 2-benzyl-3-nitropyridine

In accordance with the same procedures as in Preparation 9, except for using benzylboronic acid, the titled compound was obtained as a white solid. (Yield: 51%)

1H-NMR(400 MHz, CDCl$_3$) δ 8.77 (d, 1H), 8.22 (d, 1H), 7.35 (m, 1H), 7.27 (m, 4H), 7.21 (m, 1H), 4.52 (s, 2H)

Preparation 19. 3-phenethyl-2-nitropyridine

In accordance with the same procedures as in Preparation 9, except for using phenethylboronic acid, the titled compound was obtained as a white solid. (Yield: 55%)

1H-NMR(400 MHz, CDCl$_3$) δ 8.78 (d, 1H), 8.21 (d, 1H), 7.35 (m, 1H), 7.29 (m, 4H), 7.22 (m, 1H), 3.42 (m, 2H), 3.11 (m, 2H)

Preparation 20. 2-(3-nitropyridin-2-yl)-1,2,3,4-tetrahydroisoquinoline

2-Chloro-3-nitropyridine (3.0 g, 18.92 mmol), 1,2,3,4-tetrahydroisoquinoline (2.37 ml, 18.92 mmol), and sodium carbonate (3.1 g, 28.62 mmol) were added to anhydrous N,N-dimethylformamide (30 ml). The reaction mixture was stirred for 1 hour at 100° C. The reaction mixture was cooled to room temperature, diluted with ethyl acetate, washed with water three times, and then washed with a saturated sodium chloride solution. The organic layer was dried on anhydrous magnesium sulfate and then concentrated under reduced pressure to give 4.8 g of the titled compound as yellow oil. (Yield: 98%).

1H-NMR(400 MHz, CDCl$_3$) δ 8.35 (d, 1H), 8.17 (d, 1H), 7.19 (m, 3H), 7.11 (m, 1H), 6.73 (m, 1H), 4.48 (s, 2H), 3.76 (t, 2H), 3.01 (t, 2H)

Preparation 21. 7-methoxy-1-methyl-2-(3-nitropyridin-2-yl)-1,2,3,4-tetrahydroisoquinoline

Step 1: N-[2-(4-methoxyphenyl)-ethyl]-acetamide

4-Methoxyphenethylamine (50 g, 330 mmol) was added to dichloromethane (50 ml) and then 2N sodium hydroxide solution (25 ml) was added thereto. Acetyl chloride (26 ml, 364 mmol) was slowly added at 0° C. to the reaction mixture, which was then stirred overnight. The reaction mixture was diluted with dichloromethane, washed with water and a saturated sodium chloride solution, and then extracted with dichloromethane. The organic layer was dried on anhydrous magnesium sulfate and then concentrated under reduced pressure to give 68 g of the titled compound as a white solid. The product was used in the subsequent step without further purification.

Step 2: 7-methoxy-1-methyl-3,4-dihydroisoquinoline

Phosphorus pentoxide (22 g, 155.24 mmol) was added to a mixture of N-[2-(4-methoxyphenyl)-ethyl]-acetamide (50 g, 258.73 mmol) prepared in Step 1 and phosphorus oxychloride (48 ml, 517.46 mmol). The reaction mixture was refluxed for 3 hours. The reaction mixture was cooled to room temperature, added to ice water, basified with 2N potassium hydroxide solution, and then extracted with ethyl acetate. The organic layer washed with a saturated sodium chloride solution, dried on anhydrous magnesium sulfate, filtered, and then concentrated under reduced pressure. The resulting residue was purified with silica gel column chromatography to give 14.72 g of the titled compound as brown oil. (Yield: 32%) The product was used in the subsequent step without further purification.

Step 3: 7-methoxy-1-methyl-1,2,3,4-tetrahydroisoquinoline

Sodium borohydride (3.81 g, 100.8 mmol) was slowly added at 0° C. to a solution of 7-methoxy-1-methyl-3,4-dihydroisoquinoline (14.72 g, 84 mmol) prepared in Step 2 in anhydrous methanol (100 ml). The reaction mixture was stirred overnight at room temperature. 1N hydrochloric acid was added to the reaction mixture, which was concentrated under reduced pressure, basified with potassium hydroxide, and then extracted with dichloromethane. The organic layer washed with a saturated sodium chloride solution, dried on anhydrous magnesium sulfate, and then concentrated under reduced pressure to give 11.01 g of the titled compound as brown oil. (Yield: 74%) The product was used in the subsequent step without further purification.

Step 4: 7-methoxy-1-methyl-2-(3-nitropyridin-2-yl)-1,2,3,4-tetrahydroisoquinoline In accordance with the same procedures as in Preparation 20, except for using 7-methoxy-1-methyl-1,2,3,4-tetrahydroisoquinoline prepared in Step 3, the titled compound was obtained. (Yield: 94%) The product was used in the subsequent step without further purification.

Preparation 22. 7-chloro-1-methyl-2-(3-nitropyridin-2-yl)-1,2,3,4-tetrahydroisoquinoline In accordance with the same procedures as in Steps 1, 2, and 3 of Preparation 21, except for using 4-chlorophenethylamine and acetyl chloride, 7-chloro-1-methyl-1,2,3,4-tetrahydroisoquinoline was obtained. In accordance with the same procedures as in Preparation 20, the titled compound was obtained as pale yellow oil. (Yield: 67%) The product was used in the subsequent step without further purification.

Preparation 23. 7-fluoro-1-methyl-2-(3-nitropyridin-2-yl)-1,2,3,4-tetrahydroisoquinoline In accordance with the same procedures as in Steps 1, 2, and 3 of Preparation 21, except for using 4-fluorophenethylamine and acetyl chloride, 7-fluoro-1-methyl-1,2,3,4-tetrahydroisoquinoline was obtained. In accordance with the same procedures as in Preparation 20, the titled compound was obtained as pale yellow oil. (Yield: 69%) The product was used in the subsequent step without further purification.

Preparation 24. 1-methyl-2-(3-nitropyridin-2-yl)-1,2,3,4-tetrahydroisoquinoline

In accordance with the same procedures as in Steps 1, 2, and 3 of Preparation 21, except for using phenethylamine and acetyl chloride, 1-methyl-1,2,3,4-tetrahydroisoquinoline was obtained. In accordance with the same procedures as in Preparation 20, the titled compound was obtained as pale yellow oil. (Yield: 91%) The product was used in the subsequent step without further purification.

Preparation 25. 6-fluoro-1-methyl-2-(3-nitropyridin-2-yl)-1,2,3,4-tetrahydroisoquinoline In accordance with the same procedures as in Steps 1, 2, and 3 of Preparation 21, except for using 3-fluorophenethylamine and acetyl chloride, 6-fluoro-1-methyl-1,2,3,4-tetrahydroisoquinoline was obtained. In accordance with the same procedures as in Preparation 20, the titled compound was obtained as pale yellow oil. (Yield: 55%) The product was used in the subsequent step without further purification.

Preparation 26. 1-cyclopropyl-2-(3-nitropyridin-2-yl)-1,2,3,4-tetrahydroisoquinoline In accordance with the same procedures as in Steps 1, 2, and 3 of Preparation 21, except for using phenethylamine and cyclopropanecarbonyl chloride, 1-cyclopropyl-1,2,3,4-tetrahydroisoquinoline was obtained. In accordance with the same procedures as in Preparation 20, the titled compound was obtained as pale yellow oil. (Yield: 82%) The product was used in the subsequent step without further purification.

Preparation 27. 1-ethyl-2-(3-nitropyridin-2-yl)-1,2,3,4-tetrahydroisoquinoline

In accordance with the same procedures as in Steps 1, 2, and 3 of Preparation 21, except for using phenethylamine and propionyl chloride, 1-ethyl-1,2,3,4-tetrahydroisoquinoline was obtained. In accordance with the same procedures as in Preparation 20, the titled compound was obtained as pale yellow oil. (Yield: 78%) The product was used in the subsequent step without further purification.

Preparation 28. 7-chloro-2-ethyl-3-methyl-1H-pyrrolo[2,3-c]pyridine

Step 1: (2-chloropyridin-3-yl)-hydrazine

A solution of 3-amino-2-chloropyridine (5 g, 38.9 mmol) in concentrated hydrochloric acid (50 ml) was cooled to −5° C. and a solution of sodium nitrite (2.7 g, 38.9 mmol) in water (25 ml) was added thereto. The reaction mixture was stirred for 15 minutes at 0° C. and a solution of tin(II) chloride dihydrate (17.6 g, 77.8 mmol) in concentrated hydrochloric acid (17.5 ml) was slowly added thereto. The reaction mixture was stirred for 1 hour at room temperature, basified with 2N sodium hydroxide solution, and then extracted with dichloromethane. The organic layer was dried on anhydrous magnesium sulfate, filtered, and then concentrated under reduced pressure. The resulting residue was crystallized with ethyl ether to give 2 g of the titled compound as a pale yellow solid. (Yield: 36%).

1H-NMR(400 MHz, CDCl$_3$) δ 7.80 (d, 1H), 7.47 (d, 1H), 7.17 (m, 1H), 5.76 (brs, 1H), 3.65 (brs, 2H)

Step 2: N-(2-chloropyridin-3-yl)-N'-(1-ethylpropylidene)-hydrazine

3-Pentanone (1.1 ml, 10.4 mmol) was added to a solution of (2-chloropyridin-3-yl)-hydrazine (1 g, 6.96 mmol) prepared in Step 1 in ethanol (35 ml). The reaction mixture was refluxed overnight. The reaction mixture was concentrated under reduced pressure and then purified with silica gel column chromatography to give 1.3 g of the titled compound as pale yellow oil. (Yield: 88%).

1H-NMR(400 MHz, CDCl$_3$) δ 7.83 (d, 1H), 7.76 (dd, 1H), 7.52 (s, 1H), 7.16 (m, 1H), 2.35 (m, 2+2H), 1.18 (m, 3+3H)

Step 3: 7-chloro-2-ethyl-3-methyl-1H-pyrrolo[2,3-c]pyridine

A solution of N-(2-chloropyridin-3-yl)-N'-(1-ethylpropylidene)-hydrazine (1.3 g, 6.1 mmol) prepared in Step 2 in diphenyl ether was stirred for 3 hours at 300□. The reaction mixture was cooled to room temperature and then purified with silica gel column chromatography to give 850 mg of the titled compound as a pale yellow solid. (Yield: 72%).

1H-NMR(400 MHz, CDCl$_3$) δ 8.80 (brs, 1H), 7.98 (d, 1H), 7.32 (d, 1H), 2.82 (q, 2H), 2.21 (s, 3H), 1.31 (t, 3H)

EXAMPLE 1

7-(4-fluorophenoxymethyl)-2,3-dimethyl-1H-pyrrolo[2,3-c]pyridine

1-Methyl-1-propenyl magnesium bromide (0.5 M in tetrahydrofuran solution, 1.7 ml, 0.851 mmol) was added at −78° C. to a solution of 2-(4-fluorophenoxymethyl)-3-nitropyridine (71 mg, 0.284 mmol) prepared in Preparation 1 in anhydrous tetrahydrofuran (5 ml). The reaction mixture was stirred overnight and a saturated ammonium chloride solution was added thereto. The reaction mixture was extracted with ethyl acetate (15 ml). The organic layer washed with water (5 ml), dried on anhydrous magnesium sulfate, and then concentrated under reduced pressure. The resulting residue was purified with silica gel column chromatography (dichloromethane/n-hexane=2/1, v/v) to give 15 mg of the titled compound as brown oil.

1H-NMR(400 MHz, CDCl$_3$) δ 8.46 (brs, 1H), 8.15 (d, 1H), 7.33 (d, 1H), 6.98 (m, 4H), 5.48 (s, 2H), 2.41 (s, 3H), 2.21 (s, 3H)

EXAMPLE 2

1-allyl-7-(4-fluorophenoxymethyl)-2,3-dimethyl-1H-pyrrolo[2,3-c]pyridine hydrochloride Allyl bromide (11.77 μl, 0.14 mmol) was added to a solution of 7-(4-fluorophenoxymethyl)-2,3-dimethyl-1H-pyrrolo[2,3-c]pyridine (15 mg, 0.054 mmol) prepared in Example 1, potassium tert-butoxide (20.68 mg, 0.18 mmol), and 18-crown-6 (487 mg, 0.02 mmol) in anhydrous tetrahydrofuran (2 ml). The reaction mixture was stirred overnight at room temperature and then concentrated under reduced pressure. The resulting residue was purified with silica gel column chromatography (ethyl acetate/n-hexane=1/2, v/v). The residue was dissolved in ethyl acetate, saturated with hydrochloric acid gas, and then filtered. The resulting solid was dried under reduced pressure to give 1.9 mg of the titled compound as a white solid.

1H-NMR(400 MHz, CDCl$_3$) δ 8.18 (m, 1H), 7.74 (d, 1H), 7.12 (m, 2H), 6.98 (t, 2H), 6.03 (m, 1H), 5.88 (s, 2H), 5.30 (d, 1H), 5.13 (s, 2H), 4.40 (d, 1H), 2.50 (s, 3H), 2.27 (s, 3H)

EXAMPLES 3 to 13

The titled compounds of Examples 3 to 13 were prepared, in accordance with the same procedures as in Example 2, using 7-(4-fluorophenoxymethyl)-2,3-dimethyl-1H-pyrrolo[2,3-c]pyridine prepared in Example 1; and, benzyl bromide, 3-methoxybenzyl bromide, 4-methylbenzyl bromide, 2-bromoethyl methyl ether, (bromomethyl)cyclopropane, 1-iodopropane, 2-fluorobenzyl chloride, iodoethane, 4-fluorobenzyl chloride, 4-bromo-2-methyl-2-butene, or propargyl bromide.

EXAMPLE 3

1-benzyl-7-(4-fluorophenoxymethyl)-2,3-dimethyl-1H-pyrrolo[2,3-c]pyridine hydrochloride 1H-NMR(400 MHz, CDCl$_3$) δ 8.19 (m, 1H) 7.80 (m, 1H), 7.28 (m, 3H), 6.97 (m, 4H), 6.77 (m, 2H), 5.73 (s, 2H), 5.61 (s, 2H), 2.50 (s, 3H), 2.40 (s, 3H); (Yield: 45%)

EXAMPLE 4

7-(4-fluorophenoxymethyl)-1-(3-methoxybenzyl)-2,3-dimethyl-1H-pyrrolo[2,3-c]pyridine hydrochloride 1H-NMR(400 MHz, CDCl$_3$) δ 8.19 (t, 1H), 7.78 (d, 1H), 7.20 (d, 1H), 6.98 (m, 4H), 6.80 (d, 1H), 6.20 (d, 1H), 6.12 (s, 1H), 5.69 (s, 2H), 5.61 (s, 2H), 3.70 (s, 3H), 2.55 (s, 3H), 2.39 (s, 3H); (Yield: 55%)

EXAMPLE 5

7-(4-fluorophenoxymethyl)-2,3-dimethyl-1-(4-methylbenzyl)-1H-pyrrolo[2,3-c]pyridine hydrochloride 1H-NMR(400 MHz, CDCl$_3$) δ 8.18 (m, 1H), 7.77 (m, 1H), 7.08 (m, 2H), 6.96 (m, 4H), 6.50 (m, 2H), 5.69 (s, 2H), 5.61 (s, 2H), 2.60 (s, 3H), 2.50 (s, 3H), 2.32 (s, 3H); (Yield: 44%)

EXAMPLE 6

7-(4-fluorophenoxymethyl)-1-(2-methoxyethyl)-2,3-dimethyl-1H-pyrrolo[2,3-c]pyridine hydrochloride 1H-NMR(400 MHz, CDCl$_3$) δ 8.19 (m, 1H), 7.70 (m, 1H), 7.13 (m, 2H), 7.00 (m, 2H), 6.10-5.80 (m, 2H), 4.73-4.00 (m, 2H), 3.59 (m, 2H), 3.23 (s, 3H), 2.52 (s, 3H), 2.34 (s, 3H); (Yield: 74%)

EXAMPLE 7

1-cyclopropylmethyl-7-(4-fluorophenoxymethyl)-2,3-dimethyl-1H-pyrrolo[2,3-c]pyridine hydrochloride 1H-NMR(400 MHz, CDCl$_3$) δ 8.17 (m, 1H), 7.71 (m, 1H), 7.02 (m, 2H), 6.98 (m, 2H), 6.01 (s, 2H), 4.53 (s, 2H), 2.57 (s, 3H), 2.33 (s, 3H), 1.03 (m, 1H), 0.61 (m, 2H), 0.24 (m, 2H); (Yield: 70%)

EXAMPLE 8

7-(4-fluorophenoxymethyl)-2,3-dimethyl-1-propyl-1H-pyrrolo[2,3-c]pyridine hydrochloride 1H-NMR(400 MHz, CDCl$_3$) δ 8.16 (m, 1H), 7.71 (m, 1H), 7.15 (m, 2H), 7.01 (m, 2H), 5.93 (s, 2H), 4.36 (m, 2H), 2.55 (s, 3H), 2.33 (s, 3H), 1.76 (m, 2H), 0.93 (t, 3H); (Yield: 60%)

EXAMPLE 9

1-(2-fluorobenzyl)-7-(4-fluorophenoxymethyl)-2,3-dimethyl-1H-pyrrolo[2,3-c]pyridine hydrochloride 1H-NMR(400 MHz, CDCl$_3$) δ 8.22 (m, 1H), 7.81 (m, 1H), 7.30 (m, 1H), 7.11 (m, 1H), 6.96 (m, 5H), 6.12 (m, 1H), 5.79 (s, 2H), 5.68 (s, 2H), 2.48 (s, 3H), 2.39 (s, 3H); (Yield: 68%)

EXAMPLE 10

1-ethyl-7-(4-fluorophenoxymethyl)-2,3-dimethyl-1H-pyrrolo[2,3-c]pyridine hydrochloride 1H-NMR(400 MHz, CDCl$_3$) δ 8.16 (m, 1H), 7.72 (m, 1H), 7.15 (m, 2H), 7.00 (m, 2H), 5.96 (s, 2H), 4.52 (q, 2H), 2.56 (s, 3H), 2.33 (s, 3H), 1.40 (t, 3H); (Yield: 88%)

EXAMPLE 11

1-(4-fluorobenzyl)-7-(4-fluorophenoxymethyl)-2,3-dimethyl-1H-pyrrolo[2,3-c]pyridine hydrochloride 1H-NMR(400 MHz, CDCl$_3$) δ 8.20 (m, 1H), 7.79 (m, 1H), 7.01 (m, 6H), 6.63 (m, 2H), 5.72 (s, 2H), 5.65 (s, 2H), 2.49 (s, 3H), 2.39 (s, 3H); (Yield: 81%)

EXAMPLE 12

7-(4-fluorophenoxymethyl)-2,3-dimethyl-1-(3-methylbut-2-enyl)-1H-pyrrolo[2,3-c]pyridine hydrochloride 1H-NMR(400 MHz, CDCl$_3$) δ 8.14 (m, 1H), 7.70 (m, 1H), 7.12 (m, 2H), 6.97 (m, 2H), 5.93 (s, 2H), 5.08 (m, 2H), 4.96 (m, 1H), 2.52 (s, 3H), 2.32 (s, 3H), 1.71 (s, 3H), 1.65 (s, 3H); (Yield: 80%)

EXAMPLE 13

7-(4-fluorophenoxymethyl)-2,3-dimethyl-1-(prop-2-ynyl)-1H-pyrrolo[2,3-c]pyridine hydrochloride 1H-NMR(400 MHz, CDCl$_3$) δ 8.22 (m, 1H), 7.74 (m, 1H), 7.14 (m, 2H), 7.00 (m, 2H), 5.97 (s, 2H), 5.44 (d, 2H), 2.56 (s, 3H), 2.33 (s, 1+3H); (Yield: 70%)

EXAMPLE 14

2,3-dimethyl-7-(4-methylphenoxymethyl)-1H-pyrrolo[2,3-c]pyridine

Step 1: 2-(4-methylphenoxymethyl)-3-nitropyridine

In accordance with the same procedures as in Step 3 of Preparation 1, except for using 2-bromomethyl-3-nitropyridine prepared in Step 2 of Preparation 1 and 4-methylphenol, the titled compound was obtained as yellow solid. (Yield: 85%)

1H-NMR(400 MHz, CDCl$_3$) δ 8.85 (d, 1H), 8.30 (d, 1H), 7.49 (m, 1H), 7.06 (d, 2H), 6.85 (d, 2H), 5.54 (s, 2H), 2.28 (s, 3H)

Step 2: 2,3-dimethyl-7-(4-methylphenoxymethyl)-1H-pyrrolo[2,3-c]pyridine

In accordance with the same procedures as in Example 1, except for using 2-(4-methylphenoxymethyl)-3-nitropyridine prepared in Step 1, the titled compound was obtained as brown oil. (Yield: 20%)

1H-NMR(400 MHz, CDCl$_3$) δ 8.60 (brs, NH), 8.15 (d, 1H), 7.31 (d, 1H), 7.07 (m, 2H), 6.93 (m, 2H), 5.48 (s, 2H), 2.39 (s, 3H), 2.24 (s, 3H), 2.20 (s, 3H)

EXAMPLES 15 To 31

The titled compounds of Examples 15 to 31 were prepared, in accordance with the same procedures as in Example 2, using 2,3-dimethyl-7-(4-methylphenoxymethyl)-1H-pyrrolo[2,3-c]pyridine prepared in Example 14; and, benzyl bromide, 3-methoxybenzyl bromide, 4-methylbenzyl bromide, (bromomethyl)cyclopropane, 4-fluorobenzyl chloride, 4-chlorobenzyl chloride, 3,4-dichlorobenzyl chloride, 3-methylbenzyl bromide, 4-chloromethyl-2-methylthiazole, 4-bromo-2-methyl-2-butene, 2-bromoethyl methyl ether, 1-iodopropane, iodoethane, 2-methylbenzyl chloride, 4-tert-butylbenzyl chloride, 2,5-dimethylbenzyl chloride, or 4-trifluoromethylbenzyl chloride.

EXAMPLE 15

1-benzyl-2,3-dimethyl-7-(p-tolyloxymethyl)-1H-pyrrolo[2,3-c]pyridine hydrochloride 1H-NMR(400 MHz, CDCl$_3$) δ 8.19 (t, 1H), 7.76 (d, 1H), 7.28 (m, 3H), 7.07 (d, 2H), 6.88 (d, 2H), 5.59 (m, 2H), 5.73 (s, 2H), 5.58 (s, 2H), 2.50 (s, 3H), 2.39 (s, 3H), 2.28 (s, 3H); (Yield: 35%)

EXAMPLE 16

1-(3-methoxybenzyl)-2,3-dimethyl-7-(p-tolyloxymethyl)-1H-pyrrolo[2,3-c]pyridine hydrochloride 1H-NMR(400 MHz, CDCl$_3$) δ 8.19 (t, 1H), 7.76 (d, 1H), 7.19 (t, 1H), 7.09 (d, 2H), 6.90 (d, 2H), 6.79 (d, 1H), 6.18 (d, 1H), 6.11 (s, 1H), 5.69 (s, 2H), 5.57 (s, 2H), 3.69 (s, 3H), 2.50 (s, 3H), 2.39 (s, 3H), 2.28 (s, 3H); (Yield: 45%)

EXAMPLE 17

2,3-dimethyl-1-(4-methylbenzyl)-7-(p-tolyloxymethyl)-1H-pyrrolo[2,3-c]pyridine hydrochloride 1H-NMR(400 MHz, CDCl$_3$) δ 8.18 (t, 1H) 7.77 (d, 1H), 7.07 (m, 4H), 6.89 (d, 2H), 6.48 (d, 2H), 5.68 (s, 2H), 5.57 (s, 2H), 2.49 (s, 3H), 2.39 (s, 3H), 2.31 (s, 3H), 2.28 (s, 3H); (Yield: 41%)

EXAMPLE 18

1-cyclopropylmethyl-2,3-dimethyl-7-(p-tolyloxymethyl)-1H-pyrrolo[2,3-c]pyridine hydrochloride 1H-NMR(400 MHz, CDCl$_3$) δ 8.19 (t, 1H), 7.70 (d, 1H), 7.10 (d, 2H), 7.00 (d, 2H), 5.90 (s, 2H), 4.44 (d, 2H), 2.55 (s, 3H), 2.33 (s, 3H), 2.28 (s, 3H), 1.07 (m, 1H), 0.58 (m, 2H), 0.21 (m, 2H); (Yield: 71%)

EXAMPLE 19

1-(4-fluorobenzyl)-2,3-dimethyl-7-(p-tolyloxymethyl)-1H-pyrrolo[2,3-c]pyridine hydrochloride 1H-NMR(400 MHz, CDCl$_3$) δ 8.20 (t, 1H), 7.77 (d, 1H), 7.07 (d, 2H), 6.97 (t, 2H), 6.89 (d, 2H), 6.60 (m, 2H), 5.78 (s, 2H), 5.61 (s, 2H), 2.48 (s, 3H), 2.39 (s, 3H), 2.28 (s, 3H); (Yield: 45%)

EXAMPLE 20

1-(4-chlorobenzyl)-2,3-dimethyl-7-(p-tolyloxymethyl)-1H-pyrrolo[2,3-c]pyridine hydrochloride 1H-NMR(400 MHz, CDCl$_3$) δ 8.21 (t, 1H), 7.77 (d, 1H), 7.24 (d, 2H), 7.07 (d, 2H), 6.86 (d, 2H), 6.55 (d, 2H), 5.70 (s, 2H), 5.61 (s, 2H), 2.47 (s, 3H), 2.39 (s, 3H), 2.28 (s, 3H); (Yield: 55%)

EXAMPLE 21

1-(3,4-dichlorobenzyl)-2,3-dimethyl-7-(p-tolyloxymethyl)-1H-pyrrolo[2,3-c]pyridine hydrochloride 1H-NMR(400 MHz, CDCl$_3$) δ 8.07 (m, 1H), 7.58 (m, 2H), 7.43 (d, 1H), 7.33 (d, 1H), 7.06-7.01 (m, 4H), 6.98 (s, 2H), 6.00 (s, 2H), 2.60 (s, 3H), 2.29 (s, 3H), 2.25 (s, 3H); (Yield: 75%)

EXAMPLE 22

2,3-dimethyl-1-(3-methylbenzyl)-7-(p-tolyloxymethyl)-1H-pyrrolo[2,3-c]pyridine hydrochloride 1H-NMR(400 MHz, CDCl$_3$) δ 8.19 (t, 1H), 7.76 (d, 1H), 7.16-7.07 (m, 4H), 6.88 (d, 2H), 6.41 (s, 1H), 6.35 (d, 1H), 5.68 (s, 2H), 5.56 (s, 2H), 2.50 (s, 3H), 2.39 (s, 3H), 2.28 (s, 3H), 2.23 (s, 3H); (Yield: 79%)

EXAMPLE 23

2,3-dimethyl-1-(2-methylthiazol-4-ylmethyl)-7-(p-tolyloxymethyl)-1H-pyrrolo[2,3-c]pyridine hydrochloride 1H-NMR(400 MHz, CDCl$_3$) δ 8.17 (t, 1H), 7.71 (d, 1H), 7.13-7.00 (m, 4H), 6.61 (s, 1H), 6.02 (s, 2H), 5.73 (s, 2H), 2.60 (s, 3H), 2.56 (s, 3H), 2.33 (s, 3H), 2.26 (s, 3H); (Yield: 69%)

EXAMPLE 24

2,3-dimethyl-1-(3-methylbut-2-enyl)-7-(p-tolyloxymethyl)-1H-pyrrolo[2,3-c]pyridine hydrochloride 1H-NMR(400 MHz, CDCl$_3$) δ 8.15 (t, 1H), 7.68 (d, 1H), 7.11 (d, 2H), 7.01 (d, 2H), 5.89 (s, 2H), 5.08 (m, 2H), 4.94 (m, 1H), 2.50 (s, 3H), 2.27 (s, 3H), 2.18 (s, 3H), 1.70 (s, 3H), 1.63 (s, 3H); (Yield: 60%)

EXAMPLE 25

1-(2-methoxyethyl)-2,3-dimethyl-7-(p-tolyloxymethyl)-1H-pyrrolo[2,3-c]pyridine hydrochloride 1H-NMR(400 MHz, CDCl$_3$) δ 8.17 (t, 1H), 7.68 (d, 1H), 7.11-7.01 (m, 4H), 6.02 (s, 2H), 4.69 (m, 2H), 3.58 (m, 2H), 3.20 (s, 3H), 2.53 (s, 3H), 2.32 (s, 3H), 2.29 (s, 3H); (Yield: 65%)

EXAMPLE 26

2,3-dimethyl-1-propyl-7-(p-tolyloxymethyl)-1H-pyrrolo[2,3-c]pyridine hydrochloride 1H-NMR(400 MHz, CDCl$_3$) δ 8.17 (t, 1H), 7.70 (d, 1H), 7.10 (d, 2H), 7.01 (d, 2H), 5.90 (s, 2H), 4.35 (t, 2H), 2.54 (s, 3H), 2.32 (s, 3H), 2.28 (s, 3H), 1.72 (m, 2H), 0.90 (t, 3H); (Yield: 95%)

EXAMPLE 27

1-ethyl-2,3-dimethyl-7-(p-tolyloxymethyl)-1H-pyrrolo[2,3-c]pyridine hydrochloride 1H-NMR(400 MHz, CDCl$_3$) δ 8.17 (t, 1H), 7.70 (d, 1H), 7.11 (d, 2H), 7.03 (d, 2H), 5.93 (s, 2H), 4.50 (q, 2H), 2.55 (s, 3H), 2.32 (s, 3H), 2.28 (s, 3H), 1.38 (t, 3H); (Yield: 90%)

EXAMPLE 28

2,3-dimethyl-1-(2-methylbenzyl)-7-(p-tolyloxymethyl)-1H-pyrrolo[2,3-c]pyridine hydrochloride 1H-NMR(400 MHz, CDCl$_3$) δ 8.20 (t, 1H), 7.79 (d, 1H), 7.26 (m, 1H), 7.20 (d, 2H), 7.05 (d, 2H), 6.82 (d, 2H), 5.71 (d, 1H), 5.62 (s, 2H), 5.42 (m, 2H), 2.46 (s, 3H), 2.41 (s, 3H), 2.27 (s, 3H), 2.17 (s, 3H); (Yield: 70%)

EXAMPLE 29

1-(4-tert-butylbenzyl)-2,3-dimethyl-7-(p-tolyloxymethyl)-1H-pyrrolo[2,3-c]pyridine hydrochloride 1H-NMR(400 MHz, CDCl$_3$) δ 8.19 (t, 1H), 7.75 (d, 1H), 7.26 (d, 2H), 7.07 (d, 2H), 6.89 (d, 2H), 6.51 (d, 2H), 5.69 (s, 2H), 5.59 (s, 2H), 2.51 (s, 3H), 2.39 (s, 3H), 2.28 (s, 3H), 1.28 (s, 9H); (Yield: 75%)

EXAMPLE 30

2,3-dimethyl-1-(2,5-dimethylbenzyl)-7-(p-tolyloxymethyl)-1H-pyrrolo[2,3-c]pyridine hydrochloride 1H-NMR(400 MHz, CDCl$_3$) δ 8.21 (t, 1H), 7.79 (d, 1H), 7.08-7.00 (m, 4H), 6.82 (d, 2H), 5.53-5.58 (m, 3H), 5.44 (brs, 2H), 2.46 (s, 3H), 2.42 (s, 3H), 2.27 (s, 3H), 2.06 (s, 3H), 2.01 (s, 3H); (Yield: 78%)

EXAMPLE 31

2,3-dimethyl-7-(p-tolyloxymethyl)-1-(4-trifluoromethylbenzyl)-1H-pyrrolo[2,3-c]pyridine hydrochloride 1H-NMR(400 MHz, CDCl$_3$) δ 8.22 (t, 1H), 7.79 (d, 1H), 7.53 (d, 2H), 7.07 (d, 2H), 6.84 (d, 2H), 6.74 (d, 2H), 5.80 (s, 2H), 5.62 (s, 2H), 2.50 (s, 3H), 2.40 (s, 3H), 2.27 (s, 3H); (Yield: 72%)

EXAMPLE 32

7-(2,4-difluorophenoxymethyl)-2,3-dimethyl-1H-pyrrolo[2,3-c]pyridine

Step 1: 2-(2,4-difluorophenoxymethyl)-3-nitropyridine

In accordance with the same procedures as in Step 3 of Preparation 1, except for using 2-bromomethyl-3-nitropyridine prepared in Step 2 of Preparation 1 and 2,4-difluorophenol, the titled compound was obtained as yellow solid. (Yield: 98%)

1H-NMR(400 MHz, CDCl$_3$) δ 8.87 (d, 1H), 8.38 (d, 1H), 7.54 (m, 1H), 7.00 (m, 1H), 6.86 (m, 1H), 6.78 (m, 1H), 5.60 (s, 2H)

Step 2: 7-(2,4-difluorophenoxymethyl)-2,3-dimethyl-1H-pyrrolo[2,3-c]pyridine

In accordance with the same procedures as in Example 1, except for using 2-(2,4-difluorophenoxymethyl)-3-nitropyridine prepared in Step 1, the titled compound was obtained as brown oil. (Yield: 30%)

1H-NMR(400 MHz, CDCl$_3$) δ 8.80 (brs, 1H), 8.13 (d, 1H), 7.34 (m, 1H), 7.08 (m, 1H), 6.82 (m, 2H), 5.56 (s, 2H), 2.43 (s, 3H), 2.22 (s, 3H)

EXAMPLES 33 TO 40

The titled compounds of Examples 33 to 40 were prepared, in accordance with the same procedures as in Example 2, using 7-(2,4-difluorophenoxymethyl)-2,3-dimethyl-1H-pyrrolo[2,3-c]pyridine prepared in Example 32; and, 1-iodopropane, 2-bromoethyl methyl ether, (bromomethyl)cyclopropane, iodoethane, allyl bromide, 4-bromo-2-methyl-2-butene, iodomethane, or 4-fluorobenzyl chloride.

EXAMPLE 33

7-(2,4-difluorophenoxymethyl)-2,3-dimethyl-1-propyl-1H-pyrrolo[2,3-c]pyridine hydrochloride 1H-NMR(400 MHz, CDCl$_3$) δ 8.13 (m, 1H), 7.73 (m, 2H), 6.90-6.77 (m, 2H), 6.01 (s, 2H), 4.53 (m, 2H), 2.61 (s, 3H), 2.33 (s, 3H), 1.78 (m, 2H), 1.01 (m, 3H); (Yield: 60%)

EXAMPLE 34

7-(2,4-difluorophenoxymethyl)-1-(2-methoxyethyl)-2,3-dimethyl-1H-pyrrolo[2,3-c]pyridine hydrochloride 1H-NMR(400 MHz, CDCl$_3$) δ 8.11 (m, 1H), 7.77-7.70 (m, 2H), 6.89 (m, 1H), 6.74 (m, 1H), 6.21 (s, 2H), 4.85 (s, 2H), 3.68 (s, 2H), 3.23 (s, 3H), 2.57 (s, 3H), 2.10 (s, 3H); (Yield: 63%)

EXAMPLE 35

1-cyclopropylmethyl-7-(2,4-difluorophenoxymethyl)-2,3-dimethyl-1H-pyrrolo[2,3-c]pyridine hydrochloride 1H-NMR(400 MHz, CDCl$_3$) δ 8.14 (m, 1H), 7.71 (m, 2H), 6.69-6.60 (m, 2H), 6.10 (s, 2H), 4.59 (m, 2H), 2.59 (s, 3H), 2.35 (s, 3H), 1.10 (m, 1H), 0.63 (m, 2H), 0.29 (m, 2H); (Yield: 53%)

EXAMPLE 36

1-ethyl-7-(2,4-difluorophenoxymethyl)-2,3-dimethyl-1H-pyrrolo[2,3-c]pyridine hydrochloride 1H-NMR(400 MHz, CDCl$_3$) δ 8.13 (m, 1H), 7.81-7.71 (m, 2H), 6.90 (m, 1H), 6.77 (t, 1H), 6.04 (s, 2H), 4.66 (m, 2H), 2.58 (s, 3H), 2.33 (s, 3H), 1.42 (t, 3H); (Yield: 59%)

EXAMPLE 37

1-allyl-7-(2,4-difluorophenoxymethyl)-2,3-dimethyl-1H-pyrrolo[2,3-c]pyridine hydrochloride 1H-NMR(400 MHz, CDCl$_3$) δ 8.19 (m, 1H), 7.69 (m, 2H), 6.89-6.77 (m, 2H), 6.08 (m, 1H), 5.86 (s, 2H), 5.23-5.16 (m, 4H), 4.42 (d, 1H), 2.54 (s, 3H), 2.27 (s, 3H); (Yield: 59%)

EXAMPLE 38

7-(2,4-difluorophenoxymethyl)-2,3-dimethyl-1-(3-methylbut-2-enyl)-1H-pyrrolo[2,3-c]pyridine hydrochloride 1H-NMR(400 MHz, CDCl$_3$) δ 8.10 (m, 1H), 7.78-7.66 (m, 2H), 6.89-6.77 (m, 2H), 5.94 (s, 2H), 5.31 (s, 2H), 4.97 (m, 1H), 2.53 (s, 3H), 2.32 (s, 3H), 1.76 (s, 3H), 1.72 (s, 3H); (Yield: 55%)

EXAMPLE 39

7-(2,4-difluorophenoxymethyl)-1,2,3-trimethyl-1H-pyrrolo[2,3-c]pyridine hydrochloride 1H-NMR(400 MHz, CDCl$_3$) δ 8.11 (t, 1H), 7.78 (m, 1H), 7.70 (d, 1H), 6.90 (t, 1H), 6.78 (t, 1H), 6.14 (s, 2H), 4.23 (s, 2H), 2.56 (s, 3H), 2.33 (s, 3H); (Yield: 85%)

EXAMPLE 40

1-(4-fluorobenzyl)-7-(2,4-difluorophenoxymethyl)-2,3-dimethyl-1H-pyrrolo[2,3-c]pyridine hydrochloride 1H-NMR(400 MHz, CDCl$_3$) δ 8.14 (m, 1H), 7.80 (d, 1H), 7.78 (m, 1H), 7.01 (m, 2H), 6.72 (m, 1H), 6.73 (m, 1H), 6.69 (t, 2H), 5.87 (s, 2H), 5.70 (s, 2H), 2.52 (s, 3H), 2.40 (s, 3H); (Yield: 85%)

EXAMPLE 41

7-(4-chlorophenoxymethyl)-2,3-dimethyl-1H-pyrrolo[2,3-c]pyridine

Step 1: 2-(4-chlorophenoxymethyl)-3-nitropyridine

In accordance with the same procedures as in Step 3 of Preparation 1, except for using 2-bromomethyl-3-nitropyridine prepared in Step 2 of Preparation 1 and 4-chlorophenol, the titled compound was obtained as yellow solid. (Yield: 90%)

1H-NMR(400 MHz, CDCl$_3$) δ 8.86 (d, 1H), 8.34 (d, 1H), 7.52 (m, 1H), 7.24 (m, 2H), 6.89 (m, 2H), 5.55 (s, 2H)

Step 2: 7-(4-chlorophenoxymethyl)-2,3-dimethyl-1H-pyrrolo[2,3-c]pyridine

In accordance with the same procedures as in Example 1, except for using 2-(4-chlorophenoxymethyl)-3-nitropyridine prepared in Step 1, the titled compound was obtained as brown oil. (Yield: 24%)

1H-NMR(400 MHz, CDCl$_3$) δ 8.48 (brs, 1H), 8.16 (d, 1H), 7.34 (d, 1H), 7.23 (m, 2H), 6.98 (m, 2H), 5.30 (s, 2H), 2.40 (s, 3H), 2.20 (s, 3H)

EXAMPLE 42

7-(4-chlorophenoxymethyl)-2,3-dimethyl-1H-pyrrolo[2,3-c]pyridine hydrochloride A solution of 7-(4-chlorophenoxymethyl)-2,3-dimethyl-1H-pyrrolo[2,3-c]pyridine prepared in Example 41 in ethyl acetate (10 ml) was saturated with hydrochloric acid gas and then filtered. The resulting solid was dried under reduced pressure to give the titled compound as a white solid. (Yield: 90%)

1H-NMR(400 MHz, CDCl$_3$) δ 8.04 (m, 1H), 7.59 (m, 1H), 7.01 (m, 4H), 5.98 (s, 2H), 2.61 (s, 3H), 2.29 (s, 3H)

EXAMPLES 43 TO 52

The titled compounds of Examples 43 to 52 were prepared, in accordance with the same procedures as in Example 2, using 7-(4-chlorophenoxymethyl)-2,3-dimethyl-1H-pyrrolo[2,3-c]pyridine prepared in Example 41; and, benzyl bromide, (bromomethyl)cyclopropane, 3-methoxybenzyl chloride, 1-iodopropane, iodoethane, 4-bromo-2-methyl-2-butene, 2-fluorobenzyl chloride, iodomethane, 4-methylbenzyl chloride, or 4-fluorobenzyl chloride

EXAMPLE 43

1-benzyl-7-(4-chlorophenoxymethyl)-2,3-dimethyl-1H-pyrrolo[2,3-c]pyridine hydrochloride 1H-NMR(400 MHz, CDCl$_3$) δ 8.19 (t, 1H), 7.78 (d, 1H), 7.29-7.22 (m, 5H), 6.95 (m, 2H), 6.61 (m, 2H), 5.71 (s, 2H), 5.63 (s, 2H), 2.50 (s, 3H), 2.40 (s, 3H); (Yield: 65%)

EXAMPLE 44

7-(4-chlorophenoxymethyl)-1-cyclopropylmethyl-2,3-dimethyl-1H-pyrrolo[2,3-c]pyridine hydrochloride 1H-NMR(400 MHz, CDCl$_3$) δ 8.17 (m, 1H), 7.73 (m, 1H), 7.26 (m, 2H), 7.11 (m, 2H), 6.04 (s, 2H), 4.43 (s, 2H), 2.56 (s, 3H), 2.33 (s, 3H), 1.05 (m, 1H), 0.63 (m, 2H), 0.23 (m, 2H); (Yield: 49%)

EXAMPLE 45

7-(4-chlorophenoxymethyl)-1-(3-methoxybenzyl)-2,3-dimethyl-1H-pyrrolo[2,3-c]pyridine hydrochloride 1H-NMR(400 MHz, CDCl$_3$) δ 8.19 (m, 1H), 7.79 (m, 1H), 7.26 (m, 3H), 6.98 (m, 2H), 6.82 (m, 1H), 6.12 (m, 2H), 5.63 (m, 4H), 3.65 (s, 3H), 2.52 (s, 3H), 2.39 (s, 3H); (Yield: 35%)

EXAMPLE 46

7-(4-chlorophenoxymethyl)-2,3-dimethyl-1-propyl-1H-pyrrolo[2,3-c]pyridine hydrochloride 1H-NMR(400 MHz, CDCl$_3$) δ 8.17 (m, 1H), 7.72 (m, 1H), 7.26 (m, 2H), 7.13 (m, 2H), 5.96 (s, 2H), 4.35 (m, 2H), 2.55 (s, 3H), 2.33 (s, 3H), 1.74 (m, 2H), 0.93 (m, 3H); (Yield: 89%)

EXAMPLE 47

7-(4-chlorophenoxymethyl)-1-ethyl-2,3-dimethyl-1H-pyrrolo[2,3-c]pyridine hydrochloride 1H-NMR(400 MHz, CDCl$_3$) δ 8.16 (m, 1H), 7.71 (m, 1H), 7.26 (m, 2H), 7.12 (m, 2H), 5.98 (s, 2H), 4.50 (m, 2H), 2.56 (s, 3H), 2.33 (s, 3H), 1.39 (t, 3H); (Yield: 65%)

EXAMPLE 48

7-(4-chlorophenoxymethyl)-2,3-dimethyl-1-(3-methylbut-2-enyl)-1H-pyrrolo[2,3-c]pyridine hydrochloride 1H-NMR(400 MHz, CDCl$_3$) δ 8.16 (t, 1H), 7.71 (d, 1H), 7.26 (m, 2H), 7.10 (d, 2H), 5.95 (s, 2H), 5.06 (s, 2H), 4.95 (s, 1H), 1.70 (s, 3H), 1.65 (s, 3H); (Yield: 60%)

EXAMPLE 49

7-(4-chlorophenoxymethyl)-1-(2-fluorobenzyl)-2,3-dimethyl-1H-pyrrolo[2,3-c]pyridine hydrochloride 1H-NMR(400 MHz, CDCl$_3$) δ 8.22 (m, 1H), 7.80 (m, 1H), 7.32 (m, 2H), 7.21 (m, 2H), 7.13 (t, 1H), 7.01-6.93 (m, 3H), 6.12 (t, 1H), 5.77 (s, 2H), 5.70 (s, 2H), 2.48 (s, 3H), 2.39 (s, 3H); (Yield: 60%)

EXAMPLE 50

7-(4-chlorophenoxymethyl)-1,2,3-trimethyl-1H-pyrrolo[2,3-c]pyridine hydrochloride 1H-NMR(400 MHz, CDCl$_3$) δ 8.14 (m, 1H), 7.71 (m, 1H), 7.26 (m, 2H), 7.12 (m, 2H), 6.02 (s, 2H), 4.18 (s, 3H), 2.54 (s, 3H), 2.33 (s, 3H); (Yield: 70%)

EXAMPLE 51

7-(4-chlorophenoxymethyl)-2,3-dimethyl-1-(4-methylbenzyl)-1H-pyrrolo[2,3-c]pyridine hydrochloride 1H-NMR(400 MHz, CDCl$_3$) δ 8.19 (m, 1H), 7.74 (m, 1H), 7.26-6.96 (m, 6H), 6.52 (m, 2H), 5.67-5.59 (m, 4H), 2.51 (s, 3H), 2.40 (s, 3H), 2.33 (s, 3H); (Yield: 75%)

EXAMPLE 52

7-(4-chlorophenoxymethyl)-1-(4-fluorobenzyl)-2,3-dimethyl-1H-pyrrolo[2,3-c]pyridine hydrochloride 1H-NMR(400 MHz, CDCl$_3$) δ 8.20 (m, 1H), 7.78 (m, 1H), 7.20 (m, 2H), 6.99 (m, 4H), 6.64 (m, 2H), 5.67 (m, 4H), 2.49 (s, 3H), 2.39 (s, 3H); (Yield: 55%)

EXAMPLE 53

7-(2-chlorophenoxymethyl)-2,3-dimethyl-1H-pyrrolo[2,3-c]pyridine

Step 1: 2-(2-chlorophenoxymethyl)-3-nitropyridine

In accordance with the same procedures as in Step 3 of Preparation 1, except for using 2-bromomethyl-3-nitropyridine prepared in Step 2 of Preparation 1 and 2-chlorophenol, the titled compound was obtained as yellow oil. (Yield: 85%)
1H-NMR(400 MHz, CDCl$_3$) δ 8.85 (d, 1H), 8.37 (d, 1H), 7.50 (m, 1H), 7.38 (d, 1H), 7.10 (m, 1H), 6.97 (m, 2H), 5.64 (s, 2H)

Step 2: 7-(2-chlorophenoxymethyl)-2,3-dimethyl-1H-pyrrolo[2,3-c]pyridine

In accordance with the same procedures as in Example 1, except for using 2-(2-chlorophenoxymethyl)-3-nitropyridine prepared in Step 1, the titled compound was obtained as brown oil. (Yield: 30%)
1H-NMR(400 MHz, CDCl$_3$) δ 9.50 (brs, 1H), 8.13 (d, 1H), 7.33 (m, 3H), 6.92 (m, 2H), 5.41 (s, 2H), 2.43 (s, 3H), 2.22 (s, 3H)

EXAMPLES 54 TO 64

The titled compounds of Examples 54 to 64 were prepared, in accordance with the same procedures as in Example 2, using 7-(2-chlorophenoxymethyl)-2,3-dimethyl-1H-pyrrolo[2,3-c]pyridine prepared in Example 53; and, allyl bromide, 2-bromoethyl methyl ether, (bromomethyl)cyclopropane, 4-methylbenzyl bromide, 4-fluorobenzyl bromide, benzyl bromide, 4-bromo-2-methyl-2-butene, 1-iodopropane, iodomethane, iodoethane, or 3-methoxybenzyl chloride.

EXAMPLE 54

1-allyl-7-(2-chlorophenoxymethyl)-2,3-dimethyl-1H-pyrrolo[2,3-c]pyridine hydrochloride 1H-NMR(400 MHz, CDCl$_3$) δ 8.16 (m, 1H), 7.81-7.73 (m, 2H), 7.35-7.26 (m, 2H), 6.95 (m, 1H), 6.12-6.03 (m, 3H), 5.32 (m, 2H), 5.16 (d, 1H), 4.31 (d, 1H), 2.57 (s, 3H), 2.37 (s, 3H); (Yield: 65%)

EXAMPLE 55

7-(2-chlorophenoxymethyl)-1-(2-methoxyethyl)-2,3-dimethyl-1H-pyrrolo[2,3-c]pyridine hydrochloride 1H-NMR(400 MHz, CDCl$_3$) δ 8.12 (m, 1H), 7.80 (m, 1H), 7.70 (m, 1H), 7.26 (m, 2H), 6.92 (t, 1H), 6.28 (s, 2H), 4.90 (m, 2H), 3.64 (m, 2H), 3.21 (s, 3H), 2.55 (s, 3H), 2.32 (s, 3H); (Yield: 44%)

EXAMPLE 56

7-(2-chlorophenoxymethyl)-1-cyclopropylmethyl-2,3-dimethyl-1H-pyrrolo[2,3-c]pyridine hydrochloride 1H-NMR(400 MHz, CDCl$_3$) δ 8.15 (t, 1H), 7.79 (m, 1H), 7.70 (m, 1H), 7.26 (m, 2H), 6.92 (t, 1H), 6.18 (s, 2H), 4.65 (m, 2H), 2.57 (s, 3H), 2.33 (s, 3H), 1.07 (m, 1H), 0.62 (m, 2H), 0.24 (m, 2H); (Yield: 40%)

EXAMPLE 57

7-(2-chlorophenoxymethyl)-2,3-dimethyl-1-(4-methylbenzyl)-1H-pyrrolo[2,3-c]pyridine hydrochloride 1H-NMR(400 MHz, CDCl$_3$) δ 8.14 (m, 1H), 7.76-7.62 (m, 2H), 7.33-6.92 (m, 5H), 6.94 (m, 1H), 6.56 (m, 2H), 5.88 (s, 2H), 5.71 (s, 2H), 2.57 (s, 3H), 2.35 (s, 3H), 2.31 (s, 3H); (Yield: 48%)

EXAMPLE 58

7-(2-chlorophenoxymethyl)-1-(4-fluorobenzyl)-2,3-dimethyl-1H-pyrrolo[2,3-c]pyridine hydrochloride 1H-NMR(400 MHz, CDCl$_3$) δ 8.18 (m, 1H), 7.79-7.68 (m, 2H), 7.26 (m, 1H), 6.99 (m, 4H), 6.68 (m, 2H), 5.93 (s, 2H), 5.75 (s, 2H), 2.54 (s, 3H), 2.39 (s, 3H); (Yield: 45%)

EXAMPLE 59

1-benzyl-7-(2-chlorophenoxymethyl)-2,3-dimethyl-1H-pyrrolo[2,3-c]pyridine hydrochloride 1H-NMR(400 MHz, CDCl$_3$) δ 8.16 (m, 1H), 7.78 (m, 1H), 7.66 (m, 1H), 7.26 (m, 5H), 6.95 (m, 1H), 6.69 (m, 2H), 5.72 (s, 2H), 5.30 (s, 2H), 2.54 (s, 3H), 2.40 (s, 3H); (Yield: 95%)

EXAMPLE 60

7-(2-chlorophenoxymethyl)-2,3-dimethyl-1-(3-methylbut-2-enyl)-1H-pyrrolo[2,3-c]pyridine hydrochloride 1H-NMR(400 MHz, CDCl$_3$) δ 8.12 (m, 1H), 7.77 (m, 1H), 7.69 (m, 1H), 7.26 (m, 2H), 6.93 (t, 1H), 6.09 (s, 2H), 5.30 (m, 2H), 4.95 (s, 1H), 2.53 (s, 3H), 2.32 (s, 3H), 1.72-1.70 (d, 6H); (Yield: 92%)

EXAMPLE 61

7-(2-chlorophenoxymethyl)-2,3-dimethyl-1-propyl-1H-pyrrolo[2,3-c]pyridine hydrochloride 1H-NMR(400 MHz, CDCl$_3$) δ 8.13 (m, 1H), 7.73 (m, 2H), 7.26 (m, 2H), 6.95 (m, 1H), 6.09 (s, 2H), 4.59 (m, 2H), 2.55 (s, 3H), 2.32 (s, 3H), 1.75 (m, 2H), 0.95 (t, 3H); (Yield: 82%)

EXAMPLE 62

7-(2-chlorophenoxymethyl)-1,2,3-trimethyl-1H-pyrrolo[2,3-c]pyridine hydrochloride 1H-NMR(400 MHz, CDCl$_3$) δ 8.11 (t, 1H), 7.75 (d, 1H), 7.70 (d, 1H), 7.35 (m, 2H), 6.97 (t, 1H), 6.16 (s, 2H), 4.19 (s, 3H), 2.55 (s, 3H), 2.32 (s, 3H); (Yield: 89%)

EXAMPLE 63

7-(2-chlorophenoxymethyl)-1-ethyl-2,3-dimethyl-1H-pyrrolo[2,3-c]pyridine hydrochloride 1H-NMR(400 MHz, CDCl$_3$) δ 8.13 (t, 1H), 7.79 (d, 1H), 7.70 (d, 1H), 7.35 (m, 2H), 6.97 (t, 1H), 6.12 (s, 2H), 4.71 (m, 2H), 2.57 (s, 3H), 2.32 (s, 3H), 1.40 (t, 3H); (Yield: 69%)

EXAMPLE 64

7-(2-chlorophenoxymethyl)-1-(3-methoxybenzyl)-2,3-dimethyl-1H-pyrrolo[2,3-c]pyridine hydrochloride 1H-NMR(400 MHz, CDCl$_3$) δ 8.17 (m, 1H), 7.78-7.63 (m, 2H), 7.26 (m, 3H), 6.97-6.79 (m, 2H), 6.24 (m, 2H), 5.90 (s, 2H), 5.72 (s, 2H), 3.70 (s, 3H), 2.54 (s, 3H), 2.32 (s, 3H); (Yield: 66%)

EXAMPLE 65

2,3-dimethyl-7-(2,4-dimethylphenoxymethyl)-1H-pyrrolo[2,3-c]pyridine

Step 1: 2-(2,4-dimethylphenoxymethyl)-3-nitropyridine

In accordance with the same procedures as in Step 3 of Preparation 1, except for using 2-bromomethyl-3-nitropyridine prepared in Step 2 of Preparation 1 and 2,4-dimethylphenol, the titled compound was obtained as yellow solid. (Yield: 78%)

1H-NMR(400 MHz, CDCl$_3$) δ 8.82 (d, 1H), 8.27 (d, 1H), 7.49 (m, 1H), 6.92 (m, 2H), 6.74 (d, 1H), 5.52 (s, 2H), 2.24 (s, 3H), 2.14 (s, 3H)

Step 2: 2,3-dimethyl-7-(2,4-dimethylphenoxymethyl)-1H-pyrrolo[2,3-c]pyridine In accordance with the same procedures as in Example 1, except for using 2-(2,4-dimethylphenoxymethyl)-3-nitropyridine prepared in Step 1, the titled compound was obtained as brown oil. (Yield: 35%)

1H-NMR(400 MHz, CDCl$_3$) δ 8.74 (brs, 1H), 8.16 (d, 1H), 7.33 (d, 1H), 6.95 (m, 3H), 5.49 (s, 2H), 2.35 (s, 3H), 2.26 (s, 3H), 2.24 (s, 3H), 2.12 (s, 3H)

EXAMPLES 66 TO 77

The titled compounds of Examples 66 to 77 were prepared, in accordance with the same procedures as in Example 2, using 2,3-dimethyl-7-(2,4-dimethylphenoxymethyl)-1H-pyrrolo[2,3-c]pyridine prepared in Example 65; and, allyl bromide, benzyl bromide, 3-methoxybenzyl bromide, (bromomethyl)cyclopropane, 4-bromo-2-methyl-2-butene, 2-bromoethyl methyl ether, 1-iodopropane, 2-fluorobenzyl chloride, iodomethane, iodoethane, 4-methylbenzyl chloride, or 4-fluorobenzyl chloride.

EXAMPLE 66

1-allyl-2,3-dimethyl-7-(2,4-dimethylphenoxymethyl)-1H-pyrrolo[2,3-c]pyridine hydrochloride 1H-NMR(400 MHz, CDCl$_3$) δ 8.24 (m, 1H), 7.77 (m, 1H), 7.26 (m, 1H), 7.03 (m, 1H), 6.93 (m, 2H), 6.03-5.82 (m, 4H), 5.24-5.10 (m, 2H), 4.34 (m, 2H), 2.54 (s, 3H), 2.36 (s, 3H), 2.18 (s, 3H), 2.10 (s, 3H); (Yield: 25%)

EXAMPLE 67

1-benzyl-2,3-dimethyl-7-(2,4-dimethylphenoxymethyl)-1H-pyrrolo[2,3-c]pyridine hydrochloride 1H-NMR(400 MHz, CDCl$_3$) δ 8.20 (m, 1H), 7.78 (m, 1H), 7.26 (m, 2H), 7.15 (m, 1H), 6.97 (m, 3H), 6.60 (m, 2H), 5.74 (s, 2H), 5.56 (s, 2H), 2.53 (s, 3H), 2.40 (s, 3H), 2.25 (s, 3H), 2.12 (s, 3H); (Yield: 35%)

EXAMPLE 68

1-(3-methoxybenzyl)-2,3-dimethyl-7-(2,4-dimethylphenoxymethyl)-1H-pyrrolo[2,3-c]pyridine hydrochloride 1H-NMR(400 MHz, CDCl$_3$) δ 8.21 (m, 1H) 7.78 (m, 1H), 7.26 (m, 2H), 6.97 (m, 2H), 6.80 (m, 1H), 6.14-6.08 (m, 2H), 5.71 (s, 2H), 5.56 (s, 2H), 3.68 (s, 3H), 2.56 (s, 3H), 2.49 (s, 3H), 2.25 (s, 3H), 2.12 (s, 3H); (Yield: 45%)

EXAMPLE 69

1-cyclopropylmethyl-2,3-dimethyl-7-(2,4-dimethylphenoxymethyl)-1H-pyrrolo[2,3-c]pyridine hydrochloride 1H-NMR(400 MHz, CDCl$_3$) δ 8.19 (m, 1H), 7.70 (m, 1H), 7.17 (m, 1H), 7.02 (m, 1H), 6.91 (m, 1H), 6.00 (s, 2H), 4.47 (m, 2H), 2.58 (s, 3H), 2.36 (s, 3H), 2.24 (s, 3H), 2.07 (s, 3H), 1.03 (m, 1H), 0.58 (m, 2H), 0.21 (m, 2H); (Yield: 75%)

EXAMPLE 70

2,3-dimethyl-1-(3-methylbut-2-enyl)-7-(2,4-dimethylphenoxymethyl)-1H-pyrrolo[2,3-c]pyridine hydrochloride 1H-NMR(400 MHz, CDCl$_3$) δ 8.17 (t, 1H), 7.70 (m, 1H), 7.18 (m, 1H), 7.01 (m, 1H), 6.91 (m, 1H), 5.90 (s, 2H), 5.11 (m, 2H), 4.85 (m, 1H), 2.52 (s, 3H), 2.34 (s, 3H), 2.23 (s, 3H), 2.12 (s, 3H), 1.69 (s, 3H), 1.63 (s, 3H); (Yield: 55%)

EXAMPLE 71

1-(2-methoxyethyl)-2,3-dimethyl-7-(2,4-dimethylphenoxymethyl)-1H-pyrrolo[2,3-c]pyridine hydrochloride 1H-NMR(400 MHz, CDCl$_3$) δ 8.14 (m, 1H), 7.65 (m, 1H), 7.23 (m, 1H), 7.01 (m, 1H), 6.90 (m, 1H), 6.00 (s, 2H), 4.73 (m, 2H), 3.58 (m, 2H), 3.18 (s, 3H), 2.58 (s, 3H), 2.35 (s, 3H), 2.28 (s, 3H), 2.05 (s, 3H); (Yield: 95%)

EXAMPLE 72

2,3-dimethyl-7-(2,4-dimethylphenoxymethyl)-1-propyl-1H-pyrrolo[2,3-c]pyridine hydrochloride 1H-NMR(400 MHz, CDCl$_3$) δ 8.17 (t, 1H), 7.72 (m, 1H), 7.13 (d, 1H), 7.02 (m, 1H), 6.92 (s, 1H), 5.88 (s, 2H), 4.36 (t, 2H), 2.54 (s, 3H), 2.33 (s, 3H), 2.24 (s, 3H), 2.08 (s, 3H), 1.73 (m, 2H), 0.86 (t, 3H); (Yield: 90%)

EXAMPLE 73

1-(2-fluorobenzyl)-2,3-dimethyl-7-(2,4-dimethylphenoxymethyl)-1H-pyrrolo[2,3-c]pyridine hydrochloride 1H-NMR(400 MHz, CDCl$_3$) δ 8.22 (m, 1H), 7.78 (m, 1H), 7.13-6.91 (m, 6H), 6.20 (m, 1H), 5.85 (s, 2H), 5.64 (s, 2H), 2.47 (s, 3H), 2.39 (s, 3H), 2.23 (s, 3H), 2.12 (s, 3H); (Yield: 90%)

EXAMPLE 74

7-(2,4-dimethylphenoxymethyl)-1,2,3-trimethyl-1H-pyrrolo[2,3-c]pyridine hydrochloride 1H-NMR(400 MHz, CDCl$_3$) δ 8.16 (m, 1H), 7.70 (m, 1H), 7.15 (m, 1H), 7.04 (m, 1H), 6.94 (m, 1H), 5.94 (s, 2H), 4.03 (s, 3H), 2.53 (s, 3H), 2.33 (s, 3H), 2.25 (s, 3H), 2.11 (s, 3H); (Yield: 91%)

EXAMPLE 75

1-ethyl-2,3-dimethyl-7-(2,4-dimethylphenoxymethyl)-1H-pyrrolo[2,3-c]pyridine hydrochloride 1H-NMR(400 MHz, CDCl$_3$) δ 8.17 (m, 1H), 7.70 (m, 1H), 7.16 (m, 1H), 7.02 (m, 1H), 6.92 (s, 1H), 5.91 (s, 2H), 4.50 (m, 2H), 2.55 (s, 3H), 2.33 (s, 3H), 2.24 (s, 3H), 2.08 (s, 3H), 1.35 (t, 3H); (Yield: 71%)

EXAMPLE 76

2,3-dimethyl-1-(4-methylbenzyl)-7-(2,4-dimethylphenoxymethyl)-1H-pyrrolo[2,3-c]pyridine hydrochloride 1H-NMR(400 MHz, CDCl$_3$) δ 8.19 (m, 1H), 7.76 (m, 1H), 7.26 (m, 2H), 7.07-6.93 (m, 4H), 6.48 (m, 1H), 5.68 (s, 2H), 5.56 (s, 2H), 2.50 (s, 3H), 2.39 (s, 3H), 2.31 (s, 3H), 2.25 (s, 3H), 2.12 (s, 3H); (Yield: 76%)

EXAMPLE 77

1-(4-fluorobenzyl)-2,3-dimethyl-7-(2,4-dimethylphenoxymethyl)-1H-pyrrolo[2,3-c]pyridine hydrochloride 1H-NMR(400 MHz, CDCl$_3$) δ 8.21 (m, 1H), 7.80 (m, 1H), 6.97-6.93 (m, 5H), 6.57 (m, 2H), 5.70 (s, 2H), 5.58 (s, 2H), 2.49 (s, 3H), 2.40 (s, 3H), 2.17 (s, 3H), 2.11 (s, 3H); (Yield: 86%)

EXAMPLE 78

7-(3,4-dichlorophenoxymethyl)-1-(2-methoxyethyl)-2,3-dimethyl-1H-pyrrolo[2,3-c]pyridine hydrochloride Step 1: 2-(3,4-dichlorophenoxymethyl)-3-nitropyridine In accordance with the same procedures as in Step 3 of Preparation 1, except for using 2-bromomethyl-3-nitropyridine prepared in Step 2 of Preparation 1 and 3,4-dichlorophenol, the titled compound was obtained as yellow solid. (Yield: 72%)

1H-NMR(400 MHz, CDCl$_3$) δ 8.86 (d, 1H), 8.36 (d, 1H), 7.53 (d, 1H), 7.34 (d, 1H), 7.07 (s, 1H), 6.82 (d, 1H), 5.56 (s, 2H)

Step 2: 7-(3,4-dichlorophenoxymethyl)-2,3-dimethyl-1H-pyrrolo[2,3-c]pyridine

In accordance with the same procedures as in Example 1, except for using 2-(3,4-dichlorophenoxymethyl)-3-nitropyridine prepared in Step 1, the titled compound was obtained as brown oil. (Yield: 55%)

1H-NMR(400 MHz, CDCl$_3$) δ 8.48 (brs, 1H), 8.17 (d, 1H), 7.32 (m, 1H), 7.17 (s, 1H), 6.91 (m, 2H), 5.49 (s, 2H), 2.47 (s, 3H), 2.21 (s, 3H)

Step 3: 7-(3,4-dichlorophenoxymethyl)-1-(2-methoxyethyl)-2,3-dimethyl-1H-pyrrolo[2,3-c]pyridine hydrochloride In accordance with the same procedures as in Example 2, except for using 7-(3,4-dichlorophenoxymethyl)-2,3-dimethyl-1H-pyrrolo[2,3-c]pyridine prepared in Step 2 and 2-bromoethyl methyl ether, the titled compound was obtained as a white solid. (Yield: 70%)

1H-NMR(400 MHz, CDCl$_3$) δ 8.20 (m, 1H), 7.69 (m, 1H), 7.34 (m, 1H), 7.19 (m, 2H), 6.15 (s, 2H), 4.68 (s, 2H), 3.63 (s, 2H), 3.21 (s, 3H) 2.55 (s, 3H), 2.33 (s, 3H)

EXAMPLES 79 TO 87

The titled compounds of Examples 79 to 87 were prepared, in accordance with the same procedures as in Example 2, using 7-(3,4-dichlorophenoxymethyl)-2,3-dimethyl-1H-pyrrolo[2,3-c]pyridine prepared in Step 2 of Example 78; and, iodoethane, allyl bromide, 4-methylbenzyl bromide, 4-fluorobenzyl bromide, benzyl bromide, 4-bromo-2-methyl-2-butene, (bromomethyl)cyclopropane, 1-iodopropane, or iodomethane.

EXAMPLE 79

7-(3,4-dichlorophenoxymethyl)-1-ethyl-2,3-dimethyl-1H-pyrrolo[2,3-c]pyridine hydrochloride 1H-NMR(400 MHz, CDCl$_3$) δ 8.18 (m, 1H), 7.73 (m, 1H), 7.38 (m, 2H), 7.20 (m, 1H), 6.09 (m, 2H), 4.50 (m, 2H), 2.57 (s, 3H), 2.34 (s, 3H), 1.33 (m, 3H); (Yield: 90%)

EXAMPLE 80

1-allyl-7-(3,4-dichlorophenoxymethyl)-2,3-dimethyl-1H-pyrrolo[2,3-c]pyridine hydrochloride 1H-NMR(400 MHz, CDCl$_3$) δ 8.20 (m, 1H), 7.77 (m, 1H), 7.36 (m, 2H), 7.17 (m, 1H), 6.09-5.92 (m, 2H), 5.22 (m, 2H), 5.08 (m, 2H), 4.37 (d, 1H), 2.51 (s, 3H), 2.36 (s, 3H); (Yield: 80%)

EXAMPLE 81

7-(3,4-dichlorophenoxymethyl)-2,3-dimethyl-1-(4-methylbenzyl)-1H-pyrrolo[2,3-c]pyridine hydrochloride 1H-NMR(400 MHz, CDCl$_3$) δ 8.19 (m, 1H), 7.79 (m, 1H), 7.40 (m, 2H), 7.16 (m, 3H), 6.88 (m, 2H), 6.53 (m, 2H), 5.64 (m, 2H), 2.59 (s, 3H), 2.42 (s, 3H), 2.33 (s, 3H); (Yield: 84%)

EXAMPLE 82

7-(3,4-dichlorophenoxymethyl)-1-(4-fluorobenzyl)-2,3-dimethyl-1H-pyrrolo[2,3-c]pyridine hydrochloride 1H-NMR(400 MHz, CDCl$_3$) δ 8.22 (m, 1H), 7.80 (m, 1H), 7.03 (m, 5H), 6.66 (m, 2H), 5.70 (m, 4H), 2.50 (s, 3H), 2.40 (s, 3H); (Yield: 88%)

EXAMPLE 83

1-benzyl-7-(3,4-dichlorophenoxymethyl)-2,3-dimethyl-1H-pyrrolo[2,3-c]pyridine hydrochloride 1H-NMR(400 MHz, CDCl$_3$) δ 8.19 (m, 1H), 7.81 (m, 1H), 7.30 (m, 4H), 7.04 (m, 1H), 6.91 (s, 1H), 6.64 (m, 2H), 5.69 (m, 4H), 2.51 (s, 3H), 2.40 (s, 3H); (Yield: 68%)

EXAMPLE 84

7-(3,4-dichlorophenoxymethyl)-2,3-dimethyl-1-(3-methylbut-2-enyl)-1H-pyrrolo[2,3-c]pyridine hydrochloride 1H-NMR(400 MHz, CDCl$_3$) δ 8.15 (m, 1H), 7.73 (m, 1H), 7.41 (m, 2H), 7.16 (s, 1H), 6.01 (s, 2H), 5.07 (s, 2H), 4.96 (m, 1H), 2.60 (s, 3H), 2.37 (s, 3H), 1.77 (s, 3H), 1.74 (s, 3H); (Yield: 65%)

EXAMPLE 85

1-cyclopropylmethyl-7-(3,4-dichlorophenoxymethyl)-2,3-dimethyl-1H-pyrrolo[2,3-c]pyridine hydrochloride 1H-NMR(400 MHz, CDCl$_3$) δ 8.18 (m, 1H), 7.72 (m, 1H), 7.26 (m, 1H), 7.05 (m, 2H), 6.05 (s, 2H), 4.42 (s, 2H), 2.57 (s, 3H), 2.34 (s, 3H), 0.83 (m, 1H), 0.64 (m, 2H), 0.26 (m, 2H); (Yield: 62%)

EXAMPLE 86

7-(3,4-dichlorophenoxymethyl)-2,3-dimethyl-1-propyl-1H-pyrrolo[2,3-c]pyridine hydrochloride 1H-NMR(400 MHz, CDCl$_3$) δ 8.17 (m, 1H), 7.72 (m, 1H), 7.39 (m, 1H), 7.19 (m, 2H), 5.99 (s, 2H), 4.34 (s, 2H), 2.56 (s, 3H), 2.33 (s, 3H), 1.76 (m, 2H), 0.95 (m, 3H); (Yield: 72%)

EXAMPLE 87

7-(3,4-dichlorophenoxymethyl)-1,2,3-trimethyl-1H-pyrrolo[2,3-c]pyridine hydrochloride 1H-NMR(400 MHz, CDCl$_3$) δ 8.14 (m, 1H), 7.70 (m, 1H), 7.36 (m, 1H), 7.22 (m, 2H), 6.07 (s, 2H), 4.08 (s, 3H), 2.55 (s, 3H), 2.33 (s, 3H); (Yield: 75%)

EXAMPLE 88

N-(1-allyl-2,3-dimethyl-1H-pyrrolo[2,3-c]pyridin-7-ylmethyl)-4-fluorophenylamine hydrochloride Step 1. (2,3-dimethyl-1H-pyrrolo[2,3-c]pyridin-7-ylmethyl)-(4-fluorophenyl)-carbamic acid tert-butyl ester In accordance with the same procedures as in Example 1, except for using (4-fluorophenyl)-(3-nitropyridin-2-ylmethyl)-carbamic acid tert-butyl ester prepared in Preparation 2, the titled compound was obtained as a white solid. (Yield: 33%)

1H-NMR(400 MHz, CDCl$_3$) δ 9.99 (brs, NH), 8.40 (d, 1H), 7.27 (d, 1H), 6.85 (m, 2H), 6.76 (m, 2H), 5.09 (s, 2H), 2.50 (s, 3H), 2.26 (s, 3H), 1.37 (s, 9H)

Step 2. N-(1-allyl-2,3-dimethyl-1H-pyrrolo[2,3-c]pyridin-7-ylmethyl)-4-fluorophenylamine hydrochloride Allyl bromide (43 μl, 0.493 mmol) was added to a solution of (2,3-dimethyl-1H-pyrrolo[2,3-c]pyridin-7-ylmethyl)-(4-fluorophenyl)-carbamic acid tert-butyl ester (150 mg, 0.328 mmol) prepared in Step 1 and sodium hydride (60%, 25 mg, 0.616 mmol) in anhydrous N,N-dimethylformamide (5 ml). The reaction mixture was stirred overnight at room temperature. The reaction mixture was diluted with ethyl acetate (15 ml), washed with water (20 ml), dried on anhydrous magnesium sulfate, and then concentrated under reduced pressure. The resulting residue was purified with silica gel column chromatography (ethyl acetate/n-hexane=1/6, v/v). The resulting yellow oil was dissolved in ethyl acetate, saturated with hydrochloric acid gas, and then filtered. The resulting solid was dried under reduced pressure to give 7.7 mg of the titled compound as a white solid.

1H-NMR(400 MHz, CDCl$_3$) δ 8.15 (m, 3H) 7.78 (m, 1H), 7.19 (m, 2H), 6.10 (m, 1H), 5.50 (s, 2H), 5.29 (d, 1H), 4.96 (s, 2H), 4.58 (d, 1H), 2.51 (s, 3H), 2.35 (s, 3H)

EXAMPLES 89 TO 107

The titled compounds of Examples 89 to 107 were prepared, in accordance with the same procedures as in Step 2 of Example 88, using (2,3-dimethyl-1H-pyrrolo[2,3-c]pyridin-7-ylmethyl)-(4-fluorophenyl)-carbamic acid tert-butyl ester prepared in Step 1 of Example 88; and, benzyl bromide, (bromomethyl)cyclopropane, 3-fluorobenzyl bromide, 3-methoxybenzyl bromide, 4-chlorobenzyl bromide, 2-bromoethyl methyl ether, 2-methylbenzyl chloride, 4-tert-butylbenzyl chloride, 2-chlorobenzyl chloride, 3,4-dichlorobenzyl chloride, 2,5-dimethylbenzyl chloride, iodoethane, 1-iodopropane, 3-methylbenzyl chloride, propargyl bromide, 4-trifluoromethylbenzyl bromide, iodomethane, 2-bromoethyl ethyl ether, or 4-methylbenzyl chloride.

EXAMPLE 89

N-(1-benzyl-2,3-dimethyl-1H-pyrrolo[2,3-c]pyridin-7-ylmethyl)-4-fluorophenylamine hydrochloride 1H-NMR(400 MHz, CDCl$_3$) δ 8.14 (m, 1H), 7.72 (m, 1H), 7.36 (m, 4H), 6.81 (m, 5H), 5.82 (s, 2H), 4.81 (s, 2H), 2.56 (s, 3H), 2.39 (s, 3H); (Yield: 85%)

EXAMPLE 90

N-(1-cyclopropylmethyl-2,3-dimethyl-1H-pyrrolo[2,3-c]pyridin-7-ylmethyl)-4-fluorophenylamine hydrochloride 1H-NMR(400 MHz, CDCl$_3$) δ 8.12 (m, 1H), 7.68 (d, 1H), 7.36 (m, 2H), 7.00 (t, 2H), 5.21 (s, 2H), 4.55 (m, 2H), 2.54 (s, 3H), 2.32 (s, 3H), 1.20 (m, 1H), 0.69 (m, 2H), 0.32 (m, 2H); (Yield: 73%)

EXAMPLE 91

N-[1-(3-fluorobenzyl)-2,3-dimethyl-1H-pyrrolo[2,3-c]pyridin-7-ylmethyl]-4-fluorophenylamine hydrochloride 1H-NMR(400 MHz, CDCl$_3$) δ 8.16 (d, 1H), 7.70 (d, 1H), 7.35 (q, 2H), 7.06 (t, 2H), 6.76 (t, 2H), 6.64 (d, 1H), 6.47 (m, 3H), 5.74 (s, 2H), 4.82 (s, 2H), 2.51 (s, 3H), 2.39 (s, 3H); (Yield: 89%)

EXAMPLE 92

N-[1-(3-methoxybenzyl)-2,3-dimethyl-1H-pyrrolo[2,3-c]pyridin-7-ylmethyl]-4-fluorophenylamine hydrochloride 1H-NMR(400 MHz, CDCl$_3$) δ 8.12 (d, 1H), 7.66 (d, 1H), 7.31 (m, 1H), 6.88 (d, 1H), 6.71 (t, 2H), 6.47 (m, 2H), 6.32 (m, 2H), 5.69 (s, 2H), 4.84 (s, 2H), 3.76 (s, 3H), 2.51 (s, 3H), 2.37 (s, 3H); (Yield: 89%)

EXAMPLE 93

N-[1-(4-chlorobenzyl)-2,3-dimethyl-1H-pyrrolo[2,3-c]pyridin-7-ylmethyl]-4-fluorophenylamine hydrochloride 1H-NMR(400 MHz, CDCl$_3$) δ 8.14 (d, 1H), 7.68 (d, 1H), 7.33 (d, 2H), 6.74 (m, 4H), 6.42 (m, 2H), 5.69 (s, 2H), 4.83 (s, 2H), 2.49 (s, 3H), 2.38 (s, 3H); (Yield: 65%)

EXAMPLE 94

N-[1-(2-methoxyethyl)-2,3-dimethyl-1H-pyrrolo[2,3-c]pyridin-7-ylmethyl]-4-fluorophenylamine hydrochloride 1H-NMR(400 MHz, CDCl$_3$) δ 8.12 (m, 1H), 7.72 (m, 3H), 7.09 (m, 2H), 5.40 (m, 2H), 4.88 (m, 2H), 3.76 (m, 2H), 3.24 (s, 3H), 2.57 (s, 3H), 2.24 (s, 3H); (Yield: 65%)

EXAMPLE 95

N-[2,3-dimethyl-1-(2-methylbenzyl)-1H-pyrrolo[2,3-c]pyridin-7-ylmethyl]-4-fluorophenylamine hydrochloride 1H-NMR(400 MHz, CDCl$_3$) δ 8.15 (m, 1H), 7.70 (m, 1H), 7.12 (m, 1H), 6.72 (m, 2H), 6.45 (m, 2H), 6.05 (m, 1H), 5.62 (m, 2H), 4.73 (m, 2H), 2.49 (s, 3H), 2.40 (s, 3H), 2.32 (s, 3H); (Yield: 60%)

EXAMPLE 96

N-[1-(4-tert-butylbenzyl)-2,3-dimethyl-1H-pyrrolo[2,3-c]pyridin-7-ylmethyl]-4-fluorophenylamine hydrochloride 1H-NMR(400 MHz, CDCl$_3$) δ 8.12 (d, 1H), 7.67 (d, 1H), 7.37 (d, 2H), 6.73 (m, 4H), 6.46 (m, 2H), 5.68 (s, 2H), 4.86 (s, 2H), 2.53 (s, 3H), 2.38 (s, 3H), 1.30 (s, 9H); (Yield: 69%)

EXAMPLE 97

N-[1-(2-chlorobenzyl)-2,3-dimethyl-1H-pyrrolo[2,3-c]pyridin-7-ylmethyl]-4-fluorophenylamine hydrochloride 1H-NMR(400 MHz, CDCl$_3$) δ 8.15 (d, 1H), 7.75 (d, 1H), 7.51 (d, 1H), 7.35 (m, 1H), 7.20 (m, 1H), 6.70 (t, 2H), 6.32 (m, 2H), 6.10 (d, 1H), 5.72 (s, 2H), 4.75 (s, 2H), 2.46 (s, 3H), 2.41 (s, 3H); (Yield: 69%)

EXAMPLE 98

N-[1-(3,4-dichlorobenzyl)-2,3-dimethyl-1H-pyrrolo[2,3-c]pyridin-7-ylmethyl]-4-fluorophenylamine hydrochloride 1H-NMR(400 MHz, CDCl$_3$) δ 8.15 (m, 1H), 7.79 (m, 1H), 7.43 (d, 1H), 7.35 (m, 1H), 7.01 (m, 2H), 6.90 (s, 1H), 6.72 (m, 1H), 5.92 (s, 2H), 4.74 (s, 2H), 2.52 (s, 3H), 2.40 (s, 3H); (Yield: 73%)

EXAMPLE 99

N-[1-(2,5-dimethylbenzyl)-2,3-dimethyl-1H-pyrrolo[2,3-c]pyridin-7-ylmethyl]-4-fluorophenylamine hydrochloride 1H-NMR(400 MHz, CDCl$_3$) δ 8.15 (d, 1H), 7.70 (d, 1H), 7.15 (d, 1H), 7.08 (d, 1H), 6.73 (t, 2H), 6.69 (m, 2H), 5.86 (s, 1H), 5.57 (s, 2H), 4.74 (s, 2H), 2.57 (s, 3H), 2.41 (s, 3H), 2.21 (s, 3H), 2.11 (s, 3H); (Yield: 53%)

EXAMPLE 100

N-(1-ethyl-2,3-dimethyl-1H-pyrrolo[2,3-c]pyridin-7-ylmethyl)-4-fluorophenylamine hydrochloride 1H-NMR(400 MHz, CDCl$_3$) δ 8.11 (d, 1H), 7.82 (m, 2H), 7.71 (d, 1H), 7.10 (t, 2H), 5.11 (s, 2H), 4.67 (q, 2H), 2.56 (s, 3H), 2.32 (s, 3H), 1.48 (t, 3H); (Yield: 59%)

EXAMPLE 101

N-(2,3-dimethyl-1-propyl-1H-pyrrolo[2,3-c]pyridin-7-ylmethyl)-4-fluorophenylamine hydrochloride 1H-NMR(400 MHz, CDCl$_3$) δ 8.20 (d, 1H), 7.63 (d, 1H), 7.20 (m, 2H), 6.94 (t, 2H), 5.09 (s, 2H), 4.41 (t, 2H), 2.55 (s, 3H), 2.31 (s, 3H), 1.85 (q, 2H), 1.01 (t, 3H); (Yield: 79%)

EXAMPLE 102

N-[2,3-dimethyl-1-(3-methylbenzyl)-1H-pyrrolo[2,3-c]pyridin-7-ylmethyl]-4-fluorophenylamine hydrochloride 1H-NMR(400 MHz, CDCl$_3$) δ 8.12 (d, 1H), 7.66 (d, 1H), 7.16 (d, 1H), 6.69 (t, 3H), 6.54 (d, 1H), 6.39 (m, 2H), 5.67 (s, 2H), 4.86 (s, 2H), 2.52 (s, 3H), 2.39 (s, 3H), 2.31 (s, 3H); (Yield: 72%)

EXAMPLE 103

N-[2,3-dimethyl-1-(propa-1,2-dienyl)-1H-pyrrolo[2,3-c]pyridin-7-ylmethyl]-4-fluorophenylamine hydrochloride 1H-NMR(400 MHz, CDCl$_3$) δ 8.20 (m, 1H), 7.61 (m, 1H), 7.20 (m, 1H), 6.83 (m, 4H), 5.57 (m, 2H), 5.25 (m, 2H), 2.54 (s, 3H), 2.31 (s, 3H); (Yield: 82%)

EXAMPLE 104

N-[2,3-dimethyl-1-(4-trifluoromethylbenzyl)-1H-pyrrolo[2,3-c]pyridin-7-ylmethyl]-4-fluorophenylamine hydrochloride 1H-NMR(400 MHz, CDCl$_3$) δ 8.20 (d, 1H), 7.77 (d, 1H), 7.60 (d, 2H), 6.93 (d, 2H), 6.85 (m, 3H), 5.90 (s, 2H), 4.78 (s, 2H), 2.51 (s, 3H), 2.40 (s, 3H); (Yield: 88%)

EXAMPLE 105

N-(1,2,3-trimethyl-1H-pyrrolo[2,3-c]pyridin-7-ylmethyl)-4-fluorophenylamine hydrochloride 1H-NMR(400 MHz, CDCl$_3$) δ 8.10 (d, 1H), 7.68 (d, 1H), 7.46 (m, 2H), 7.01 (t, 2H), 5.19 (s, 2H), 4.22 (s, 3H), 2.55 (s, 3H), 2.32 (s, 3H); (Yield: 80%)

EXAMPLE 106

N-[1-(2-ethoxyethyl)-2,3-dimethyl-1H-pyrrolo[2,3-c]pyridin-7-ylmethyl]-4-fluorophenylamine hydrochloride 1H-NMR(400 MHz, CDCl$_3$) δ 8.11 (d, 1H), 7.67 (d, 1H), 6.97 (t, 2H), 5.27 (s, 2H), 4.57 (m, 2H), 3.74 (m, 2H), 3.40 (q, 2H), 2.55 (s, 3H), 2.32 (s, 3H), 1.03 (t, 3H); (Yield: 40%)

EXAMPLE 107

N-[2,3-dimethyl-1-(4-methylbenzyl)-1H-pyrrolo[2,3-c]pyridin-7-ylmethyl]-4-fluorophenylamine hydrochloride 1H-NMR(400 MHz, CDCl$_3$) δ 8.12 (m, 1H), 7.65 (d, 1H), 7.17 (d, 2H), 6.69 (m, 4H), 6.28 (m, 2H), 5.64 (s, 2H), 4.88 (s, 2H), 2.52 (s, 3H), 2.38 (s, 3H), 2.36 (s, 3H); (Yield: 45%)

EXAMPLE 108

N-(2,3-dimethyl-1-propenyl-1H-pyrrolo[2,3-c]pyridin-7-ylmethyl)-4-fluorophenylamine hydrochloride The compound prepared in Example 88 was treated with a saturated sodium bicarbonate solution to obtain N-(1-allyl-2,3-dimethyl-1H-pyrrolo[2,3-c]pyridin-7-ylmethyl)-4-fluorophenylamine. A solution of N-(1-allyl-2,3-dimethyl-1H-pyrrolo[2,3-c]pyridin-7-ylmethyl)-4-fluorophenylamine (40 mg, 0.13 mmol) and sodium hydride (60%, 7.8 mg, 0.19 mmol) in anhydrous N,N-dimethylformamide (5 ml) was stirred overnight at room temperature. The reaction mixture was diluted with ethyl acetate (115 ml), washed with water (20 ml), dried on anhydrous magnesium sulfate, and then concentrated under reduced pressure. The resulting residue was purified with silica gel column chromatography (ethyl acetate/n-hexane=1/1, v/v). The resulting yellow oil was dissolved in ethyl acetate, saturated with hydrochloric acid gas, and then filtered. The resulting solid was dried under reduced pressure to give 3.3 mg of the titled compound as a white solid.

1H-NMR(400 MHz, CDCl$_3$) δ 8.11 (d, 1H), 8.01 (m, 2H), 7.75 (d, 1H), 7.44 (d, 1H), 7.12 (t, 2H), 6.33 (m, 1H), 5.31 (d, 1H), 5.09 (d, 1H), 2.46 (s, 3H), 2.33 (s, 3H), 1.59 (d, 3H)

EXAMPLE 109

N-(2,3-dimethyl-1H-pyrrolo[2,3-c]pyridin-7-ylmethyl)-4-fluorophenylamine hydrochloride In accordance with the same procedures as in Example 42, except for using (2,3-dimethyl-1H-pyrrolo[2,3-c]pyridin-7-ylmethyl)-(4-fluorophenyl)-carbamic acid tert-butyl ester prepared in Step 1 of Example 88, the titled compound was obtained as a white solid. (Yield: 79%)

1H-NMR(400 MHz, CDCl$_3$) δ 7.93 (d, 1H), 7.58 (d, 1H), 7.19 (m, 2H), 6.87 (t, 2H), 5.23 (s, 2H), 2.60 (s, 3H), 2.27 (s, 3H)

EXAMPLE 110

N-(2,3-dimethyl-1H-pyrrolo[2,3-c]pyridin-7-ylmethyl)-N-(4-fluorophenyl)-methylamine Step 1: (4-fluorophenyl)-methyl-(3-nitropyridin-2-ylmethyl)-amine In accordance with the same procedures as in Step 1 of Preparation 2, except for using 2-bromomethyl-3-nitropyridine prepared in Step 2 of Preparation 1 and (4-fluorophenyl)-methylamine, the titled compound was obtained as yellow solid. (Yield: 80%)

1H-NMR(400 MHz, CDCl$_3$) δ 8.75 (d, 1H) 8.12 (d, 1H), 7.38 (m, 1H), 6.89 (m, 2H), 6.63 (m, 2H), 4.93 (s, 2H), 3.02 (s, 3H)

Step 2: N-(2,3-dimethyl-1H-pyrrolo[2,3-c]pyridin-7-ylmethyl)-N-(4-fluorophenyl)-methylamine In accordance with the same procedures as in Example 1, except for using (4-fluorophenyl)-methyl-(3-nitropyridin-2-ylmethyl)-amine prepared in Step 1, the titled compound was obtained as brown oil. (Yield: 27%)

1H-NMR(400 MHz, CDCl$_3$) δ 8.15 (d, 1H), 7.31 (d, 1H), 7.00 (m, 5H), 4.77 (s, 2H), 2.91 (s, 3H), 2.32 (s, 3H), 2.20 (s, 3H)

EXAMPLES 111 TO 134

The titled compounds of Examples 111 to 134 were prepared, in accordance with the same procedures as in Example 2, using N-(2,3-dimethyl-1H-pyrrolo[2,3-c]pyridin-7-ylmethyl)-N-(4-fluorophenyl)-methylamine prepared in Example 110; and, benzyl bromide, (bromomethyl)cyclopropane, 4-chlorobenzyl bromide, 3-fluorobenzyl bromide, 2-fluorobenzyl bromide, 3-methoxybenzyl bromide, 4-methylbenzyl bromide, 4-fluorobenzyl bromide, 4-bromo-2-methyl-2-butene, 2-bromoethyl methyl ether, 2-chlorobenzyl bromide, 3,4-dichlorobenzyl bromide, iodoethane, 1-iodopropane, 4-methoxybenzyl chloride, 3-methylbenzyl chloride, propargyl bromide, allyl bromide, 3,4-dimethylbenzyl bromide, 2-methylbenzyl bromide, 4-tert-butylbenzyl bromide, 2,5-dimethylbenzyl bromide, iodomethane, or 2-bromoethyl ethyl ether.

EXAMPLE 111

N-(1-benzyl-2,3-dimethyl-1H-pyrrolo[2,3-c]pyridin-7-ylmethyl)-N-(4-fluorophenyl)-methylamine hydrochloride 1H-NMR(400 MHz, CDCl$_3$) δ 8.23 (m, 1H) 7.74 (d, 1H), 7.20 (m, 1H), 6.94 (t, 2H), 6.86 (m, 2H), 6.42 (d, 2H), 5.74 (s, 2H), 4.79 (s, 2H), 2.80 (s 3H), 2.44 (s, 3H), 2.39 (s, 3H); (Yield: 75%)

EXAMPLE 112

N-(1-cyclopropylmethyl-2,3-dimethyl-1H-pyrrolo[2,3-c]pyridin-7-ylmethyl)-N-(4-fluorophenyl)-methylamine hydrochloride 1H-NMR(400 MHz, CDCl$_3$) δ 8.21 (t, 1H) 7.69 (d, 1H), 7.05 (m, 4H), 5.17 (s, 2H), 4.43 (d, 2H), 2.84 (s, 3H), 2.52 (s, 3H), 2.32 (s, 3H), 0.95 (m, 1H), 0.58 (q, 2H), 0.12 (q, 2H); (Yield: 72%)

EXAMPLE 113

N-[1-(4-chlorobenzyl)-2,3-dimethyl-1H-pyrrolo[2,3-c]pyridin-7-ylmethyl]-N-(4-fluorophenyl)-methylamine hydrochloride 1H-NMR(400 MHz, CDCl$_3$) δ 8.23 (m, 1H), 7.77 (d, 1H), 7.19 (d, 2H), 6.97 (t, 2H), 6.35 (m, 2H), 6.33 (d, 2H), 5.69 (s, 2H), 4.79 (s, 2H), 2.77 (s, 3H), 2.41 (s, 3H), 2.38 (s, 3H); (Yield: 77%)

EXAMPLE 114

N-[1-(3-fluorobenzyl)-2,3-dimethyl-1H-pyrrolo[2,3-c]pyridin-7-ylmethyl]-N-(4-fluorophenyl)-methylamine hydrochloride 1H-NMR(400 MHz, CDCl$_3$) δ 8.24 (m, 1H), 7.76 (d, 1H), 7.20 (m, 1H), 6.96 (m, 3H), 6.84 (m, 2H), 6.22 (d, 1H), 6.08 (d, 1H), 5.73 (s, 2H), 4.80 (s, 2H), 2.79 (s, 3H), 2.43 (s, 3H), 2.39 (s, 3H); (Yield: 55%)

EXAMPLE 115

N-[1-(2-fluorobenzyl)-2,3-dimethyl-1H-pyrrolo[2,3-c]pyridin-7-ylmethyl]-N-(4-fluorophenyl)-methylamine hydrochloride 1H-NMR(400 MHz, CDCl$_3$) δ 8.25 (m, 1H), 7.75 (d, 1H), 7.07-6.87 (m, 7H), 6.01 (t, 1H), 5.82 (s, 2H), 4.83 (s, 2H), 2.81 (s, 3H), 2.42 (s, 3H), 2.38 (s, 3H); (Yield: 73%)

EXAMPLE 116

N-(4-fluorophenyl)-N-[1-(3-methoxybenzyl)-2,3-dimethyl-1H-pyrrolo[2,3-c]pyridin-7-ylmethyl]-methylamine hydrochloride 1H-NMR(400 MHz, CDCl$_3$) δ 8.23 (m, 1H) 7.73 (d, 1H), 7.15 (t, 1H), 6.94 (m, 2H), 6.81 (m, 3H), 5.96 (m, 2H), 5.69 (s, 2H), 4.77 (s, 2H), 3.68 (s, 3H), 2.78 (s, 3H), 2.43 (s, 3H), 2.38 (s, 3H); (Yield: 45%)

EXAMPLE 117

N-[2,3-dimethyl-1-(4-methylbenzyl)-1H-pyrrolo[2,3-c]pyridin-7-ylmethyl]-N-(4-fluorophenyl)-methylamine hydrochloride 1H-NMR(400 MHz, CDCl$_3$) δ 8.23 (m, 1H), 7.73 (d, 1H), 7.03 (d, 2H), 6.96 (t, 2H), 6.85 (m, 2H), 6.29 (d, 2H), 5.69 (s, 2H), 4.78 (s, 2H), 2.80 (s, 3H), 2.44 (s, 3H), 2.38 (s, 3H), 2.17 (s, 3H); (Yield: 75%)

EXAMPLE 118

N-[1-(4-fluorobenzyl)-2,3-dimethyl-1H-pyrrolo[2,3-c]pyridin-7-ylmethyl]-N-(4-fluorophenyl)-methylamine hydrochloride 1H-NMR(400 MHz, CDCl$_3$) δ 8.24 (m, 1H), 7.77 (d, 1H), 6.95 (m, 4H), 6.81 (m, 2H), 6.38 (t, 2H), 5.69 (s, 2H), 4.79 (s, 2H), 2.93 (s, 3H), 2.42 (s, 3H), 2.38 (s, 3H); (Yield: 70%)

EXAMPLE 119

N-[2,3-dimethyl-1-(3-methylbut-2-enyl)-1H-pyrrolo[2,3-c]pyridin-7-ylmethyl]-N-(4-fluorophenyl)-methylamine hydrochloride 1H-NMR(400 MHz, CDCl$_3$) δ 8.20 (m, 1H), 7.66 (d, 1H), 6.99 (m, 4H), 5.06-5.03 (m, 4H), 4.87 (m, 1H), 2.98 (s, 3H), 2.46 (s, 3H), 2.04 (s, 3H), 1.66 (s, 3H), 1.41 (s, 3H); (Yield: 80%)

EXAMPLE 120

N-(4-fluorophenyl)-N-[1-(2-methoxyethyl)-2,3-dimethyl-1H-pyrrolo[2,3-c]pyridin-7-ylmethyl]-methylamine hydrochloride 1H-NMR(400 MHz, CDCl$_3$) δ 8.19 (m, 1H), 7.66 (m, 1H), 6.98 (m, 4H), 5.23 (s, 2H), 4.66 (m, 2H), 3.53 (m, 2H), 3.21 (s, 3H), 2.81 (s, 3H), 2.51 (s, 3H), 2.32 (s, 3H); (Yield: 85%)

EXAMPLE 121

N-[1-(2-chlorobenzyl)-2,3-dimethyl-1H-pyrrolo[2,3-c]pyridin-7-ylmethyl]-N-(4-fluorophenyl)-methylamine hydrochloride 1H-NMR(400 MHz, CDCl$_3$) δ 8.25 (m, 1H), 7.77 (d, 1H), 7.37 (d, 1H), 7.10 (t, 1H), 6.91-6.80 (m, 4H), 5.84 (d, 1H), 5.78 (s, 2H), 4.76 (s, 2H), 2.78 (s, 3H), 2.39 (s, 6H); (Yield: 75%)

EXAMPLE 122

N-[1-(3,4-dichlorobenzyl)-2,3-dimethyl-1H-pyrrolo[2,3-c]pyridin-7-ylmethyl]-N-(4-fluorophenyl)-methylamine hydrochloride 1H-NMR(400 MHz, CDCl$_3$) δ 8.24 (m, 1H), 7.77 (d, 1H), 7.30 (m, 1H), 7.00 (t, 2H), 6.85 (m, 2H), 6.49 (s, 1H), 6.20 (d, 1H), 5.68 (s, 2H), 4.82 (s, 2H), 2.78 (s, 3H), 2.42 (s, 3H), 2.39 (s, 3H); (Yield: 70%)

EXAMPLE 123

N-(1-ethyl-2,3-dimethyl-1H-pyrrolo[2,3-c]pyridin-7-ylmethyl)-N-(4-fluorophenyl)-methylamine hydrochloride 1H-NMR(400 MHz, CDCl$_3$) δ 8.20 (m, 1H), 7.65 (d, 1H), 7.03 (m, 4H), 5.10 (s, 2H), 4.44 (q, 2H), 2.86 (s, 3H), 2.53 (s, 3H), 2.32 (s, 3H), 1.26 (t, 3H); (Yield: 90%)

EXAMPLE 124

N-(2,3-dimethyl-1-propyl-1H-pyrrolo[2,3-c]pyridin-7-ylmethyl)-N-(4-fluorophenyl)-methylamine hydrochloride 1H-NMR(400 MHz, CDCl$_3$) δ 8.21 (t, 1H), 7.69 (d, 1H), 7.00 (m, 4H), 5.07 (s, 2H), 4.31 (q, 2H), 2.85 (s, 3H), 2.50 (s, 3H), 2.31 (s, 3H), 1.59 (m, 2H), 0.77 (t, 3H); (Yield: 97%)

EXAMPLE 125

N-(4-fluorophenyl)-N-[1-(4-methoxybenzyl)-2,3-dimethyl-1H-pyrrolo[2,3-c]pyridin-7-ylmethyl]-methylamine hydrochloride 1H-NMR(400 MHz, CDCl$_3$) δ 8.21 (m, 1H), 7.72 (d, 1H), 6.92 (m, 3H), 6.77 (m, 3H), 6.33 (d, 2H), 5.63 (s, 2H), 4.77 (s, 2H), 3.78 (s, 3H), 2.84 (s, 3H), 2.44 (s, 3H), 2.38 (s, 3H); (Yield: 97%)

EXAMPLE 126

N-[2,3-dimethyl-1-(3-methylbenzyl)-1H-pyrrolo[2,3-c]pyridin-7-ylmethyl]-N-(4-fluorophenyl)-methylamine hydrochloride 1H-NMR(400 MHz, CDCl$_3$) δ 8.23 (d, 1H), 7.76 (d, 1H), 7.07 (q, 2H), 6.96 (t, 2H), 6.84 (m, 2H), 6.22 (s, 1H), 6.14 (d, 1H), 5.69 (s, 2H), 4.77 (s, 2H), 2.79 (s, 3H), 2.48 (s, 3H), 2.44 (s, 3H), 2.18 (s, 3H); (Yield: 77%)

EXAMPLE 127

N-[2,3-dimethyl-1-(propa-1,2-dienyl)-1H-pyrrolo[2,3-c]pyridin-7-ylmethyl]-N-(4-fluorophenyl)-methylamine hydrochloride 1H-NMR(400 MHz, CDCl$_3$) δ 8.25 (d, 1H), 7.68 (d, 1H), 7.35 (t, 1H), 7.00 (m, 4H), 5.40 (d, 2H), 5.13 (s, 2H), 2.90 (s, 3H), 2.57 (s, 3H), 2.32 (s, 3H); (Yield: 37%)

EXAMPLE 128

N-(1-allyl-2,3-dimethyl-1H-pyrrolo[2,3-c]pyridin-7-ylmethyl)-N-(4-fluorophenyl)-methylamine hydrochloride 1H-NMR(400 MHz, CDCl$_3$) δ 8.21 (m, 1H), 7.71 (d, 1H), 7.01 (d, 4H), 5.80 (m, 1H), 5.16 (m, 3H), 5.00 (s, 2H), 4.25 (d, 1H), 2.83 (s, 3H), 2.45 (s, 3H), 2.34 (s, 3H); (Yield: 39%)

EXAMPLE 129

N-[2,3-dimethyl-1-(3,4-dimethylbenzyl)-1H-pyrrolo[2,3-c]pyridin-7-ylmethyl]-N-(4-fluorophenyl)-methylamine hydrochloride 1H-NMR(400 MHz, CDCl$_3$) δ 8.23 (d, 1H), 7.73 (d, 1H), 6.97-6.87 (m, 5H), 6.19 (s, 1H), 6.07 (d, 1H), 5.65 (s, 2H), 4.78 (s, 2H), 2.81 (s, 3H), 2.44 (s, 3H), 2.39 (s, 3H), 2.17 (s, 3H), 2.10 (s, 3H); (Yield: 69%)

EXAMPLE 130

N-[2,3-dimethyl-1-(2-methylbenzyl)-1H-pyrrolo[2,3-c]pyridin-7-ylmethyl]-N-(4-fluorophenyl)-methylamine hydrochloride 1H-NMR(400 MHz, CDCl$_3$) δ 8.24 (m, 1H), 7.77 (d, 1H), 7.16 (m, 1H), 7.10 (m, 1H), 6.91 (m, 1H), 6.87 (m, 2H), 6.67 (m, 2H), 5.71 (d, 1H), 5.54 (s, 2H), 4.71 (s, 2H), 2.75 (s, 3H), 2.40 (s, 3H), 2.37 (s, 3H), 1.80 (s, 3H); (Yield: 60%)

EXAMPLE 131

N-[1-(4-tert-butylbenzyl)-2,3-dimethyl-1H-pyrrolo[2,3-c]pyridin-7-ylmethyl]-N-(4-fluorophenyl)-methylamine hydrochloride 1H-NMR(400 MHz, CDCl$_3$) δ 8.22 (m, 1H), 7.74 (d, 1H), 7.22 (m, 2H), 6.98 (m, 4H), 6.33 (d, 2H), 5.71 (s, 2H), 2.85 (s, 3H), 2.47 (s, 3H), 2.39 (s, 3H), 1.31 (s, 9H); (Yield: 66%)

EXAMPLE 132

N-[1-(2,5-dimethylbenzyl)-2,3-dimethyl-1H-pyrrolo[2,3-c]pyridin-7-ylmethyl]-N-(4-fluorophenyl)-methylamine hydrochloride 1H-NMR(400 MHz, CDCl$_3$) δ 8.25 (m, 1H), 7.80 (d, 1H), 6.98 (m, 6H), 5.60 (m, 2H), 5.48 (s, 1H), 4.80 (s, 2H), 2.90 (s, 3H), 2.41 (s, 6H), 2.04 (s, 3H), 1.85 (s, 3H); (Yield: 86%)

EXAMPLE 133

N-(4-fluorophenyl)-N-(1,2,3-trimethyl-1H-pyrrolo[2,3-c]pyridin-7-ylmethyl)-methylamine hydrochloride 1H-NMR(400 MHz, CDCl$_3$) δ 8.17 (m, 1H), 7.65 (d, 1H), 7.05 (m, 4H), 5.12 (s, 2H), 4.00 (s, 3H), 2.84 (s, 3H), 2.49 (s, 3H), 2.31 (s, 3H); (Yield: 80%)

EXAMPLE 134

N-[1-(2-ethoxyethyl)-2,3-dimethyl-1H-pyrrolo[2,3-c]pyridin-7-ylmethyl]-N-(4-fluorophenyl)-methylamine hydrochloride 1H-NMR(400 MHz, CDCl$_3$) δ 8.04 (d, 1H), 7.60 (d, 1H), 6.97 (m, 4H), 5.30 (m, 4H), 3.48 (m, 2H), 3.01 (s, 3H), 2.53 (s, 3H), 2.28 (s, 3H), 2.10 (s, 2H), 1.28 (t, 3H); (Yield: 88%)

EXAMPLE 135

N-[1-(1-allyl-2,3-dimethyl-1H-pyrrolo[2,3-c]pyridin-7-yl)-ethyl]-4-fluorophenylamine hydrochloride Step 1: N-(1-allyl-2,3-dimethyl-1H-pyrrolo[2,3-c]pyridin-7-ylmethylene)-4-fluorophenylamine A solution of 1-allyl-2,3-dimethyl-1H-pyrrolo[2,3-c]pyridin-7-carbaldehyde (1.214 g, 5.67 mmol) prepared in Preparation 3 and 4-fluoroaniline (0.54 ml, 5.67 mmol) in ethanol (10 ml) was refluxed for 1 hour. The reaction mixture was cooled to room temperature and then concentrated under reduced pressure to give 2,3 g of the titled compound as a brown solid. The product was used in the subsequent step without further purification.

Step 2: N-[1-(1-allyl-2,3-dimethyl-1H-pyrrolo[2,3-c]pyridin-7-yl)-ethyl]-4-fluorophenylamine hydrochloride Methylmagnesium bromide (3.0M in ethyl ether solution, 37 μl, 1.12 mmol) was added at 0° C. to a solution of N-(1-allyl-2,3-dimethyl-1H-pyrrolo[2,3-c]pyridin-7-ylmethylene)-4-fluorophenylamine (30 mg, 0.112 mmol) prepared in Step 1 in anhydrous ethyl ether (5 ml). The reaction mixture was stirred for 2 hours at room temperature and then a saturated ammonium chloride solution (5 ml) was added thereto.

The reaction mixture was extracted with ethyl acetate (15 ml), dried on anhydrous magnesium sulfate, and then concentrated under reduced pressure. The resulting residue was purified with silica gel column chromatography (ethyl acetate/n-hexane=1/1, v/v). The resulting yellow oil was dissolved in ethyl acetate, saturated with hydrochloric acid gas, and then filtered. The resulting solid was dried under reduced pressure to give 1.4 mg of the titled compound as a white solid.

1H-NMR(400 MHz, CDCl$_3$) δ 8.12 (d, 1H) 7.57 (d, 1H), 6.81-6.71 (m, 4H), 6.23 (m, 1H), 5.45 (d, 1H), 5.36 (m, 1H), 5.16 (q, 2H), 4.99 (m, 2H), 4.70 (δ, 1H), 2.51 (s, 3H), 2.32 (s, 3H), 1.91 (d, 3H)

EXAMPLE 136

N-[1-(1-allyl-2,3-dimethyl-1H-pyrrolo[2,3-c]pyridin-7-yl)-2-phenylethyl]-4-fluorophenylamine hydrochloride In accordance with the same procedures as in Step 2 of Example 135, except for using N-(1-allyl-2,3-dimethyl-1H-pyrrolo[2,3-c]pyridin-7-ylmethylene)-4-fluorophenylamine prepared in Step 1 of Example 135 and benzylmagnesium chloride, the titled compound was obtained as a white solid. (Yield: 33%)

1H-NMR(400 MHz, CDCl$_3$) δ 8.19 (t, 1H), 7.60 (d, 1H), 7.24-7.17 (m, 5H), 6.75 (brs, 1H), 6.72-6.68 (m, 4H), 6.08 (m, 1H), 5.41 (m, 2H), 4.71 (s, 2H), 4.61 (d, 1H), 3.78 (m, 1H), 3.41 (m, 1H), 2.42 (s, 3H), 2.31 (s, 3H)

EXAMPLE 137

(1-allyl-2,3-dimethyl-1H-pyrrolo[2,3-c]pyridin-7-yl)-(4-fluorophenylamino)-acetonitrile hydrochloride Acetic acid (0.5 ml) and potassium cyanide (10.2 mg, 0.157 mmol) was added at 0° C. to a solution of N-(1-allyl-2,3-dimethyl-1H-pyrrolo[2,3-c]pyridin-7-ylmethylene)-4-fluorophenylamine (35 mg, 0.131 mmol) prepared in Step 1 of Example 135 in methanol (10 ml). The reaction mixture was stirred overnight at room temperature. The reaction mixture was basified with a saturated sodium bicarbonate solution and then extracted with ethyl acetate (15 ml). The organic layer was dried on anhydrous magnesium sulfate and then concentrated under reduced pressure. The resulting residue was purified with silica gel column chromatography (ethyl acetate/n-hexane=1/10, v/v). The resulting yellow oil was dissolved in ethyl acetate and then saturated with hydrochloric acid gas to give 7.1 mg of the titled compound as a white solid.

1H-NMR(400 MHz, CDCl$_3$/DMSO-d$_6$) δ 8.36 (d, 1H) 7.80 (d, 1H), 7.80-7.35 (m, 5H), 5.89 (m, 1H), 5.04 (m, 3H), 4.43 (d, 1H), 2.49 (s, 3H), 2.28 (s, 3H)

EXAMPLE 138

7-[N-(4-fluorobenzyl)-N-methyl]amino-2,3-dimethyl-1H-pyrrolo[2,3-c]pyridine

2-[N-(4-fluorobenzyl)-N-methyl]amino-3-nitropyridine (8.26 g, 31.6 mmol) prepared in Preparation 4 was dissolved in anhydrous tetrahydrofuran (100 ml) under a nitrogen atmosphere. 1-Methyl-1-propenylmagnesium bromide (0.5M in tetrahydrofuran solution, 190 ml, 94.8 mmol) was slowly added at −78° C. to the solution, which was then stirred for 2 hours at −20° C. 20% ammonium chloride solution (60 ml) was added to the reaction mixture, which was extracted with ethyl acetate. The organic layer was dried on anhydrous magnesium sulfate, and then concentrated under reduced pressure. The resulting residue was purified with silica gel column chromatography (ethyl acetate/n-hexane=1/1, v/v) to give 3.94 g of the titled compound as yellow oil. (Yield: 44%)

1H-NMR (400 MHz, CDCl$_3$) δ 10.74 (brs, 1H), 7.61 (d, 1H), 7.16 (m, 2H), 6.91 (m, 3H), 5.00 (s, 2H), 3.41 (s, 3H), 2.47 (s, 3H), 2.15 (s, 3H)

EXAMPLE 139

7-[N-(4-fluorobenzyl)-N-methyl]amino-2,3-dimethyl-1H-pyrrolo[2,3-c]pyridine hydrochloride In accordance with the same procedures as in Example 42, except for using 7-[N-(4-fluorobenzyl)-N-methyl]amino-2,3-dimethyl-1H-pyrrolo[2,3-c]pyridine prepared in Example 138, the titled compound was obtained as a white solid. (Yield: 87%)

1H-NMR (400 MHz, CDCl$_3$) δ 10.74 (brs, 1H), 7.61 (d, 1H), 7.16 (m, 2H), 6.91 (m, 3H), 5.00 (s, 2H), 3.41 (s, 3H), 2.47 (s, 3H), 2.15 (s, 3H); (Yield: 95%)

EXAMPLE 140

1-allyl-7-[N-(4-fluorobenzyl)-N-methyl]amino-2,3-dimethyl-1H-pyrrolo[2,3-c]pyridine hydrochloride Potassium tert-butoxide (29 mg, 0.260 mmol) was added to a solution of 7-[N-(4-fluorobenzyl)-N-methyl]amino-2,3-dimethyl-1H-pyrrolo[2,3-c]pyridine (49 mg, 0.173 mmol) prepared in Example 138 and 18-crown-6 (4.6 mg, 0.0171 mmol) in anhydrous tetrahydrofuran (2 ml). The reaction mixture was stirred for 1 hour at room temperature and allyl iodide (23.9 μl, 0.260 mmol) was added thereto. The reaction mixture was stirred overnight at room temperature and then concentrated under reduced pressure. The resulting residue was purified with silica gel column chromatography (ethyl acetate/n-hexane=1/5, v/v). The resulting residue was dissolved in ethyl acetate and then saturated with hydrochloric acid gas to give 8.4 mg of the titled compound as a white solid. (Yield: 15%).

1H-NMR (400 MHz, CDCl$_3$) δ 8.08 (d, 1H), 7.38 (m, 3H), 6.97 (t, 2H), 5.87 (m, 1H), 5.17 (m, 3H), 4.72 (brs, 2H), 4.52 (d, 1H), 2.97 (s, 3H), 2.41 (s, 3H), 2.27 (s, 3H)

EXAMPLES 141 TO 174

The titled compounds of Examples 141 to 174 were prepared, in accordance with the same procedures as in Example 140, using 7-[N-(4-fluorobenzyl)-N-methyl]amino-2,3-dimethyl-1H-pyrrolo[2,3-c]pyridine prepared in Example 138; and, benzyl bromide, 4-bromo-2-methyl-2-butene, 2-bromoethyl methyl ether, (bromomethyl)cyclopropane, 4-chlorobenzyl chloride, 1,3-dichlorobutane, 2-fluorobenzyl chloride, iodoethane, 1-iodo-2-methylpropane, 1-iodopropane, 3-methoxybenzyl chloride, 4-methylbenzyl chloride, propargyl bromide, 2-bromoethyl ethyl ether, 4-fluorobenzyl chloride, 4-methoxybenzyl chloride, 4-bromo-1-butene, 2-bromomethyl-1,3-dioxolane, 3-fluorobenzyl chloride, 3-methylbenzyl chloride, 1-chloro-3-methylbutane, 4-tert-butylbenzyl chloride, bromoacetonitrile, 1-bromomethoxy-2-methoxyethane, 4-trifluoromethylbenzyl chloride, iodomethane, 2-bromoethyl-1, 3-dioxane, 2-chlorobenzyl chloride, bromomethyl methyl ether, 2-chloroethanol, 5-chloro-1-pentyne, 2-(chloromethyl)tetrahydro-2H-pyran, bromomethyl acetate, or 4-chloromethyl-2-methylthiazole.

EXAMPLE 141

1-benzyl-7-[N-(4-fluorobenzyl)-N-methyl]amino-2,3-dimethyl-1H-pyrrolo[2,3-c]pyridine hydrochloride 1H-NMR (400 MHz, CDCl$_3$) δ 8.12 (d, 1H), 7.47 (d, 1H), 7.30 (m, 2H), 7.10 (m, 2H), 6.95 (m, 1H), 6.79 (t, 2H), 6.62 (d, 2H), 5.82 (s, 2H), 4.71 (s, 2H), 2.91 (s, 3H), 2.30 (s, 3H), 2.29 (s, 3H); (Yield: 25%)

EXAMPLE 142

7-[N-(4-fluorobenzyl)-N-methyl]amino-2,3-dimethyl-1-(3-methylbut-2-enyl)-1H-pyrrolo[2,3-c]pyridine hydrochloride 1H-NMR (400 MHz, CDCl$_3$) δ 8.06 (t, 1H), 7.38 (m, 3H), 6.96 (t, 2H), 5.16 (d, 2H), 4.88 (t, 1H), 4.79 (s, 2H), 3.04 (s, 3H), 2.41 (s, 3H), 2.24 (s, 3H), 1.75 (s, 3H), 1.72 (s, 3H); (Yield: 34%)

EXAMPLE 143

7-[N-(4-fluorobenzyl)-N-methyl]amino-1-(2-methoxyethyl)-2,3-dimethyl-1H-pyrrolo[2,3-c]pyridine hydrochloride 1H-NMR (400 MHz, CDCl$_3$) δ 8.12 (brs, 1H), 7.39 (brs, 3H), 7.00 (brs, 2H), 4.67 (brs, 2H), 4.66 (brs, 2H), 3.48 (m, 2H), 3.20 (brs, 3H), 3.02 (brs, 3H), 2.50 (s, 3H), 2.27 (s, 3H); (Yield: 41%)

EXAMPLE 144

1-cyclopropylmethyl-7-[N-(4-fluorobenzyl)-N-methyl]amino-2,3-dimethyl-1H-pyrrolo[2,3-c]pyridine hydrochloride 1H-NMR (400 MHz, CDCl$_3$) δ 8.13 (t, 1H), 7.37 (m, 3H), 7.02 (t, 2H), 4.75 (s, 2H), 4.34 (d, 2H), 3.01 (s, 3H), 2.51 (s, 3H), 2.28 (s, 3H), 0.95 (m, 1H), 0.53 (q, 2H), 0.27 (q, 2H); (Yield: 48%)

EXAMPLE 145

1-(4-chlorobenzyl)-7-[N-(4-fluorobenzyl)-N-methyl]amino-2,3-dimethyl-1H-pyrrolo[2,3-c]pyridine hydrochloride 1H-NMR (400 MHz, CDCl$_3$) δ 8.14 (t, 1H), 7.48 (d, 1H), 7.17 (t, 2H), 7.12 (m, 2H), 6.81 (t, 2H), 6.56 (d, 2H), 5.80 (s, 2H), 4.72 (s, 2H), 2.93 (s, 3H), 2.29 (s, 6H); (Yield: 24%)

EXAMPLE 146

1-(3-chlorobutyl)-7-[N-(4-fluorobenzyl)-N-methyl]amino-2,3-dimethyl-1H-pyrrolo[2,3-c]pyridine hydrochloride 1H-NMR (400 MHz, CDCl$_3$/MeOH-d$_4$) δ 8.01 (t, 1H), 7.44 (d, 1H), 7.33 (m, 2H), 6.99 (t, 2H), 5.09 (brs, 2H), 4.67 (s, 2H), 3.00 (s, 3H), 2.44 (s, 3H), 2.26 (m, 4H), 1.78 (m, 1H), 1.65 (d, 3H), 1.51 (m, 1H); (Yield: 19%)

EXAMPLE 147

1-(2-fluorobenzyl)-7-[N-(4-fluorobenzyl)-N-methyl]amino-2,3-dimethyl-1H-pyrrolo[2,3-c]-pyridine hydrochloride 1H-NMR (400 MHz, CDCl$_3$) δ 8.14 (t, 1H) 7.49 (d, 1H), 7.30 (m, 1H), 7.13 (m, 3H), 6.96 (t, 1H), 6.81 (t, 2H), 5.97 (t, 1H), 5.86 (s, 2H), 4.71 (s, 2H), 2.90 (s, 3H), 2.33 (s, 3H), 2.30 (s, 3H); (Yield: 46%)

EXAMPLE 148

1-ethyl-7-[N-(4-fluorobenzyl)-N-methyl]amino-2,3-dimethyl-1H-pyrrolo[2,3-c]pyridine hydrochloride 1H-NMR (400 MHz, CDCl$_3$) δ 8.10 (t, 1H), 7.41 (m, 3H), 7.00 (m, 2H), 4.79 (s, 2H), 4.54 (q, 2H), 3.05 (s, 3H), 2.48 (s, 3H), 2.26 (s, 3H), 1.24 (t, 3H); (Yield: 51%)

EXAMPLE 149

7-[N-(4-fluorobenzyl)-N-methyl]amino-1-isobutyl-2,3-dimethyl-1H-pyrrolo[2,3-c]pyridine hydrochloride 1H-NMR(400 MHz, CDCl$_3$) δ 8.12 (t, 1H), 7.39 (d, 1H), 7.32 (m, 2H), 7.03 (t, 2H), 4.73 (s, 2H), 4.18 (d, 2H), 3.02 (s, 3H), 2.47 (s, 3H), 2.27 (s, 3H), 1.93 (m, 1H), 0.70 (d, 6H); (Yield: 50%)

EXAMPLE 150

7-[N-(4-fluorobenzyl)-N-methyl]amino-2,3-dimethyl-1-propyl-1H-pyrrolo[2,3-c]pyridine hydrochloride 1H-NMR(400 MHz, CDCl$_3$/MeOH-d$_4$) δ 8.06 (d, 1H), 7.43 (m, 1H), 7.34 (m, 2H), 7.03 (m, 2H), 4.70 (s, 2H), 4.36 (t, 2H), 3.03 (s, 3H), 2.48 (s, 3H), 2.27 (s, 3H), 1.59 (q, 2H), 0.87 (t, 3H); (Yield: 39%)

EXAMPLE 151

7-[N-(4-fluorobenzyl)-N-methyl]amino-1-(3-methoxybenzyl)-2,3-dimethyl-1H-pyrrolo[2,3-c]pyridine hydrochloride 1H-NMR(400 MHz, CDCl$_3$) δ 8.12 (t, 1H), 7.47 (d, 1H), 7.22 (t, 1H), 7.11 (m, 2H), 6.80 (m 3H), 6.19 (d, 1H), 6.15 (s, 1H), 5.79 (s, 2H), 4.71 (s, 2H), 3.73 (s, 3H), 2.92 (s, 3H), 2.31 (s, 3H), 2.29 (s, 3H); (Yield: 36%)

EXAMPLE 152

7-[N-(4-fluorobenzyl)-N-methyl]amino-2,3-dimethyl-1-(4-methylbenzyl)-1H-pyrrolo[2,3-c]pyridine hydrochloride 1H-NMR(400 MHz, CDCl$_3$) δ 8.12 (brs, 1H), 7.46 (d, 1H), 7.10 (m, 4H), 6.80 (t, 2H), 6.52 (d, 2H), 5.78 (s, 2H), 4.71 (s, 2H), 2.91 (s, 3H), 2.33 (s, 3H), 2.30 (s, 3H), 2.28 (s, 3H); (Yield: 56%)

EXAMPLE 153

7-[N-(4-fluorobenzyl)-N-methyl]amino-2,3-dimethyl-1-(prop-2-ynyl)-1H-pyrrolo[2,3-c]pyridine hydrochloride 1H-NMR(400 MHz, CDCl$_3$) δ 8.10 (d, 1H), 7.45 (m, 3H), 6.98 (m, 2H), 5.37 (s, 2H), 4.83 (s, 2H), 3.10 (s, 3H), 2.58 (s, 3H), 2.43 (s, 1H), 2.27 (s, 3H); (Yield: 16%)

EXAMPLE 154

1-(2-ethoxyethyl)-7-[N-(4-fluorobenzyl)-N-methyl]amino-2,3-dimethyl-1H-pyrrolo[2,3-c]-pyridine hydrochloride 1H-NMR(400 MHz, CDCl$_3$) δ 8.11 (brs, 1H), 7.41 (m, 3H), 7.00 (t, 2H), 4.77 (s, 2H), 4.66 (brs, 2H), 3.49 (brs, 2H), 3.29 (q, 2H), 3.01 (s, 3H), 2.50 (s, 3H), 2.26 (s, 3H), 1.04 (t, 3H); (Yield: 43%)

EXAMPLE 155

1-(4-fluorobenzyl)-7-[N-(4-fluorobenzyl)-N-methyl]amino-2,3-dimethyl-1H-pyrrolo[2,3-c]pyridine hydrochloride 1H-NMR(400 MHz, CDCl$_3$) δ 8.14 (d, 1H), 7.48 (d, 1H), 7.12 (m, 2H), 6.99 (t, 2H), 6.82 (t, 2H), 6.61 (m, 2H), 5.80 (s, 2H), 4.71 (s, 2H), 2.92 (s, 3H), 2.29 (s, 6H); (Yield: 25%)

EXAMPLE 156

7-[N-(4-fluorobenzyl)-N-methyl]amino-1-(4-methoxybenzyl)-2,3-dimethyl-1H-pyrrolo[2,3-c]pyridine hydrochloride 1H-NMR(400 MHz, CDCl$_3$) δ 8.12 (brs, 1H), 7.47 (brs, 1H), 7.15 (brs, 2H), 6.81 (brs, 4H), 6.57 (brs, 2H), 5.78 (brs, 2H), 4.73 (brs, 2H), 3.78 (s, 3H), 2.96 (brs, 3H), 2.30 (brs, 6H); (Yield: 38%)

EXAMPLE 157

1-(but-3-enyl)-7-[N-(4-fluorobenzyl)-N-methyl]amino-2,3-dimethyl-1H-pyrrolo[2,3-c]pyridine hydrochloride 1H-NMR(400 MHz, CDCl$_3$) δ 8.12 (m, 1H), 7.38 (m, 3H), 6.99 (t, 2H), 5.61 (m, 1H), 5.04 (m, 2H), 4.78 (s, 2H), 4.51 (t, 2H), 3.04 (s, 3H), 2.48 (s, 3H), 2.29 (m, 2H), 2.26 (s, 3H); (Yield: 33%)

EXAMPLE 158

1-(1,3-dioxolan-2-ylmethyl)-7-[N-(4-fluorobenzyl)-N-methyl]amino-2,3-dimethyl-1H-pyrrolo[2,3-c]pyridine hydrochloride 1H-NMR(400 MHz, CDCl$_3$) δ 8.14 (brs, 1H), 7.44 (m, 3H), 6.70 (t, 2H), 4.94 (brs, 1H), 4.76 (brs, 2H), 4.67 (brs, 2H), 3.75 (brs, 2H), 3.47 (brs, 2H), 2.97 (s, 3H), 2.51 (s, 3H), 2.27 (s, 3H); (Yield: 39%)

EXAMPLE 159

1-(3-fluorobenzyl)-7-[N-(4-fluorobenzyl)-N-methyl]amino-2,3-dimethyl-1H-pyrrolo[2,3-c]pyridine hydrochloride 1H-NMR (400 MHz, CDCl$_3$) δ 8.15 (m, 1H), 7.49 (d, 1H), 7.28 (m, 1H), 7.11 (m, 2H), 7.01 (m, 1H), 6.81 (m, 2H), 6.40 (d, 1H), 6.32 (d, 1H), 5.82 (s, 2H), 4.72 (s, 2H), 2.92 (s, 3H), 2.31 (s, 3H), 2.30 (s, 3H); (Yield: 42%)

EXAMPLE 160

7-[N-(4-fluorobenzyl)-N-methyl]amino-2,3-dimethyl-1-(3-methylbenzyl)-1H-pyrrolo[2,3-c]pyridine hydrochloride 1H-NMR(400 MHz, CDCl$_3$) δ 8.13 (brs, 1H), 7.47 (d, 1H), 7.13 (m, 4H), 6.79 (t, 2H), 6.50 (s, 1H), 6.34 (d, 1H), 5.79 (s, 2H), 4.70 (s, 2H), 2.91 (s, 3H), 2.30 (s, 3H), 2.29 (s, 3H), 2.28 (s, 3H); (Yield: 82%)

EXAMPLE 161

7-[N-(4-fluorobenzyl)-N-methyl]amino-2,3-dimethyl-1-(3-methylbutyl)-1H-pyrrolo[2,3-c]pyridine hydrochloride 1H-NMR(400 MHz, CDCl$_3$/MeOH-d$_4$) δ 8.06 (d, 1H), 7.41 (d, 1H), 7.33 (m, 2H), 7.00 (t, 2H), 4.69 (s, 2H), 4.42 (t, 2H), 3.06 (s, 3H), 2.47 (s, 3H), 2.26 (s, 3H), 1.61 (m, 1H), 1.40 (q, 2H), 0.97 (s, 3H), 0.95 (s, 3H); (Yield: 80%)

EXAMPLE 162

1-(4-tert-butylbenzyl)-7-[N-(4-fluorobenzyl)-N-methyl]amino-2,3-dimethyl-1H-pyrrolo[2,3-c]pyridine hydrochloride 1H-NMR(400 MHz, CDCl$_3$) δ 8.12 (t, 1H), 7.47 (d, 1H), 7.29 (m, 2H), 7.06 (m, 2H), 6.77 (t, 2H), 6.53 (d, 2H), 5.77 (s, 2H), 4.69 (s, 2H), 2.92 (s, 3H), 2.32 (s, 3H), 2.29 (s, 3H), 1.29 (s, 9H); (Yield: 70%)

EXAMPLE 163

1-cyanomethyl-7-[N-(4-fluorobenzyl)-N-methyl]amino-2,3-dimethyl-1H-pyrrolo[2,3-c]pyridine hydrochloride 1H-NMR(400 MHz, CDCl$_3$) δ 8.19 (d, 1H), 7.50 (d, 1H), 7.41 (m, 2H), 6.99 (t, 2H), 5.60 (s, 2H), 4.83 (s, 2H), 3.12 (s, 3H), 2.59 (s, 3H), 2.29 (s, 3H); (Yield: 40%)

EXAMPLE 164

7-[N-(4-fluorobenzyl)-N-methyl]amino-1-(2-methoxyethoxymethyl)-2,3-dimethyl-1H-pyrrolo[2,3-c]pyridine hydrochloride 1H-NMR(400 MHz, CDCl$_3$) δ 8.12 (brs, 1H), 7.38 (brs, 3H), 6.99 (brs, 2H), 5.83 (s, 2H), 4.80 (s, 2H), 3.48 (m, 4H), 3.32 (s, 3H), 3.09 (s, 3H), 2.53 (s, 3H), 2.26 (s, 3H); (Yield: 40%)

EXAMPLE 165

7-[N-(4-fluorobenzyl)-N-methyl]amino-2,3-dimethyl-1-(4-trifluoromethylbenzyl)-1H-pyrrolo[2,3-c]pyridine hydrochloride 1H-NMR(400 MHz, CDCl$_3$) δ 8.16 (brs, 1H), 7.54 (m, 3H), 7.07 (m, 2H), 6.77 (m, 4H), 5.90 (s, 2H), 4.71 (s, 2H), 2.94 (s, 3H), 2.31 (s, 3H), 2.29 (s, 3H); (Yield: 70%)

EXAMPLE 166

7-[N-(4-fluorobenzyl)-N-methyl]amino-1,2,3-trimethyl-1H-pyrrolo[2,3-c]pyridine hydrochloride 1H-NMR(400 MHz, CDCl$_3$) δ 8.02 (brs, 1H), 7.35 (m, 3H), 6.99 (t, 2H), 4.82 (s, 2H), 4.04 (s, 3H), 3.07 (s, 3H), 2.46 (s, 3H), 2.25 (s, 3H); (Yield: 70%)

EXAMPLE 167

1-(2-[1,3]dioxan-2-ylethyl)-7-[N-(4-fluorobenzyl)-N-methyl]amino-2,3-dimethyl-1H-pyrrolo[2,3-c]pyridine hydrochloride 1H-NMR(400 MHz, CDCl$_3$) δ 8.10 (brs, 1H), 7.48 (brs, 3H), 7.00 (brs, 2H), 4.79 (brs, 2H), 4.62 (brs, 2H), 4.46 (brs, 1H), 4.09 (brs, 2H), 3.71 (brs, 2H), 3.08 (brs, 3H), 2.49 (brs, 3H), 2.28 (brs, 3H), 2.06 (brs, 2H), 1.84 (brs, 2H); (Yield: 45%)

EXAMPLE 168

1-(2-chlorobenzyl)-7-[N-(4-fluorobenzyl)-N-methyl]amino-2,3-dimethyl-1H-pyrrolo[2,3-c]pyridine hydrochloride 1H-NMR(400 MHz, CDCl$_3$) δ 8.14 (brs, 1H), 7.49 (t, 2H), 7.29 (m, 1H), 7.08 (m, 3H), 6.80 (t, 2H), 5.84-5.79 (m, 3H), 4.69 (s, 2H), 2.85 (s, 3H), 2.33 (s, 6H); (Yield: 60%)

EXAMPLE 169

7-[N-(4-fluorobenzyl)-N-methyl]amino-1-methoxymethyl-2,3-dimethyl-1H-pyrrolo[2,3-c]pyridine hydrochloride 1H-NMR(400 MHz, CDCl$_3$) δ 8.12 (m, 1H), 7.38 (m, 3H), 6.99 (m, 2H), 5.70 (s, 2H), 4.80 (s, 2H), 3.24 (s, 3H), 3.07 (s, 3H), 2.52 (s, 3H), 2.26 (s, 3H); (Yield: 52%)

EXAMPLE 170

7-[N-(4-fluorobenzyl)-N-methyl]amino-1-(2-hydroxyethyl)-2,3-dimethyl-1H-pyrrolo[2,3-c]pyridine hydrochloride 1H-NMR(400 MHz, CDCl$_3$) δ 7.95 (m, 1H), 7.33 (m, 3H), 6.97 (t, 2H), 4.61 (brs, 4H), 3.78 (brs, 2H), 3.01 (brs, 1H), 2.91 (s, 3H), 2.53 (s, 3H), 2.25 (s, 3H); (Yield: 50%)

EXAMPLE 171

7-[N-(4-fluorobenzyl)-N-methyl]amino-2,3-dimethyl-1-(pent-4-ynyl)-1H-pyrrolo[2,3-c]pyridine hydrochloride 1H-NMR(400 MHz, CDCl$_3$) δ 8.12 (brs, 1H), 7.38 (m, 3H), 7.00 (t, 2H), 4.78 (s, 2H), 4.54 (m, 2H), 3.08 (s, 3H), 2.49 (s, 3H), 2.26 (s, 3H), 2.18 (m, 2H), 2.05 (s, 1H), 1.75 (m, 2H); (Yield: 62%)

EXAMPLE 172

7-[N-(4-fluorobenzyl)-N-methyl]amino-2,3-dimethyl-1-(tetrahydropyran-2-ylmethyl)-1H-pyrrolo[2,3-c]pyridine hydrochloride 1H-NMR(400 MHz, CDCl$_3$) δ 8.12 (m, 1H), 7.41 (m, 3H), 7.00 (t, 2H), 4.74 (m, 2H), 4.42 (m, 2H), 3.82 (m, 1H), 3.35 (m, 1H), 3.12 (m, 1H), 2.99 (s, 3H), 2.48 (s, 3H), 2.26 (s, 3H), 1.50 (m, 2H), 1.39 (m, 2H), 1.25 (m, 1H); (Yield: 39%)

EXAMPLE 173

7-[N-(4-fluorobenzyl)-N-methyl]amino-1-methoxycarbonylmethyl-2,3-dimethyl-1H-pyrrolo[2,3-c]pyridine hydrochloride 1H-NMR(400 MHz, CDCl$_3$) δ 8.13 (brs, 1H), 7.46 (d, 1H), 7.35 (m, 2H), 6.97 (t, 2H), 5.36 (s, 2H), 4.75 (s, 2H), 3.78 (s, 3H), 2.99 (s, 3H), 2.38 (s, 3H), 2.28 (s, 3H); (Yield: 43%)

EXAMPLE 174

7-[N-(4-fluorobenzyl)-N-methyl]amino-2,3-dimethyl-1-(2-methylthiazol-4-ylmethyl)-1H-pyrrolo[2,3-c]pyridine hydrochloride 1H-NMR(400 MHz, CDCl$_3$) δ 8.13 (brs, 1H), 7.46 (brs, 1H), 7.22 (brs, 2H), 6.87 (m, 2H), 6.10 (s, 1H), 5.87 (s, 2H), 4.75 (s, 2H), 2.99 (s, 3H), 2.71 (s, 3H), 2.40 (s, 3H), 2.29 (s, 3H); (Yield: 60%)

EXAMPLE 175

7-benzylamino-2,3-dimethyl-1H-pyrrolo[2,3-c]pyridine hydrochloride

Step 1: 7-(N-benzyl-N-tert-butoxycarbonyl)amino-2,3-dimethyl-1H-pyrrolo[2,3-c]pyridine 1-Methyl-1-propenylmagnesium bromide (0.5M in tetrahydrofuran solution, 318 ml, 159 mmol) was slowly added at −78° C. to a solution of 2-(N-benzyl-N-tert-butoxycarbonyl)amino-3-nitropyridine (17.5 g, 53.1 mmol) prepared in Preparation 5 in anhydrous tetrahydrofuran (100 ml). The reaction mixture was stirred for 1 hour at −78° C. An ammonium chloride solution was added to the reaction mixture, which was then extracted with ethyl acetate. The organic layer was dried on anhydrous magnesium sulfate and then concentrated under reduced pressure. The resulting residue was purified with silica gel column chromatography (ethyl acetate/n-hexane=1/5, v/v) to give 7.5 g of the titled compound as yellow solid.

1H-NMR(400 MHz, CDCl$_3$) δ 7.30 (m, 2H), 7.13 (m, 2H), 7.11 (m, 1H), 7.04 (d, 1H), 6.78 (d, 1H), 4.74 (s, 2H), 2.44 (s, 3H), 2.15 (s, 3H)

Step 2: 7-benzylamino-2,3-dimethyl-1H-pyrrolo[2,3-c]pyridine hydrochloride

A solution of 7-(N-benzyl-N-tert-butoxycarbonyl)amino-2,3-dimethyl-1H-pyrrolo[2,3-c]pyridine (37.0 mg) prepared in Step 1 in ethyl acetate (5 ml) was saturated with hydrochloric acid gas and then filtered to give 29.0 mg of the titled compound as a white solid. (Yield: 96%)

1H-NMR(400 MHz, CDCl$_3$/MeOH-d$_4$) δ 7.42 (m, 2H), 7.32 (m, 2H), 7.24 (m, 1H), 7.14 (d, 1H), 6.84 (d, 1H), 4.74 (s, 2H), 2.44 (s, 3H), 2.15 (s, 3H)

EXAMPLE 176

1-allyl-7-benzylamino-2,3-dimethyl-1H-pyrrolo[2,3-c]pyridine hydrochloride

Potassium tert-butoxide (27.1 mg, 0.242 mmol) was added to a solution of 7-(N-benzyl-N-tert-butoxycarbonyl)amino-2,3-dimethyl-1H-pyrrolo[2,3-c]pyridine (57 mg, 0.161 mmol) prepared in Step 1 of Example 175 and 18-crown-6 (4.3 mg, 0.016 mmol) in anhydrous tetrahydrofuran (2 ml). The reaction mixture was stirred for 30 minutes at room temperature. Allyl iodide (22.1 µl, 0.242 mmol) was added at the same temperature to the reaction mixture, which was then stirred overnight at room temperature. The reaction mixture was concentrated under reduced pressure and then purified with silica gel column chromatography (ethyl acetate/n-hexane=1/7, v/v). The resulting product was dissolved in ethyl acetate, saturated with hydrochloric acid gas, and then filtered to give the titled compound as a pale yellow solid. (Yield: 42%)

1H-NMR(400 MHz, CDCl$_3$) δ 7.78 (t, 1H), 7.43-7.33 (m, 5H), 6.97 (d, 1H), 5.98 (m, 1H), 5.83 (brs, 1H), 5.26 (d, 1H), 5.05 (d, 2H), 4.84 (d, 2H), 4.73 (d, 1H), 2.33 (s, 3H), 2.21 (s, 3H)

EXAMPLES 177 TO 197

The titled compounds of Examples 177 to 197 were prepared, in accordance with the same procedures as in Example 176, using 7-(N-benzyl-N-tert-butoxycarbonyl)amino-2,3-dimethyl-1H-pyrrolo[2,3-c]pyridine prepared in Step 1 of Example 175; and, 1-iodopropane, benzyl bromide, 1-bromomethyl-2-methoxyethane, 4-methylbenzyl chloride, 4-bromo-1-butene, 2-bromoethyl methyl ether, 1,3-dichlorobutane, 1-iodo-2-methylpropane, (bromomethyl)cyclopropane, 4-chlorobenzyl chloride, 3-methoxybenzyl chloride, 4-methoxybenzyl chloride, 4-tert-butylbenzyl chloride, iodoethane, 4-bromo-2-methyl-2-butene, 2-bromoethyl-1,3-dioxane, iodomethane, 2-fluorobenzyl chloride, 3-methylbenzyl chloride, 4-fluorobenzyl chloride, or 1-bromo-3-methylbutane.

EXAMPLE 177

7-benzylamino-2,3-dimethyl-1-propyl-1H-pyrrolo[2,3-c]pyridine hydrochloride

1H-NMR(400 MHz, CDCl$_3$) δ 7.69 (t, 1H), 7.50 (d, 1H), 7.37-7.28 (m, 3H), 6.88 (d, 1H), 6.13 (brs, 1H), 5.11 (d, 2H), 4.19 (t, 2H), 2.35 (s, 3H), 2.16 (s, 3H), 1.67 (m, 2H), 0.80 (t, 3H); (Yield: 46%)

EXAMPLE 178

1-benzyl-7-benzylamino-2,3-dimethyl-1H-pyrrolo[2,3-c]pyridine hydrochloride

1H-NMR(400 MHz, CDCl$_3$) δ 7.70 (brs, 1H), 7.33-7.18 (m, 6H), 6.94 (m, 3H), 6.76 (m, 2H), 5.86 (brs, 1H), 5.56 (brs, 2H), 4.82 (brs, 2H), 2.40 (s, 3H), 2.25 (s, 3H); (Yield: 48%)

EXAMPLE 179

7-benzylamino-1-(2-methoxyethoxymethyl)-2,3-dimethyl-1H-pyrrolo[2,3-c]pyridine hydrochloride 1H-NMR(400 MHz, CDCl$_3$) δ 7.82 (t, 1H), 7.70 (brs, 1H), 7.49 (m, 2H), 7.39-7.30 (m, 3H), 6.91 (d, 1H), 5.52 (s, 2H), 5.08 (d, 2H), 3.63 (m, 2H), 3.39 (m, 2H), 3.23 (s, 3H), 2.41 (s, 3H), 2.18 (s, 3H); (Yield: 52%)

EXAMPLE 180

7-benzylamino-2,3-dimethyl-1-(4-methylbenzyl)-1H-pyrrolo[2,3-c]pyridine hydrochloride 1H-NMR(400 MHz, CDCl$_3$) δ 7.73 (t, 1H), 7.30-7.20 (m, 3H), 7.02-6.94 (m, 5H), 6.64 (d, 2H), 5.57 (brs, 1H), 5.42 (s, 2H), 4.80 (d, 2H), 3.40 (s, 3H), 2.33 (s, 3H), 2.25 (s, 3H); (Yield: 47%)

EXAMPLE 181

7-benzylamino-1-(but-3-enyl)-2,3-dimethyl-1H-pyrrolo[2,3-c]pyridine hydrochloride 1H-NMR(400 MHz, CDCl$_3$) δ 7.72 (m, 1H), 7.47 (m, 2H), 7.35 (m, 3H), 6.92 (d, 1H), 6.10 (brs, 1H), 5.55 (m, 1H), 5.09 (d, 2H), 4.96 (d, 1H), 4.84 (d, 1H), 4.30 (t, 2H), 2.36 (m, 5H), 2.17 (s, 3H); (Yield: 52%)

EXAMPLE 182

7-benzylamino-1-(2-methoxyethyl)-2,3-dimethyl-1H-pyrrolo[2,3-c]pyridine hydrochloride 1H-NMR(400 MHz, CDCl$_3$) δ 7.79 (m, 2H), 7.46 (m, 2H), 7.39-7.32 (m, 3H), 6.93 (d, 1H), 5.01 (d, 2H), 4.36 (m, 2H), 3.68 (m, 2H), 3.05 (s, 3H), 2.34 (s, 3H), 2.19 (s, 3H); (Yield: 50%)

EXAMPLE 183

7-benzylamino-1-(but-2-enyl)-2,3-dimethyl-1H-pyrrolo[2,3-c]pyridine hydrochloride 1H-NMR(400 MHz, CDCl$_3$) δ 7.76 (t, 1H), 7.43-7.34 (m, 5H), 6.65 (m, 1H), 5.99 (brs, 1H), 5.55 (m, 1H) 5.15 (m, 1H), 5.03 (m, 2H), 4.75 (m, 2H), 2.33 (s, 3H), 2.19 (s, 3H), 1.53 (d, 3H); (Yield: 39%)

EXAMPLE 184

7-benzylamino-1-isobutyl-2,3-dimethyl-1H-pyrrolo[2,3-c]pyridine hydrochloride

1H-NMR(400 MHz, CDCl$_3$) δ 7.74 (m, 1H), 7.48 (m, 2H), 7.40-7.34 (m, 3H), 6.92 (d, 1H), 5.80 (brs, 1H), 5.09 (d, 2H), 4.12 (d, 2H), 2.35 (s, 3H), 2.18 (s, 3H), 1.93 (m, 1H), 0.75 (d, 6H); (Yield: 15%)

EXAMPLE 185

7-benzylamino-1-cyclopropylmethyl-2,3-dimethyl-1H-pyrrolo[2,3-c]pyridine hydrochloride 1H-NMR(400 MHz, CDCl$_3$) δ 7.72 (t, 1H), 7.51 (m, 2H), 7.38-7.31 (m, 3H), 6.91 (d, 1H), 6.29 (brs, 1H), 5.13 (d, 2H), 4.29 (d, 2H), 2.34 (s, 3H), 2.17 (s, 3H), 0.98 (m, 1H), 0.50 (m, 2H), 0.18 (m, 2H); (Yield: 75%)

EXAMPLE 186

7-benzylamino-1-(4-chlorobenzyl)-2,3-dimethyl-1H-pyrrolo[2,3-c]pyridine hydrochloride 1H-NMR(400 MHz, CDCl$_3$) δ 7.62 (t, 1H), 7.21-7.14 (m, 5H) 6.89-6.83 (m, 3H), 6.72 (d, 2H), 6.51 (brs, 1H), 5.69 (s, 2H), 4.85 (d, 2H), 2.38 (s, 3H), 2.22 (s, 3H); (Yield: 75%)

EXAMPLE 187

7-benzylamino-1-(3-methoxybenzyl)-2,3-dimethyl-1H-pyrrolo[2,3-c]pyridine hydrochloride 1H-NMR(400 MHz, CDCl$_3$) δ 7.72 (t, 1H), 7.26-7.13 (m, 4H), 6.98-6.92 (m, 3H), 6.83 (d, 1H), 6.31 (m, 2H), 5.71 (brs, 1H), 5.47 (s, 2H), 4.83 (d, 2H), 3.67 (s, 3H), 2.39 (s, 3H), 2.24 (s, 3H); (Yield: 70%)

EXAMPLE 188

7-benzylamino-1-(4-methoxybenzyl)-2,3-dimethyl-1H-pyrrolo[2,3-c]pyridine hydrochloride 1H-NMR(400 MHz, CDCl$_3$) δ 7.74 (t, 1H), 7.31-7.22 (m, 3H), 7.01 (d, 2H), 6.96 (d, 1H), 6.72 (d, 2H), 6.65 (d, 2H), 5.57 (brs, 1H), 5.38 (s, 2H), 4.81 (d, 2H), 3.79 (s, 3H), 2.40 (s, 3H), 2.25 (s, 3H); (Yield: 55%)

EXAMPLE 189

7-benzylamino-1-(4-tert-butylbenzyl)-2,3-dimethyl-1H-pyrrolo[2,3-c]pyridine hydrochloride 1H-NMR(400 MHz, CDCl$_3$) δ 7.78 (t, 1H), 7.35-7.22 (m, 5H), 7.02 (m, 3H), 6.64 (d, 2H), 5.36 (s, 2H), 5.30 (brs, 1H), 4.77 (d, 2H), 2.41 (s, 3H), 2.27 (s, 3H), 1.30 (s, 9H); (Yield: 73%)

EXAMPLE 190

7-benzylamino-1-ethyl-2,3-dimethyl-1H-pyrrolo[2,3-c]pyridine hydrochloride

1H-NMR(400 MHz, CDCl$_3$) δ 7.66 (m, 1H), 7.52 (m, 2H), 7.36-7.29 (m, 3H), 6.86 (d, 1H), 6.47 (brs, 1H), 5.15 (d, 2H), 4.37 (q, 2H), 2.36 (s, 3H), 2.15 (s, 3H), 1.30 (t, 3H); (Yield: 65%)

EXAMPLE 191

7-benzylamino-2,3-dimethyl-1-(3-methylbut-2-enyl)-1H-pyrrolo[2,3-c]pyridine hydrochloride 1H-NMR(400 MHz, CDCl$_3$) δ 7.78 (m, 1H), 7.38-7.32 (m, 5H), 6.95 (d, 1H), 5.89 (brs, 1H), 5.14 (m, 1H), 4.98 (d, 2H), 4.74 (brs, 2H), 2.35 (s, 3H), 2.19 (s, 3H), 1.59 (s, 3H), 1.15 (s, 3H); (Yield: 55%)

EXAMPLE 192

3-[7-benzylamino-1H-pyrrolo[2,3-c]pyridin-1-yl]-propionaldehyde hydrochloride

1H-NMR(400 MHz, CDCl$_3$) δ 7.62 (brs, 1H), 7.35 (m, 2H), 7.18 (m, 3H), 6.84 (d, 1H), 5.91 (d, 1H), 5.58 (brs, 1H), 5.31 (d, 1H), 4.51 (m, 1H), 4.10 (m, 1H), 2.54 (m, 1H), 2.39 (s, 3H), 2.36 (m, 1H), 2.18 (s, 3H); (Yield: 50%)

EXAMPLE 193

7-benzylamino-1,2,3-trimethyl-1H-pyrrolo[2,3-c]pyridine hydrochloride

1H-NMR (400 MHz, CDCl$_3$) δ 7.57-7.44 (m, 4H), 7.29-7.20 (m, 3H), 6.70 (d, 1H), 5.12 (d, 2H), 4.12 (s, 3H), 2.33 (s, 3H), 2.12 (s, 3H); (Yield: 75%)

EXAMPLE 194

7-benzylamino-1-(2-fluorobenzyl)-2,3-dimethyl-1H-pyrrolo[2,3-c]pyridine hydrochloride 1H-NMR (400 MHz, CDCl$_3$) δ 7.80 (t, 1H), 7.30-7.21 (m, 4H), 7.07-7.00 (m, 4H), 6.94 (t, 1H), 6.48 (t, 1H), 5.47 (s, 2H), 5.29 (brs, 1H), 4.84 (d, 2H), 2.39 (s, 3H), 2.26 (s, 3H); (Yield: 70%)

EXAMPLE 195

7-benzylamino-2,3-dimethyl-1-(3-methylbenzyl)-1H-pyrrolo[2,3-c]pyridine hydrochloride 1H-NMR (400 MHz, CDCl$_3$) δ 7.77 (m, 1H), 7.28-7.21 (m, 3H), 7.12 (d, 2H), 6.99 (m, 3H), 6.53 (m, 2H), 5.46 (brs, 1H), 5.40 (s, 2H), 4.80 (d, 2H), 2.46 (s, 3H), 2.26 (s, 3H), 2.20 (s, 3H); (Yield: 77%)

EXAMPLE 196

7-benzylamino-1-(4-fluorobenzyl)-2,3-dimethyl-1H-pyrrolo[2,3-c]pyridine hydrochloride 1H-NMR (400 MHz, CDCl$_3$) δ 7.69 (t, 1H), 7.24-7.18 (m, 3H) 6.97-6.87 (m, 5H), 6.74 (m, 2H), 5.96 (brs, 1H), 5.55 (s, 2H), 4.84 (d, 2H), 2.39 (s, 3H), 2.24 (s, 3H); (Yield: 74%)

EXAMPLE 197

7-benzylamino-2,3-dimethyl-1-(3-methylbutyl)-1H-pyrrolo[2,3-c]pyridine hydrochloride 1H-NMR (400 MHz, CDCl$_3$) δ 7.71 (m, 1H), 7.49 (m, 2H), 7.38-7.30 (m, 3H), 6.89 (d, 1H), 5.99 (brs, 1H), 5.09 (d, 2H), 4.17 (m, 2H), 2.34 (s, 3H), 2.16 (s, 3H), 1.49 (m, 3H), 0.78 (d, 6H); (Yield: 58%)

EXAMPLE 198

1-isobutyl-2,3-dimethyl-7-(4-methylbenzylamino)-1H-pyrrolo[2,3-c]pyridine hydrochloride Step 1.
7-chloro-2,3-dimethyl-1H-pyrrolo[2,3-c]pyridine 2-Chloro-3-nitropyridine (8 g, 50.46 mmol) was dissolved in anhydrous tetrahydrofuran (200 ml) at nitrogen atmosphere. 1-Methyl-1-propenyl magnesium bromide (0.5M in tetrahydrofuran solution, 252 ml, 126.15 mmol) was slowly added at −78° C. to the solution. The reaction mixture was stirred for 2 hours at −20° C. and 20% ammonium chloride solution was added thereto. The reaction mixture was extracted with ethyl acetate and then concentrated under reduced pressure. The resulting residue was purified with silica gel column chromatography (ethyl acetate/n-hexane=1/3, v/v) to give 2.73 g of the titled compound as a pale yellow solid. (Yield: 30%)

1H-NMR (400 MHz, CDCl$_3$) δ 8.45 (brs, 1H), 7.97 (d, 1H), 7.30 (d, 1H), 2.43 (s, 3H), 2.21 (s, 3H)

Step 2. 7-chloro-1-isobutyl-2,3-dimethyl-1H-pyrrolo[2,3-c]pyridine

Sodium hydride (60%, 33 mg, 0.83 mmol) was added to a solution of 7-chloro-2,3-dimethyl-1H-pyrrolo[2,3-c]pyridine (100 mg, 0.53 mmol) prepared in Step 1 in anhydrous tetrahydrofuran (2.8 ml). The reaction mixture was stirred for 30 minutes at room temperature. 1-Iodo-2-methylpropane (64 t, 0.67 mmol) was added to the reaction mixture, which was then stirred overnight at room temperature. Water was added to the reaction mixture, which was then extracted with dichloromethane. The organic layer was dried on anhydrous magnesium sulfate and then concentrated under reduced pressure. The resulting residue was purified with silica gel column chromatography (ethyl acetate/n-hexane=1/9, v/v) to give 108 mg of the titled compound as a white solid. (Yield: 86%)

1H-NMR (400 MHz, CDCl$_3$) δ 7.94 (d, 1H), 7.29 (d, 1H), 4.25 (brs, 2H), 2.38 (s, 3H), 2.22 (m, 4H), 0.89 (d, 6H)

Step 3. 1-isobutyl-2,3-dimethyl-7-(4-methylbenzylamino)-1H-pyrrolo[2,3-c]pyridine hydrochloride Cesium carbonate (97 mg, 0.317 mmol) and (S)-2,2'-bis(diphenylphosphino)-1,1'-binaphthyl (20 mg, 0.0317 mmol) were added to a solution of 7-chloro-1-isobutyl-2,3-dimethyl-1H-pyrrolo[2,3-c]pyridine (50 mg, 0.211 mmol) prepared in Step 2, tris(dibenzylideneacetone)dipalladium (0) (11 mg, 0.0106 mmol), and 4-methylbenzylamine (40 ml, 0.317 mmol) in anhydrous toluene (1.1 ml). The reaction mixture was refluxed for 40 hours and then concentrated under reduced pressure. The resulting residue was purified with silica gel column chromatography (ethyl acetate/n-hexane=15/85, v/v). The resulting product was dissolved in ethyl acetate, saturated with hydrochloric acid gas, and then filtered to give 15 mg of the titled compound as a white solid. (Yield: 21%).

1H-NMR(400 MHz, CDCl$_3$) δ 7.73 (t, 1H), 7.35 (d, 2H), 7.17 (d, 2H), 6.90 (d, 1H), 5.79 (brs, 1H), 5.03 (d, 2H), 3.97 (d, 2H), 2.34 (s, 6H), 2.17 (s, 3H), 1.93 (m, 1H), 0.76 (d, 6H)

EXAMPLE 199

1-(2-methoxyethyl)-2,3-dimethyl-7-(4-methylbenzylamino)-1H-pyrrolo[2,3-c]pyridine hydrochloride Step 1. 7-chloro-1-(2-methoxyethyl)-2,3-dimethyl-1H-pyrrolo[2,3-c]pyridine In accordance with the same procedures as in Step 2 of Example 198, except for using 7-chloro-2,3-dimethyl-1H-pyrrolo[2,3-c]pyridine prepared in Step 1 of Example 198 and 2-bromoethyl methyl ether, the titled compound was obtained as a white solid. (Yield: 80%)

1H-NMR (400 MHz, CDCl$_3$) δ 7.94 (d, 1H), 7.29 (d, 1H), 4.64 (t, 2H), 3.72 (t, 2H), 3.28 (s, 3H), 2.41 (s, 3H), 2.21 (s, 3H)

Step 2. 1-(2-methoxyethyl)-2,3-dimethyl-7-(4-methylbenzylamino)-1H-pyrrolo[2,3-c]pyridine hydrochloride In accordance with the same procedures as in Step 3 of Example 198, except for using 7-chloro-1-(2-methoxyethyl)-2,3-dimethyl-1H-pyrrolo[2,3-c]pyridine prepared in Step 1 and 4-methylbenzylamine, the titled compound was obtained as a white solid. (Yield: 47%)

1H-NMR(400 MHz, CDCl$_3$) δ 7.78 (t, 1H), 7.77 (brs, 1H), 7.34 (d, 2H), 7.17 (d, 2H), 6.93 (d, 1H), 4.95 (d, 2H), 4.35 (t, 2H), 3.68 (t, 2H), 3.07 (s, 3H), 2.35 (s, 3H), 2.33 (s, 3H), 2.16 (s, 3H)

EXAMPLE 200

1-benzyl-2,3-dimethyl-7-(4-methylbenzylamino)-1H-pyrrolo[2,3-c]pyridine hydrochloride Step 1. 1-benzyl-7-chloro-2,3-dimethyl-1H-pyrrolo[2,3-c]pyridine In accordance with the same procedures as in Step 2 of Example 198, except for using 7-chloro-2,3-dimethyl-1H-pyrrolo[2,3-c]pyridine prepared in Step 1 of Example 198 and benzyl bromide, the titled compound was obtained as a white solid. (Yield: 42%)

1H-NMR (400 MHz, CDCl$_3$) δ 7.97 (d, 1H), 7.34 (d, 1H), 7.27-7.21 (m, 3H), 6.87 (d, 2H), 5.75 (s, 2H), 2.27 (s, 3H), 2.24 (s, 3H)

Step 2. 1-benzyl-2,3-dimethyl-7-(4-methylbenzylamino)-1H-pyrrolo[2,3-c]pyridine hydrochloride In accordance with the same procedures as in Step 3 of Example 198, except for using 1-benzyl-7-chloro-2,3-dimethyl-1H-pyrrolo[2,3-c]pyridine prepared in Step 1 and 4-methylbenzylamine, the titled compound was obtained as a white solid. (Yield: 50%)

1H-NMR(400 MHz, CDCl$_3$) δ 7.72 (t, 1H), 7.32-7.22 (m, 3H), 7.00 (d, 2H), 6.94 (d, 1H), 6.83 (d, 2H), 6.75 (d, 2H), 5.61 (brs, 1H), 5.49 (s, 2H), 4.73 (d, 2H), 2.40 (s, 3H), 2.33 (s, 3H), 2.25 (s, 3H)

EXAMPLE 201

1-(4-fluorobenzyl)-2,3-dimethyl-7-(4-methylbenzylamino)-1H-pyrrolo[2,3-c]pyridine hydrochloride Step 1. 7-chloro-1-(4-fluorobenzyl)-2,3-dimethyl-1H-pyrrolo[2,3-c]pyridine In accordance with the same procedures as in Step 2 of Example 198, except for using 7-chloro-2,3-dimethyl-1H-pyrrolo[2,3-c]pyridine prepared in Step 1 of Example 198 and 4-fluorobenzyl chloride, the titled compound was obtained as a pale yellow solid. (Yield: 86%)

1H-NMR(400 MHz, CDCl$_3$) δ 7.97 (d, 1H), 7.34 (d, 1H), 6.94 (dd, 2H), 6.85 (dd, 1H), 5.71 (s, 2H), 2.27 (s, 3H), 2.24 (s, 3H)

Step 2. 1-(4-fluorobenzyl)-2,3-dimethyl-7-(4-methylbenzylamino)-1H-pyrrolo[2,3-c]pyridine hydrochloride In accordance with the same procedures as in Step 3 of Example 198, except for using 7-chloro-1-(4-fluorobenzyl)-2,3-dimethyl-1H-pyrrolo[2,3-c]pyridine prepared in Step 1 and 4-methylbenzylamine, the titled compound was obtained as a white solid. (Yield: 45%)

1H-NMR(400 MHz, CDCl$_3$) δ 7.64 (t, 1H), 6.97 (d, 2H), 7.00 (d, 2H), 6.90-6.85 (m, 3H), 6.81 (d, 2H), 6.75 (dd, 2H), 6.16 (brs, 1H), 5.60 (s, 2H), 4.78 (d, 2H), 2.38 (s, 3H), 2.30 (s, 3H), 2.22 (s, 3H)

EXAMPLE 202

2,3-dimethyl-1-(4-methylbenzyl)-7-(4-methylbenzylamino)-1H-pyrrolo[2,3-c]pyridine hydrochloride Step 1. 7-chloro-2,3-dimethyl-1-(4-methylbenzyl)-1H-pyrrolo[2,3-c]pyridine In accordance with the same procedures as in Step 2 of Example 198, except for using 7-chloro-2,3-dimethyl-1H-pyrrolo[2,3-c]pyridine prepared in Step 1 of Example 198 and 4-methylbenzyl chloride, the titled compound was obtained as a white solid. (Yield: 75%)

1H-NMR(400 MHz, CDCl$_3$) δ 7.93 (d, 1H), 7.29 (d, 1H), 7.07 (d, 2H), 6.79 (d, 2H), 5.71 (s, 2H), 2.30 (s, 3H), 2.27 (s, 3H), 2.24 (s, 3H)

Step 2. 2,3-dimethyl-1-(4-methylbenzyl)-7-(4-methylbenzylamino)-1H-pyrrolo[2,3-c]pyridine hydrochloride In accordance with the same procedures as in Step 3 of Example 198, except for using 7-chloro-2,3-dimethyl-1-(4-methylbenzyl)-1H-pyrrolo[2,3-c]pyridine prepared in Step 1 and 4-methylbenzylamine, the titled compound was obtained as a white solid. (Yield: 31%)

1H-NMR(400 MHz, CDCl$_3$) δ 7.72 (t, 1H), 7.01 (d, 4H), 6.93 (d, 2H), 6.85 (d, 2H), 6.64 (d, 2H), 5.56 (brs, 1H), 5.41 (s, 2H), 4.74 (d, 2H), 2.39 (s, 3H), 2.34 (s, 6H), 2.24 (s, 3H)

EXAMPLE 203

1-ethyl-2,3-dimethyl-7-(4-methylbenzylamino)-1H-pyrrolo[2,3-c]pyridine hydrochloride Step 1. 7-chloro-1-ethyl-2,3-dimethyl-1H-pyrrolo[2,3-c]pyridine In accordance with the same procedures as in Step 2 of Example 198, except for using 7-chloro-2,3-dimethyl-1H-pyrrolo[2,3-c]pyridine prepared in Step 1 of Example 198 and iodoethane, the titled compound was obtained as a white solid. (Yield: 42%)

1H-NMR(400 MHz, CDCl$_3$) δ 7.91 (d, 1H), 7.25 (d, 1H), 4.46 (q, 2H), 2.34 (s, 3H), 2.19 (s, 3H), 1.33 (t, 3H)

Step 2. 1-ethyl-2,3-dimethyl-7-(4-methylbenzylamino)-1H-pyrrolo[2,3-c]pyridine hydrochloride In accordance with the same procedures as in Step 3 of Example 198, except for using 7-chloro-1-ethyl-2,3-dimethyl-1H-pyrrolo[2,3-c]pyridine prepared in Step 1 and 4-methylbenzylamine, the titled compound was obtained as a white solid. (Yield: 39%)

1H-NMR(400 MHz, CDCl$_3$) δ 7.64 (t, 1H), 7.41 (d, 2H), 7.12 (d, 2H), 6.82 (d, 1H), 6.59 (brs, 1H), 5.10 (s, 2H), 4.40 (brs, 2H), 2.35 (s, 3H), 2.30 (s, 3H), 2.14 (s, 3H), 1.31 (brs, 3H)

EXAMPLE 204

1-cyclopropylmethyl-2,3-dimethyl-7-(4-methylbenzylamino)-1H-pyrrolo[2,3-c]pyridine hydrochloride Step 1. 7-chloro-1-cyclopropylmethyl-2,3-dimethyl-1H-pyrrolo[2,3-c]pyridine In accordance with the same procedures as in Step 2 of Example 198, except for using 7-chloro-2,3-dimethyl-1H-pyrrolo[2,3-c]pyridine prepared in Step 1 of Example 198 and (bromomethyl)cyclopropane, the titled compound was obtained as a white solid. (Yield: 92%)

1H-NMR(400 MHz, CDCl$_3$) δ 7.93 (d, 1H), 7.29 (d, 1H), 4.43 (d, 2H), 2.38 (s, 3H), 2.22 (s, 3H), 1.26-1.21 (m, 1H), 0.53-0.48 (m, 2H), 0.40-0.36 (m, 2H)

Step 2. 1-cyclopropylmethyl-2,3-dimethyl-7-(4-methylbenzylamino)-1H-pyrrolo[2,3-c]pyridine hydrochloride In accordance with the same procedures as in Step 3 of Example 198, except for using 7-chloro-1-cyclopropylmethyl-2,3-dimethyl-1H-pyrrolo[2,3-c]pyridine prepared in Step 1 and 4-methylbenzylamine, the titled compound was obtained as a white solid. (Yield: 47%)

1H-NMR(400 MHz, CDCl$_3$) δ 7.74 (t, 1H), 7.37 (d, 2H), 7.16 (d, 2H), 6.92 (d, 1H), 6.10 (brs, 1H), 5.07 (d, 2H), 4.26 (d, 2H), 2.34 (s, 6H), 2.17 (s, 3H), 0.99 (m, 1H), 0.52 (dd, 2H), 0.18 (dd, 2H)

EXAMPLE 205

2,3-dimethyl-7-(4-methylbenzylamino)-1-propyl-1H-pyrrolo[2,3-c]pyridine hydrochloride Step 1. 7-chloro-2,3-dimethyl-1-propyl-1H-pyrrolo[2,3-c]pyridine In accordance with the same procedures as in Step 2 of Example 198, except for using 7-chloro-2,3-dimethyl-1H-pyrrolo[2,3-c]pyridine prepared in Step 1 of Example 198 and 1-iodopropane, the titled compound was obtained as a white solid. (Yield: 95%)

1H-NMR(400 MHz, CDCl$_3$) δ 7.91 (d, 1H), 7.27 (d, 1H), 4.36 (dd, 2H), 2.36 (s, 3H), 2.20 (s, 3H), 1.75 (m, 2H), 0.96 (t, 3H)

Step 2. 2,3-dimethyl-7-(4-methylbenzylamino)-1-propyl-1H-pyrrolo[2,3-c]pyridine hydrochloride In accordance with the same procedures as in Step 3 of Example 198, except for using 7-chloro-2,3-dimethyl-1-propyl-1H-pyrrolo[2,3-c]pyridine prepared in Step 1 and 4-methylbenzylamine, the titled compound was obtained as a white solid. (Yield: 35%)

1H-NMR(400 MHz, CDCl$_3$) δ 7.67 (t, 1H), 7.38 (d, 2H), 7.14 (d, 2H), 6.85 (d, 1H), 6.19 (brs, 1H), 5.06 (d, 2H), 4.21 (t, 2H), 2.34 (s, 3H), 2.32 (s, 3H), 2.15 (s, 3H), 1.67 (m, 2H), 0.81 (t, 3H)

EXAMPLE 206

1-allyl-2,3-dimethyl-7-(4-methylbenzylamino)-1H-pyrrolo[2,3-c]pyridine hydrochloride Step 1. 1-allyl-7-chloro-2,3-dimethyl-1H-pyrrolo[2,3-c]pyridine In accordance with the same procedures as in Step 2 of Example 198, except for using 7-chloro-2,3-dimethyl-1H-pyrrolo[2,3-c]pyridine prepared in Step 1 of Example 198 and allyl iodide, the titled compound was obtained as a white solid. (Yield: 75%)
1H-NMR(400 MHz, CDCl$_3$) δ 2.27 (s, 3H), 2.41 (s, 3H), 4.52 (m, 2H), 4.72 (t, 1H), 6.97 (d, 2H), 7.38 (d, 1H), 8.08 (d, 1H)

Step 2. 1-allyl-2,3-dimethyl-7-(4-methylbenzylamino)-1H-pyrrolo[2,3-c]pyridine hydrochloride In accordance with the same procedures as in Step 3 of Example 198, except for using 1-allyl-7-chloro-2,3-dimethyl-1H-pyrrolo[2,3-c]pyridine prepared in Step 1 and 4-methylbenzylamine, the titled compound was obtained as a white solid. (Yield: 29%)
1H-NMR(400 MHz, CDCl$_3$) δ 7.78 (t, 1H), 7.45-7.30 (m, 4H), 6.93 (d, 1H), 5.98 (m, 1H), 5.83 (brs, 1H), 5.31 (d, 1H), 5.05 (d, 2H), 4.80 (d, 2H), 4.66 (d, 1H), 2.36 (s, 3H), 2.33 (s, 3H), 2.21 (s, 3H)

EXAMPLE 207

1-(3-fluorobenzyl)-7-(4-fluorobenzylamino)-2,3-dimethyl-1H-pyrrolo[2,3-c]pyridine hydrochloride Step 1. 7-chloro-1-(3-fluorobenzyl)-2,3-dimethyl-1H-pyrrolo[2,3-c]pyridine In accordance with the same procedures as in Step 2 of Example 198, except for using 7-chloro-2,3-dimethyl-1H-pyrrolo[2,3-c]pyridine prepared in Step 1 of Example 198 and 3-fluorobenzyl chloride, the titled compound was obtained as a white solid. (Yield: 72%)
1H-NMR(400 MHz, CDCl$_3$) δ 7.98 (d, 1H), 7.35 (d, 1H), 7.27-7.21 (m, 1H), 6.92 (dd, 1H), 6.69 (d, 1H), 6.54 (d, 1H), 5.76 (s, 2H), 2.29 (s, 3H), 2.26 (s, 3H)

Step 2. 1-(3-fluorobenzyl)-7-(4-fluorobenzylamino)-2,3-dimethyl-1H-pyrrolo[2,3-c]pyridine hydrochloride In accordance with the same procedures as in Step 3 of Example 198, except for using 7-chloro-2,3-dimethyl-1-(3-fluorobenzyl)-1H-pyrrolo[2,3-c]pyridine prepared in Step 1 and 4-fluorobenzylamine, the titled compound was obtained as a white solid. (Yield: 70%)
1H-NMR(400 MHz, CDCl$_3$) δ 7.60 (t, 1H), 7.22 (dd, 1H), 6.99 (t, 1H), 6.92-6.77 (m, 5H), 6.65 (d, 1H), 6.61 (brs, —NH, 1H), 6.43 (d, 1H), 5.74 (s, 2H), 4.84 (d, 2H), 2.38 (s, 3H), 2.22 (s, 3H)

EXAMPLES 208 TO 210

The titled compounds of Examples 208 to 210 were prepared, in accordance with the same procedures as in Step 3 of Example 198, using 7-chloro-1-isobutyl-2,3-dimethyl-1H-pyrrolo[2,3-c]pyridine prepared in Step 2 of Example 198; and, 4-fluorobenzylamine, 4-chlorobenzylamine, or 2-methylbenzylamine.

EXAMPLE 208

7-(4-fluorobenzylamino)-1-isobutyl-2,3-dimethyl-1H-pyrrolo[2,3-c]pyridine hydrochloride 1H-NMR(400 MHz, CDCl$_3$) δ 7.60 (t, 1H), 7.52 (dd, 2H), 6.99 (t, 2H), 6.82 (d, 1H), 6.68 (brs, 1H), 5.07 (d, 2H), 4.15 (d, 2H), 2.33 (s, 3H), 2.15 (s, 3H), 1.86 (m, 1H), 0.75 (d, 6H); (Yield: 97%)

EXAMPLE 209

7-(4-chlorobenzylamino)-1-isobutyl-2,3-dimethyl-1H-pyrrolo[2,3-c]pyridine hydrochloride 1H-NMR(400 MHz, CDCl$_3$) δ 7.64 (t, 1H), 7.46 (d, 2H), 7.29 (d, 2H), 6.87 (d, 1H), 6.43 (brs, 1H), 5.09 (d, 2H), 4.11 (d, 2H), 2.35 (s, 3H), 2.16 (s, 3H), 1.89 (m, 1H), 0.77 (d, 6H); (Yield: 21%)

EXAMPLE 210

1-isobutyl-2,3-dimethyl-7-(2-methylbenzylamino)-1H-pyrrolo[2,3-c]pyridine hydrochloride 1H-NMR(400 MHz, CDCl$_3$) δ 7.79 (t, 1H), 7.35 (d, 1H), 7.29-7.19 (m, 3H), 6.96 (d, 1H), 5.34 (brs, 1H), 5.07 (d, 2H), 3.88 (d, 2H), 2.42 (s, 3H), 2.37 (s, 3H), 2.19 (s, 3H), 1.89 (m, 1H), 0.71 (d, 6H); (Yield: 21%)

EXAMPLES 211 TO 213

The titled compounds of Examples 211 to 213 were prepared, in accordance with the same procedures as in Step 3 of Example 198, using 7-chloro-1-(2-methoxyethyl)-2,3-dimethyl-1H-pyrrolo[2,3-c]pyridine prepared in Step 1 of Example 199; and, 4-fluorobenzylamine, 4-chlorobenzylamine, or 2-methylbenzylamine.

EXAMPLE 211

7-(4-fluorobenzylamino)-1-(2-methoxyethyl)-2,3-dimethyl-1H-pyrrolo[2,3-c]pyridine hydrochloride 1H-NMR(400 MHz, CDCl$_3$) δ 7.79 (d, 1H), 7.46 (dd, 2H), 7.06 (t, 2H), 6.95 (d, 1H), 5.01 (d, 2H), 4.36 (s, 2H), 3.70 (s, 2H), 3.10 (s, 3H), 2.34 (s, 3H), 2.19 (s, 3H); (Yield: 22%)

EXAMPLE 212

7-(4-chlorobenzylamino)-1-(2-methoxyethyl)-2,3-dimethyl-1H-pyrrolo[2,3-c]pyridine hydrochloride 1H-NMR(400 MHz, CDCl$_3$) δ 7.82 (brs, 1H), 7.76 (t, 1H), 7.43 (d, 2H), 7.34 (d, 2H), 6.95 (d, 1H), 5.01 (d, 2H), 4.38 (t, 2H), 3.71 (t, 2H), 3.12 (s, 3H), 2.35 (s, 3H), 2.19 (s, 3H); (Yield: 19%)

EXAMPLE 213

1-(2-methoxyethyl)-2,3-dimethyl-7-(2-methylbenzylamino)-1H-pyrrolo[2,3-c]pyridine hydrochloride 1H-NMR(400 MHz, CDCl$_3$) δ 7.82 (t, 1H), 7.69 (brs, 1H), 7.34 (d, 1H), 7.28-7.21 (m, 3H), 6.95 (d, 1H), 4.99 (d, 2H), 4.31 (s, 2H), 3.65 (s, 2H), 2.95 (s, 3H), 2.44 (s, 3H), 2.33 (s, 3H), 2.19 (s, 3H); (Yield: 29%)

EXAMPLES 214 TO 216

The titled compounds of Examples 214 to 216 were prepared, in accordance with the same procedures as in Step 3 of Example 198, using 1-benzyl-7-chloro-2,3-dimethyl-1H-pyrrolo[2,3-c]pyridine prepared in Step 1 of Example 200; and, 4-fluorobenzylamine, 4-chlorobenzylamine, or 2-methylbenzylamine.

EXAMPLE 214

1-benzyl-7-(4-fluorobenzylamino)-2,3-dimethyl-1H-pyrrolo[2,3-c]pyridine hydrochloride 1H-NMR(400 MHz, CDCl$_3$) δ 13.85 (brs, 1H), 7.63 (d, 1H), 7.34-7.24 (m, 4H), 6.88-6.79 (m, 6H), 6.25 (brs, 1H), 5.66 (s, 2H), 4.82 (d, 2H), 2.40 (s, 3H), 2.23 (s, 3H); (Yield: 90%)

EXAMPLE 215

1-benzyl-7-(4-chlorobenzylamino)-2,3-dimethyl-1H-pyrrolo[2,3-c]pyridine hydrochloride 1H-NMR(400 MHz, CDCl$_3$) δ 7.60 (t, 1H), 7.33-7.24 (m, 3H), 7.07 (d, 2H), 6.87 (d, 1H), 6.80 (d, 4H), 6.32 (brs, 1H), 5.67 (s, 2H), 4.82 (d, 2H), 2.40 (s, 3H), 2.23 (s, 3H); (Yield: 30%)

EXAMPLE 216

1-benzyl-2,3-dimethyl-7-(2-methylbenzylamino)-1H-pyrrolo[2,3-c]pyridine hydrochloride 1H-NMR(400 MHz, CDCl$_3$) δ 7.76 (t, 1H), 7.25 (m, 2H), 7.15-7.10 (m, 4H), 6.99 (brs, 1H), 6.89 (brs, 1H), 6.65 (brs, 2H), 5.40 (brs, 2H), 5.21 (brs, 1H), 4.76 (d, 2H), 2.42 (s, 3H), 2.28 (s, 3H), 2.28 (s, 3H); (Yield: 30%)

EXAMPLES 217 TO 219

The titled compounds of Examples 217 to 219 were prepared, in accordance with the same procedures as in Step 3 of Example 198, using 7-chloro-1-(4-fluorobenzyl)-2,3-dimethyl-1H-pyrrolo[2,3-c]pyridine prepared in Step 1 of Example 201; and, 4-fluorobenzylamine, 4-chlorobenzylamine, or 2-methylbenzylamine.

EXAMPLE 217

1-(4-fluorobenzyl)-7-(4-fluorobenzylamino)-2,3-dimethyl-1H-pyrrolo[2,3-c]pyridine hydrochloride 1H-NMR(400 MHz, CDCl$_3$) δ 7.58 (d, 1H), 7.26 (d, 1H), 6.94-6.76 (m, 8H), 6.60 (brs, 1H), 5.71 (s, 2H), 4.84 (d, 2H), 2.38 (s, 3H), 2.22 (s, 3H); (Yield: 66%)

EXAMPLE 218

7-(4-chlorobenzylamino)-1-(4-fluorobenzyl)-2,3-dimethyl-1H-pyrrolo[2,3-c]pyridine hydrochloride 1H-NMR(400 MHz, CDCl$_3$) δ 7.54 (t, 1H), 7.05 (d, 2H), 6.93 (t, 2H), 6.83-6.78 (m, 6H), 5.76 (s, 2H), 4.84 (d, 2H), 2.38 (s, 3H), 2.22 (s, 3H); (Yield: 29%)

EXAMPLE 219

1-(4-fluorobenzyl)-2,3-dimethyl-7-(2-methylbenzylamino)-1H-pyrrolo[2,3-c]pyridine hydrochloride 1H-NMR(400 MHz, CDCl$_3$) δ 7.72 (t, 1H), 7.21 (t, 1H), 7.09 (d, 1H), 7.05 (t, 1H), 6.94 (d, 2H), 6.84-6.80 (m, 3H), 6.56 (dd, 2H), 5.51 (brs, 1H), 5.45 (s, 2H), 4.78 (d, 2H), 2.40 (s, 3H), 2.25 (s, 3H), 2.04 (s, 3H); (Yield: 86%)

EXAMPLES 220 TO 222

The titled compounds of Examples 220 to 222 were prepared, in accordance with the same procedures as in Step 3 of Example 198, using 7-chloro-2,3-dimethyl-1-(4-methylbenzyl)-1H-pyrrolo[2,3-c]pyridine prepared in Step 1 of Example 202; and, 4-fluorobenzylamine, 4-chlorobenzylamine, or 2-methylbenzylamine.

EXAMPLE 220

7-(4-fluorobenzylamino)-2,3-dimethyl-1-(4-methylbenzyl)-1H-pyrrolo[2,3-c]pyridine hydrochloride 1H-NMR(400 MHz, CDCl$_3$) δ 7.68 (t, 1H), 7.04 (d, 2H), 6.94 (d, 1H), 6.92 (d, 2H), 6.85 (d, 2H), 6.67 (d, 2H), 5.84 (brs, 1H), 5.49 (d, 2H), 4.81 (d, 2H), 2.40 (s, 3H), 2.34 (s, 3H), 2.24 (s, 3H); (Yield: 23%)

EXAMPLE 221

7-(4-chlorobenzylamino)-2,3-dimethyl-1-(4-methylbenzyl)-1H-pyrrolo[2,3-c]pyridine hydrochloride 1H-NMR(400 MHz, CDCl$_3$) δ 7.64 (t, 1H), 7.12 (d, 2H), 7.03 (d, 2H), 6.92 (d, 1H), 6.87 (d, 2H), 6.68 (d, 2H), 5.87 (brs, 1H), 5.51 (s, 2H), 4.79 (d, 2H), 2.40 (s, 3H), 2.35 (s, 3H), 2.24 (s, 3H); (Yield: 15%)

EXAMPLE 222

2,3-dimethyl-1-(4-methylbenzyl)-7-(2-methylbenzylamino)-1H-pyrrolo[2,3-c]pyridine hydrochloride 1H-NMR (400 MHz, CDCl$_3$) δ 7.79 (t, 1H), 7.26 (dd, 2H), 7.10 (dd, 2H), 6.99 (d, 1H), 6.91 (d, 2H), 6.53 (d, 2H), 5.30 (s, 2H), 5.13 (brs, 1H), 4.75 (d, 2H), 2.40 (s, 3H), 2.32 (s, 3H), 2.27 (s, 3H), 2.05 (s, 3H); (Yield: 22%)

EXAMPLES 223 TO 225

The titled compounds of Examples 223 to 225 were prepared, in accordance with the same procedures as in Step 3 of Example 198, using 7-chloro-1-ethyl-2,3-dimethyl-1H-pyrrolo[2,3-c]pyridine prepared in Step 1 of Example 203; and, 4-fluorobenzylamine, 4-chlorobenzylamine, or 2-methylbenzylamine.

EXAMPLE 223

1-ethyl-7-(4-fluorobenzylamino)-2,3-dimethyl-1H-pyrrolo[2,3-c]pyridine hydrochloride 1H-NMR(400 MHz, CDCl$_3$) δ 7.59-7.54 (m, 3H), 7.25 (brs, 1H), 6.94 (t, 2H), 6.79 (d, 1H), 5.16 (d, 2H), 4.51 (q, 2H), 2.35 (s, 3H), 2.13 (s, 3H), 1.28 (t, 3H); (Yield: 52%)

EXAMPLE 224

7-(4-chlorobenzylamino)-1-ethyl-2,3-dimethyl-1H-pyrrolo[2,3-c]pyridine hydrochloride 1H-NMR(400 MHz, CDCl$_3$) δ 7.55 (t, 1H), 7.52 (d, 2H), 7.34 (brs, 1H), 7.20 (d, 2H), 6.79 (d, 1H), 5.16 (d, 2H), 4.52 (q, 2H), 2.35 (s, 3H), 2.14 (s, 3H), 1.29 (t, 3H); (Yield: 37%)

EXAMPLE 225

1-ethyl-2,3-dimethyl-7-(2-methylbenzylamino)-1H-pyrrolo[2,3-c]pyridine hydrochloride 1H-NMR(400 MHz, CDCl$_3$) δ 7.68 (t, 1H), 7.38 (d, 1H), 7.23-7.17 (m, 4H), 6.88 (d, 2H), 6.11 (brs, 1H), 5.12 (d, 2H), 4.32 (q, 2H), 2.41 (s, 3H), 2.37 (s, 3H), 2.17 (s, 3H), 1.28 (t, 3H); (Yield: 76%)

EXAMPLES 226 AND 227

The titled compounds of Examples 226 and 227 were prepared, in accordance with the same procedures as in Step 3 of Example 198, using 7-chloro-1-cyclopropylmethyl-2,3-dimethyl-1H-pyrrolo[2,3-c]pyridine prepared in Step 1 of Example 204; and, 4-fluorobenzylamine or 4-chlorobenzylamine.

EXAMPLE 226

1-cyclopropylmethyl-7-(4-fluorobenzylamino)-2,3-dimethyl-1H-pyrrolo[2,3-c]pyridine hydrochloride 1H-NMR (400 MHz, CDCl$_3$) δ 7.69 (d, 1H), 7.52 (t, 2H), 7.04 (t, 2H), 6.90 (d, 1H), 6.41 (s, 1H), 5.12 (s, 2H), 4.32 (d, 2H), 2.34 (s, 3H), 2.17 (s, 3H), 0.98 (m, 1H), 0.50 (d, 2H), 0.19 (d, 2H)

EXAMPLE 227

7-(4-chlorobenzylamino)-1-cyclopropylmethyl-2,3-dimethyl-1H-pyrrolo[2,3-c]pyridine hydrochloride 1H-NMR(400 MHz, CDCl$_3$) δ 7.65 (t, 1H), 7.49 (d, 2H), 7.27 (d, 2H), 6.88 (d, 1H), 6.69 (brs, 1H), 5.13 (s, 2H), 4.36 (s, 2H), 2.34 (s, 3H), 2.16 (s, 3H), 0.50 (d, 2H), 0.20 (d, 2H); (Yield: 25%)

EXAMPLES 228 TO 236

The titled compounds of Examples 228 to 236 were prepared, in accordance with the same procedures as in Step 3 of Example 198, using 7-chloro-2,3-dimethyl-1-propyl-1H-pyrrolo[2,3-c]pyridine prepared in Step 1 of Example 205; and, 4-fluorobenzylamine, 4-chlorobenzylamine, 2-methylbenzylamine, 2-chlorobenzylamine, 3-fluorobenzylamine, 4-trifluoromethoxybenzylamine, 3-methylbenzylamine, piperonylamine, or 3-chlorobenzylamine.

EXAMPLE 228

7-(4-fluorobenzylamino)-2,3-dimethyl-1-propyl-1H-pyrrolo[2,3-c]pyridine hydrochloride 1H-NMR(400 MHz, CDCl$_3$) δ 7.60-7.52 (m, 3H), 6.97 (t, 2H), 6.81 (d, 1H), 5.11 (d, 2H), 4.35 (t, 2H), 2.34 (s, 3H), 2.14 (s, 3H), 1.66-1.60 (m, 1H), 0.82 (t, 3H); (Yield: 29%)

EXAMPLE 229

7-(4-chlorobenzylamino)-2,3-dimethyl-1-propyl-1H-pyrrolo[2,3-c]pyridine hydrochloride 1H-NMR(400 MHz, CDCl$_3$) δ 7.59 (brs, 1H), 7.48 (brs, 2H), 7.26 (brs, 2H), 6.84 (brs, 1H), 6.67 (brs, 1H), 5.12 (brs, 2H), 4.31 (brs, 2H), 2.35 (s, 3H), 2.15 (s, 3H), 1.66 (brs, 2H), 0.84 (brs, 3H); (Yield: 15%)

EXAMPLE 230

2,3-dimethyl-7-(2-methylbenzylamino)-1-propyl-1H-pyrrolo[2,3-c]pyridine hydrochloride 1H-NMR(400 MHz, CDCl$_3$) δ 7.77 (t, 1H), 7.36 (d, 1H), 7.29-7.19 (m, 3H), 6.95 (d, 1H), 5.48 (brs, 1H), 5.09 (d, 2H), 4.07 (t, 2H), 2.42 (s, 3H), 2.36 (s, 3H), 2.19 (s, 3H), 1.65 (m, 1H), 0.73 (t, 3H); (Yield: 22%)

EXAMPLE 231

7-(2-chlorobenzylamino)-2,3-dimethyl-1-propyl-1H-pyrrolo[2,3-c]pyridine hydrochloride 1H-NMR(400 MHz, CDCl$_3$) δ 8.13 (m, 1H), 7.75 (t, 1H), 7.39 (m, 1H), 7.31-7.27 (m, 2H), 6.93 (d, 1H), 6.13 (brs, 1H), 5.33 (d, 2H), 4.17 (t, 2H), 2.36 (s, 3H), 2.17 (s, 3H), 1.73 (m, 2H), 0.88 (t, 3H); (Yield: 30%)

EXAMPLE 232

7-(3-fluorobenzylamino)-2,3-dimethyl-1-propyl-1H-pyrrolo[2,3-c]pyridine hydrochloride 1H-NMR(400 MHz, CDCl$_3$) δ 7.61 (t, 1H), 7.33 (t, 1H), 7.29 (d, 1H), 7.20 (d, 1H), 6.96 (t, 1H), 6.85 (d, 1H), 6.73 (brs, 1H), 5.15 (d, 2H), 4.33 (t, 2H), 2.36 (s, 3H), 2.15 (s, 3H), 1.67 (m, 2H), 0.85 (t, 3H); (Yield: 22%)

EXAMPLE 233

2,3-dimethyl-1-propyl-7-(4-trifluoromethoxybenzylamino)-1H-pyrrolo[2,3-c]pyridine hydrochloride 1H-NMR(400 MHz, CDCl$_3$) δ 7.59 (m, 3H), 7.13 (d, 2H), 6.84 (d, 2H), 5.19 (d, 2H), 4.33 (t, 2H), 2.35 (s, 3H), 2.14 (s, 3H), 1.62 (m, 2H), 0.82 (t, 3H); (Yield: 13%)

EXAMPLE 234

2,3-dimethyl-7-(3-methylbenzylamino)-1-propyl-1H-pyrrolo[2,3-c]pyridine hydrochloride 1H-NMR(400 MHz, CDCl$_3$) δ 7.70 (d, 1H), 7.28-7.22 (m, 3H), 7.13 (d, 1H), 6.88 (d, 1H), 6.09 (brs, 1H), 5.07 (d, 2H), 4.19 (t, 2H), 2.35 (s, 3H), 2.33 (s, 3H), 2.16 (s, 3H), 1.68 (m, 2H), 0.82 (t, 3H); (Yield: 53%)

EXAMPLE 235

2,3-dimethyl-1-propyl-7-(1,3-benzodioxol-5-ylmethylamino)-1H-pyrrolo[2,3-c]pyridine hydrochloride 1H-NMR(400 MHz, CDCl$_3$) δ 7.65 (t, 1H), 7.02 (d, 1H), 6.96 (s, 1H), 6.86 (d, 1H), 6.75 (d, 1H), 6.33 (brs, 1H), 5.92 (s, 2H), 5.02 (d, 2H), 4.25 (t, 2H), 2.35 (s, 3H), 2.15 (s, 3H), 1.68 (m, 2H), 0.84 (t, 3H); (Yield: 75%)

EXAMPLE 236

7-(3-chlorobenzylamino)-2,3-dimethyl-1-propyl-1H-pyrrolo[2,3-c]pyridine hydrochloride 1H-NMR(400 MHz, CDCl$_3$) δ 7.61 (d, 1H), 7.45 (m, 2H), 7.25 (m, 2H), 6.86 (d, 1H), 6.76 (brs, 1H), 5.13 (d, 2H), 4.33 (t, 2H), 2.36 (s, 3H), 2.16 (s, 3H), 1.65 (m, 2H), 0.87 (t, 3H); (Yield: 72%)

EXAMPLES 237 TO 241

The titled compounds of Examples 237 to 241 were prepared, in accordance with the same procedures as in Step 3 of Example 198, using 1-allyl-7-chloro-2,3-dimethyl-1H-pyrrolo[2,3-c]pyridine prepared in Step 1 of Example 206; and, 4-fluorobenzylamine, 4-chlorobenzylamine, 3-fluorobenzylamine, 4-trifluoromethoxybenzylamine, or 3-methylbenzylamine.

EXAMPLE 237

1-allyl-7-(4-fluorobenzylamino)-2,3-dimethyl-1H-pyrrolo[2,3-c]pyridine hydrochloride 1H-NMR(400 MHz, CDCl$_3$) δ 7.78 (t, 1H), 7.54-7.48 (m, 4H), 7.02 (d, 1H), 6.03 (m, 1H), 5.83 (brs, 1H), 5.26 (d, 1H), 5.05 (d, 2H), 4.88 (d, 2H), 4.73 (d, 1H), 2.33 (s, 3H), 2.30 (s, 3H); (Yield: 80%)

EXAMPLE 238

1-allyl-7-(4-chlorobenzylamino)-2,3-dimethyl-1H-pyrrolo[2,3-c]pyridine hydrochloride 1H-NMR(400 MHz, CDCl$_3$) δ 7.80 (t, 1H), 7.44-7.40 (m, 4H), 6.97 (d, 1H), 5.98 (m, 1H), 5.90 (brs, 1H), 5.33 (d, 1H), 5.05 (d, 2H), 4.84 (d, 2H), 4.73 (d, 1H), 2.35 (s, 3H), 2.33 (s, 3H); (Yield: 35%)

EXAMPLE 239

1-allyl-7-(3-fluorobenzylamino)-2,3-dimethyl-1H-pyrrolo[2,3-c]pyridine hydrochloride 1H-NMR(400 MHz, CDCl$_3$) δ 7.90 (t, 1H), 7.66-7.43 (m, 4H), 6.97 (d, 1H), 5.88 (m, 1H), 5.83 (brs, 1H), 5.21 (d, 1H), 5.05 (d, 2H), 4.84 (d, 2H), 4.73 (d, 1H), 2.33 (s, 3H), 2.25 (s, 3H); (Yield: 28%)

EXAMPLE 240

1-allyl-2,3-dimethyl-7-(4-trifluoromethoxybenzylamino)-1H-pyrrolo[2,3-c]pyridine hydrochloride 1H-NMR(400 MHz, CDCl$_3$) δ 8.01 (t, 1H), 7.66-7.43 (m, 4H), 6.90 (d, 1H), 5.88 (m, 1H), 5.73 (brs, 1H), 5.26 (d, 1H), 5.05 (d, 2H), 4.84 (d, 2H), 4.73 (d, 1H), 2.33 (s, 3H), 2.29 (s, 3H); (Yield: 83%)

EXAMPLE 241

1-allyl-2,3-dimethyl-7-(3-methylbenzylamino)-1H-pyrrolo[2,3-c]pyridine hydrochloride 1H-NMR(400 MHz, CDCl$_3$) δ 7.89 (t, 1H), 7.63-7.43 (m, 4H), 7.00 (d, 1H), 5.98 (m, 1H), 5.63 (brs, 1H), 5.33 (d, 1H), 5.05 (d, 2H), 4.84 (d, 2H), 4.73 (d, 1H), 2.35 (s, 3H), 2.33 (s, 3H), 2.19 (s, 3H); (Yield: 43%)

EXAMPLE 242

2,3-dimethyl-7-(4-vinylphenyl)-1H-pyrrolo[2,3-c]pyridine

A solution of 3-nitro-2-(4-vinylphenyl)pyridine (4.9 g, 21.6 mmol) prepared in Preparation 9 in anhydrous tetrahydrofuran (150 ml) was cooled to −78° C. and 1-methyl-1-propenyl magnesium bromide (0.5M in anhydrous tetrahydrofuran solution; 130 ml) was slowly added thereto. The reaction mixture was stirred for 1 hour at the same temperature, slowly warmed to room temperature, and then stirred overnight. 20% (w/v) ammonium chloride solution was added to the reaction mixture, which was then extracted with ethyl acetate. The reaction mixture was dried on anhydrous magnesium sulfate, filtered, and then concentrated under reduced pressure. The resulting residue was purified with silica gel column chromatography and then crystallized with ethyl ether to give 612 mg of the titled compound as a white solid.

1H-NMR(400 MHz, CDCl$_3$) δ 8.33 (d, 1H), 8.23 (brs, 1H), 7.86 (d, 2H), 7.58 (d, 2H), 7.36 (d, 1H), 6.80 (dd, 1H), 5.86 (d, 1H), 5.33 (d, 1H), 2.42 (s, 3H), 2.25 (s, 3H)

EXAMPLE 243

1-(3-fluorobenzyl)-2,3-dimethyl-7-(4-vinylphenyl)-1H-pyrrolo[2,3-c]pyridine hydrochloride 18-Crown-6 (2.5 mg, 0.0097 mmol) and potassium tert-butoxide (33 mg, 0.291 mmol) were added to a solution of 2,3-dimethyl-7-(4-vinylphenyl)-1H-pyrrolo[2,3-c]pyridine (24 mg, 0.097 mmol) prepared in Example 242 in anhydrous tetrahydrofuran (0.5 ml). The reaction mixture was stirred for 30 minutes at room temperature and 3-fluorobenzyl chloride (20 μl, 0.16 mmol) was added thereto. The reaction mixture was stirred overnight and then concentrated under reduced pressure. The resulting residue was purified with silica gel column chromatography. The resulting product was dissolved in ethyl acetate, saturated with hydrochloric acid gas, and then filtered to give 3.8 mg of the titled compound as a white solid.

1H-NMR(400 MHz, CDCl$_3$) δ 8.41 (d, 1H), 7.77 (d, 1H), 7.41 (d, 2H), 7.34 (d, 2H), 7.15 (m, 1H), 6.95 (m, 1H), 6.75 (dd, 1H), 6.15 (d, 1H), 6.15 (d, 1H), 5.86 (d, 1H), 5.40 (d, 1H), 5.11 (s, 2H), 2.43 (s, 3H), 2.41 (s, 3H)

EXAMPLES 244 TO 261

The titled compounds of Examples 244 to 261 were prepared, in accordance with the same procedures as in Example 243, using 2,3-dimethyl-7-(4-vinylphenyl)-1H-pyrrolo[2,3-c]pyridine prepared in Example 242; and, 4-methylbenzyl chloride, allyl bromide, benzyl bromide, 2-bromoethyl methyl ether, (bromomethyl)cyclopropane, propargyl bromide, 2,5-dimethylbenzyl chloride, iodoethane, 1-iodopropane, 3-methoxybenzyl chloride, 4-methoxybenzyl chloride, 3-methylbenzyl chloride, 1-chloro-3-methylbutane, 2-(bromomethyl)naphthalene, 4-fluorobenzyl chloride, 2-fluorobenzyl chloride, 4-tert-butylbenzyl chloride, or 4-bromo-2-methyl-2-butene.

EXAMPLE 244

2,3-dimethyl-1-(4-methylbenzyl)-7-(4-vinylphenyl)-1H-pyrrolo[2,3-c]pyridine hydrochloride 1H-NMR(400 MHz, CDCl$_3$) δ 8.41 (d, 1H), 7.74 (d, 1H), 7.39 (d, 2H), 6.97 (d, 2H), 6.73 (dd, 1H), 6.25 (d, 2H), 5.85 (d, 1H), 5.39 (d, 1H), 5.06 (s, 2H), 2.41 (s, 3H), 2.39 (s, 3H), 2.28 (s, 3H); (Yield: 52%)

EXAMPLE 245

1-allyl-2,3-dimethyl-7-(4-vinylphenyl)-1H-pyrrolo[2,3-c]pyridine hydrochloride

1H-NMR(400 MHz, CDCl$_3$) δ 8.37 (d, 1H), 7.72 (d, 1H), 7.58 (s, 4H), 6.78 (dd, 1H), 5.91 (d, 1H), 5.61 (m, 1H), 5.43 (d, 1H), 5.05 (d, 1H), 4.45 (s, 2H), 4.37 (d, 1H), 2.45 (s, 3H), 2.25 (s, 3H); (Yield: 68%)

EXAMPLE 246

1-benzyl-2,3-dimethyl-7-(4-vinylphenyl)-1H-pyrrolo[2,3-c]pyridine hydrochloride

1H-NMR(400 MHz, CDCl$_3$) δ 8.40 (d, 1H), 7.75 (d, 1H), 7.51 (m, 4H), 7.21 (m, 3H), 6.75 (dd, 1H), 6.36 (d, 2H), 5.84 (d, 1H), 5.39 (d, 1H), 5.11 (s, 2H), 2.42 (s, 3H), 2.41 (s, 3H); (Yield: 52%)

EXAMPLE 247

1-(2-methoxyethyl)-2,3-dimethyl-7-(4-vinylphenyl)-1H-pyrrolo[2,3-c]pyridine hydrochloride 1H-NMR(400 MHz, CDCl$_3$) δ 8.31 (d, 1H), 7.67 (d, 1H), 7.56 (s, 4H), 6.77 (dd, 1H), 5.89 (d, 1H), 5.42 (d, 1H), 4.08 (t, 2H), 3.03 (t, 2H), 3.00 (s, 3H), 2.51 (s, 3H), 2.35 (s, 3H); (Yield: 43%)

EXAMPLE 248

1-cyclopropylmethyl-2,3-dimethyl-7-(4-vinylphenyl)-1H-pyrrolo[2,3-c]pyridine hydrochloride 1H-NMR(400 MHz, CDCl$_3$) δ 8.41 (d, 1H), 7.65 (m, 1+4H), 6.80 (dd, 1H), 5.93 (d, 1H), 5.44 (d, 1H), 3.87 (d, 2H), 2.53 (s, 3H), 2.37 (s, 3H), 0.63 (m 1H), 0.26 (m, 2H), −0.17 (m, 2H); (Yield: 54%)

EXAMPLE 249

2,3-dimethyl-1-(prop-2-ynyl)-7-(4-vinylphenyl)-1H-pyrrolo[2,3-c]pyridine hydrochloride 1H-NMR(400 MHz, CDCl$_3$) δ 8.41 (d, 1H), 7.77 (d, 2H), 7.70 (d, 2H), 7.64 (d, 2H), 6.79 (dd, 1H), 5.93 (d, 1H), 5.44 (d, 1H), 4.53 (s, 2H), 2.59 (s, 3H), 2.36 (d, 1+3H); (Yield: 49%)

EXAMPLE 250

2,3-dimethyl-1-(2,5-dimethylbenzyl)-7-(4-vinylphenyl)-1H-pyrrolo[2,3-c]pyridine hydrochloride 1H-NMR(400 MHz, CDCl$_3$) δ 8.35 (d, 1H), 7.77 (d, 1H), 7.23 (d, 2H), 7.13 (d, 2H), 6.98 (dd, 2H), 6.70 (dd, 1H), 5.77 (d, 1H), 5.68 (s, 1H), 5.35 (d, 1H), 4.87 (s, 2H), 2.44 (s, 3H), 2.40 (s, 3H), 2.12 (s, 3H), 1.68 (s, 3H); (Yield: 69%)

EXAMPLE 251

1-ethyl-2,3-dimethyl-7-(4-vinylphenyl)-1H-pyrrolo[2,3-c]pyridine hydrochloride

1H-NMR(400 MHz, CDCl$_3$) δ 8.43 (d, 1H), 7.69 (d, 2H), 7.63 (s, 1+2H), 6.85 (dd, 1H), 5.96 (d, 1H), 5.43 (d, 1H), 3.92 (q, 2H), 2.49 (s, 3H), 2.35 (s, 3H), 0.91 (t, 3H); (Yield: 63%)

EXAMPLE 252

2,3-dimethyl-1-propyl-7-(4-vinylphenyl)-1H-pyrrolo[2,3-c]pyridine hydrochloride

1H-NMR(400 MHz, CDCl$_3$) δ 8.37 (d, 1H), 7.69 (d, 1H), 7.63 (s, 3+1H), 6.80 (dd, 1H), 5.92 (d, 1H), 5.43 (d, 1H), 3.78 (t, 2H), 2.48 (s, 3H), 2.34 (s, 3H), 1.26 (m, 2H), 0.45 (t, 3H); (Yield: 68%)

EXAMPLE 253

2,3-dimethyl-1-(3-methoxybenzyl)-7-(4-vinylphenyl)-1H-pyrrolo[2,3-c]pyridine hydrochloride 1H-NMR(400 MHz, CDCl$_3$) δ 8.35 (d, 1H), 7.74 (d, 1H), 7.34 (m, 4H), 7.06 (t, 1H), 6.74 (m, 1+1H), 5.90 (m, 2H), 5.82 (d, 1H), 5.38 (d, 1H), 5.07 (s, 2H), 3.68 (s, 3H), 2.43 (s, 3H), 2.40 (s, 3H); (Yield: 68%)

EXAMPLE 254

2,3-dimethyl-1-(4-methoxybenzyl)-7-(4-vinylphenyl)-1H-pyrrolo[2,3-c]pyridine hydrochloride 1H-NMR(400 MHz, CDCl$_3$) δ 8.34 (s, 1H), 7.74 (d, 1H), 7.39 (m, 4H), 6.87 (m, 1H), 6.68 (t, 3H), 6.27 (d, 1H), 5.84 (d, 1H), 5.38 (d, 1H), 5.05 (s, 2H), 3.74 (s, 3H), 2.42 (s, 3H), 2.39 (s, 3H); (Yield: 68%)

EXAMPLE 255

2,3-dimethyl-1-(3-methylbenzyl)-7-(4-vinylphenyl)-1H-pyrrolo[2,3-c]pyridine hydrochloride 1H-NMR(400 MHz, CDCl$_3$) δ 8.40 (d, 1H), 7.75 (d, 1H), 7.40 (d, 2H), 7.34 (d, 2H), 7.02 (m, 2H), 6.76 (dd, 1H), 6.14 (s, 1H), 6.09 (d, 1H), 5.85 (d, 1H), 5.39 (d, 1H), 5.08 (s, 2H), 2.43 (s, 3H), 2.41 (s, 3H), 2.18 (s, 3H); (Yield: 68%)

EXAMPLE 256

2,3-dimethyl-1-(3-methylbutyl)-7-(4-vinylphenyl)-1H-pyrrolo[2,3-c]pyridine hydrochloride 1H-NMR(400 MHz, CDCl$_3$) δ 8.26 (d, 1H), 7.94 (d, 1H), 7.69 (m, 1H), 7.58 (dd, 2H), 7.34 (m, 1H), 6.73 (dd, 1H), 5.85

(d, 1H), 5.40 (d, 1H), 3.86 (m, 2H), 2.47 (s, 3H), 2.27 (s, 3H), 1.06 (m, 2H), 0.58 (s, 3H), 0.56 (s, 3H); (Yield: 67%)

EXAMPLE 257

2,3-dimethyl-1-(naphthalen-2-ylmethyl)-7-(4-vinylphenyl)-1H-pyrrolo[2,3-c]pyridine hydrochloride 1H-NMR(400 MHz, CDCl$_3$) δ 8.38 (d, 1H), 7.78 (t, H), 7.66 (d, 1H), 7.56 (d, 2H), 7.48 (m, 2H), 7.28 (s, 3H), 6.71 (s, 1H), 6.69 (dd, 1H), 6.54 (d, 1H), 5.79 (d, 1H), 5.37 (d, 1H), 5.25 (s, 2H), 2.45 (s, 3H), 2.43 (s, 3H); (Yield: 55%)

EXAMPLE 258

2,3-dimethyl-1-(4-fluorobenzyl)-7-(4-vinylphenyl)-1H-pyrrolo[2,3-c]pyridine hydrochloride 1H-NMR(400 MHz, CDCl$_3$) δ 8.41 (d, 1H), 7.75 (d, 1H), 7.42 (d, 2H), 7.36 (d, 2H), 6.87 (t, 2H), 6.73 (dd, 1H), 6.33 (m, 2H), 5.86 (d, 1H), 5.40 (d, 1H), 5.09 (s, 2H), 2.42 (s, 3H), 2.40 (s, 3H); (Yield: 75%)

EXAMPLE 259

2,3-dimethyl-1-(2-fluorobenzyl)-7-(4-vinylphenyl)-1H-pyrrolo[2,3-c]pyridine hydrochloride 1H-NMR(400 MHz, CDCl$_3$) δ 8.42 (d, 1H), 7.76 (d, 1H), 7.38 (d, 2H), 7.32 (d, 2H), 7.15 (m, 1H), 6.94 (m, 2H), 6.77 (dd, 1H), 6.03 (t, 1H), 5.83 (d, 1H), 5.39 (d, 1H), 5.12 (s, 2H), 2.42 (s, 3H), 2.41 (s, 3H); (Yield: 70%)

EXAMPLE 260

1-(4-tert-butylbenzyl)-2,3-dimethyl-7-(4-vinylphenyl)-1H-pyrrolo[2,3-c]pyridine hydrochloride 1H-NMR(400 MHz, CDCl$_3$) δ 8.39 (d, 1H), 7.74 (d, 1H), 7.36 (dd, 4H), 7.14 (d, 2H), 6.76 (dd, 1H), 6.24 (d, 1H), 5.74 (d, 1H), 5.39 (d, 1H), 5.09 (s, 2H), 2.44 (s, 3H), 2.40 (s, 3H), 1.25 (s, 9H); (Yield: 76%)

EXAMPLE 261

2,3-dimethyl-1-(3-methylbut-2-enyl)-7-(4-vinylphenyl)-1H-pyrrolo[2,3-c]pyridine hydrochloride 1H-NMR(400 MHz, CDCl$_3$) δ 8.29 (d, 1H), 7.68 (d, 1H), 7.59 (m, 4H), 6.74 (dd, 1H), 5.87 (d, 1H), 5.40 (d, 1H), 4.65 (s, 1H), 4.46 (s, 2H), 2.46 (s, 3H), 2.27 (s, 3H), 1.26 (s, 3+3H); (Yield: 68%)

EXAMPLE 262

2,3-dimethyl-7-(4-methylsulfanylphenyl)-1H-pyrrolo[2,3-c]pyridine

In accordance with the same procedures as in Example 242, except for using 3-nitro-2-(4-methylthiophenyl)pyridine prepared in Preparation 10, the titled compound was obtained as a white solid. (Yield: 35%)
1H-NMR(400 MHz, CDCl$_3$) δ 8.31 (d, 1H), 8.17 (brs, 1H), 7.82 (d, 2H), 7.41 (d, 2H), 7.35 (d, 1H), 2.54 (s, 3H), 2.41 (s, 3H), 2.24 (s, 3H)

EXAMPLES 263 TO 275

The titled compounds of Examples 263 to 275 were prepared, in accordance with the same procedures as in Example 243, using 2,3-dimethyl-7-(4-methylsulfanylphenyl)-1H-pyrrolo[2,3-c]pyridine prepared in Example 262; and, allyl bromide, 2-bromoethyl methyl ether, iodoethane, 3-methoxybenzyl chloride, 4-methylbenzyl chloride, benzyl bromide, 4-bromo-2-methyl-2-butene, (bromomethyl)cyclopropane, 4-chlorobenzyl chloride, 3-fluorobenzyl chloride, 3-methylbenzyl chloride, 4-fluorobenzyl chloride, or 2-fluorobenzyl chloride.

EXAMPLE 263

1-allyl-2,3-dimethyl-7-(4-methylsulfanylphenyl)-1H-pyrrolo[2,3-c]pyridine hydrochloride 1H-NMR(400 MHz, CDCl$_3$) δ 8.35 (d, 1H), 7.66 (d, 1H), 7.53 (d, 2H), 7.36 (d, 2H), 5.54 (m, 1H), 5.07 (d, 1H), 4.46 (d, 2H), 4.38 (d, 1H), 2.54 (s, 3H), 2.42 (s, 3H), 2.35 (s, 3H); (Yield: 57%)

EXAMPLE 264

1-(2-methoxyethyl)-2,3-dimethyl-7-(4-methylsulfanylphenyl)-1H-pyrrolo[2,3-c]pyridine hydrochloride 1H-NMR(400 MHz, CDCl$_3$) δ 8.35 (d, 1H), 7.65 (d, 1H), 7.55 (d, 2H), 7.40 (d, 2H), 4.11 (t, 2H), 3.05 (t, 2H), 3.01 (s, 3H), 2.55 (s, 3H), 2.47 (s, 3H), 2.34 (s, 3H); (Yield: 53%)

EXAMPLE 265

1-ethyl-2,3-dimethyl-7-(4-methylsulfanylphenyl)-1H-pyrrolo[2,3-c]pyridine hydrochloride 1H-NMR(400 MHz, CDCl$_3$) δ 8.35 (d, 1H), 7.65 (d, 1H), 7.58 (d, 2H), 7.42 (d, 2H), 3.92 (q, 2H), 2.56 (s, 3H), 2.48 (s, 3H), 2.33 (s, 3H), 0.91 (t, 3H); (Yield: 56%)

EXAMPLE 266

1-(3-methoxybenzyl)-2,3-dimethyl-7-(4-methylsulfanylphenyl)-1H-pyrrolo[2,3-c]pyridine hydrochloride 1H-NMR(400 MHz, CDCl$_3$) δ 8.37 (d, 1H), 7.70 (d, 1H), 7.28 (d, 2H), 7.18 (d, 2H), 7.07 (t, 1H), 6.74 (d, 1H), 5.94 (d, 1H), 5.92 (s, 1H), 5.07 (s, 2H), 3.69 (s,3H), 2.49 (s, 3H), 2.40 (s, 3H), 2.38 (s, 3H); (Yield: 48%)

EXAMPLE 267

2,3-dimethyl-1-(4-methylbenzyl)-7-(4-methylsulfanylphenyl)-1H-pyrrolo[2,3-c]pyridine hydrochloride 1H-NMR(400 MHz, CDCl$_3$) δ 8.41 (d, 1H), 7.72 (d, 1H), 7.32 (d, 2H), 7.20 (m, 2H), 6.97 (d, 2H), 6.28 (d, 2H), 5.07 (s, 2H), 2.50 (s, 3H), 2.40 (s, 3H), 2.38 (s, 3H), 2.28 (s, 3H); (Yield: 62%)

EXAMPLE 268

1-benzyl-2,3-dimethyl-7-(4-methylsulfanylphenyl)-1H-pyrrolo[2,3-c]pyridine hydrochloride 1H-NMR(400 MHz, CDCl$_3$) δ 8.35 (d, 1H), 7.69 (d, 1H), 7.24 (d, 2H), 7.15 (m, 5H), 6.38 (d, 2H), 5.10 (s, 2H), 2.49 (s, 3H), 2.39 (s, 3+3H); (Yield: 82%)

EXAMPLE 269

2,3-dimethyl-1-(3-methylbut-2-enyl)-7-(4-methylsulfanylphenyl)-1H-pyrrolo[2,3-c]pyridine hydrochloride 1H-NMR(400 MHz, CDCl$_3$) δ 8.30 (d, 1H), 7.65 (d, 1H), 7.55 (d, 2H), 7.34 (d, 2H), 4.65 (t, 1H), 4.47 (d, 2H), 2.50 (s, 3H), 2.45 (s, 3H), 2.30 (s, 3H), 1.55 (s, 3H), 1.29 (s, 3H); (Yield: 80%)

EXAMPLE 270

1-cyclopropylmethyl-2,3-dimethyl-7-(4-methylsulfanylphenyl)-1H-pyrrolo[2,3-c]pyridine hydrochloride 1H-NMR(400 MHz, CDCl$_3$) δ 8.34 (d, 1H), 7.56 (d, 2+1H), 7.40 (d, 2H), 3.83 (d, 2H), 2.55 (s, 3H), 2.46 (s, 3H), 2.32 (s, 3H), 0.61 (m, 1H), 0.24 (m, 2H), −0.16 (m, 2H); (Yield: 88%)

EXAMPLE 271

1-(4-chlorobenzyl)-2,3-dimethyl-7-(4-methylsulfanylphenyl)-1H-pyrrolo[2,3-c]pyridine hydrochloride 1H-NMR(400 MHz, CDCl$_3$) δ 8.37 (d, 1H), 7.67 (d, 2H), 7.28 (d, 2H), 7.19 (d, 2H), 7.12 (d, 2H), 6.33 (d, 2H), 5.07 (s, 2H), 2.50 (s, 3H), 2.38 (s, 3+3H); (Yield: 68%)

EXAMPLE 272

2,3-dimethyl-1-(3-fluorobenzyl)-7-(4-methylsulfanylphenyl)-1H-pyrrolo[2,3-c]pyridine hydrochloride 1H-NMR(400 MHz, CDCl$_3$) δ 8.36 (d, 1H), 7.70 (d, 1H), 7.24 (d, 3H), 7.14 (m, 2H), 6.90 (t, 1H), 6.15 (d, 1H), 6.09 (d, 1H), 5.09 (s, 2H), 2.49 (s, 3H), 2.40 (s, 3H), 2.39 (s, 3H); (Yield: 60%)

EXAMPLE 273

2,3-dimethyl-1-(3-methylbenzyl)-7-(4-methylsulfanylphenyl)-1H-pyrrolo[2,3-c]pyridine hydrochloride 1H-NMR(400 MHz, CDCl$_3$) δ 8.34 (d, 1H), 7.66 (d, 1H), 7.27 (d, 2H), 7.17 (d, 2H), 7.00 (m, 2H), 6.20 (s, 1H), 6.12 (d, 1H), 5.06 (s, 2H), 2.49 (s, 3H), 2.39 (s, 3H), 2.38 (s, 3H), 2.20 (s, 3H); (Yield: 90%)

EXAMPLE 274

2,3-dimethyl-1-(4-fluorobenzyl)-7-(4-methylsulfanylphenyl)-1H-pyrrolo[2,3-c]pyridine hydrochloride 1H-NMR(400 MHz, CDCl$_3$) δ 8.33 (d, 1H), 7.61 (d, 1H), 7.25 (d, 2H), 7.18 (d, 2H), 6.84 (t, 2H), 6.36 (m, 2H), 5.05 (s, 2H), 2.49 (s, 3H), 2.36 (s, 3H), 2.35 (s, 3H); (Yield: 95%)

EXAMPLE 275

2,3-dimethyl-1-(2-fluorobenzyl)-7-(4-methylsulfanylphenyl)-1H-pyrrolo[2,3-c]pyridine hydrochloride 1H-NMR(400 MHz, CDCl$_3$) δ 8.36 (d, 1H), 7.65 (d, 1H), 7.22 (d, 3H), 7.16 (d, 2H), 6.92 (m, 2H), 6.06 (t, 1H), 5.09 (s, 2H), 2.49 (s, 3H), 2.37 (s, 3H), 2.36 (s, 3H); (Yield: 95%)

EXAMPLE 276

2,3-dimethyl-7-(p-tolyl)-1H-pyrrolo[2,3-c]pyridine

In accordance with the same procedures as in Example 242, except for using 3-nitro-2-(4-methylphenyl)pyridine prepared in Preparation 11, the titled compound was obtained as a white solid. (Yield: 42%)

1H-NMR(400 MHz, CDCl$_3$) δ 8.31 (d, 1H), 8.22 (brs, 1H), 7.78 (d, 2H), 7.34 (d, 2+1H), 2.43 (s, 3H), 2.40 (s, 3H), 2.24 (s 3H)

EXAMPLES 277 TO 298

The titled compounds of Examples 277 to 298 were prepared, in accordance with the same procedures as in Example 243, using 2,3-dimethyl-7-(p-tolyl)-1H-pyrrolo[2,3-c]pyridine prepared in Example 276; and, allyl bromide, 3-methoxybenzyl chloride, 4-methylbenzyl chloride, propargyl bromide, benzyl bromide, 2-bromoethyl methyl ether, 4-chlorobenzyl chloride, 3-fluorobenzyl chloride, 1-iodo-2-methylpropane, 1-iodopropane, 4-methoxybenzyl chloride, 4-fluorobenzyl chloride, (bromomethyl)cyclobutane, 2-fluorobenzyl chloride, 4-bromo-2-methyl-2-butene, 1-bromo-3-methylbutane, (bromomethyl)cyclopropane, 2,5-dimethylbenzyl bromide, 2-chlorobenzyl bromide, 3,4-dichlorobenzyl bromide, iodoethane, or 3-methylbenzyl bromide.

EXAMPLE 277

1-allyl-2,3-dimethyl-7-(p-tolyl)-1H-pyrrolo[2,3-c]pyridine hydrochloride

1H-NMR(400 MHz, CDCl$_3$) δ 8.36 (t, 1H), 7.70 (d, 1H), 7.51 (d, 2H), 7.36 (d, 2H), 5.53 (m, 1H), 5.07 (d, 1H), 4.43 (s, 2H), 4.37 (d, 1H), 2.45 (s, 3H), 2.44 (s, 3H), 2.36 (s, 3H); (Yield: 51%)

EXAMPLE 278

1-(3-methoxybenzyl)-2,3-dimethyl-7-(p-tolyl)-1H-pyrrolo[2,3-c]pyridine hydrochloride 1H-NMR(400 MHz, CDCl$_3$) δ 8.38 (t, 1H), 7.73 (d, 1H), 7.28 (d, 2H), 7.18 (d, 2H), 7.08 (t, 1H), 6.72 (d, 1H), 5.91 (m, 2H), 5.06 (s, 2H), 3.69 (s, 3H), 2.41 (s, 3H), 2.39 (s, 3+3H); (Yield: 65%)

EXAMPLE 279

2,3-dimethyl-1-(4-methylbenzyl)-7-(p-tolyl)-1H-pyrrolo[2,3-c]pyridine hydrochloride 1H-NMR(400 MHz, CDCl$_3$) δ 8.40 (t, 1H), 7.72 (d, 1H), 7.31 (d, 2H), 7.19 (d, 2H), 6.97 (d, 2H), 6.27 (d, 2H), 5.05 (s, 2H), 2.39 (s, 3+3+3H), 2.19 (s, 3H); (Yield: 42%)

EXAMPLE 280

2,3-dimethyl-1-(prop-2-ynyl)-7-(p-tolyl)-1H-pyrrolo[2,3-c]pyridine hydrochloride 1H-NMR(400 MHz, CDCl$_3$) δ 8.40 (brs, 1H), 7.69 (brs, 3H), 7.42 (brs, 2H), 4.52 (s, 2H), 2.60 (s, 3H), 2.48 (s, 3H), 2.36 (s, 3+1H); (Yield: 67%)

EXAMPLE 281

1-benzyl-2,3-dimethyl-7-(p-tolyl)-1H-pyrrolo[2,3-c]pyridine hydrochloride

1H-NMR(400 MHz, CDCl$_3$) δ 8.38 (t, 1H), 7.73 (d, 1H), 7.27 (m, 2H), 7.18 (m, 5H), 6.37 (d, 2H), 5.10 (s, 2H), 2.40 (s, 3+3H), 2.39 (s, 3H); (Yield: 62%)

EXAMPLE 282

2,3-dimethyl-1-(2-methoxyethyl)-7-(p-tolyl)-1H-pyrrolo[2,3-c]pyridine hydrochloride 1H-NMR(400 MHz, CDCl$_3$) δ 8.34 (t, 1H), 7.67 (d, 1H), 7.52 (d, 2H), 7.38 (d, 2H), 4.08 (t, 2H), 3.04 (t, 2H), 3.02 (s, 3H), 2.48 (s, 3H), 2.45 (s, 3H), 2.34 (s, 3H); (Yield: 72%)

EXAMPLE 283

1-(4-chlorobenzyl)-2,3-dimethyl-7-(p-tolyl)-1H-pyrrolo[2,3-c]pyridine hydrochloride 1H-NMR(400 MHz, CDCl$_3$) δ 8.40 (s, 1H), 7.75 (s, 1H), 7.30 (m, 1H), 7.15 (m, 4H), 6.89 (d, 1H), 6.32 (d, 2H), 5.07 (s, 2H), 2.40 (s, 3+3+3H); (Yield: 79%)

EXAMPLE 284

2,3-dimethyl-1-(3-fluorobenzyl)-7-(p-tolyl)-1H-pyrrolo[2,3-c]pyridine hydrochloride 1H-NMR(400 MHz, CDCl$_3$) δ 8.40 (t, 1H), 7.76 (d, 1H), 7.25 (d, 2H), 7.20 (d, 2H), 7.13 (m, 1H), 6.91 (t, 1H), 6.10 (dd, 2H), 5.10 (s, 2H), 2.42 (s, 3+3+3H); (Yield: 49%)

EXAMPLE 285

1-isobutyl-2,3-dimethyl-7-(p-tolyl)-1H-pyrrolo[2,3-c]pyridine hydrochloride

1H-NMR(400 MHz, CDCl$_3$) δ 8.36 (brs, 1H), 7.67 (d, 1H), 7.53 (brs, 2H), 7.40 (d, 2H), 3.76 (d, 2H), 2.49 (s, 3H), 2.45 (s, 3H), 2.35 (s, 3H), 1.25 (m, 1H), 0.39 (s, 3H), 0.37 (s, 3H); (Yield: 40%)

EXAMPLE 286

2,3-dimethyl-1-propyl-7-(p-tolyl)-1H-pyrrolo[2,3-c]pyridine hydrochloride

1H-NMR(400 MHz, CDCl$_3$) δ 8.35 (t, 1H), 7.67 (d, 1H), 7.53 (d, 2H), 7.39 (d, 2H), 3.76 (t, 2H), 2.48 (s, 3H), 2.46 (s, 3H), 2.34 (s, 3H), 1.27 (q, 2H), 0.45 (t, 3H); (Yield: 40%)

EXAMPLE 287

2,3-dimethyl-1-(4-methoxybenzyl)-7-(p-tolyl)-1H-pyrrolo[2,3-c]pyridine hydrochloride 1H-NMR(400 MHz, CDCl$_3$) δ 8.38 (brs, 1H), 7.31 (brs, 2H), 7.19 (brs, 2H), 6.72 (t, 1H), 6.38 (d, 1H), 6.28 (d, 1H), 5.68 (d, 2H), 3.68 (s, 3H), 2.40 (s, 3+3+3H); (Yield: 80%)

EXAMPLE 288

2,3-dimethyl-1-(4-fluorobenzyl)-7-(p-tolyl)-1H-pyrrolo[2,3-c]pyridine hydrochloride 1H-NMR(400 MHz, CDCl$_3$) δ 8.40 (t, 1H), 7.74 (d, 2H), 7.27 (d, 2H), 7.21 (d, 2H), 6.88 (t, 2H), 6.33 (m, 2H), 5.08 (s, 2H), 2.41 (s, 3+3+3H); (Yield: 85%)

EXAMPLE 289

1-cyclobutylmethyl-2,3-dimethyl-7-(p-tolyl)-1H-pyrrolo[2,3-c]pyridine hydrochloride 1H-NMR(400 MHz, CDCl$_3$) δ 8.35 (t, 1H), 7.66 (d, 1H), 7.56 (d, 2H), 7.40 (d, 2H), 3.96 (d, 2H), 2.45 (s, 3H), 2.39 (s, 3H), 2.31 (s, 3H), 2.09 (m, 1H), 1.56 (m, 4H), 1.30 (m, 2H); (Yield: 75%)

EXAMPLE 290

2,3-dimethyl-1-(2-fluorobenzyl)-7-(p-tolyl)-1H-pyrrolo[2,3-c]pyridine hydrochloride 1H-NMR(400 MHz, CDCl$_3$) δ 8.40 (t, 1H), 7.75 (d, 1H), 7.23 (d, 3H), 7.16 (d, 2H), 6.95 (t, 2H), 6.04 (t, 1H), 5.10 (s, 2H), 2.41 (s, 3+3+3H); (Yield: 77%)

EXAMPLE 291

2,3-dimethyl-1-(3-methylbut-2-enyl)-7-(p-tolyl)-1H-pyrrolo[2,3-c]pyridine hydrochloride 1H-NMR(400 MHz, CDCl$_3$) δ 8.32 (t, 1H), 7.66 (d, 1H), 7.53 (m, 2H), 7.35 (m, 2H), 4.66 (t, 1H), 4.46 (d, 2H), 2.45 (s, 3H), 2.44 (s, 3H), 2.34 (s, 3H), 1.47 (s, 3H), 1.22 (s, 3H); (Yield: 74%)

EXAMPLE 292

2,3-dimethyl-1-(3-methylbutyl)-7-(p-tolyl)-1H-pyrrolo[2,3-c]pyridine hydrochloride 1H-NMR(400 MHz, CDCl$_3$) δ 8.35 (t, 1H), 7.66 (d, 1H), 7.56 (d, 2H), 7.40 (d, 2H), 3.86 (m, 2H), 2.47 (s, 3H), 2.45 (s, 3H), 2.33 (s, 3H), 1.08 (m, 2+1H), 0.60 (s, 3H), 0.59 (s, 3H); (Yield: 74%)

EXAMPLE 293

1-cyclopropylmethyl-2,3-dimethyl-7-(p-tolyl)-1H-pyrrolo[2,3-c]pyridine hydrochloride 1H-NMR(400 MHz, CDCl$_3$) δ 8.39 (t, 1H), 7.68 (d, 1H), 7.58 (d, 2H), 7.41 (d, 2H), 3.86 (d, 2H), 2.53 (s, 3H), 2.47 (s, 3H), 2.36 (s, 3H), 1.57 (m, 1H), 0.28 (d, 2H), −0.18 (d, 2H); (Yield: 72%)

EXAMPLE 294

1-(2,5-dimethylbenzyl)-2,3-dimethyl-7-(p-tolyl)-1H-pyrrolo[2,3-c]pyridine hydrochloride 1H-NMR(400 MHz, CDCl$_3$) δ 8.39 (t, 1H), 7.76 (d, 1H), 7.12 (d, 2H), 7.06 (d, 2H), 6.96 (s, 2H), 5.67 (s, 1H), 4.87 (s, 2H), 2.44 (s, 3H), 2.39 (s, 3H), 2.36 (s, 3H), 2.12 (s, 3H), 1.71 (s, 3H); (Yield: 68%)

EXAMPLE 295

1-(2-chlorobenzyl)-2,3-dimethyl-7-(p-tolyl)-1H-pyrrolo[2,3-c]pyridine hydrochloride 1H-NMR(400 MHz, CDCl$_3$) δ 8.39 (t, 1H), 7.77 (d, 1H), 7.29 (m, 2H), 7.23 (t, 1H), 7.09 (m, 4H), 5.92 (d, 1H), 5.04 (s, 2H), 2.42 (s, 3H), 2.39 (s, 3H), 2.38 (s, 3H); (Yield: 71%)

EXAMPLE 296

1-(3,4-dichlorobenzyl)-2,3-dimethyl-7-(p-tolyl)-1H-pyrrolo[2,3-c]pyridine hydrochloride 1H-NMR(400 MHz, CDCl$_3$) δ 8.40 (t, 1H), 7.75 (d, 1H), 7.26 (m, 5H), 6.42 (s, 1H), 6.10 (d, 1H), 5.07 (s, 2H), 2.44 (s, 3+3H), 2.41 (s, 3H); (Yield: 67%)

EXAMPLE 297

1-ethyl-2,3-dimethyl-7-(p-tolyl)-1H-pyrrolo[2,3-c]pyridine hydrochloride

1H-NMR(400 MHz, CDCl$_3$) δ 8.40 (t, 1H), 7.76 (d, 1H), 7.25 (d, 2H), 7.20 (d, 2H), 7.13 (m, 1H), 6.91 (t, 1H), 6.10 (dd, 2H), 5.10 (s, 2H), 2.42 (s, 3+3+3H), 1.54 (t, 3H); (Yield: 81%)

EXAMPLE 298

2,3-dimethyl-1-(3-methylbenzyl)-7-(p-tolyl)-1H-pyrrolo[2,3-c]pyridine hydrochloride 1H-NMR(400 MHz, CDCl$_3$) δ 8.39 (brs, 1H), 7.30 (brs, 1H), 7.28 (brs, 2H), 7.18 (d, 2H), 7.03 (brs, 2H), 6.12 (m, 2H), 5.07 (s, 2H), 2.40 (s, 3+3+3H), 2.19 (s, 3H); (Yield: 75%)

EXAMPLE 299

7-(4-chlorophenyl)-2,3-dimethyl-1H-pyrrolo[2,3-c]pyridine hydrochloride

In accordance with the same procedures as in Example 242, using 3-nitro-2-(4-chlorophenyl)pyridine prepared in Preparation 12, 7-(4-chlorophenyl)-2,3-dimethyl-1H-pyrrolo[2,3-c]pyridine was obtained. The product was dissolved in ethyl acetate, saturated with hydrochloric acid gas, and then filtered to give the titled compound as a white solid. (Yield: 36%)

1H-NMR(400 MHz, CDCl$_3$) δ 8.09 (s, 1H), 7.47 (t, 2H), 7.05 (m, 3H), 5.46 (s, 2H), 2.33 (s, 3H), 2.13 (s, 3H)

EXAMPLES 300 TO 324

The titled compounds of Examples 300 to 324 were prepared, in accordance with the same procedures as in Example 243, using 7-(4-chlorophenyl)-2,3-dimethyl-1H-pyrrolo[2,3-c]pyridine obtained by treating the compound prepared in Example 299 with a saturated sodium carbonate solution; and, allyl bromide, benzyl bromide, 2-bromoethyl methyl ether, 3-fluorobenzyl chloride, 1-iodo-2-methylpropane, 4-methylbenzyl chloride, 3-methoxybenzyl chloride, 4-methoxybenzyl chloride, propargyl bromide, bromomethyl methyl ether, 4-bromo-2-methyl-2-butene, 1-bromo-3-methylbutane, (bromomethyl)cyclopropane, 2-(bromomethyl)naphthalene, 4-tert-butylbenzyl bromide, 4-chlorobenzyl chloride, epibromohydrin, 2,5-dimethylbenzyl bromide, iodoethane, 1-bromopropane, 3-methylbenzyl bromide, α-bromo-m-tolunitrile, 4-fluorobenzyl bromide, 3-chlorobenzyl chloride, or (bromomethyl)cyclobutane.

EXAMPLE 300

1-allyl-7-(4-chlorophenyl)-2,3-dimethyl-1H-pyrrolo[2,3-c]pyridine hydrochloride

1H-NMR(400 MHz, CDCl$_3$) δ 8.34 (brs, 1H), 7.56 (brs, 2H), 7.26 (brs, 3H), 5.60 (brs, 1H), 5.30 (brs, 1H), 4.41 (brs, 1+2H), 2.44 (d, 3+3H); (Yield: 48%)

EXAMPLE 301

1-benzyl-7-(4-chlorophenyl)-2,3-dimethyl-1H-pyrrolo[2,3-c]pyridine hydrochloride 1H-NMR(400 MHz, CDCl$_3$) δ 8.39 (s, 1H), 7.79 (d, 1H), 7.29 (m, 5H), 7.20 (m, 2H), 6.35 (d, 2H), 5.09 (s, 2H), 2.44 (s, 3H), 2.42 (s, 3H); (Yield: 62%)

EXAMPLE 302

7-(4-chlorophenyl)-1-(2-methoxyethyl)-2,3-dimethyl-1H-pyrrolo[2,3-c]pyridine hydrochloride 1H-NMR(400 MHz, CDCl$_3$) δ 8.31 (s, 1H), 7.72 (s, 1H), 7.58 (brs, 4H), 4.01 (s, 2H), 3.08 (s, 2H), 3.04 (s, 3H), 2.53 (s, 3H), 2.36 (s, 3H); (Yield: 43%)

EXAMPLE 303

7-(4-chlorophenyl)-1-(3-fluorobenzyl)-2,3-dimethyl-1H-pyrrolo[2,3-c]pyridine hydrochloride 1H-NMR(400 MHz, CDCl$_3$) δ 8.38 (t, 1H), 7.80 (d, 1H), 7.36 (d, 2H), 7.28 (d, 2H), 7.18 (q, 1H), 6.94 (t, 1H), 6.14 (d, 1H), 6.06 (d, 1H), 5.08 (s, 2H), 2.44 (s, 3H), 2.42 (s, 3H); (Yield: 52%)

EXAMPLE 304

7-(4-chlorophenyl)-1-isobutyl-2,3-dimethyl-1H-pyrrolo[2,3-c]pyridine hydrochloride 1H-NMR(400 MHz, CDCl$_3$) δ 8.32 (d, 1H), 7.71 (d, 1H), 7.59 (m, 4H), 3.73 (d, 2H), 2.51 (s, 3H), 2.36 (s, 3H), 1.38 (m, 1H), 0.43 (s, 3H), 0.41 (s, 3H); (Yield: 59%)

EXAMPLE 305

7-(4-chlorophenyl)-2,3-dimethyl-1-(4-methylbenzyl)-1H-pyrrolo[2,3-c]pyridine hydrochloride 1H-NMR(400 MHz, CDCl$_3$) δ 8.35 (t, 1H), 7.78 (d, 1H), 7.34 (m, 4H), 6.99 (d, 2H), 6.24 (d, 2H), 5.03 (s, 2H), 2.42 (s, 3H), 2.41 (s, 3H), 2.31 (s, 3H); (Yield: 56%)

EXAMPLE 306

7-(4-chlorophenyl)-2,3-dimethyl-1-(3-methoxybenzyl)-1H-pyrrolo[2,3-c]pyridine hydrochloride 1H-NMR(400 MHz, CDCl$_3$) δ 8.35 (t, 1H), 7.78 (d, 1H), 7.34 (m, 4H), 7.10 (t, 1H), 6.79 (d, 1H), 5.91 (d, 2H), 5.04 (s, 2H), 3.70 (s, 3H), 2.44 (s, 3H), 2.41 (s, 3H); (Yield: 76%)

EXAMPLE 307

7-(4-chlorophenyl)-2,3-dimethyl-1-(4-methoxybenzyl)-1H-pyrrolo[2,3-c]pyridine hydrochloride 1H-NMR(400 MHz, CDCl$_3$) δ 8.38 (t, 1H), 7.78 (d, 1H), 7.37 (m, 4H), 6.71 (d, 1H), 6.27 (d, 1H), 5.02 (s, 2H), 3.75 (s, 3H), 2.43 (s, 3H), 2.40 (s, 3H); (Yield: 76%)

EXAMPLE 308

7-(4-chlorophenyl)-2,3-dimethyl-1-(prop-2-ynyl)-1H-pyrrolo[2,3-c]pyridine hydrochloride 1H-NMR(400 MHz, CDCl$_3$) δ 8.41 (d, 1H), 7.73 (d, 1H), 7.70 (d, 2H), 7.57 (d, 2H), 6.39 (t, 1H), 5.08 (d, 2H), 2.52 (s, 3H), 2.37 (s, 3H); (Yield: 36%)

EXAMPLE 309

7-(4-chlorophenyl)-1-methoxymethyl-2,3-dimethyl-1H-pyrrolo[2,3-c]pyridine hydrochloride 1H-NMR(400 MHz, CDCl$_3$) δ 8.32 (s, 1H), 7.70 (m, 4H), 7.26 (s, 1H), 4.97 (brs, 2H), 3.42 (s, 3H), 2.51 (s, 3H), 2.37 (s, 3H); (Yield: 39%)

EXAMPLE 310

7-(4-chlorophenyl)-2,3-dimethyl-1-(3-methylbut-2-enyl)-1H-pyrrolo[2,3-c]pyridine hydrochloride 1H-NMR(400 MHz, CDCl$_3$) δ 8.33 (s, 1H), 7.71 (d, 1H), 7.60 (d, 2H), 7.55 (d, 2H), 4.66 (s, 1H), 4.44 (s, 2H), 2.47 (s, 3H), 2.35 (s, 3H), 1.60 (s, 3+3H); (Yield: 45%)

EXAMPLE 311

7-(4-chlorophenyl)-2,3-dimethyl-1-(3-methylbutyl)-1H-pyrrolo[2,3-c]pyridine hydrochloride 1H-NMR(400 MHz, CDCl$_3$) δ 8.33 (t, 1H), 7.71 (d, 1H), 7.60 (m, 4H), 3.85 (m, 2H), 2.49 (s, 3H), 2.35 (s, 3H), 1.12 (m, 3H), 0.65 (s, 3H), 0.63 (s, 3H); (Yield: 42%)

EXAMPLE 312

7-(4-chlorophenyl)-1-cyclopropylmethyl-2,3-dimethyl-1H-pyrrolo[2,3-c]pyridine hydrochloride 1H-NMR(400 MHz, CDCl$_3$) δ 8.38 (t, 1H), 7.73 (d, 1H), 7.65 (m, 4H), 3.82 (d, 2H), 2.54 (s, 3H), 2.37 (s, 3H), 0.60 (m, 1H), 0.33 (m, 2H), −0.12 (m, 2H); (Yield: 54%)

EXAMPLE 313

7-(4-chlorophenyl)-2,3-dimethyl-1-(naphthalen-2-ylmethyl)-1H-pyrrolo[2,3-c]pyridine hydrochloride 1H-NMR(400 MHz, CDCl$_3$) δ 8.39 (s, 1H), 7.80 (m, 2H), 7.70 (d, 1H), 7.59 (m, 1H), 7.49 (m, 4H), 6.70 (s, 1H), 6.54 (d, 1H), 5.24 (s, 2H), 2.48 (s, 3H), 2.45 (s, 3H); (Yield: 36%)

EXAMPLE 314

1-(4-tert-butylbenzyl)-7-(4-chlorophenyl)-2,3-dimethyl-1H-pyrrolo[2,3-c]pyridine hydrochloride 1H-NMR(400 MHz, CDCl$_3$) δ 8.35 (s, 1H), 7.77 (s, 1H), 7.32 (m, 3H), 7.17 (m, 3H), 6.24 (s, 2H), 5.12 (s, 2H), 2.43 (s, 3+3H), 1.26 (s, 9H); (Yield: 47%)

EXAMPLE 315

1-(4-chlorobenzyl)-7-(4-chlorophenyl)-2,3-dimethyl-1H-pyrrolo[2,3-c]pyridine hydrochloride 1H-NMR(400 MHz, CDCl$_3$) δ 8.38 (s, 1H), 7.79 (d, 1H), 7.36 (m, 4H), 7.18 (d, 2H), 6.31 (d, 2H), 5.05 (s, 2H), 2.42 (s, 3H), 2.41 (s, 3H); (Yield: 47%)

EXAMPLE 316

7-(4-chlorophenyl)-2,3-dimethyl-1-oxiranylmethyl-1H-pyrrolo[2,3-c]pyridine hydrochloride 1H-NMR(400 MHz, CDCl$_3$) δ 8.14 (d, 1H), 8.04 (d, 1H), 7.69 (t, 1H), 7.39 (m, 3H), 4.13 (d, 1H), 4.02 (d, 1H), 3.67 (s, 2H), 3.29 (m, 1H), 3.10 (m, 1H), 2.61 (s, 3H), 2.37 (s, 3H); (Yield: 37%)

EXAMPLE 317

7-(4-chlorophenyl)-1-(2,5-dimethylbenzyl)-2,3-dimethyl-1H-pyrrolo[2,3-c]pyridine hydrochloride 1H-NMR(400 MHz, CDCl$_3$) δ 8.35 (t, 1H), 7.81 (d, 1H), 7.22 (d, 2H), 7.15 (d, 2H), 7.00 (s, 2H), 5.66 (s, 1H), 4.86 (s, 2H), 2.45 (s, 3H), 2.43 (s, 3H), 2.12 (s, 3H), 1.76 (s, 3H); (Yield: 36%)

EXAMPLE 318

7-(4-chlorophenyl)-1-ethyl-2,3-dimethyl-1H-pyrrolo[2,3-c]pyridine hydrochloride

1H-NMR(400 MHz, CDCl$_3$) δ 8.34 (t, 1H), 7.80 (d, 1H), 7.72 (d, 1H), 7.64 (m, 4H), 3.89 (q, 2H), 2.50 (s, 3H), 2.35 (s, 3H), 0.93 (t, 3H); (Yield: 52%)

EXAMPLE 319

7-(4-chlorophenyl)-2,3-dimethyl-1-propyl-1H-pyrrolo[2,3-c]pyridine hydrochloride 1H-NMR(400 MHz, CDCl$_3$) δ 8.34 (t, 1H), 7.72 (d, 1H), 7.61 (m, 4H), 3.76 (t, 2H), 2.49 (s, 3H), 2.35 (s, 3H), 1.29 (q, 2H), 0.50 (t, 3H); (Yield: 49%)

EXAMPLE 320

7-(4-chlorophenyl)-2,3-dimethyl-1-(3-methylbenzyl)-1H-pyrrolo[2,3-c]pyridine hydrochloride 1H-NMR(400 MHz, CDCl$_3$) δ 8.37 (t, 1H), 7.78 (d, 1H), 7.34 (d, 2H), 7.28 (d, 2H), 7.04 (s, 2H), 6.15 (s, 1H), 6.07 (d, 2H), 5.05 (s, 2H), 2.45 (s, 3H), 2.42 (s, 3H), 2.22 (s, 3H); (Yield: 39%)

EXAMPLE 321

3-[7-(4-chlorophenyl)-2,3-dimethylpyrrolo[2,3-c]pyridin-1-ylmethyl]-benzonitrile hydrochloride 1H-NMR(400 MHz, CDCl$_3$) δ 8.38 (d, 1H), 7.74 (d, 1H), 7.54 (d, 1H), 7.47 (d, 1H), 7.33 (t, 2H), 7.32 (m, 2H), 6.62 (s, 1H), 6.58 (d, 1H), 5.11 (s, 2H), 2.42 (s, 3+3H); (Yield: 47%)

EXAMPLE 322

7-(4-chlorophenyl)-1-(4-fluorobenzyl)-2,3-dimethyl-1H-pyrrolo[2,3-c]pyridine hydrochloride 1H-NMR(400 MHz, CDCl$_3$) δ 8.37 (s, 1H), 7.79 (t, 1H), 7.34 (m, 4H), 6.91 (m 2H), 6.32 (m, 2H), 5.06 (s, 2H), 2.42 (d, 3+3H); (Yield: 57%)

EXAMPLE 323

7-(4-chlorophenyl)-1-(3-chlorobenzyl)-2,3-dimethyl-1H-pyrrolo[2,3-c]pyridine hydrochloride 1H-NMR(400 MHz, CDCl$_3$) δ 8.38 (t, 1H), 7.81 (d, 1H), 7.35 (d, 2H), 7.29 (d, 2H), 7.18 (q, 1H), 6.92 (t, 1H), 6.15 (d, 1H), 6.07 (d, 1H), 5.07 (s, 2H), 2.45 (s, 3H), 2.43 (s, 3H); (Yield: 43%)

EXAMPLE 324

7-(4-chlorophenyl)-1-cyclobutylmethyl-2,3-dimethyl-1H-pyrrolo[2,3-c]pyridine hydrochloride 1H-NMR(400 MHz, CDCl$_3$) δ 8.37 (t, 1H), 7.72 (d, 1H), 7.66 (m, 4H), 3.82 (d, 2H), 2.53 (s, 3H), 2.35 (s, 3H), 2.09 (m, 1H), 1.57 (m, 2+2H), 1.30 (t, 2H); (Yield: 57%)

EXAMPLE 325

7-(4-fluorophenyl)-2,3-dimethyl-1H-pyrrolo[2,3-c]pyridine hydrochloride

In accordance with the same procedures as in Example 242, using 3-nitro-2-(4-fluorophenyl)pyridine prepared in Preparation 13, 7-(4-fluorophenyl)-2,3-dimethyl-1H-pyrrolo[2,3-c]pyridine was obtained. The product was dissolved in ethyl acetate, saturated with hydrochloric acid gas, and then filtered to give the titled compound as a white solid. (Yield: 39%)

1H-NMR(400 MHz, CDCl$_3$) δ 8.09 (m, 1H), 7.95 (t, 2H), 7.73 (m, 1H), 7.59 (d, 1H), 6.90 (m, 2H), 2.64 (s, 3H), 2.32 (s, 3H)

EXAMPLES 326 TO 348

The titled compounds of Examples 326 to 348 were prepared, in accordance with the same procedures as in Example 243, using 7-(4-fluorophenyl)-2,3-dimethyl-1H-pyrrolo[2,3-c]pyridine obtained by treating the compound prepared in Example 325 with a saturated sodium carbonate solution; and, allyl bromide, 2-bromoethyl methyl ether, 3-fluorobenzyl chloride, benzyl chloride, bromomethyl methyl ether, 4-bromo-2-methyl-2-butene, 1-bromo-3-methylbutane, (bromomethyl)cyclopropane, 2-(bromomethyl)naphthalene, 4-tert-butylbenzyl bromide, 4-chlorobenzyl chloride, 2,5-dimethylbenzyl bromide, epibromohydrin, iodoethane, 1-iodo-2-methylpropane, 1-bromopropane, 3-methoxybenzyl bromide, 4-methoxybenzyl bromide, 3-methylbenzyl bromide, 4-methylbenzyl bromide, α-bromo-m-tolunitrile, 4-fluorobenzyl bromide, or propargyl bromide.

EXAMPLE 326

1-allyl-7-(4-fluorophenyl)-2,3-dimethyl-1H-pyrrolo[2,3-c]pyridine hydrochloride

1H-NMR(400 MHz, CDCl$_3$) δ 8.35 (s, 1H), 7.74 (s, 1H), 7.64 (s, 2H), 7.26 (s, 2H), 5.55 (m, 1H), 5.10 (d, 1H), 2.42 (s, 2+1H), 2.45 (s, 3H), 2.37 (s, 3H); (Yield: 52%)

EXAMPLE 327

7-(4-fluorophenyl)-1-(2-methoxyethyl)-2,3-dimethyl-1H-pyrrolo[2,3-c]pyridine hydrochloride 1H-NMR(400 MHz, CDCl$_3$) δ 8.34 (s, 1H), 7.71 (m, 3H), 7.30 (t, 2H), 4.06 (s, 2H), 3.06 (s, 2H), 3.04 (s, 3H), 2.52 (s, 3H), 2.35 (s, 3H); (Yield: 57%)

EXAMPLE 328

1-(3-fluorobenzyl)-7-(4-fluorophenyl)-2,3-dimethyl-1H-pyrrolo[2,3-c]pyridine hydrochloride 1H-NMR(400 MHz, CDCl$_3$) δ 8.38 (t, 1H), 7.80 (d, 1H), 7.38 (m, 2H), 7.16 (q, 1H), 7.08 (t, 2H), 6.94 (t, 1H), 6.14 (d, 1H), 6.13 (d, 1H), 5.08 (s, 2H), 2.44 (s, 3H), 2.42 (s, 3H); (Yield: 50%)

EXAMPLE 329

1-benzyl-7-(4-fluorophenyl)-2,3-dimethyl-1H-pyrrolo[2,3-c]pyridine hydrochloride 1H-NMR(400 MHz, CDCl$_3$) δ 8.36 (t, 1H), 7.78 (d, 1H), 7.35 (m, 2H), 7.21 (m, 3H), 7.06 (t, 2H), 6.35 (d, 2H), 5.08 (s, 2H), 2.43 (s, 3H), 2.41 (s, 3H); (Yield: 82%)

EXAMPLE 330

7-(4-fluorophenyl)-1-methoxymethyl-2,3-dimethyl-1H-pyrrolo[2,3-c]pyridine hydrochloride 1H-NMR(400 MHz, CDCl$_3$) δ 8.40 (s, 1H), 8.32 (t, 1H), 7.69 (m, 4H), 4.95 (s, 2H), 3.40 (s, 3H), 2.35 (s, 3+3H); (Yield: 56%)

EXAMPLE 331

7-(4-fluorophenyl)-2,3-dimethyl-1-(3-methylbut-2-enyl)-1H-pyrrolo[2,3-c]pyridine hydrochloride 1H-NMR(400 MHz, CDCl$_3$) δ 8.33 (s, 1H), 7.69 (s, 3H), 7.26 (s, 2H), 4.67 (s, 1H), 4.44 (s, 2H), 2.47 (s, 3H), 2.35 (s, 3H), 1.60 (s,3H), 1.58 (s, 3H); (Yield: 51%)

EXAMPLE 332

7-(4-fluorophenyl)-2,3-dimethyl-1-(3-methylbutyl)-1H-pyrrolo[2,3-c]pyridine hydrochloride 1H-NMR(400 MHz, CDCl$_3$) δ 8.34 (s, 1H), 7.71 (s, 3H), 7.33 (s, 2H), 3.87 (s, 2H), 2.50 (s, 3H), 2.36 (s, 3H), 1.14 (s, 1+2H), 0.65 (s, 3+3H); (Yield: 51%)

EXAMPLE 333

1-cyclopropylmethyl-7-(4-fluorophenyl)-2,3-dimethyl-1H-pyrrolo[2,3-c]pyridine hydrochloride 1H-NMR(400 MHz, CDCl$_3$) δ 8.37 (t, 1H), 7.72 (d, 3H), 7.32 (t, 2H), 3.83 (d, 2H), 2.53 (s, 3H), 2.37 (s, 3H), 0.60 (m, 1H), 0.32 (d, 2H), 0.13 (d, 2H); (Yield: 57%)

EXAMPLE 334

7-(4-fluorophenyl)-2,3-dimethyl-1-(naphthalen-2-ylmethyl)-1H-pyrrolo[2,3-c]pyridine hydrochloride 1H-NMR(400 MHz, CDCl$_3$) δ 8.38 (t, 1H), 7.81 (d, 2H), 7.70 (t, 1H), 7.56 (t, 1H), 7.48 (m, 2H), 7.35 (m, 2H), 7.24 (t, 2H), 6.71 (d, 1H), 6.55 (t, 1H), 5.23 (s, 2H), 2.45 (s, 3+3H); (Yield: 53%)

EXAMPLE 335

1-(4-tert-butylbenzyl)-7-(4-fluorophenyl)-2,3-dimethyl-1H-pyrrolo[2,3-c]pyridine hydrochloride 1H-NMR(400 MHz, CDCl$_3$) δ 8.36 (t, 1H), 7.77 (t, 1H), 7.35 (m, 2H), 7.16 (t, 2H), 7.04 (m, 2H), 6.24 (t, 2H), 5.06 (s, 2H), 2.43 (s, 3H), 2.41 (s, 3H), 1.26 (s, 9H); (Yield: 53%)

EXAMPLE 336

1-(4-chlorobenzyl)-7-(4-fluorophenyl)-2,3-dimethyl-1H-pyrrolo[2,3-c]pyridine hydrochloride 1H-NMR(400 MHz, CDCl$_3$) δ 8.38 (s, 1H), 7.79 (d, 1H), 7.39 (m, 2H), 7.18 (t, 2H), 7.09 (t, 2H), 6.31 (t, 2H), 5.05 (s, 2H), 2.41 (s, 3+3H); (Yield: 49%)

EXAMPLE 337

1-(2,5-dimethylbenzyl)-7-(4-fluorophenyl)-2,3-dimethyl-1H-pyrrolo[2,3-c]pyridine hydrochloride 1H-NMR(400 MHz, CDCl$_3$) δ 8.35 (t, 1H), 7.80 (d, 1H), 7.21 (q, 2H), 6.99 (s, 2H), 6.94 (t, 2H), 5.67 (s, 1H), 4.87 (s, 2H), 2.45 (s, 3H), 2.42 (s, 3H), 2.12 (s, 3H), 1.77 (s, 3H); (Yield: 56%)

EXAMPLE 338

7-(4-fluorophenyl)-2,3-dimethyl-1-oxiranylmethyl-1H-pyrrolo[2,3-c]pyridine hydrochloride 1H-NMR(400 MHz, CDCl$_3$/MeOH-d$_4$) δ 8.17 (d, 1H), 8.06 (d, 1H), 7.82 (d, 2H), 7.61 (t, 3H), 3.91 (s, 2H), 3.52 (m, 1H), 3.09 (d, 2H), 2.59 (s, 3H), 2.38 (s, 3H); (Yield: 36%)

EXAMPLE 339

1-ethyl-7-(4-fluorophenyl)-2,3-dimethyl-1H-pyrrolo[2,3-c]pyridine hydrochloride

1H-NMR(400 MHz, CDCl$_3$) δ 8.34 (q, 1H), 7.68 (m, 3H), 7.33 (m, 2H), 3.87 (q, 2H), 2.50 (s, 3H), 2.35 (s, 3H), 0.91 (t, 3H); (Yield: 57%)

EXAMPLE 340

7-(4-fluorophenyl)-1-isobutyl-2,3-dimethyl-1H-pyrrolo[2,3-c]pyridine hydrochloride 1H-NMR(400 MHz, CDCl$_3$) δ 8.35 (q, 1H), 7.71 (m, 3H), 7.33 (t, 2H), 3.74 (d, 2H), 2.51 (s, 3H), 2.36 (s, 3H), 1.39 (m, 1H), 0.44 (d, 3+3H); (Yield: 50%)

EXAMPLE 341

7-(4-fluorophenyl)-2,3-dimethyl-1-propyl-1H-pyrrolo[2,3-c]pyridine hydrochloride 1H-NMR(400 MHz, CDCl$_3$) δ 8.36 (t, 1H), 7.68 (m, 3H), 7.32 (t, 2H), 3.76 (t, 2H), 2.50 (s, 3H), 2.35 (s, 3H), 1.29 (q, 2H), 0.50 (t, 3H); (Yield: 57%)

EXAMPLE 342

7-(4-fluorophenyl)-1-(3-methoxybenzyl)-2,3-dimethyl-1H-pyrrolo[2,3-c]pyridine hydrochloride 1H-NMR(400 MHz, CDCl$_3$) δ 8.35 (t, 1H), 7.77 (d, 1H), 7.37 (t, 2H), 7.09 (m, 3H), 6.76 (d, 1H), 5.90 (s, 2H), 3.69 (s, 3H), 2.43 (s, 3H), 2.41 (s, 3H); (Yield: 55%)

EXAMPLE 343

7-(4-fluorophenyl)-1-(4-methoxybenzyl)-2,3-dimethyl-1H-pyrrolo[2,3-c]pyridine hydrochloride 1H-NMR(400 MHz, CDCl$_3$) δ 8.33 (s, 1H), 7.77 (d, 1H), 7.37 (t, 1H), 7.28 (t, 1H), 7.09 (t, 2H), 6.72 (d, 2H), 6.27 (d, 2H), 5.01 (s, 2H), 3.76 (s, 3H), 2.43 (s, 3H), 2.41 (s, 3H); (Yield: 58%)

EXAMPLE 344

7-(4-fluorophenyl)-1-(3-methylbenzyl)-2,3-dimethyl-1H-pyrrolo[2,3-c]pyridine hydrochloride 1H-NMR(400 MHz, CDCl$_3$) δ 8.36 (t, 1H), 7.77 (d, 1H), 7.36 (t, 2H), 7.05 (m, 4H), 6.16 (s, 1H), 6.09 (d, 1H), 5.05 (s, 2H), 2.44 (s, 3H), 2.42 (s, 3H), 2.21 (s, 3H); (Yield: 59%)

EXAMPLE 345

7-(4-fluorophenyl)-1-(4-methylbenzyl)-2,3-dimethyl-1H-pyrrolo[2,3-c]pyridine hydrochloride 1H-NMR(400 MHz, CDCl$_3$) δ 8.37 (t, 1H), 7.77 (d, 1H), 7.38 (m, 2H), 7.08 (t, 2H), 6.99 (d, 2H), 6.25 (d, 2H), 5.03 (s, 2H), 2.42 (s, 3H), 2.41 (s, 3H), 2.29 (s, 3H); (Yield: 51%)

EXAMPLE 346

3-[7-(4-fluorophenyl)-2,3-dimethylpyrrolo[2,3-c]pyridin-1-ylmethyl]-benzonitrile hydrochloride 1H-NMR(400 MHz, CDCl$_3$/MeOH-d$_4$) δ 8.24 (s, 1H), 7.85 (d, 1H), 7.57 (m, 2H), 7.37 (m, 2H), 6.67 (s, 2H), 5.15 (s, 2H), 2.46 (s, 3H), 2.44 (s, 3H); (Yield: 51%)

EXAMPLE 347

1-(4-fluorobenzyl)-7-(4-fluorophenyl)-2,3-dimethyl-1H-pyrrolo[2,3-c]pyridine hydrochloride 1H-NMR(400 MHz, MeOH-$d_4$) δ 8.17 (t, 1H), 7.97 (d, 1H), 7.48 (m, 2H), 7.26 (d, 2H), 6.94 (t, 2H), 6.36 (t, 2H), 5.12 (s, 2H), 2.51 (s, 3H), 2.47 (s, 3H); (Yield: 50%)

EXAMPLE 348

7-(4-fluorophenyl)-2,3-dimethyl-1-(prop-2-ynyl)-1H-pyrrolo[2,3-c]pyridine hydrochloride 1H-NMR(400 MHz, $CDCl_3$) δ 8.40 (s, 1H), 7.73 (m, 3H), 7.26 (m, 2H), 6.39 (s, 1H), 5.07 (s, 2H), 2.60 (s, 3H), 2.37 (s, 3H); (Yield: 47%)

EXAMPLE 349

7-(4-methoxyphenyl)-2,3-dimethyl-1H-pyrrolo[2,3-c]pyridine

In accordance with the same procedures as in Example 242, except for using 3-nitro-2-(4-methoxyphenyl)pyridine prepared in Preparation 14, the titled compound was obtained as a white solid. (Yield: 45%)

1H-NMR(400 MHz, $CDCl_3$) δ 8.30 (d, 1H), 8.19 (brs, 1H), 7.83 (d, 2H), 7.32 (d, 1H), 7.07 (d, 2H), 3.88 (s, 3H), 2.41 (s, 3H), 2.24 (s, 3H)

EXAMPLES 350 TO 370

The titled compounds of Examples 350 to 370 were prepared, in accordance with the same procedures as in Example 243, using 7-(4-methoxyphenyl)-2,3-dimethyl-1H-pyrrolo[2,3-c]pyridine prepared in Example 349; and, benzyl bromide, (bromomethyl)cyclopropane, 3-fluorobenzyl chloride, 2-fluorobenzyl chloride, propargyl bromide, 2-bromoethyl methyl ether, 2-(bromomethyl)naphthalene, 4-chlorobenzyl bromide, 1-iodo-2-methylpropane, (bromomethyl)cyclobutane, allyl bromide, 4-bromo-2-methyl-2-butene, 1-bromo-3-methylbutane, 4-tert-butylbenzyl bromide, 2,5-dimethylbenzyl chloride, epibromohydrin, iodoethane, 1-bromopropane, 3-methoxybenzyl bromide, 4-methoxybenzyl bromide, or 4-fluorobenzyl chloride.

EXAMPLE 350

1-benzyl-7-(4-methoxyphenyl)-2,3-dimethyl-1H-pyrrolo[2,3-c]pyridine hydrochloride 1H-NMR(400 MHz, $CDCl_3$) δ 8.38 (s, 1H), 7.72 (d, 1H), 7.34 (d, 2H), 7.18 (m, 3H), 6.88 (d, 2H), 6.40 (d, 2H), 5.13 (s, 2H), 3.88 (s, 3H), 2.41 (s, 3H), 2.39 (s, 3H); (Yield: 65%)

EXAMPLE 351

1-cyclopropylmethyl-7-(4-methoxyphenyl)-2,3-dimethyl-1H-pyrrolo[2,3-c]pyridine hydrochloride 1H-NMR(400 MHz, $CDCl_3$) δ 8.54 (t, 1H), 7.83 (m, 3H), 7.28 (d, 2H), 4.07 (s, 3H), 4.05 (d, 2H), 2.69 (s, 3H), 2.52 (s, 3H), 0.77 (m, 1H), 0.44 (m, 2H), 0.00 (m, 2H); (Yield: 63%)

EXAMPLE 352

1-(3-fluorobenzyl)-7-(4-methoxyphenyl)-2,3-dimethyl-1H-pyrrolo[2,3-c]pyridine hydrochloride 1H-NMR(400 MHz, $CDCl_3$) δ 8.37 (s, 1H), 7.75 (s, 1H), 7.33 (s, 2H), 7.15 (t, 1H), 6.91 (m, 3H), 6.15 (m, 2H), 5.14 (s, 2H), 3.85 (s, 3H), 2.43 (s, 3H), 2.41 (s, 3H); (Yield: 52%)

EXAMPLE 353

1-(2-fluorobenzyl)-7-(4-methoxyphenyl)-2,3-dimethyl-1H-pyrrolo[2,3-c]pyridine hydrochloride 1H-NMR(400 MHz, $CDCl_3$) δ 8.38 (t, 1H), 7.73 (d, 1H), 7.30 (d, 2H), 7.22 (m, 1H), 6.96 (m, 2H), 6.87 (d, 2H), 6.04 (t, 1H), 5.14 (s, 2H), 3.84 (s, 3H), 2.41 (s, 3H), 2.40 (s, 3H); (Yield: 55%)

EXAMPLE 354

7-(4-methoxyphenyl)-2,3-dimethyl-1-(prop-2-ynyl)-1H-pyrrolo[2,3-c]pyridine hydrochloride 1H-NMR(400 MHz, $CDCl_3$) δ 8.39 (d, 1H), 7.75 (d, 2H), 7.67 (d, 1H), 7.13 (d, 2H), 4.55 (s, 2H), 3.91 (s, 3H), 2.59 (s, 3H), 2.36 (s, 1H), 2.35 (s, 3H); (Yield: 57%)

EXAMPLE 355

7-(4-methoxyphenyl)-2,3-dimethyl-1-(2-methoxyethyl)-1H-pyrrolo[2,3-c]pyridine hydrochloride 1H-NMR(400 MHz, $CDCl_3$) δ 8.33 (t, 1H), 7.65 (d, 1H), 7.57 (m, 2H), 7.09 (m, 2H), 4.11 (s, 2H), 3.89 (s, 3H), 3.04 (s, 2H), 3.02 (s, 3H), 2.51 (s, 3H), 2.34 (s, 3H); (Yield: 57%)

EXAMPLE 356

7-(4-methoxyphenyl)-2,3-dimethyl-1-(naphthalen-2-ylmethyl)-1H-pyrrolo[2,3-c]pyridine hydrochloride 1H-NMR(400 MHz, $CDCl_3$) δ 8.36 (d, 1H), 7.76 (m, 1H), 7.72 (d, 1H), 7.67 (d, 1H), 7.56 (m, 1H), 7.47 (m, 2H), 7.31 (d, 2H), 6.78 (d, 3H), 6.58 (d, 1H), 5.27 (s, 2H), 3.78 (s, 3H), 2.44 (s, 3H), 2.42 (s, 3H); (Yield: 97%)

EXAMPLE 357

1-(4-chlorobenzyl)-7-(4-methoxyphenyl)-2,3-dimethyl-1H-pyrrolo[2,3-c]pyridine hydrochloride 1H-NMR(400 MHz, $CDCl_3$) δ 8.35 (s, 1H), 7.72 (s, 1H), 7.33 (s, 2H), 7.16 (d, 2H), 6.88 (s, 2H), 6.32 (d, 2H), 5.10 (s, 2H), 3.84 (s, 3H), 2.40 (s, 3+3H); (Yield: 90%)

EXAMPLE 358

1-isobutyl-7-(4-methoxyphenyl)-2,3-dimethyl-1H-pyrrolo[2,3-c]pyridine hydrochloride 1H-NMR(400 MHz, $CDCl_3$) δ 8.33 (s, 1H), 7.66 (m, 3H), 7.11 (d 2H), 3.90 (s, 3H), 3.79 (d, 2H), 2.49 (s, 3H), 2.35 (s, 3H), 1.41 (m, 1H), 0.41 (s, 3H), 0.39 (s, 3H); (Yield: 92%)

EXAMPLE 359

1-cyclobutylmethyl-7-(4-methoxyphenyl)-2,3-dimethyl-1H-pyrrolo[2,3-c]pyridine hydrochloride 1H-NMR(400 MHz, CDCl$_3$) δ 8.34 (d, 1H), 7.63 (m, 3H), 7.11 (d, 2H), 3.99 (d, 2H), 3.90 (s, 3H), 2.49 (s, 3H), 2.33 (s, 3H), 2.08 (m, 1H), 1.58 (m, 2+2H), 1.30 (t, 2H); (Yield: 62%)

EXAMPLE 360

1-allyl-7-(4-methoxyphenyl)-2,3-dimethyl-1H-pyrrolo[2,3-c]pyridine hydrochloride 1H-NMR(400 MHz, CDCl$_3$) δ 8.36 (t, 1H), 7.69 (d, 1H), 7.57 (d, 2H), 7.07 (d, 2H), 5.55 (m, 1H), 5.09 (d, 1H), 4.47 (s, 2H), 4.39 (d, 1H), 3.90 (s, 3H), 2.45 (s, 3H), 2.36 (s, 3H); (Yield: 52%)

EXAMPLE 361

7-(4-methoxyphenyl)-2,3-dimethyl-1-(3-methylbut-2-enyl)-1H-pyrrolo[2,3-c]pyridine hydrochloride 1H-NMR(400 MHz, CDCl$_3$) δ 8.33 (s, 1H), 7.63 (t, 3H), 7.07 (d, 2H), 4.68 (s, 1H), 4.49 (s, 2H), 3.89 (s, 3H), 2.45 (s, 3H), 2.33 (s, 3H), 1.59 (s, 3H), 1.33 (s, 3H); (Yield: 57%)

EXAMPLE 362

7-(4-methoxyphenyl)-2,3-dimethyl-1-(3-methylbutyl)-1H-pyrrolo[2,3-c]pyridine hydrochloride 1H-NMR(400 MHz, CDCl$_3$) δ 8.33 (t, 1H), 7.64 (m, 3H), 7.11 (d, 2H), 3.89 (s, 2+3H), 2.48 (s, 3H), 2.34 (s, 3H), 1.09 (m, 1+2H), 0.63 (s, 3H), 0.61 (s, 3H); (Yield: 57%)

EXAMPLE 363

1-(4-tert-butylbenzyl)-7-(4-methoxyphenyl)-2,3-dimethyl-1H-pyrrolo[2,3-c]pyridine hydrochloride 1H-NMR(400 MHz, CDCl$_3$) δ 8.34 (d, 1H), 7.70 (m, 1H), 7.31 (m, 2H), 7.16 (m, 2H), 6.86 (m, 2H), 6.29 (m, 2H), 5.11 (s, 2H), 3.85 (s, 3H), 2.43 (s, 3H), 2.39 (s, 3H), 1.25 (s, 9H); (Yield: 57%)

EXAMPLE 364

1-(2,5-dimethylbenzyl)-7-(4-methoxyphenyl)-2,3-dimethyl-1H-pyrrolo[2,3-c]pyridine hydrochloride 1H-NMR(400 MHz, CDCl$_3$) δ 8.37 (s, 1H), 7.75 (s, 1H), 7.18 (s, 2H), 6.97 (s, 2H), 6.76 (s, 2H), 5.72 (s, 1H), 4.92 (s, 2H), 3.81 (s, 3H), 2.44 (s, 3H), 2.40 (s, 3H), 2.13 (s, 3H), 1.78 (s, 3H); (Yield: 53%)

EXAMPLE 365

7-(4-methoxyphenyl)-2,3-dimethyl-1-oxiranylmethyl-1H-pyrrolo[2,3-c]pyridine hydrochloride 1H-NMR(400 MHz, CDCl$_3$) δ 8.08 (s, 1H), 7.59 (m, 1H), 7.43 (m, 2H), 6.96 (s, 2H), 4.12 (m, 2H), 3.87 (s, 3H), 3.77 (s, 1H), 3.13 (m, 1H), 3.05 (m, 1H), 2.56 (s, 3H), 2.37 (s, 3H); (Yield: 47%)

EXAMPLE 366

1-ethyl-7-(4-methoxyphenyl)-2,3-dimethyl-1H-pyrrolo[2,3-c]pyridine hydrochloride 1H-NMR(400 MHz, CDCl$_3$) δ 8.33 (s, 1H), 7.66 (m, 3H), 7.08 (s, 2H), 3.90 (s, 2+3H), 2.50 (s, 3H), 2.35 (s, 3H), 0.91 (t, 3H); (Yield: 59%)

EXAMPLE 367

7-(4-methoxyphenyl)-2,3-dimethyl-1-propyl-1H-pyrrolo[2,3-c]pyridine hydrochloride 1H-NMR(400 MHz, CDCl$_3$) δ 8.33 (s, 1H), 7.65 (d, 1H), 7.59 (s,2H), 7.10 (s, 2H), 3.90 (s, 3H), 3.82 (t, 2H), 2.49 (s, 3H), 2.34 (s, 3H), 1.27 (m, 2H), 0.50 (t, 3H); (Yield: 58%)

EXAMPLE 368

1-(3-methoxybenzyl)-7-(4-methoxyphenyl)-2,3-dimethyl-1H-pyrrolo[2,3-c]pyridine hydrochloride 1H-NMR(400 MHz, CDCl$_3$) δ 8.32 (s, 1H), 7.71 (d, 1H), 7.31 (s, 2H), 7.08 (t, 1H), 6.84 (s, 2H), 6.74 (d, 1H), 5.94 (d, 2H), 5.09 (s, 2H), 3.82 (s, 3H), 3.68 (s, 3H), 2.42 (s, 3H), 2.39 (s, 3H); (Yield: 51%)

EXAMPLE 369

1-(4-methoxybenzyl)-7-(4-methoxyphenyl)-2,3-dimethyl-1H-pyrrolo[2,3-c]pyridine hydrochloride 1H-NMR(400 MHz, CDCl$_3$) δ 8.33 (s, 1H), 7.70 (s, 1H), 7.36 (s,2H), 6.89 (s, 2H), 6.70 (d, 2H), 6.31 (d, 2H), 5.07 (s, 2H), 3.83 (s, 3H), 3.75 (s, 3H), 2.42 (s, 3H), 2.39 (s, 3H); (Yield: 51%)

EXAMPLE 370

1-(4-fluorobenzyl)-7-(4-methoxyphenyl)-2,3-dimethyl-1H-pyrrolo[2,3-c]pyridine hydrochloride 1H-NMR(400 MHz, CDCl$_3$) δ 8.36 (s, 1H), 7.72 (d, 1H), 7.34 (s, 2H), 6.88 (m, 4H), 6.35 (t, 2H), 5.11 (s, 2H), 3.84 (s 3H), 2.42 (s, 3H), 2.39 (s, 3H); (Yield: 50%)

EXAMPLE 371

2,3-dimethyl-7-phenyl-1H-pyrrolo[2,3-c]pyridine hydrochloride

In accordance with the same procedures as in Example 242, except for using 3-nitro-2-phenylpyridine prepared in Preparation 15, 2,3-dimethyl-7-phenyl-1H-pyrrolo[2,3-c]pyridine was obtained. The product was dissolved in ethyl acetate, saturated with hydrochloric acid gas, and then filtered to give the titled compound as a white solid. (Yield: 45%)

1H-NMR(400 MHz, CDCl$_3$) δ 8.34 (d, 1H), 8.18 (brs, 1H), 7.89 (d, 2H), 7.54 (t, 2H), 7.45 (t, 1H), 7.35 (d, 1H), 2.41 (s, 3H), 2.25 (s, 3H)

EXAMPLES 372 TO 394

The titled compounds of Examples 372 to 394 were prepared, in accordance with the same procedures as in Example 243, using 2,3-dimethyl-7-phenyl-1H-pyrrolo[2,3-c]pyridine hydrochloride prepared in Example 371; and, allyl bromide, 4-methylbenzyl bromide, iodoethane, 3-fluorobenzyl chloride, benzyl chloride, 1-iodo-2-methylpropane, bromomethyl methyl ether, 2-bromoethyl methyl ether, 4-methoxybenzyl bromide, 4-chlorobenzyl bromide, 2-chlorobenzyl bromide, 4-bromo-2-methyl-2-butene, (bromomethyl)cyclopropane, (bromomethyl)cyclohexane, 1-bromopentane, 2,5-dimethylbenzyl chloride, 3,4-dichlorobenzyl chloride, 1-bromopropane, 3-methoxybenzyl bromide, 3-methylbenzyl bromide, 4-fluorobenzyl bromide, (bromomethyl)cyclobutane, or 2-fluorobenzyl bromide.

EXAMPLE 372

1-allyl-2,3-dimethyl-7-phenyl-1H-pyrrolo[2,3-c]pyridine hydrochloride

1H-NMR(400 MHz, CDCl$_3$) δ 8.39 (s, 1H), 7.64 (m, 6H), 5.52 (m, 1H), 5.08 (m, 1H), 4.42 (m, 1+2H), 2.47 (s, 3H), 2.40 (s, 3H); (Yield: 62%)

EXAMPLE 373

2,3-dimethyl-1-(4-methylbenzyl)-7-phenyl-1H-pyrrolo[2,3-c]pyridine hydrochloride 1H-NMR(400 MHz, CDCl$_3$) δ 8.32 (s, 1H), 7.74 (s, 1H), 7.48 (s, 1H), 7.27 (brs, 4H), 6.96 (d, 2H), 6.22 (d, 2H), 5.02 (s, 2H), 2.42 (s, 3+3H), 2.28 (s, 3H); (Yield: 81%)

EXAMPLE 374

1-ethyl-2,3-dimethyl-7-phenyl-1H-pyrrolo[2,3-c]pyridine hydrochloride

1H-NMR(400 MHz, CDCl$_3$) δ 8.39 (s, 1H), 7.64 (m, 6H), 3.87 (q, 2H), 2.50 (s, 3H), 2.37 (s, 3H), 0.92 (t, 3H); (Yield: 51%)

EXAMPLE 375

2,3-dimethyl-1-(3-fluorobenzyl)-7-phenyl-1H-pyrrolo[2,3-c]pyridine hydrochloride 1H-NMR(400 MHz, CDCl$_3$) δ 8.37 (d, 1H), 7.61 (m, 1H), 7.45 (m, 1H), 7.30 (m, 4H), 7.11 (m, 1H), 6.87 (t, 1H), 6.13 (d, 1H), 6.06 (d, 1H), 5.01 (s, 2H), 2.37 (s, 3H), 2.35 (s, 3H); (Yield: 59%)

EXAMPLE 376

1-benzyl-2,3-dimethyl-7-phenyl-1H-pyrrolo[2,3-c]pyridine hydrochloride

1H-NMR(400 MHz, CDCl$_3$) δ 8.44 (m, 1H), 7.84 (m, 1H), 7.50 (m, 1H), 7.42 (m, 4H), 7.25 (m, 3H), 6.39 (d, 2H), 5.14 (m, 2H), 2.50 (s 3H), 2.42 (s, 3H); (Yield: 58%)

EXAMPLE 377

1-isobutyl-2,3-dimethyl-7-phenyl-1H-pyrrolo[2,3-c]pyridine hydrochloride

1H-NMR(400 MHz, CDCl$_3$) δ 8.40 (s, 1H), 7.70 (m, 6H), 3.76 (brs, 2H), 2.52 (s, 3H), 2.38 (s, 3H), 1.26 (m, 1H), 0.39 (s, 3+3H); (Yield: 57%)

EXAMPLE 378

1-methoxymethyl-2,3-dimethyl-7-phenyl-1H-pyrrolo[2,3-c]pyridine hydrochloride

1H-NMR(400 MHz, CDCl$_3$) δ 8.40 (s, 1H), 8.01 (m, 1H), 7.70 (m, 2H), 7.60 (m, 3H), 4.95 (s, 2H), 2.91 (s, 3H), 2.54 (s, 3H), 2.36 (s, 3H); (Yield: 49%)

EXAMPLE 379

1-(2-methoxyethyl)-2,3-dimethyl-7-phenyl-1H-pyrrolo[2,3-c]pyridine hydrochloride 1H-NMR(400 MHz, CDCl$_3$) δ 8.26 (m, 1H), 7.57 (m, 6H), 4.05 (m, 2H), 3.32 (m, 2H), 3.03 (s, 3H), 2.37 (s, 3H), 2.33 (s, 3H); (Yield: 46%)

EXAMPLE 380

1-(4-methoxybenzyl)-2,3-dimethyl-7-phenyl-1H-pyrrolo[2,3-c]pyridine hydrochloride 1H-NMR(400 MHz, CDCl$_3$) δ 8.37 (m, 1H), 7.78 (m, 1H), 7.56 (m, 2H), 7.42 (m, 3H), 6.75 (s, 2H), 6.31 (s, 2H), 5.09 (s, 2H), 3.76 (s, 3H), 2.45 (s, 3+3H); (Yield: 47%)

EXAMPLE 381

1-(4-chlorobenzyl)-2,3-dimethyl-7-phenyl-1H-pyrrolo[2,3-c]pyridine hydrochloride 1H-NMR(400 MHz, CDCl$_3$) δ 8.39 (s, 1H), 7.77 (s, 1H), 7.53 (s, 1H), 7.38 (m, 4H), 7.12 (s, 2H), 6.26 (s, 2H), 5.05 (s, 2H), 2.42 (s, 3+3H); (Yield: 51%)

EXAMPLE 382

1-(2-chlorobenzyl)-2,3-dimethyl-7-phenyl-1H-pyrrolo[2,3-c]pyridine hydrochloride 1H-NMR(400 MHz, CDCl$_3$) δ 8.44 (s, 1H), 7.81 (s, 1H), 7.52 (s, 1H), 7.29 (m, 3H), 7.26 (m, 3H), 7.10 (s, 1H), 5.94 (s, 1H), 5.03 (s, 2H), 2.45 (s, 3H), 2.42 (s, 3H); (Yield: 51%)

EXAMPLE 383

2,3-dimethyl-1-(3-methylbut-2-enyl)-7-phenyl-1H-pyrrolo[2,3-c]pyridine hydrochloride 1H-NMR(400 MHz, CDCl$_3$) δ 8.39 (brs, 1H), 7.69-7.56 (m, 6H), 4.66 (t, 1H), 4.43 (d, 3H), 2.45 (s, 3H), 2.35 (s, 3H), 1.57 (s, 3H), 1.21 (s, 3H); (Yield: 48%)

EXAMPLE 384

1-cyclopropylmethyl-2,3-dimethyl-7-phenyl-1H-pyrrolo[2,3-c]pyridine hydrochloride 1H-NMR(400 MHz, CDCl$_3$) δ 8.37 (d, 1H), 7.64-7.56 (m, 6H), 3.79 (d, 2H), 2.49 (s, 3H), 2.35 (s, 3H), 0.65 (m, 1H), 0.25 (m, 2H), −0.19 (m, 2H); (Yield: 56%)

EXAMPLE 385

1-cyclohexylmethyl-2,3-dimethyl-7-phenyl-1H-pyrrolo[2,3-c]pyridine hydrochloride 1H-NMR(400 MHz, CDCl$_3$) δ 8.37 (t, 1H), 7.70-7.59 (m, 6H), 3.74 (d, 2H), 2.49 (s, 3H), 2.32 (s, 3H), 1.47 (m, 2H), 1.05 (m, 1H), 0.81 (m, 4H), 0.72 (m, 2H), 0.55 (m, 2H); (Yield: 52%)

EXAMPLE 386

2,3-dimethyl-1-pentyl-7-phenyl-1H-pyrrolo[2,3-c]pyridine hydrochloride

1H-NMR(400 MHz, CDCl$_3$) δ 8.37 (d, 1H), 7.65 (m, 6H), 3.77 (t, 2H), 2.48 (s, 3H), 2.34 (s, 3H), 1.21 (m, 2H), 1.03 (m, 2H), 0.85 (m, 2H), 0.73 (t, 3H); (Yield: 50%)

EXAMPLE 387

1-(2,5-dimethylbenzyl)-2,3-dimethyl-7-phenyl-1H-pyrrolo[2,3-c]pyridine hydrochloride 1H-NMR(400 MHz, CDCl$_3$) δ 8.42 (t, 1H), 7.79 (d, 1H), 7.48 (t, 1H), 7.28 (m, 2H), 7.22 (m, 2H), 6.95 (m, 2H), 5.67 (s, 1H), 4.85 (s, 2H), 2.45 (s, 3H), 2.40 (s, 3H), 2.12 (s, 3H), 1.69 (s, 3H); (Yield: 48%)

EXAMPLE 388

1-(3,4-dichlorobenzyl)-2,3-dimethyl-7-phenyl-1H-pyrrolo[2,3-c]pyridine hydrochloride 1H-NMR(400 MHz, CDCl$_3$) δ 8.36 (d, 1H), 7.59 (m, 1H), 7.46 (m, 2H), 7.32 (m, 3H), 7.19 (d, 1H), 6.44 (s, 1H), 6.15 (d, 1H), 4.96 (s, 2H), 2.36 (s, 3H), 2.34 (s, 3H); (Yield: 48%)

EXAMPLE 389

2,3-dimethyl-7-phenyl-1-propyl-1H-pyrrolo[2,3-c]pyridine hydrochloride

1H-NMR(400 MHz, CDCl$_3$) δ 8.35 (m, 1H), 8.01 (m, 1H), 7.68 (d, 1H), 7.58 (m, 4H), 3.71 (t, 2H), 2.48 (s, 3H), 2.35 (s, 3H), 0.83 (m, 2H), 0.45 (t, 3H); (Yield: 57%)

EXAMPLE 390

1-(3-methoxybenzyl)-2,3-dimethyl-7-phenyl-1H-pyrrolo[2,3-c]pyridine hydrochloride 1H-NMR(400 MHz, CDCl$_3$) δ 8.31 (m, 1H), 7.91 (d, 1H), 7.55 (m, 1H), 7.39 (m, 1H), 7.28 (m, H), 7.04 (t, 1H), 6.70 (d, 1H), 5.96 (d, 1H), 5.91 (s, 1H), 4.96 (s, 2H), 3.66 (s, 3H), 2.35 (s, 3H), 2.32 (s, 3H); (Yield: 54%)

EXAMPLE 391

1-(3-methylbenzyl)-2,3-dimethyl-7-phenyl-1H-pyrrolo[2,3-c]pyridine hydrochloride 1H-NMR(400 MHz, CDCl$_3$) δ 8.40 (t, 1H), 7.76 (d, 1H), 7.53 (m, 1H), 7.37 (m, 4H), 7.02 (m, 2H), 6.12 (s, 1H), 6.08 (d, 1H), 5.03 (s, 2H), 2.43 (s, 3H), 2.41 (s, 3H), 2.19 (s, 3H); (Yield: 51%)

EXAMPLE 392

1-(4-fluorobenzyl)-2,3-dimethyl-7-phenyl-1H-pyrrolo[2,3-c]pyridine hydrochloride 1H-NMR(400 MHz, CDCl$_3$) δ 8.35 (d, 1H), 7.57 (d, 1H), 7.39 (m, 1H), 7.30 (m, 4H), 6.83 (t, 2H), 6.30 (m, 2H), 4.98 (s, 2H), 2.35 (s, 3H), 2.33 (s, 3H); (Yield: 49%)

EXAMPLE 393

1-cyclobutylmethyl-2,3-dimethyl-7-phenyl-1H-pyrrolo[2,3-c]pyridine hydrochloride 1H-NMR(400 MHz, CDCl$_3$) δ 8.32 (m, 1H), 8.01 (m, 1H), 7.63 (m, 4H), 7.57 (m, 1H), 3.92 (d, 2H), 2.50 (s, 3H), 2.34 (s, 3H), 1.01 (m, 1H), 0.81 (m, 6H); (Yield: 59%)

EXAMPLE 394

1-(2-fluorobenzyl)-2,3-dimethyl-7-phenyl-1H-pyrrolo[2,3-c]pyridine hydrochloride 1H-NMR(400 MHz, CDCl$_3$) δ 8.43 (d, 1H), 7.77 (d, 1H), 7.53 (t, 1H), 7.33 (m, 4H), 7.23 (m, 1H), 6.94 (m, 2H), 6.00 (t, 1H), 5.07 (s, 2H), 2.41 (s, 3+3H); (Yield: 48%)

EXAMPLE 395

(1-benzyl-2-methyl-7-phenyl-1H-pyrrolo[2,3-c]pyridin-3-yl)-methanol hydrochloride The compound prepared in Example 376 was treated with a saturated sodium carbonate solution to obtain 1-benzyl-2,3-dimethyl-7-phenyl-1H-pyrrolo[2,3-c]pyridine. 1-Benzyl-2,3-dimethyl-7-phenyl-1H-pyrrolo[2,3-c]pyridine (130 mg, 0.42 mmol) was dissolved in acetic acid (4 ml) and ammonium cerium (IV) nitrate (690 mg, 1.25 mmol) was added thereto at room temperature. The reaction mixture was stirred for 3 hours at 55° C. and then cooled to room temperature. Water was added to the reaction mixture, which was then extracted with ethyl acetate. The organic layer washed with a saturated sodium chloride solution, dried on anhydrous magnesium sulfate, and then concentrated under reduced pressure. The resulting residue was dissolved in methanol (5 ml) and then 2N lithium hydroxide (3 ml) was added thereto. The reaction mixture was stirred overnight at room temperature, neutralized with 1N hydrochloric acid, and then concentrated under reduced pressure. The resulting residue was extracted with dichloromethane. The organic layer was dried on anhydrous magnesium sulfate and then concentrated under reduced pressure. The resulting residue was purified with silica gel column chromatography (n-hexane/ethyl acetate=1/5, v/v). The resulting product was dissolved in ethyl acetate and then saturated with hydrochloric acid gas to give 2.8 mg of the titled compound as a white solid.

1H-NMR(400 MHz, CDCl$_3$) δ 8.21 (brs, 1H), 8.00 (brs, 1H), 7.54 (t, 1H), 7.37 (m, 4H), 7.16 (m, 3H), 6.35 (d, 2H), 5.08 (s, 2H), 4.99 (s, 2H), 2.52 (s, 3H)

EXAMPLE 396

(1-benzyl-2-methyl-7-phenyl-1H-pyrrolo[2,3-c]pyridin-3-yl)-acetic acid methyl ester The compound prepared in Example 376 was treated with a saturated sodium carbonate solution to obtain 1-benzyl-2, 3-dimethyl-7-phenyl-1H-pyrrolo[2,3-c]pyridine. 1-Benzyl-2,3-dimethyl-7-phenyl-1H-pyrrolo[2,3-c]pyridine (130 mg, 0.42 mmol) was dissolved in acetic acid (4 ml) and ammonium cerium (IV) nitrate (690 mg, 1.25 mmol) was added thereto at room temperature. The reaction mixture was stirred for 3 hours at 55□ and then cooled to room temperature. Water was added to the reaction mixture, which was then extracted with ethyl acetate. The organic layer washed with a saturated sodium chloride solution, dried on anhydrous magnesium sulfate, and then concentrated under reduced pressure. The resulting residue was dissolved in methanol (5 ml) and then 2N lithium hydroxide (3 ml) was added thereto. The reaction mixture was stirred overnight at room temperature, neutralized with 1N hydrochloric acid, and then concentrated under reduced pressure. The resulting residue was extracted with dichloromethane. The organic layer was dried on anhydrous magnesium sulfate and then concentrated under reduced pressure. The resulting residue was purified with silica gel column chromatography (n-hexane/ethyl acetate=1/4, v/v) to give 1 mg of the titled compound as a white solid.

1H-NMR(400 MHz, CDCl$_3$) δ 8.34 (d, 1H), 7.72 (brs, 2H), 7.60 (d, 1H), 7.54 (m, 2H), 7.23 (m, 2H), 7.13 (m, 2H), 6.39 (d, 2H), 5.37 (s, 2H), 5.01 (s, 3H), 2.38 (s, 3H), 2.09 (s, 3H)

EXAMPLE 397

2,3-dimethyl-7-(naphthalen-1-yl)-1H-pyrrolo[2,3-c]pyridine

Step 1: 2-(naphthalen-1-yl)-3-nitropyridine

In accordance with the same procedures as Preparation 9, except for using 1-naphthaleneboronic acid, the titled compound was obtained as a white solid. (Yield: 56%)

Step 2: 2,3-dimethyl-7-(naphthalen-1-yl)-1H-pyrrolo[2,3-c]pyridine

In accordance with the same procedures as in Example 242, except for using 2-(naphthalen-1-yl)-3-nitropyridine prepared in Step 1, the titled compound was obtained as a white solid. (Yield: 35%)

1H-NMR(400 MHz, CDCl$_3$) δ 8.41 (d, 1H), 7.96 (t, 2H), 7.79 (d, 1H), 7.69 (m, 2H), 7.62 (t, 1H), 7.60 (t, 1H), 7.44 (m, 2H), 2.31 (s, 3H), 2.28 (s, 3H)

EXAMPLES 398 TO 401

The titled compounds of Examples 398 to 401 were prepared, in accordance with the same procedures as in Example 243, using 2,3-dimethyl-7-(naphthalen-1-yl)-1H-pyrrolo[2,3-c]pyridine prepared in Example 397; and, benzyl bromide, 1-iodo-2-methylpropane, 1-bromopropane, or 3-methoxybenzyl bromide.

EXAMPLE 398

1-benzyl-2,3-dimethyl-7-(naphthalen-1-yl)-1H-pyrrolo[2,3-c]pyridine hydrochloride 1H-NMR(400 MHz, CDCl$_3$) δ 9.30 (brs, 1H), 8.16 (brs, 1H), 8.15 (brs, 1H), 8.01 (brs, 1H), 7.21 (m, 2H), 7.01 (m, 2H), 6.77 (m, 2H), 6.01 (s, 2H), 5.71 (d, 1H), 5.40 (d, 1H), 4.59 (d, 1H), 4.39 (d, 1H), 2.45 (s, 3H), 2.30 (s, 3H); (Yield: 37%)

EXAMPLE 399

1-isobutyl-2,3-dimethyl-7-(naphthalen-1-yl)-1H-pyrrolo[2,3-c]pyridine hydrochloride 1H-NMR(400 MHz, CDCl$_3$) δ 8.41 (d, 1H), 7.96 (t, 2H), 7.79 (d, 1H), 7.71 (m, 2H), 7.70 (m, 1H), 7.45 (m, 1H), 7.44 (m, 1H), 3.66 (s, 2H), 2.55 (s, 1H), 2.31 (s, 3H), 2.28 (s, 3H), 0.79 (d, 2H), 0.65 (d, 3H); (Yield: 42%)

EXAMPLE 400

2,3-dimethyl-7-(naphthalen-1-yl)-1-propyl-1H-pyrrolo[2,3-c]pyridine hydrochloride 1H-NMR(400 MHz, CDCl$_3$) δ 9.02 (d, 1H), 8.24 (d, 1H), 8.05 (m, 2H), 7.86 (d, 1H), 7.77 (d, 1H), 7.66 (d, 1H), 7.56 (m, 1H), 7.11 (d, 1H), 4.41 (m, 1H), 4.05 (m, 1H), 3.12 (m, 1H), 3.01 (m, 1H), 2.45 (s, 3H), 2.38 (s, 3H), 0.75 (t, 3H); (Yield: 41%)

EXAMPLE 401

1-(3-methoxybenzyl)-2,3-dimethyl-7-(naphthalen-1-yl)-1H-pyrrolo[2,3-c]pyridine hydrochloride 1H-NMR(400 MHz, CDCl$_3$) δ 8.41 (d, 1H), 8.01 (d, 1H), 7.88 (d, 1H), 7.56 (m, 2H), 7.40 (m, 2H), 7.21 (m, 1H), 7.12 (m, 1H), 6.98 (m, 1H), 6.72 (d, 1H), 6.32 (d, 1H), 6.22 (s, 1H), 4.92 (d, 2H), 3.65 (s, 3H), 2.48 (s, 3H), 2.33 (s, 3H); (Yield: 36%)

EXAMPLE 402

2,3-dimethyl-7-(naphthalen-2-yl)-1H-pyrrolo[2,3-c]pyridine hydrochloride

In accordance with the same procedures as in Example 242, using 2-(naphthalen-2-yl)-3-nitropyridine prepared in Preparation 16, 2,3-dimethyl-7-(naphthalen-2-yl)-1H-pyrrolo[2,3-c]pyridine was obtained. The product was dissolved in ethyl acetate, saturated with hydrochloric acid gas, and then filtered to give the titled compound as a white solid. (Yield: 46%)

1H-NMR(400 MHz, CDCl$_3$) δ 8.37 (d, 1H), 8.33 (s, 1H), 8.20 (d, 1H), 8.01 (s, 1H), 7.95 (m, 1H), 7.85 (m, 1H), 7.55 (m, 2H), 7.35 (d, 1H), 7.10 (d, 1H), 2.44 (s, 3H), 2.17 (s, 3H)

EXAMPLES 403 TO 409

The titled compounds of Examples 403 to 409 were prepared, in accordance with the same procedures as in Example 243, using 2,3-dimethyl-7-(naphthalen-2-yl)-1H-pyrrolo[2,3-c]pyridine hydrochloride prepared in Example 402; and, (bromomethyl)cyclopropane, iodoethane, 3-fluorobenzyl chloride, 4-tert-butylbenzyl chloride, 1-iodopropane, propargyl bromide, or 2-fluorobenzyl bromide.

EXAMPLE 403

1-cyclopropylmethyl-2,3-dimethyl-7-(naphthalen-2-yl)-1H-pyrrolo[2,3-c]pyridine hydrochloride 1H-NMR(400 MHz, CDCl$_3$) δ 8.19 (s, 2H), 7.91 (m, 3H), 7.63 (m, 2H), 7.52 (m, 2H), 3.80 (d, 2H), 2.54 (s, 3H), 2.38 (s, 3H), 0.56 (m, 1H), 0.19 (m, 2H), −0.30 (m, 2H); (Yield: 52%)

EXAMPLE 404

1-ethyl-2,3-dimethyl-7-(naphthalen-2-yl)-1H-pyrrolo[2,3-c]pyridine hydrochloride 1H-NMR(400 MHz, CDCl$_3$) δ 8.21 (s, 1H), 8.01 (m, 2H), 7.89 (m, 2H), 7.77 (m, 2H), 7.56 (m, 2H), 3.82 (q, 2H), 2.50 (s, 3H), 2.36 (s, 3H), 1.25 (t, 3H); (Yield: 59%)

EXAMPLE 405

1-(3-fluorobenzyl)-2,3-dimethyl-7-(naphthalen-2-yl)-1H-pyrrolo[2,3-c]pyridine hydrochloride 1H-NMR(400 MHz, CDCl$_3$) δ 8.23 (s, 1H), 8.15 (s, 1H), 7.82 (m, 2H), 7.76 (d, 2H), 7.56 (m, 3H), 7.08 (m, 1H), 6.91 (t, 1H), 5.98 (d, 1H), 5.90 (d, 1H), 5.01 (s, 2H), 2.43 (s, 3+3H); (Yield: 43%)

EXAMPLE 406

1-(4-tert-butylbenzyl)-2,3-dimethyl-7-(naphthalen-2-yl)-1H-pyrrolo[2,3-c]pyridine hydrochloride 1H-NMR(400 MHz, CDCl$_3$) δ 8.17 (s, 1H), 7.93 (m, 3H), 7.67 (m, 3H), 7.56 (m, 2H), 7.04 (d, 2H), 6.09 (d, 2H), 5.00 (s,2H), 2.45 (s, 3H), 2.43 (s, 3H), 1.25 (s, 9H); (Yield: 73%)

EXAMPLE 407

2,3-dimethyl-7-(naphthalen-2-yl)-1-propyl-1H-pyrrolo[2,3-c]pyridine hydrochloride 1H-NMR(400 MHz, CDCl$_3$) δ 8.21 (s, 1H), 8.05 (s, 1H), 7.92 (m, 2H), 7.61 (m, 2H), 7.55 (m,3H), 3.70 (t, 2H), 2.49 (s, 3H), 2.36 (s, 3H), 0.82 (m, 2H), 0.24 (t, 3H); (Yield: 70%)

EXAMPLE 408

2,3-dimethyl-7-(naphthalen-2-yl)-1-(prop-2-ynyl)-1H-pyrrolo[2,3-c]pyridine hydrochloride 1H-NMR(400 MHz, CDCl$_3$) δ 8.28 (s, 1H), 8.25 (s, 1H), 8.01 (m, 3H), 7.82 (m, 2H), 7.52 (m, 2H), 5.16 (s, 2H), 2.55 (s, 1H), 2.41 (s, 3H), 2.11 (s, 3H); (Yield: 60%)

EXAMPLE 409

1-(2-fluorobenzyl)-2,3-dimethyl-7-(naphthalen-2-yl)-1H-pyrrolo[2,3-c]pyridine hydrochloride 1H-NMR(400 MHz, CDCl$_3$) δ 8.20 (s, 1H), 8.07 (s, 1H), 7.98 (d, 1H), 7.89 (d, 1H), 7.65 (m, 2H), 7.55 (m, 3H), 7.19 (m, 1H), 6.92 (t, 1H), 6.71 (t, 1H), 6.01 (t, 1H), 5.02 (s, 2H), 2.43 (s, 3H), 2.08 (s, 3H); (Yield: 66%)

EXAMPLE 410

2,3-dimethyl-7-(naphthalen-2-yl)-1H-pyrrolo[2,3-c]pyridine sodium

The compound prepared in Example 402 was treated with a saturated sodium bicarbonate solution to obtain 2,3-dimethyl-7-(naphthalen-2-yl)-1H-pyrrolo[2,3-c]pyridine. A solution of 2,3-dimethyl-7-(naphthalen-2-yl)-1H-pyrrolo[2,3-c]pyridine (73.5 mg, 0.27 mmol) and sodium hydride (6.5 mg, 0.27 mmol) in anhydrous tetrahydrofuran (2 ml) was stirred for 2 hours at room temperature and then concentrated under reduced pressure. The resulting residue was re-crystallized with ethyl ether to give 73 mg of the titled compound as a pale yellow solid.

1H-NMR(400 MHz, MeOH-d$_4$) δ 8.48 (brs, 1H), 8.24 (m, 1H), 8.16 (m, 2H), 8.06 (m, 2H), 7.92 (m, 1H), 7.70 (m, 2H), 2.59 (s, 3H), 2.39 (s, 3H)

EXAMPLE 411

1-(3-fluorobenzyl)-3-hydroxymethyl-2-methyl-7-(naphthalen-2-yl)-1H-pyrrolo[2,3-c]pyridine hydrochloride The compound prepared in Example 405 was treated with a saturated sodium bicarbonate solution to obtain 1-(3-fluorobenzyl)-2,3-dimethyl-7-(naphthalen-2-yl)-1H-pyrrolo[2,3-c]pyridine. 1-(3-Fluorobenzyl)-2,3-dimethyl-7-(naphthalen-2-yl)-1H-pyrrolo[2,3-c]pyridine (225 mg, 0.59 mmol) was dissolved in acetic acid (5 ml) and ammonium cerium (IV) nitrate (973 mg, 1.77 mmol) was added thereto at room temperature. The reaction mixture was stirred for 3 hours at 55° C. and then cooled to room temperature. Water was added to the reaction mixture, which was then extracted with ethyl acetate. The organic layer washed with a saturated sodium chloride solution, dried on anhydrous magnesium sulfate, and then concentrated under reduced pressure. The resulting residue was dissolved in methanol (10 ml) and then 2N lithium hydroxide (2.5 ml) was added thereto. The reaction mixture was stirred for 1 hour at room temperature, neutralized with 1N hydrochloric acid solution, and then concentrated under reduced pressure. The resulting residue was extracted with ethyl acetate. The organic layer was dried on anhydrous magnesium sulfate and then concentrated under reduced pressure. The resulting residue was purified with silica gel column chromatography. The resulting product was dissolved in ethyl acetate, saturated with hydrochloric acid gas, and then filtered to give 45 mg of the titled compound as a white solid.

1H-NMR(400 MHz, CDCl$_3$) δ 8.17 (s, 1H), 8.04 (s, 1H), 7.86 (t, 2H), 7.74 (s, 1H), 7.57 (m, 3H), 7.41 (m, 1H), 7.01 (m, 1H), 6.86 (t, 1H), 6.01 (d, 1H), 5.92 (d, 1H), 5.03 (s, 2H), 4.98 (s, 2H), 2.51 (s, 3H)

EXAMPLE 412

1-benzyl-3-hydroxymethyl-2-methyl-7-(4-methylsulfanylphenyl)-1H-pyrrolo[2,3-c]pyridine hydrochloride 18-Crown-6 (26 mg, 0.098 mmol) and potassium tert-butoxide (253 mg, 2.25 mmol) were added to a solution of 2,3-dimethyl-7-(4-methylsulfanylphenyl)-1H-pyrrolo[2,3-c]pyridine (300 mg, 0.98 mmol) prepared in Example 262 in anhydrous tetrahydrofuran (9 ml). The reaction mixture was stirred for 30 minutes at room temperature and benzyl bromide (175 µl, 1.47 mmol) was added thereto. The reaction mixture was stirred overnight. The reaction mixture was diluted with ethyl acetate and water was added thereto. The separated organic layer was dried on anhydrous magnesium sulfate, and then concentrated under reduced pressure. The resulting residue was purified with silica gel column chromatography. The resulting pale yellow solid (242 mg, 0.67 mmol) was dissolved in 6 ml of acetic acid. Ammonium cerium (IV) nitrate (1.11 g, 2.01 mmol) was added at room temperature to the resulting solution, which was stirred for 3 hours at 55° C. and then cooled to room temperature. Water was added to the reaction mixture, which was then extracted with ethyl acetate. The organic layer washed with a saturated sodium chloride solution, dried on anhydrous magnesium sulfate, and then concentrated under reduced pressure. The resulting residue was dissolved in methanol (11 ml) and 2N lithium hydroxide (3 ml) was added thereto. The reaction mixture was stirred for 1 hour at room temperature, neutralized with 1N hydrochloric acid, and then concentrated under reduced pressure. The resulting residue was extracted with ethyl acetate. The organic layer was dried on anhydrous magnesium sulfate and then concentrated under reduced pressure. The resulting residue was purified with silica gel column chromatography to obtain 1-benzyl-3-hydroxymethyl-2-methyl-7-(4-methylsulfanylphenyl)-1H-pyrrolo[2,3-c]pyridine. The product was dissolved in ethyl acetate, saturated with hydrochloric acid gas, and then filtered to give 48 mg of the titled compound as a white solid.

1H-NMR(400 MHz, CDCl$_3$) δ 8.23 (brs, 1H), 8.09 (d, 1H), 7.75 (m, 1H), 7.48 (brs, 3H), 7.20 (m, 1H), 7.15 (m, 2H), 6.31 (d, 2H), 5.09 (s, 2H), 4.93 (s, 2H), 2.79 (s, 3H), 2.55 (s, 3H)

EXAMPLE 413

1-benzyl-3-ethoxymethyl-2-methyl-7-(4-methylsulfanylphenyl)-1H-pyrrolo[2,3-c]pyridine hydrochloride 18-Crown-6 (3 mg, 0.011 mmol) and potassium tert-butoxide (37 mg, 0.291 mmol) were added to a solution of 1-benzyl-3-hydroxymethyl-2-methyl-7-(4-methylsulfanylphenyl)-1H-pyrrolo[2,3-c]pyridine hydrochloride (48 mg, 0.11 mmol) prepared in Example 412 in anhydrous tetrahydrofuran (1 ml). The reaction mixture was stirred for 30 minutes at room temperature and iodoethane (10 μl, 0.165 mmol) was added thereto. The reaction mixture was stirred overnight and then concentrated under reduced pressure. The resulting residue was purified with silica gel column chromatography. The resulting product was dissolved in ethyl acetate, saturated with hydrochloric acid gas, and then filtered to give 6.7 mg of the titled compound as a white solid.

1H-NMR(400 MHz, CDCl$_3$) δ 8.35 (s, 1H), 7.97 (d, 1H), 7.23 (m, 7H), 6.36 (d, 2H), 5.10 (s, 2H), 4.76 (s, 2H), 3.67 (q, 2H), 2.79 (s, 3H), 2.51 (s, 3H), 1.32 (t, 3H)

EXAMPLE 414

2,3-dimethyl-7-styryl-1H-pyrrolo[2,3-c]pyridine hydrochloride

In accordance with the same procedures as in Example 242, using 3-nitro-2-styrylpyridine prepared in Preparation 17 as a starting matertal, 2,3-dimethyl-7-styryl-1H-pyrrolo[2,3-c]pyridine was obtained. The product was dissolved in ethyl acetate, saturated with hydrochloric acid gas, and then filtered to give the titled compound as a white solid. (Yield: 32%)

1H-NMR(400 MHz, CDCl$_3$) δ 7.94 (s, 1H), 7.79 (t, 1H), 7.47 (m, 2H), 7.20 (m, 2H), 7.07 (m, 3H), 2.59 (s, 3H), 2.06 (s, 3H)

EXAMPLES 415 TO 427

The titled compounds of Examples 415 to 427 were prepared, in accordance with the same procedures as in Example 243, using 2,3-dimethyl-7-styryl-1H-pyrrolo[2,3-c]pyridine hydrochloride prepared in Example 414; and, iodoethane, allyl bromide, 4-methylbenzyl chloride, benzyl bromide, 3-fluorobenzyl bromide, 2-bromoethyl methyl ether, 1-bromo-2-methylpropane, 3-methoxybenzyl chloride, (bromomethyl)cyclopropane, iodomethane, bromomethyl methyl ether, 4-methoxybenzyl bromide, or 4-chlorobenzyl bromide.

EXAMPLE 415

1-ethyl-2,3-dimethyl-7-styryl-1H-pyrrolo[2,3-c]pyridine hydrochloride

1H-NMR(400 MHz, CDCl$_3$) δ 8.50 (m, 1H), 8.26 (s, 1H), 7.72 (brs, 2H), 7.52 (m, 2H), 7.41 (s, 3H), 4.50 (s, 2H), 2.53 (s, 3H), 2.30 (s, 3H); (Yield: 52%)

EXAMPLE 416

1-allyl-2,3-dimethyl-7-styryl-1H-pyrrolo[2,3-c]pyridine hydrochloride

1H-NMR(400 MHz, CDCl$_3$) δ 8.07 (d, 1H), 7.89 (d, 1H), 7.70 (d, 3H), 7.50 (m, 4H), 6.23 (m, 1H), 5.33 (d, 1H), 5.16 (s, 2H), 4.68 (d, 1H), 2.54 (s, 3H), 2.39 (s, 3H); (Yield: 48%)

EXAMPLE 417

2,3-dimethyl-1-(4-methylbenzyl)-7-styryl-1H-pyrrolo[2,3-c]pyridine hydrochloride 1H-NMR(400 MHz, CDCl$_3$) δ 8.05 (d, 1H), 7.92 (d, 1H), 7.41 (brs, 7H), 7.16 (d, 2H), 6.84 (d, 2H), 5.76 (s, 2H), 2.56 (s, 3H), 2.43 (s, 3H), 2.29 (s, 3H); (Yield: 39%)

EXAMPLE 418

1-benzyl-2,3-dimethyl-7-styryl-1H-pyrrolo[2,3-c]pyridine hydrochloride

1H-NMR(400 MHz, CDCl$_3$) δ 8.11 (d, 1H), 7.92 (m, 2H), 7.72 (m, 2H), 7.54 (m, 1H), 7.45 (m, 4H), 7.33 (m, 2H), 6.95 (d, 2H), 5.82 (s, 2H), 2.57 (s, 3H), 2.44 (s, 3H); (Yield: 52%)

EXAMPLE 419

1-(3-fluorobenzyl)-2,3-dimethyl-7-styryl-1H-pyrrolo[2,3-c]pyridine hydrochloride 1H-NMR(400 MHz, CDCl$_3$) δ 7.87 (t, 1H), 7.75 (d, 1H), 7.59 (t, 1H), 7.59 (m, 2H), 7.55 (m, 3H), 7.44 (m, 5H), 5.83 (s, 2H), 2.57 (s, 3H), 2.44 (s, 3H); (Yield: 44%)

EXAMPLE 420

1-(2-methoxyethyl)-2,3-dimethyl-7-styryl-1H-pyrrolo[2,3-c]pyridine hydrochloride 1H-NMR(400 MHz, CDCl$_3$) δ 8.03 (d, 1H), 8.08 (d, 1H), 7.86 (m, 1H), 7.75 (m,2H), 7.68 (m, 1H), 7.48 (m, 3H), 4.72 (t, 2H), 3.81 (t, 2H), 3.29 (d, 3H), 2.59 (s, 3H), 2.36 (s, 3H); (Yield: 74%)

EXAMPLE 421

1-isobutyl-2,3-dimethyl-7-styryl-1H-pyrrolo[2,3-c]pyridine hydrochloride

1H-NMR(400 MHz, CDCl$_3$) δ 8.05 (s, 1H), 7.87 (brs, 2H), 7.77 (m, 2H), 7.49 (m, 4H), 4.38 (brs, 2H), 2.60 (s, 3H), 2.37 (s, 3H), 2.15 (m, 1H), 0.87 (brs, 3+3H); (Yield: 44%)

EXAMPLE 422

1-(3-methoxybenzyl)-2,3-dimethyl-7-styryl-1H-pyrrolo[2,3-c]pyridine hydrochloride 1H-NMR(400 MHz, CDCl$_3$) δ 7.91 (d, 1H), 7.73 (m, 1H), 7.68 (m, 1H), 7.59 (m, 1H), 7.25 (m, 5H), 6.87 (d, 2H), 6.57 (s, 1H), 6.45 (d, 1H), 5.77 (s, 2H), 3.67 (s, 2H), 2.58 (s, 3H), 2.44 (s, 3H); (Yield: 49%)

EXAMPLE 423

1-cyclopropylmethyl-2,3-dimethyl-7-styryl-1H-pyrrolo[2,3-c]pyridine hydrochloride 1H-NMR(400 MHz, CDCl$_3$) δ 8.28 (d, 1H) 7.38-7.55 (m, 7H), 3.72 (d, 2H), 2.39 (s, 3H), 2.29 (s, 3H), 0.51 (m, 1H), 0.17 (m, 2H), −0.20 (m, 2H); (Yield: 51%)

EXAMPLE 424

1,2,3-trimethyl-7-styryl-1H-pyrrolo[2,3-c]pyridine hydrochloride

1H-NMR(400 MHz, CDCl$_3$) δ 8.01 (s, 2H), 7.84 (d, 1H), 7.79 (d, 2H), 7.50 (m, 4H), 4.13 (s, 3H), 2.58 (s, 3H), 2.36 (s, 3H); (Yield: 51%)

EXAMPLE 425

1-methoxymethyl-2,3-dimethyl-7-styryl-1H-pyrrolo[2,3-c]pyridine hydrochloride

1H-NMR(400 MHz, CDCl$_3$) δ 8.14 (d, 1H), 8.04 (d, 1H), 7.90 (d, 1H), 7.74 (d, 2H), 7.65 (d, 1H), 7.46 (m, 3H), 5.73 (s, 2H), 3.45 (s, 3H), 2.66 (s, 3H), 2.37 (s, 3H); (Yield: 39%)

EXAMPLE 426

1-(4-methoxybenzyl)-2,3-dimethyl-7-styryl-1H-pyrrolo[2,3-c]pyridine hydrochloride 1H-NMR(400 MHz, CDCl$_3$) δ 8.04 (d, 1H), 7.91 (d, 1H), 7.45 (m, 7H), 6.87 (s, 4H), 5.73 (s, 2H), 3.72 (s, 3H), 2.56 (s, 3H), 2.42 (s 3H); (Yield: 42%)

EXAMPLE 427

1-(4-chlorobenzyl)-2,3-dimethyl-7-styryl-1H-pyrrolo[2,3-c]pyridine hydrochloride 1H-NMR(400 MHz, CDCl$_3$) δ 8.15 (d, 1H), 7.95 (m, 2H), 7.77 (m, 2H), 7.42 (brs, 4H), 7.32 (m, 2H), 6.92 (d, 2H), 5.80 (s, 2H), 2.56 (s, 3H), 2.42 (s, 3H); (Yield: 47%)

EXAMPLE 428

7-benzyl-2,3-dimethyl-1H-pyrrolo[2,3-c]pyridine hydrochloride

In accordance with the same procedures as in Example 242, using 2-benzyl-3-nitropyridine prepared in Preparation 18, 7-benzyl-2,3-dimethyl-1H-pyrrolo[2,3-c]pyridine was obtained. The product was dissolved in ethyl acetate, saturated with hydrochloric acid gas, and then filtered to give the titled compound as a white solid. (Yield: 35%)

1H-NMR(400 MHz, DMSO-d$_6$) δ 8.11 (d, 1H), 7.83 (d, 1H), 7.44 (d, 2H), 7.34 (m, 2H), 7.25 (m, 1H), 4.64 (s, 2H), 2.56 (s, 3H), 2.26 (s, 3H)

EXAMPLES 429 TO 439

The titled compounds of Examples 429 to 439 were prepared, in accordance with the same procedures as in Example 243, using 7-benzyl-2,3-dimethyl-1H-pyrrolo[2,3-c]pyridine hydrochloride prepared in Example 428; and, benzyl bromide, (bromomethyl)cyclopropane, 4-chlorobenzyl chloride, 3-fluorobenzyl bromide, iodoethane, 3-methylbenzyl bromide, 4-methylbenzyl bromide, 4-fluorobenzyl chloride, allyl bromide, 3-chlorobenzyl chloride, or 4-methoxybenzyl bromide.

EXAMPLE 429

1,7-dibenzyl-2,3-dimethyl-1H-pyrrolo[2,3-c]pyridine hydrochloride

1H-NMR(400 MHz, CDCl$_3$) δ 8.24 (s, 1H), 7.73 (s, 1H), 7.33 (s, 3H), 7.26 (s, 3H), 6.99 (s, 2H), 6.66 (s, 2H), 5.30 (s, 2H), 4.69 (s, 2H), 2.37 (s, 3+3H); (Yield: 38%)

EXAMPLE 430

7-benzyl-1-cyclopropylmethyl-2,3-dimethyl-1H-pyrrolo[2,3-c]pyridine hydrochloride 1H-NMR(400 MHz, CDCl$_3$) δ 8.22 (t, 1H), 7.65 (d, 1H), 7.22 (m, 3H), 7.09 (d, 2H), 5.09 (s, 2H), 4.13 (d, 2H), 2.45 (s, 3H), 2.30 (s, 3H), 1.01 (m, 1H), 0.63 (m, 2H), 0.24 (m, 2H); (Yield: 39%)

EXAMPLE 431

7-benzyl-1-(4-chlorobenzyl)-2,3-dimethyl-1H-pyrrolo[2,3-c]pyridine hydrochloride 1H-NMR(400 MHz, CDCl$_3$) δ 8.25 (t, 1H), 7.74 (d, 1H), 7.23 (m, 5H), 6.96 (d, 2H), 6.59 (d, 2H), 5.28 (s, 2H), 4.72 (s, 2H), 2.36 (s, 3H), 2.35 (s, 3H); (Yield: 42%)

EXAMPLE 432

7-benzyl-1-(3-fluorobenzyl)-2,3-dimethyl-1H-pyrrolo[2,3-c]pyridine hydrochloride 1H-NMR(400 MHz, CDCl$_3$) δ 8.25 (t, 1H), 7.75 (d, 1H), 7.24 (m, 4H), 7.02 (t, 2H), 6.97 (d, 2H), 6.46 (d, 1H), 6.32 (d, 1H), 5.29 (s, 2H), 4.72 (s, 2H), 2.37 (s, 3+3H); (Yield: 42%)

EXAMPLE 433

7-benzyl-1-ethyl-2,3-dimethyl-1H-pyrrolo[2,3-c]pyridine hydrochloride

1H-NMR(400 MHz, CDCl$_3$) δ 8.19 (t, 1H), 7.65 (d, 1H), 7.27 (m, 3H), 7.09 (d, 2H), 5.02 (s, 2H), 4.21 (q, 2H), 2.45 (s, 3H), 2.30 (s, 3H), 1.21 (t, 3H); (Yield: 46%)

EXAMPLE 434

7-benzyl-2,3-dimethyl-1-(3-methylbenzyl)-1H-pyrrolo[2,3-c]pyridine hydrochloride 1H-NMR(400 MHz, CDCl$_3$) δ 8.23 (t, 1H), 7.73 (d, 1H), 7.23 (m, 4H), 7.13 (d, 1H), 6.99 (d, 2H), 6.45 (s, 1H), 6.43 (d, 1H), 5.26 (s, 2H), 4.70 (s, 2H), 2.37 (s, 3+3H), 2.29 (s, 3H); (Yield: 39%)

EXAMPLE 435

7-benzyl-2,3-dimethyl-1-(4-methylbenzyl)-1H-pyrrolo[2,3-c]pyridine hydrochloride 1H-NMR(400 MHz, CDCl$_3$) δ 8.22 (t, 1H), 7.72 (d, 1H), 7.24 (m, 3H), 7.13 (d, 2H), 6.99 (d, 2H), 6.56 (d, 2H), 5.25 (s, 2H), 4.69 (s, 2H), 2.37 (s, 3H), 2.36 (s, 3H), 2.34 (s, 3H); (Yield: 39%)

EXAMPLE 436

7-benzyl-1-(4-fluorobenzyl)-2,3-dimethyl-1H-pyrrolo[2,3-c]pyridine hydrochloride 1H-NMR(400 MHz, CDCl$_3$) δ 8.24 (t, 1H), 7.74 (d, 1H), 7.21 (m, 3H), 7.04 (t, 2H), 6.97 (d, 2H), 6.63 (m, 2H), 5.28 (s, 2H), 4.72 (s, 2H), 2.36 (s, 3+3H); (Yield: 47%)

EXAMPLE 437

1-allyl-7-benzyl-2,3-dimethyl-1H-pyrrolo[2,3-c]pyridine hydrochloride

1H-NMR(400 MHz, CDCl$_3$) δ 8.23 (t, 1H), 7.69 (d, 1H), 7.25 (m, 3H), 7.05 (d, 2H), 5.94 (m, 1H), 5.21 (d, 1H), 4.96 (s, 2H), 4.70 (s, 2H), 4.43 (d, 1H), 2.32 (s, 3H), 2.28 (s, 3H); (Yield: 45%)

EXAMPLE 438

7-benzyl-1-(3-chlorobenzyl)-2,3-dimethyl-1H-pyrrolo[2,3-c]pyridine hydrochloride 1H-NMR(400 MHz, CDCl$_3$) δ 8.26 (t, 1H), 7.75 (d, 1H), 7.23 (m, 5H), 6.96 (d, 2H), 6.62 (s, 1H), 6.52 (d, 1H), 5.28 (s, 2H), 4.73 (s, 2H), 2.37 (s, 3H), 2.35 (s, 3H); (Yield: 41%)

EXAMPLE 439

7-benzyl-1-(4-methoxybenzyl)-2,3-dimethyl-1H-pyrrolo[2,3-c]pyridine hydrochloride 1H-NMR(400 MHz, CDCl$_3$) δ 8.21 (t, 1H), 7.71 (d, 1H), 7.21 (m, 2H), 6.98 (d, 2H), 6.85 (d, 2H), 6.61 (m, 2+1H), 5.23 (s, 2H), 4.70 (s, 2H), 3.81 (s, 3H), 2.37 (s, 3H), 2.36 (s, 3H); (Yield: 39%)

EXAMPLE 440

2,3-dimethyl-7-phenethyl-1H-pyrrolo[2,3-c]pyridine hydrochloride

In accordance with the same procedures as in Example 242, using 3-phenethyl-2-nitropyridine prepared in Preparation 19, 2,3-dimethyl-7-phenethyl-1H-pyrrolo[2,3-c]pyridine was obtained. The product was dissolved in ethyl acetate, saturated with hydrochloric acid gas, and then filtered to give the titled compound as a white solid. (Yield: 43%)

1H-NMR(400 MHz, CDCl$_3$) δ 7.92 (d, 1H), 7.73 (d, 1H), 7.22 (m, 3H), 7.11 (d, 2H), 3.54 (t, 2H), 3.16 (t, 2H), 2.54 (s, 3H), 2.30 (s, 3H)

EXAMPLE 441 TO 462

The titled compounds of Examples 441 to 462 were prepared, in accordance with the same procedures as in Example 243, using 2,3-dimethyl-7-phenethyl-1H-pyrrolo[2,3-c]pyridine hydrochloride prepared in Example 440; and, iodoethane, benzyl bromide, 2-bromoethyl methyl ether, 4-methylbenzyl chloride, 4-methoxybenzyl chloride, 4-chlorobenzyl chloride, 1-iodo-2-methylpropane, allyl bromide, 3-fluorobenzyl chloride, 2-fluorobenzyl chloride, 3,4-dichlorobenzyl chloride, 4-chloromethyl-2-methylthiazole, (bromomethyl)cyclopropane, cinnamyl chloride, 4-fluorobenzyl chloride, 4-chloromethyl-3,5-dimethylisoxazole, 4-bromo-2-methyl-2-butene, propargyl bromide, propargyl bromide, iodomethane, 2-chlorobenzyl chloride, or epibromohydrin.

EXAMPLE 441

1-ethyl-2,3-dimethyl-7-phenethyl-1H-pyrrolo[2,3-c]pyridine hydrochloride

1H-NMR(400 MHz, CDCl$_3$) δ 8.13 (s, 1H), 7.58 (s, 1H), 7.31 (m, 5H), 4.27 (q, 2H), 3.82 (brs, 2H), 3.30 (brs, 2H), 2.50 (s, 3H), 2.30 (s, 3H), 1.37 (t, 3H); (Yield: 67%)

EXAMPLE 442

1-benzyl-2,3-dimethyl-7-phenethyl-1H-pyrrolo[2,3-c]pyridine hydrochloride

1H-NMR(400 MHz, CDCl$_3$) δ 8.16 (brs, 1H), 7.64 (brs, 1H), 7.31 (m, 3H), 7.23 (m, 3H), 7.12 (brs, 2H), 6.71 (brs, 2H), 5.40 (brs, 2H), 3.57 (brs, 2H), 3.14 (brs, 2H), 2.42 (s, 3H), 2.37 (s, 3H); (Yield: 52%)

EXAMPLE 443

1-(2-methoxyethyl)-2,3-dimethyl-7-phenethyl-1H-pyrrolo[2,3-c]pyridine hydrochloride 1H-NMR(400 MHz, CDCl$_3$) δ 8.13 (s, 1H), 7.56 (s, 1H), 7.29 (m, 4H), 7.23 (m, 1H), 4.36 (brs, 2H), 3.85 (brs, 2H), 3.58 (s, 3H), 3.24 (brs, 2H), 3.20 (s, 3H), 2.48 (s, 3H), 2.29 (s, 3H); (Yield: 49%)

EXAMPLE 444

2,3-dimethyl-1-(4-methylbenzyl)-7-phenethyl-1H-pyrrolo[2,3-c]pyridine hydrochloride 1H-NMR(400 MHz, CDCl$_3$) δ 8.16 (s, 1H), 7.63 (s, 1H), 7.25 (m, 3H), 7.03 (m, 4H), 6.59 (brs, 2H), 3.58 (brs, 2H), 3.14 (brs, 2H), 2.41 (s, 3H), 2.35 (s, 3H), 2.31 (s,3H); (Yield: 56%)

EXAMPLE 445

1-(4-methoxybenzyl)-2,3-dimethyl-7-phenethyl-1H-pyrrolo[2,3-c]pyridine hydrochloride 1H-NMR(400 MHz, CDCl$_3$) δ 7.13 (m, 5H), 6.95 (m, 2H), 6.73 (m, 2H), 6.62 (brs, 2H), 5.34 (brs, 2H), 3.76 (brs, 3H), 3.47 (brs, 2H), 3.15 (brs, 2H), 2.42 (s, 3H), 2.36 (s, 3H); (Yield: 62%)

EXAMPLE 446

1-(4-chlorobenzyl)-2,3-dimethyl-7-phenethyl-1H-pyrrolo[2,3-c]pyridine hydrochloride 1H-NMR(400 MHz, CDCl$_3$) δ 8.19 (s, 1H), 7.71 (s, 1H), 7.26 (m, 5H), 7.04 (brs, 2H), 6.64 (brs, 2H), 5.34 (brs, 2H), 3.48 (brs, 2H), 3.17 (brs, 2H), 2.40 (s, 3H), 2.37 (s, 3H); (Yield: 52%)

EXAMPLE 447

1-isobutyl-2,3-dimethyl-7-phenethyl-1H-pyrrolo[2,3-c]pyridine hydrochloride

1H-NMR(400 MHz, CDCl$_3$) δ 7.21 (m, 7H), 3.99 (brs, 2H), 3.81 (brs, 2H), 3.28 (brs, 2H), 2.50 (brs, 3H), 2.33 (brs, 3H), 2.10 (brs, 1H), 0.88 (brs, 6H); (Yield: 39%)

EXAMPLE 448

1-allyl-2,3-dimethyl-7-phenethyl-1H-pyrrolo[2,3-c]pyridine hydrochloride

1H-NMR(400 MHz, CDCl$_3$) δ 8.16 (brs, 1H), 7.60 (brs, 1H), 7.31 (m, 3H), 7.22 (m, 2H), 5.98 (m, 1H), 5.25 (d, 1H), 4.80 (s, 2H), 4.48 (d, 1H), 3.74 (brs, 2H), 3.28 (brs, 2H), 2.49 (s, 3H), 2.35 (s, 3H); (Yield: 58%)

EXAMPLE 449

1-(3-fluorobenzyl)-2,3-dimethyl-7-phenethyl-1H-pyrrolo[2,3-c]pyridine hydrochloride 1H-NMR(400 MHz, CDCl$_3$) δ 8.20 (brs, 1H), 7.65 (brs, 1H), 7.25 (m, 3H), 7.12 (m, 2H), 7.01 (m, 2H), 6.51 (m, 1H), 6.38 (m, 1H), 5.34 (s, 2H), 3.49 (brs, 2H), 3.16 (brs, 2H), 2.42 (s, 3H), 2.37 (s, 3H); (Yield: 51%)

EXAMPLE 450

1-(2-fluorobenzyl)-2,3-dimethyl-7-phenethyl-1H-pyrrolo[2,3-c]pyridine hydrochloride 1H-NMR(400 MHz, CDCl$_3$) δ 8.20 (brs, 1H), 7.67 (brs, 1H), 7.25 (m, 3H), 7.17 (m, 3H), 7.00 (m, 2H), 6.10 (m, 1H), 5.45 (s, 2H), 3.54 (brs, 2H), 3.17 (brs, 2H), 2.42 (s, 3H), 2.37 (s, 3H); (Yield: 63%)

EXAMPLE 451

1-(3,4-dichlorobenzyl)-2,3-dimethyl-7-phenethyl-1H-pyrrolo[2,3-c]pyridine hydrochloride 1H-NMR(400 MHz, CDCl$_3$) δ 8.20 (brs, 1H), 7.66 (brs, 1H), 7.38 (brs, 1H), 7.15 (m, 3H), 7.09 (m, 2H), 6.83 (s, 1H), 6.53 (m, 1H), 5.27 (s, 2H), 3.55 (brs, 2H), 3.17 (brs, 2H), 2.40 (s, 3H), 2.37 (s, 3H); (Yield: 59%)

EXAMPLE 452

2,3-dimethyl-1-(2-methylthiazol-4-ylmethyl)-7-phenethyl-1H-pyrrolo[2,3-c]pyridine hydrochloride 1H-NMR(400 MHz, CDCl$_3$) δ 8.18 (brs, 1H), 7.62 (brs, 1H), 7.22 (m, 5H), 6.33 (brs, 1H), 5.45 (s, 2H), 3.73 (brs, 2H), 3.21 (brs, 2H), 2.67 (s, 3H), 2.48 (s, 3H), 2.34 (s, 3H); (Yield: 51%)

EXAMPLE 453

1-cyclopropylmethyl-2,3-dimethyl-7-phenethyl-1H-pyrrolo[2,3-c]pyridine hydrochloride 1H-NMR(400 MHz, CDCl$_3$) δ 8.15 (s, 1H), 7.58 (s, 1H), 7.28 (m, 5H), 4.17 (d, 2H), 3.90 (t, 2H), 3.28 (t, 2H), 2.47 (s, 3H), 2.30 (s, 3H), 1.05 (m, 1H), 0.62 (m, 2H), 0.26 (m, 2H); (Yield: 57%)

EXAMPLE 454

2,3-dimethyl-7-phenethyl-1-(3-phenylallyl)-1H-pyrrolo[2,3-c]pyridine hydrochloride 1H-NMR(400 MHz, CDCl$_3$) δ 8.12 (m, 1H), 7.58 (m, 2H), 7.26 (m, 5H), 7.13 (m, 3H), 6.88 (brs, 1H), 6.28 (brs, 1H), 5.90 (s, 1H), 3.48 (brs, 2H), 3.23 (brs, 2H), 2.49 (s, 3H), 2.20 (s, 3H); (Yield: 52%)

EXAMPLE 455

1-(4-fluorobenzyl)-2,3-dimethyl-7-phenethyl-1H-pyrrolo[2,3-c]pyridine hydrochloride 1H-NMR(400 MHz, CDCl$_3$) δ 8.18 (brs, 1H), 7.61 (brs, 1H), 7.26 (m, 3H), 7.13 (m, 2H), 7.02 (m, 2H), 6.68 (m, 2H), 5.36 (s, 2H), 3.48 (brs, 2H), 3.18 (brs, 2H), 2.41 (s, 3H), 2.37 (s, 3H); (Yield: 43%)

EXAMPLE 456

1-(3,5-dimethylisoxazol-4-ylmethyl)-2,3-dimethyl-7-phenethyl-1H-pyrrolo[2,3-c]pyridine hydrochloride 1H-NMR(400 MHz, CDCl$_3$) δ 8.43 (m, 1H), 8.22 (m, 1H), 7.66 (m, 1H), 7.18 (m, 3H), 6.72 (m, 1H), 5.06 (m, 2H), 3.35 (m, 2H), 3.22 (m, 2H), 2.45 (s, 3H), 2.35 (s, 3H), 2.07 (s, 3+3H); (Yield: 61%)

EXAMPLE 457

1-(3-methylbut-2-enyl)-2,3-dimethyl-7-phenethyl-1H-pyrrolo[2,3-c]pyridine hydrochloride 1H-NMR(400 MHz, CDCl$_3$) δ 8.05 (s, 1H), 7.54 (s, 1H), 7.27 (m, 3H), 6.86 (brs, 2H), 4.93 (brs, 1H), 4.85 (brs, 2H), 3.76 (brs, 2H), 3.26 (brs, 2H), 2.45 (brs, 3H), 2.30 (bs, 3H), 1.69 (brs, 3+3H); (Yield: 65%)

EXAMPLE 458

2,3-dimethyl-7-phenethyl-1-(prop-2-ynyl)-1H-pyrrolo[2,3-c]pyridine hydrochloride 1H-NMR(400 MHz, CDCl$_3$) δ 8.15 (s, 1H), 7.58 (s, 1H), 7.40 (m, 2H), 7.15 (m, 2H), 6.70 (brs, 1H), 5.48 (brs, 2H), 3.92 (brs, 2H), 3.25 (brs, 2H), 2.46 (s, 1H), 2.31 (s, 3H), 2.17 (s, 3H); (Yield: 65%)

EXAMPLE 459

2,3-dimethyl-7-phenethyl-1-(prop-1-ynyl)-1H-pyrrolo[2,3-c]pyridine hydrochloride 1H-NMR(400 MHz, CDCl$_3$) δ 8.22 (s, 1H), 7.59 (s, 1H), 7.41 (m, 2H), 7.27 (m, 2H), 7.24 (m, 1H), 4.08 (brs, 2H), 3.28 (brs, 2H), 2.55 (s, 3H), 2.30 (s, 3H), 2.09 (s, 3H); (Yield: 24%)

EXAMPLE 460

1,2,3-trimethyl-7-phenethyl-1H-pyrrolo[2,3-c]pyridine hydrochloride

1H-NMR(400 MHz, CDCl$_3$) δ 8.11 (brs, 1H), 7.57 (brs, 1H), 7.23 (m, 5H), 3.88 (brs, 3+2H), 3.31 (brs, 2H), 2.48 (s, 3H), 2.31 (s, 3H); (Yield: 86%)

EXAMPLE 461

1-(2-chlorobenzyl)-2,3-dimethyl-7-phenethyl-1H-pyrrolo[2,3-c]pyridine hydrochloride 1H-NMR(400 MHz, CDCl$_3$) δ 8.22 (brs, 1H), 7.68 (brs, 1H), 7.47 (m, 1H), 6.90 (m, 8H), 5.32 (s, 2H), 3.47 (brs, 2H), 3.01 (brs, 2H), 2.46 (brs, 6H); (Yield: 78%)

EXAMPLE 462

2,3-dimethyl-1-oxiranylmethyl-7-phenethyl-1H-pyrrolo[2,3-c]pyridine hydrochloride 1H-NMR(400 MHz, CDCl$_3$) δ 7.80 (s, 1H), 7.37 (s, 1H), 7.21 (m, 3H), 7.10 (m, 2H), 4.36 (m, 1H), 4.23 (m, 2H), 3.92 (m, 1H), 3.57 (m, 1H), 3.50 (m, 2H), 2.99 (m, 2H), 2.51 (s, 3H), 2.27 (s, 3H); (Yield: 77%)

EXAMPLE 463

7-(4-chlorophenyl)-2-methyl-1H-pyrrolo[2,3-c]pyridine

In accordance with the same procedures as in Example 242, except for using 3-nitro-2-(4-chlorophenyl)pyridine prepared in Preparation 12 and isopropenylmagnesium bromide, the titled compound was obtained as a white solid. (Yield: 32%)

1H-NMR(400 MHz, CDCl$_3$) δ 8.45 (brs, 1H), 8.30 (d, 1H), 7.83 (d, 2H), 7.51 (d, 2H), 7.45 (d, 1H), 6.34 (s, 1H), 2.52 (s, 3H)

EXAMPLE 464

1-benzyl-2-methyl-7-phenyl-1H-pyrrolo[2,3-c]pyridine hydrochloride

Step 1: 2-methyl-7-phenyl-1H-pyrrolo[2,3-c]pyridine

In accordance with the same procedures as in Example 242, except for using 3-nitro-2-phenylpyridine prepared in Preparation 15 and isopropenylmagnesium bromide, the titled compound was obtained as a white solid. (Yield: 37%)

Step 2: 1-benzyl-2-methyl-7-phenyl-1H-pyrrolo[2,3-c]pyridine hydrochloride

18-Crown-6 (2 mg, 0.006 mmol) and potassium tert-butoxide (7 mg, 0.066 mmol) were added to a solution of 2-methyl-7-phenyl-1H-pyrrolo[2,3-c]pyridine (20 mg, 0.066 mmol) prepared in Step 1 in anhydrous tetrahydrofuran (1 ml). The reaction mixture was stirred for 30 minutes at room temperature and benzyl bromide (11.8 μl, 0.099 mmol) was added thereto. The reaction mixture was stirred overnight and then concentrated under reduced pressure. The resulting residue was purified with silica gel column chromatography (ethyl acetate/n-hexane=1/8, v/v). The resulting product was dissolved in ethyl acetate, saturated with hydrochloric acid gas, and then filtered to give 10 mg of the titled compound as a white solid.

1H-NMR(400 MHz, CDCl$_3$) δ 10.39 (s, 1H), 8.67 (dd, 2H), 7.57 (t, 1H), 7.39 (m, 3H), 7.22 (m, 4H), 6.36 (d, 2H), 5.17 (d, 2H), 2.81 (s, 3H)

EXAMPLE 465

1-allyl-7-(4-fluorophenyl)-2-methyl-1H-pyrrolo[2,3-c]pyridine hydrochloride

Step 1: 7-(4-fluorophenyl)-2-methyl-1H-pyrrolo[2,3-c]pyridine

In accordance with the same procedures as in Example 242, except for using 3-nitro-2-(4-fluorophenyl)pyridine prepared in Preparation 13 and isopropenyl magnesium bromide, the titled compound was obtained as a white solid. (Yield: 37%)

Step 2: 1-allyl-7-(4-fluorophenyl)-2-methyl-1H-pyrrolo[2,3-c]pyridine hydrochloride In accordance with the same procedures as in Step 2 of Example 464, except for using 7-(4-fluorophenyl)-2-methyl-1H-pyrrolo[2,3-c]pyridine prepared in Step 1 and allyl bromide, 9 mg of the titled compound was obtained as a white solid.

1H-NMR(400 MHz, CDCl$_3$) δ 10.36 (s, 1H), 8.67 (d, 1H), 8.57 (d, 1H), 7.64 (s, 2H), 7.28 (t, 2H), 5.58 (m, 1H), 5.22 (d, 1H), 4.51 (s, 2H), 4.46 (d, 1H), 2.83 (s, 3H)

EXAMPLE 466

7-(4-chlorophenyl)-3-ethoxymethyl-2-methyl-1H-pyrrolo[2,3-c]pyridine

A solution of 7-(4-chlorophenyl)-2-methyl-1H-pyrrolo[2,3-c]pyridine (170 mg, 0.07 mmol) prepared in Example 463, dimethylamine (2.0M tetrahydrofuran solution; 375 μl, 0.75 mmol), acetic acid (0.36 ml) and formaldehyde (0.68 ml) in ethanol (10 ml) was refluxed for 60 hours. The reaction mixture was concentrated under reduced pressure. The resulting residue was diluted with a sodium hydroxide solution and then extracted with ethyl acetate. The organic layer was dried on anhydrous magnesium sulfate and then concentrated under reduced pressure. The resulting residue was purified with silica gel column chromatography (ethyl acetate/n-hexane=1/5, v/v) to give 85 mg of the titled compound as a white solid.

1H-NMR(400 MHz, CDCl$_3$) δ 8.41 (brs, 1H), 8.34 (d, 1H), 7.79 (d, 2H), 7.50 (m, 2+1H), 4.65 (s, 2H), 3.58 (q, 2H), 2.50 (s, 3H), 1.25 (t, 3H)

EXAMPLE 467

1-benzyl-7-(4-chlorophenyl)-3-ethoxymethyl-2-methyl-1H-pyrrolo[2,3-c]pyridine hydrochloride 18-Crown-6 (2 mg, 0.006 mmol) and potassium tert-butoxide (7 mg, 0.066 mmol) were added to a solution of 7-(4-chlorophenyl)-3-ethoxymethyl-2-methyl-1H-pyrrolo[2,3-c]pyridine (20 mg, 0.066 mmol) prepared in Example 466 in anhydrous tetrahydrofuran (1 ml). The reaction mixture was stirred for 30 minutes at room temperature and then benzyl bromide (11.8 µl, 0.099 mmol) was added thereto. The reaction mixture was stirred overnight and then concentrated under reduced pressure. The resulting residue was purified with silica gel column chromatography (ethyl acetate/n-hexane=1/5, v/v). The resulting product was dissolved in ethyl acetate, saturated with hydrochloric acid gas, and then filtered to give 10 mg of the titled compound as a white solid.

1H-NMR(400 MHz, CDCl$_3$) δ 8.35 (s, 1H), 7.97 (d, 1H), 7.23 (m, 7H), 6.36 (d, 2H), 5.10 (s, 2H), 4.76 (s, 2H), 3.67 (q, 2H), 2.51 (s, 3H), 1.32 (t, 3H)

EXAMPLE 468

7-(1,2,3,4-tetrahydroisoquinolin-2-yl)-2,3-dimethyl-1H-pyrrolo[2,3-c]pyridine hydrochloride 1-Methyl-1-propenyl magnesium bromide (0.5M in tetrahydrofuran solution; 112 ml) was slowly added at −78° C. to a solution of 2-(1,2,3,4-tetrahydroisoquinolin-2-yl)-3-nitropyridine (4.8 g, 18.8 mmol) prepared in Preparation 20 in anhydrous tetrahydrofuran (150 ml). The reaction mixture was stirred for 4 hours at −20° C. 20% ammonium chloride solution was added to the reaction mixture, which was then extracted with ethyl acetate. The separated organic layer was dried on anhydrous magnesium sulfate and then concentrated under reduced pressure. The resulting residue was purified with silica gel column chromatography (ethyl acetate/n-hexane=1/1, v/v). The resulting product was dissolved in ethyl acetate, saturated with hydrochloric acid gas, and then filtered to give 1.3 g of the titled compound as yellow solid.

1H-NMR(400 MHz, CDCl$_3$) δ 13.05 (brs, 1H), 11.59 (brs, 1H), 7.54 (brs, 1H), 7.08 (brs, 1H), 6.98 (m, 1H), 6.91 (brs, 1H), 6.78 (s, 2H), 5.04 (s, 2H), 3.97 (s, 2H), 2.89 (s, 2H), 2.63 (s, 3H), 2.14 (s, 3H)

EXAMPLE 469

1-benzyl-7-(1,2,3,4-tetrahydroisoquinolin-2-yl)-2,3-dimethyl-1H-pyrrolo[2,3-c]pyridine hydrochloride Sodium hydride (60%; 40 mg, 0.999 mmol) and benzyl bromide (0.475 ml, 0.399 mmol) were added at 0° C. to a solution of 7-(1,2,3,4-tetrahydroisoquinolin-2-yl)-2,3-dimethyl-1H-pyrrolo[2,3-c]pyridine hydrochloride (92,3 mg, 0.333 mmol) prepared in Example 468 in anhydrous tetrahydrofuran (10 ml). The reaction mixture was stirred for 12 hours at room temperature and ice was added thereto. The reaction mixture was extracted with ethyl acetate. The separated organic layer was dried on anhydrous magnesium sulfate and then concentrated under reduced pressure. The resulting residue was purified with silica gel column chromatography (ethyl acetate/n-hexane=1/5, v/v). The resulting product was dissolved in ethyl acetate, saturated with hydrochloric acid gas, and then filtered to give 23.7 mg of the titled compound as a white solid.

1H-NMR(400 MHz, CDCl$_3$) δ 8.17 (brs, 1H), 7.51 (d, 1H), 7.19 (m, 4H), 7.10 (m, 2H), 6.69 (d, 1H), 6.55 (d, 2H), 5.64 (s, 2H), 4.50 (brs, 2H), 3.89 (brs, 2H), 2.86 (s, 2H), 2.35 (s, 3H), 2.33 (s, 3H)

EXAMPLES 470 TO 484

The titled compounds of Examples 470 to 484 were prepared, in accordance with the same procedures as in Example 469, using 7-(1,2,3,4-tetrahydroisoquinolin-2-yl)-2,3-dimethyl-1H-pyrrolo[2,3-c]pyridine hydrochloride prepared in Example 468; and, iodomethane, 4-fluorobenzyl chloride, 2-chlorobenzyl chloride, 1-iodopropane, 4-chloromethyl-2-methyl thiazole, 4-bromo-2-methyl-2-butene, 1-iodo-2-methylpropane, 4-methylbenzyl chloride, 4-chlorobenzyl chloride, 4-(trifluoromethoxy)benzyl chloride, 3-fluorobenzyl chloride, iodoethane, 4-methoxybenzyl chloride, 2-fluorobenzyl chloride, or allyl bromide.

EXAMPLE 470

7-(1,2,3,4-tetrahydroisoquinolin-2-yl)-1,2,3-trimethyl-1H-pyrrolo[2,3-c]pyridine hydrochloride 1H-NMR(400 MHz, CDCl$_3$) δ 8.08 (t, 1H), 7.38 (d, 1H), 7.23 (m, 3H), 7.12 (d, 1H), 4.64 (s, 2H), 3.99 (t, 2H), 3.92 (s, 3H), 3.19 (t, 2H), 2.44 (s, 3H), 2.27 (s, 3H); (Yield: 50%)

EXAMPLE 471

1-(4-fluorobenzyl)-7-(1,2,3,4-tetrahydroisoquinolin-2-yl)-2,3-dimethyl-1H-pyrrolo[2,3-c]pyridine hydrochloride 1H-NMR(400 MHz, CDCl$_3$) δ 8.18 (t, 1H), 7.51 (d, 1H), 7.19 (m, 1H), 7.12 (m, 2H), 6.89 (t, 2H), 6.74 (d, 1H), 6.52 (m, 2H), 5.61 (s, 2H), 4.43 (brs, 2H), 3.86 (brs, 2H), 2.90 (t, 2H), 2.35 (s, 3H), 2.33 (s, 3H); (Yield: 53%)

EXAMPLE 472

1-(2-chlorobenzyl)-7-(1,2,3,4-tetrahydroisoquinolin-2-yl)-2,3-dimethyl-1H-pyrrolo[2,3-c]pyridine hydrochloride 1H-NMR(400 MHz, CDCl$_3$) δ 8.19 (m, 1H), 7.23 (m, 1H), 7.17 (m, 3H), 7.10 (t, 1H), 6.47 (d, 2H), 5.10 (d, 2H), 5.68 (s, 2H), 4.30 (brs, 2H), 3.85 (brs, 2H), 2.87 (brs, 2H), 2.35 (s, 3H), 2.33 (s, 3H); (Yield: 63%)

EXAMPLE 473

1-propyl-7-(1,2,3,4-tetrahydroisoquinolin-2-yl)-2,3-dimethyl-1H-pyrrolo[2,3-c]pyridine hydrochloride 1H-NMR(400 MHz, CDCl₃) δ 8.14 (brs, 1H), 7.44 (m, 1H), 7.22 (m, 2H), 7.08 (m, 2H), 4.60 (brs, 2H), 4.23 (t, 2H), 4.04 (t, 2H), 3.18 (t, 2H), 2.46 (s, 3H), 2.29 (s, 3H), 1.59 (t, 2H), 0.59 (t, 3H); (Yield: 68%)

EXAMPLE 474

1-(2-methylthiazol-4-ylmethyl)-7-(1,2,3,4-tetrahydroisoquinolin-2-yl)-2,3-dimethyl-1H-pyrrolo[2,3-c]pyridine hydrochloride 1H-NMR(400 MHz, CDCl₃) δ 8.18 (t, 1H), 7.48 (d, 1H), 7.16 (m, 2H), 7.08 (m, 1H), 6.32 (s, 1H), 5.68 (s, 2H), 4.53 (brs, 2H), 3.91 (t, 2H), 3.02 (t, 2H), 2.55 (s, 3H), 2.45 (s, 3H), 2.30 (s, 3H); (Yield: 76%)

EXAMPLE 475

1-(3-methylbut-2-enyl)-7-(1,2,3,4-tetrahydroisoquinolin-2-yl)-2,3-dimethyl-1H-pyrrolo[2,3-c]pyridine hydrochloride 1H-NMR(400 MHz, CDCl₃) δ 8.11 (m, 1H), 7.40 (d, 1H), 7.19 (m, 3H), 7.00 (d, 1H), 5.00 (d, 2H), 4.94 (d, 1H), 4.58 (brs, 2H), 3.97 (t, 2H), 3.13 (t, 2H), 2.42 (s, 3H), 2.27 (s, 3H), 1.63 (s, 3H), 1.32 (s, 3H); (Yield: 56%)

EXAMPLE 476

1-isobutyl-7-(1,2,3,4-tetrahydroisoquinolin-2-yl)-2,3-dimethyl-1H-pyrrolo[2,3-c]pyridine hydrochloride 1H-NMR(400 MHz, CDCl₃) δ 8.13 (t, 1H), 7.42 (d, 1H), 7.18 (m, 3H), 7.06 (d, 1H), 4.52 (s, 2H), 4.02 (brs, 2+2H), 3.18 (t, 2H), 2.45 (s, 3H), 2.28 (s, 3H), 1.90 (m, 1H), 0.56 (s, 3H), 0.52 (s, 3H); (Yield: 45%)

EXAMPLE 477

1-(4-methylbenzyl)-7-(1,2,3,4-tetrahydroisoquinolin-2-yl)-2,3-dimethyl-1H-pyrrolo[2,3-c]pyridine hydrochloride 1H-NMR(400 MHz, CDCl₃) δ 7.51 (brs, 1H), 7.11 (m, 7H), 6.49 (m, 2H), 5.76 (s, 2H), 4.65 (brs, 2H), 4.11 (brs, 2H), 2.97 (t, 2H), 2.41 (s, 3H), 2.31 (s, 3H), 1.48 (s, 3H); (Yield: 65%)

EXAMPLE 478

1-(4-chlorobenzyl)-7-(1,2,3,4-tetrahydroisoquinolin-2-yl)-2,3-dimethyl-1H-pyrrolo[2,3-c]pyridine hydrochloride 1H-NMR(400 MHz, CDCl₃) δ 8.20 (brs, 1H), 7.52 (brs, 1H), 7.18 (m, 5H), 6.78 (m, 1H), 6.51 (m, 2H), 5.64 (s, 2H), 4.48 (brs, 2H), 3.91 (brs, 2H), 2.92 (brs, 2H), 2.38 (s, 3+3H); (Yield: 56%)

EXAMPLE 479

1-(4-trifluoromethoxybenzyl)-7-(1,2,3,4-tetrahydroisoquinolin-2-yl)-2,3-dimethyl-1H-pyrrolo[2,3-c]pyridine hydrochloride 1H-NMR(400 MHz, CDCl₃) δ 8.18 (d, 1H), 7.53 (d, 1H), 7.18 (m, 5H), 6.65 (d, 1H), 6.56 (d, 2H), 5.64 (s, 2H), 4.41 (brs, 2H), 3.84 (brs, 2H), 2.89 (t, 2H), 2.36 (s, 3H), 2.34 (s, 3H); (Yield: 55%)

EXAMPLE 480

1-(3-fluorobenzyl)-7-(1,2,3,4-tetrahydroisoquinolin-2-yl)-2,3-dimethyl-1H-pyrrolo[2,3-c]pyridine hydrochloride 1H-NMR(400 MHz, CDCl₃) δ 8.18 (brs, 1H), 7.53 (brs, 1H), 7.20 (m, 4H), 6.94 (brs, 1H), 6.73 (brs, 1H), 6.33 (brs, 1H), 6.24 (d, 1H), 5.65 (s, 2H), 4.41 (brs, 2H), 3.89 (brs, 2H), 2.89 (t, 2H), 2.36 (brs, 3+3H); (Yield: 63%)

EXAMPLE 481

1-ethyl-7-(1,2,3,4-tetrahydroisoquinolin-2-yl)-2,3-dimethyl-1H-pyrrolo[2,3-c]pyridine hydrochloride 1H-NMR(400 MHz, CDCl₃) δ 8.14 (brs, 1H), 7.47 (brs, 1H), 7.24 (m, 4H), 4.69 (m, 2H), 4.44 (s, 2H), 4.05 (brs, 2H), 3.21 (t, 2H), 2.51 (s, 3H), 2.33 (s, 3H), 1.23 (t, 3H); (Yield: 52%)

EXAMPLE 482

1-(4-methoxybenzyl)-7-(1,2,3,4-tetrahydroisoquinolin-2-yl)-2,3-dimethyl-1H-pyrrolo[2,3-c]pyridine hydrochloride 1H-NMR(400 MHz, CDCl₃) δ 8.23 (brs, 1H), 7.52 (brs, 1H), 7.20 (m, 3H), 6.74 (m, 3H), 6.53 (brs, 2H), 5.63 (s, 2H), 4.57 (brs, 2H), 3.81 (s, 3H), 2.96 (t, 2H), 2.38 (brs, 3+3H); (Yield: 46%)

EXAMPLE 483

1-(2-fluorobenzyl)-7-(1,2,3,4-tetrahydroisoquinolin-2-yl)-2,3-dimethyl-1H-pyrrolo[2,3-c]pyridine hydrochloride 1H-NMR(400 MHz, CDCl₃) δ 8.51 (brs, 1H), 7.72 (brs, 1H), 7.13 (m, 5H), 6.80 (m, 2H), 6.31 (brs, 1H), 5.72 (s, 2H), 4.58 (brs, 2H), 3.93 (brs, 2H), 2.98 (t, 2H), 2.40 (s, 3+3H); (Yield: 44%)

EXAMPLE 484

1-allyl-7-(1,2,3,4-tetrahydroisoquinolin-2-yl)-2,3-dimethyl-1H-pyrrolo[2,3-c]pyridine hydrochloride 1H-NMR(400 MHz, CDCl₃) δ 8.14 (d, 1H), 7.46 (d, 1H), 7.21 (m, 3H), 7.03 (d, 1H), 5.18 (m, 1H), 5.14 (d, 1H), 5.05 (s, 2H), 4.55 (brs, 2H), 4.50 (d, 1H), 3.91 (t, 2H), 3.12 (t, 2H), 2.42 (s, 3H), 2.30 (s, 3H); (Yield: 63%)

EXAMPLE 485

1-allyl-7-(1,2,3,4-tetrahydroisoquinolin-2-yl)-2,3-dimethyl-1H-pyrrolo[2,3-c]pyridine citrate The compound prepared in Example 484 was treated with a saturated sodium carbonate solution to obtain 1-allyl-7-(1,2,3,4-tetrahydroisoquinolin-2-yl)-2,3-dimethyl-1H-pyrrolo[2,3-c]pyridine. A solution of citric acid (11.2 t, 0.09 mmol) in ethyl acetate (0.5 ml) was added to a solution of 1-allyl-7-(1,2,3,4-tetrahydroisoquinolin-2-yl)-2,3-dimethyl-1H-pyrrolo[2,3-c]pyridine (30 mg, 0.08 mmol) in ethyl acetate (3 ml). The reaction mixture was stirred overnight at room temperature. The resulting solid was filtered and then dried to give 17.3 mg of the titled compound as a pink solid.

1H-NMR(400 MHz, CDCl$_3$) δ 8.11 (d, 1H), 7.43 (d, 1H), 7.20 (m, 3H), 7.06 (d, 1H), 5.81 (m, 1H), 5.14 (d, 1H), 5.03 (s, 2H), 4.53 (d, 1H), 4.48 (s, 2H), 3.70 (m, 2H), 3.08 (m, 2H), 2.83 (m, 4H), 2.40 (s, 3H), 2.28 (s, 3H)

EXAMPLES 486 TO 494

The titled compounds of Examples 486 to 494 were prepared, in accordance with the same procedures as in Example 485, using 1-allyl-7-(1,2,3,4-tetrahydroisoquinolin-2-yl)-2,3-dimethyl-1H-pyrrolo[2,3-c]pyridine obtained by treating the compound prepared in Example 484 with a saturated sodium carbonate solution; and, tartaric acid, methanesulfonic acid, sulfuric acid, p-toluenesulfonic acid, nitric acid, maleic acid, phosphoric acid, benzenesulfonic acid, or hydrobromic acid.

EXAMPLE 486

1-allyl-7-(1,2,3,4-tetrahydroisoquinolin-2-yl)-2,3-dimethyl-1H-pyrrolo[2,3-c]pyridine tartrate 1H-NMR(400 MHz, CDCl$_3$) δ 8.41 (m, 1H), 7.43 (m, 1H), 7.22 (m, 3H), 7.05 (m, 1H), 5.80 (m, 1H), 5.28 (d, 1H), 5.05 (s, 2H), 4.57 (m, 1+2H), 4.21 (m, 2H), 3.61 (m, 2H), 3.10 t(m, 2H), 2.41 (s, 3H), 2.29 (s, 3H); (Yield: 83%)

EXAMPLE 487

1-allyl-7-(1,2,3,4-tetrahydroisoquinolin-2-yl)-2,3-dimethyl-1H-pyrrolo[2,3-c]pyridine methanesulfonate 1H-NMR(400 MHz, CDCl$_3$) δ 8.30 (t, 1H), 7.44 (d, 1H), 7.22 (m, 3H), 7.06 (d, 1H), 5.78 (m, 1H), 5.16 (d, 1H), 5.01 (s, 2H), 4.53 (m, 1+2H), 3.81 (m, 2H), 3.14 (m, 2H), 2.89 (s, 3H), 2.41 (s, 3H), 2.29 (s, 3H); (Yield: 86%)

EXAMPLE 488

1-allyl-7-(1,2,3,4-tetrahydroisoquinolin-2-yl)-2,3-dimethyl-1H-pyrrolo[2,3-c]pyridine sulfate 1H-NMR(400 MHz, CDCl$_3$) δ 8.24 (t, 1H), 7.44 (d, 1H), 7.18 (m, 3H), 7.05 (m, 1H), 5.78 (m, 1H), 5.16 (d, 1H), 4.97 (d, 2H), 4.58 (m, 1+2H), 3.83 (t, 2H), 3.13 (m, 2H), 2.40 (s, 3H), 2.26 (s, 3H); (Yield: 96%)

EXAMPLE 489

1-allyl-7-(1,2,3,4-tetrahydroisoquinolin-2-yl)-2,3-dimethyl-1H-pyrrolo[2,3-c]pyridine p-toluenesulfonate 1H-NMR(400 MHz, CDCl$_3$) δ 8.27 (t, 1H), 7.86 (d, 2H), 7.42 (d, 1H), 7.19 (m, 2+3H), 6.99 (d, 1H), 5.81 (m, 1H), 5.15 (d, 1H), 5.00 (s, 2H), 4.54 (m, 1+2H), 4.54 (d, 1+2H), 3.77 (s, 2H), 3.07 (m, 2H), 2.41 (s, 3H), 2.34 (s, 3H), 2.28 (s, 3H); (Yield: 90%)

EXAMPLE 490

1-allyl-7-(1,2,3,4-tetrahydroisoquinolin-2-yl)-2,3-dimethyl-1H-pyrrolo[2,3-c]pyridine nitrate 1H-NMR(400 MHz, CDCl$_3$) δ 8.14 (m, 1H), 7.47 (d, 2H), 7.20 (m, 3H), 7.02 (d, 1H), 5.79 (m, 1H), 5.16 (d, 1H), 5.03 (s, 2H), 4.53 (m, 1+2H), 3.78 (m, 2H), 3.09 (m, 2H), 2.42 (s, 3H), 2.30 (s, 3H); (Yield: 93%)

EXAMPLE 491

1-allyl-7-(1,2,3,4-tetrahydroisoquinolin-2-yl)-2,3-dimethyl-1H-pyrrolo[2,3-c]pyridine maleate 1H-NMR(400 MHz, CDCl$_3$) δ 8.19 (d, 1H), 7.46 (d, 1H), 7.34 (m, 3H), 7.05 (d, 1H), 6.33 (s, 2H), 5.80 (m, 1H), 5.16 (d, 1H), 5.04 (s, 2H), 4.54 (d, 1+2H), 3.76 (m, 2H), 3.11 (m, 2H), 2.42 (s, 3H), 2.24 (s, 3H); (Yield: 82%)

EXAMPLE 492

1-allyl-7-(1,2,3,4-tetrahydroisoquinolin-2-yl)-2,3-dimethyl-1H-pyrrolo[2,3-c]pyridine phosphate 1H-NMR(400 MHz, MeOH-d$_4$) δ 7.93 (d, 1H), 7.66 (d, 1H), 7.23 (m, 3H), 7.11 (d, 1H), 5.88 (m, 1H), 5.10 (m, 1+2H), 3.71 (m, 2H), 3.14 (m, 2H), 2.47 (s, 3H), 2.33 (s, 3H); (Yield: 86%)

EXAMPLE 493

1-allyl-7-(1,2,3,4-tetrahydroisoquinolin-2-yl)-2,3-dimethyl-1H-pyrrolo[2,3-c]pyridine benzenesulfonate 1H-NMR(400 MHz, CDCl$_3$) δ 8.26 (t, 1H), 7.98 (m, 2H), 7.43 (d, 1H), 7.36 (m, 3H), 7.34 (t, 3H), 7.01 (d, 1H), 5.78 (m, 1H), 5.15 (d, 1H), 5.00 (s, 2H), 4.54 (d, 1+2H), 3.73 (t, 2H), 3.09 (m, 2H), 2.41 (s, 3H), 2.29 (s, 3H); (Yield: 77%)

EXAMPLE 494

1-allyl-7-(1,2,3,4-tetrahydroisoquinolin-2-yl)-2,3-dimethyl-1H-pyrrolo[2,3-c]pyridine hydrobromide 1H-NMR(400 MHz, CDCl$_3$) δ 8.20 (t, 1H), 7.48 (d, 1H), 7.22 (m, 3H), 7.05 (d, 1H), 5.79 (m, 1H), 5.17 (d, 1H), 5.04 (d, 2H), 4.55 (m, 1+2H), 3.93 (m, 2H), 3.12 (m, 2H), 2.42 (s, 3H), 2.30 (s, 3H); (Yield: 75%)

EXAMPLES 495 TO 525

The titled compounds of Examples 495 to 525 were prepared, in accordance with the same procedures as in Example 469, using 7-(1,2,3,4-tetrahydroisoquinolin-2-yl)-2,3-dimethyl-1H-pyrrolo[2,3-c]pyridine hydrochloride prepared in Example 468; and, 3,4-dichlorobenzyl chloride, bromomethyl methyl ether, (bromomethyl)cyclopropane, cyanomethyl iodide, 2-bromoethyl methyl ether, 4-trifluoromethylbenzyl chloride, methyl bromoacetate, 2-(bromomethyl)naphthalene, 2-bromoethyl ethyl ether, chloromethyl methyl sulfide, (bromomethyl)cyclobutane, propargyl bromide, 4-tert-butylbenzyl chloride, 4-chloro-1-butene, 1-bromopentane, 3-methoxybenzyl chloride, 2-chloroethyl vinyl ether, 2-bromoethyl-4-methanesulfonylbenzene, 1-bromo-3-chlorobutane, 2-chloro-5-chloromethylthiophene, 3-methylbenzyl chloride, 3-picolyl chloride, 2-picolyl chloride, 4-picolyl chloride, 2,3-dichlorobenzyl chloride, 1-bromo-3-methylbutane, $\alpha^2$-chloroisodurene, 2,5-dimethylbenzyl chloride, 5-chloro-1-pentyne, 4-(chloromethyl)-3,5-dimethylisoxazole, or 1-iodobutane.

EXAMPLE 495

1-(3,4-dichlorobenzyl)-7-(1,2,3,4-tetrahydroisoquinolin-2-yl)-2,3-dimethyl-1H-pyrrolo[2,3-c]pyridine hydrochloride 1H-NMR(400 MHz, CDCl$_3$) δ 8.21 (brs, 1H), 7.55 (m, 2H), 7.17 (m, 3H), 6.67 (m, 2H), 6.34 (brs, 1H), 5.60 (s, 2H), 4.49 (brs, 2H), 4.08 (brs, 2H), 3.02 (t, 2H), 2.38 (s, 3+3H); (Yield: 45%)

EXAMPLE 496

1-methoxymethyl-7-(1,2,3,4-tetrahydroisoquinolin-2-yl)-2,3-dimethyl-1H-pyrrolo[2,3-c]pyridine hydrochloride 1H-NMR(400 MHz, CDCl$_3$) δ 8.17 (s, 1H), 7.42 (s, 1H), 7.23 (m, 3H), 7.10 (m, 1H), 5.71 (s, 2H), 4.64 (s, 2H), 4.04 (s, 2H), 3.18 (s, 2H), 3.05 (s, 3H), 2.51 (s, 3H), 2.28 (s, 3H); (Yield: 63%)

EXAMPLE 497

1-cyclopropylmethyl-7-(1,2,3,4-tetrahydroisoquinolin-2-yl)-2,3-dimethyl-1H-pyrrolo[2,3-c]pyridine hydrochloride 1H-NMR(400 MHz, CDCl$_3$) δ 8.15 (brs, 1H), 7.44 (m, 1H), 7.19-7.30 (m, 3H), 7.05 (m, 1H), 4.53 (m, 2H), 4.20 (m, 2H), 4.02 (m, 2H), 3.18 (m, 2H), 2.52 (s, 3H), 2.30 (s, 3H), 1.21 (m, 1H), 0.33 (m, 2H), 0.03 (m, 2H); (Yield: 57%)

EXAMPLE 498

1-cyanomethyl-7-(1,2,3,4-tetrahydroisoquinolin-2-yl)-2,3-dimethyl-1H-pyrrolo[2,3-c]pyridine hydrochloride 1H-NMR(400 MHz, CDCl$_3$) δ 8.25 (s, 1H), 7.54 (d, 1H), 7.24 (m, 3H), 7.14 (d, 1H), 5.42 (s, 2H), 4.80 (brs, 2H), 4.01 (brs, 2H), 3.24 (brs, 2H), 2.59 (s, 3H), 2.34 (s, 3H); (Yield: 62%)

EXAMPLE 499

1-(2-methoxyethyl)-7-(1,2,3,4-tetrahydroisoquinolin-2-yl)-2,3-dimethyl-1H-pyrrolo[2,3-c]pyridine hydrochloride 1H-NMR(400 MHz, CDCl$_3$) δ 8.15 (s, 1H), 7.47 (s, 1H), 7.18 (m, 3H), 7.05 (d, 1H), 4.60 (brs, 2H), 4.50 (s, 2H), 3.92 (brs, 2H), 3.41 (s, 2H), 3.12 (s, 2H), 3.08 (s, 3H), 2.49 (s, 3H), 2.28 (s, 3H); (Yield: 71%)

EXAMPLE 500

7-(1,2,3,4-tetrahydroisoquinolin-2-yl)-1-(4-trifluoromethylbenzyl)-2,3-dimethyl-1H-pyrrolo[2,3-c]pyridine hydrochloride 1H-NMR(400 MHz, CDCl$_3$) δ 8.21 (brs, 1H), 7.54 (brs, 1H), 7.45 (d, 2H), 7.29 (m, 1H), 7.22 (d, 1H), 7.18 (d, 1H), 7.06 (m, 1H), 6.65 (m, 2H), 5.71 (s, 2H), 4.39 (brs, 2H), 3.49 (brs, 2H), 2.88 (s, 2H), 2.42 (d, 3+3H); (Yield: 65%)

EXAMPLE 501

1-methoxycarbonylmethyl-7-(1,2,3,4-tetrahydroisoquinolin-2-yl)-2,3-dimethyl-1H-pyrrolo[2,3-c]pyridine hydrochloride 1H-NMR(400 MHz, CDCl$_3$) δ 8.17 (t, 1H), 7.52 (d, 1H), 7.21 (m, 3H), 7.01 (d, 1H), 5.27 (brs, 2H), 5.08 (brs, 2H), 4.16 (s, 2H), 3.49 (s, 3H), 3.12 (s, 2H), 2.41 (s, 3H), 2.31 (s, 3H); (Yield: 53%)

EXAMPLE 502

1-(naphthalen-2-ylmethyl)-7-(1,2,3,4-tetrahydroisoquinolin-2-yl)-2,3-dimethyl-1H-pyrrolo[2,3-c]pyridine hydrochloride 1H-NMR(400 MHz, CDCl$_3$) δ 8.35 (s, 1H), 7.80 (d, 1H), 7.69 (d, 1H), 7.54 (m, 4H), 7.27 (m, 1H), 7.15 (m, 2H), 6.98 (m, 2H), 6.73 (d, 1H), 6.56 (d, 1H), 5.81 (s, 2H), 4.46 (s, 2H), 3.84 (s, 2H), 2.83 (s, 2H), 2.38 (s, 3H), 2.36 (s, 3H); (Yield: 39%)

EXAMPLE 503

1-(2-ethoxyethyl)-7-(1,2,3,4-tetrahydroisoquinolin-2-yl)-2,3-dimethyl-1H-pyrrolo[2,3-c]pyridine hydrochloride 1H-NMR(400 MHz, CDCl$_3$) δ 8.15 (brs, 1H), 7.46 (d, 1H), 7.21 (m, 3H), 7.05 (d, 1H), 4.51 (brs, 2H), 3.97 (brs, 4H), 3.44 (m, 2H), 3.17 (m, 4H), 2.50 (s, 3H), 2.29 (s, 3H) 1.95 (t, 3H); (Yield: 75%)

EXAMPLE 504

1-methylsulfanylmethyl-7-(1,2,3,4-tetrahydroisoquinolin-2-yl)-2,3-dimethyl-1H-pyrrolo[2,3-c]pyridine hydrochloride 1H-NMR(400 MHz, CDCl$_3$) δ 8.20 (s, 1H), 7.46 (s, 1H), 7.19 (m, 3H), 7.08 (d, 1H), 5.43 (s, 2H), 4.59 (s, 2H), 4.02 (s, 2H), 3.22 (s, 2H), 2.55 (s, 3H), 2.20 (s, 3H), 1.81 (s, 3H); (Yield: 43%)

EXAMPLE 505

1-cyclobutylmethyl-7-(1,2,3,4-tetrahydroisoquinolin-2-yl)-2,3-dimethyl-1H-pyrrolo[2,3-c]pyridine hydrochloride 1H-NMR(400 MHz, CDCl$_3$) δ 8.13 (s, 1H), 7.40 (d, 1H), 7.23 (m, 3H), 7.09 (d, 1H), 4.58 (s, 2H), 4.29 (s, 2H), 4.03 (s, 2H), 3.21 (s, 2H), 2.46 (s, 3+1H), 2.27 (s, 3H), 1.66 (m, 4H), 1.42 (m, 2H); (Yield: 53%)

EXAMPLE 506

1-(prop-2-ynyl)-7-(1,2,3,4-tetrahydroisoquinolin-2-yl)-2,3-dimethyl-1H-pyrrolo[2,3-c]pyridine hydrochloride 1H-NMR(400 MHz, CDCl$_3$) δ 8.17 (s, 1H), 7.43 (s, 1H), 7.25 (m, 3H), 7.13 (d, 1H), 5.22 (s, 2H), 4.73 (s, 2H), 3.98 (s, 2H), 3.22 (s, 2H), 2.58 (s, 3H), 2.42 (s, 1H), 2.18 (s, 3H); (Yield: 52%)

EXAMPLE 507

1-(4-tert-butylbenzyl)-7-(1,2,3,4-tetrahydroisoquinolin-2-yl)-2,3-dimethyl-1H-pyrrolo[2,3-c]pyridine hydrochloride 1H-NMR(400 MHz, CDCl$_3$) δ 8.16 (m, 1H), 7.48 (d, 1H), 7.16 (m, 3H), 7.13 (d, 1H), 7.04 (t, 1H), 6.60 (d, 1H), 6.47 (d, 2H), 5.60 (s, 2H), 4.38 (s, 2H), 3.87 (s, 2H), 2.91 (t, 2H), 2.36 (s, 3H), 2.32 (s, 3H), 1.28 (s, 9H); (Yield: 51%)

EXAMPLE 508

1-(but-3-enyl)-7-(1,2,3,4-tetrahydroisoquinolin-2-yl)-2,3-dimethyl-1H-pyrrolo[2,3-c]pyridine hydrochloride 1H-NMR(400 MHz, CDCl$_3$) δ 8.15 (s, 1H), 7.45 (d, 1H), 7.18 (m, 3H), 7.05 (d, 1H), 5.321 (m, 1H), 4.80 (d, 1H), 4.69 (d, 1H), 4.65 (brs, 2H), 4.36 (s, 2H), 4.01 (s, 2H), 3.17 (s, 2H), 2.47 (s, 3H), 2.28 (s, 3H), 2.21 (d, 2H); (Yield: 62%)

EXAMPLE 509

1-pentyl-7-(1,2,3,4-tetrahydroisoquinolin-2-yl)-2,3-dimethyl-1H-pyrrolo[2,3-c]pyridine hydrochloride 1H-NMR(400 MHz, CDCl$_3$) δ 8.13 (m, 1H), 7.44 (d, 1H), 7.22 (m, 3H), 7.06 (d, 1H), 4.70 (brs, 1H), 4.26 (m, 2H), 4.05 (brs, 2H), 3.17 (s, 2H), 2.45 (s, 3H), 2.28 (s, 3H), 1.46 (m, 2H), 1.08 (m, 2H), 0.89 (m, 2H), 0.69 (m, 3H); (Yield: 57%)

EXAMPLE 510

1-(3-methoxybenzyl)-7-(1,2,3,4-tetrahydroisoquinolin-2-yl)-2,3-dimethyl-1H-pyrrolo[2,3-c]pyridine hydrochloride 1H-NMR(400 MHz, CDCl$_3$) δ 8.17 (s, 1H), 7.51 (s, 1H), 7.13 (m, 4H), 6.78 (d, 1H), 6.68 (d, 1H), 6.09 (s, 2H), 5.62 (s, 2H), 4.44 (brs, 2H), 3.86 (brs, 2H), 3.64 (s, 3H), 2.90 (s, 2H), 2.36 (s, 3H), 2.33 (s, 3H); (Yield: 42%)

EXAMPLE 511

1-(2-vinyloxyethyl)-7-(1,2,3,4-tetrahydroisoquinolin-2-yl)-2,3-dimethyl-1H-pyrrolo[2,3-c]pyridine hydrochloride 1H-NMR(400 MHz, CDCl$_3$) δ 8.09 (s, 1H), 7.45 (s, 1H), 7.28 (m, 3H), 7.05 (d, 1H), 4.80 (brs, 2H), 4.47 (m, 2+1H), 3.98 (brs, 1H), 3.72 (m, 2+1H), 3.12 (m, 2+1H), 2.53 (s, 3H), 2.29 (s, 3H); (Yield: 48%)

EXAMPLE 512

1-[2-(4-methylsulfonylphenyl)ethyl]-7-(1,2,3,4-tetrahydroisoquinolin-2-yl)-2,3-dimethyl-1H-pyrrolo[2,3-c]pyridine hydrochloride 1H-NMR(400 MHz, CDCl$_3$) δ 8.12 (s, 1H), 7.25 (m, 4H), 7.19 (m, 2H), 7.11 (m, 2H), 6.84 (m, 1H), 5.23 (m, 2H), 5.10 (m, 2H), 4.70 (s, 3H), 3.97 (t, 2H), 3.15 (t, 2H), 2.48 (s, 3H), 2.27 (s, 3H), 2.15 (m, 2H); (Yield: 47%)

EXAMPLE 513

1-(3-chlorobutyl)-7-(1,2,3,4-tetrahydroisoquinolin-2-yl)-2,3-dimethyl-1H-pyrrolo[2,3-c]pyridine hydrochloride 1H-NMR(400 MHz, CDCl$_3$) δ 8.14 (s, 1H), 7.44 (s, 1H), 7.22 (m, 3H), 7.03 (m, 1H), 5.34 (m, 2H), 4.95 (m, 2H), 4.60 (s, 2H), 4.46 (d, 2H), 3.95 (t, 2H), 3.48 (m, 1H), 3.14 (t, 2H), 2.43 (s, 3H), 2.29 (s, 3H); (Yield: 39%)

EXAMPLE 514

1-(5-chlorothiophene-2-ylmethyl)-7-(1,2,3,4-tetrahydroisoquinolin-2-yl)-2,3-dimethyl-1H-pyrrolo[2,3-c]pyridine hydrochloride 1H-NMR(400 MHz, CDCl$_3$) δ 8.21 (s, 1H), 7.48 (s, 1H), 7.21 (m, 3H), 6.98 (d, 2H), 6.64 (s, 1H), 6.33 (s, 1H), 5.61 (s, 2H), 4.52 (brs, 2H), 4.04 (brs, 2H), 3.12 (s, 2H), 2.47 (s, 3H), 2.29 (s, 3H); (Yield: 52%)

EXAMPLE 515

1-(3-methylbenzyl)-7-(1,2,3,4-tetrahydroisoquinolin-2-yl)-2,3-dimethyl-1H-pyrrolo[2,3-c]pyridine hydrochloride 1H-NMR(400 MHz, CDCl$_3$) δ 8.17 (s, 1H), 7.51 (d, 1H), 7.17 (d, 1H), 7.09 (m, 4H), 6.66 (d, 1H), 6.40 (s, 1H), 6.28 (d, 1H), 5.60 (s, 2H), 4.39 (brs, 2H), 3.85 (brs, 2H), 2.88 (t, 2H), 2.36 (s, 3H), 2.33 (s, 3H), 2.19 (s, 3H); (Yield: 55%)

EXAMPLE 516

1-(pyridin-3-ylmethyl)-7-(1,2,3,4-tetrahydroisoquinolin-2-yl)-2,3-dimethyl-1H-pyrrolo[2,3-c]pyridine hydrochloride 1H-NMR(400 MHz, CDCl$_3$) δ 8.51 (s, 2H), 8.19 (d, 1H), 7.62 (d, 1H), 7.24 (t, 1H), 7.13 (d, 2H), 6.88 (s, 2H), 6.66 (d, 1H), 5.87 (s, 2H), 4.52 (brs, 2H), 3.85 (brs, 2H), 2.86 (brs, 2H), 2.40 (s, 3H), 2.36 (s, 3H); (Yield: 38%)

EXAMPLE 517

1-(pyridin-2-ylmethyl)-7-(1,2,3,4-tetrahydroiso-quinolin-2-yl)-2,3-dimethyl-1H-pyrrolo[2,3-c]pyridine hydrochloride 1H-NMR(400 MHz, CDCl$_3$) δ 8.41 (s, 1H), 8.16 (s, 1H), 7.50 (m, 2H), 7.09 (m, 3H), 7.03 (m, 1H), 6.63 (m, 2H), 5.75 (s, 2H), 4.54 (brs, 2H), 3.85 (brs, 2H), 2.91 (brs, 2H), 2.34 (s, 3H), 2.31 (s, 3H); (Yield: 62%)

EXAMPLE 518

1-(pyridin-4-ylmethyl)-7-(1,2,3,4-tetrahydroiso-quinolin-2-yl)-2,3-dimethyl-1H-pyrrolo[2,3-c]pyridine hydrochloride 1H-NMR(400 MHz, CDCl$_3$) δ 8.51 (s, 1H), 8.19 (d, 1H), 7.62 (d, 1H), 7.22 (m, 1H), 7.13 (d, 2H), 6.88 (s, 1H), 6.66 (d, 1H), 5.85 (s, 2H), 4.45 (m, 2H), 3.85 (m, 2H), 2.86 (s, 2H), 2.40 (s, 3H), 2.36 (s, 3H); (Yield: 60%)

EXAMPLE 519

1-(2,3-dichlorobenzyl)-7-(1,2,3,4-tetrahydroiso-quinolin-2-yl)-2,3-dimethyl-1H-pyrrolo[2,3-c]pyridine hydrochloride 1H-NMR(400 MHz, CDCl$_3$) δ 8.18 (brs, 1H), 7.54 (m, 1H), 7.39 (d, 1H), 7.18 (m, 2H), 7.10 (m, 2H), 7.02 (m, 1H), 6.34 (d, 1H), 6.04 (s, 2H), 5.66 (brs, 2H), 3.84 (brs, 2H), 2.90 (t, 2H), 2.36 (s, 3H), 2.34 (s, 3H); (Yield: 63%)

EXAMPLE 520

1-(3-methylbutyl)-7-(1,2,3,4-tetrahydroisoquinolin-2-yl)-2,3-dimethyl-1H-pyrrolo[2,3-c]pyridine hydrochloride 1H-NMR(400 MHz, CDCl$_3$) δ 8.13 (t, 1H), 7.43 (d, 1H), 7.21 (m, 3H), 7.06 (d, 1H), 4.65 (s, 2H), 4.27 (t, 2H), 4.03 (s, 2H), 3.18 (s, 2H), 2.45 (s, 3H), 2.28 (s, 3H), 1.30 (m, 2+1H), 0.68 (s, 3H), 0.66 (s, 3H); (Yield: 56%)

EXAMPLE 521

1-(2,4,6-trimethylbenzyl)-7-(1,2,3,4-tetrahydroiso-quinolin-2-yl)-2,3-dimethyl-1H-pyrrolo[2,3-c]pyridine hydrochloride 1H-NMR(400 MHz, CDCl$_3$) δ 8.14 (s, 1H), 7.41 (m, 1H), 7.18 (m, 3H), 7.08 (m, 1H), 6.75 (s, 2H), 5.89 (brs, 2H), 4.85 (brs, 2H), 4.04 (s, 2H), 3.14 (s, 2H), 2.21 (s, 3H), 2.20 (s, 3H), 1.97 (s, 3H), 1.56 (s, 6H); (Yield: 75%)

EXAMPLE 522

1-(2,5-dimethylbenzyl)-7-(1,2,3,4-tetrahydroiso-quinolin-2-yl)-2,3-dimethyl-1H-pyrrolo[2,3-c]pyridine hydrochloride 1H-NMR(400 MHz, CDCl$_3$) δ 8.15 (s, 1H), 7.53 (s, 1H), 7.16 (m, 1H), 7.08 (m, 1H), 6.99 (m, 2H), 6.90 (m, 1H), 6.31 (d, 1H), 5.82 (s, 1H), 5.48 (brs, 2H), 4.30 (brs, 2H), 3.84 (brs, 2H), 2.81 (s, 2H), 2.37 (s, 3H), 2.32 (s, 3H), 2.15 (s, 3H), 1.60 (s, 3H); (Yield: 68%)

EXAMPLE 523

1-(pent-4-ynyl)-7-(1,2,3,4-tetrahydroisoquinolin-2-yl)-2,3-dimethyl-1H-pyrrolo[2,3-c]pyridine hydrochloride 1H-NMR(400 MHz, CDCl$_3$) δ 8.16 (m, 1H), 7.46 (d, 1H), 7.18 (m, 3H), 7.07 (d, 1H), 4.75 (brs, 1H), 4.42 (t, 2H), 4.00 (brs, 2H), 3.19 (s, 2H), 2.50 (s, 3H), 2.29 (s, 3H), 1.88 (m, 2H), 1.75 (m, 2+1H); (Yield: 72%)

EXAMPLE 524

1-(3,5-dimethylisoxazol-4-ylmethyl)-7-(1,2,3,4-tetrahydroisoquinolin-2-yl)-2,3-dimethyl-1H-pyrrolo[2,3-c]pyridine hydrochloride 1H-NMR(400 MHz, CDCl$_3$) δ 8.19 (s, 1H), 7.51 (d, 1H), 7.22 (m, 3H), 6.84 (d, 1H), 5.44 (s, 2H), 4.59 (brs, 2H), 4.04 (brs, 2H), 3.04 (t, 2H), 2.34 (s, 3H), 2.31 (s, 3H), 1.73 (s, 3H), 1.54 (s, 3H); (Yield: 51%)

EXAMPLE 525

1-butyl-7-(1,2,3,4-tetrahydroisoquinolin-2-yl)-2,3-dimethyl-1H-pyrrolo[2,3-c]pyridine hydrochloride 1H-NMR(400 MHz, CDCl$_3$) δ 8.13 (m, 1H), 7.44 (d, 1H), 7.18 (m, 3H), 7.06 (d, 1H), 4.52 (s, 2H), 4.26 (t, 2H), 4.02 (s, 2H), 3.17 (s, 2H), 2.46 (s, 3H), 2.28 (s, 3H), 1.45 (m, 2H), 0.95 (m, 2H), 0.70 (t, 3H); (Yield: 52%)

EXAMPLE 526

1-(propa-1,2-dienyl)-7-(1,2,3,4-tetrahydroisoquinolin-2-yl)-2,3-dimethyl-1H-pyrrolo[2,3-c]pyridine hydrochloride Sodium hydride (60%; 80 mg, 1.80 mmol) and propargyl bromide (35.6 µl, 1.40 mmol) were added at 0° C. to a solution of 7-(1,2,3,4-tetrahydroisoquinolin-2-yl)-2,3-dimethyl-1H-pyrrolo[2,3-c]pyridine hydrochloride (92,3 mg, 0.33 mol) prepared in Example 468 in anhydrous tetrahydrofuran (10 ml). The reaction mixture was stirred for 12 hours at room temperature. Ice was added to the reaction mixture, which was then extracted with ethyl acetate. The organic layer was dried on anhydrous magnesium sulfate and then concentrated under reduced pressure. The resulting residue was purified with silica gel column chromatography (n-hexane/ethyl acetate=1/1, v/v). The resulting product was dissolved in ethyl acetate, saturated with hydrochloric acid gas, and then filtered to give 32.5 mg of the titled compound as a white solid.

1H-NMR(400 MHz, CDCl$_3$) δ 8.11 (t, 1H), 7.29 (d, 2H), 7.20 (m, 4H), 5.32 (d, 2H), 4.83 (s, 2H), 3.97 (t, 2H), 3.20 (t, 2H), 2.48 (s, 3H), 2.29 (s, 3H)

EXAMPLE 527

2-(2,3-dimethyl-1H-pyrrolo[2,3-c]pyridin-7-yl)-7-methoxy-1-methyl-1,2,3,4-tetrahydroisoquinoline hydrochloride In accordance with the same procedures as in Example 468, except for using 7-methoxy-1-methyl-2-(3-nitropyridin-2-yl)-1,2,3,4-tetrahydroisoquinoline prepared in Preparation 21, the titled compound was obtained as a white solid. (Yield: 35%)

1H-NMR(400 MHz, CDCl$_3$) δ 8.75 (s, 1H), 7.92 (d, 1H), 7.03 (m, 2H), 6.73 (m, 2H), 5.22 (q, 1H), 3.68 (s, 3H), 3.61 (m, 1H), 3.49 (m, 1H), 3.35 (m, 1H), 2.72 (m, 1H), 2.32 (s, 3H), 2.18 (s, 3H), 1.31 (d, 3H)

EXAMPLES 528 AND 529

The titled compounds of Examples 528 and 529 were prepared, in accordance with the same procedures as in Example 469, using 2-(2,3-dimethyl-1H-pyrrolo[2,3-c]pyridin-7-yl)-7-methoxy-1-methyl-1,2,3,4-tetrahydroisoquinoline hydrochloride prepared in Example 527; and, allyl bromide or 3-fluorobenzyl bromide.

EXAMPLE 528

2-(1-allyl-2,3-dimethyl-1H-pyrrolo[2,3-c]pyridin-7-yl)-7-methoxy-1-methyl-1,2,3,4-tetrahydroisoquinoline hydrochloride 1H-NMR(400 MHz, CDCl$_3$) δ 8.08 (brs, 1H), 7.37 (m, 1H), 7.10 (t, 1H), 6.80 (t, 1H), 6.52 (m, 1H), 5.83 (m, 1H), 5.72 (m, 1H), 5.56 (m, 1H), 5.30 (m, 1H), 4.85 (m. 1H), 4.11 (m, 1H), 3.88 (m, 1H), 3.07 (m, 1H), 2.98 (m, 1H), 2.51 (brs, 1H), 2.33 (s, 3H), 2.27 (s, 3H), 1.33 (d, 3H); (Yield: 56%)

EXAMPLE 529

2-[1-(3-fluorobenzyl)-2,3-dimethyl-1H-pyrrolo[2,3-c]pyridin-7-yl]-7-methoxy-1-methyl-1,2,3,4-tetrahydroisoquinoline hydrochloride 1H-NMR(400 MHz, CDCl$_3$) δ 8.13 (brs, 2H), 7.38 (m, 1H), 7.17 (m, 2H), 6.82 (m, 2H), 6.61 (m, 2H), 5.73 (m, 2H), 4.88 (m, 2H), 3.97 (m, 1H), 3.80 (s, 3H), 3.07 (m. 2H), 2.52 (s, 3H), 2.23 (s, 3H), 1.34 (brs, 3H); (Yield: 49%)

EXAMPLE 530

7-chloro-2-(2,3-dimethyl-1H-pyrrolo[2,3-c]pyridin-7-yl)-1-methyl-1,2,3,4-tetrahydroisoquinoline hydrochloride In accordance with the same procedures as in Example 468, except for using 7-chloro-1-methyl-2-(3-nitropyridin-2-yl)-1,2,3,4-tetrahydroisoquinoline prepared in Preparation 22, the titled compound was obtained as a white solid. (Yield: 37%)

1H-NMR(400 MHz, CDCl$_3$) δ 8.77 (s, 1H), 7.95 (d, 1H), 7.00 (m, 2H), 6.73 (m, 2H), 5.22 (q, 1H), 3.61 (m, 1H), 3.49 (m, 1H), 3.37 (m, 1H), 2.75 (m, 1H), 2.32 (s, 3H), 2.18 (s, 3H), 1.32 (d, 3H)

EXAMPLES 531 TO 540

The titled compounds of Examples 531 to 540 were prepared, in accordance with the same procedures as in Example 469, using 7-chloro-2-(2,3-dimethyl-1H-pyrrolo[2,3-c]pyridin-7-yl)-1-methyl-1,2,3,4-tetrahydroisoquinoline hydrochloride prepared in Example 530; and, allyl bromide, iodoethane, iodomethane, 4-bromo-2-methyl-2-butene, benzyl bromide, 4-methylbenzyl chloride, bromomethyl methyl ether, 4-chloromethyl-2-methylthiazole, 3-fluorobenzyl chloride, or 4-fluorobenzyl chloride.

EXAMPLE 531

7-chloro-2-(1-allyl-2,3-dimethyl-1H-pyrrolo[2,3-c]pyridin-7-yl)-1-methyl-1,2,3,4-tetrahydroisoquinoline hydrochloride 1H-NMR(400 MHz, CDCl$_3$) δ 8.08 (brs, 1H), 7.36 (s, 1H), 7.19 (d, 1H), 7.13 (d, 1H), 6.98 (s, 1H), 6.53 (d, 1H), 5.83 (s, 1H), 5.57 (t, 1H), 4.80 (m, 1H), 4.19 (m. 1H), 3.89 (m, 1H), 3.01 (brs, 2H), 2.54 (s, 2H), 2.34 (s, 3H), 2.30 (s, 3H), 1.34 (d, 3H); (Yield: 42%)

EXAMPLE 532

7-chloro-2-(1-ethyl-2,3-dimethyl-1H-pyrrolo[2,3-c]pyridin-7-yl)-1-methyl-1,2,3,4-tetrahydroisoquinoline hydrochloride 1H-NMR(400 MHz, CDCl$_3$) δ 8.12 (brs, 1H), 7.45 (brs, 1H), 7.21 (m, 1H), 7.16 (t, 1H), 7.08 (m, 1H), 4.59 (m, 1H), 4.49 (m, 1H), 4.27 (m, 2H), 3.83 (m, 1H), 3.10 (brs, 2H), 2.48 (s, 3H), 2.29 (s, 3H), 1.34 (d, 3H), 1.09 (brs, 3H); (Yield: 56%)

EXAMPLE 533

7-chloro-1-methyl-2-(1,2,3-trimethyl-1H-pyrrolo[2,3-c]pyridin-7-yl)-1,2,3,4-tetrahydroisoquinoline hydrochloride 1H-NMR(400 MHz, CDCl$_3$) δ 8.08 (brs, 1H), 7.41 (brs, 1H), 7.21 (d, 1H), 7.17 (d, 1H), 7.09 (brs, 1H), 4.82 (m, 1H), 4.31 (m, 1H), 3.87 (brs, 3H), 3.10 (brs, 2H), 2.45 (s. 3H), 2.29 (s, 3H), 1.38 (brs, 3H); (Yield: 66%)

EXAMPLE 534

7-chloro-2-[2,3-dimethyl-1-(3-methylbut-2-enyl)-1H-pyrrolo[2,3-c]pyridin-7-yl]-1-methyl-1,2,3,4-tetrahydroisoquinoline hydrochloride 1H-NMR(400 MHz, CDCl$_3$) δ 8.09 (brs, 1H), 7.40 (brs, 1H), 7.19 (d, 1H), 7.14 (d, 1H), 6.91 (brs, 1H), 5.19 (m, 1H), 4.98 (m, 1H), 4.50 (m, 2H), 3.81 (m, 1H), 3.07 (bs. 2H), 2.42 (s, 3H), 2.28 (s, 3H), 1.68 (s, 3H), 1.58 (s, 3H), 1.35 (brs, 3H); (Yield: 75%)

EXAMPLE 535

7-chloro-2-(1-benzyl-2,3-dimethyl-1H-pyrrolo[2,3-c]pyridin-7-yl)-1-methyl-1,2,3,4-tetrahydroisoquinoline hydrochloride 1H-NMR(400 MHz, CDCl$_3$) δ 8.15 (brs, 2H), 7.50 (brs, 2H), 7.15 (d, 2H), 7.05 (m, 2H), 6.62 (brs, 2H), 6.39 (m, 1H), 5.69 (m, 1H), 5.30 (m, 1H), 4.57 (m, 1H), 3.69 (m. 1H), 2.89 (m, 2H), 2.35 (s, 3+3H), 1.21 (brs, 3H); (Yield: 57%)

EXAMPLE 536

7-chloro-2-[2,3-dimethyl-1-(4-methylbenzyl)-1H-pyrrolo[2,3-c]pyridin-7-yl]-1-methyl-1,2,3,4-tetrahydroisoquinoline hydrochloride 1H-NMR(400 MHz, CDCl$_3$) δ 8.15 (m, 2H), 7.46 (m, 2H), 7.16 (d, 2H), 6.47 (d, 2H), 6.22 (m, 1H), 5.72 (m, 1H), 5.24

(m, 2H), 4.54 (m, 1H), 4.43 (m, 1H), 3.74 (m. 1H), 2.91 (m, 2H), 2.34 (s, 3+3+3H), 1.27 (brs, 3H); (Yield: 63%)

EXAMPLE 537

7-chloro-2-(1-methoxymethyl-2,3-dimethyl-1H-pyrrolo[2,3-c]pyridin-7-yl)-1-methyl-1,2,3,4-tetrahydroisoquinoline hydrochloride 1H-NMR(400 MHz, CDCl$_3$) δ 8.16 (m, 1H), 7.43 (m, 1H), 7.21 (m, 2H), 7.12 (m, 1H), 5.65 (m, 1H), 5.23 (m, 1H), 4.99 (m, 1H), 4.25 (m, 1H), 3.85 (m, 1H), 3.16 (brs, 2H), 3.02 (s, 3H), 2.51 (s, 3H), 2.30 (s, 3H), 1.36 (brs, 3H); (Yield: 74%)

EXAMPLE 538

7-chloro-2-[2,3-dimethyl-1-(2-methylthiazol-4-ylmethyl)-1H-pyrrolo[2,3-c]pyridin-7-yl]-1-methyl-1,2,3,4-tetrahydroisoquinoline hydrochloride 1H-NMR(400 MHz, CDCl$_3$) δ 8.15 (brs, 1H), 7.48 (brs, 1H), 7.16 (m, 3H), 6.43 (m, 1H), 5.92 (m, 1H), 5.20 (m, 1H), 4.78 (m, 1H), 4.38 (m, 1H), 3.77 (m, 1H), 2.97 (brs, 2H), 2.66 (s, 3H), 2.40 (s, 3H), 2.31 (s, 3H), 1.29 (brs, 3H); (Yield: 64%)

EXAMPLE 539

7-chloro-2-[1-(3-fluorobenzyl)-2,3-dimethyl-1H-pyrrolo[2,3-c]pyridin-7-yl]-1-methyl-1,2,3,4-tetrahydroisoquinoline hydrochloride 1H-NMR(400 MHz, CDCl$_3$) δ 8.18 (m, 1H), 7.52 (m, 1H), 7.18 (m, 2H), 7.08 (m, 1H), 6.98 (m, 1H), 6.42 (m, 1H), 6.27 (m, 2H), 5.70 (m, 1H), 5.30 (m, 1H), 4.49 (m. 2H), 3.63 (m, 1H), 2.91 (m, 1H), 2.80 (m, 1H), 2.35 (s, 3+3H), 1.32 (brs, 3H); (Yield: 43%)

EXAMPLE 540

7-chloro-2-[1-(4-fluorobenzyl)-2,3-dimethyl-1H-pyrrolo[2,3-c]pyridin-7-yl]-1-methyl-1,2,3,4-tetrahydroisoquinoline hydrochloride 1H-NMR(400 MHz, CDCl$_3$) δ 8.31 (m, 1H), 7.55 (m, 1H), 7.16 (m, 2H), 6.95 (m, 1H), 6.51 (m, 2H), 6.16 (m, 1H), 5.65 (m, 1H), 5.31 (m, 1H), 5.15 (m, 1H), 4.55 (m. 1H), 4.21 (m, 1H), 3.69 (m, 1H), 2.91 (m, 2H), 2.35 (s, 3+3H), 1.28 (brs, 3H); (Yield: 56%)

EXAMPLE 541

7-fluoro-2-(2,3-dimethyl-1H-pyrrolo[2,3-c]pyridin-7-yl)-1-methyl-1,2,3,4-tetrahydroisoquinoline hydrochloride In accordance with the same procedures as in Example 468, except for using 7-fluoro-1-methyl-2-(3-nitropyridin-2-yl)-1,2,3,4-tetrahydroisoquinoline prepared in Preparation 23, the titled compound was obtained as a white solid. (Yield: 33%)

1H-NMR(400 MHz, CDCl$_3$) δ 8.45 (brs, 1H), 7.91 (d, 1H), 7.05 (d, 2H), 6.83 (m, 2H), 5.17 (q, 1H), 3.86 (m, 1H), 3.57 (t, 1H), 2.95 (m, 1H), 2.83 (t, 1H), 2.36 (s, 3H), 2.19 (s, 3H), 1.32 (d, 3H)

EXAMPLES 542 TO 551

The titled compounds of Examples 542 to 551 were prepared, in accordance with the same procedures as in Example 469, using 7-fluoro-2-(2,3-dimethyl-1H-pyrrolo[2,3-c]pyridin-7-yl)-1-methyl-1,2,3,4-tetrahydroisoquinoline hydrochloride prepared in Example 541; and, 3-fluorobenzyl chloride, iodoethane, allyl bromide, 4-bromomethyl-2-methyl-2-butene, 2-bromoethyl methyl ether, benzyl bromide, 4-methylbenzyl bromide, 4-fluorobenzyl chloride, bromomethyl methyl ether, or 4-chloromethyl-2-methylthiazole.

EXAMPLE 542

7-fluoro-2-[1-(3-fluorobenzyl)-2,3-dimethyl-1H-pyrrolo[2,3-c]pyridin-7-yl]-1-methyl-1,2,3,4-tetrahydroisoquinoline hydrochloride 1H-NMR(400 MHz, CDCl$_3$) δ 8.18 (brs, 1H), 7.52 (m, 1H), 7.19 (d, 1H), 7.10 (brs, 1H), 6.96 (m, 2H), 6.21 (m, 1+2H), 5.65 (m, 1H), 5.30 (m, 1H), 4.51 (m, 2H), 3.63 (m. 1H), 2.89 (m, 1H), 2.77 (m, 1H), 2.34 (s, 3+3H), 1.33 (brs, 3H); (Yield: 57%)

EXAMPLE 543

2-(1-ethyl-2,3-dimethyl-1H-pyrrolo[2,3-c]pyridin-7-yl)-7-fluoro-1-methyl-1,2,3,4-tetrahydroisoquinoline hydrochloride 1H-NMR(400 MHz, CDCl$_3$) δ 8.23 (brs, 1H), 7.46 (brs, 1H), 7.18 (brs, 1H), 7.02 (s, 1H), 6.84 (m, 1H), 4.80 (m, 1H), 4.50 (m, 1H), 4.30 (m, 2H), 4.01 (m, 1H), 3.09 (brs, 2H), 2.48 (s, 3H), 2.30 (s, 3H), 1.36 (brs, 3H), 1.11 (brs, 3H); (Yield: 45%)

EXAMPLE 544

2-(1-allyl-2,3-dimethyl-1H-pyrrolo[2,3-c]pyridin-7-yl)-7-fluoro-1-methyl-1,2,3,4-tetrahydroisoquinoline hydrochloride 1H-NMR(400 MHz, CDCl$_3$) δ 8.16 (brs, 1H), 7.48 (brs, 1H), 7.17 (brs, 1H), 6.95 (brs, 1H), 6.73 (m, 1H), 5.75 (m, 2H), 5.13 (d, 2H), 4.75 (m, 2H), 4.48 (d, 1H), 3.80 (m, 1H), 3.06 (brs, 2H), 2.43 (s, 3H), 2.31 (s, 3H), 1.35 (brs, 3H); (Yield: 66%)

EXAMPLE 545

2-[2,3-dimethyl-1-(3-methylbut-2-enyl)-1H-pyrrolo[2,3-c]pyridin-7-yl]-7-fluoro-1-methyl-1,2,3,4-tetrahydroisoquinoline hydrochloride 1H-NMR(400 MHz, CDCl$_3$) δ 8.11 (brs, 1H), 7.41 (brs, 1H), 7.16 (brs, 1H), 6.95 (brs, 1H), 6.68 (m, 1H), 5.16 (m, 2H), 4.97 (brs, 1H), 4.73 (m, 2H), 4.35 (m, 1H), 3.85 (m, 1H), 3.07 (brs, 2H), 2.43 (s, 3H), 2.29 (s, 3H), 1.65 (s, 3H), 1.57 (s, 3H), 1.35 (brs, 3H); (Yield: 35%)

EXAMPLE 546

7-fluoro-2-[1-(2-methoxyethyl)-2,3-dimethyl-1H-pyrrolo[2,3-c]pyridin-7-yl]-1-methyl-1,2,3,4-tetrahydroisoquinoline hydrochloride 1H-NMR(400 MHz, CDCl$_3$) δ 8.15 (brs, 1H), 7.46 (brs, 1H), 7.16 (brs, 1H), 6.95 (brs, 1H), 6.82 (m, 1H), 4.49 (m, 1H), 4.36 (brs, 2H), 4.21 (m, 1H), 3.75 (m, 1H), 3.32 (m, 2H), 3.08 (brs, 2+3H), 2.49 (s, 3H), 2.30 (s, 3H), 1.35 (brs, 3H); (Yield: 45%)

EXAMPLE 547

2-(1-benzyl-2,3-dimethyl-1H-pyrrolo[2,3-c]pyridin-7-yl)-7-fluoro-1-methyl-1,2,3,4-tetrahydroisoquinoline hydrochloride 1H-NMR(400 MHz, CDCl$_3$) δ 8.17 (brs, 1H), 7.50 (brs, 1H), 7.24 (brs, 2H), 7.08 (brs, 1H), 6.89 (brs, 1H), 6.53 (brs, 2H), 6.14 (m, 1H), 5.65 (m, 1H), 5.37 (m, 2H), 4.55 (m, 1H), 4.38 (m, 1H), 3.67 (m, 1H), 2.89 (m, 2H), 2.34 (s, 3+3H), 1.30 (brs, 3H); (Yield: 55%)

EXAMPLE 548

2-[2,3-dimethyl-1-(4-methylbenzyl)-1H-pyrrolo[2,3-c]pyridin-7-yl]-7-fluoro-1-methyl-1,2,3,4-tetrahydroisoquinoline hydrochloride 1H-NMR(400 MHz, CDCl$_3$) δ 8.16 (brs, 1H), 7.49 (brs, 1H), 7.02 (m, 3H), 6.89 (brs, 1H), 6.44 (brs, 2H), 6.11 (brs, 2H), 5.59 (m, 1H), 5.30 (m, 1H), 4.57 (m, 1H), 4.38 (m, 1H), 3.70 (m, 1H), 2.85 (m, 2H), 2.33 (m, 3+3+3H), 1.27 (brs, 3H); (Yield: 69%)

EXAMPLE 549

7-fluoro-2-[1-(4-fluorobenzyl)-2,3-dimethyl-1H-pyrrolo[2,3-c]pyridin-7-yl]-1-methyl-1,2,3,4-tetrahydroisoquinoline hydrochloride 1H-NMR(400 MHz, CDCl$_3$) δ 8.18 (brs, 1H), 7.52 (brs, 1H), 7.10 (brs, 1H), 6.93 (brs, 3H), 6.50 (brs, 2H), 6.27 (m, 1H), 5.58 (m, 1H), 5.36 (m, 1H), 4.55 (m, 1H), 4.41 (m, 1H), 3.74 (m, 1H), 2.79 (m, 2H), 2.34 (m, 3+3H), 1.33 (brs, 3H); (Yield: 54%)

EXAMPLE 550

7-fluoro-2-(1-methoxymethyl-2,3-dimethyl-1H-pyrrolo[2,3-c]pyridin-7-yl)-1-methyl-1,2,3,4-tetrahydroisoquinoline hydrochloride 1H-NMR(400 MHz, CDCl$_3$) δ 8.15 (brs, 1H), 7.43 (brs, 1H), 7.19 (t, 1H), 6.97 (t, 1H), 6.80 (m, 1H), 5.79 (m, 1H), 5.15 (m, 1H), 4.99 (m, 1H), 4.34 (m, 1H), 3.87 (m, 1H), 3.09 (brs, 2H), 3.02 (brs, 3H), 2.50 (s, 3H), 2.29 (s, 3H), 1.34 (d, 3H); (Yield: 53%)

EXAMPLE 551

2-[2,3-dimethyl-1-(2-methylthiazol-4-ylmethyl)-1H-pyrrolo[2,3-c]pyridin-7-yl]-7-fluoro-1-methyl-1,2,3,4-tetrahydroisoquinoline hydrochloride 1H-NMR(400 MHz, CDCl$_3$) δ 7.66 (brs, 1H), 7.11 (brs, 1H), 6.96 (m, 2H), 6.79 (d, 1H), 5.85 (m, 1H), 5.25 (m, 1H), 4.35 (m, 1H), 4.11 (m, 1H), 3.92 (m, 1H), 3.72 (m, 1H), 3.09 (brs, 2H), 2.65 (brs, 3H), 2.21 (s, 3+3H), 1.51 (brs, 3H); (Yield: 42%)

EXAMPLE 552

2-(2,3-dimethyl-1H-pyrrolo[2,3-c]pyridin-7-yl)-1-methyl-1,2,3,4-tetrahydroisoquinoline hydrochloride In accordance with the same procedures as in Example 468, except for using 1-methyl-2-(3-nitropyridin-2-yl)-1,2,3,4-tetrahydroisoquinoline prepared in Preparation 24, the titled compound was obtained as a white solid. (Yield: 40%)

1H-NMR(400 MHz, CDCl$_3$) δ 8.58 (brs, 1H), 7.93 (m, 1H), 6.97 (m, 5H), 5.20 (q, 1H), 3.91 (m, 1H), 3.59 (t, 1H), 3.02 (m, 1H), 2.83 (d, 1H), 2.35 (s, 3H), 2.19 (s, 3H), 1.27 (d, 3H)

EXAMPLES 553 TO 559

The titled compounds of Examples 553 to 559 were prepared, in accordance with the same procedures as in Example 469, using 2-(2,3-dimethyl-1H-pyrrolo[2,3-c]pyridin-7-yl)-1-methyl-1,2,3,4-tetrahydroisoquinoline hydrochloride prepared in Example 552; and, allyl bromide, iodoethane, 2-bromoethyl methyl ether, benzyl bromide, 3-fluorobenzyl chloride, 4-methoxybenzyl bromide, or 4-chloromethyl-2-methylthiazole.

EXAMPLE 553

2-(1-allyl-2,3-dimethyl-1H-pyrrolo[2,3-c]pyridin-7-yl)-1-methyl-1,2,3,4-tetrahydroisoquinoline hydrochloride 1H-NMR(400 MHz, CDCl$_3$) δ 8.07 (brs, 1H), 7.52 (d, 1H), 7.19 (m, 3H), 6.99 (d, 1H), 6.52 (d, 1H), 5.83 (s, 1H), 5.51 (m, 1H), 4.85 (m, 1H), 4.19 (m, 1H), 3.89 (m. 1H), 3.13 (m, 1H), 3.05 (brs, 2H), 2.51 (d, 1H), 2.33 (s, 3H), 2.29 (s, 3H), 1.33 (d, 3H); (Yield: 53%)

EXAMPLE 554

2-(1-ethyl-2,3-dimethyl-1H-pyrrolo[2,3-c]pyridin-7-yl)-1-methyl-1,2,3,4-tetrahydroisoquinoline hydrochloride 1H-NMR(400 MHz, CDCl$_3$) δ 8.13 (brs, 1H), 7.42 (s, 1H), 7.22 (m, 3H), 7.09 (m, 1H), 4.65 (m, 1H), 4.44 (m, 1H), 4.29 (brs, 2H), 3.84 (brs, 1H), 3.12 (brs, 2H), 2.53 (s. 3H), 2.29 (s, 3H), 1.33 (d, 3H), 1.08 (brs, 3H); (Yield: 65%)

EXAMPLE 555

2-[1-(2-methoxyethyl)-2,3-dimethyl-1H-pyrrolo[2,3-c]pyridin-7-yl]-1-methyl-1,2,3,4-tetrahydroisoquinoline hydrochloride 1H-NMR(400 MHz, CDCl$_3$) δ 8.13 (s, 1H), 7.59 (s, 1H), 7.45 (s, 1H), 7.22 (s, 2H), 7.09 (s, 1H), 4.78 (m, 1H), 4.41 (m, 1H), 3.84 (s, 2H), 3.28 (s, 3H), 2.96 (m, 3H), 2.56 (s, 1H), 2.40 (s, 1H), 2.20 (s, 3+3H), 1.22 (brs, 3H); (Yield: 66%)

EXAMPLE 556

2-(1-benzyl-2,3-dimethyl-1H-pyrrolo[2,3-c]pyridin-7-yl)-1-methyl-1,2,3,4-tetrahydroisoquinoline hydrochloride 1H-NMR(400 MHz, CDCl$_3$) δ 8.23 (s, 1H), 7.61 (m, 1H), 7.44 (m, 1H), 7.30 (s, 1H), 7.21 (m, 3H), 7.11 (m, 1H), 6.85 (m, 1H), 6.48 (m, 1H), 5.82 (m, 1H), 5.39 (m, 1H), 4.72 (m, 1H), 4.35 (m, 1H), 3.75 (m, 1H), 2.98 (m, 2H), 2.43 (s, 1H), 2.33 (s, 3+3H), 1.20 (brs, 3H); (Yield: 69%)

EXAMPLE 557

2-[1-(3-fluorobenzyl)-2,3-dimethyl-1H-pyrrolo[2,3-c]pyridin-7-yl]-1-methyl-1,2,3,4-tetrahydroisoquinoline hydrochloride 1H-NMR(400 MHz, CDCl$_3$) δ 8.17 (s, 1H), 7.48 (m, 1H), 7.01 (m, 3H), 6.99 (t, 1H), 6.65 (d, 1H), 6.53 (d, 1H), 6.51 (m, 2H), 5.79 (s, 1H), 5.41 (m, 1H), 4.55 (m, 1H), 4.35 (m, 1H), 3.65 (m, 1H), 2.85 (m, 1H), 2.75 (m, 1H), 2.33 (s, 3+3H), 1.26 (s, 3H); (Yield: 57%)

EXAMPLE 558

2-[1-(4-methoxybenzyl)-2,3-dimethyl-1H-pyrrolo[2,3-c]pyridin-7-yl]-1-methyl-1,2,3,4-tetrahydroisoquinoline hydrochloride 1H-NMR(400 MHz, CDCl$_3$) δ 8.15 (s, 1H), 7.57 (d, 1H), 7.17 (m, 1H), 7.12 (m, 1H), 6.81 (m, 4H), 6.73 (d, 1H), 6.43 (m, 1H), 5.73 (s, 2H), 5.39 (m, 1H), 4.65 (m, 1H), 4.41 (m, 1H), 3.81 (s, 3H), 3.61 (m, 1H), 2.98 (m, 1H), 2.31 (s, 3+3H), 1.30 (brs, 3H); (Yield: 52%)

EXAMPLE 559

2-[2,3-dimethyl-1-(2-methylthiazol-4-ylmethyl)-1H-pyrrolo[2,3-c]pyridin-7-yl]-1-methyl-1,2,3,4-tetrahydroisoquinoline hydrochloride 1H-NMR(400 MHz, CDCl$_3$) δ 8.11 (s, 1H), 7.72 (d, 1H), 7.62 (s, 1H), 7.12 (m, 1H), 6.95 (m, 1H), 6.64 (s, 1H), 5.80 (s, 2H), 5.76 (m, 1H), 4.40 (m, 1H), 3.96 (m, 1H), 2.88 (m, 1H), 2.62 (s, 3+3H), 2.27 (s, 3H), 2.17 (s, 3H), 1.61 (s, 3H); (Yield: 51%)

EXAMPLE 560

2-(2,3-dimethyl-1H-pyrrolo[2,3-c]pyridin-7-yl)-1-methyl-1,2,3,4-tetrahydroisoquinoline sodium In accordance with the same procedures as in Example 410, except for using 2-(2,3-dimethyl-1H-pyrrolo[2,3-c]pyridin-7-yl)-1-methyl-1,2,3,4-tetrahydroisoquinoline obtained by treating the compound prepared in Example 552 with a saturated sodium bicarbonate solution, the titled compound was obtained as a white solid. (Yield: 91%)

1H-NMR(400 MHz, CDCl$_3$) δ 7.94 (d, 1H), 7.90 (brs, 1H), 7.20 (s, 4H), 7.05 (d, 1H), 5.19 (m, 1H), 3.90 (m, 1H), 3.65 (m, 1H), 3.10 (m, 1H), 2.94 (dd, 1H), 2.38 (s, 3H), 2.19 (s, 3H), 1.37 (d, 3H)

EXAMPLE 561

6-fluoro-2-(2,3-dimethyl-1H-pyrrolo[2,3-c]pyridin-7-yl)-1-methyl-1,2,3,4-tetrahydroisoquinoline hydrochloride In accordance with the same procedures as in Example 468, except for using 6-fluoro-1-methyl-2-(3-nitropyridin-2-yl)-1,2,3,4-tetrahydroisoquinoline prepared in Preparation 25, the titled compound was obtained as a white solid. (Yield: 32%)

1H-NMR(400 MHz, CDCl$_3$) δ 8.59 (brs, 1H), 7.91 (d, 1H), 7.05 (d, 1H), 6.92 (m, 1H), 6.84 (m, 1H), 6.75 (m, 1H), 5.14 (q, 1H), 3.88 (m, 1H), 3.56 (t, 1H), 2.99 (m, 1H), 2.80 (d, 1H), 2.36 (s, 3H), 2.19 (s, 3H), 1.25 (d, 3H)

EXAMPLES 562 TO 566

The titled compounds of Examples 562 to 566 were prepared, in accordance with the same procedures as in Example 469, using 6-fluoro-2-(2,3-dimethyl-1H-pyrrolo[2,3-c]pyridin-7-yl)-1-methyl-1,2,3,4-tetrahydroisoquinoline hydrochloride prepared in Example 561; and, iodoethane, allyl bromide, 2-bromoethyl methyl ether, 3-fluorobenzyl chloride, or 4-methoxybenzyl chloride.

EXAMPLE 562

2-(1-ethyl-2,3-dimethyl-1H-pyrrolo[2,3-c]pyridin-7-yl)-6-fluoro-1-methyl-1,2,3,4-tetrahydroisoquinoline hydrochloride 1H-NMR(400 MHz, CDCl$_3$) δ 8.14 (s, 1H), 7.44 (s, 1H), 7.06 (m, 1H), 6.92 (m, 2H), 4.28 (m, 2H), 3.82 (m, 2H), 3.49 (m, 1H), 3.10 (m, 2H), 2.47 (s, 3H), 2.29 (s, 3H), 1.35 (m, 3H), 1.09 (m, 3H); (Yield: 62%)

EXAMPLE 563

2-(1-allyl-2,3-dimethyl-1H-pyrrolo[2,3-c]pyridin-7-yl)-6-fluoro-1-methyl-1,2,3,4-tetrahydroisoquinoline hydrochloride 1H-NMR(400 MHz, CDCl$_3$) δ 8.14 (s, 1H), 7.43 (s, 1H), 6.91 (m, 3H), 5.70 (m, 1H), 5.13 (d, 2H), 4.72 (m, 2H), 4.49 (d, 2H), 3.78 (m, 1H), 3.01 (m, 2H), 2.41 (s, 3H), 2.30 (s, 3H), 1.27 (brs, 3H); (Yield: 53%)

EXAMPLE 564

6-fluoro-2-[1-(2-methoxyethyl)-2,3-dimethyl-1H-pyrrolo[2,3-c]pyridin-7-yl]-1-methyl-1,2,3,4-tetrahydroisoquinoline hydrochloride 1H-NMR(400 MHz, CDCl$_3$) δ 8.14 (s, 1H), 7.45 (m, 1H), 6.92 (m, 3H), 4.55 (m, 1H), 4.34 (m, 1H), 4.22 (m, 1H), 3.87 (m, 1H), 3.71 (m, 1H), 3.31 (m, 2H), 3.11 (brs, 3+2H), 2.48 (s, 3H), 2.29 (s, 3H), 1.35 (brs, 3H); (Yield: 71%)

EXAMPLE 565

6-fluoro-2-[1-(3-fluorobenzyl)-2,3-dimethyl-1H-pyrrolo[2,3-c]pyridin-7-yl]-1-methyl-1,2,3,4-tetrahydroisoquinoline hydrochloride 1H-NMR(400 MHz, CDCl$_3$) δ 8.16 (s, 1H), 7.45 (m, 1H), 7.25 (m, 1H), 6.98 (t, 1H), 6.82 (m, 2H), 6.51 (m, 1H), 6.22 (m, 2H), 5.55 (m, 1H), 5.35 (m, 1H), 4.44 (m, 2H), 3.59 (m, 1H), 2.75 (m, 2H), 2.35 (s, 3+3H), 1.31 (brs, 3H); (Yield: 52%)

EXAMPLE 566

6-fluoro-2-[1-(4-methoxybenzyl)-2,3-dimethyl-1H-pyrrolo[2,3-c]pyridin-7-yl]-1-methyl-1,2,3,4-tetrahydroisoquinoline hydrochloride 1H-NMR(400 MHz, CDCl$_3$) δ 8.14 (s, 1H), 7.45 (m, 1H), 6.85 (m, 3H), 6.75 (d, 1H), 6.44 (m, 3H), 5.44 (m, 1H), 5.35 (m, 1H), 4.51 (m, 1H), 4.41 (m, 1H), 3.76 (s, 3H), 3.59 (m, 1H), 2.89 (m, 2H), 2.33 (s, 3H), 2.31 (s, 3H), 1.22 (brs, 3H); (Yield: 43%)

EXAMPLE 567

6-fluoro-2-(2,3-dimethyl-1H-pyrrolo[2,3-c]pyridin-7-yl)-1-methyl-1,2,3,4-tetrahydroisoquinoline sodium The compound prepared in Example 561 was treated with a saturated sodium bicarbonate solution to obtain 6-fluoro-2-(2,3-dimethyl-1H-pyrrolo[2,3-c]pyridin-7-yl)-1-methyl-1,2,3,4-tetrahydroisoquinoline. A solution of 6-fluoro-2-(2,3-dimethyl-1H-pyrrolo[2,3-c]pyridin-7-yl)-1-methyl-1,2,3,4-tetrahydroisoquinoline (73.5 mg, 0.25 mmol) and sodium hydride (6.0 mg, 0.25 mmol) in anhydrous tetrahydrofuran (2 ml) was stirred for 2 hours at room temperature and then concentrated under reduced pressure. The resulting residue was recrystallized with ethyl ether to give 73 mg of the titled compound as a pale yellow solid.

1H-NMR(400 MHz, CDCl$_3$) δ 8.58 (brs, 1H), 7.91 (d, 1H), 7.06 (d, 1H), 6.92 (m, 1H), 6.84 (m, 1H), 6.74 (m, 1H), 5.14 (q, 1H), 3.87 (m, 1H), 3.56 (t, 1H), 2.99 (m, 1H), 2.80 (d, 1H), 2.36 (s, 3H), 2.20 (s, 3H), 1.26 (d, 3H)

EXAMPLE 568

1-cyclopropyl-2-(2,3-dimethyl-1H-pyrrolo[2,3-c]pyridin-7-yl)-1,2,3,4-tetrahydroisoquinoline hydrochloride In accordance with the same procedures as in Example 468, except for using 1-cyclopropyl-2-(3-nitropyridin-2-yl)-1,2,3,4-tetrahydroisoquinoline prepared in Preparation 26, the titled compound was obtained as a white solid. (Yield: 34%)

1H-NMR(400 MHz, CDCl$_3$) δ 8.31 (s, 1H), 7.91 (d, 1H), 7.19 (m, 4H), 7.04 (d, 1H), 4.45 (d, 1H), 3.86 (m, 1H), 3.77 (m, 1H), 3.08 (m, 1H), 2.91 (m, 1H), 2.31 (s, 3H), 2.18 (s, 3H), 0.98 (m, 1H), 0.45 (m, 1H), 0.30 (m, 1H), 0.20 (m, 1H)

EXAMPLES 569 TO 573

The titled compounds of Examples 569 to 573 were prepared, in accordance with the same procedures as in Example 469, using 1-cyclopropyl-2-(2,3-dimethyl-1H-pyrrolo[2,3-c]pyridin-7-yl)-1,2,3,4-tetrahydroisoquinoline hydrochloride prepared in Example 568; and, iodoethane, allyl bromide, 2-bromoethyl methyl ether, 3-fluorobenzyl chloride, or 4-methoxybenzyl bromide.

EXAMPLE 569

1-cyclopropyl-2-(1-ethyl-2,3-dimethyl-1H-pyrrolo[2,3-c]pyridin-7-yl)-1,2,3,4-tetrahydroisoquinoline hydrochloride 1H-NMR(400 MHz, CDCl$_3$) δ 8.17 (m, 1H), 7.11 (m, 5H), 6.30 (m, 1H), 5.84 (m, 1H), 5.67 (m, 1H), 5.26 (m, 1H), 4.37 (m, 2H), 3.82 (m, 1H), 2.83 (m, 4H), 2.29 (s, 3+3H), 1.75 (m, 1H), 0.64 (m, 3H); (Yield: 56%)

EXAMPLE 570

2-(1-allyl-2,3-dimethyl-1H-pyrrolo[2,3-c]pyridin-7-yl)-1-cyclopropyl-1,2,3,4-tetrahydroisoquinoline hydrochloride 1H-NMR(400 MHz, CDCl$_3$) δ 8.10 (m, 1H), 7.07 (m, 5H), 6.01 (m, 1H), 4.62 (m, 1H), 4.01 (m, 2H), 3.88 (m, 2H), 3.22 (m, 2H), 3.14 (m, 2H), 2.69 (s, 3H), 2.44 (s, 3H), 1.55 (m, 1H), 0.44 (m, 2H), 0.22 (m, 2H); (Yield: 43%)

EXAMPLE 571

1-cyclopropyl-2-[1-(2-methoxyethyl)-2,3-dimethyl-1H-pyrrolo[2,3-c]pyridin-7-yl]-1,2,3,4-tetrahydroisoquinoline hydrochloride 1H-NMR(400 MHz, CDCl$_3$) δ 8.10 (s, 1H), 7.06 (m, 5H), 6.09 (m, 1H), 5.69 (m, 2H), 4.62 (m, 2H), 3.64 (m, 2H), 3.49 (m, 2H), 3.12 (m, 3H), 2.39 (s, 3H), 2.29 (s, 3H), 0.88 (m, 1H), 0.47 (m, 2+2H); (Yield: 35%)

EXAMPLE 572

1-cyclopropyl-2-[1-(3-fluorobenzyl)-2,3-dimethyl-1H-pyrrolo[2,3-c]pyridin-7-yl]-1,2,3,4-tetrahydroisoquinoline hydrochloride 1H-NMR(400 MHz, CDCl$_3$) δ 8.10 (s, 1H), 7.18 (m, 9H), 6.05 (m, 1H), 4.65 (m, 1H), 4.28 (m, 2H), 3.75 (m, 2H), 3.25 (m, 1H), 2.45 (s, 3H), 2.28 (s, 3H), 1.55 (m, 1H), 0.55 (m, 2H), 0.22 (m, 2H); (Yield: 56%)

EXAMPLE 573

1-cyclopropyl-2-[1-(4-methoxybenzyl)-2,3-dimethyl-1H-pyrrolo[2,3-c]pyridin-7-yl]-1,2,3,4-tetrahydroisoquinoline hydrochloride 1H-NMR(400 MHz, CDCl$_3$) δ 8.10 (s, 1H), 7.11 (m, 9H), 6.59 (m, 2H), 6.17 (m, 2H), 5.55 (m, 1H), 5.23 (m, 1H), 2.32 (s, 3+3+3H), 1.44 (m, 1H), 0.49 (m, 2+2H); (Yield: 56%)

EXAMPLE 574

2-(2,3-dimethyl-1H-pyrrolo[2,3-c]pyridin-7-yl)-1-ethyl-1,2,3,4-tetrahydroisoquinoline hydrochloride In accordance with the same procedures as in Example 468, except for using 1-ethyl-2-(3-nitropyridin-2-yl)-1,2,3,4-tetrahydroisoquinoline prepared in Preparation 27, the titled compound was obtained as a white solid. (Yield: 33%)

1H-NMR(400 MHz, CDCl$_3$) δ 8.25 (s, 1H), 7.86 (d, 1H), 7.15 (m, 5H), 5.12 (m, 1H), 3.85 (m, 1H), 3.65 (m, 1H), 3.35 (m, 1H), 2.84 (m, 1H), 2.35 (s, 3H), 2.12 (s, 3H), 1.23 (t, 3H)

EXAMPLES 575 TO 590

The titled compounds of Examples 575 to 590 were prepared, in accordance with the same procedures as in Example 469, using 2-(2,3-dimethyl-1H-pyrrolo[2,3-c]pyridin-7-yl)-1-ethyl-1,2,3,4-tetrahydroisoquinoline hydrochloride prepared in Example 574; and, iodomethane, iodoethane, allyl bromide, 4-bromo-2-methyl-2-butene, benzyl bromide, 4-methylbenzyl bromide, 4-fluorobenzyl chloride, 3-fluorobenzyl chloride, 4-methoxybenzyl chloride, bromomethyl methyl ether, 2-bromoethyl methyl ether, 4-chloromethyl-2-methylthiazole, 2-chloromethoxyethyl methyl ether, 4-bromo-1-butene, 2-chloroethyl vinyl ether, or 2-fluorobenzyl chloride.

EXAMPLE 575

1-ethyl-2-(1,2,3-trimethyl-1H-pyrrolo[2,3-c]pyridin-7-yl)-1,2,3,4-tetrahydroisoquinoline hydrochloride 1H-NMR(400 MHz, CDCl$_3$) δ 8.12 (s, 1H), 7.12 (m, 5H), 5.37 (m, 1H), 4.36 (m, 1H), 3.12 (m, 1H), 2.88 (m, 1H), 2.75 (m, 1H), 2.30 (s, 3+3+3H), 2.09 (m, 1H), 1.75 (m, 1H), 0.64 (brs, 3H); (Yield: 45%)

EXAMPLE 576

1-ethyl-2-(1-ethyl-2,3-dimethyl-1H-pyrrolo[2,3-c]pyridin-7-yl)-1,2,3,4-tetrahydroisoquinoline hydrochloride 1H-NMR(400 MHz, CDCl$_3$) δ 8.17 (s, 1H), 7.20 (m, 5H), 5.79 (s, 1H), 5.42 (m, 1H), 5.22 (m, 1H), 4.51 (m, 1H), 4.22 (m, 1H), 3.75 (m, 1H), 3.05 (m, 1H), 2.33 (s, 3+3H), 1.97 (m, 1H), 1.79 (m, 1H), 1.25 (m, 3H), 0.66 (m, 3H); (Yield: 63%)

EXAMPLE 577

2-(1-allyl-2,3-dimethyl-1H-pyrrolo[2,3-c]pyridin-7-yl)-1-ethyl-1,2,3,4-tetrahydroisoquinoline hydrochloride 1H-NMR(400 MHz, CDCl$_3$) δ 8.18 (s, 1H), 7.18 (m, 5H), 5.82 (s, 1H), 5.45 (m, 1H), 5.25 (m, 1H), 4.35 (m, 1H), 3.75 (m, 1H), 3.05 (m, 1H), 2.95 (m, 1H), 2.85 (m, 1H), 2.32 (s, 3+3H), 1.95 (m, 1H), 1.75 (m, 1H), 0.67 (s, 3H); (Yield: 72%)

EXAMPLE 578

2-[2,3-dimethyl-1-(3-methylbut-2-enyl)-1H-pyrrolo[2,3-c]pyridin-7-yl]-1-ethyl-1,2,3,4-tetrahydroisoquinoline hydrochloride 1H-NMR(400 MHz, CDCl$_3$) δ 7.68 (s, 1H), 7.12 (m, 5H), 5.74 (s, 1H), 5.25 (m, 1H), 4.25 (m, 1H), 4.15 (m, 1H), 3.85 (m, 2H), 3.75 (s, 3+3H), 3.15 (m, 1H), 2.95 (m, 1H), 2.33 (s, 3+3H), 2.12 (m, 1H), 1.85 (m, 1H), 0.63 (m, 3H); (Yield: 65%)

EXAMPLE 579

2-(1-benzyl-2,3-dimethyl-1H-pyrrolo[2,3-c]pyridin-7-yl)-1-ethyl-1,2,3,4-tetrahydroisoquinoline hydrochloride 1H-NMR(400 MHz, CDCl$_3$) δ 8.06 (s, 1H), 7.25 (m, 5+5H), 5.83 (s, 1H), 5.58 (s, 1H), 5.05 (m, 1H), 4.95 (m, 1H), 4.33 (m, 1H), 4.05 (m, 1H), 3.75 (m, 1H), 2.60 (s, 3H), 2.33 (s, 3H), 2.12 (m, 1H), 1.89 (m, 1H), 0.70 (m, 3H); (Yield: 32%)

EXAMPLE 580

2-[2,3-dimethyl-1-(4-methylbenzyl)-1H-pyrrolo[2,3-c]pyridin-7-yl]-1-ethyl-1,2,3,4-tetrahydroisoquinoline hydrochloride 1H-NMR(400 MHz, CDCl$_3$) δ 8.06 (s, 1H), 7.27 (m, 5+4H), 6.02 (m, 1H), 5.45 (m, 1H), 5.22 (m, 1H), 4.55 (m, 1H), 3.76 (s, 3H), 3.19 (m, 1H), 2.95 (m, 1H), 2.67 (m, 1H), 2.31 (s, 3H), 2.30 (s, 3H), 1.43 (m, 1H), 1.22 (m, 1H), 0.43 (m, 3H); (Yield: 42%)

EXAMPLE 581

1-ethyl-2-[1-(4-fluorobenzyl)-2,3-dimethyl-1H-pyrrolo[2,3-c]pyridin-7-yl]-1,2,3,4-tetrahydroisoquinoline hydrochloride 1H-NMR(400 MHz, CDCl$_3$) δ 8.02 (s, 2H), 7.29 (m, 2H), 7.23 (m, 3H), 7.15 (m, 3H), 4.02 (m, 2H), 3.74 (m, 3H), 2.96 (m, 2H), 2.42 (s, 3H), 2.30 (s, 3H), 2.05 (m, 1H), 1.85 (m, 1H), 0.71 (m, 3H); (Yield: 36%)

EXAMPLE 582

1-ethyl-2-[1-(3-fluorobenzyl)-2,3-dimethyl-1H-pyrrolo[2,3-c]pyridin-7-yl]-1,2,3,4-tetrahydroisoquinoline hydrochloride 1H-NMR(400 MHz, CDCl$_3$) δ 8.08 (s, 2H), 7.33 (m, 2H), 7.22 (m, 6H), 4.58 (m, 2H), 4.19 (m, 2H), 3.98 (m, 1H), 3.13 (m, 2H), 2.45 (s, 3H), 2.27 (s, 3H), 2.00 (m, 1H), 1.86 (m, 1H), 0.70 (m, 3H); (Yield: 55%)

EXAMPLE 583

1-ethyl-2-[1-(4-methoxybenzyl)-2,3-dimethyl-1H-pyrrolo[2,3-c]pyridin-7-yl]-1,2,3,4-tetrahydroisoquinoline hydrochloride 1H-NMR(400 MHz, CDCl$_3$) δ 8.10 (s, 1H), 7.56 (m, 2H), 7.37 (m, 2H), 7.11 (m, 5H), 6.02 (m, 2H), 5.17 (m, 2H), 4.55 (m, 2H), 3.15 (m, 1H), 2.44 (s, 3H), 2.35 (s, 3H), 3.33 (s, 3H), 1.12 (m, 1H), 0.82 (m, 1H), 0.65 (m, 3H); (Yield: 46%)

EXAMPLE 584

1-ethyl-2-(1-methoxymethyl-2,3-dimethyl-1H-pyrrolo[2,3-c]pyridin-7-yl)-1,2,3,4-tetrahydroisoquinoline hydrochloride 1H-NMR(400 MHz, CDCl$_3$) δ 8.05 (m, 1H), 7.42 (m, 1H), 7.17 (m, 4H), 5.11 (m, 1H), 4.82 (m, 1H), 4.55 (m, 2H), 4.01 (m, 2H), 3.11 (m, 3H), 2.89 (m, 1H), 2.45 (s, 3H), 2.22 (s, 3H), 0.69 (m, 3H); (Yield: 55%)

EXAMPLE 585

1-ethyl-2-[1-(2-methoxyethyl)-2,3-dimethyl-1H-pyrrolo[2,3-c]pyridin-7-yl]-1,2,3,4-tetrahydroisoquinoline hydrochloride 1H-NMR(400 MHz, CDCl$_3$) δ 8.12 (m, 1H), 7.19 (m, 5H), 5.80 (m, 1H), 5.45 (m, 1H), 5.25 (m, 1H), 5.01 (m, 1H), 4.43 (m, 1H), 4.22 (m, 1H), 3.95 (m, 1H), 3.75 (m, 1H), 3.11 (m, 1H), 2.45 (s, 3H), 2.33 (s, 3+3H), 1.44 (m, 1H), 1.33 (m, 1H), 0.65 (m, 3H); (Yield: 57%)

EXAMPLE 586

1-ethyl-2-[2,3-dimethyl-1-(2-methylthiazol-4-ylmethyl)-1H-pyrrolo[2,3-c]pyridin-7-yl]-1,2,3,4-tetrahydroisoquinoline hydrochloride 1H-NMR(400 MHz, CDCl$_3$) δ 8.07 (m, 1H), 7.92 (m, 1H), 7.22 (m, 3H), 7.14 (m, 2H), 5.05 (m, 1H), 4.72 (m, 1H), 4.33 (m, 1H), 4.22 (m, 1H), 3.95 (m, 1H), 3.70 (m, 3H), 3.22 (m, 1H), 3.12 (m, 3H), 2.55 (s, 3H), 2.05 (m, 1H), 1.86 (m, 1H), 0.82 (m, 3H); (Yield: 65%)

EXAMPLE 587

1-ethyl-2-[1-(2-methoxyethoxymethyl)-2,3-dimethyl-1H-pyrrolo[2,3-c]pyridin-7-yl]-1,2,3,4-tetrahydroisoquinoline hydrochloride 1H-NMR(400 MHz, CDCl$_3$) δ 8.05 (s, 1H), 7.19 (m, 5H), 5.85 (m, 1H), 5.04 (m, 2H), 4.72 (m, 1H), 4.58 (m, 1H), 4.44 (m, 2H), 4.22 (m, 1H), 4.01 (m, 2H), 3.12 (m, 2H), 2.44 (s, 3H), 2.26 (s, 3H), 1.99 (m, 1H), 1.86 (m, 1H), 0.82 (m, 3H), 0.69 (m, 3H); (Yield: 35%)

EXAMPLE 588

2-[1-(but-3-enyl)-2,3-dimethyl-1H-pyrrolo[2,3-c]pyridin-7-yl]-1-ethyl-1,2,3,4-tetrahydroisoquinoline hydrochloride 1H-NMR(400 MHz, CDCl$_3$) δ 8.00 (m, 1H), 7.18 (m, 5H), 6.47 (m, 1H), 6.08 (m, 1H), 5.35 (m, 1H), 5.04 (m, 1H), 4.72 (m, 1H), 4.31 (m, 1H), 4.17 (m, 1H), 4.01 (m, 1H), 3.45 (m, 2H), 3.22 (m, 1H), 3.01 (m, 1H), 2.22 (s, 3+3H), 1.55 (m, 1H), 1.33 (m, 1H), 0.83 (m, 3H); (Yield: 35%)

EXAMPLE 589

2-[1-(2-allyloxyethyl)-2,3-dimethyl-1H-pyrrolo[2,3-c]pyridin-7-yl]-1-ethyl-1,2,3,4-tetrahydroisoquinoline hydrochloride 1H-NMR(400 MHz, CDCl$_3$) δ 8.03 (s, 1H), 7.11 (m, 5H), 6.45 (m, 1H), 6.22 (m, 1H), 5.66 (m, 1H), 5.22 (m, 1H), 5.05 (m, 1H), 4.55 (m, 1H), 4.15 (m, 1H), 3.75 (m, 1H), 3.33 (m, 1H), 2.95 (m, 3H), 2.55 (m, 3H), 2.33 (s, 3H), 2.22 (s, 3H), 1.88 (m, 1H), 1.66 (m, 1H), 0.76 (m, 3H); (Yield: 39%)

EXAMPLE 590

1-ethyl-2-[1-(2-fluorobenzyl)-2,3-dimethyl-1H-pyrrolo[2,3-c]pyridin-7-yl]-1,2,3,4-tetrahydroisoquinoline hydrochloride 1H-NMR(400 MHz, CDCl$_3$) δ 8.08 (s, 1H), 7.27 (m, 9H), 5.65 (m, 1H), 5.22 (m, 1H), 4.75 (m, 1H), 4.33 (m, 1H), 4.00 (m, 1H), 3.66 (m, 1H), 3.55 (m, 1H), 2.49 (s, 3H), 2.26 (s, 3H), 1.94 (m, 1H), 1.83 (m, 1H), 0.68 (m, 3H); (Yield: 39%)

EXAMPLE 591

2-ethyl-3-methyl-7-(1,2,3,4-tetrahydroisoquinolin-2-yl)-1H-pyrrolo[2,3-c]pyridine 1,2,3,4-Tetrahydroisoquinoline (1 ml) was added to 7-chloro-2-ethyl-3-methyl-1H-pyrrolo[2,3-c]pyridine (850 mg, 4.37 mmol) prepared in Preparation 28. The reaction mixture was stirred overnight at 140° C., cooled to room temperature, and then purified with silica gel column chromatography to give 660 mg of the titled compound as a pale yellow solid.

1H-NMR(400 MHz, CDCl$_3$) δ 8.07 (brs, 1H), 7.98 (d, 1H), 7.32 (d, 1H), 2.82 (q, 2H), 2.21 (s, 3H), 1.31 (t, 3H)

EXAMPLE 592

1-benzyl-2-ethyl-3-methyl-7-(1,2,3,4-tetrahydroisoquinolin-2-yl)-1H-pyrrolo[2,3-c]pyridine hydrochloride 18-Crown-6 (2.5 mg, 0.0097 mmol) and potassium tert-butoxide (11 mg, 0.097 mmol) was added to a solution of 2-ethyl-3-methyl-7-(1,2,3,4-tetrahydroisoquinolin-2-yl)-1H-pyrrolo[2,3-c]pyridine (28.3 mg, 0.097 mmol) prepared in Example 591 in anhydrous tetrahydrofuran (0.5 ml). The reaction mixture was stirred for 30 minutes at room temperature and benzyl bromide (17.4 μl, 0.146 mmol) was added thereto. The reaction mixture was stirred overnight and then concentrated under reduced pressure. The resulting residue was purified with silica gel column chromatography (ethyl acetate/n-hexane=1/5, v/v). The resulting product was dissolved in ethyl acetate, saturated with hydrochloric acid gas, and then filtered to give 7.8 mg of the titled compound as a white solid.

1H-NMR(400 MHz, CDCl$_3$) δ 8.17 (m, 1H), 7.52 (d, 2H), 7.16 (m, 5H), 6.72 (m, 1H), 6.46 (m, 2H), 5.55 (s, 2H), 4.43 (m, 2H), 3.72 (m, 2H), 2.87 (m, 2H), 2.75 (m, 2H), 2.41 (s, 3H), 1.17 (t, 3H)

EXAMPLES 593 TO 611

The titled compounds of Examples 593 to 611 were prepared, in accordance with the same procedures as in Example 592, using 2-ethyl-3-methyl-7-(1,2,3,4-tetrahydroisoquinolin-2-yl)-1H-pyrrolo[2,3-c]pyridine prepared in Example 591; and, 3-fluorobenzyl chloride, 3-methoxybenzyl chloride, allyl bromide, 4-bromo-2-methylbutene, 2-bromoethyl methyl ether, (bromomethyl)cyclopropane, 4-chlorobenzyl chloride, 3,4-dichlorobenzyl chloride, iodoethane, 4-methoxybenzyl chloride, 3-methylbenzyl chloride, 4-methylbenzyl chloride, propargyl bromide, 4-fluorobenzyl chloride, 4-trifluoromethylbenzyl chloride, 2-fluorobenzyl chloride, iodomethane, 3-chlorobenzyl chloride, or 1-bromopropane.

EXAMPLE 593

2-ethyl-1-(3-fluorobenzyl)-3-methyl-7-(1,2,3,4-tetrahydroisoquinolin-2-yl)-1H-pyrrolo[2,3-c]pyridine hydrochloride 1H-NMR(400 MHz, CDCl$_3$) δ 8.18 (d, 1H), 7.54 (d, 1H), 7.26 (m, 1H), 7.13 (m, 3H), 6.92 (t, 1H), 6.74 (d, 1H), 6.23 (d, 1H), 6.16 (d, 1H), 5.63 (s, 2H), 4.32 (m, 2H), 3.65 (m, 2H), 2.83 (m, 2H), 2.75 (m, 2H), 2.40 (s, 3H), 1.21 (t, 3H); (Yield: 35%)

EXAMPLE 594

2-ethyl-1-(3-methoxybenzyl)-3-methyl-7-(1,2,3,4-tetrahydroisoquinolin-2-yl)-1H-pyrrolo[2,3-c]pyridine hydrochloride 1H-NMR (400 MHz, CDCl$_3$) δ 8.16 (d, 1H), 7.52 (d, 1H), 7.18 (m, 1H), 7.10 (m, 3H), 6.75 (d, 1H), 6.69 (d, 1H), 6.02 (s, 2H), 5.62 (s, 2H), 4.52 (m, 2H), 3.78 (m, 2H), 3.61 (s, 3H), 2.86 (m, 2H), 2.75 (m, 2H), 2.34 (s, 3H), 1.19 (t, 3H); (Yield: 45%)

EXAMPLE 595

1-allyl-2-ethyl-3-methyl-7-(1,2,3,4-tetrahydroiso-quinolin-2-yl)-1H-pyrrolo[2,3-c]pyridine hydrochloride 1H-NMR(400 MHz, CDCl₃) δ 8.15 (d, 1H), 7.48 (d, 1H), 7.39 (m, 1H), 7.20 (m, 2H), 7.04 (d, 1H), 5.87 (m, 1H), 5.15 (d, 1H), 5.10 (s, 2H), 4.52 (m, 2H), 4.45 (d, 1H), 3.93 (s, 2H), 3.15 (s, 2H), 2.87 (m, 2H), 2.31 (s, 3H), 1.25 (t, 3H); (Yield: 63%)

EXAMPLE 596

2-ethyl-3-methyl-1-(3-methylbut-2-enyl)-7-(1,2,3,4-tetrahydroisoquinolin-2-yl)-1H-pyrrolo[2,3-c]pyridine hydrochloride 1H-NMR(400 MHz, CDCl₃) δ 8.09 (s, 1H), 7.42 (d, 1H), 7.21 (m, 3H), 7.01 (d, 1H), 5.01 (s, 1H), 4.93 (s, 1H), 4.79 (s, 1H), 4.52 (m, 2H), 3.95 (m, 2H), 3.12 (m, 2H), 2.83 (q, 2H), 2.28 (s, 3H), 1.56 (s, 3H), 1.35 (s, 3H), 1.28 (t, 3H); (Yield: 69%)

EXAMPLE 597

2-ethyl-1-(2-methoxyethyl)-3-methyl-7-(1,2,3,4-tetrahydroisoquinolin-2-yl)-1H-pyrrolo[2,3-c]pyridine hydrochloride 1H-NMR(400 MHz, CDCl₃) δ 8.16 (d, 1H), 7.39 (d, 1H), 7.21 (m, 3H), 6.91 (d, 1H), 4.50 (s, 2H), 4.12 (s, 1H), 3.92 (s, 2H), 3.55 (m, 1H), 3.31 (t, 2H), 3.15 (t, 2H), 3.07 (s, 3H), 2.92 (q, 2H), 2.25 (s, 3H), 1.28 (t, 3H); (Yield: 89%)

EXAMPLE 598

1-cyclopropylmethyl-2-ethyl-3-methyl-7-(1,2,3,4-tetrahydroisoquinolin-2-yl)-1H-pyrrolo[2,3-c]pyridine hydrochloride 1H-NMR(400 MHz, CDCl₃) δ 8.15 (s, 1H), 7.44 (d, 1H), 7.24 (t, 3H), 7.07 (d, 1H), 4.51 (m, 1H), 4.21 (d, 2H), 4.01 (m, 2H), 3.48 (m, 1H), 3.17 (s, 2H), 2.90 (q, 2H), 2.29 (s, 3H), 1.29 (t, 3H), 0.89 (m, 1H), 0.33 (d, 2H), 0.04 (m, 2H); (Yield: 81%)

EXAMPLE 599

1-(4-chlorobenzyl)-2-ethyl-3-methyl-7-(1,2,3,4-tetrahydroisoquinolin-2-yl)-1H-pyrrolo[2,3-c]pyridine hydrochloride 1H-NMR(400 MHz, CDCl₃) δ 8.17 (s, 1H), 7.54 (d, 1H), 7.20 (m, 2H), 7.12 (m, 3H), 6.76 (s, 1H), 6.41 (d, 2H), 5.61 (s, 2H), 4.72 (m, 1H), 4.35 (m, 1H), 3.75 (m, 2H), 2.85 (s, 2H), 2.74 (q, 2H), 2.34 (s, 3H), 1.28 (t, 3H); (Yield: 51%)

EXAMPLE 600

1-(3,4-dichlorobenzyl)-2-ethyl-3-methyl-7-(1,2,3,4-tetrahydroisoquinolin-2-yl)-1H-pyrrolo[2,3-c]pyridine hydrochloride 1H-NMR(400 MHz, CDCl₃) δ 8.25 (m, 1H), 7.55 (d, 1H), 7.23 (d, 2H), 7.13 (m, 2H), 6.74 (m, 1H), 6.59 (s, 1H), 6.24 (d, 1H), 5.48 (s, 2H), 4.67 (m, 1H), 3.75 (m, 1H), 3.33 (m, 1H), 3.05 (m, 1H), 2.85 (s, 2H), 2.79 (q, 2H), 2.35 (s, 3H), 1.22 (t, 3H); (Yield: 51%)

EXAMPLE 601

1,2-diethyl-3-methyl-7-(1,2,3,4-tetrahydroisoquinolin-2-yl)-1H-pyrrolo[2,3-c]pyridine hydrochloride 1H-NMR(400 MHz, CDCl₃) δ 8.15 (m, 1H), 7.45 (d, 1H), 7.23 (m, 3H), 7.08 (d, 1H), 4.55 (m, 2H), 4.35 (q, 2H), 3.97 (m, 2H), 3.17 (s, 2H), 2.85 (q, 2H), 2.29 (s, 3H), 1.31 (t, 3H), 1.21 (t, 3H); (Yield: 61%)

EXAMPLE 602

2-ethyl-1-(4-methoxybenzyl)-3-methyl-7-(1,2,3,4-tetrahydroisoquinolin-2-yl)-1H-pyrrolo[2,3-c]pyridine hydrochloride 1H-NMR(400 MHz, CDCl₃) δ 8.15 (m, 1H), 7.50 (d, 1H), 7.18 (m, 1H), 7.11 (m, 2H), 6.89 (m, 1H), 6.70 (d, 2H), 6.42 (d, 2H), 5.58 (s, 2H), 4.56 (m, 1H), 4.35 (m, 1H), 3.85 (m, 2H), 3.74 (s, 3H), 2.86 (s, 2H), 2.75 (q, 2H), 2.33 (s, 3H), 1.19 (t, 3H); (Yield: 63%)

EXAMPLE 603

2-ethyl-3-methyl-1-(3-methylbenzyl)-7-(1,2,3,4-tetrahydroisoquinolin-2-yl)-1H-pyrrolo[2,3-c]pyridine hydrochloride 1H-NMR(400 MHz, CDCl₃) δ 8.16 (m, 1H), 7.52 (d, 1H), 7.15 (m, 1H), 7.11 (m, 4H), 6.65 (d, 1H), 6.31 (s, 1H), 6.21 (d, 1H), 5.55 (s, 2H), 4.33 (m, 2H), 3.75 (m, 2H), 2.75 (m, 2H), 2.65 (q, 2H), 2.34 (s, 3H), 2.18 (s, 3H), 1.19 (t, 3H); (Yield: 73%)

EXAMPLE 604

2-ethyl-3-methyl-1-(4-methylbenzyl)-7-(1,2,3,4-tetrahydroisoquinolin-2-yl)-1H-pyrrolo[2,3-c]pyridine hydrochloride 1H-NMR(400 MHz, CDCl₃) δ 8.15 (m, 1H), 7.51 (d, 1H), 7.18 (m, 1H), 7.08 (m, 1H), 6.97 (d, 3H), 6.76 (d, 1H), 6.38 (d, 2H), 5.60 (s, 2H), 4.44 (m, 2H), 3.75 (m, 2H), 2.84 (t, 2H), 2.76 (q, 2H), 2.33 (s, 3H), 2.22 (s, 3H), 1.15 (t, 3H); (Yield: 73%)

EXAMPLE 605

2-ethyl-3-methyl-1-(prop-2-ynyl)-7-(1,2,3,4-tetrahydroisoquinolin-2-yl)-1H-pyrrolo[2,3-c]pyridine hydrochloride 1H-NMR(400 MHz, CDCl₃) δ 8.14 (m, 1H), 7.46 (d, 1H), 7.18 (m, 2H), 7.11 (m, 2H), 5.22 (s, 2H), 4.69 (m, 1H), 4.45 (m, 1H), 3.95 (m, 2H), 3.19 (m, 2H), 2.97 (m, 2H), 2.42 (s, 3H), 2.41 (s, 1H), 1.33 (t, 3H); (Yield: 77%)

EXAMPLE 606

2-ethyl-1-(4-fluorobenzyl)-3-methyl-7-(1,2,3,4-tetrahydroisoquinolin-2-yl)-1H-pyrrolo[2,3-c]pyridine hydrochloride 1H-NMR(400 MHz, CDCl$_3$) δ 8.17 (m, 1H), 7.53 (d, 1H), 7.15 (m, 2H), 6.90 (m, 2H), 6.75 (d, 2H), 6.45 (m, 1H), 5.61 (s, 2H), 4.55 (m, 1H), 4.23 (m, 1H), 3.75 (m, 2H), 2.81 (t, 2H), 2.76 (q, 2H), 2.30 (s, 3H), 1.18 (t, 3H); (Yield: 67%)

EXAMPLE 607

2-ethyl-1-(4-trifluoromethylbenzyl)-3-methyl-7-(1,2,3,4-tetrahydroisoquinolin-2-yl)-1H-pyrrolo[2,3-c]pyridine hydrochloride 1H-NMR(400 MHz, CDCl$_3$) δ 8.17 (s, 1H), 7.56 (s, 1H), 7.41 (d, 2H), 7.19 (m, 1H), 7.09 (m, 2H), 6.66 (d, 1H), 6.55 (d, 2H), 5.71 (s, 2H), 4.51 (m, 2H), 3.99 (m, 1H), 3.65 (m, 1H), 3.21 (m, 1H), 2.77 (s, 2H), 2.75 (q, 2H), 2.36 (s, 3H), 1.20 (t, 3H); (Yield: 69%)

EXAMPLE 608

2-ethyl-1-(2-fluorobenzyl)-3-methyl-7-(1,2,3,4-tetrahydroisoquinolin-2-yl)-1H-pyrrolo[2,3-c]pyridine hydrochloride 1H-NMR(400 MHz, CDCl$_3$) δ 8.17 (d, 1H), 7.54 (d, 1H), 7.16 (m, 2H), 7.09 (m, 1H), 7.05 (m, 2H), 6.89 (t, 1H), 6.67 (d, 1H), 6.12 (t, 1H), 5.71 (s, 2H), 4.44 (m, 2H), 3.75 (m, 2H), 2.88 (t, 2H), 2.77 (q, 2H), 2.40 (s, 3H), 1.20 (t, 3H); (Yield: 89%)

EXAMPLE 609

2-ethyl-1,3-dimethyl-7-(1,2,3,4-tetrahydroisoquinolin-2-yl)-1H-pyrrolo[2,3-c]pyridine hydrochloride 1H-NMR(400 MHz, CDCl$_3$) δ 8.08 (d, 1H), 7.39 (d, 1H), 7.22 (m, 3H), 7.13 (d, 1H), 4.65 (s, 2H), 3.97 (s, 2H), 3.96 (s, 3H), 3.19 (t, 2H), 2.85 (q, 2H), 2.28 (s, 3H), 1.25 (t, 3H); (Yield: 80%)

EXAMPLE 610

1-(3-chlorobenzyl)-2-ethyl-3-methyl-7-(1,2,3,4-tetrahydroisoquinolin-2-yl)-1H-pyrrolo[2,3-c]pyridine hydrochloride 1H-NMR(400 MHz, CDCl$_3$) δ 8.08 (s, 1H), 7.54 (m, 1H), 7.14 (m, 2H), 7.09 (m, 3H), 6.73 (d, 2H), 6.49 (s, 1H), 6.27 (s, 1H), 5.60 (s, 2H), 4.44 (m, 2H), 3.75 (m, 2H), 2.82 (s, 2H), 2.75 (m, 2H), 2.35 (s, 3H), 1.20 (t, 3H); (Yield: 85%)

EXAMPLE 611

2-(2-ethyl-3-methyl-1-propyl-1H-pyrrolo[2,3-c]pyridin-7-yl)-1,2,3,4-tetrahydroisoquinoline hydrochloride 1H-NMR(400 MHz, CDCl$_3$) δ 8.12 (m, 1H), 7.55 (m, 2H), 7.19 (m, 2H), 7.05 (d, 1H), 4.56 (m, 1H), 4.19 (m, 1H), 4.09 (m, 1H), 3.91 (m, 1H), 3.51 (m, 1H), 3.25 (m, 1H), 3.15 (m, 2H), 2.85 (q, 2H), 2.28 (s, 3H), 1.29 (t, 3H), 0.79 (m, 2H), 0.60 (t, 3H); (Yield: 89%)

EXAMPLE 612

2-{2-[1-(3-fluorobenzyl)-2,3-dimethyl-1H-pyrrolo[2,3-c]pyridin-7-ylamino]-ethyl}-benzaldehyde hydrochloride The compound prepared in Example 480 was treated with a saturated sodium bicarbonate solution to obtain 1-(3-fluorobenzyl)-7-(1,2,3,4-tetrahydroisoquinolin-2-yl)-2,3-dimethyl-1H-pyrrolo[2,3-c]pyridine. Ammonium cerium (IV) nitrate (973 mg, 1.77 mmol) was added at room temperature to a solution of 1-(3-fluorobenzyl)-7-(1,2,3,4-tetrahydroisoquinolin-2-yl)-2,3-dimethyl-1H-pyrrolo[2,3-c]pyridine (225 mg, 0.58 mmol) in acetic acid (5 ml). The reaction mixture was stirred for 3 hours at 55□ and then cooled to room temperature. Water was added to the reaction mixture, which was then extracted with ethyl acetate. The organic layer was washed with a saturated sodium hydroxide solution, dried on anhydrous magnesium sulfate, and then concentrated under reduced pressure. The resulting residue was dissolved in methanol (10 ml) and then 2N lithium hydroxide (2.5 ml) was added thereto. The reaction mixture was stirred for 1 hour at room temperature, neutralized with 1N hydrochloric acid, and then concentrated under reduced pressure. The resulting residue was extracted with ethyl acetate. The organic layer was dried on anhydrous magnesium sulfate and then concentrated under reduced pressure. The resulting residue was purified with silica gel column chromatography (n-hexane/ethyl acetate=1/3, v/v). The resulting product was dissolved in ethyl acetate, saturated with hydrochloric acid gas, and then filtered to give 35 mg of the titled compound as a white solid.

1H-NMR(400 MHz, CDCl$_3$) δ 9.95 (s, 1H), 8.10 (s, 1H), 7.74 (d, 1H), 7.58 (m, 2H), 7.48 (m, 1H), 7.23 (s, 1H), 6.99 (d, 1H), 6.89 (m, 2H), 6.48 (d, 1H), 5.97 (s, 2H), 3.81 (t, 2H), 3.30 (t, 2H), 2.38 (s, 3H), 2.26 (s, 3H)

EXAMPLE 613

2-[1-(3-fluorobenzyl)-2-methyl-1H-pyrrolo[2,3-c]pyridin-7-yl]-1,2,3,4-tetrahydroisoquinoline hydrochloride Step 1: (2-methyl-1H-pyrrolo[2,3-c]pyridin-7-yl)-1,2,3,4-tetrahydroisoquinoline hydrochloride In accordance with the same procedures as in Example 468, except for using 2-(1,2,3,4-tetrahydroisoquinolin-2-yl)-3-nitropyridine prepared in Preparation 20 and isopropenyl magnesium bromide, the titled compound was obtained. (Yield: 39%) The product was used in the subsequent step without further purification.

Step 2: 2-[1-(3-fluorobenzyl)-2-methyl-1H-pyrrolo[2,3-c]pyridin-7-yl]-1,2,3,4-tetrahydroisoquinoline hydrochloride In accordance with the same procedures as in Example 469, except for using 2-methyl-1H-pyrrolo[2,3-c]pyridin-7-yl]-1,2,3,4-tetrahydroisoquinoline hydrochloride prepared in Step 1 and 3-fluorobenzyl chloride, the titled compound was obtained as a white solid. (Yield: 79%)

1H-NMR(400 MHz, CDCl$_3$) δ 8.02 (d, 1H), 7.28 (d, 1H), 7.12 (m, 4H), 6.87 (m, 2H), 6.49 (d, 1H), 6.38 (s, 1H), 6.36 (d, 1H), 5.82 (brs, 1H), 5.51 (brs, 1H), 4.33 (brs, 1H), 4.07 (brs, 1H), 3.45 (brs, 1H), 3.28 (brs, 1H), 2.91 (brs, 1H), 2.76 (brs, 1H), 2.30 (s, 3H)

EXAMPLE 614

2-(1-benzyl-2-methyl-1H-pyrrolo[2,3-c]pyridin-7-yl)-1,2,3,4-tetrahydroisoquinoline hydrochloride In accordance with the same procedures as in Example 469, except for using (2-methyl-1H-pyrrolo[2,3-c]pyridin-7-yl)-1,2,3,4-tetrahydroisoquinoline hydrochloride prepared in Step 1 of Example 613 and benzyl bromide, the titled compound was obtained as a white solid. (Yield: 75%)

1H-NMR(400 MHz, CDCl$_3$) δ 8.15 (s, 1H), 7.54 (s, 1H), 7.39 (s, 1H), 7.25 (m, 5H), 7.12 (brs, 2H), 6.68 (m, 1H), 6.53 (s, 1H), 5.64 (brs, 2H), 4.45 (brs, 2H), 3.82 (brs, 2H), 2.84 (brs, 2H), 2.43 (s, 3H)

EXAMPLE 615

2-[3-bromo-1-(3-fluorobenzyl)-2-methyl-1H-pyrrolo[2,3-c]pyridin-7-yl]-1,2,3,4-tetrahydroisoquinoline hydrochloride N-Bromosuccinimide (41 mg, 0.23 mmol) and silica gel (100 mg) were added to a solution of 2-[1-(3-fluorobenzyl)-2-methyl-1H-pyrrolo[2,3-c]pyridin-7-yl]-1,2,3,4-tetrahydroisoquinoline hydrochloride (88 mg, 0.23 mmol) prepared in Example 613 in dichloromethane (2 ml). The reaction mixture was stirred for 1 hour and then filtered. The resulting filtrate was concentrated under reduced pressure. The resulting residue was purified with silica gel column chromatography (ethyl acetate/n-hexane=1/5, v/v). The resulting product was dissolved in ethyl acetate, saturated with hydrochloric acid gas, and then filtered to give 10 mg of the titled compound as a white solid.

1H-NMR(400 MHz, CDCl$_3$) δ 8.10 (d, 1H), 7.27 (d, 1H), 7.12 (m, 4H), 6.91 (m, 2H), 6.52 (d, 1H), 6.44 (d, 1H), 5.88 (m, 1H), 5.72 (m, 1H), 4.42 (brs, 1H), 4.14 (brs, 1H), 3.48 (brs, 1H), 3.22 (brs, 1H), 2.92 (brs, 1H), 2.79 (brs, 1H), 2.18 (s, 3H)

EXAMPLE 616

7-(3,4-dihydro-1H-isoquinolin-2-yl)-1-(3-fluorobenzyl)-2-methyl-1H-pyrrolo[2,3-c]pyridin-3-carbaldehyde hydrochloride Phosphorus oxychloride (44 μl, 0.47 mmol) was added to a solution of 2-[1-(3-fluorobenzyl)-2-methyl-1H-pyrrolo[2,3-c]pyridin-7-yl]-1,2,3,4-tetrahydroisoquinoline hydrochloride (115 mg, 0.31 mmol) prepared in Example 613 in N,N-dimethylformamide (2 ml). The reaction mixture was stirred overnight at 100° C. under heating. The reaction mixture was cooled to room temperature, added to ice water, basified with a sodium bicarbonate solution, and then extracted with ethyl acetate. The organic layer was dried on anhydrous magnesium sulfate and then concentrated under reduced pressure. The resulting residue was purified with silica gel column chromatography (ethyl acetate/n-hexane=1/1, v/v). The resulting product was dissolved in ethyl acetate, saturated with hydrochloric acid gas, and then filtered to give 28 mg of the titled compound as a white solid.

1H-NMR(400 MHz, CDCl$_3$) δ 10.31 (s, 1H), 8.36 (s, 2H), 7.22 (m, 2H), 7.12 (m, 2H), 7.01 (d, 1H), 6.71 (s, 1H), 6.35 (m, 2H), 5.74 (brs, 2H), 4.45 (brs, 2H), 3.88 (brs, 2H), 2.90 (brs, 2H), 2.75 (s, 3H)

EXAMPLE 617

[7-(3,4-dihydro-1H-isoquinolin-2-yl)-1-(3-fluorobenzyl)-2-methyl-1H-pyrrolo[2,3-c]pyridin-3-yl]-methanol hydrochloride Sodium borohydride (4.7 mg, 0.124 mmol) was added to a solution of 7-(3,4-dihydro-1H-isoquinolin-2-yl)-1-(3-fluorobenzyl)-2-methyl-1H-pyrrolo[2,3-c]pyridin-3-carbaldehyde hydrochloride (25 mg) prepared in Example 616 in methanol (2 ml). The reaction mixture was stirred for 1 hour and water was added thereto. The reaction mixture was extracted with ethyl acetate and then concentrated under reduced pressure. The resulting residue was purified with silica gel column chromatography (ethyl acetate/n-hexane=1/1, v/v). The resulting product was dissolved in ethyl acetate, saturated with hydrochloric acid gas, and then filtered to give 8 mg of the titled compound as a white solid.

1H-NMR(400 MHz, CDCl$_3$) δ 8.08 (d, 1H), 7.42 (d, 1H), 7.15 (m, 4H), 6.87 (m, 2H), 6.51 (d, 1H), 6.40 (d, 1H), 5.85 (brs, 1H), 5.69 (brs, 1H), 4.85 (s, 2H), 4.35 (brs, 1H), 4.11 (brs, 1H), 3.47 (brs, 1H), 3.29 (brs, 1H), 2.90 (brs, 1H), 2.76 (brs, 1H), 2.32 (s, 3H)

EXAMPLE 618

2-[1-(3-fluorobenzyl)-2-methyl-3-(morpholin-4-ylmethyl)-1H-pyrrolo[2,3-c]pyridin-7-yl]-1,2,3,4-tetrahydroisoquinoline hydrochloride The compound prepared in Example 613 was treated with a saturated sodium bicarbonate solution to obtain 2-[1-(3-fluorobenzyl)-2-methyl-1H-pyrrolo[2,3-c]pyridin-7-yl]-1,2,3,4-tetrahydroisoquinoline. Morpholine (25 μl, 0.297 mmol), acetic acid (0.13 ml), and formaldehyde (70 μl) were added to a solution of 2-[1-(3-fluorobenzyl)-2-methyl-1H-pyrrolo[2,3-c]pyridin-7-yl]-1,2,3,4-tetrahydroisoquinoline (100 mg, 0.27 mmol) in ethanol (1.5 ml). The reaction mixture was refluxed overnight and then concentrated under reduced pressure. The resulting residue was dissolved in ethyl acetate and then washed with a sodium bicarbonate solution. The organic layer was dried on anhydrous magnesium sulfate and then concentrated under reduced pressure. The resulting residue was purified with silica gel column chromatography (ethyl acetate/dichloromethane=1/1, v/v) to give the titled compound as a pale yellow solid (Yield: 65%).

1H-NMR(400 MHz, CDCl$_3$) δ 8.07 (d, 1H), 7.42 (d, 1H), 7.13 (m, 4H), 6.88 (m, 2H), 6.47 (d, 1H), 6.35 (d, 1H), 5.84 (d, 1H), 5.70 (d, 1H), 4.32 (brs, 1H), 4.11 (brs, 1H), 3.72 (s, 2H), 3.71 (brs, 4H), 3.46 (brs, 1H), 3.29 (brs, 1H), 2.91 (brs, 1H), 2.76 (brs, 1H), 2.54 (brs, 4H), 2.28 (s, 3H)

EXAMPLE 619

[7-(3,4-dihydro-1H-isoquinolin-2-yl)-1-(3-fluorobenzyl)-2-methyl-1H-pyrrolo[2,3-c]pyridin-3-ylmethyl]-dimethylamine hydrochloride The compound prepared in Example 613 was treated with a saturated sodium bicarbonate solution to obtain 2-[1-(3-fluorobenzyl)-2-methyl-1H-pyrrolo[2,3-c]pyridin-7-yl]-1,2,3,4-tetrahydroisoquinoline. Dimethylamine (2.0M in tetrahydrofuran solution; 378 μl, 0.75 mmol), acetic acid (0.03 ml), and formaldehyde (163 μl) were added to a solution of 2-[1-(3-fluorobenzyl)-2-methyl-1H-pyrrolo[2,3-c]pyridin-7-yl]-1,2,3,4-tetrahydroisoquinoline (234 mg, 0.63 mmol) in ethanol (3.5 ml). The reaction mixture was refluxed overnight and then concentrated under reduced pressure. The resulting residue was dissolved in ethyl acetate and then washed with a sodium bicarbonate solution. The organic layer was dried on anhydrous magnesium sulfate and then concentrated under reduced pressure. The resulting residue was purified with silica gel column chromatography (ethyl acetate/dichloromethane=1/1, v/v). The resulting product was dissolved in ethyl acetate, saturated with hydrochloric acid gas, and then filtered to give the titled compound as a white solid (Yield: 68%).

1H-NMR(400 MHz, CDCl$_3$) δ 8.05 (d, 1H), 7.37 (d, 1H), 7.13 (m, 4H), 6.86 (m, 2H), 6.48 (d, 1H), 6.37 (d, 1H), 5.84 (d, 1H), 5.71 (d, 1H), 4.33 (brs, 1H), 4.08 (brs, 1H), 3.62 (s, 2H), 3.47 (brs, 1H), 3.27 (brs, 1H), 2.30 (s, 6H), 2.28 (s, 3H)

EXAMPLE 620

[7-(3,4-dihydro-1H-isoquinolin-2-yl)-1-(3-fluorobenzyl)-2-methyl-1H-pyrrolo[2,3-c]pyridin-3-ylmethyl]-trimethylammonium iodide The compound prepared in Example 619 was treated with a saturated sodium bicarbonate solution to obtain [7-(3,4-dihydro-1H-isoquinolin-2-yl)-1-(3-fluorobenzyl)-2-methyl-1H-pyrrolo[2,3-c]pyridin-3-ylmethyl]-dimethylamine. Iodomethane (40 μl, 0.64 mmol) was added to a solution of [7-(3,4-dihydro-1H-isoquinolin-2-yl)-1-(3-fluorobenzyl)-2-methyl-1H-pyrrolo[2,3-c]pyridin-3-ylmethyl]-dimethylamine (136 mg, 0.32 mmol) in ethanol (2 ml). The reaction mixture was stirred overnight at room temperature. The resulting precipitate was filtered and then dried to give the titled compound as a white solid (Yield 82%).

1H-NMR(400 MHz, CDCl$_3$) δ 8.16 (d, 1H), 7.57 (d, 1H), 7.14 (m, 4H), 6.92 (d, 2H), 6.47 (d, 1H), 6.33 (d, 1H), 5.90 (d, 1H), 5.78 (d, 1H), 5.16 (brs, 2H), 4.34 (brs, 1H), 4.10 (brs, 1H), 3.48 (brs, 1H), 3.44 (s, 9H), 3.30 (brs, 1H), 2.95 (brs, 1H), 2.81 (brs, 1H), 2.60 (s, 3H)

EXAMPLE 621

[7-(3,4-dihydro-1H-isoquinolin-2-yl)-1-(3-fluorobenzyl)-2-methyl-1H-pyrrolo[2,3-c]pyridin-3-yl]-acetonitrile hydrochloride Sodium cyanide (34 mg, 0.72 mmol) was added to a solution of [7-(3,4-dihydro-1H-isoquinolin-2-yl)-1-(3-fluorobenzyl)-2-methyl-1H-pyrrolo[2,3-c]pyridin-3-ylmethyl]-trimethylammonium iodide (100 mg, 0.27 mmol) prepared in Example 620 in N,N-dimethylformamide (3 ml). The reaction mixture was stirred for 5 hours at 100° C. Water was added to the reaction mixture, which was then extracted with ethyl acetate. The organic layer was dried on anhydrous magnesium sulfate and then concentrated under reduced pressure. The resulting residue was purified with silica gel column chromatography (ethyl acetate/n-hexane=1/1, v/v). The resulting product was dissolved in ethyl ether, saturated with hydrochloric acid gas, and then filtered to give 17 mg of the titled compound as a white solid.

1H-NMR(400 MHz, CDCl$_3$) δ 8.28 (brs, 1H), 7.67 (brs, 1H), 7.24 (m, 3H), 7.19 (m, 1H), 7.13 (m, 2H), 6.68 (m, 2H), 5.68 (brs, 2H), 4.51 (brs, 2H), 3.92 (brs, 2H), 3.89 (brs, 2H), 2.88 (brs, 2H), 2.45 (s, 3H)

EXAMPLE 622

[1-benzyl-7-(3,4-dihydro-1H-isoquinolin-2-yl)-2-methyl-1H-pyrrolo[2,3-c]pyridin-3-ylmethyl]-dimethylamine hydrochloride In accordance with the same procedures as in Example 619, except for using 2-(1-benzyl-2-methyl-1H-pyrrolo[2,3-c]pyridin-7-yl)-1,2,3,4-tetrahydroisoquinoline obtained by treating the compound prepared in Example 614 with a saturated sodium bicarbonate solution, the titled compound was obtained as a white solid. (Yield: 72%)

1H-NMR(400 MHz, CDCl$_3$) δ 8.15 (s, 1H), 7.52 (m, 1H), 7.17 (m, 4H), 7.11 (m, 2H), 6.85 (d, 1H), 6.65 (m, 2H), 5.78 (brs, 2H), 4.37 (s, 2H), 4.34 (brs, 2H), 3.50 (brs, 2H), 2.86 (brs, 2H), 2.82 (s, 3+3H), 2.54 (s, 3H)

EXAMPLE 623

[1-benzyl-7-(3,4-dihydro-1H-isoquinolin-2-yl)-2-methyl-1H-pyrrolo[2,3-c]pyridin-3-ylmethyl]-trimethylammonium iodide In accordance with the same procedures as in Example 620, except for using [1-benzyl-7-(3,4-dihydro-1H-isoquinolin-2-yl)-2-methyl-1H-pyrrolo[2,3-c]pyridin-3-ylmethyl]-dimethylamine obtained by treating the compound prepared in Example 622 with a saturated sodium bicarbonate solution, the titled compound was obtained as a white solid. (Yield: 83%)

1H-NMR(400 MHz, CDCl$_3$) δ 8.14 (d, 1H), 7.65 (d, 1H), 7.16 (m, 4H), 7.12 (m, 2H), 6.88 (d, 1H), 6.67 (brs, 2H), 5.92 (brs, 1H), 5.75 (brs, 1H), 5.14 (s, 2H), 4.35 (brs, 1H), 4.14 (brs, 1H), 3.54 (brs, 1H), 3.45 (s, 3+3+3H), 3.26 (brs, 1H), 2.93 (brs, 1H), 2.77 (brs, 1H), 2.56 (s, 3H)

EXAMPLE 624

[1-benzyl-7-(3,4-dihydro-1H-isoquinolin-2-yl)-2-methyl-1H -pyrrolo[2,3-c]pyridin-3-yl]-acetonitrile hydrochloride Sodium cyanide (34 mg, 0.72 mmol) was added to a solution [1-benzyl-7-(3,4-dihydro-1H-isoquinolin-2-yl)-2-methyl-1H-pyrrolo[2,3-c]pyridin-3-ylmethyl]-trimethylammonium iodide (100 mg, 0.18 mmol) prepared in Example 623 in N,N-dimethylformamide (3 ml). The reaction mixture was stirred for 5 hours at 100° C. Water was added to the reaction mixture, which was then extracted with ethyl acetate. The organic layer was dried on anhydrous magnesium sulfate and then concentrated under reduced pressure. The resulting residue was purified with silica gel column chromatography (ethyl acetate/n-hexane=1/1, v/v). The resulting product was dissolved in ethyl ether, saturated with hydrochloric acid gas, and then filtered to give 15 mg of the titled compound as a white solid.

1H-NMR(400 MHz, CDCl$_3$) δ 8.27 (brs, 1H), 7.63 (brs, 1H), 7.25 (m, 3H), 7.18 (m, 1H), 7.13 (m, 2H), 6.68 (m, 1H), 6.57 (brs, 2H), 5.68 (brs, 2H), 4.50 (brs, 2H), 3.88 (brs, 2H), 3.86 (brs, 2H), 2.89 (brs, 2H), 2.45 (s, 3H)

EXAMPLE 625

2-(2-methyl-3-methylsulfanyl-1H-pyrrolo[2,3-c]pyridin-7-yl)-1,2,3,4-tetrahydroisoquinoline hydrochloride

Step 1. 7-chloro-2-methyl-3-methylsulfanyl-1H-pyrrolo[2,3-c]pyridine

A solution of 3-amino-2-chloropyridine (1.13 g, 8.84 mmol) in dichloromethane (22.7 ml) was cooled to −78° C. A solution of tert-butyl hyperchloride (2 ml, 17.7 mmol) in dichloromethane (6.8 ml) was added to the solution. The reaction mixture was stirred for 15 minutes and a solution of methylthioacetone (0.91 ml, 8.84 mmol) in dichloromethane (6.8 ml) was slowly added thereto. The reaction mixture was stirred for 90 minutes at the same temperature and a solution of triethylamine (1.36 ml, 8.84 mmol) in dichloromethane (6.8 ml) was added thereto. The reaction mixture was warmed to room temperature and water was added thereto. The separated organic layer was dried on anhydrous magnesium sulfate and then concentrated under reduced pressure. The resulting residue was purified with silica gel column chromatography to give 100 mg of the titled compound as a white solid.

1H-NMR(400 MHz, CDCl$_3$) δ 8.61 (brs, 1H), 8.07 (d, 1H), 7.52 (d, 1H), 2.61 (s, 3H), 2.26 (s, 3H)

Step 2: 2-(2-methyl-3-methylsulfanyl-1H-pyrrolo[2,3-c]pyridin-7-yl)-1,2,3,4-tetrahydroisoquinoline 7-Chloro-2-methyl-3-methylsulfanyl-1H-pyrrolo[2,3-c]pyridine (418 mg) prepared in Step 1 was added to 1,2,3,4-tetrahydroisoquinoline (3 ml). The reaction mixture was stirred overnight at 140° C., cooled to room temperature, and then purified with silica gel column chromatography to give 440 mg of the titled compound as pale yellow oil.

Step 3: 2-(2-methyl-3-methylsulfanyl-1H-pyrrolo[2,3-c]pyridin-7-yl)-1,2,3,4-tetrahydroisoquinoline hydrochloride A solution of 2-(2-methyl-3-methylsulfanyl-1H-pyrrolo[2,3-c]pyridin-7-yl)-1,2,3,4-tetrahydroisoquinoline prepared in Step 2 in ethyl acetate was saturated with hydrochloric acid gas and then filtered to give the titled compound as a white solid (Yield: 54%)

1H-NMR(400 MHz, CDCl$_3$) δ 9.64 (brs, 1H), 8.00 (d, 1H), 7.28 (d, 1H), 7.04 (m, 3H), 6.87 (d, 1H), 4.48 (s, 2H), 3.62 (t, 2H), 2.89 (t, 2H), 2.52 (s, 3H), 2.25 (s, 3H)

EXAMPLES 626 TO 631

The titled compounds of Examples 626 to 631 were prepared, in accordance with the same procedures as in Example 592, using 2-(2-methyl-3-methylsulfanyl-1H-pyrrolo[2,3-c]pyridin-7-yl)-1,2,3,4-tetrahydroisoquinoline prepared in Step 2 of Example 625; and, benzyl bromide, 3-fluorobenzyl chloride, (bromomethyl)cyclopropane, 1-bromopropane, 2-bromoethyl methyl ether, or allyl bromide.

EXAMPLE 626

2-(1-benzyl-2-methyl-3-methylsulfanyl-1H-pyrrolo[2,3-c]pyridin-7-yl)-1,2,3,4-tetrahydroisoquinoline hydrochloride 1H-NMR(400 MHz, CDCl$_3$) δ 8.25 (d, 1H), 7.76 (d, 1H), 7.21 (m, 4H), 7.17 (m, 2H), 6.68 (d, 1H), 6.53 (d, 2H), 5.67 (s, 2H), 4.45 (brs, 2H), 3.85 (brs, 2H), 2.87 (m, 2H), 2.54 (s, 3H), 2.29 (s, 3H); (Yield: 51%)

EXAMPLE 627

2-[1-(3-fluorobenzyl)-2-methyl-3-methylsulfanyl-1H-pyrrolo[2,3-c]pyridin-7-yl]-1,2,3,4-tetrahydroisoquinoline hydrochloride 1H-NMR(400 MHz, CDCl$_3$) δ 8.19 (d, 1H), 7.63 (d, 1H), 7.09 (m, 4H), 6.93 (t, 1H), 6.78 (d, 1H), 6.40 (d, 2H), 6.33 (d, 2H), 5.73 (s, 2H), 4.33 (brs, 2H), 3.61 (brs, 2H), 2.86 (s, 2H), 2.48 (s, 3H), 2.28 (s, 3H); (Yield: 49%)

EXAMPLE 628

2-(1-cyclopropylmethyl-2-methyl-3-methylsulfanyl-1H-pyrrolo[2,3-c]pyridin-7-yl)-1,2,3,4-tetrahydroisoquinoline hydrochloride 1H-NMR(400 MHz, CDCl$_3$) δ 8.23 (d, 1H), 7.69 (d, 1H), 7.23 (m, 3H), 7.07 (d, 1H), 4.45 (brs, 2H), 4.26 (d, 2H), 4.02 (brs, 2H), 3.18 (t, 2H), 2.71 (s, 3H), 2.28 (s, 3H), 0.95 (m, 1H), 0.38 (d, 2H), 0.07 (brs, 2H); (Yield: 43%)

EXAMPLE 629

2-(2-methyl-3-methylsulfanyl-1-propyl-1H-pyrrolo[2,3-c]pyridin-7-yl)-1,2,3,4-tetrahydroisoquinoline hydrochloride 1H-NMR(400 MHz, CDCl$_3$) δ 8.22 (d, 1H), 7.71 (d, 1H), 7.22 (m, 3H), 7.06 (t, 1H), 4.55 (brs, 2H), 4.26 (t, 2H), 4.05 (t, 2H), 3.16 (t, 2H), 2.66 (s, 3H), 2.26 (s, 3H), 1.57 (m, 1H), 0.59 (t, 3H); (Yield: 43%)

EXAMPLE 630

2-[1-(2-methoxyethyl)-2-methyl-3-methylsulfanyl-1H-pyrrolo[2,3-c]pyridin-7-yl]-1,2,3,4-tetrahydroisoquinoline hydrochloride 1H-NMR(400 MHz, CDCl$_3$) δ 8.25 (t, 1H), 7.74 (d, 1H), 7.22 (m, 3H), 7.06 (d, 1H), 4.55 (m, 2+2H), 4.01 (m, 2H), 3.44 (t, 2H), 3.13 (brs, 2H), 3.08 (s, 3H), 2.69 (s, 3H), 2.26 (s, 3H); (Yield: 42%)

EXAMPLE 631

2-(1-allyl-2-methyl-3-methylsulfanyl-1H-pyrrolo[2,3-c]pyridin-7-yl)-1,2,3,4-tetrahydroisoquinoline hydrochloride 1H-NMR(400 MHz, CDCl$_3$) δ 8.22 (t, 1H), 7.73 (d, 1H), 7.20 (m, 3H), 7.03 (d, 1H), 5.82 (m, 1H), 5.20 (d, 1H), 5.08 (s, 2H), 4.57 (m, 2+1H), 3.95 (brs, 2H), 3.11 (brs, 2H), 2.62 (s, 3H), 2.27 (s, 3H); (Yield: 51%)

EXAMPLE 632

2-(1-allyl-3-methylsulfinyl-2-methyl-1H-pyrrolo[2,3-c]pyridin-7-yl)-1,2,3,4-tetrahydroisoquinoline hydrochloride Hydrogen peroxide (50 wt. %, 100 µl) was added to a solution of 2-(1-allyl-2-methyl-3-methylsulfanyl-1H-pyrrolo[2,3-c]pyridin-7-yl)-1,2,3,4-tetrahydroisoquinoline hydrochloride (45 mg, 0.12 mmol) prepared in Example 631 in acetic acid (3 ml). The reaction mixture was stirred for 30 minutes at room temperature and sodium thiosulfate was added thereto. The reaction mixture was basified with a potassium carbonate solution and then extracted with dichloromethane. The organic layer was dried on anhydrous magnesium sulfate and concentrated under reduced pressure. The resulting residue was dissolved in ethyl ether, saturated with hydrochloric acid gas, and then filtered to give 5.5 mg of the titled compound as a white solid.

1H-NMR(400 MHz, CDCl$_3$) δ 8.29 (d, 1H), 8.12 (d, 1H), 7.21 (m, 3H), 7.04 (d, 1H), 5.81 (m, 1H), 5.25 (d, 1H), 5.10 (m, 2H), 4.64 (m, 2+1H), 4.01 (brs, 2H), 3.13 (t, 2H), 3.03 (s, 3H), 2.64 (s, 3H)

EXAMPLES 633 TO 636

The titled compounds of Examples 633 to 636 were prepared, in accordance with the same procedures as in Example 632, using the compounds prepared in Examples 627 to 630.

EXAMPLE 633

2-[1-(3-fluorobenzyl)-3-methylsulfinyl-2-methyl-1H-pyrrolo[2,3-c]pyridin-7-yl]-1,2,3,4-tetrahydroisoquinoline hydrochloride 1H-NMR(400 MHz, CDCl$_3$) δ 8.28 (d, 1H), 8.15 (d, 1H), 7.21 (m, 2H), 7.13 (m, 2H), 7.09 (t, 1H), 6.71 (d, 1H), 6.33 (t, 2H), 5.66 (dd, 2H), 4.55 (brs, 2H), 3.83 (brs, 2H), 3.06 (s, 3H), 2.89 (brs, 2H), 2.56 (s, 3H); (Yield: 51%)

EXAMPLE 634

2-(1-cyclopropylmethyl-3-methylsulfinyl-2-methyl-1H-pyrrolo[2,3-c]pyridin-7-yl)-1,2,3,4-tetrahydroisoquinoline hydrochloride 1H-NMR(400 MHz, CDCl$_3$) δ 8.29 (d, 1H), 8.08 (d, 1H), 7.22 (m, 3H), 7.07 (d, 1H), 4.55 (brs, 2H), 4.25 (d, 2H), 4.04 (brs, 2H), 3.18 (brs, 2H), 3.04 (s, 3H), 2.74 (s, 3H), 0.92 (m, 1H), 0.40 (m, 2H), 0.07 (m, 2H); (Yield: 58%)

EXAMPLE 635

2-(3-methylsulfinyl-2-methyl-1-propyl-1H-pyrrolo[2,3-c]pyridin-7-yl)-1,2,3,4-tetrahydroisoquinoline hydrochloride 1H-NMR(400 MHz, CDCl$_3$) δ 8.27 (d, 1H), 8.09 (d, 1H), 7.22 (m, 3H), 7.08 (d, 1H), 4.55 (brs, 2H), 4.24 (brs, 2H), 4.04 (brs, 2H), 3.18 (brs, 2H), 3.03 (s, 3H), 2.68 (s, 3H), 1.55 (m, 2H), 0.61 (t, 3H); (Yield: 57%)

EXAMPLE 636

2-[1-(2-methoxyethyl)-3-methylsulfinyl-2-methyl-1H-pyrrolo[2,3-c]pyridin-7-yl]-1,2,3,4-tetrahydroisoquinoline hydrochloride 1H-NMR(400 MHz, CDCl$_3$) δ 8.30 (d, 1H), 8.14 (d, 1H), 7.22 (m, 3H), 7.07 (d, 1H), 4.53 (m, 2+2H), 3.97 (brs, 2H), 3.45 (brs, 2H), 3.14 (brs, 2H), 3.10 (s, 3H), 3.02 (s, 3H), 2.69 (s, 3H); (Yield: 51%)

EXAMPLE 637

2-(1-allyl-3-methylsulfonyl-2-methyl-1H-pyrrolo[2,3-c]pyridin-7-yl)-1,2,3,4-tetrahydroisoquinoline hydrochloride Hydrogen peroxide (50 wt. %, 100 µl) was added to a solution of 2-(1-allyl-3-methylsulfinyl-2-methyl-1H-pyrrolo[2,3-c]pyridin-7-yl)-1,2,3,4-tetrahydroisoquinoline hydrochloride (30 mg, 0.07 mmol) prepared in Example 632 in acetic acid (3 ml). The reaction mixture was stirred for 1 hour at 60° C., cooled to room temperature, basified with a potassium carbonate solution, and then extracted with dichloromethane. The organic layer was dried on anhydrous magnesium sulfate and then concentrated under reduced pressure. The resulting residue was purified with silica gel column chromatography. The resulting product was dissolved in ethyl ether, saturated with hydrochloric acid gas, and then filtered to give 8 mg of the titled compound as a white solid.

1H-NMR(400 MHz, CDCl$_3$) δ 8.34 (d, 1H), 8.14 (d, 1H), 7.23 (m, 3H), 7.04 (d, 1H), 5.83 (m, 1H), 5.28 (d, 1H), 5.16 (s, 2H), 4.67 (brs, 2H), 4.62 (d, 1H), 3.97 (brs, 2H), 3.16 (s, 3H), 3.14 (brs, 2H), 2.81 (s, 3H)

EXAMPLES 638 TO 641

The titled compounds of Examples 638 to 641 were prepared, in accordance with the same procedures as in Example 637, using the compounds prepared in Examples 633 to 636.

EXAMPLE 638

2-(1-cyclopropylmethyl-3-methylsulfonyl-2-methyl-1H-pyrrolo[2,3-c]pyridin-7-yl)-1,2,3,4-tetrahydroisoquinoline hydrochloride 1H-NMR(400 MHz, CDCl$_3$) δ 8.41 (m, 2H), 8.10 (d, 1H), 7.62 (t, 1H), 7.45 (t, 1H), 7.36 (d, 1H), 5.22 (t, 1H), 4.29 (m, 1H), 4.07 (m, 2H), 3.47 (m, 2H), 3.28 (s, 3H), 2.88 (s, 3H), 1.09 (m, 1H), 0.63 (m, 2H), 0.25 (m, 2H); (Yield: 51%)

EXAMPLE 639

2-(3-methylsulfonyl-2-methyl-1-propyl-1H-pyrrolo[2,3-c]pyridin-7-yl)-1,2,3,4-tetrahydroisoquinoline hydrochloride 1H-NMR(400 MHz, CDCl$_3$) δ 8.40 (s, 2H), 8.11 (d, 1H), 7.62 (t, 1H), 7.45 (t, 1H), 7.34 (d, 1H), 5.17 (t, 1H), 4.21 (t, 2H), 3.94 (m, 1H), 3.50 (m, 1H), 3.28 (m, 1H), 3.18 (s, 3H), 2.87 (s, 3H), 1.75 (m, 2H), 0.811 (t, 3H); (Yield: 59%)

EXAMPLE 640

2-[3-methylsulfonyl-1-(2-methoxyethyl)-2-methyl-1H-pyrrolo[2,3-c]pyridin-7-yl]-1,2,3,4-tetrahydroisoquinoline hydrochloride 1H-NMR(400 MHz, CDCl$_3$) δ 8.40 (m, 2H), 8.09 (d, 1H), 7.61 (t, 1H), 7.44 (t, 1H), 7.34 (d, 1H), 5.22 (t, 1H), 4.51 (m, 1H), 4.40 (m, 1H), 3.98 (m, 1H), 3.48 (m, 2+2H), 3.18 (s, 3+3H), 2.88 (s, 3H); (Yield: 54%)

EXAMPLE 641

2-[1-(3-fluorobenzyl)-3-methylsulfonyl-2-methyl-1H-pyrrolo[2,3-c]pyridin-7-yl]-1,2,3,4-tetrahydroisoquinoline hydrochloride 1H-NMR(400 MHz, CDCl$_3$) δ 8.42 (s, 2H), 8.09 (d, 1H), 7.56 (t, 1H), 7.44 (t, 1H), 7.21 (m, 2H), 7.01 (t, 1H), 6.34 (m, 2H), 5.60 (d, 1H), 5.45 (d, 1H), 4.72 (t, 1H), 3.22 (s, 3H), 3.11 (m, 2H), 2.82 (s, 3H), 2.33 (t, 1H)

EXAMPLE 642

2-(1-benzyl-5-fluoro-2,3-dimethyl-1H-pyrrolo[2,3-c]pyridin-7-yl)-1,2,3,4-tetrahydroisoquinoline hydrochloride

Step 1: 2,6-difluoro-3-nitropyridine

Trifluoromethanesulfonic anhydride (69.51 ml, 0.41 mol) was added to a mixture solution of tetramethylammonium nitrate (56.26 g, 0.41 mol) in dichloromethane (167 ml) under a nitrogen atmosphere. The reaction mixture was stirred for 1.5 hours at room temperature and then 2,6-difluoropyridine (25 ml, 0.28 mol) and dichloromethane (50 ml) were added thereto. The reaction mixture was refluxed for 8 hours, cooled to room temperature, and then brought to pH 8 with a saturated sodium bicarbonate solution. The separated organic layer washed with a saturated sodium chloride solution, dried on anhydrous magnesium sulfate, and then concentrated under reduced pressure. The resulting residue was dried under reduced pressure to give 34.55 g of the titled compound as yellow oil.

1H-NMR(400 MHz, CDCl$_3$) δ 8.69 (q, 1H), 7.04 (d, 1H)

Step 2: 2-(6-fluoro-3-nitropyridin-2-yl)-1,2,3,4-tetrahydroisoquinoline 1,2,3,4-Tetrahydroisoquinoline (34.8 ml, 0.28 mol) was added to a solution of 2,6-difluoro-3-nitropyridine (44.55 g, 0.28 mol) prepared in Step 1 in toluene (200 ml). The reaction mixture was stirred overnight at 60° C. and then concentrated under reduced pressure. The resulting residue was purified with silica gel column chromatography (dichloromethane/n-hexane=1/4, v/v) to give 5.38 g of the titled compound as yellow solid.

1H-NMR (400 MHz, CDCl$_3$) δ 8.34 (brs, 2H), 7.49 (brs, 1H), 7.16-7.13 (m, 1H), 7.10-7.03 (m, 3H), 6.95-6.87 (m, 2H), 6.40-6.38 (d, 2H), 5.67 (s, 2H), 4.18 (brs, 2H), 4.17 (s, 2H), 3.43 (brs, 2H), 2.76 (brs, 2H), 2.18 (s, 3H), 2.14 (s, 3H)

Step 3: 2-(5-fluoro-2,3-dimethyl-1H-pyrrolo[2,3-c]pyridin-7-yl)-1,2,3,4-tetrahydroisoquinoline 1-Methyl-1-propenyl magnesium bromide (0.5M in tetrahydrofuran solution; 138 ml, 68.9 mmol) was slowly added at −78° C. to a solution of 2-(6-fluoro-3-nitropyridin-2-yl)-1,2,3,4-tetrahydroisoquinoline (5.38 g, 19.7 mmol) prepared in Step 2 in anhydrous tetrahydrofuran (150 ml). The reaction mixture was stirred for 1 hour at the same temperature, slowly warmed to room temperature, and then stirred overnight. 20% (w/v) Ammonium chloride solution was added to the reaction mixture, which was then extracted with ethyl acetate. The resulting organic layer was dried on anhydrous magnesium sulfate and then filtered. The resulting filtrate was concentrated under reduced pressure. The resulting residue was purified with silica gel column chromatography. The resulting product was crystallized with ethyl ether to give the titled compound as red oil. (Yield: 32%)

1H-NMR(400 MHz, CDCl$_3$) δ 7.71 (brs, 1H), 7.26-7.17 (m, 4H), 6.47 (brs, 1H), 4.56 (s, 2H), 3.83 (m, 2H), 3.01 (m, 2H), 2.36 (s, 3H), 2.17 (s, 3H)

Step 4: 2-(1-benzyl-5-fluoro-2,3-dimethyl-1H-pyrrolo[2,3-c]pyridin-7-yl)-1,2,3,4-tetrahydroisoquinoline hydrochloride A solution of 2-(5-fluoro-2,3-dimethyl-1H-pyrrolo[2,3-c]pyridin-7-yl)-1,2,3,4-tetrahydroisoquinoline (117.4 mg, 0.40 mmol) prepared in Step 3, sodium hydride (60%, 23.85 mg, 0.60 mmol), and benzyl bromide (56.73 μl, 0.48 mmol) in anhydrous N,N-dimethylformamide (1 ml) was stirred for 30 minutes at room temperature. Water was added to the reaction mixture, which was then extracted with ethyl acetate. The organic layer was dried on anhydrous magnesium sulfate and then concentrated under reduced pressure. The resulting residue was dissolved in ethyl acetate, saturated with hydrochloric acid gas, and then filtered to give 8.9 mg of the titled compound as a pale yellow solid.

1H-NMR(400 MHz, CDCl$_3$) δ 7.37-7.23 (m, 6H), 7.08 (d, 1H), 6.93 (d, 2H), 5.51 (s, 2H), 4.79 (brs, 2H), 3.87 (brs, 2H), 2.35 (s, 3H), 2.29 (s, 3H)

EXAMPLES 643 TO 646

The titled compounds of Examples 643 to 646 were prepared, in accordance with the same procedures as in Step 4 of Example 642, using 2-(5-fluoro-2,3-dimethyl-1H-pyrrolo[2,3-c]pyridin-7-yl)-1,2,3,4-tetrahydroisoquinoline prepared in Step 3 of Example 642; and, (bromomethyl)cyclopropane, 3-chlorobenzyl bromide, 3-fluorobenzyl chloride, or allyl bromide.

EXAMPLE 643

2-(1-cyclopropylmethyl-5-fluoro-2,3-dimethyl-1H-pyrrolo[2,3-c]pyridin-7-yl)-1,2,3,4-tetrahydroisoquinoline hydrochloride 1H-NMR(400 MHz, CDCl$_3$) δ 8.42 (s, 1H), 7.26-7.23 (m, 3H), 7.08 (d, 1H), 4.79 (brs, 2H), 4.17 (d, 2H), 3.87 (brs, 2H), 2.43 (s, 3H), 2.27 (s, 3H); (Yield: 65%)

EXAMPLE 644

2-[1(3-chlorobenzyl)-5-fluoro-2,3-dimethyl-1H-pyrrolo[2,3-c]pyridin-7-yl]-1,2,3,4-tetrahydroisoquinoline hydrochloride 1H-NMR(400 MHz, MeOH-d$_4$) δ 7.63 (s, 1H), 7.35-7.25 (m, 6H), 6.93-6.89 (m, 2H), 5.60 (s, 2H), 4.89 (s, 2H), 4.05 (t, 2H), 3.37 (t, 2H), 2.41 (s, 3H), 2.34 (s, 3H); (Yield: 69%)

EXAMPLE 645

2-[5-fluoro-1-(3-fluorobenzyl)-2,3-dimethyl-1H-pyrrolo[2,3-c]pyridin-7-yl]-1,2,3,4-tetrahydroisoquinoline hydrochloride 1H-NMR(400 MHz, CDCl$_3$) δ 8.49 (s, 1H), 7.32-7.24 (m, 4H), 7.08 (d, 1H), 6.98 (m, 1H), 6.72 (d, 1H), 6.60 (d, 1H), 5.49 (s, 2H), 4.79 (brs, 2H), 3.49 (brs, 2H), 2.35 (s, 3H), 2.30 (s, 3H); (Yield: 85%)

EXAMPLE 646

2-(1-allyl-5-fluoro-2,3-dimethyl-1H-pyrrolo[2,3-c]pyridin-7-yl)-1,2,3,4-tetrahydroisoquinoline hydrochloride 1H-NMR(400 MHz, CDCl$_3$) δ 8.43 (s, 1H), 7.26-7.24 (m, 3H), 7.08 (d, 1H), 5.94 (m, 1H), 5.16 (d, 1H), 4.88 (s, 2H), 4.78 (s, 2H), 4.74 (s, 2H), 3.68 (brs, 2H), 2.38 (s, 3H), 2.27 (s, 3H); (Yield: 86%)

EXAMPLE 647

4-fluoro-2,3-dimethyl-7-(1,2,3,4-tetrahydroisoquinolin-2-yl)-1H-pyrrolo[2,3-c]pyridine In accordance with the same procedures as in Step 3 of Example 642, except for using 2-(5-fluoro-3-nitropyridin-2-yl)-1,2,3,4-tetrahydroisoquinoline prepared in Preparation 6, the titled compound was obtained as yellow oil. (Yield: 43%)

1H-NMR(400 MHz, CDCl$_3$) δ 8.11 (brs, 1H), 7.72 (d, 1H), 7.17 (m, 4H), 4.47 (s, 2H), 3.59 (t, 2H), 3.10 (t, 2H), 2.38 (s, 3H), 2.33 (s, 3H)

EXAMPLE 648

1-allyl-4-fluoro-2,3-dimethyl-7-(1,2,3,4-tetrahydroisoquinolin-2-yl)-1H-pyrrolo[2,3-c]pyridine hydrochloride A solution of 4-fluoro-2,3-dimethyl-7-(1,2,3,4-tetrahydroisoquinolin-2-yl)-1H-pyrrolo[2,3-c]pyridine (38.5 mg, 0.13 mmol) prepared in Example 647, sodium hydride (60%, 10.4 mg, 0.261 mmol), and allyl bromide (12.1 μl, 0.143 mmol) in anhydrous N,N-dimethylformamide (1 ml) was stirred for 30 minutes at room temperature. Water was added to the reaction mixture, which was then extracted with ethyl acetate. The organic layer was dried on anhydrous magnesium sulfate and then concentrated under reduced pressure. The resulting residue was dissolved in ethyl acetate, saturated with hydrochloric acid gas, and then filtered to give 2.6 mg of the titled compound as a pale yellow solid. (Yield: 6%)

1H-NMR(400 MHz, CDCl$_3$) δ 8.03 (d, 1H), 7.22 (m, 3H), 7.01 (d, 1H), 5.81 (m, 1H), 5.18-3.51 (m, 8H), 3.09 (m, 2H), 2.44 (s, 3H), 2.41 (s, 3H)

EXAMPLES 649 TO 651

The titled compounds of Examples 649 to 651 were prepared, in accordance with the same procedures as in Example 648, using 4-fluoro-2,3-dimethyl-7-(1,2,3,4-tetrahydroisoquinolin-2-yl)-1H-pyrrolo[2,3-c]pyridine prepared in Example 647; and, 1-bromopropane, 2-bromoethyl methyl ether, or benzyl bromide.

EXAMPLE 649

2,3-dimethyl-4-fluoro-1-propyl-7-(1,2,3,4-tetrahydroisoquinolin-2-yl)-1H-pyrrolo[2,3-c]pyridine hydrochloride 1H-NMR(400 MHz, CDCl$_3$) δ 8.02 (d, 1H), 7.20 (m, 3H), 7.04 (d, 1H), 4.79 (brs, 1H), 4.18 (m, 4H), 3.51 (brs, 1H), 3.14 (brs, 2H), 2.45 (s, 3H), 2.42 (s, 3H), 1.55 (m, 2H), 0.60 (t, 3H); (Yield: 56%)

EXAMPLE 650

2,3-dimethyl-4-fluoro-1-(2-methoxyethyl)-7-(1,2,3,4-tetrahydroisoquinolin-2-yl)-1H-pyrrolo[2,3-c]pyridine hydrochloride 1H-NMR(400 MHz, CDCl$_3$) δ 8.00 (d, 1H), 7.21 (m, 3H), 7.01 (d, 1H), 5.04-3.95 (m, 6H), 3.42 (m, 2H), 3.11 (m, 5H), 2.48 (s, 3H), 2.42 (s, 3H); (Yield: 53%)

EXAMPLE 651

1-benzyl-2,3-dimethyl-4-fluoro-7-(1,2,3,4-tetrahydroisoquinolin-2-yl)-1H-pyrrolo[2,3-c]pyridine hydrochloride 1H-NMR(400 MHz, CDCl$_3$) δ 8.05 (brs, 1H), 7.16 (m, 6H), 6.54 (d, 1H), 6.54 (m, 2H), 5.69 (brs, 2H), 4.71-2.82 (m, 4H), 2.74 (brs, 2H), 2.46 (s, 3H), 2.34 (s, 3H); (Yield: 61%)

EXAMPLE 652

2-[2-(4-fluoro-2,3-dimethyl-1H-pyrrolo[2,3-c]pyridin-7-ylamino)-ethyl]-benzaldehyde hydrochloride Step 1: 2-[2-(4-fluoro-2,3-dimethyl-1H-pyrrolo[2,3-c]pyridin-7-ylamino)-ethyl]-benzaldehyde In accordance with the same procedures as in Step 3 of Example 642, except for using 5-fluoro-3-nitro-2-(1,2,3,4-tetrahydroisoquinolin-2-yl)pyridine prepared in Preparation 6, the titled compound was obtained as a white solid. (Yield: 20%)

Step 2: 2-[2-(4-fluoro-2,3-dimethyl-1H-pyrrolo[2,3-c]pyridin-7-ylamino)-ethyl]-benzaldehyde hydrochloride A solution of the compound (5 mg) prepared in Step 1 in ethyl acetate was saturated with hydrochloric acid gas and then filtered to give 2,3 mg of the titled compound as a pale yellow solid.

1H-NMR(400 MHz, CDCl$_3$) δ 8.03 (brs, 1H), 7.88 (brs, 1H), 7.50 (brs, 1H), 7.31 (brs, 1H), 7.24 (brs, 1H), 4.48 (brs, 2H), 3.26 (brs, 2H), 2.44 (s, 3H), 2.40 (s, 3H)

EXAMPLES 653 TO 655

The titled compounds of Examples 653 to 655 were prepared, in accordance with the same procedures as in Example 648, using 2-[2-(4-fluoro-2,3-dimethyl-1H-pyrrolo[2,3-c]

pyridin-7-ylamino)-ethyl]-benzaldehyde prepared in Step 1 of Example 652; and, 1-bromopropane, benzyl bromide, or allyl iodide.

EXAMPLE 653

2-[2-(4-fluoro-2,3-dimethyl-1-propyl-1H-pyrrolo[2,3-c]pyridin-7-ylamino)-ethyl]-benzaldehyde hydrochloride 1H-NMR(400 MHz, CDCl$_3$) δ 8.12 (d, 1H), 8.05 (d, 1H), 7.57 (t, 1H), 7.41 (t, 1H), 7.32 (d, 1H), 5.05 (m, 1H), 4.13 (m, 2H), 3.88 (m, 1H), 3.53 (m, 1H), 3.29 (m, 1H), 2.47 (s, 3H), 2.46 (s, 3H), 1.69 (m, 2H), 0.78 (t, 3H); (Yield: 65%)

EXAMPLE 654

2-[2-(1-benzyl-4-fluoro-2,3-dimethyl-1H-pyrrolo[2,3-c]pyridin-7-ylamino)-ethyl]-benzaldehyde hydrochloride 1H-NMR(400 MHz, CDCl$_3$) δ 8.09 (m, 2H), 7.52 (t, 1H), 7.39 (t, 1H), 7.23 (m, 3H), 7.14 (d, 1H), 6.52 (d, 2H), 5.56 (d, 1H), 5.35 (d, 1H), 4.60 (m, 1H), 3.10 (m, 1H), 2.98 (m, 1H), 2.52 (s, 3H), 2.41 (s, 3H), 2.25 (m, 1H); (Yield: 57%)

EXAMPLE 655

2-[2-(1-allyl-4-fluoro-2,3-dimethyl-1H-pyrrolo[2,3-c]pyridin-7-ylamino)-ethyl]-benzaldehyde hydrochloride 1H-NMR(400 MHz, CDCl$_3$) δ 8.10 (d, 1H), 8.06 (d, 1H), 7.56 (t, 1H), 7.30 (d, 1H), 7.41 (t, 1H), 5.92 (m, 1H), 5.15 (d, 1H), 4.90 (m, 2H), 4.73 (m, 1H), 4.41 (d, 1H), 3.77 (m, 1H), 3.45 (m, 1H), 3.25 (m, 1H), 2.48 (s, 3H), 2.42 (s, 3H); (Yield: 67%)

EXAMPLE 656

2-(5-chloro-2,3-dimethyl-1H-pyrrolo[2,3-c]pyridin-7-yl)-1,2,3,4-tetrahydroisoquinoline 2-(6-Chloro-3-nitropyridin-2-yl)-1,2,3,4-tetrahydroisoquinoline (16 g, 56.6 mmol) prepared in Preparation 7 was dissolved in anhydrous tetrahydrofuran (300 ml) under a nitrogen atmosphere. 1-Methyl-1-propenyl magnesium bromide (0.5M in tetrahydrofuran solution, 283 ml, 141.5 mmol) was slowly added at −78° C. to the solution. The reaction mixture was stirred for 2 hours at −20° C. and then 20% (w/v) ammonium chloride solution was added thereto. The reaction mixture was extracted with ethyl acetate and then concentrated under reduced pressure. The resulting residue was purified with silica gel column chromatography (ethyl acetate/n-hexane=1/10, v/v) to give 7.8 g of the titled compound as yellow oil. (Yield: 45%)

1H-NMR(400 MHz, CDCl$_3$) δ 8.12 (s, 1H), 7.15 (m, 4H), 6.98 (s, 1H), 4.60 (s, 2H), 3.71 (t, 2H), 3.04 (t, 2H), 2.36 (s, 3H), 2.13 (s, 3H)

EXAMPLE 657

5-chloro-[1-(3-fluorobenzyl)-7-(1,2,3,4-tetrahydroisoquinolin-2-yl)]-2,3-dimethyl-1H-pyrrolo[2,3-c]pyridine hydrochloride Sodium hydride (60%, 2,3 mg, 0.075 mmol) and 3-fluorobenzyl chloride (9.2 µl, 0.075 mmol) were added to a solution of 2-(5-chloro-2,3-dimethyl-1H-pyrrolo[2,3-c]pyridin-7-yl)-1,2,3,4-tetrahydroisoquinoline (15 mg, 0.048 mmol) prepared in Example 656 in anhydrous N,N-dimethylformamide (0.5 ml). The reaction mixture was stirred for 12 hours at room temperature. Water was added to the reaction mixture, which was then extracted with ethyl acetate. The organic layer was dried on anhydrous magnesium sulfate and then concentrated under reduced pressure. The resulting residue was purified with silica gel column chromatography (ethyl acetate/n-hexane=1/10, v/v) to give the titled compound as a white solid (Yield: 35%)

1H-NMR(400 MHz, CDCl$_3$) δ 8.52 (s, 1H), 7.21 (m, 3H), 7.07 (d, 1H), 6.98 (m, 3H), 6.88 (s, 1H), 5.68 (s, 2H), 4.35 (s, 2H), 3.49 (t, 2H), 3.15 (t, 2H), 2.54 (s, 3H), 2.27 (s, 3H)

EXAMPLES 658 TO 681

The titled compounds of Examples 658 to 681 were prepared, in accordance with the same procedures as in Example 657, using 2-(5-chloro-2,3-dimethyl-1H-pyrrolo[2,3-c]pyridin-7-yl)-1,2,3,4-tetrahydroisoquinoline prepared in Example 656; and, benzyl bromide, propargyl bromide, 2-bromoethyl methyl ether, allyl bromide, 3-fluorobenzyl bromide, 4-bromo-1-butene, 4-bromo-2-methyl-2-butene, 1-bromo-3-methylbutane, (bromomethyl)cyclopropane, 2-(bromomethyl)naphthalene, 4-tert-butylbenzyl chloride, 4-chlorobenzyl chloride, 2,5-dimethylbenzyl chloride, iodoethane, 1-iodo-2-methylpropane, 1-bromopropane, 3-methoxybenzyl bromide, 4-methoxybenzyl bromide, 3-methylbenzyl bromide, 4-methylbenzyl bromide, 4-fluorobenzyl bromide, (bromomethyl)cyclobutane, 2-fluorobenzyl chloride, or iodomethane.

EXAMPLE 658

2-(1-benzyl-5-chloro-2,3-dimethyl-1H-pyrrolo[2,3-c]pyridin-7-yl)-1,2,3,4-tetrahydroisoquinoline 1H-NMR(400 MHz, CDCl$_3$) δ 7.12 (m, 7H), 6.88 (d, 1H), 6.71 (m, 2H), 5.67 (brs, 2H), 4.26 (brs, 2H), 3.40 (brs, 2H), 2.76 (brs, H), 2.19 (s, 3+3H); (Yield: 79%)

EXAMPLE 659

2-[5-chloro-2,3-dimethyl-1-(prop-2-ynyl)-1H-pyrrolo[2,3-c]pyridin-7-yl]-1,2,3,4-tetrahydroisoquinoline 1H-NMR(400 MHz, CDCl$_3$) δ 7.19 (m, 5H), 5.25 (brs, 2H), 4.42 (brs, 2H), 3.65 (brs, 2H), 3.15 (brs, 2H), 2.45 (s, 3H), 2.31 (s, 1H), 2.17 (s, 3H); (Yield: 86%)

EXAMPLE 660

2-[5-chloro-1-(2-methoxyethyl)-2,3-dimethyl-1H-pyrrolo[2,3-c]pyridin-7-yl]-1,2,3,4-tetrahydroisoquinoline 1H-NMR(400 MHz, CDCl₃) δ 7.15 (m, 4H), 7.10 (d, 1H), 4.43 (s, 2H), 4.20 (brs, 2H), 3.49 (brs, 2H), 3.37 (t, 2H), 3.06 (s, 3H), 2.37 (s, 3H), 2.17 (s, 3H); (Yield: 76%)

EXAMPLE 661

2-(1-allyl-5-chloro-2,3-dimethyl-1H-pyrrolo[2,3-c]pyridin-7-yl)-1,2,3,4-tetrahydroisoquinoline 1H-NMR(400 MHz, CDCl₃) δ 7.19 (m, 4H), 7.10 (d, 1H), 5.81 (m, 1H), 5.06 (d, 2+1H), 4.65 (d, 1H), 4.33 (m, 2H), 3.38 (brs, 2H), 3.05 (brs, 2H), 2.30 (s, 3H), 2.18 (s, 3H); (Yield: 69%)

EXAMPLE 662

2-[5-chloro-1-(3-fluorobenzyl)-2,3-dimethyl-1H-pyrrolo[2,3-c]pyridin-7-yl]-1,2,3,4-tetrahydroisoquinoline 1H-NMR(400 MHz, CDCl₃) δ 7.21 (s, 1H), 7.14 (m, 4H), 6.89 (d, 2H), 6.49 (d, 1H), 6.39 (d, 1H), 5.66 (brs, 2H), 4.23 (brs, 2H), 3.38 (brs, 2H), 2.84 (brs, 2H), 2.20 (s, 3+3H); (Yield: 66%)

EXAMPLE 663

2-[1-(but-3-enyl)-5-chloro-2,3-dimethyl-1H-pyrrolo[2,3-c]pyridin-7-yl]-1,2,3,4-tetrahydroisoquinoline 1H-NMR(400 MHz, CDCl₃) δ 7.16 (m, 4H), 7.10 (d, 1H), 5.40 (m, 1H), 4.78 (dd, 1+1H), 4.28 (brs, 2+2H), 3.51 (brs, 2H), 3.01 (brs, 2H), 2.34 (s, 3H), 2.17 (s, 3H); (Yield: 65%)

EXAMPLE 664

2-[5-chloro-2,3-dimethyl-1-(3-methylbut-2-enyl)-1H-pyrrolo[2,3-c]pyridin-7-yl]-1,2,3,4-tetrahydroisoquinoline 1H-NMR(400 MHz, CDCl₃) δ 7.15 (m, 4H), 7.08 (d, 1H), 5.00 (m, 2+1H), 4.35 (s, 2H), 3.45 (brs, 2H), 3.10 (brs, 2H), 2.30 (s, 3H), 2.16 (s, 3H), 1.61 (s, 3H), 1.43 (s, 3H); (Yield: 65%)

EXAMPLE 665

2-[5-chloro-2,3-dimethyl-1-(3-methylbutyl)-1H-pyrrolo[2,3-c]pyridin-7-yl]-1,2,3,4-tetrahydroisoquinoline 1H-NMR(400 MHz, CDCl₃) δ 1H NMR (400 MHz, CDCl3) 7.17 (m, 4H), 7.08 (d, 1H), 4.31 (s, 2H), 4.26 (q, 2H), 3.49 (brs, 2H), 3.03 (brs, 2H), 2.33 (s, 3H), 2.17 (s, 3H), 1.27 (m, 1+2H), 0.70 (s, 3H), 0.69 (s, 3H); (Yield: 69%)

EXAMPLE 666

2-(5-chloro-1-cyclopropylmethyl-2,3-dimethyl-1H-pyrrolo[2,3-c]pyridin-7-yl)-1,2,3,4-tetrahydroisoquinoline 1H-NMR(400 MHz, CDCl₃) δ 7.15 (m, 4H), 7.10 (d, 1H), 4.29 (brs, 2H), 4.19 (s, 2H), 3.49 (brs, 2H), 3.21 (brs, 2H), 2.39 (s, 3H), 2.17 (s, 3H), 0.86 (m, 1H), 0.25 (m, 2H), 0.09 (m, 2H); (Yield: 71%)

EXAMPLE 667

2-[5-chloro-2,3-dimethyl-1-(naphthalen-2-ylmethyl)-1H-pyrrolo[2,3-c]pyridin-7-yl]-1,2,3,4-tetrahydroisoquinoline 1H-NMR(400 MHz, CDCl₃) δ 7.84 (m, 4H), 7.48 (m, 4H), 7.05 (m, 4H), 5.89 (brs, 2H), 4.32 (brs, 2H), 3.45 (brs, 2H), 2.75 (brs, 2H), 2.21 (s, 3+3H); (Yield: 71%)

EXAMPLE 668

2-[1-(4-tert-butylbenzyl)-5-chloro-2,3-dimethyl-1H-pyrrolo[2,3-c]pyridin-7-yl]-1,2,3,4-tetrahydroisoquinoline 1H-NMR(400 MHz, CDCl₃) δ 7.32 (d, 1H), 7.25 (d, 1H), 7.09 (m, 4H), 6.74 (d, 1H), 6.56 (d, 2H), 5.55 (s, 2H), 4.17 (brs, 2H), 3.30 (brs, 3H), 2.80 (brs, 2H), 2.14 (s, 3H), 2.11 (s, 3H), 1.18 (s, 9H); (Yield: 70%)

EXAMPLE 669

2-[5-chloro-1-(4-chlorobenzyl)-2,3-dimethyl-1H-pyrrolo[2,3-c]pyridin-7-yl]-1,2,3,4-tetrahydroisoquinoline 1H-NMR(400 MHz, CDCl₃) δ 7.14 (m, 6H), 7.09 (d, 1H), 6.63 (d, 2H), 5.63 (brs, 2H), 4.22 (brs, 2H), 3.37 (brs, 2H), 2.84 (brs, 2H), 2.19 (s, 3+3H); (Yield: 70%)

EXAMPLE 670

2-[5-chloro-1-(2,5-dimethylbenzyl)-2,3-dimethyl-1H-pyrrolo[2,3-c]pyridin-7-yl]-1,2,3,4-tetrahydroisoquinoline 1H-NMR(400 MHz, CDCl₃) δ 7.14 (d, 1H), 7.07 (d, 2H), 7.02 (t, 1H), 6.54 (s, 2H), 6.54 (d, 1H), 6.01 (s, 1H), 5.56 (brs, 2H), 4.06 (brs, 2H), 3.34 (brs, 2H), 2.74 (brs, 2H), 2.24 (s, 3H), 2.18 (s, 3H), 2.12 (s, 3H), 1.79 (s, 3H); (Yield: 68%)

EXAMPLE 671

2-(5-chloro-1-ethyl-2,3-dimethyl-1H-pyrrolo[2,3-c]pyridin-7-yl)-1,2,3,4-tetrahydroisoquinoline 1H-NMR(400 MHz, CDCl₃) δ 7.16 (m, 5H), 4.34 (brs, 2+2H), 3.46 (brs, 2H), 3.03 (brs, 2H), 2.34 (s, 3H), 2.17 (s, 3H), 1.06 (t, 3H); (Yield: 79%)

EXAMPLE 672

2-(5-chloro-1-isobutyl-2,3-dimethyl-1H-pyrrolo[2,3-c]pyridin-7-yl)-1,2,3,4-tetrahydroisoquinoline 1H-NMR(400 MHz, CDCl$_3$) δ 7.16 (m, 4H), 7.10 (d, 1H), 4.28 (brs, 2H), 3.99 (brs, 2H), 3.48 (brs, 2H), 3.02 (brs, 2H), 2.33 (s, 3H), 2.17 (s, 3H), 1.87 (m, 1H), 0.56 (s, 3H), 0.54 (s, 3H); (Yield: 79%)

EXAMPLE 673

2-(5-chloro-2,3-dimethyl-1-propyl-1H-pyrrolo[2,3-c]pyridin-7-yl)-1,2,3,4-tetrahydroisoquinoline 1H-NMR(400 MHz, CDCl$_3$) δ 7.16 (m, 4H), 7.10 (d, 1H), 4.30 (brs, 2H), 4.17 (m, 2H), 3.48 (brs, 2H), 3.02 (brs, 2H), 2.33 (s, 3H), 2.17 (s, 3H), 1.43 (q, 2H), 0.60 (t, 3H); (Yield: 79%)

EXAMPLE 674

2-[5-chloro-1-(3-methoxybenzyl)-2,3-dimethyl-1H-pyrrolo[2,3-c]pyridin-7-yl]-1,2,3,4-tetrahydroisoquinoline 1H-NMR(400 MHz, CDCl$_3$) δ 7.20 (s, 1H), 7.09 (m, 4H), 6.87 (d, 1H), 6.72 (d, 1H), 6.29 (m, 2H), 5.65 (brs, 2H), 4.24 (brs, 2H), 3.63 (s, 3H), 3.41 (brs, 2H), 2.85 (brs, 2H), 2.21 (s, 3H), 2.19 (s, 3H); (Yield: 71%)

EXAMPLE 675

2-[5-chloro-1-(4-methoxybenzyl)-2,3-dimethyl-1H-pyrrolo[2,3-c]pyridin-7-yl]-1,2,3,4-tetrahydroisoquinoline 1H-NMR(400 MHz, CDCl$_3$) δ 7.31 (t, 2H), 7.12 (m, 1H), 6.91 (m, 2H), 6.88 (d, 2H), 6.66 (d, 2H), 5.59 (brs, 2H), 4.24 (brs, 2H), 3.74 (s, 3H), 3.38 (brs, 2H), 2.87 (brs, 2H), 2.20 (s, 3H), 2.18 (s, 3H); (Yield: 71%)

EXAMPLE 676

2-[5-chloro-2,3-dimethyl-1-(3-methylbenzyl)-1H-pyrrolo[2,3-c]pyridin-7-yl]-1,2,3,4-tetrahydroisoquinoline 1H-NMR(400 MHz, CDCl$_3$) δ 7.20 (s, 1H), 7.08 (m, 4H), 7.04 (d, 1H), 6.85 (d, 1H), 6.57 (s, 1H), 6.45 (d, 1H), 5.62 (s, 2H), 4.24 (brs, 2H), 3.39 (brs, 2H), 2.83 (brs, 2H), 2.20 (s, 3+3+3H); (Yield: 71%)

EXAMPLE 677

2-[5-chloro-2,3-dimethyl-1-(4-methylbenzyl)-1H-pyrrolo[2,3-c]pyridin-7-yl]-1,2,3,4-tetrahydroisoquinoline 1H-NMR(400 MHz, CDCl$_3$) δ 7.19 (s, 1H), 7.09 (m, 3H), 6.99 (d, 2H), 6.91 (d, 1H), 6.62 (d, 2H), 5.65 (brs, 2H), 4.25 (brs, 2H), 3.37 (brs, 2H), 2.84 (brs, 2H), 2.27 (s, 3H), 2.19 (s, 3H), 2.18 (s, 3H); (Yield: 71%)

EXAMPLE 678

2-[5-chloro-1-(4-fluorobenzyl)-2,3-dimethyl-1H-pyrrolo[2,3-c]pyridin-7-yl]-1,2,3,4-tetrahydroisoquinoline 1H-NMR(400 MHz, CDCl$_3$) δ 7.20 (s, 1H), 7.12 (m, 3H), 6.88 (m, 3H), 6.65 (m, 2H), 5.62 (brs, 2H), 4.24 (brs, 2H), 3.47 (brs, 2H), 2.85 (brs, 2H), 2.20 (s, 3H), 2.19 (s, 3H); (Yield: 68%)

EXAMPLE 679

2-(5-chloro-1-cyclobutylmethyl-2,3-dimethyl-1H-pyrrolo[2,3-c]pyridin-7-yl)-1,2,3,4-tetrahydroisoquinoline 1H-NMR(400 MHz, CDCl$_3$) δ 7.12 (m, 2H), 7.07 (m, 1H), 7.04 (m, 2H), 4.21 (d, 2+2H), 3.52 (brs, 2H), 3.05 (brs, 2H), 2.26 (s, 3H), 2.09 (s, 3H), 1.53 (m, 2+2H), 1.36 (brs, 2H); (Yield: 75%)

EXAMPLE 680

2-[5-chloro-1-(2-fluorobenzyl)-2,3-dimethyl-1H-pyrrolo[2,3-c]pyridin-7-yl]-1,2,3,4-tetrahydroisoquinoline 1H-NMR(400 MHz, CDCl$_3$) δ 7.14 (s, 1H), 7.04 (m, 4H), 6.83 (m, 2H), 6.77 (d, 1H), 6.22 (t, 1H), 5.65 (s, 2H), 4.15 (brs, 2H), 3.27 (brs, 2H), 2.78 (brs, 2H), 2.13 (s, 3+3H); (Yield: 68%)

EXAMPLE 681

2-(5-chloro-1,2,3-trimethyl-1H-pyrrolo[2,3-c]pyridin-7-yl)-1,2,3,4-tetrahydroisoquinoline 1H-NMR(400 MHz, CDCl$_3$) δ 7.14 (m, 5H), 4.38 (brs, 2H), 3.88 (brs, 3H), 3.50 (brs, 2H), 3.12 (brs, 2H), 2.32 (brs, 3H), 2.16 (brs, 3H); (Yield: 80%)

EXAMPLE 682

7-(3,4-dihydro-1H-isoquinolin-2-yl)-2,3-dimethyl-1H-pyrrolo[2,3-c]pyridin-5-carbonitrile Copper(I) cyanide (9.3 g, 102.6 mmol) was added to a solution of 2-(5-chloro-2,3-dimethyl-1H-pyrrolo[2,3-c]pyridin-7-yl)-1,2,3,4-tetrahydroisoquinoline (3.2 g, 10.3 mmol) prepared in Example 656 in anhydrous N,N-dimethylformamide (100 ml). The reaction mixture was refluxed for 24 hours and then cooled to room temperature. Ethyl acetate was added to the reaction mixture, which was then filtered to discard insoluble matertals. The reaction mixture washed with water. The organic layer was dried on anhydrous magnesium sulfate and then concentrated under reduced pressure. The resulting residue was purified with silica gel column chromatography (ethyl acetate/n-hexane=1/3, v/v) to give 750 mg of the titled compound as a white solid. (Yield: 26%)

1H-NMR(400 MHz, CDCl$_3$) δ 8.12 (s, 1H), 7.50 (s, 1H), 7.20 (m, 4H), 4.67 (s, 2H), 3.78 (t, 2H), 3.11 (t, 2H), 2.42 (s, 3H), 2.20 (s, 3H)

EXAMPLES 683 TO 729

The titled compounds of Examples 683 to 729 were prepared, in accordance with the same procedures as in Example 657, using 7-(3,4-dihydro-1H-isoquinolin-2-yl)-2,3-dimethyl-1H-pyrrolo[2,3-c]pyridin-5-carbonitrile prepared in Example 682; and, 4-bromo-1-butene, allyl iodide, 2-chloroethyl vinyl ether, benzyl bromide, 2-bromoethyl methyl ether, propargyl bromide, 3-chlorobenzyl chloride, 4-fluorobenzyl chloride, 3-methoxybenzyl chloride, 4-methoxybenzyl chloride, 4-methylbenzyl chloride, 4-bromo-2-methyl-2-butene, 3-fluorobenzyl chloride, iodoethane, 1-bromopropane, 1-bromobutane, bromomethyl methyl ether, (bromomethyl)cyclopropane, 4-tert-butylbenzyl chloride, 4-chlorobenzyl chloride, 2-chlorobenzyl chloride, 3,4-dichlorobenzyl chloride, 2,5-dimethylbenzyl chloride, 3-methylbenzyl chloride, iodomethane, 1-iodo-2-methylpropane, 1-bromo-3-methylbutane, 1-bromo-3-phenylpropane, 2-bromoethyl acetate, 2-bromoethyl-1,3-dioxane, 2-(bromoethyl)benzene, (bromomethyl)cyclobutane, (bromomethyl)cyclohexane, 2-(bromomethyl)naphthalene, 2-methylbenzyl bromide, 5-chloro-1-pentyne, 5-chloro-2-pentanone ethylene ketal, 1-chloroheptane, chloromethyl pivalate, 3-chloromethyl pentane, cis, trans-crotyl chloride, 2-fluorobenzyl chloride, 2-methoxyethoxymethyl chloride, methyl bromoacetate, methyl-(4-bromomethyl)benzoate, 4-(trifluoromethyl)benzyl bromide, or 2-methoxybenzyl bromide.

EXAMPLE 683

1-(but-3-enyl)-7-(3,4-dihydro-1H-isoquinolin-2-yl)-2,3-dimethyl-1H-pyrrolo[2,3-c]pyridin-5-carbonitrile 1H-NMR(400 MHz, CDCl$_3$) δ 7.65 (s, 1H), 7.18 (m, 3H), 7.10 (d, 1H), 5.44 (m, 1H), 4.78 (m, 2H), 4.36 (brs, 4H), 4.26-2.96 (brs, 6H), 2.38 (s, 3H), 2.22 (s, 3H); (Yield: 66%)

EXAMPLE 684

1-allyl-7-(3,4-dihydro-1H-isoquinolin-2-yl)-2,3-dimethyl-1H-pyrrolo[2,3-c]pyridin-5-carbonitrile 1H-NMR(400 MHz, CDCl$_3$) δ 7.66 (s, 1H), 7.17 (m, 3H), 7.09 (m, 1H), 5.84 (m, 1H), 5.10 (d, 3H), 4.63 (d, 1H), 4.34 (brs, 2H), 3.44 (brs, 2H), 3.07 (brs, 2H), 2.33 (s, 3H), 2.17 (s, 3H); (Yield: 56%)

EXAMPLE 685

7-(3,4-dihydro-1H-isoquinolin-2-yl)-2,3-dimethyl-1-(2-vinyloxyethyl)-1H-pyrrolo[2,3-c]pyridin-5-carbonitrile 1H-NMR(400 MHz, CDCl$_3$) δ 7.67 (s, 1H), 7.20 (m, 3H), 7.10 (d, 1H), 6.14 (m, 1H), 4.58 (brs, 2H), 4.40-4.30 (brs, 2H), 4.18 (d, 1H), 3.96 (d, 1H), 3.84 (t, 2H), 3.58-2.99 (brs, 4H), 2.41 (s, 3H), 2.23 (s, 3H); (Yield: 76%)

EXAMPLE 686

1-benzyl-7-(3,4-dihydro-1H-isoquinolin-2-yl)-2,3-dimethyl-1H-pyrrolo[2,3-c]pyridin-5-carbonitrile 1H-NMR(400 MHz, CDCl$_3$) δ 7.70 (s, 1H), 7.16 (m, 7H), 6.85 (d, 1H), 6.71 (d, 2H), 5.73 (brs, 2H), 4.28 (brs, 2H), 2.84 (brs, 2H), 2.25 (s, 3H), 2.17 (s, 3H); (Yield: 64%)

EXAMPLE 687

7-(3,4-dihydro-1H-isoquinolin-2-yl)-1-(2-methoxyethyl)-2,3-dimethyl-1H-pyrrolo[2,3-c]pyridin-5-carbonitrile 1H-NMR(400 MHz, CDCl$_3$) δ 7.66 (s, 1H), 7.20 (m, 3H), 7.10 (m, 1H), 4.50 (s, 2H), 3.41 (t, 2H), 3.08 (s, 3H), 4.50-3.08 (brs, 6H), 2.40 (s, 3H), 2.23 (s, 3H); (Yield: 70%)

EXAMPLE 688

7-(3,4-dihydro-1H-isoquinolin-2-yl)-2,3-dimethyl-1-(prop-2-ynyl)-1H-pyrrolo[2,3-c]pyridin-5-carbonitrile 1H-NMR(400 MHz, CDCl$_3$) δ 7.64 (s, 1H), 7.20 (m, 4H), 5.59 (brs, 1H), 5.12 (brs, 1H), 4.46 (m, 2H), 3.74 (brs, 1H), 3.30 (brs, 2H), 2.92 (brs, 1H), 2.43 (s, 3H), 2.38 (s, 1H), 2.23 (s, 3H); (Yield: 63%)

EXAMPLE 689

1-(3-chlorobenzyl)-7-(3,4-dihydro-1H-isoquinolin-2-yl)-2,3-dimethyl-1H-pyrrolo[2,3-c]pyridin-5-carbonitrile 1H-NMR(400 MHz, CDCl$_3$) δ 7.71 (s, 1H), 7.15 (m, 5H), 6.84 (d, 1H), 6.74 (s, 1H), 6.53 (d, 1H), 5.72 (s, 2H), 4.26 (brs, 2H), 3.48 (brs, 2H), 2.89 (brs, 2H), 2.26 (s, 3H), 2.23 (s, 3H); (Yield: 65%)

EXAMPLE 690

7-(3,4-dihydro-1H-isoquinolin-2-yl)-1-(4-fluorobenzyl)-2,3-dimethyl-1H-pyrrolo[2,3-c]pyridin-5-carbonitrile 1H-NMR(400 MHz, CDCl$_3$) δ 7.70 (s, 1H), 7.17 (m, 3H), 6.89 (m, 3H), 6.67 (m, 2H), 5.71 (brs, 2H), 4.13 (brs, 2H), 3.36 (brs, 2H), 2.89 (brs, 2H), 2.25 (s, 3H), 2.23 (s, 3H); (Yield: 67%)

EXAMPLE 691

7-(3,4-dihydro-1H-isoquinolin-2-yl)-1-(3-methoxybenzyl)-2,3-dimethyl-1H-pyrrolo[2,3-c]pyridin-5-carbonitrile 1H-NMR(400 MHz, CDCl$_3$) δ 7.69 (s, 1H), 7.13 (m, 4H), 6.85 (d, 1H), 6.74 (d, 1H), 6.28 (d, 1H), 6.25 (s, 1H), 5.72 (brs, 2H), 4.26 (brs, 2H), 3.65 (s, 3H), 3.35 (brs, 2H), 2.88 (brs, 2H), 2.25 (s, 3H), 2.23 (s, 3H); (Yield: 84%)

EXAMPLE 692

7-(3,4-dihydro-1H-isoquinolin-2-yl)-1-(4-methoxybenzyl)-2,3-dimethyl-1H-pyrrolo[2,3-c]pyridin-5-carbonitrile 1H-NMR(400 MHz, CDCl$_3$) δ 7.68 (s, 1H), 7.15 (m, 3H), 6.92 (d, 1H), 6.75 (m, 2H), 6.67 (m, 2H), 5.30 (brs, 2H), 4.22 (brs, 2H), 3.80 (s, 3H), 3.52 (brs, 2H), 2.89 (brs, 2H), 2.17 (s, 6H); (Yield: 81%)

EXAMPLE 693

7-(3,4-dihydro-1H-isoquinolin-2-yl)-2,3-dimethyl-1-(4-methylbenzyl)-1H-pyrrolo[2,3-c]pyridin-5-carbonitrile 1H-NMR(400 MHz, CDCl$_3$) δ 7.69 (s, 1H), 7.11 (m, 3H), 7.02 (d, 2H), 6.88 (m, 1H), 6.61 (d, 2H), 5.78 (brs, 2H), 4.26 (brs, 2H), 3.40 (brs, 2H), 2.83 (brs, 2H), 2.37 (s, 3H), 2.29 (s, 3H), 2.24 (s, 3H); (Yield: 70%)

EXAMPLE 694

7-(3,4-dihydro-1H-isoquinolin-2-yl)-2,3-dimethyl-1-(3-methylbut-2-enyl)-1H-pyrrolo[2,3-c]pyridin-5-carbonitrile 1H-NMR(400 MHz, CDCl$_3$) δ 7.82 (s, 1H), 7.18 (m, 3H), 7.08 (m, 1H), 5.09 (brs, 2H), 5.00 (brs, 1H), 4.43 (brs, 2H), 3.49 (brs, 2H), 3.06 (brs, 2H), 2.33 (s, 3H), 2.24 (s, 3H), 1.68 (s, 3H), 1.47 (s, 3H); (Yield: 34%)

EXAMPLE 695

7-(3,4-dihydro-1H-isoquinolin-2-yl)-1-(3-fluorobenzyl)-2,3-dimethyl-1H-pyrrolo[2,3-c]pyridin-5-carbonitrile 1H-NMR(400 MHz, CDCl$_3$) δ 7.83 (s, 1H), 7.15 (m, 4H), 6.90 (m, 2H), 6.49 (d, 1H), 6.38 (d, 1H), 5.74 (brs, 2H), 4.13 (brs, 2H), 3.44 (brs, 2H), 2.85 (brs, 2H), 2.26 (s, 3H), 2.23 (s, 3H); (Yield: 84%)

EXAMPLE 696

7-(3,4-dihydro-1H-isoquinolin-2-yl)-1-ethyl-2,3-dimethyl-1H-pyrrolo[2,3-c]pyridin-5-carbonitrile 1H-NMR(400 MHz, CDCl$_3$) δ 7.64 (s, 1H), 7.20 (m, 3H), 7.12 (m, 1H), 4.41 (brs, 4H), 3.59-2.90 (brs, 4H), 2.39 (s, 3H), 2.23 (s, 3H), 1.12 (t, 3H); (Yield: 84%)

EXAMPLE 697

7-(3,4-dihydro-1H-isoquinolin-2-yl)-2,3-dimethyl-1-propyl-1H-pyrrolo[2,3-c]pyridin-5-carbonitrile 1H-NMR(400 MHz, CDCl$_3$) δ 7.65 (s, 1H), 7.18 (m, 3H), 7.10 (m, 1H), 4.27 (t, 2H), 3.70-3.00 (dr, 6H), 2.38 (s, 3H), 2.23 (s, 3H), 1.52 (m, 2H), 0.61 (t, 3H); (Yield: 86%)

EXAMPLE 698

1-butyl-7-(3,4-dihydro-1H-isoquinolin-2-yl)-2,3-dimethyl-1H-pyrrolo[2,3-c]pyridin-5-carbonitrile 1H-NMR(400 MHz, CDCl$_3$) δ 7.73 (s, 1H), 7.20 (m, 3H), 7.09 (m, 1H), 4.31 (t, 2H), 4.31 (brs, 2H), 3.49 (brs, 2H), 3.01 (brs, 2H), 2.37 (s, 3H), 2.24 (s, 3H), 1.45 (m, 2H), 0.99 (m, 2H), 0.71 (t, 3H); (Yield: 86%)

EXAMPLE 699

7-(3,4-dihydro-1H-isoquinolin-2-yl)-1-methoxymethyl-2,3-dimethyl-1H-pyrrolo[2,3-c]pyridin-5-carbonitrile 1H-NMR(400 MHz, CDCl$_3$) δ 7.63 (s, 1H), 7.18 (m, 3H), 7.12 (m, 1H), 5.72 (s, 2H), 4.35 (s, 2H), 3.55 (brs, 2H), 3.12 (brs, 2H), 3.06 (s, 3H), 2.42 (s, 3H), 2.23 (s, 3H); (Yield: 71%)

EXAMPLE 700

1-cyclopropylmethyl-7-(3,4-dihydro-1H-isoquinolin-2-yl)-2,3-dimethyl-1H-pyrrolo[2,3-c]pyridin-5-carbonitrile 1H-NMR(400 MHz, CDCl$_3$) δ 7.65 (s, 1H), 7.17 (m, 3H), 7.09 (m, 1H), 5.30 (s, 2H), 4.26 (brs, 4H), 3.64-3.00 (brs, 4H), 2.44 (s, 3H), 2.25 (s, 3H), 1.11 (s, 1H), 0.28 (m, 2H), 0.15 (m, 2H); (Yield: 79%)

EXAMPLE 701

1-(4-tert-butylbenzyl)-7-(3,4-dihydro-1H-isoquinolin-2-yl)-2,3-dimethyl-1H-pyrrolo[2,3-c]pyridin-5-carbonitrile 1H-NMR(400 MHz, CDCl$_3$) δ 7.69 (s, 1H), 7.17 (m, 5H), 6.78 (d, 1H), 6.64 (d, 2H), 5.70 (s, 2H), 4.22 (brs, 2H), 3.48 (brs, 2H), 2.93 (brs, 2H), 2.24 (s, 6H), 1.27 (s, 9H); (Yield: 79%)

EXAMPLE 702

1-(4-chlorobenzyl)-7-(3,4-dihydro-1H-isoquinolin-2-yl)-2,3-dimethyl-1H-pyrrolo[2,3-c]pyridin-5-carbonitrile 1H-NMR(400 MHz, CDCl$_3$) δ 7.70 (s, 1H), 7.18 (m, 5H), 6.88 (d, 1H), 6.64 (d, 2H), 5.75 (brs, 2H), 4.20 (brs, 2H), 3.47 (brs, 2H), 2.84 (brs, 2H), 2.25 (s, 3H), 2.22 (s, 3H); (Yield: 77%)

EXAMPLE 703

1-(2-chlorobenzyl)-7-(3,4-dihydro-1H-isoquinolin-2-yl)-2,3-dimethyl-1H-pyrrolo[2,3-c]pyridin-5-carbonitrile 1H-NMR(400 MHz, CDCl$_3$) δ 7.72 (s, 1H), 7.17 (m, 3H), 7.07 (m, 3H), 6.70 (d, 1H), 6.14 (d, 1H), 5.80 (s, 2H), 4.17 (brs, 2H), 3.31 (s, 2H), 3.03 (brs, 2H), 2.28 (s, 3H), 2.21 (s, 3H); (Yield: 77%)

EXAMPLE 704

1-(3,4-dichlorobenzyl)-7-(3,4-dihydro-1H-isoquinolin-2-yl)-2,3-dimethyl-1H-pyrrolo[2,3-c]pyridin-5-carbonitrile 1H-NMR(400 MHz, CDCl$_3$) δ 7.71 (s, 1H), 7.17 (m, 4H), 6.86 (m, 2H), 6.47 (d, 1H), 5.67 (brs, 2H), 4.13 (brs, 2H), 3.39 (brs, 2H), 2.89 (brs, 2H), 2.26 (s, 3H), 224 (s, 3H); (Yield: 77%)

EXAMPLE 705

7-(3,4-dihydro-1H-isoquinolin-2-yl)-1-(2,5-dimethylbenzyl)-2,3-dimethyl-1H-pyrrolo[2,3-c]pyridin-5-carbonitrile 1H-NMR(400 MHz, CDCl$_3$) δ 7.73 (s, 1H), 7.14-6.96 (m, 5H), 6.94 (s, 1H), 6.48 (d, 1H), 6.01 (s, 2H), 4.06 (brs, 2H), 3.42 (brs, 2H), 2.78 (brs, 2H), 2.30 (s, 3H), 2.20 (s, 3H), 2.15 (s, 3H), 1.80 (s, 3H); (Yield: 76%)

EXAMPLE 706

7-(3,4-dihydro-1H-isoquinolin-2-yl)-2,3-dimethyl-1-(3-methylbenzyl)-1H-pyrrolo[2,3-c]pyridin-5-carbonitrile 1H-NMR(400 MHz, CDCl$_3$) δ 7.70 (s, 1H), 7.10 (m, 4H), 7.01 (m, 1H), 6.81 (d, 1H), 6.58 (s, 1H), 6.45 (d, 1H), 5.71 (s, 2H), 4.24 (brs, 2H), 3.47 (brs, 2H), 2.84 (brs, 2H), 2.25 (s, 3H), 2.23 (s, 3H), 2.21 (s, 3H); (Yield: 76%)

EXAMPLE 707

7-(3,4-dihydro-1H-isoquinolin-2-yl)-1,2,3-trimethyl-1H-pyrrolo[2,3-c]pyridin-5-carbonitrile 1H-NMR(400 MHz, CDCl$_3$) δ 7.61 (s, 1H), 7.19 (m, 4H), 4.38 (s, 2H), 3.97 (s, 3H), 3.50 (brs, 2H), 3.13 (brs, 2H), 2.36 (s, 3H), 2.22 (s, 3H); (Yield: 83%)

EXAMPLE 708

7-(3,4-dihydro-1H-isoquinolin-2-yl)-1-isobutyl-2,3-dimethyl-1H-pyrrolo[2,3-c]pyridin-5-carbonitrile 1H-NMR(400 MHz, CDCl$_3$) δ 7.64 (s, 1H), 7.18 (m, 3H), 7.09 (d, 1H), 4.24 (brs, 2H), 4.11 (m, 1H), 4.11 (brs, 2H), 3.45 (brs, 4H), 2.37 (s, 3H), 2.23 (s, 3H), 1.88 (m, 1H), 0.56 (d, 6H); (Yield: 81%)

EXAMPLE 709

7-(3,4-dihydro-1H-isoquinolin-2-yl)-1-(3-methylbutyl)-2,3-dimethyl-1H-pyrrolo[2,3-c]pyridin-5-carbonitrile 1H-NMR(400 MHz, CDCl$_3$) δ 7.63 (s, 1H), 7.18 (m, 3H), 7.09 (d, 1H), 4.32 (m, 4H), 3.68-2.96 (brs, 4H), 2.37 (s, 3H), 2.22 (s, 3H), 0.90 (m, 3H), 0.71 (d, 6H); (Yield: 81%)

EXAMPLE 710

7-(3,4-dihydro-1H-isoquinolin-2-yl)-2,3-dimethyl-1-(3-phenylpropyl)-1H-pyrrolo[2,3-c]pyridin-5-carbonitrile 1H-NMR(400 MHz, CDCl$_3$) δ 7.63 (s, 1H), 7.22 (m, 3H), 7.11 (m, 4H), 6.88 (d, 2H), 4.30 (m, 2H), 4.31 (brs, 2H), 3.60-2.96 (brs, 4H), 2.34 (m, 2H), 2.33 (s, 3H), 2.21 (s, 3H), 1.78 (m, 2H); (Yield: 68%)

EXAMPLE 711

2-[5-cyano-7-(3,4-dihydro-1H-isoquinolin-2-yl)-2,3-dimethyl-pyrrolo[2,3-c]pyridin-1-yl]-acetic acid ethyl ester 1H-NMR(400 MHz, CDCl$_3$) δ 7.66 (s, 1H), 7.20 (m, 3H), 7.10 (d, 1H), 4.60 (brs, 2H), 4.38 (brs, 1H), 4.15 (brs, 1H), 4.11 (t, 2H), 3.61-2.97 (brs, 4H), 2.41 (s, 3H), 2.24 (s, 3H); (Yield: 67%)

EXAMPLE 712

7-(3,4-dihydro-1H-isoquinolin-2-yl)-1-[2-[1,3]dioxan-2-ylethyl]-2,3-dimethyl-1H-pyrrolo[2,3-c]pyridin-5-carbonitrile 1H-NMR(400 MHz, CDCl$_3$) δ 7.64 (s, 1H), 7.20 (m 3H), 7.12 (d, 1H), 4.41 (brs, 2H), 4.06 (t, 1H), 3.85 (m, 2H), 3.77 (m, 2H), 3.51 (t, 2H), 3.39 (brs, 2H), 2.90 (brs, 2H), 2.38 (s, 3H), 2.22 (s, 3H), 2.09 (m, 2H), 1.86 (m, 2H); (Yield: 67%)

EXAMPLE 713

7-(3,4-dihydro-1H-isoquinolin-2-yl)-2,3-dimethyl-1-phenethyl-1H-pyrrolo[2,3-c]pyridin-5-carbonitrile 1H-NMR(400 MHz, CDCl$_3$) δ 7.66 (s, 1H), 7.22 (m, 3H), 7.12 (m, 2H), 6.99 (m, 2H), 6.65 (d, 2H), 4.50 (brs, 3H), 4.25 (brs, 1H), 3.59 (brs, 1H), 3.40 (brs, 2H), 2.96 (brs, 1H), 2.70 (brs, 2H), 2.27 (s, 3H), 2.22 (s, 3H); (Yield: 68%)

EXAMPLE 714

1-cyclobutylmethyl-7-(3,4-dihydro-1H-isoquinolin-2-yl)-2,3-dimethyl-1H-pyrrolo[2,3-c]pyridin-5-carbonitrile 1H-NMR(400 MHz, CDCl$_3$) δ 7.63 (s, 1H), 7.21 (m, 3H), 7.11 (d, 1H), 4.36 (d, 2H), 4.28 (brs, 2H), 3.60 (brs, 1H), 3.28 (brs, 2H), 3.00 (brs, 1H), 2.42 (m, 1H), 2.37 (s, 3H), 2.22 (s, 3H), 1.65 (m, 4H), 1.48 (m, 2H); (Yield: 72%)

EXAMPLE 715

1-cyclohexylmethyl-7-(3,4-dihydro-1H-isoquinolin-2-yl)-2,3-dimethyl-1H-pyrrolo[2,3-c]pyridin-5-carbonitrile 1H-NMR(400 MHz, CDCl$_3$) δ 7.64 (s, 1H), 7.20 (m, 3H), 7.09 (d, 1H), 4.22 (brs, 2H) 4.10 (brs, 2H), 3.64-2.96 (brs, 4H), 2.37 (s, 3H), 2.23 (s, 3H), 1.52 (m, 4H), 1.26 (m, 1H), 1.04 (m, 2H), 0.88 (brs, 2H), 0.75 (brs, 2H); (Yield: 65%)

EXAMPLE 716

7-(3,4-dihydro-1H-isoquinolin-2-yl)-2,3-dimethyl-1-(naphthalen-2-ylmethyl)-1H-pyrrolo[2,3-c]pyridin-5-carbonitrile 1H-NMR(400 MHz, CDCl$_3$) δ 7.79 (m, 1H), 7.73 (s, 1H), 7.70 (d, 1H), 7.62 (m, 1H), 7.45 (m, 2H), 7.14-7.04 (m, 4H), 6.88 (dd, 1H), 6.77 (d, 1H), 5.93 (brs, 2H), 4.13 (brs, 2H), 3.40 (brs, 2H), 2.89 (brs, 2H), 2.27 (s, 3H), 2.25 (s, 3H); (Yield: 66%)

EXAMPLE 717

7-(3,4-dihydro-1H-isoquinolin-2-yl)-2,3-dimethyl-1-(2-methylbenzyl)-1H-pyrrolo[2,3-c]pyridin-5-carbonitrile 1H-NMR(400 MHz, CDCl$_3$) δ 7.73 (s, 1H), 7.20-6.98 (m, 6H), 6.48 (d, 2H), 6.15 (d, 2H), 4.05 (brs, 2H), 3.39 (brs, 2H), 2.77 (brs, 2H), 2.34 (s, 3H), 2.21 (s, 3H), 1.84 (s, 3H); (Yield: 76%)

EXAMPLE 718

7-(3,4-dihydro-1H-isoquinolin-2-yl)-2,3-dimethyl-1-(pent-4-ynyl)-1H-pyrrolo[2,3-c]pyridin-5-carbonitrile 1H-NMR(400 MHz, CDCl$_3$) δ 7.65 (s, 1H), 7.17 (m, 3H), 7.10 (d, 1H), 4.42 (brs, 3H), 4.25 (brs, 1H), 3.63-2.96 (brs, 6H), 2.41 (s, 3H), 2.23 (s, 3H), 1.91 (t, 2H), 1.65 (s, 1H); (Yield: 68%)

EXAMPLE 719

7-(3,4-dihydro-1H-isoquinolin-2-yl)-2,3-dimethyl-1-[3-(2-methyl-[1,3]dioxolan-2-yl)-propyl]-1H-pyrrolo[2,3-c]pyridin-5-carbonitrile 1H-NMR(400 MHz, CDCl$_3$) δ 7.65 (s, 1H), 7.20 (m, 4H), 4.30 (m, 4H), 3.81 (s, 2H), 3.66 (s, 2H) 3.40 (brs, 2H), 2.99 (brs, 2H), 2.38 (s, 3H), 2.23 (s, 3H), 1.36 (t, 4H), 1.11 (s, 3H); (Yield: 68%)

EXAMPLE 720

7-(3,4-dihydro-1H-isoquinolin-2-yl)-1-heptyl-2,3-dimethyl-1H-pyrrolo[2,3-c]pyridin-5-carbonitrile 1H-NMR(400 MHz, CDCl$_3$) δ 7.64 (s, 1H), 7.18 (m, 3H), 7.09 (m, 1H), 4.29 (t, 4H), 4.60-2.96 (brs, 4H), 2.37 (s, 3H), 2.22 (s, 3H), 1.45 (m, 2H), 1.30 (m, 2H), 1.06 (m, 6H), 0.80 (t, 3H); (Yield: 68%)

EXAMPLE 721

[5-cyano-7-(3,4-dihydro-1H-isoquinolin-2-yl)-2,3-dimethyl-1H-pyrrolo[2,3-c]pyridin-1-yl]methyl-2,2-dimethylpropanate 1H-NMR(400 MHz, CDCl$_3$) δ 7.64 (s, 1H), 7.19 (m, 3H), 7.10 (m, 1H), 6.45 (brs, 2H), 4.37 (brs, 2H), 3.49 (brs, 2H), 3.03 (brs, 2H), 2.36 (s, 3H), 2.23 (s, 3H), 1.11 (s, 9H); (Yield: 68%)

EXAMPLE 722

7-(3,4-dihydro-1H-isoquinolin-2-yl)-1-(2-ethylbutyl)-2,3-dimethyl-1H-pyrrolo[2,3-c]pyridin-5-carbonitrile 1H-NMR(400 MHz, CDCl$_3$) δ 7.64 (s, 1H), 7.18 (m, 3H), 7.10 (m, 1H), 4.25 (brs, 4H), 3.80-2.90 (brs, 4H), 2.37 (s, 3H), 2.23 (s, 3H), 0.97 (brs, 4H), 0.87 (m, 1H), 0.60 (brs, 6H); (Yield: 58%)

EXAMPLE 723

1-(but-2-ynyl)-7-(3,4-dihydro-1H-isoquinolin-2-yl)-2,3-dimethyl-1H-pyrrolo[2,3-c]pyridin-5-carbonitrile 1H-NMR(400 MHz, CDCl$_3$) δ 7.65 (s, 1H), 7.20 (m, 3H), 7.08 (m, 1H), 5.42 (d, 1H), 5.18 (m, 1H), 5.03 (brs, 2H), 4.34 (brs, 2H), 3.80-2.90 (brs, 4H), 2.34 (s, 3H), 2.23 (s, 3H), 1.61 (d, 3H); (Yield: 58%)

EXAMPLE 724

7-(3,4-dihydro-1H-isoquinolin-2-yl)-1-(2-fluorobenzyl)-2,3-dimethyl-1H-pyrrolo[2,3-c]pyridin-5-carbonitrile 1H-NMR(400 MHz, CDCl$_3$) δ 7.71 (s, 1H), 7.13 (m, 4H), 6.94 (m, 2H), 6.82 (d, 1H), 6.29 (m, 1H), 5.81 (s, 2H), 4.23 (brs, 2H), 3.37 (brs, 2H), 2.87 (brs, 2H), 2.26 (s, 3H) 2.23 (s, 3H); (Yield: 69%)

EXAMPLE 725

7-(3,4-dihydro-1H-isoquinolin-2-yl)-1-(2-methoxyethoxymethyl)-2,3-dimethyl-1H-pyrrolo[2,3-c]pyridin-5-carbonitrile 1H-NMR(400 MHz, CDCl$_3$) δ 7.73 (s, 1H), 7.18 (m, 3H), 7.11 (m, 1H), 5.85 (brs, 2H), 4.35 (s, 2H), 3.31 (s, 4H), 3.22 (s, 3H), 2.42 (s, 3H), 2.22 (s, 3H); (Yield: 56%)

EXAMPLE 726

[5-cyano-7-(3,4-dihydro-1H-isoquinolin-2-yl)-2,3-dimethyl-pyrrolo[2,3-c]pyridin-1-yl]-acetic acid methyl ester 1H-NMR(400 MHz, CDCl$_3$) δ 7.68 (s, 1H), 7.19 (m, 3H), 7.10 (m, 1H), 5.30 (brs, 2H), 4.10 (brs, 2H), 3.57 (s, 3H), 2.90 (brs, 2H), 2.28 (s, 3H), 2.42 (s, 3H); (Yield: 57%)

EXAMPLE 727

4-[5-cyano-7-(3,4-dihydro-1H-isoquinolin-2-yl)-2,3-dimethyl-pyrrolo[2,3-c]pyridin-1-ylmethyl]-benzoic acid methyl ester 1H-NMR(400 MHz, CDCl$_3$) δ 7.88 (d, 2H), 7.71 (s, 1H), 7.16 (m, 1H), 7.11 (d, 2H), 6.84 (d, 2H), 6.77 (d, 2H), 4.10 (brs, 2H), 3.89 (s, 3H), 3.50 (brs, 2H), 2.80 (brs, 2H), 2.26 (s, 3H), 2.21 (s, 3H); (Yield: 57%)

EXAMPLE 728

7-(3,4-dihydro-1H-isoquinolin-2-yl)-2,3-dimethyl-1-(4-trifluoromethylbenzyl)-1H-pyrrolo[2,3-c]pyridin-5-carbonitrile 1H-NMR(400 MHz, CDCl$_3$) δ 7.72 (s, 1H), 7.45 (d, 2H), 7.11 (m, 3H), 6.80 (m, 3H), 5.80 (brs, 2H), 4.10 (brs, 2H), 3.40 (brs, 2H), 2.80 (brs, 2H), 2.26 (s, 3H), 2.23 (s, 3H); (Yield: 57%)

EXAMPLE 729

7-(3,4-dihydro-1H-isoquinolin-2-yl)-1-(2-methoxybenzyl)-2,3-dimethyl-1H-pyrrolo[2,3-c]pyridin-5-carbonitrile 1H-NMR(400 MHz, CDCl$_3$) δ 7.83 (s, 1H), 7.19-7.04 (m, 4H), 6.75 (m, 2H), 6.65 (d, 1H), 6.16 (d, 1H), 5.69 (brs, 2H), 4.10 (brs, 2H), 3.52 (s, 3H), 3.33 (brs, 2H), 2.80 (brs, 2H), 2.28 (s, 3H), 2.24 (s, 3H); (Yield: 69%)

EXAMPLE 730

7-(3,4-dihydro-1H-isoquinolin-2-yl)-1-(3-fluorobenzyl)-2-methyl-1H-pyrrolo[2,3-c]pyridin-3,5-dicarbonitrile

Step 1: (2-methyl-1H-pyrrolo[2,3-c]pyridin-7-yl)-1,2,3,4-tetrahydroisoquinoline hydrochloride In accordance with the same procedures as in Example 656, except for using 2-(1,2,3,4-tetrahydroisoquinolin-2-yl)-3-nitropyridine prepared in Preparation 20 and isopropenyl magnesium bromide, the titled compound was obtained. (Yield: 39%) The product was used in the subsequent step without further purification.

Step 2: 2-[1-(3-fluorobenzyl)-2-methyl-1H-pyrrolo[2,3-c]pyridin-7-yl]-1,2,3,4-tetrahydroisoquinoline In accordance with the same procedures as in Example 657, except for using 2-methyl-1H-pyrrolo[2,3-c]pyridin-7-yl]-1,2,3,4-tetrahydroisoquinoline hydrochloride prepared in Step 1 and 3-fluorobenzyl chloride, the titled compound was obtained as a white solid. (Yield: 79%)

1H-NMR(400 MHz, CDCl$_3$) δ 8.02 (d, 1H), 7.28 (d, 1H), 7.12 (m, 4H), 6.87 (m, 2H), 6.49 (d, 1H), 6.38 (s, 1H), 6.36 (d, 1H), 5.82 (brs, 1H), 5.51 (brs, 1H), 4.33 (brs, 1H), 4.07 (brs, 1H), 3.45 (brs, 1H), 3.28 (brs, 1H), 2.91 (brs, 1H), 2.76 (brs, 1H), 2.30 (s, 3H)

Step 3: 2-[3,5-d]bromo-1-(4-fluorobenzyl)-2-methyl-1H-pyrrolo[2,3-c]pyridin-7-yl]-1,2,3,4-tetrahydroisoquinoline N-Bromosuccinimide (53 mg, 0.30 mmol) and silica gel (100 mg) was added to a solution of 2-[1-(3-fluorobenzyl)-2-methyl-1H-pyrrolo[2,3-c]pyridin-7-yl]-1,2,3,4-tetrahydroisoquinoline (110 mg, 0.30 mmol) prepared in Step 2 in dichloromethane (2 ml). The reaction mixture was stirred for 1 hour at 40° C. and then filtered. The filtrate was concentrated under reduced pressure. The resulting residue was purified with silica gel column chromatography to give 110 mg of the titled compound as a white solid.

Step 4: 7-(3,4-dihydro-1H-isoquinolin-2-yl)-1-(3-fluorobenzyl)-2-methyl-1H-pyrrolo[2,3-c]pyridin-3,5-dicarbonitrile Copper(I) cyanide (107 mg, 1.2 mmol) was added to a solution of 2-[3,5-dibromo-1-(4-fluorobenzyl)-2-methyl-1H-pyrrolo[2,3-c]pyridin-7-yl]-1,2,3,4-tetrahydroisoquinoline (110 mg, 0.24 mmol) prepared in Step 3 in anhydrous N,N-dimethylformamide (2 ml). The reaction mixture was refluxed overnight and then cooled to room temperature. Water was added to the reaction mixture, which was then filtered. The filtrate was extracted with ethyl acetate and then concentrated under reduced pressure. The resulting residue was purified with silica gel column chromatography to give 15 mg of the titled compound as a white solid.

1H-NMR(400 MHz, CDCl$_3$) δ 8.44 (s, 1H), 7.28 (d, 1H), 7.20 (m, 2H), 7.15 (d, 2H), 6.99 (t, 1H), 6.85 (d, 1H), 6.47 (t, 2H), 5.72 (s, 2H), 4.29 (brs, 2H), 3.49 (brs, 2H), 2.90 (brs, 2H), 2.52 (s, 3H)

EXAMPLE 731

7-(3,4-dihydro-1H-isoquinolin-2-yl)-1-(4-fluorobenzyl)-2,3-dimethyl-1H-pyrrolo[2,3-c]pyridin-5-carboxylic acid 7-(3,4-dihydro-1H-isoquinolin-2-yl)-1-(4-fluorobenzyl)-2,3-dimethyl-1H-pyrrolo[2,3-c]pyridin-5-carbonitrile (300 mg, 0.73 mmol) prepared in Example 690 was diluted with a mixture of ethanol (7 ml) and water (1 ml). Potassium hydroxide (410 mg, 7.3 mmol) was added to the solution, which was then refluxed for 72 hours. 1N hydrochloric acid was added to the reaction mixture, which was then extracted with ethyl acetate. The organic layer was dried on anhydrous magnesium sulfate and then concentrated under reduced pressure. The resulting residue was purified with silica gel column chromatography (ethyl acetate/n-hexane=1/1, v/v) to give 250 mg of the titled compound as a white solid. (Yield: 81%)

1H-NMR(400 MHz, CDCl$_3$) δ 10.13 (brs, 1H), 8.74 (s, 1H), 7.30 (m, 4H), 7.12 (m, 4H), 6.77 (s, 1H), 6.04 (s, 1H), 5.69 (s, 2H), 4.51 (brs, 2H), 3.90 (brs, 2H), 2.26 (brs, 6H)

EXAMPLES 732 TO 742

The titled compounds of Examples 732 to 742 were prepared, in accordance with the same procedures as in Example 731, using the compounds prepared in Examples 684, 686, 687, 689, 691, 695, 696, 697, 700, 706, and 708.

EXAMPLE 732

1-allyl-7-(3,4-dihydro-1H-isoquinolin-2-yl)-2,3-dimethyl-1H-pyrrolo[2,3-c]pyridin-5-carboxylic acid 1H-NMR(400 MHz, CDCl$_3$) δ 8.21 (s, 1H), 7.21 (m, 3H), 7.09 (m, 1H), 5.86 (m, 1H), 5.12 (brs, 2H), 5.09 (d, 1H), 4.65 (d, 1H), 4.36 (brs, 2H), 3.50 (brs, 2H), 3.00 (brs, 2H), 2.33 (s, 3H), 2.10 (s, 3H); (Yield: 73%)

EXAMPLE 733

1-benzyl-7-(3,4-dihydro-1H-isoquinolin-2-yl)-2,3-dimethyl-1H-pyrrolo[2,3-c]pyridin-5-carboxylic acid 1H-NMR(400 MHz, CDCl$_3$) δ 8.34 (s, 1H), 7.22 (m, 3H), 7.12 (m, 3H), 6.87 (d, 1H), 6.71 (m, 2H), 5.75 (brs, 2H), 4.25 (brs, 2H), 3.47 (brs, 2H), 2.83 (brs, 2H), 2.29 (s, 3H), 2.24 (s, 3H); (Yield: 83%)

EXAMPLE 734

7-(3,4-dihydro-1H-isoquinolin-2-yl)-1-(2-methoxyethyl)-2,3-dimethyl-1H-pyrrolo[2,3-c]pyridin-5-carboxylic acid 1H-NMR(400 MHz, CDCl$_3$) δ 8.21 (s, 1H), 7.22 (m, 3H), 7.13 (m, 1H), 4.52 (t, 2H), 4.30-4.10 (brs, 2H), 3.80-3.40 (brs, 2H), 3.44 (t, 2H), 3.30-2.90 (brs, 2H), 3.10 (s, 3H), 2.43 (s, 3H), 2.27 (s, 3H); (Yield: 88%)

EXAMPLE 735

1-(3-chlorobenzyl)-7-(3,4-dihydro-1H-isoquinolin-2-yl)-2,3-dimethyl-1H-pyrrolo[2,3-c]pyridin-5-carboxylic acid 1H-NMR(400 MHz, CDCl$_3$) δ 8.25 (s, 1H), 7.20 (m, 1H), 7.15 (m, 4H), 6.87 (d, 1H), 6.76 (s, 1H), 6.54 (d, 1H), 5.73 (s, 2H), 4.30 (brs, 2H), 3.55-3.31 (brs, 2H), 2.93-2.82 (brs, 2H), 2.30 (s, 3H), 2.26 (s, 3H); (Yield: 91%)

EXAMPLE 736

7-(3,4-dihydro-1H-isoquinolin-2-yl)-1-(3-methoxybenzyl)-2,3-dimethyl-1H-pyrrolo[2,3-c]pyridin-5-carboxylic acid 1H-NMR(400 MHz, CDCl$_3$) δ 8.24 (s, 1H), 7.20 (m, 1H), 7.16-7.08 (m, 3H), 7.02 (d, 1H), 6.84 (d, 1H), 6.59 (s, 1H), 6.47 (d, 1H), 5.73 (s, 2H), 4.30 (brs, 2H), 3.60-3.30 (brs, 2H), 2.90-2.70 (brs, 2H), 2.30 (s, 3H), 2.25 (s, 3H), 2.22 (s, 3H); (Yield: 89%)

EXAMPLE 737

7-(3,4-dihydro-1H-isoquinolin-2-yl)-1-(3-fluorobenzyl)-2,3-dimethyl-1H-pyrrolo[2,3-c]pyridin-5-carboxylic acid 1H-NMR(400 MHz, CDCl$_3$) δ 8.25 (s, 1H), 7.21 (m, 4H), 6.90 (m, 2H), 6.50 (d, 1H), 6.40 (d, 1H), 5.78 (brs, 2H), 4.32-4.18 (brs, 2H), 3.57-3.33 (brs, 2H), 2.91-2.80 (brs, 2H), 2.30 (s, 3H), 2.25 (s, 3H); (Yield: 82%)

EXAMPLE 738

7-(3,4-dihydro-1H-isoquinolin-2-yl)-1-ethyl-2,3-dimethyl-1H-pyrrolo[2,3-c]pyridin-5-carboxylic acid 1H-NMR(400 MHz, CDCl$_3$) δ 8.19 (s, 1H), 7.22 (m, 3H), 7.13 (m, 1H), 4.43 (brs, 4H), 3.69-2.97 (brs, 4H), 2.40 (s, 3H), 2.26 (s, 3H), 1.15 (t, 3H); (Yield: 93%)

EXAMPLE 739

7-(3,4-dihydro-1H-isoquinolin-2-yl)-2,3-dimethyl-1-propyl-1H-pyrrolo[2,3-c]pyridin-5-carboxylic acid 1H-NMR(400 MHz, CDCl$_3$) δ 8.19 (s, 1H), 7.22 (m, 3H), 7.13 (m, 1H), 4.36-4.28 (brs, 2H), 4.30 (t, 2H), 3.67-3.39 (brs, 2H), 3.22-2.96 (brs, 2H), 2.40 (s, 3H), 2.27 (brs, 3H), 1.54 (m, 2H), 0.64 (t, 3H); (Yield: 92%)

EXAMPLE 740

1-cyclopropylmethyl-7-(3,4-dihydro-1H-isoquinolin-2-yl)-2,3-dimethyl-1H-pyrrolo[2,3-c]pyridin-5-carboxylic acid 1H-NMR(400 MHz, CDCl$_3$) δ 8.19 (s, 1H), 7.20 (m, 3H), 7.12 (m, 1H), 4.29 (brs, 2+2H), 3.69 (brs, 1H), 3.30 (brs, 1H), 3.10 (brs, 1H), 2.90 (brs, 1H), 2.46 (s, 3H), 2.29 (s, 3H), 0.31 (d, 2H), 0.15 (brs, 2H); (Yield: 81%)

EXAMPLE 741

7-(3,4-dihydro-1H-isoquinolin-2-yl)-2,3-dimethyl-1-(3-methylbenzyl)-1H-pyrrolo[2,3-c]pyridin-5-carboxylic acid 1H-NMR(400 MHz, CDCl$_3$) δ 8.25 (s, 1H), 7.20-7.08 (m, 4H), 7.02 (d, 1H), 6.83 (d, 1H), 6.59 (s, 1H), 6.47 (d, 1H), 5.73 (s, 2H), 4.30-4.21 (brs, 2H), 3.55-3.31 (brs, 2H), 2.93-2.84 (brs, 2H), 2.30 (s, 3H), 2.22 (s, 3H), 2.18 (s, 3H); (Yield: 83%)

EXAMPLE 742

7-(3,4-dihydro-1H-isoquinolin-2-yl)-1-isobutyl-2,3-dimethyl-1H-pyrrolo[2,3-c]pyridin-5-carboxylic acid 1H-NMR(400 MHz, CDCl$_3$) δ 8.12 (s, 1H), 7.19 (m, 3H), 7.08 (d, 1H), 4.25 (brs, 2H), 4.10 (m, 1H), 4.11-4.09 (brs, 2H), 3.48 (brs, 4H), 2.35 (s, 3H), 2.23 (s, 3H), 1.89 (m, 1H), 0.56 (d, 6H); (Yield: 79%)

EXAMPLE 743

1-benzyl-7-(3,4-dihydro-1H-isoquinolin-2-yl)-2,3-dimethyl-1H-pyrrolo[2,3-c]pyridin-5-carboxylic acid methyl ester A solution of 1-benzyl-7-(3,4-dihydro-1H-isoquinolin-2-yl)-2,3-dimethyl-1H-pyrrolo[2,3-c]pyridin-5-carboxylic acid (20 mg, 0.05 mmol) prepared in Example 733, potassium hydroxide (10.1 mg, 0.07 mmol) and iodomethane (4.3 μl, 0.07 mmol) in anhydrous N,N-dimethylformamide (1 ml) was stirred for 10 hours at room temperature. Water was added to the reaction mixture, which was then extracted with ethyl acetate. The organic layer was dried on anhydrous magnesium sulfate and then concentrated under reduced pressure. The resulting residue was purified with silica gel column chromatography (ethyl acetate/n-hexane=1/10, v/v) to give the titled compound as a white solid. (Yield: 35%)

1H-NMR(400 MHz, CDCl$_3$) δ 8.20 (s, 1H), 7.17 (m, 3H), 7.11 (m, 1H), 7.11 (m, 2H), 6.90 (d, 1H), 6.72 (d, 2H), 5.80 (brs, 2H), 4.30 (brs, 2H), 3.99 (s, 3H), 3.53 (brs, 2H), 2.90 (brs, 2H), 2.28 (s, 3H), 2.22 (s, 3H)

EXAMPLE 744

1-benzyl-7-(3,4-dihydro-1H-isoquinolin-2-yl)-2,3-dimethyl-1H-pyrrolo[2,3-c]pyridin-5-carboxylate sodium 1-Benzyl-7-(3,4-dihydro-1H-isoquinolin-2-yl)-2,3-dimethyl-1H-pyrrolo[2,3-c]pyridin-5-carboxylic acid (28 mg, 0.068 mmol) prepared in Example 733 and sodium hydride (2.6 mg, 0.068 mmol) were dripped into anhydrous tetrahydrofuran (1 ml). The reaction mixture was stirred for 2 hours at room temperature and then concentrated under reduced pressure. The resulting residue was re-crystallized with methanol to give the titled compound as a white solid. (Yield: 82%)

1H-NMR(400 MHz, CDCl$_3$) δ 7.91 (s, 1H), 7.04 (m, 3H), 6.92 (m, 1H), 6.76 (s, 2H), 6.54 (m, 2H), 6.31 (brs, 1H), 5.50 (brs, 2H), 4.92 (s, 2H), 3.75 (brs, 2H), 3.20 (brs, 2H), 2.6 (s, 3H), 1.94 (s, 3H)

EXAMPLE 745

1-benzyl-7-(3,4-dihydro-1H-isoquinolin-2-yl)-2,3-dimethyl-1H-pyrrolo[2,3-c]pyridin-5-carboxamide 1-Benzyl-7-(3,4-dihydro-1H-isoquinolin-2-yl)-2,3-dimethyl-1H-pyrrolo[2,3-c]pyridin-5-carbonitrile (300 mg, 0.76 mmol) prepared in Example 686 was diluted with a mixture of ethanol (7 ml) and water (1 ml). Potassium hydroxide (426 mg, 7.6 mmol) was added to the solution, which was then refluxed for 2 hours. Water was added to the reaction mixture, which was then extracted with ethyl acetate. The organic layer was dried on anhydrous magnesium sulfate and then concentrated under reduced pressure. The resulting residue was purified with silica gel column chromatography (ethyl acetate/n-hexane=1/1, v/v) to give 260 mg of the titled compound as a white solid. (Yield: 84%)

1H-NMR(400 MHz, CDCl$_3$) δ 8.25 (s, 1H), 8.24 (brs, 1H), 7.21 (m, 3H), 7.15 (m, 1H), 713 (m, 2H), 6.88 (m, 1H), 6.73 (m, 2H), 5.81 (brs, 2H), 5.42 (brs, 1H), 4.30 (brs, 2H), 3.40 (brs, 2H), 2.90 (brs, 2H), 2.29 (s, 3H), 2.22 (s, 3H)

EXAMPLES 746 TO 755

The titled compounds of Examples 746 to 755 were prepared, in accordance with the same procedures as in Example 745, using the compounds prepared in Example 682, 684, 687, 688, 689, 691, 695, 697, 700, and 708.

EXAMPLE 746

7-(3,4-dihydro-1H-isoquinolin-2-yl)-2,3-dimethyl-1H-pyrrolo[2,3-c]pyridin-5-carboxamide 1H-NMR(400 MHz, CDCl$_3$) δ 8.08 (s, 1H), 8.05 (brs, 1H), 7.82 (brs, 1H), 7.20 (m, 4H), 5.42 (brs, 1H), 4.63 (s, 2H), 3.77 (t, 2H), 3.08 (t, 2H), 2.42 (s, 3H), 2.23 (s, 3H); (Yield: 85%)

EXAMPLE 747

1-allyl-7-(3,4-dihydro-1H-isoquinolin-2-yl)-2,3-dimethyl-1H-pyrrolo[2,3-c]pyridin-5-carboxamide 1H-NMR(400 MHz, CDCl$_3$) δ 8.20 (s, 1H), 7.79 (brs, 1H), 7.20 (m, 3H), 7.11 (d, 1H), 5.87 (m, 1H), 5.43 (s, 1H), 5.30-4.90 (brs, 2H), 5.09 (d, 1H), 4.66 (d, 1H), 4.35 (brs, 2H), 3.65-3.28 (brs, 2H), 3.20-2.90 (brs, 2H), 2.33 (s, 3H), 2.27 (s, 3H); (Yield: 89%)

EXAMPLE 748

7-(3,4-dihydro-1H-isoquinolin-2-yl)-1-(2-methoxyethyl)-2,3-dimethyl-1H-pyrrolo[2,3-c]pyridin-5-carboxamide 1H-NMR(400 MHz, CDCl$_3$) δ 8.20 (s, 1H), 8.80 (brs, 1H), 7.20 (m, 3H), 7.13 (m, 1H), 5.50 (brs, 1H), 4.52 (t, 2H), 4.52-4.20 (brs, 2H), 3.80-3.40 (brs, 2H), 3.44 (t, 2H), 3.20-2.90 (brs, 2H), 3.10 (s, 3H), 2.40 (s, 3H), 2.26 (s, 3H); (Yield: 95%)

EXAMPLE 749

7-(3,4-dihydro-1H-isoquinolin-2-yl)-2,3-dimethyl-1-(prop-2-ynyl)-1H-pyrrolo[2,3-c]pyridin-5-carboxamide 1H-NMR(400 MHz, CDCl$_3$) δ 8.12 (s, 1H), 7.76 (brs, 1H), 7.20 (m, 4H), 5.41 (brs, 1H), 4.50 (s, 2H), 3.55 (brs, 2H), 3.07 (brs, 2H), 2.43 (s, 3H), 2.25 (s, 3H), 2.05 (s, 1H); (Yield: 81%)

EXAMPLE 750

1-(3-chlorobenzyl)-7-(3,4-dihydro-1H-isoquinolin-2-yl)-2,3-dimethyl-1H-pyrrolo[2,3-c]pyridin-5-carboxamide 1H-NMR(400 MHz, CDCl$_3$) δ 8.25 (s, 1H), 7.76 (s, —NH), 7.14 (m, 5H), 6.88 (d, 1H), 6.77 (s, 1H), 6.54 (d, 1H), 5.73 (s, 2H), 5.46 (s, —NH), 4.15 (brs, 2H), 3.49 (brs, 2H), 2.89 (brs, 2H), 2.30 (s, 3H), 2.23 (s, 3H); (Yield: 86%)

EXAMPLE 751

7-(3,4-dihydro-1H-isoquinolin-2-yl)-1-(3-methoxybenzyl)-2,3-dimethyl-1H-pyrrolo[2,3-c]pyridin-5-carboxamide 1H-NMR(400 MHz, CDCl$_3$) δ 8.24 (s, 1H), 7.79 (s, 1H), 7.18-7.06 (m, 4H), 7.00 (d, 1H), 6.86 (d, 1H), 6.60 (s, 1H), 6.48 (d, 1H), 5.75 (brs, 2H), 5.42 (s, 1H), 4.32-4.16 (brs, 2H), 3.55-3.24 (brs, 2H), 2.94-2.75 (brs, 2H), 2.29 (s, 3H), 2.23 (s, 3H), 2.21 (s, 3H); (Yield: 92%)

EXAMPLE 752

7-(3,4-dihydro-1H-isoquinolin-2-yl)-1-(3-fluorobenzyl)-2,3-dimethyl-1H-pyrrolo[2,3-c]pyridin-5-carboxamide 1H-NMR(400 MHz, CDCl$_3$) δ 8.25 (s, 1H), 7.75 (brs, 1H), 7.17 (m, 4H), 6.88 (m, 2H), 6.50 (d, 1H), 6.41 (d, 1H), 5.72 (brs, 2H), 5.41 (brs, 1H), 4.23 (brs, 2H), 3.46-3.30 (brs, 2H), 2.89 (brs, 2H), 2.29 (s, 3H), 2.23 (s, 3H); (Yield: 75%)

EXAMPLE 753

7-(3,4-dihydro-1H-isoquinolin-2-yl)-2,3-dimethyl-1-propyl-1H-pyrrolo[2,3-c]pyridin-5-carboxamide 1H-NMR(400 MHz, CDCl$_3$) δ 8.25 (s, 1H), 7.82 (brs, 1H), 7.21 (m, 3H), 7.13 (m, 1H), 5.51 (brs, 1H), 4.39 (brs, 2H), 4.29 (t, 2H), 3.67-3.28 (brs, 2H), 3.20-2.92 (brs, 2H), 2.38 (s, 3H), 2.26 (s, 3H), 1.45 (m, 2H), 0.64 (t, 3H); (Yield: 82%)

EXAMPLE 754

1-cyclopropylmethyl-7-(3,4-dihydro-1H-isoquinolin-2-yl)-2,3-dimethyl-1H-pyrrolo[2,3-c]pyridin-5-carboxamide 1H-NMR(400 MHz, CDCl$_3$) δ 8.19 (s, 1H), 7.80 (s, 1H), 7.20 (m, 3H), 7.12 (d, 1H), 5.45 (s, 1H), 4.27 (m, 2+2H), 4.70 (brs, 1H), 4.40-4.10 (brs, 2H), 2.90 (brs, 1H), 2.43 (s, 3H), 2.28 (s, 3H), 0.29 (d, 2H), 0.20 (brs, 2H); (Yield: 82%)

EXAMPLE 755

7-(3,4-dihydro-1H-isoquinolin-2-yl)-1-isobutyl-2,3-dimethyl-1H-pyrrolo[2,3-c]pyridin-5-carboxamide 1H-NMR(400 MHz, CDCl$_3$) δ 8.18 (s, 1H), 7.80 (s, 1H), 7.19 (m, 3H), 7.13 (m, 1H), 5.49 (s, 1H), 4.38-4.28 (m, 2H), 4.10 (s, 2H), 3.67 (brs, 1H), 3.35-3.21 (brs, 2H), 2.92 (brs, 1H), 2.37 (s, 3H), 2.27 (s, 3H), 1.95 (m, 1H), 0.59 (d, 6H); (Yield: 75%)

EXAMPLE 756

1-allyl-7-(3,4-dihydro-1H-isoquinolin-2-yl)-2,3-dimethyl-N-(4-methylbenzyl)-1H-pyrrolo[2,3-c]pyridin-5-carboxamide hydrochloride Step 1: 1-allyl-7-(3,4-dihydro-1H-isoquinolin-2-yl)-2,3-dimethyl-N-(4-methylbenzyl)-1H-pyrrolo[2,3-c]pyridin-5-carboxamide A solution of 1-allyl-7-(3,4-dihydro-1H-isoquinolin-2-yl)-2,3-dimethyl-1H-pyrrolo[2,3-c]pyridin-5-carboxylic acid (30 mg, 0.083 mmol) prepared in Example 732, 1-hydroxybenzotriazole hydrate (16.9 mg, 0.125 mmol), 1-(3-dimethylaminopropyl)-3-ethylcarbodiimide hydrochloride (23.9 mg, 0.125 mmol), diisopropylethylamine (43,4 µl, 0.25 mmol), and 4-methylbenzylamine (15.9 µl, 0.125 mmol) in dichloromethane (1 ml) was stirred for 2 hours at room temperature and then concentrated under reduced pressure. The resulting residue was purified with silica gel column chromatography (ethyl acetate/n-hexane=1/3, v/v) to give 9.1 mg of the titled compound as a white solid. (Yield: 45%).

Step 2: 1-allyl-7-(3,4-dihydro-1H-isoquinolin-2-yl)-2,3-dimethyl-N-(4-methylbenzyl)-1H-pyrrolo[2,3-c]pyridin-5-carboxamide hydrochloride A solution of 1-allyl-7-(3,4-dihydro-1H-isoquinolin-2-yl)-2,3-dimethyl-N-(4-methylbenzyl)-1H-pyrrolo[2,3-c]pyridin-5-carboxamide prepared in Step 1 in ethyl acetate was saturated with hydrochloric acid gas and then filtered to give the titled compound as a white solid. (Yield: 90%)

1H-NMR(400 MHz, CDCl$_3$) δ 11.23 (brs, 1H), 8.83 (s, 1H), 7.43 (d, 2H), 7.20 (m, 3H), 7.12 (d, 2H), 7.02 (d, 1H), 5.80 (m, 1H), 5.15 (d, 1H), 5.05 (s, 2H), 4.71 (s, 2H), 4.42 (d, 1H), 4.07 (brs, 2H), 3.53 (brs, 2H), 3.07 (s, 2H), 2.41 (s, 3H), 2.36 (s, 3H), 2.30 (s, 3H)

EXAMPLES 757 TO 760

The titled compounds of Examples 757 to 760 were prepared, in accordance with the same procedures as in Example 756, using 1-allyl-7-(3,4-dihydro-1H-isoquinolin-2-yl)-2,3-dimethyl-1H-pyrrolo[2,3-c]pyridin-5-carboxylic acid prepared in Example 732; and, monomethylamine hydrochloride, 3-chlorobenzylamine, 2,2,2-trifluoroethylamine hydrochloride, or piperonylamine.

EXAMPLE 757

1-allyl-7-(3,4-dihydro-1H-isoquinolin-2-yl)-2,3-dimethyl-N-methyl-1H-pyrrolo[2,3-c]pyridin-5-carboxamide hydrochloride 1H-NMR(400 MHz, CDCl$_3$) δ 10.53 (brs, 1H), 8.80 (s, 1H), 7.23 (m, 3H), 7.03 (d, 1H), 5.80 (m, 1H), 5.15 (d, 1H), 5.07 (s, 2H), 4.70 (brs, 2H), 4.45 (d, 1H), 4.18 (brs, 2H), 3.49 (brs, 2H), 3.09 (s, 3H), 2.43 (s, 3H), 2.39 (s, 3H); (Yield: 47%)

EXAMPLE 758

1-allyl-7-(3,4-dihydro-1H-isoquinolin-2-yl)-2,3-dimethyl-N-(3-chlorobenzyl)-1H-pyrrolo[2,3-c]pyridin-5-carboxamide hydrochloride 1H-NMR(400 MHz, CDCl$_3$) δ 11.22 (brs, 1H), 8.90 (brs, 1H), 7.48 (s, 1H), 7.44 (brs, 2H), 7.21 (brs, 3H), 7.04 (brs, 2H), 5.82 (m, 1H), 5.16-5.08 (m, 2H), 4.67 (s, 2H), 4.46 (d, 1H), 4.11 (m, 2H), 3.10 (s, 2H), 2.44 (s, 3H), 2.40 (s, 3H); (Yield: 72%)

EXAMPLE 759

1-allyl-7-(3,4-dihydro-1H-isoquinolin-2-yl)-2,3-dimethyl-N-(2,2,2-trifluoroethyl)-1H-pyrrolo[2,3-c]pyridin-5-carboxamide hydrochloride 1H-NMR(400 MHz, CDCl$_3$) δ 8.75 (s, 1H), 7.21 (m, 3H), 7.04 (m, 1H), 5.82 (m, 1H), 5.18 (d, 1H), 5.09 (s, 2H), 4.73 (brs, 2H), 4.45 (s, 1H), 4.18 (brs, 2H), 3.99 (brs, 2H), 3.08 (s, 3H), 2.45 (s 3H), 2.39 (s, 3H); (Yield: 82%)

EXAMPLE 760

1-allyl-7-(3,4-dihydro-1H-isoquinolin-2-yl)-2,3-dimethyl-N-(benzo[1,3]dioxol-5-ylmethyl)-1H-pyrrolo[2,3-c]pyridin-5-carboxamide hydrochloride 1H-NMR(400 MHz, CDCl$_3$) δ 8.41 (brs, 1H), 7.18 (m, 3H), 7.06 (m, 1H), 6.93 (m, 2H), 6.77 (brs, 1H), 5.93 (s, 2H), 5.85 (m, 1H), 5.10 (m, 3H), 4.59 (m, 3H), 4.49 (brs, 2H), 3.62 (brs, 2H), 3.00 (brs, 2H), 2.36 (s, 3H), 2.17 (s, 3H); (Yield: 62%)

EXAMPLES 761 TO 763

The titled compounds of Examples 761 to 763 were prepared, in accordance with the same procedures as in Step 1 of Example 756, using 1-allyl-7-(3,4-dihydro-1H-isoquinolin-2-yl)-2,3-dimethyl-1H-pyrrolo[2,3-c]pyridin-5-carboxylic acid prepared in Example 732; and, cyclopropylamine, 2,2,2-trifluoroethylamine hydrochloride, or tert-butylamine.

EXAMPLE 761

1-allyl-7-(3,4-dihydro-1H-isoquinolin-2-yl)-2,3-dimethyl-N-cyclopropyl-1H-pyrrolo[2,3-c]pyridin-5-carboxamide 1H-NMR(400 MHz, CDCl$_3$) δ 8.16 (s, 1H), 7.85 (s, 1H), 7.18 (m, 3H), 7.11 (m, 1H), 5.85 (m, 1H), 5.10 (brs, 2H), 5.05 (d, 1H), 4.62 (d, 1H), 4.30 (brs, 2H), 3.40 (brs, 2H), 3.00 (brs, 2H), 2.90 (m, 1H), 2.32 (s, 3H), 2.27 (s, 3H), 0.84 (t, 2H), 0.58 (t, 2H); (Yield: 79%)

EXAMPLE 762

1-allyl-7-(3,4-dihydro-1H-isoquinolin-2-yl)-2,3-dimethyl-N-(2,2,2-trifluoroethyl)-1H-pyrrolo[2,3-c]pyridin-5-carboxamide 1H-NMR(400 MHz, CDCl$_3$) δ 8.18 (s, 1H+1H), 7.20 (m, 3H), 7.12 (m, 1H), 5.87 (m, 1H), 5.16 (brs, 2H), 5.08 (d, 1H), 4.63 (d, 1H), 4.38 (m, 2H), 4.09 (m, 2H), 3.47 (brs, 2H), 2.90 (brs, 2H), 2.33 (s, 3H), 2.27 (s, 3H); (Yield: 82%)

EXAMPLE 763

1-allyl-7-(3,4-dihydro-1H-isoquinolin-2-yl)-2,3-dimethyl-N-tert-butyl-1H-pyrrolo[2,3-c]pyridin-5-carboxamide 1H-NMR(400 MHz, CDCl$_3$) δ 8.15 (s, 1H), 7.95 (s, 1H), 7.20 (m, 3H), 7.12 (s, 1H), 5.85 (m, 1H), 5.10 (brs, 2H), 5.05 (d, 1H), 4.61 (d, 1H), 4.36 (m, 2H), 4.20 (brs, 2H), 2.90 (brs, 2H), 2.31 (s, 3H), 2.25 (s, 3H), 1.46 (s, 9H); (Yield: 72%)

EXAMPLES 764 TO 768

The titled compounds of Examples 764 to 768 were prepared, in accordance with the same procedures as in Step 1 of Example 756, using 1-benzyl-7-(3,4-dihydro-1H-isoquinolin-2-yl)-2,3-dimethyl-1H-pyrrolo[2,3-c]pyridin-5-carboxylic acid prepared in Example 733; and, morpholine, ethylamine, tert-butylamine, 2,2,2,-trifluoroethylamine, or 4-methylbenzylamine.

EXAMPLE 764

[1-benzyl-7-(3,4-dihydro-1H-isoquinolin-2-yl)-2,3-dimethyl-1H-pyrrolo[2,3-c]pyridin-5-yl]-(morpholin-4-yl)-methanone 1H-NMR(400 MHz, CDCl$_3$) δ 7.83 (s, 1H), 7.19 (m, 3H), 7.12 (m, 3H), 6.86 (d, 1H), 6.71 (d, 2H), 5.73 (brs, 2H), 5.30 (brs, 2H), 3.83 (s, 6H), 3.67 (s, 2H), 3.41 (brs, 2H), 2.73 (brs, 2H), 2.26 (s, 3H), 2.21 (s, 3H); (Yield: 60%)

EXAMPLE 765

1-benzyl-7-(3,4-dihydro-1H-isoquinolin-2-yl)-2,3-dimethyl-N-ethyl-1H-pyrrolo[2,3-c]pyridin-5-carboxamide 1H-NMR(400 MHz, CDCl$_3$) δ 8.20 (s, 1H), 7.85 (t, 1H), 7.20-7.10 (m, 6H), 6.93 (d, 1H), 6.73 (d, 2H), 5.76 (brs, 2H), 4.20 (brs, 2H), 3.50 (m, 2H), 3.40 (br 2H), 2.70 (brs, 2H), 2.28 (s, 3H), 2.21 (s, 3H), 1.24 (t, 3H); (Yield: 90%)

EXAMPLE 766

1-benzyl-7-(3,4-dihydro-1H-isoquinolin-2-yl)-2,3-dimethyl-N-tert-butyl-1H-pyrrolo[2,3-c]pyridin-5-carboxamide 1H-NMR(400 MHz, CDCl$_3$) δ 8.18 (s, 1H), 7.93 (s, 1H), 7.17-7.10 (m, 6H), 6.93 (s, 1H), 6.72 (d, 2H), 5.74 (brs, 2H), 4.30 (brs, 2H), 3.40 (brs, 2H), 2.90 (brs, 2H), 2.26 (s, 3H), 2.21 (s, 3H), 1.46 (s, 9H); (Yield: 57%)

EXAMPLE 767

1-benzyl-7-(3,4-dihydro-1H-isoquinolin-2-yl)-2,3-dimethyl-N-(2,2,2,-trifluoroethyl)-1H-pyrrolo[2,3-c]pyridin-5-carboxamide 1H-NMR(400 MHz, CDCl$_3$) δ 8.22 (s, 1H), 8.16 (t, 1H), 7.21-7.10 (m, 6H), 6.92 (d, 1H), 6.73 (d, 2H), 5.77 (brs, 2H), 4.33 (brs, 2H), 4.09 (m, 2H), 3.40 (brs, 2H), 2.80 (brs, 2H), 2.28 (s, 3H), 2.22 (s, 3H); (Yield: 68%)

EXAMPLE 768

1-benzyl-7-(3,4-dihydro-1H-isoquinolin-2-yl)-2,3-dimethyl-N-(4-methylbenzyl)-1H-pyrrolo[2,3-c]pyridin-5-carboxamide 1H-NMR(400 MHz, CDCl$_3$) δ 8.25 (s, 1H), 8.20 (brs, 1H), 7.26 (m, 3H), 7.15-7.10 (m, 7H), 6.85 (d, 2H), 6.72 (m, 2H), 6.78 (brs, 2H), 4.63 (d, 2H), 4.20 (brs, 2H), 3.30 (brs, 2H), 2.70 (brs, 2H), 2.33 (s, 3H), 2.29 (s, 3H), 2.21 (s, 3H); (Yield: 58%)

EXAMPLES 769 TO 775

The titled compounds of Examples 769 to 775 were prepared, in accordance with the same procedures as in Example 756, using 1-benzyl-7-(3,4-dihydro-1H-isoquinolin-2-yl)-2,3-dimethyl-1H-pyrrolo[2,3-c]pyridin-5-carboxylic acid prepared in Example 733; and, morpholine, diethylamine, dimethylamine hydrochloride, monomethylamine hydrochloride, 3-chlorobenzylamine, piperonylamine, or ethylamine.

EXAMPLE 769

[1-benzyl-7-(3,4-dihydro-1H-isoquinolin-2-yl)-2,3-dimethyl-1H-pyrrolo[2,3-c]pyridin-5-yl]-(morpholin-4-yl)-methanone hydrochloride 1H-NMR(400 MHz, CDCl$_3$) δ 7.50 (s, 1H), 7.17 (m, 4H), 7.08 (m, 2H), 6.67 (d, 1H), 6.50 (d, 2H), 5.63 (s, 2H), 4.30 (brs, 2H), 4.10-3.47 (brs, 2H), 3.90 (brs, 6H), 3.64 (brs, 2H), 2.79 (s, 2H), 2.33 (s, 3H), 2.32 (s, 3H); (Yield: 60%)

EXAMPLE 770

1-benzyl-7-(3,4-dihydro-1H-isoquinolin-2-yl)-2,3-dimethyl-N-diethyl-1H-pyrrolo[2,3-c]pyridin-5-carboxamide hydrochloride 1H-NMR(400 MHz, CDCl$_3$) δ 7.72 (s, 1H), 7.15 (m, 5H), 6.89 (m, 2H), 6.38 (m, 2H), 5.74 (brs, 2H), 4.35 (brs, 2H), 3.61-3.49 (m, 6H), 2.84 (brs, 2H), 2.30 (s, 6H), 1.26 (s, 6H); (Yield: 66%)

EXAMPLE 771

1-benzyl-7-(3,4-dihydro-1H-isoquinolin-2-yl)-2,3-dimethyl-N-dimethyl-1H-pyrrolo[2,3-c]pyridin-5-carboxamide hydrochloride 1H-NMR(400 MHz, CDCl$_3$) δ 7.58 (s, 1H), 7.20 (m, 3H), 7.07 (m, 2H), 6.68 (d, 1H), 6.50 (d, 2H), 5.66 (s, 2H), 3.21 (s, 3H), 3.19 (s, 3H), 2.77 (s, 2H), 2.36 (s, 3H), 2.32 (s, 3H); (Yield: 52%)

EXAMPLE 772

1-benzyl-7-(3,4-dihydro-1H-isoquinolin-2-yl)-2,3-dimethyl-N-methyl-1H-pyrrolo[2,3-c]pyridin-5-carboxamide hydrochloride 1H-NMR(400 MHz, CDCl$_3$) δ 10.50 (s, 1H), 8.78 (s, 1H), 7.20 (m, 3H), 7.10 (m, 2H), 6.68 (d, 1H), 6.47 (d, 2H), 5.66 (s, 2H), 4.50 (brs, 2H), 4.11 (brs, 2H), 3.09 (s, 3H), 2.76 (s, 2H), 2.41 (s, 3H), 2.35 (s, 3H); (Yield: 48%)

EXAMPLE 773

1-benzyl-7-(3,4-dihydro-1H-isoquinolin-2-yl)-2,3-dimethyl-N-(3-chlorobenzyl)-1H-pyrrolo[2,3-c]pyridin-5-carboxamide hydrochloride 1H-NMR(400 MHz, CDCl$_3$) δ 10.85 (brs, 1H), 8.80 (brs, 1H), 7.66-7.42 (m, 3H), 7.25 (m, 4H), 7.10 (brs, 2H), 6.72 (brs, 1H), 6.50 (s, 2H), 5.70 (brs, 2H), 4.67 (s, 2H), 4.67 (brs, 2H), 4.13 (brs, 2H), 2.78 (s, 2H), 2.43 (s, 3H), 2.37 (s, 3H); (Yield: 58%)

EXAMPLE 774

1-benzyl-7-(3,4-dihydro-1H-isoquinolin-2-yl)-2,3-dimethyl-N-(1,3-benzodioxol-5-ylmethyl)-1H-pyrrolo[2,3-c]pyridin-5-carboxamide hydrochloride 1H-NMR(400 MHz, CDCl$_3$) δ 10.59 (brs, 1H), 8.71 (brs, 1H), 7.22 (m, 3H), 7.09 (d, 2H), 7.03 (m, 2H), 6.75 (d, 2H), 6.70 (d, 1H), 6.49 (m, 2H), 5.91 (s, 2H), 5.67 (brs, 2H), 4.51 (s, 2H), 3.84 (brs, 2H), 3.47 (brs, 2H), 2.76 (s, 2H), 2.39 (s, 3H), 2.33 (s, 3H); (Yield: 58%)

EXAMPLE 775

1-benzyl-7-(3,4-dihydro-1H-isoquinolin-2-yl)-2,3-dimethyl-N-ethyl-1H-pyrrolo[2,3-c]pyridin-5-carboxamide hydrochloride 1H-NMR(400 MHz, CDCl$_3$) δ 8.89 (s, 1H), 7.21 (m, 3H), 7.11 (m, 1H), 6.68 (s, 1H), 6.45 (d, 2H), 5.67 (s, 2H), 4.62 (brs, 2H), 3.95 (brs, 2H), 3.61 (s, 2H), 2.77 (s, 2H), 2.44 (s, 3H), 2.37 (s, 3H), 1.38 (s, 3H); (Yield: 76%)

EXAMPLE 776

[7-(3,4-dihydro-1H-isoquinolin-2-yl)-2,3-dimethyl-1H-pyrrolo[2,3-c]pyridin-5-yl]-(morpholin-4-yl)-methanone Step 1: 7-(3,4-dihydro-1H-isoquinolin-2-yl)-2,3-dimethyl-1H-pyrrolo[2,3-c]pyridin-5-carboxylic acid In accordance with the same procedures as in Example 731, except for using 7-(3,4-dihydro-1H-isoquinolin-2-yl)-2,3-dimethyl-1H-pyrrolo[2,3-c]pyridin-5-carbonitrile prepared in Example 682, the titled compound was obtained as a pale yellow solid. (Yield: 59%) The product was used in the subsequent step without further purification.

Step 2: [7-(3,4-dihydro-1H-isoquinolin-2-yl)-2,3-dimethyl-1H-pyrrolo[2,3-c]pyridin-5-yl]-(morpholin-4-yl)-methanone In accordance with the same procedures as in Step 1 of Example 756, except for using 7-(3,4-dihydro-1H-isoquinolin-2-yl)-2,3-dimethyl-1H-pyrrolo[2,3-c]pyridin-5-carboxylic acid prepared in Step 1 and morpholine, the titled compound was obtained as a white solid. (Yield: 69%)

1H-NMR(400 MHz, CDCl$_3$) δ 8.04 (brs, 1H), 7.61 (s, 1H), 7.20 (m, 4H), 4.60 (s, 2H), 3.76 (m, 6H), 3.73 (t, 2H), 3.63 (brs, 2H), 3.04 (t, 2H), 2.40 (s, 3H), 2.20 (s, 3H)

EXAMPLES 777 TO 781

The titled compounds of Examples 777 to 781 were prepared, in accordance with the same procedures as in Example 657, using [7-(3,4-dihydro-1H-isoquinolin-2-yl)-2,3-dimethyl-1H-pyrrolo[2,3-c]pyridin-5-yl]-(morpholin-4-yl)-methanone prepared in Example 776; and, allyl bromide, (bromomethyl)cyclopropane, 3-fluorobenzyl chloride, 3-methoxybenzyl bromide, or 1-iodopropane.

EXAMPLE 777

[1-allyl-7-(3,4-dihydro-1H-isoquinolin-2-yl)-2,3-dimethyl-1H-pyrrolo[2,3-c]pyridin-5-yl]-(morpholin-4-yl)-methanone hydrochloride 1H-NMR(400 MHz, CDCl$_3$) δ 7.45 (brs, 1H), 7.22 (m, 3H), 7.00 (m, 1H), 5.79 (m, 1H), 5.17 (d, 1H), 5.03 (s, 2H), 4.75 (brs, 2H), 4.51 (d, 1H), 4.03 (brs, 2H), 3.90 (m, 6H), 3.61 (brs, 2H), 3.04 (s, 2H), 2.37 (s, 3H), 2.31 (s, 3H); (Yield: 69%)

EXAMPLE 778

[1-cyclopropylmethyl-7-(3,4-dihydro-1H-isoquinolin-2-yl)-2,3-dimethyl-1H-pyrrolo[2,3-c]pyridin-5-yl]-(morpholin-4-yl)-methanone hydrochloride 1H-NMR(400 MHz, CDCl$_3$) δ 7.41 (brs, 1H), 7.21 (m, 3H), 7.16 (brs, 1H), 4.21 (s, 2H), 3.91 (m, 6H), 3.49 (m, 2H), 3.15 (brs, 2H), 2.54 (s, 3H), 2.31 (s, 3H), 0.95 (brs, 1H), 0.35 (s, 2H), 0.32 (s, 1H); (Yield: 47%)

EXAMPLE 779

[7-(3,4-dihydro-1H-isoquinolin-2-yl)-1-(3-fluorobenzyl)-2,3-dimethyl-1H-pyrrolo[2,3-c]pyridin-5-yl]-(morpholin-4-yl)-methanone hydrochloride 1H-NMR(400 MHz, CDCl$_3$) δ 7.52 (brs, 1H), 7.19 (m, 2H), 7.10 (m, 2H), 6.95 (m, 1H), 6.67 (m, 1H), 6.25 (s, 1H), 6.19 (d, 1H), 5.63 (s, 2H), 3.91 (m, 6H), 3.49 (m, 2H), 2.83 (m, 2H), 2.38 (s, 3H), 2.36 (s, 3H); (Yield: 68%)

EXAMPLE 780

[7-(3,4-dihydro-1H-isoquinolin-2-yl)-1-(3-methoxybenzyl)-2,3-dimethyl-1H-pyrrolo[2,3-c]pyridin-5-yl]-(morpholin-4-yl)-methanone hydrochloride 1H-NMR(400 MHz, CDCl$_3$) δ 7.53 (brs, 1H), 7.17-7.05 (m, 4H), 6.78 (d, 1H), 6.62 (brs, 1H), 6.05 (m, 2H), 5.62 (brs, 2H), 3.90 (m, 6H), 3.79 (m, 2H), 3.73 (s, 3H), 2.78 (m, 2H), 2.38 (s, 3H), 2.36 (s, 3H); (Yield: 64%)

EXAMPLE 781

[7-(3,4-dihydro-1H-isoquinolin-2-yl)-2,3-dimethyl-1-propyl-1H-pyrrolo[2,3-c]pyridin-5-yl]-(morpholin-4-yl)-methanone hydrochloride 1H-NMR(400 MHz, CDCl$_3$) δ 7.44 (brs, 1H), 7.20 (m, 3H), 7.04 (brs, 1H), 3.89 (m, 6H), 3.64 (brs, 2H), 4.31 (brs, 2H), 3.10 (m, 2H), 2.49 (s, 3H), 2.39 (s, 3H), 1.46 (m, 2H), 0.58 (t, 3H); (Yield: 63%)

EXAMPLE 782

[7-(3,4-dihydro-1H-isoquinolin-2-yl)-1-ethyl-2,3-dimethyl-1H-pyrrolo[2,3-c]pyridin-5-yl]-(4-methylpiperazin-1-yl)-methanone hydrochloride In accordance with the same procedures as in Example 756, except for using 7-(3,4-dihydro-1H-isoquinolin-2-yl)-1-ethyl-2,3-dimethyl-1H-pyrrolo[2,3-c]pyridin-5-carboxylic acid prepared in Example 738 and 1-methylpiperazine, the titled compound was obtained as a white solid. (Yield: 56%)

1H-NMR(400 MHz, CDCl$_3$) δ 7.38 (s, 1H), 7.24 (m, 3H), 7.08 (m, 1H), 4.88 (d, 1H), 4.70 (brs, 1H), 4.52 (brs, 1H), 4.35 (m, 3H), 4.03 (brs, 1H), 3.86 (m, 3H), 3.38 (d, 1H), 3.17 (s, 3H), 2.87 (s, 3H), 2.50 (s, 3H), 2.29 (s, 3H), 1.15 (s, 3H)

EXAMPLES 783 AND 784

The titled compounds of Examples 783 and 784 were prepared, in accordance with the same procedures as in Example 756, using 7-(3,4-dihydro-1H-isoquinolin-2-yl)-1-(3-methoxybenzyl)-2,3-dimethyl-1H-pyrrolo[2,3-c]pyridin-5-carboxylic acid prepared in Example 736; and, 1-methylpiperazine or thiomorpholine.

EXAMPLE 783

[7-(3,4-dihydro-1H-isoquinolin-2-yl)-1-(3-methoxybenzyl)-2,3-dimethyl-1H-pyrrolo[2,3-c]pyridin-5-yl]-(4-methylpiperazin-1-yl)-methanone hydrochloride 1H-NMR(400 MHz, CDCl$_3$) δ 7.45 (brs, 1H), 7.21-7.07 (m, 3H), 6.80 (m, 1H), 6.60 (brs, 1H), 6.07 (s, 2H), 6.70 (brs, 1H), 6.50 (brs, 1H), 5.68 (brs, 2H), 4.86 (brs, 1H), 4.53 (brs, 3H), 4.00-3.86 (brs, 4H), 3.67 (s, 3H), 3.37 (brs, 1H), 3.10 (brs, 3H), 2.86 (s, 4H), 2.37 (s, 3H), 2.34 (s, 3H); (Yield: 61%)

EXAMPLE 784

[7-(3,4-dihydro-1H-isoquinolin-2-yl)-1-(3-methoxybenzyl)-2,3-dimethyl-1H-pyrrolo[2,3-c]pyridin-5-yl]-(thiomorpholin-1-yl)-methanone hydrochloride 1H-NMR(400 MHz, CDCl$_3$) δ 7.49 (s, 1H), 7.17-7.05 (m, 4H), 6.78 (d, 1H), 6.63 (brs, 1H), 6.07 (s, 2H), 5.63 (brs, 2H), 4.13 (brs, 2H), 3.86 (brs, 2H), 3.64 (s, 3H), 2.88-2.83 (brs, 6H), 2.35 (s, 3H), 2.32 (s, 3H); (Yield: 70%)

EXAMPLES 785 and 786

The titled compounds of Examples 785 and 786 were prepared, in accordance with the same procedures as in Example 756, using 1-allyl-7-(3,4-dihydro-1H-isoquinolin-2-yl)-2,3-dimethyl-1H-pyrrolo[2,3-c]pyridin-5-carboxylic acid prepared in Example 732; and, 1-methylpiperazine or piperidine.

EXAMPLE 785

[1-allyl-7-(3,4-dihydro-1H-isoquinolin-2-yl)-2,3-dimethyl-1H-pyrrolo[2,3-c]pyridin-5-yl]-(4-methylpiperazin-1-yl)-methanone hydrochloride 1H-NMR(400 MHz, CDCl$_3$) δ 7.41 (s, 1H), 7.25 (m, 3H), 7.03 (m, 1H), 5.85 (m, 1H), 5.21-5.00 (brs, 2H), 4.88 (d, 2H), 4.57 (brs, 1H), 4.30-4.00 (m, 3H), 3.88 (m, 4H), 3.30 (brs, 1H), 3.15 (brs, 1H), 3.10 (brs, 2H), 2.88 (s, 3H), 2.44 (s, 3H), 2.30 (s, 3H); (Yield: 53%)

EXAMPLE 786

[1-allyl-7-(3,4-dihydro-1H-isoquinolin-2-yl)-2,3-dimethyl-1H-pyrrolo[2,3-c]pyridin-5-yl]-(piperidin-1-yl)-methanone hydrochloride 1H-NMR(400 MHz, CDCl$_3$) δ 7.46 (brs, 1H), 7.19 (m, 3H), 7.00 (m, 1H), 5.79 (m, 1H), 5.16 (brs, 1H), 5.05 (brs, 2H), 4.80 (brs, 1H), 4.50 (brs, 1H), 4.13 (brs, 1H), 3.85 (brs, 2H), 3.55 (brs, 2H), 3.09 (brs, 2H), 2.44 (s, 3H), 2.31 (s, 3H), 1.72 (brs, 6H); (Yield: 56%)

EXAMPLE 787

[7-(3,4-dihydro-1H-isoquinolin-2-yl)-1-ethyl-2,3-dimethyl-1H-pyrrolo[2,3-c]pyridin-5-yl]-(piperidin-1-yl)-methanone hydrochloride In accordance with the same procedures as in Example 756, except for using 7-(3,4-dihydro-1H-isoquinolin-2-yl)-1-ethyl-2,3-dimethyl-1H-pyrrolo[2,3-c]pyridin-5-carboxylic acid prepared in Example 738 and piperidine, the titled compound was obtained as a white solid. (Yield: 47%)

1H-NMR(400 MHz, CDCl$_3$) δ 7.47 (brs, 1H), 7.20 (m, 3H), 7.05 (m, 1H), 4.38 (brs, 2H), 3.83 (brs, 2H), 3.63 (m, 2H), 3.13 (brs, 2H), 2.47 (s, 3H), 2.28 (s, 3H), 1.72 (m, 6H), 1.15 (s, 3H)

EXAMPLES 788 AND 789

The titled compounds of Examples 788 and 789 were prepared, in accordance with the same procedures as in Example 756, using 1-benzyl-7-(3,4-dihydro-1H-isoquinolin-2-yl)-2,3-dimethyl-1H-pyrrolo[2,3-c]pyridin-5-carboxylic acid prepared in Example 733; and, piperidine or thiomorpholine.

EXAMPLE 788

[1-benzyl-7-(3,4-dihydro-1H-isoquinolin-2-yl)-2,3-dimethyl-1H-pyrrolo[2,3-c]pyridin-5-yl]-(piperidin-1-yl)-methanone hydrochloride H-NMR(400 MHz, CDCl$_3$) δ 7.55 (s, 1H), 7.21-7.14 (m, 4H), 7.07 (m, 2H), 6.70 (d, 1H), 6.55 (brs, 2H), 5.67 (s, 2H), 4.45 (brs, 2H), 3.96 (brs, 2H), 3.66 (brs, 2H), 2.78 (s, 2H), 2.38 (s, 6H), 1.71 (brs, 6H); (Yield: 34%)

EXAMPLE 789

[1-benzyl-7-(3,4-dihydro-1H-isoquinolin-2-yl)-2,3-dimethyl-1H-pyrrolo[2,3-c]pyridin-5-yl]-(thiomorpholin-1-yl)-methanone hydrochloride 1H-NMR(400 MHz, CDCl$_3$) δ 7.52 (s, 1H), 7.22-7.15 (m, 4H), 7.09 (m, 2H), 6.68 (brs, 1H), 6.54 (s, 2H), 5.66 (s, 2H), 4.13 (brs, 2H), 3.88 (brs, 3H), 2.86 s, 3H), 2.79 (s, 3H), 2.32 (s, 6H); (Yield: 69%)

EXAMPLE 790

[1-(3-chlorobenzyl)-7-(3,4-dihydro-1H-isoquinolin-2-yl)-2,3-dimethyl-1H-pyrrolo[2,3-c]pyridin-5-yl]-(thiomorpholin-1-yl)-methanone hydrochloride In accordance with the same procedures as in Example 756, except for using 1-(3-chlorobenzyl)-7-(3,4-dihydro-1H-isoquinolin-2-yl)-2,3-dimethyl-1H-pyrrolo[2,3-c]pyridin-5- carboxylic acid prepared in Example 737 and thiomorpholine, the titled compound was obtained as a white solid. (Yield: 69%)

1H-NMR(400 MHz, CDCl$_3$) δ 7.58 (s, 1H), 7.22-7.08 (m, 5H), 6.72 (m, 1H), 6.59 (s, 1H), 6.37 (m, 1H), 5.63 (s, 2H), 4.12 (brs, 2H), 3.90 (brs, 2H), 2.82 (brs, 6H), 2.32 (s, 6H)

EXAMPLE 791

[7-(3,4-dihydro-1H-isoquinolin-2-yl)-2,3-dimethyl-1H-pyrrolo[2,3-c]pyridin-5-yl]-(piperidin-1-yl)-methanone hydrochloride Step 1: 7-(3,4-dihydro-1H-isoquinolin-2-yl)-2,3-dimethyl-1H-pyrrolo[2,3-c]pyridin-5-carboxylic acid In accordance with the same procedures as in Example 731, except for using 7-(3,4-dihydro-1H-isoquinolin-2-yl)-2,3-dimethyl-1H-pyrrolo[2,3-c]pyridin-5-carbonitrile prepared in Example 682, the titled compound was obtained. (Yield: 59%)

Step 2: [7-(3,4-dihydro-1H-isoquinolin-2-yl)-2,3-dimethyl-1H-pyrrolo[2,3-c]pyridin-5-yl]-(piperidin-1-yl)-methanone A solution of 7-(3,4-dihydro-1H-isoquinolin-2-yl)-2,3-dimethyl-1H-pyrrolo[2,3-c]pyridin-5-carboxylic acid (450 mg, 1.4 mmol) prepared in Step 1, 1-hydroxybenzotriazole hydrate (284 mg, 2.1 mmol), 1-(3-dimethylaminopropyl)-3-ethylcarbodiimide hydrochloride (401 mg, 2.1 mmol), diisopropylethylamine (730 µl, 4.2 mmol), and piperidine (270 µl, 2.1 mmol) in dichloromethane (5 ml) was stirred overnight at room temperature and then concentrated under reduced pressure. The resulting residue was purified with silica gel column chromatography (ethyl acetate/n-hexane=1/1, v/v) to give 250 mg of the titled compound as a white solid. (Yield: 50%).

Step 3: [7-(3,4-dihydro-1H-isoquinolin-2-yl)-2,3-dimethyl-1H-pyrrolo[2,3-c]pyridin-5-yl]-(piperidin-1-yl)-methanone hydrochloride A solution of [7-(3,4-dihydro-1H-isoquinolin-2-yl)-2,3-dimethyl-1H-pyrrolo[2,3-c]pyridin-5-yl]-(piperidin-1-yl)-methanone prepared in Step 2 in ethyl acetate was saturated with hydrochloric acid gas and then filtered to give the titled compound as a white solid. (Yield: 90%)

1H-NMR(400 MHz, CDCl$_3$) δ 7.58 (s, 1H), 7.22-7.08 (m, 5H), 6.72 (m, 1H), 6.59 (s, 1H), 6.37 (m, 1H), 5.63 (s, 2H), 4.12 (brs, 2H), 3.90 (brs, 2H), 2.82 (brs, 6H), 2.32 (s, 6H)

EXAMPLES 792 TO 802

The titled compounds of Examples 792 to 802 were prepared, in accordance with the same procedures as in Example 657, using [7-(3,4-dihydro-1H-isoquinolin-2-yl)-2,3-dimethyl-1H-pyrrolo[2,3-c]pyridin-5-yl]-piperidin-1-yl-methanone prepared in Step 2 of Example 791; and, 2-bromoethyl methyl ether, (bromomethyl)cyclopropane, 1-iodo-2-methylpropane, 4-bromo-2-methyl-2-butene, 3-fluorobenzyl chloride, 4-fluorobenzyl chloride, 3-methylbenzyl bromide, 3-chlorobenzyl chloride, bromomethyl methyl ether, 1-bromopropane, or propargyl bromide.

EXAMPLE 792

[7-(3,4-dihydro-1H-isoquinolin-2-yl)-1-(2-methoxyethyl)-2,3-dimethyl-1H-pyrrolo[2,3-c]pyridin-5-yl]-(piperidin-1-yl)-methanone hydrochloride 1H-NMR(400 MHz, CDCl$_3$) δ 7.46 (s, 1H), 7.22-7.14 (m, 3H), 7.02 (m, 1H), 4.48 (brs, 2H), 3.85 (brs, 2H), 3.52 (brs, 2H), 3.39 (t, 2H), 3.12 (s, 2+3H), 2.48 (s, 3H), 2.27 (s, 3H), 1.71 (brs, 6H); (Yield: 68%)

EXAMPLE 793

[1-cyclopropylmethyl-7-(3,4-dihydro-1H-isoquinolin-2-yl)-2,3-dimethyl-1H-pyrrolo[2,3-c]pyridin-5-yl]-(piperidin-1-yl)-methanone hydrochloride 1H-NMR(400 MHz, CDCl$_3$) δ 7.42 (s, 1H), 7.20 (m, 3H), 7.02 (m, 1H), 4.21 (d, 2H), 3.85 (brs, 2H), 3.54 (brs, 2H), 3.12 (brs, 2H), 2.50 (s, 3H), 2.28 (s, 3H), 1.69 (brs, 6H), 0.92 (m, 1H), 0.35 (m, 2H), 0.03 (m, 2H); (Yield: 72%)

EXAMPLE 794

[7-(3,4-dihydro-1H-isoquinolin-2-yl)-1-isobutyl-2,3-dimethyl-1H-pyrrolo[2,3-c]pyridin-5-yl]-(piperidin-1-yl)-methanone hydrochloride 1H-NMR(400 MHz, CDCl$_3$) δ 7.44 (s, 1H), 7.20 (m, 3H), 7.03 (m, 1H), 4.00 (brs, 2H), 3.83 (brs, 2H), 3.55 (brs, 2H), 3.12 (brs, 2H), 2.44 (s, 3H), 2.26 (s, 3H), 1.90 (m, 1H), 1.70 (brs, 6H), 0.53 (d, 6H); (Yield: 59%)

EXAMPLE 795

[7-(3,4-dihydro-1H-isoquinolin-2-yl)-2,3-dimethyl-1-(3-methylbut-2-enyl)-1H-pyrrolo[2,3-c]pyridin-5-yl]-(piperidin-1-yl)-methanone hydrochloride 1H-NMR(400 MHz, CDCl$_3$) δ 7.43 (s, 1H), 7.18 (m, 3H), 6.98 (m, 1H), 5.00 (2H), 4.90 (s, 1H), 4.80-4.50 (brs, 2H), 4.10-3.90 (brs, 2H), 3.83 (brs, 2H), 3.54 (brs, 2H), 3.08 (brs, 2H), 2.40 (s, 3H), 2.25 (s, 3H), 1.70 (brs, 6H), 1.62 (s, 3H), 1.29 (s, 3H); (Yield: 69%)

EXAMPLE 796

[7-(3,4-dihydro-1H-isoquinolin-2-yl)-1-(3-fluorobenzyl)-2,3-dimethyl-1H-pyrrolo[2,3-c]pyridin-5-yl]-(piperidin-1-yl)-methanone hydrochloride 1H-NMR(400 MHz, CDCl$_3$) δ 7.53 (s, 1H), 7.18 (m, 2H), 7.07 (m, 2H), 6.93 (m, 1H), 6.67 (d, 1H), 6.25 (d, 1H), 6.20 (s, 1H), 5.63 (s, 2H), 3.84 (brs, 2H), 3.54 (brs, 2H), 2.79 (s, 2H), 2.34 (s, 3H), 2.32 (s, 3H), 1.70 (brs, 6H); (Yield: 64%)

EXAMPLE 797

[7-(3,4-dihydro-1H-isoquinolin-2-yl)-1-(4-fluorobenzyl)-2,3-dimethyl-1H-pyrrolo[2,3-c]pyridin-5-yl]-(piperidin-1-yl)-methanone hydrochloride 1H-NMR(400 MHz, CDCl$_3$) δ 7.52 (s, 1H), 7.17 (m, 1H), 7.08 (m, 2H), 6.91 (m, 2H), 6.72 (d, 1H), 6.47 (m, 2H), 5.61 (s, 2H), 3.84 (brs, 2H), 3.54 (brs, 2H), 2.80 (s, 2H), 2.32 (s, 3H), 2.31 (s, 3H), 1.70 (brs, 6H); (Yield: 67%)

EXAMPLE 798

[7-(3,4-dihydro-1H-isoquinolin-2-yl)-2,3-dimethyl-1-(3-methylbenzyl)-1H-pyrrolo[2,3-c]pyridin-5-yl]-(piperidin-1-yl)-methanone hydrochloride 1H-NMR(400 MHz, CDCl$_3$) δ 7.51 (s, 1H), 7.15 (m, 1H), 7.10-7.03 (m, 4H), 6.62 (d, 1H), 6.35 (s, 1H), 6.24 (d, 1H), 5.60 (s, 2H), 3.84 (brs, 2H), 3.55 (brs, 2H), 2.79 (s, 2H), 2.33 (s, 3H), 2.31 (s, 3H), 2.20 (s, 3H), 1.70 (brs, 6H); (Yield: 57%)

EXAMPLE 799

[1-(3-chlorobenzyl)-7-(3,4-dihydro-1H-isoquinolin-2-yl)-2,3-dimethyl-1H-pyrrolo[2,3-c]pyridin-5-yl]-(piperidin-1-yl)-methanone hydrochloride 1H-NMR(400 MHz, CDCl$_3$) δ 7.54 (s, 1H), 7.22-7.06 (m, 5H), 6.67 (d, 1H), 6.52 (s, 1H), 6.32 (d, 1H), 5.60 (s, 2H), 3.84 (brs, 2H), 3.54 (brs, 2H), 2.79 (s, 2H), 2.34 (s, 3H), 2.32 (s, 3H), 1.70 (brs, 6H); (Yield: 51%)

EXAMPLE 800

[7-(3,4-dihydro-1H-isoquinolin-2-yl)-1-methoxymethyl-2,3-dimethyl-1H-pyrrolo[2,3-c]pyridin-5-yl]-(piperidin-1-yl)-methanone hydrochloride 1H-NMR(400 MHz, CDCl$_3$) δ 7.52 (s, 1H), 7.20 (m, 3H), 7.06 (m, 1H), 5.62 (s, 2H), 4.60 (s, 2H), 3.96-3.74 (brs, 2H), 3.81 (brs, 2H), 3.54 (brs, 2H), 3.11 (s, 2H), 3.03 (s, 3H), 2.46 (s, 3H), 2.25 (s, 3H), 1.71 (brs, 6H); (Yield: 63%)

EXAMPLE 801

[7-(3,4-dihydro-1H-isoquinolin-2-yl)-2,3-dimethyl-1-propyl-1H-pyrrolo[2,3-c]pyridin-5-yl]-(piperidin-1-yl)-methanone hydrochloride 1H-NMR(400 MHz, CDCl$_3$) δ 7.44 (s, 1H), 7.20 (m, 3H), 7.04 (d, 1H), 4.19 (t, 2H), 3.84 (brs, 2H), 3.49 (brs, 2H), 3.12 (brs, 2H), 2.45 (s, 3H), 2.26 (s, 3H), 1.71 (brs, 6H), 1.52 (m, 2H), 0.57 (t, 3H); (Yield: 78%)

EXAMPLE 802

[7-(3,4-dihydro-1H-isoquinolin-2-yl)-2,3-dimethyl-1-(prop-2-ynyl)-1H-pyrrolo[2,3-c]pyridin-5-yl]-(piperidin-1-yl)-methanone hydrochloride 1H-NMR(400 MHz, CDCl$_3$) δ 7.48 (s, 1H), 7.20 (m, 3H), 7.07 (m, 1H), 5.23 (s, 2H), 3.82 (brs, 2H), 3.53 (brs, 2H), 3.17 (brs, 2H), 2.55 (s, 3H), 2.38 (s, 1H), 2.32 (s, 3H), 1.71 (brs, 6H); (Yield: 51%)

EXAMPLES 803 TO 810

The titled compounds of Examples 803 to 810 were prepared, in accordance with the same procedures as in Example 756, using 7-(3,4-dihydro-1H-isoquinolin-2-yl)-1-ethyl-2,3-dimethyl-1H-pyrrolo[2,3-c]pyridin-5-carboxylic acid prepared in Example 738; and, pyrrolidine, 4-piperidineethanol, 4-piperidinemethanol, 4-hydroxypiperidine, 3-hydroxypiperidine, thiomorpholine, 1,2,3,6-tetrahydropyridine, or 1-phenylpiperazine.

EXAMPLE 803

[7-(3,4-dihydro-1H-isoquinolin-2-yl)-1-ethyl-2,3-dimethyl-1H-pyrrolo[2,3-c]pyridin-5-yl]-(pyrrolidin-1-yl)-methanone hydrochloride 1H-NMR(400 MHz, CDCl$_3$) δ 7.79 (brs, 1H), 7.21 (m, 3H), 7.14 (m, 1H), 4.46 (brs, 3H), 4.07-3.78 (brs, 6H), 3.19 (brs, 3H), 2.49 (brs, 3H), 2.35 (brs, 3H), 2.01 (brs, 3H), 2.01 (brs, 4H), 1.21 (brs, 3H); (Yield: 59%)

EXAMPLE 804

[7-(3,4-dihydro-1H-isoquinolin-2-yl)-1-ethyl-2,3-dimethyl-1H-pyrrolo[2,3-c]pyridin-5-yl]-[4-(2-hydroxyethyl)-piperidin-1-yl]-methanone hydrochloride 1H-NMR(400 MHz, CDCl$_3$) δ 7.52 (brs, 1H), 7.20 (m, 3H), 7.06 (m, 1H), 4.57 (m, 2H), 4.40 (m, 2H), 3.74 (s, 3H), 3.40 (brs, 2H), 3.13 (brs, 2H), 2.98 (brs, 2H), 2.50 (s, 3H), 2.31 (s, 3H), 1.82 (m, 2H), 1.59 (m, 6H), 1.17 (t, 3H); (Yield: 57%)

EXAMPLE 805

[7-(3,4-dihydro-1H-isoquinolin-2-yl)-1-ethyl-2,3-dimethyl-1H-pyrrolo[2,3-c]pyridin-5-yl]-(4-hydroxymethylpiperidin-1-yl)-methanone hydrochloride 1H-NMR(400 MHz, CDCl$_3$) δ 7.56 (brs, 1H), 7.20 (m, 3H), 7.07 (m, 1H), 4.77 (brs, 1H), 4.40 (brs, 3H), 3.56 (brs, 3H), 3.19-2.95 (brs, 3H), 2.46 (s, 3H), 2.28 (s, 3H), 1.84 (brs, 2H), 1.59 (m, 6H), 1.16 (t, 3H); (Yield: 69%)

EXAMPLE 806

[7-(3,4-dihydro-1H-isoquinolin-2-yl)-1-ethyl-2,3-dimethyl-1H-pyrrolo[2,3-c]pyridin-5-yl]-(4-hydroxypiperidin-1-yl)-methanone hydrochloride 1H-NMR(400 MHz, CDCl$_3$) δ 7.70 (s, 1H), 7.20 (m, 3H), 7.11 (m, 1H), 4.42 (brs, 2H), 4.36 (brs, 2H), 4.15 (m, 1H), 3.97 (m, 1H), 3.60 (brs, 1H), 3.34 (m, 2H), 2.90 (brs, 1H), 2.38 (s, 3H), 2.23 (s, 3H), 2.02-1.94 (m, 2H), 1.64 (m, 4H), 1.12 (t, 3H); (Yield: 71%)

EXAMPLE 807

[7-(3,4-dihydro-1H-isoquinolin-2-yl)-1-ethyl-2,3-dimethyl-1H-pyrrolo[2,3-c]pyridin-5-yl]-(3-hydroxypiperidin-1-yl)-methanone hydrochloride 1H-NMR(400 MHz, CDCl$_3$) δ 7.71 (s, 1H), 7.20 (m, 3H), 7.00 (m, 1H), 4.66 (m, 1H), 4.47 (brs, 1H), 4.37 (brs, 2H), 4.06 (brs, 1H), 3.87 (brs, 3H), 3.33 (brs, 1H), 3.15 (brs, 2H), 2.93 (brs, 1H), 2.46 (s, 3H), 2.27 (s, 3H), 2.08 (brs, 1H), 1.68-1.59 (m, 4H), 1.14 (t, 3H); (Yield: 74%)

EXAMPLE 808

[7-(3,4-dihydro-1H-isoquinolin-2-yl)-1-ethyl-2,3-dimethyl-1H-pyrrolo[2,3-c]pyridin-5-yl]-(thiomorpholin-4-yl)-methanone hydrochloride 1H-NMR(400 MHz, CDCl$_3$) δ 7.65 (s, 1H), 7.20 (m, 3H), 7.0 (m, 1H), 4.41 (brs, 3H), 4.14-3.96 (m, 5H), 3.60 (brs, 2H), 3.13 (brs, 2H), 2.79 (brs, 4H), 2.40 (s, 3H), 2.29 (s, 3H), 1.13 (t, 3H); (Yield: 69%)

EXAMPLE 809

[7-(3,4-dihydro-1H-isoquinolin-2-yl)-1-ethyl-2,3-dimethyl-1H-pyrrolo[2,3-c]pyridin-5-yl]-(3,6-dihydro-2H-pyridin-1-yl)-methanone hydrochloride 1H-NMR(400 MHz, CDCl$_3$) δ 7.45 (s, 1H), 7.20 (m, 3H), 7.05 (d, 1H), 5.90-5.80 (m, 2H), 4.80-4.60 (brs, 2H), 4.38 (m, 4H), 4.13 (m, 2H), 4.00 (m, 2H), 3.67 (s, 2H), 3.13 (s, 2H), 2.47 (s, 3H), 2.24 (s, 3H), 1.15 (d, 3H); (Yield: 62%)

EXAMPLE 810

[7-(3,4-dihydro-1H-isoquinolin-2-yl)-1-ethyl-2,3-dimethyl-1H-pyrrolo[2,3-c]pyridin-5-yl]-(4-phenylpiperazin-1-yl)-methanone hydrochloride 1H-NMR(400 MHz, CDCl$_3$) δ 8.29 (d, 2H), 7.51-7.43 (m, 3H), 7.41 (s, 1H), 7.22 (m, 3H), 7.07 (d, 1H), 5.20 (brs, 1H), 4.98 (d, 1H), 4.76 (m, 2H), 4.38-4.29 (m, 4H), 4.06 (m, 1H), 3.96 (m, 1H), 3.56 (d, 1H), 3.34 (d, 1H), 3.17 (s, 2H), 2.50 (s, 3H), 2.29 (s, 3H), 1.16 (t, 3H); (Yield: 53%)

EXAMPLE 811

[1-allyl-7-(3,4-dihydro-1H-isoquinolin-2-yl)-2,3-dimethyl-1H-pyrrolo[2,3-c]pyridin-5-yl]-(piperazin-1-yl)-methanone hydrochloride In accordance with the same procedures as in Example 756, except for using 1-allyl-7-(3,4-dihydro-1H-isoquinolin-2-yl)-2,3-dimethyl-1H-pyrrolo[2,3-c]pyridin-5-carboxylic acid prepared in Example 732 and 1-piperazin-1-carboxylic acid tert-butyl ester, the titled compound was obtained as a white solid. (Yield: 57%)

1H-NMR(400 MHz, CDCl$_3$) δ 7.46 (s, 1H), 7.22 (m, 3H), 7.06 (m, 1H), 5.75 (m, 1H), 5.21 (d, 1H), 4.99 (s, 2H), 4.70 (m, 1H), 4.60 (d, 1H), 4.27 (brs, 2H), 4.13 (brs, 2H), 3.96 (brs, 2H), 3.58 (brs, 2H), 3.43 (s, 2H), 3.14 (s, 2H), 2.43 (s, 3H), 2.29 (s, 3H)

EXAMPLE 812

[1-benzyl-7-(3,4-dihydro-1H-isoquinolin-2-yl)-2,3-dimethyl-1H-pyrrolo[2,3-c]pyridin-5-yl]-(piperazin-1-yl)-methanone hydrochloride In accordance with the same procedures as in Example 756, except for using 1-benzyl-7-(3,4-dihydro-1H-isoquinolin-2-yl)-2,3-dimethyl-1H-pyrrolo[2,3-c]pyridin-5-carboxylic acid prepared in Example 733 and 1-piperazin-1-carboxylic acid tert-butyl ester, the titled compound was obtained as a white solid. (Yield: 67%)

1H-NMR(400 MHz, CDCl$_3$) δ 7.76 (brs, 1H), 7.43 (s, 1H), 7.18 (m, 3H), 6.63 (brs, 2H), 5.80 (brs, 2H), 4.22 (brs, 2H), 3.65 (brs, 2H), 3.30 (brs, 3H), 3.09 (brs, 2H), 2.90 (brs, 2H), 2.83 (brs, 2H), 2.52-2.18 (brs, 5H), 1.52 (s, 3H), 1.43 (s, 3H)

EXAMPLE 813

[7-(3,4-dihydro-1H-isoquinolin-2-yl)-2,3-dimethyl-1-propyl-1H-pyrrolo[2,3-c]pyridin-5-yl]-(piperazin-1-yl)-methanone hydrochloride In accordance with the same procedures as in Example 756, except for using 7-(3,4-dihydro-1H-isoquinolin-2-yl)-2,3-dimethyl-1-propyl-1H-pyrrolo[2,3-c]pyridin-5-carboxylic acid prepared in Example 742 and 1-piperazin-1-carboxylic acid tert-butyl ester, the titled compound was obtained as a white solid. (Yield: 64%)

1H-NMR(400 MHz, CDCl$_3$) δ 7.45 (s, 1H), 7.22 (m, 3H), 7.10 (m, 1H), 4.61 (brs, 1H), 4.26 (brs, 2H), 4.18 (brs, 4H), 4.01 (brs, 2H), 3.57 (brs, 2H), 3.47 (brs, 2H), 3.18 (s, 2H), 2.46 (s, 3H), 2.27 (s, 3H), 1.50 (m, 2H), 0.56 (t, 3H)

EXAMPLE 814

[7-(3,4-dihydro-1H-isoquinolin-2-yl)-2,3-dimethyl-1-(3-methylbenzyl)-1H-pyrrolo[2,3-c]pyridin-5-yl]-(piperazin-1-yl)-methanone hydrochloride In accordance with the same procedures as in Example 756, except for using 7-(3,4-dihydro-1H-isoquinolin-2-yl)-2,3-dimethyl-1-(3-methylbenzyl)-1H-pyrrolo[2,3-c]pyridin-5-carboxylic acid prepared in Example 740 and 1-piperazin-1-carboxylic acid tert-butyl ester, the titled compound was obtained as a white solid. (Yield: 59%)

1H-NMR(400 MHz, CDCl$_3$) δ 7.49 (s, 1H), 7.19-7.05 (m, 5H), 6.59 (d, 1H), 6.38 (s, 1H), 6.27 (d, 1H), 5.54 (s, 2H), 4.50 (brs, 1H), 4.25-4.13 (m, 4H), 3.89 (brs, 2H), 3.59 (brs, 2H), 3.42 (brs, 2H), 2.90 (s, 2H), 2.34 (s, 3H), 2.31 (s, 3H), 2.21 (s, 3H)

EXAMPLE 815

[7-(3,4-dihydro-1H-isoquinolin-2-yl)-1-isobutyl-2,3-dimethyl-1H-pyrrolo[2,3-c]pyridin-5-yl]-(piperazin-1-yl)-methanone hydrochloride In accordance with the same procedures as in Example 756, except for using 7-(3,4-dihydro-1H-isoquinolin-2-yl)-1-isobutyl-2,3-dimethyl-1H-pyrrolo[2,3-c]pyridin-5-carboxylic acid prepared in Example 741 and 1-piperazin-1-carboxylic acid tert-butyl ester, the titled compound was obtained as a white solid. (Yield: 59%)

1H-NMR(400 MHz, CDCl$_3$) δ 7.40 (s, 1H), 7.23 (m, 3H), 7.10 (m, 1H), 4.60 (brs, 2H), 4.26 (brs, 2H), 4.13 (brs, 4H), 3.97 (brs, 2H), 3.60 (brs, 2H), 3.45 (brs, 2H), 3.20 (s, 2H), 2.46 (s, 3H), 2.27 (s, 3H), 1.86 (m, 1H), 0.50 (d, 6H)

EXAMPLES 816 TO 818

The titled compounds of Examples 816 to 818 were prepared, in accordance with the same procedures as in Example 756, using 1-cyclopropylmethyl-7-(3,4-dihydro-1H-isoquinolin-2-yl)-2,3-dimethyl-1H-pyrrolo[2,3-c]pyridin-5-carboxylic acid prepared in Example 735; and, 1-piperazin-1-carboxylic acid tert-butyl ester, 1-methylpiperazine, or 1-ethylpiperazine.

EXAMPLE 816

[1-cyclopropylmethyl-7-(3,4-dihydro-1H-isoquinolin-2-yl)-2,3-dimethyl-1H-pyrrolo[2,3-c]pyridin-5-yl]-(piperazin-1-yl)-methanone hydrochloride 1H-NMR(400 MHz, CDCl$_3$) δ 7.56 (brs, 1H), 7.23 (m, 4H), 4.58 (brs, 1H), 4.22 (brs, 4H), 4.05 (brs, 3H), 3.49 (brs, 4H), 3.27 (brs, 3H), 2.52 (s, 3H), 2.41 (s, 3H), 0.93 (m, 1H), 0.34 (m, 2H), 0.06 (m, 2H); (Yield: 51%)

EXAMPLE 817

[1-cyclopropylmethyl-7-(3,4-dihydro-1H-isoquinolin-2-yl)-2,3-dimethyl-1H-pyrrolo[2,3-c]pyridin-5-yl]-(4-methylpiperazin-1-yl)-methanone hydrochloride 1H-NMR(400 MHz, CDCl$_3$) δ 7.53 (brs, 1H), 7.24 (m, 3H), 7.07 (m, 1H), 4.86 (brs, 1H), 4.67-4.58 (brs, 2H), 4.44 (m, 3H), 4.27 (m, 3H), 3.85 (m, 2H), 3.39 (brs, 1H), 3.33 (brs, 3H), 2.87 (brs, 2+3H), 2.56 (s, 3H), 2.34 (s, 3H), 0.93 (m, 1H), 0.41 (m, 2H), 0.09 (m, 2H); (Yield: 51%)

EXAMPLE 818

[1-cyclopropylmethyl-7-(3,4-dihydro-1H-isoquinolin-2-yl)-2,3-dimethyl-1H-pyrrolo[2,3-c]pyridin-5-yl]-(4-ethylpiperazin-1-yl)-methanone hydrochloride 1H-NMR(400 MHz, CDCl$_3$) δ 7.47 (s, 1H), 7.21 (m, 4H), 7.04 (m, 1H), 4.85 (d, 1H), 4.60 (brs, 2H), 4.01 (brs, 4H), 3.83 (brs, 1H), 3.60 (brs, 1H), 3.44 (brs, 2H), 3.15 (s, 4H), 2.54 (s, 3H), 2.31 (s, 3H), 1.42 (s, 3H), 0.91 (m, 1H), 0.40 (m, 2H), 0.09 (m, 2H); (Yield: 51%)

EXAMPLE 819

[1-benzyl-7-(3,4-dihydro-1H-isoquinolin-2-yl)-2,3-dimethyl-1H-pyrrolo[2,3-c]pyridin-5-yl]-(4-methylpiperazin-1-yl)-methanone hydrochloride In accordance with the same procedures as in Example 756, except for using 1-benzyl-7-(3,4-dihydro-1H-isoquinolin-2-yl)-2,3-dimethyl-1H-pyrrolo[2,3-c]pyridin-5-carboxylic acid prepared in Example 733 and 1-methylpiperazine, the titled compound was obtained as a white solid. (Yield: 44%)
1H-NMR(400 MHz, CDCl$_3$) δ 7.53 (brs, 1H), 7.20 (m, 5H), 7.10 (m, 2H), 6.56 (m, 2H), 5.71 (brs, 2H), 4.86 (brs, 1H), 4.50-4.36 (brs, 3H), 3.82 (brs, 3H), 3.39 (brs, 2H), 2.83 (brs, 5H), 2.38 (s, 3+3H)

EXAMPLE 820

[7-(3,4-dihydro-1H-isoquinolin-2-yl)-2,3-dimethyl-1-(3-methylbenzyl)-1H-pyrrolo[2,3-c]pyridin-5-yl]-(4-methylpiperazin-1-yl)-methanone hydrochloride In accordance with the same procedures as in Example 756, except for using 7-(3,4-dihydro-1H-isoquinolin-2-yl)-2,3-dimethyl-1-(3-methylbenzyl)-1H-pyrrolo[2,3-c]pyridin-5-carboxylic acid prepared in Example 740 and 1-methylpiperazine, the titled compound was obtained as a white solid. (Yield: 48%)
1H-NMR(400 MHz, CDCl$_3$) δ 7.35 (brs, 1H), 7.19-7.07 (m, 5H), 6.61 (brs, 1H), 6.44 (brs, 2H), 5.61 (brs, 2H), 4.85 (brs, 1H), 4.50-4.10 (brs, 3H), 3.82 (brs, 4H), 2.86 (brs, 5H), 2.43 (brs, 3H), 2.24 (brs, 3H)

EXAMPLE 821

[7-(3,4-dihydro-1H-isoquinolin-2-yl)-1-(2-methoxyethyl)-2,3-dimethyl-1H-pyrrolo[2,3-c]pyridin-5-yl]-(4-methylpiperazin-1-yl)-methanone hydrochloride In accordance with the same procedures as in Example 756, except for using 7-(3,4-dihydro-1H-isoquinolin-2-yl)-1-(2-methoxyethyl)-2,3-dimethyl-1H-pyrrolo[2,3-c]pyridin-5-carboxylic acid prepared in Example 739 and 1-methylpiperazine, the titled compound was obtained as a white solid. (Yield: 51%)
1H-NMR(400 MHz, CDCl$_3$) δ 7.43 (s, 1H), 7.23 (m, 3H), 7.05 (m, 1H), 4.87 (d, 1H), 4.70 (brs, 1H), 4.48 (brs, 3H), 4.32 (brs, 1H), 3.92-3.80 (m, 3H), 3.39 (s, 3H), 3.10 (s, 5H), 2.86 (s, 3H), 2.51 (s, 3H), 2.34 (s, 3H)

EXAMPLES 822 TO 824

The titled compounds of Examples 822 to 824 were prepared, in accordance with the same procedures as in Example 756, using 7-(3,4-dihydro-1H-isoquinolin-2-yl)-1-(3-methoxybenzyl)-2,3-dimethyl-1H-pyrrolo[2,3-c]pyridin-5-carboxylic acid prepared in Example 736; and, 1-piperazin-1-carboxylic acid tert-butyl ester, 4-methylpiperidine, or 1-ethylpiperazine.

EXAMPLE 822

[7-(3,4-dihydro-1H-isoquinolin-2-yl)-1-(3-methoxybenzyl)-2,3-dimethyl-1H-pyrrolo[2,3-c]pyridin-5-yl]-(piperazin-1-yl)-methanone hydrochloride 1H-NMR(400 MHz, CDCl$_3$) δ 7.59 (s, 1H), 7.15 (m, 4H), 6.78 (d, 1H), 6.65 (brs, 1H), 6.12 (s, 2H), 5.59 (s, 2H), 4.44 (brs, 1H), 4.22 (brs, 3H), 3.78 (brs, 2H), 3.66 (s, 3H), 3.57-3.40 (m, 4H), 2.81 (s, 3H), 2.33 (s, 3+3H); (Yield: 59%)

EXAMPLE 823

[7-(3,4-dihydro-1H-isoquinolin-2-yl)-1-(3-methoxybenzyl)-2,3-dimethyl-1H-pyrrolo[2,3-c]pyridin-5-yl]-(4-methylpiperidin-1-yl)-methanone hydrochloride 1H-NMR(400 MHz, CDCl$_3$) δ 7.56 (s, 1H), 7.17-7.04 (m, 4H), 6.76 (d, 1H), 6.68 (d, 1H), 6.10 (s, 2H), 5.64 (s, 2H), 4.70 (m, 1H), 3.73 (brs, 1H), 3.65 (s, 3H), 3.39 (brs, 1H), 3.00 (m, 1H), 2.81 (brs, 2H), 2.31 (s, 3H), 2.30 (s, 3H), 1.81-1.51 (m, 5H), 1.32 (m, 1H), 0.99 (d, 3H); (Yield: 34%)

EXAMPLE 824

[7-(3,4-dihydro-1H-isoquinolin-2-yl)-1-(3-methoxybenzyl)-2,3-dimethyl-1H-pyrrolo[2,3-c]pyridin-5-yl]-(4-ethylpiperazin-1-yl)-methanone hydrochloride 1H-NMR(400 MHz, CDCl$_3$) δ 7.42 (s, 1H), 7.22-7.11 (m, 3H), 7.07 (m, 1H), 6.80 (d, 1H), 6.60 (brs, 1H), 6.06 (s, 2H), 5.68 (d, 1H), 5.46 (d, 1H), 4.88 (d, 1H), 4.40-4.39 (m, 4H), 3.91 (m, 3H), 3.67 (s, 3H), 3.45 (d, 1H), 3.22 (m, 3H), 2.90 (m, 2H), 2.37 (s, 3H), 2.33 (s, 3H), 1.48 (t, 3H); (Yield: 58%)

EXAMPLE 825

[7-(3,4-dihydro-1H-isoquinolin-2-yl)-2,3-dimethyl-1-propyl-1H-pyrrolo[2,3-c]pyridin-5-yl]-(4-methylpiperazin-1-yl)-methanone hydrochloride In accordance with the same procedures as in Example 756, except for using 7-(3,4-dihydro-1H-isoquinolin-2-yl)-2,3-dimethyl-1-propyl-1H-pyrrolo[2,3-c]pyridin-5-carboxylic acid prepared in Example 742 and 1-methylpiperazine, the titled compound was obtained as a white solid. (Yield: 60%)

1H-NMR(400 MHz, CDCl$_3$) δ 7.40 (s, 1H), 7.23 (m, 3H), 7.07 (m, 1H), 4.87 (m, 1H), 4.80-4.30 (brs, 3H), 4.24 (m, 3H), 4.14 (m, 1H), 4.02 (m, 1H), 3.85 (m, 3H), 3.37 (brs, 1H), 3.16 (s, 3H), 2.87 (s, 3H), 2.49 (s, 3H), 2.30 (s, 3H), 1.52 (m, 2H), 0.57 (t, 3H)

EXAMPLE 826

[7-(3,4-dihydro-1H-isoquinolin-2-yl)-1-ethyl-2,3-dimethyl-1H-pyrrolo[2,3-c]pyridin-5-yl]-(4-ethylpiperazin-1-yl)-methanone hydrochloride In accordance with the same procedures as in Example 756, except for using 7-(3,4-dihydro-1H-isoquinolin-2-yl)-1-ethyl-2,3-dimethyl-1H-pyrrolo[2,3-c]pyridin-5-carboxylic acid prepared in Example 738 and 1-ethylpiperazine, the titled compound was obtained as a white solid. (Yield: 53%)

1H-NMR(400 MHz, CDCl$_3$) δ 7.46 (brs, 1H), 7.22 (m, 3H), 7.03 (m, 1H), 4.86 (brs, 2H), 4.59-3.80 (brs, 2H), 4.38 (m, 4H), 3.93 (brs, 4H), 3.42 (brs, 2H), 3.17 (brs, 4H), 2.55 (s, 3H), 2.35 (s, 3H), 1.47 (s, 3H), 1.20 (s, 3H)

EXAMPLE 827

[7-(3,4-dihydro-1H-isoquinolin-2-yl)-2,3-dimethyl-1H-pyrrolo[2,3-c]pyridin-5-yl]-(4-methylpiperazin-1-yl)-methanone hydrochloride

Step 1: 7-(3,4-dihydro-1H-isoquinolin-2-yl)-2,3-dimethyl-1H-pyrrolo[2,3-c]pyridin-5-carboxylic acid In accordance with the same procedures as in Example 731, except for using 7-(3,4-dihydro-1H-isoquinolin-2-yl)-2,3-dimethyl-1H-pyrrolo[2,3-c]pyridin-5-carbonitrile prepared in Example 682, the titled compound was obtained as a white solid. (Yield: 59%)

Step 2: [7-(3,4-dihydro-1H-isoquinolin-2-yl)-2,3-dimethyl-1H-pyrrolo[2,3-c]pyridin-5-yl]-(4-methylpiperazin-1-yl)-methanone A solution of 7-(3,4-dihydro-1H-isoquinolin-2-yl)-2,3-dimethyl-1H-pyrrolo[2,3-c]pyridin-5-carboxylic acid (450 mg, 1.4 mmol) prepared in Step 1, 1-hydroxybenzotriazole hydrate (284 mg, 2.1 mmol), 1-(3-dimethylaminopropyl)-3-ethylcarbodiimide hydrochloride (401 mg, 2.1 mmol), diisopropylethylamine (730 µl, 4.2 mmol), and 1-methylpiperazine (234 µl, 2.1 mmol) in dichloromethane (10 ml) was stirred overnight at room temperature and then concentrated under reduced pressure. The resulting residue was purified with silica gel column chromatography (dichloromethane/methanol=10/1, v/v) to give 300 mg of the titled compound as a white solid (Yield: 53%).

Step 3: [7-(3,4-dihydro-1H-isoquinolin-2-yl)-2,3-dimethyl-1H-pyrrolo[2,3-c]pyridin-5-yl]-(4-methylpiperazin-1-yl)-methanone hydrochloride A solution of [7-(3,4-dihydro-1H-isoquinolin-2-yl)-2,3-dimethyl-1H-pyrrolo[2,3-c]pyridin-5-yl]-(4-methylpiperazin-1-yl)-methanone prepared in Step 2 in ethyl acetate was saturated with hydrochloric acid gas and then filtered to give the titled compound as a white solid. (Yield: 90%)

1H-NMR(400 MHz, CDCl$_3$) δ 12.72 (brs, 1H), 11.25 (brs, 1H), 7.20 (m, 3H), 6.94 (m, 1H), 4.84 (brs, 4H), 3.98 (brs, 5H), 3.25 (m, 2H), 3.01 (m, 3H), 2.83 (s, 3H), 2.59 (s, 3H), 2.14 (s, 3H)

EXAMPLES 828 TO 837

The titled compounds of Examples 828 to 837 were prepared, in accordance with the same procedures as in Example 657, using [7-(3,4-dihydro-1H-isoquinolin-2-yl)-2,3-dimethyl-1H-pyrrolo[2,3-c]pyridin-5-yl]-(4-methylpiperazin-1-yl)-methanone prepared in Step 2 of Example 827; and, 4-methylbenzyl bromide, 4-methoxybenzyl bromide, (bromomethyl)cyclobutane, 4-fluorobenzyl chloride, 3-fluorobenzyl chloride, 1-iodo-2-methylpropane, 1-bromo-3-methylbutene, 4-tert-butylbenzyl chloride, 3-chlorobenzyl chloride, or ethanolamine.

EXAMPLE 828

[7-(3,4-dihydro-1H-isoquinolin-2-yl)-1-(4-methylbenzyl)-2,3-dimethyl-1H-pyrrolo[2,3-c]pyridin-5-yl]-(4-methylpiperazin-1-yl)-methanone hydrochloride 1H-NMR(400 MHz, CDCl$_3$) δ 7.46 (brs, 1H), 7.20 (m, 1H), 7.13 (m, 2H), 7.01 (m, 2H), 6.70 (m, 1H), 6.45 (d, 2H), 5.61-5.53 (m, 2H), 4.88 (m, 1H), 4.55 (brs, 2H), 4.25 (brs, 2H), 4.03 (brs, 2H), 3.80 (m, 3H), 3.38 (m, 2H), 3.17 (m, 2H), 2.85 (d, 3H), 2.34 (s, 3H), 2.31 (s, 6H); (Yield: 59%)

EXAMPLE 829

[7-(3,4-dihydro-1H-isoquinolin-2-yl)-1-(4-methoxybenzyl)-2,3-dimethyl-1H-pyrrolo[2,3-c]pyridin-5-yl]-(4-methylpiperazin-1-yl)-methanone hydrochloride 1H-NMR(400 MHz, CDCl$_3$) δ 7.47 (brs, 1H), 7.20 (m, 2H), 7.10 (m, 2H), 6.76 (d, 2H), 6.49 (m, 2H), 5.58 (m, 2H), 4.88 (m, 2H), 4.46 (brs, 2H), 4.27 (brs, 2H), 3.90 (brs, 2H), 3.81 (m, 2H), 3.73 (s, 3H), 3.38 (brs, 2H), 3.17 (brs, 2H), 2.85 (s, 3H), 2.35 (s, 3H), 2.30 (s, 3H); (Yield: 61%)

EXAMPLE 830

[1-cyclobutylmethyl-7-(3,4-dihydro-1H-isoquinolin-2-yl)-2,3-dimethyl-1H-pyrrolo[2,3-c]pyridin-5-yl]-(4-methylpiperazin-1-yl)-methanone hydrochloride 1H-NMR(400 MHz, CDCl$_3$) δ 7.36 (s, 1H), 7.20 (m, 3H), 7.08 (d, 1H), 4.88 (d, 1H), 4.65 (brs, 2H), 4.41 (brs, 2H), 4.29 (m, 2H), 4.04-3.90 (brs, 2H), 3.84 (m, 2H), 3.36 (brs, 2H), 3.17 (brs, 3H), 2.86 (d, 3H), 2.48 (s, 3H), 2.27 (s, 3H), 1.72 (m, 3H), 1.62 (m, 4H); (Yield: 66%)

EXAMPLE 831

[7-(3,4-dihydro-1H-isoquinolin-2-yl)-1-(4-fluorobenzyl)-2,3-dimethyl-1H-pyrrolo[2,3-c]pyridin-5-yl]-(4-methylpiperazin-1-yl)-methanone hydrochloride 1H-NMR(400 MHz, CDCl$_3$) δ 7.46 (s, 1H), 7.23 (m, 1H), 7.10 (m, 3H), 6.92 (m, 2H), 6.70 (brs, 1H), 6.49 (m, 1H), 5.61-5.54 (m, 2H), 4.88 (m, 1H), 4.49 (m, 2H), 4.30 (brs, 2H), 4.20-3.90 (brs, 2H), 3.82 (brs, 3H), 3.38 (brs, 2H), 3.15 (brs, 2H), 2.84 (s, 3H), 2.35 (s, 3H), 2.32 (s, 3H); (Yield: 63%)

EXAMPLE 832

[7-(3,4-dihydro-1H-isoquinolin-2-yl)-1-(3-fluorobenzyl)-2,3-dimethyl-1H-pyrrolo[2,3-c]pyridin-5-yl]-(4-methylpiperazin-1-yl)-methanone hydrochloride 1H-NMR(400 MHz, CDCl$_3$) δ 7.44 (brs, 1H), 7.22 (m, 2H), 7.15 (m, 2H), 6.99 (m, 1H), 6.66 (m, 1H), 6.27 (m, 2H), 5.71 (d, 1H), 5.50 (d, 1H), 4.88 (m, 1H), 4.58 (m, 3H), 4.33 (m, 2H), 3.87 (m, 4H), 3.37 (m, 1H), 3.19 (m, 1H), 2.87 (brs, 2+3H), 2.37 (s, 3H), 2.31 (s, 3H); (Yield: 63%)

EXAMPLE 833

[7-(3,4-dihydro-1H-isoquinolin-2-yl)-1-isobutyl-2,3-dimethyl-1H-pyrrolo[2,3-c]pyridin-5-yl]-(4-methylpiperazin-1-yl)-methanone hydrochloride 1H-NMR(400 MHz, CDCl$_3$) δ 7.36 (s, 1H), 7.24 (m, 3H), 7.06 (d, 1H), 4.88 (d, 1H), 4.56 (brs, 3H), 4.31 (m, 2H), 4.14-4.04 (m, 3H), 3.94-3.83 (m, 4H), 3.49 (d, 1H), 3.17 (s, 2H), 2.86 (d, 3H), 2.48 (s, 3H), 2.29 (s, 3H), 1.87 (m, 1H), 0.50 (d, 6H); (Yield: 59%)

EXAMPLE 834

[7-(3,4-dihydro-1H-isoquinolin-2-yl)-2,3-dimethyl-1-(3-methylbut-2-enyl)-1H-pyrrolo[2,3-c]pyridin-5-yl]-(4-methylpiperazin-1-yl)-methanone hydrochloride 1H-NMR(400 MHz, CDCl$_3$) δ 7.36 (s, 1H), 7.22 (m, 3H), 7.00 (d, 1H), 5.09 (m, 1H), 4.87 (m, 3H), 4.65 (brs, 2H), 4.50 (brs, 1H), 4.28 (m, 1H), 3.98 (brs, 2H), 3.84 (m, 2H), 3.38 (m, 1H), 3.17 (m, 3H), 2.86 (d, 3H), 2.44 (s, 3H), 2.27 (s, 3H), 1.64 (s, 3H), 1.29 (s, 3H); (Yield: 59%)

EXAMPLE 835

[1-(4-tert-butylbenzyl)-7-(3,4-dihydro-1H-isoquinolin-2-yl)-2,3-dimethyl-1H-pyrrolo[2,3-c]pyridin-5-yl]-(4-methylpiperazin-1-yl)-methanone hydrochloride 1H-NMR(400 MHz, CDCl$_3$) δ 7.45 (s, 1H), 7.21 (m, 3H), 7.13 (d, 1H), 7.05 (m, 1H), 6.55 (brs, 1H), 6.46 (d, 2H), 5.80-5.63 (m, 2H), 4.88 (d, 1H), 4.45 (brs, 2H), 4.29 (m, 2H), 3.95 (brs, 2H), 3.83 (d, 3H), 3.38 (d, 2H), 3.37 (d, 2H), 2.86 (d, 3H), 2.37 (s, 3H), 2.32 (s, 3H), 1.29 (s, 9H); (Yield: 45%)

EXAMPLE 836

[1-(3-chlorobenzyl)-7-(3,4-dihydro-1H-isoquinolin-2-yl)-2,3-dimethyl-1H-pyrrolo[2,3-c]pyridin-5-yl]-(4-methylpiperazin-1-yl)-methanone hydrochloride 1H-NMR(400 MHz, CDCl$_3$) δ 7.52 (brs, 1H), 7.15 (m, 4H), 6.70 (brs, 1H), 6.58 (brs, 2H), 6.38 (brs, 1H), 5.66 (brs, 2H), 4.86 (brs, 2H), 4.45-4.11 (brs, 4H), 4.08 (brs, 2H), 3.77 (brs, 2H), 3.40 (brs, 2H), 3.17 (brs, 2H), 2.83 (s, 3H), 2.35 (s, 3H), 2.33 (s, 3H); (Yield: 34%)

EXAMPLE 837

1-allyl-7-(3,4-dihydro-1H-isoquinolin-2-yl)-2,3-dimethyl-N-(2-hydroxyethyl)-1H-pyrrolo[2,3-c]pyridin-5-carboxamide hydrochloride 1H-NMR(400 MHz, CDCl$_3$) δ 10.32 (brs, 1H), 9.03 (s, 1H), 7.25 (m, 3H), 7.07 (m, 1H), 5.83 (m, 1H), 5.20 (d, 1H), 5.06 (s, 2H), 4.71 (brs, 2H), 4.54 (d, 1H), 4.00 (brs, 2H), 3.95 (s, 2H), 3.65 (s, 2H), 3.10 (s, 2H), 2.44 (s, 3H), 2.38 (s, 3H); (Yield: 82%)

EXAMPLE 838

[7-(3,4-dihydro-1H-isoquinolin-2-yl)-1-ethyl-2,3-dimethyl-1H-pyrrolo[2,3-c]pyridin-5-yl]-(imidazol-1-yl)-methanone hydrochloride A solution of 7-(3,4-dihydro-1H-isoquinolin-2-yl)-1-ethyl-2,3-dimethyl-1H-pyrrolo[2,3-c]pyridin-5-carboxylic acid (50 mg, 0.14 mmol) prepared in Example 738 and 1,1'-carbonyldiimidazol (227 mg, 1.4 mmol) in anhydrous tetrahydrofuran (3 ml) was refluxed for 3 hours. 10% Sodium carbonate solution and water were added to the reaction mixture, which was then extracted with dichloromethane. The organic layer was dried on anhydrous magnesium sulfate and then concentrated under reduced pressure. The resulting residue was purified with silica gel column chromatography (ethyl acetate/n-hexane=1/1, v/v). The resulting product was dissolved in ethyl acetate, saturated with hydrochloric acid gas, and then filtered to give 55.9 mg of the titled compound as a white solid.

1H-NMR(400 MHz, CDCl$_3$) δ 10.06 (s, 1H), 8.48 (s, 1H), 8.17 (s, 1H), 7.43 (s, 1H), 7.25 (m, 4H), 4.49 (m, 2H), 4.43 (s, 2H), 3.68-3.47 (brs, 2H), 3.12-2.95 (brs, 2H), 2.45 (s, 3H), 2.33 (s, 3H), 1.18 (t, 3H)

EXAMPLES 839 TO 843

The titled compounds of Examples 839 to 843 were prepared, in accordance with the same procedures as in Example 838, using the compounds prepared in Examples 733, 743, 736, 739, and 742.

EXAMPLE 839

[1-benzyl-7-(3,4-dihydro-1H-isoquinolin-2-yl)-2,3-dimethyl-1H-pyrrolo[2,3-c]pyridin-5-yl]-(imidazol-1-yl)-methanone hydrochloride 1H-NMR(400 MHz, CDCl$_3$) δ 8.98 (s, 1H), 8.28 (s, 1H), 7.26 (s, 1H), 7.24 (m, 4H), 7.18 (s, 2H), 6.76 (m, 1H), 6.64 (s, 2H), 5.71 (s, 2H), 4.51 (brs, 2H), 3.72 (brs, 2H), 2.85 (s, 2H), 2.38 (s, 3H), 2.34 (s, 3H); (Yield: 36%)

EXAMPLE 840

[7-(3,4-dihydro-1H-isoquinolin-2-yl)-1-(3-fluorobenzyl)-2,3-dimethyl-1H-pyrrolo[2,3-c]pyridin-5-yl]-(imidazol-1-yl)-methanone hydrochloride 1H-NMR(400 MHz, CDCl$_3$) δ 9.12 (s, 1H), 8.29 (s, 1H), 7.29 (s, 1H), 7.26 (m, 2H), 7.19 (m, 2H), 7.13 (m, 2H), 6.98 (m, 1H), 6.71 (d, 1H), 6.35 (d, 1H), 6.27 (d, 1H), 5.65 (s, 2H), 4.59 (brs, 2H), 3.93 (brs, 2H), 2.86 (s, 2H), 2.40 (s, 3H), 2.37 (s, 3H); (Yield: 36%)

EXAMPLE 841

[7-(3,4-dihydro-1H-isoquinolin-2-yl)-1-(3-methoxybenzyl)-2,3-dimethyl-1H-pyrrolo[2,3-c]pyridin-5-yl]-(imidazol-1-yl)-methanone hydrochloride 1H-NMR(400 MHz, CDCl$_3$) δ 8.87 (s, 1H), 8.26 (s, 1H), 7.28 (s, 1H), 7.16 (m, 4H), 6.79 (d, 1H), 6.70 (d, 1H), 6.16 (s, 2H), 5.65 (s, 3H), 4.55 (brs, 2H), 3.86 (brs, 2H), 3.67 (s, 3H), 2.88 (s, 3H), 2.38-2.17 (m, 6H); (Yield: 82%)

EXAMPLE 842

[7-(3,4-dihydro-1H-isoquinolin-2-yl)-1-(2-methoxyethyl)-2,3-dimethyl-1H-pyrrolo[2,3-c]pyridin-5-yl]-(imidazol-1-yl)-methanone hydrochloride 1H-NMR(400 MHz, CDCl$_3$) δ 9.01 (s, 1H), 8.25 (s, 1H), 7.26 (m, 3H), 7.18 (m, 1H), 4.77 (brs, 2H), 4.52 (m, 2H), 4.36 (brs, 2H), 3.46 (m, 2H), 3.10 (m, 2+3H), 2.52 (s, 3H), 2.34 (s, 3H); (Yield: 36%)

EXAMPLE 843

[7-(3,4-dihydro-1H-isoquinolin-2-yl)-2,3-dimethyl-1-propyl-1H-pyrrolo[2,3-c]pyridin-5-yl]-(imidazol-1-yl)-methanone hydrochloride 1H-NMR(400 MHz, CDCl$_3$) δ 9.05 (s, 1H), 8.22 (s, 1H), 7.30 (s, 1H), 7.26 (m, 3H), 7.13 (m, 1H), 4.82 (brs, 2H), 4.23 (s, 4H), 3.16 (s, 2H), 2.51 (s, 3H), 2.34 (s, 3H), 1.54 (m, 2H), 0.57 (t, 3H); (Yield: 41%)

EXAMPLE 844

2-[1-(3-fluorobenzyl)-2,3-dimethyl-5-(morpholin-4-yl)-1H-pyrrolo[2,3-c]pyridin-7-yl]-1,2,3,4-tetrahydroisoquinoline hydrochloride Morpholine (96.7 μl, 1.11 mmol) was added to a solution of 2-[5-chloro-1-(3-fluorobenzyl)-2,3-dimethyl-1H-pyrrolo[2,3-c]pyridin-7-yl-]1,2,3,4-tetrahydroisoquinoline (300 mg, 0.714 mmol) prepared in Example 662, tris(dibenzylideneacetone)dipalladium(0) (16.3 mg, 0.018 mmol), 4,5-bis(diphenylphosphino)-9,9-dimethyl-xanthene (31 mg, 0.054 mmol), and cesium carbonate (326 mg, 1.0 mmol) in anhydrous 1,4-dioxane (5 ml). The reaction mixture was refluxed for 40 hours at 80° C. and then concentrated under reduced pressure. The resulting residue was purified with silica gel column chromatography (ethyl acetate/n-hexane=1/5, v/v). The resulting product was dissolved in ethyl acetate, saturated with hydrochloric acid gas, and then filtered to give 115 mg of the titled compound as a white solid (Yield: 32%).

1H-NMR(400 MHz, CDCl$_3$) δ 7.18 (m, 4H), 7.13 (s, 1H), 6.91 (m, 2H), 6.46 (d, 1H), 6.37 (d, 1H), 5.67 (s, 2H), 4.28 (brs, 6H), 3.61 (brs, 6H), 2.80 (brs, 2H), 2.25 (s, 3H), 2.23 (s, 3H)

EXAMPLE 845

1-(3-chlorobenzyl)-7-(3,4-dihydro-1H-isoquinolin-2-yl)-2,3-dimethyl-1H-pyrrolo[2,3-c]pyridin-5-amine hydrochloride A solution of 1-(3-chlorobenzyl)-7-(3,4-dihydro-1H-isoquinolin-2-yl)-1-(2-methoxyethyl)-2,3-dimethyl-1H-pyrrolo[2,3-c]pyridin-5-carboxylic acid (100 mg, 0.22 mmol) prepared in Example 737, diphenyl phosphoryl azide (71 μl, 0.33 mmol), and triethylamine (61 μl, 0.44 mmol) in a mixture of tert-butylalcohol (2 ml) and toluene (2 ml) was stirred for 1.5 hours at 60° C. under heating. The reaction mixture was stirred for 3 hours at 90° C. under heating and then concentrated under reduced pressure. The resulting residue was purified with silica gel column chromatography (ethyl acetate/n-hexane=1/5, v/v). The resulting product was dissolved in ethyl acetate, saturated with hydrochloric acid gas, and then filtered to give 5.7 mg of the titled compound as a white solid.

1H-NMR(400 MHz, CDCl$_3$) δ 7.35 (m, 1H), 7.26-719 (m, 1H), 7.12 (m, 5H), 6.87 (d, 1H), 6.73 (brs, 1H), 6.53 (d, 1H), 6.40 (s, 1H), 5.53 (brs, 2H), 4.20 (brs, 2H), 3.34 (brs, 2H), 2.82 (brs, 2H), 2.17 (s, 3H), 2.15 (s, 3H)

EXAMPLES 846 TO 849

The titled compounds of Examples 846 to 849 were prepared, in accordance with the same procedures as in Example 845, using the compounds prepared in Examples 732, 734, 736, and 738.

EXAMPLE 846

1-allyl-7-(3,4-dihydro-1H-isoquinolin-2-yl)-2,3-dimethyl-1H-pyrrolo[2,3-c]pyridin-5-amine hydrochloride 1H-NMR(400 MHz, CDCl$_3$) δ 7.20 (m, 3H), 7.02 (d, 1H), 6.38 (s, 1H), 5.81 (m, 1H), 5.07 (d, 1H), 4.90 (s, 1H), 4.87 (s, 2H), 4.54 (d, 1H), 4.54-4.50 (brs, 2H), 3.80 (brs, 2H), 3.07 (brs, 2H), 2.37 (d, 1H), 2.30 (s, 3H), 2.13 (s, 3H); (Yield: 19%)

EXAMPLE 847

7-(3,4-dihydro-1H-isoquinolin-2-yl)-1-(3-fluorobenzyl)-2,3-dimethyl-1H-pyrrolo[2,3-c]pyridin-5-amine hydrochloride 1H-NMR(400 MHz, CDCl$_3$) δ 7.19-7.15 (m, 5H), 6.92-6.88 (m, 2H), 6.76 (m, 1H), 6.43 (s, 1H), 6.34 (d, 1H), 6.24 (d, 1H), 5.26 (s, 2H), 4.47-3.51 (brs, 4H), 2.80 (brs, 2H), 2.26 (s, 3H), 2.13 (s, 3H); (Yield: 19%)

EXAMPLE 848

7-(3,4-dihydro-1H-isoquinolin-2-yl)-1-(3-methoxybenzyl)-2,3-dimethyl-1H-pyrrolo[2,3-c]pyridin-5-amine hydrochloride 1H-NMR(400 MHz, CDCl$_3$) δ 7.37 (m, 1H), 7.17-7.14 (m, 2H), 7.10 (m, 3H), 6.73 (d, 2H), 6.42 (s, 1H), 6.11 (d, 2H), 5.45 (s, 2H), 4.50-4.10 (brs, 2H), 3.73-3.60 (brs, 2H), 3.61 (s, 3H), 2.81 (brs, 2H), 2.26 (s, 3H), 2.16 (s, 3H); (Yield: 18%)

EXAMPLE 849

7-(3,4-dihydro-1H-isoquinolin-2-yl)-1-ethyl-2,3-dimethyl-1H-pyrrolo[2,3-c]pyridin-5-amine hydrochloride 1H-NMR(400 MHz, CDCl$_3$) δ 7.38 (m, 1H), 7.21 (m, 3H), 7.05 (d, 1H), 6.35 (s, 1H), 4.50 (brs, 2H), 4.30 (m, 1H), 4.21 (brs, 2H), 3.88-3.82 (brs, 2H), 3.11 (brs, 2H), 3.35 (s, 3H), 2.10 (s, 3H), 1.09 (t, 3H); (Yield: 18%)

EXAMPLE 850

[1-benzyl-7-(3,4-dihydro-1H-isoquinolin-2-yl)-2,3-dimethyl-1H-pyrrolo[2,3-c]pyridin-5-yl]-methanol hydrochloride Step 1: [1-benzyl-7-(3,4-dihydro-1H-isoquinolin-2-yl)-2,3-dimethyl-1H-pyrrolo[2,3-c]pyridin-5-yl]-methanol Hydroborane tetrahydrofuran complex (1.0M in tetrahydrofuran solution; 1 ml, 1.0 mmol) was added at 0° C. to a solution of 1-benzyl-7-(3,4-dihydro-1H-isoquinolin-2-yl)-2,3-dimethyl-1H-pyrrolo[2,3-c]pyridin-5-carboxylic acid (20 mg, 0.05 mmol) prepared in Example 733 in anhydrous tetrahydrofuran (1 ml). The reaction mixture was stirred overnight at room temperature. Water was added to the reaction mixture, which was then extracted with ethyl acetate. The organic layer was dried on anhydrous magnesium sulfate and then concentrated under reduced pressure. The resulting residue was purified with silica gel column chromatography (ethyl acetate/n-hexane=1/1, v/v) to give 19 mg of the titled compound as a white solid.

Step 2: [1-benzyl-7-(3,4-dihydro-1H-isoquinolin-2-yl)-2,3-dimethyl-1H-pyrrolo[2,3-c]pyridin-5-yl]-methanol hydrochloride A solution of [1-benzyl-7-(3,4-dihydro-1H-isoquinolin-2-yl)-2,3-dimethyl-1H-pyrrolo[2,3-c]pyridin-5-yl]-methanol prepared in Step 2 in ethyl acetate was saturated with hydrochloric acid gas and then filtered to give 10.2 mg of the titled compound as a white solid.
1H-NMR(400 MHz, CDCl$_3$) δ 7.36 (s, 1H), 7.19 (m, 4H), 7.09 (m, 2H), 6.70 (d, 1H), 6.48 (d, 2H), 5.63 (s, 2H), 5.02 (s, 2H), 4.50 (brs, 2H), 3.80 (brs, 2H), 2.80 (brs, 2H), 2.34 (s, 3H), 2.31 (s, 3H)

EXAMPLE 851

7-(3,4-dihydro-1H-isoquinolin-2-yl)-1-(3-fluorobenzyl)-2,3-dimethyl-1H-pyrrolo[2,3-c]pyridin-5-yl]-methanol hydrochloride Step 1: 7-(3,4-dihydro-1H-isoquinolin-2-yl)-1-(3-fluorobenzyl)-2,3-dimethyl-1H-pyrrolo[2,3-c]pyridin-5-yl]-methanol In accordance with the same procedures as in Step 1 of Example 850, except for using 7-(3,4-dihydro-1H-isoquinolin-2-yl)-1-(3-fluorobenzyl)-2,3-dimethyl-1H-pyrrolo[2,3-c]pyridin-5-carboxylic acid prepared in Example 734, the titled compound was obtained as a pale yellow solid. (Yield: 91%)

Step 2: 7-(3,4-dihydro-1H-isoquinolin-2-yl)-1-(3-fluorobenzyl)-2,3-dimethyl-1H-pyrrolo[2,3-c]pyridin-5-yl]-methanol hydrochloride In accordance with the same procedures as in Step 2 of Example 850, except for using 7-(3,4-dihydro-1H-isoquinolin-2-yl)-1-(3-fluorobenzyl)-2,3-dimethyl-1H-pyrrolo[2,3-c]pyridin-5-yl]-methanol prepared in Step 1, the titled compound was obtained as a pale yellow solid. (Yield: 92%)
1H-NMR(400 MHz, CDCl$_3$) δ 7.37 (s, 1H), 7.22-6.95 (m, 4H), 6.93 (m, 1H), 6.73 (m, 1H), 6.25 (d, 1H), 6.16 (d, 1H), 5.62 (s, 2H), 5.03 (s, 2H), 5.00-3.00 (brs, 4H), 3.49 (s, 2H), 2.36 (s, 3H), 2.32 (s, 3H)

EXAMPLE 852

2-[1-(3-chlorobenzyl)-2,3-dimethyl-5-(1H-tetrazol-5-yl)-1H-pyrrolo[2,3-c]pyridin-7-yl]-1,2,3,4-tetrahydroisoquinoline Sodium azide (137 mg, 2.1 mmol) was added at 0° C. to a solution of 1-(3-chlorobenzyl)-7-(3,4-dihydro-1H-isoquinolin-2-yl)-2,3-dimethyl-1H-pyrrolo[2,3-c]pyridin-5-carbonitrile (300 mg, 0.7 mmol) prepared in Example 689 and ammonium chloride (74.9 mg, 1.4 mmol) in anhydrous N,N-dimethylformamide (10 ml). The reaction mixture was refluxed overnight. 6% sodium nitrite solution was added to the reaction mixture, which was then extracted with ethyl acetate. The organic layer was dried on anhydrous magnesium sulfate and then concentrated under reduced pressure. The resulting residue was purified with silica gel column chromatography (ethyl acetate/n-hexane=1/3, v/v) to give 110 mg of the titled compound as a white solid. (Yield: 33%).
1H-NMR(400 MHz, CDCl$_3$) δ 8.32 (s, 1H), 7.19-7.11 (m, 5H), 6.92 (d, 1H), 6.78 (s, 1H), 6.55 (d, 1H), 5.74 (s, 2H), 4.35 (brs, 2H), 4.30 (brs, 2H), 3.50 (brs, 2H), 2.79 (brs, 2H), 2.31 (s, 3H), 2.26 (s, 3H)

EXAMPLE 853

2-[1-(3-chlorobenzyl)-2,3-dimethyl-5-(1-methyl-1H-tetrazol-5-yl)-1H-pyrrolo[2,3-c]pyridin-7-yl]-1,2,3,4-tetrahydroisoquinoline 2-[1-(3-Chlorobenzyl)-2,3-dimethyl-5-(1H-tetrazol-5-yl)-1H-pyrrolo[2,3-c]pyridin-7-yl]-1,2,3,4-tetrahydroisoquinoline (50 mg, 0.11 mmol) prepared in Example 852 and potassium carbonate (22.1 mg, 0.16 mmol) were dripped into anhydrous N,N-dimethylformamide (1 ml). Iodomethane (10 t, 0.16 mmol) was added to the reaction mixture, which was then stirred overnight at room temperature. Water was added to the reaction mixture, which was then extracted with ethyl acetate. The organic layer was dried on anhydrous magnesium sulfate and then concentrated under reduced pressure. The resulting residue was purified with silica gel column chromatography (ethyl acetate/n-hexane=1/3, v/v) to give 18 mg of the titled compound as a white solid (Yield: 34%).
1H-NMR(400 MHz, CDCl$_3$) δ 8.38 (s, 1H), 7.17 (m, 5H), 6.90 (d, 1H), 6.78 (s, 1H), 6.55 (d, 1H), 5.74 (s, 2H), 4.38 (s, 3H), 4.30 (brs, 2H), 3.50 (brs, 2H), 2.79 (brs, 2H), 2.31 (s, 3H), 2.27 (s, 3H)

EXAMPLE 854

2-[1-(3-chlorobenzyl)-2,3-dimethyl-5-(1-ethyl-1H-tetrazol-5-yl)-1H-pyrrolo[2,3-c]pyridin-7-yl]-1,2,3,4-tetrahydroisoquinoline In accordance with the same procedures as in Example 853, except for using 2-[1-(3-chlorobenzyl)-2,3-dimethyl-5-(1H-tetrazol-5-yl)-1H-pyrrolo[2,3-c]pyridin-7-yl]-1,2,3,4-tetrahydroisoquinoline prepared in Example 852 and iodoethane, the titled compound was obtained as a white solid. (Yield: 34%)

1H-NMR(400 MHz, CDCl$_3$) δ 8.40 (s, 1H), 7.14 (m, 5H), 6.88 (d, 1H), 6.78 (s, 1H), 6.56 (d, 1H), 5.74 (brs, 2H), 4.98 (q, 2H), 4.32-4.17 (brs, 2H), 3.49-3.17 (brs, 2H), 2.91-2.79 (brs, 2H), 2.32 (s, 3H), 2.27 (s, 3H), 1.51 (t, 3H)

EXAMPLE 855

1-[7-(3,4-dihydro-1H-isoquinolin-2-yl)-1-(3-fluorobenzyl)-2,3-dimethyl-1H-pyrrolo[2,3-c]pyridin-5-yl]-ethanone hydrochloride Methyl magnesium bromide (3.0M in tetrahydrofuran solution; 244 µl, 0.74 mmol) was added at 0° C. to a solution of 7-(3,4-dihydro-1H-isoquinolin-2-yl)-1-(3-fluorobenzyl)-2,3-dimethyl-1H-pyrrolo[2,3-c]pyridin-5-carbonitrile (100 mg, 0.24 mmol) prepared in Example 695 in anhydrous tetrahydrofuran (2 ml). The reaction mixture was stirred overnight at room temperature. Water was added to the reaction mixture, which was then extracted with ethyl acetate. The organic layer was dried on anhydrous magnesium sulfate and then concentrated under reduced pressure. The resulting residue was purified with silica gel column chromatography (ethyl acetate/n-hexane=1/5, v/v). The resulting product was dissolved in ethyl acetate, saturated with hydrochloric acid gas, and then filtered to give 95 mg of the titled compound as a white solid. (Yield: 86%).

1H-NMR(400 MHz, CDCl$_3$) δ 8.14 (s, 1H), 7.18 (m, 4H), 6.91 (m, 2H), 6.49 (s, 1H), 6.36 (d, 1H), 5.76 (s, 2H), 4.38 (brs, 2H), 3.57 (brs, 2H), 2.86 (s, 2H), 2.79 (s, 3H), 2.33 (s, 3H), 2.27 (s, 3H)

EXAMPLE 856

1-[1-benzyl-7-(3,4-dihydro-1H-isoquinolin-2-yl)-2,3-dimethyl-1H-pyrrolo[2,3-c]pyridin-5-yl]-propan-1-one hydrochloride In accordance with the same procedures as in Example 855, except for using 1-benzyl-7-(3,4-dihydro-1H-isoquinolin-2-yl)-2,3-dimethyl-1H-pyrrolo[2,3-c]pyridin-5-carbonitrile prepared in Example 686 and ethyl magnesium bromide (2.0M in tetrahydrofuran solution), the titled compound was obtained as a white solid. (Yield: 61%)

1H-NMR(400 MHz, CDCl$_3$) δ 8.14 (brs, 1H), 7.20 (m, 5H), 6.87 (brs, 1H), 6.72 (s, 2H), 5.78 (bs 2H), 4.40 (brs, 2H), 3.62 (brs, 2H), 3.31 (brs, 2H), 2.92 (brs, 2H), 2.36 (s, 3H), 2.30 (s, 3H), 1.27 (s, 3H)

EXAMPLE 857

1-[1-(3-chlorobenzyl)-7-(3,4-dihydro-1H-isoquinolin-2-yl)-2,3-dimethyl-1H-pyrrolo[2,3-c]pyridin-5-yl]-propan-1-one hydrochloride In accordance with the same procedures as in Example 855, except for using 1-(3-chlorobenzyl)-7-(3,4-dihydro-1H-isoquinolin-2-yl)-2,3-dimethyl-1H-pyrrolo[2,3-c]pyridin-5-carbonitrile prepared in Example 689 and ethyl magnesium bromide (2.0M in tetrahydrofuran solution), the titled compound was obtained as a white solid. (Yield: 65%)

1H-NMR(400 MHz, CDCl$_3$) δ 8.13 (s, 1H), 7.14 (m, 5H), 6.90 (d, 1H), 6.79 (s, 1H), 6.56 (d, 1H), 5.74 (brs, 2H), 4.10 (brs, 2H), 3.49 (brs, 2H), 3.24 (q, 2H), 2.88 (brs, 2H), 2.29 (s, 3H), 2.22 (s, 3H), 1.22 (t, 3H)

EXAMPLE 858 cyclohexyl-[7-(3,4-dihydro-1H-isoquinolin-2-yl)-1-ethyl-2,3-dimethyl-1H-pyrrolo[2,3-c]pyridin-5-yl]-methanone hydrochloride In accordance with the same procedures as in Example 855, except for using 7-(3,4-dihydro-1H-isoquinolin-2-yl)-1-ethyl-2,3-dimethyl-1H-pyrrolo[2,3-c]pyridin-5-carbonitrile prepared in Example 696 and cyclohexyl magnesium chloride (2.0M in diethyl ether solution), the titled compound was obtained as a white solid. (Yield: 61%)

1H-NMR(400 MHz, CDCl$_3$) δ 7.97 (s, 1H), 7.21 (m, 3H), 7.10 (d, 1H), 4.81 (brs, 2H), 4.40 (q, 2H), 4.20 (brs, 2H), 3.83 (m, 1H), 3.13 (s, 2H), 2.48 (s, 3H), 2.33 (s, 3H), 1.99 (m, 2H), 1.84 (m, 2H), 1.74 (m, 1H), 1.53 (m, 4H), 1.20 (m, 1H), 1.17 (t, 3H)

EXAMPLE 859 cyclohexyl-[7-(3,4-dihydro-1H-isoquinolin-2-yl)-1-(3-methoxybenzyl)-2,3-dimethyl-1H-pyrrolo[2,3-c]pyridin-5-yl]-methanone hydrochloride In accordance with the same procedures as in Example 855, except for using 7-(3,4-dihydro-1H-isoquinolin-2-yl)-1-(3-methoxybenzyl)-2,3-dimethyl-1H-pyrrolo[2,3-c]pyridin-5-carbonitrile prepared in Example 691 and cyclohexyl magnesium chloride (2.0M in diethyl ether solution), the titled compound was obtained as a white solid. (Yield: 61%)

1H-NMR(400 MHz, CDCl$_3$) δ 8.08 (s, 1H), 7.16 (m, 4H), 6.81 (d, 1H), 6.76 (d, 1H), 6.24 (s, 2H), 5.73 (s, 2H), 4.50-4.20 (brs, 2H), 3.85 (m, 1H), 3.84-3.64 (brs, 2H), 3.70 (s, 3H), 2.87 (s, 2H), 2.31 (s, 3H), 2.11 (s, 3H), 1.99 (m, 2H), 1.84 (m, 2H), 1.64 (m, 1H), 1.46 (m, 4H), 1.28 (m, 1H)

EXAMPLE 860

1-[7-(3,4-dihydro-1H-isoquinolin-2-yl)-1-(3-fluorobenzyl)-2,3-dimethyl-1H-pyrrolo[2,3-c]pyridin-5-yl]-ethanol hydrochloride Sodium borohydride (5.3 mg, 0.14 mmol) was added at 0° C. to a solution of 1-[7-(3,4-dihydro-1H-isoquinolin-2-yl)-1-(3-fluorobenzyl)-2,3-dimethyl-1H-pyrrolo[2,3-c]pyridin-5-yl]-ethanone hydrochloride (20 mg, 0.05 mmol) prepared in Example 855 in anhydrous methanol (2 ml). The reaction mixture was stirred for 10 minutes at the same temperature. Water was added to the reaction mixture, which was then extracted with ethyl acetate. The organic layer was dried on anhydrous magnesium sulfate and then concentrated under reduced pressure. The resulting residue was purified with silica gel column chromatography (ethyl acetate/n-hexane=1/3, v/v). The resulting residue was dissolved in ethyl acetate, saturated with hydrochloric acid gas, and then filtered to give 7.1 mg of the titled compound as a white solid.

1H-NMR(400 MHz, CDCl$_3$) δ 7.40 (s, 1H), 7.19-7.10 (m, 4H), 6.93 (t, 1H), 6.72 (d, 1H), 6.24 (d, 1H), 6.17 (d, 1H), 5.62 (s, 2H), 5.49 (m, 1H), 4.13-4.06 (brs, 2H), 3.56-3.49 (brs, 2H), 2.81 (s, 2H), 2.36 (s, 3H), 2.27 (s, 3H), 1.82 (s, 3H)

EXAMPLE 861

1-[1-benzyl-7-(3,4-dihydro-1H-isoquinolin-2-yl)-2,3-dimethyl-1H-pyrrolo[2,3-c]pyridin-5-yl]-propan-1-ol hydrochloride In accordance with the same procedures as in Example 860, except for using 1-[1-benzyl-7-(3,4-dihydro-1H-isoquinolin-2-yl)-2,3-dimethyl-1H-pyrrolo[2,3-c]pyridin-5-yl]-propan-1-one obtained by treating the compound prepared in Example 856 with a saturated sodium bicarbonate solution, the titled compound was obtained as a white solid. (Yield: 95%)

1H-NMR (400 MHz, CDCl$_3$) δ 7.37 (s, 1H), 7.20 (m, 4H), 7.07 (m, 2H), 6.67 (d, 1H), 6.48 (d, 2H), 5.64 (s, 2H), 5.09 (brs, 1H), 4.5-3.0 (brs, 4H), 2.77 (brs, 2H), 2.34 (s, 3H), 2.32 (s, 3H), 2.15 (brs, 2H), 1.40 (t, 3H)

EXAMPLE 862

7-(3,4-dihydro-1H-isoquinolin-2-yl)-2,3-dimethyl-1H-pyrrolo[2,3-c]pyridin-5-carbaldehyde Diisobutyl aluminum hydride (1.0M in toluene solution; 1.98 ml, 1.98 mmol) was added at −78° C. to a solution of 7-(3,4-dihydro-1H-isoquinolin-2-yl)-2,3-dimethyl-1H-pyrrolo[2,3-c]pyridin-5-carbonitrile (300 mg, 099 mmol) prepared in Example 682 in anhydrous tetrahydrofuran (2 ml). The reaction mixture was stirred for 5 hours and then diluted with diethyl ether. Water (2 ml) and 15% sodium hydroxide solution (2 ml) were added to the reaction mixture, which was then stirred for 30 minutes. The organic layer was dried on anhydrous magnesium sulfate and then concentrated under reduced pressure. The resulting residue was purified with silica gel column chromatography (ethyl acetate/n-hexane=1/3, v/v) to give 50.6 mg of the titled compound as a white solid. (Yield: 16%).

1H-NMR(400 MHz, CDCl$_3$) δ 10.04 (s, 1H), 8.20 (s, 1H), 7.86 (s, 1H), 7.20 (s, 4H), 4.70 (s, 2H), 3.81 (t, 2H), 3.13 (t, 2H), 2.43 (s, 3H), 2.24 (s, 3H)

EXAMPLE 863

1-(3-chlorobenzyl)-7-(3,4-dihydro-1H-isoquinolin-2-yl)-2,3-dimethyl-1H-pyrrolo[2,3-c]pyridin-5-carbaldehyde In accordance with the same procedures as in Example 862, except for using 1-(3-chlorobenzyl-7-(3,4-dihydro-1H-isoquinolin-2-yl)-2,3-dimethyl-1H-pyrrolo[2,3-c]pyridin-5-carbonitrile prepared in Example 689, the titled compound was obtained as a pale yellow solid. (Yield: 15%)

1H-NMR(400 MHz, CDCl$_3$) δ 10.18 (s, 1H), 8.06 (s, 1H), 7.18-7.10 (m, 5H), 6.88 (d, 1H), 6.76 (s, 1H), 6.56 (d, 1H), 5.77 (brs, 2H), 4.42-4.11 (brs, 2H), 3.55-3.37 (brs, 2H), 2.90 (brs, 2H), 2.30 (s, 3H), 2.24 (s, 3H)

EXAMPLE 864

7-(3,4-dihydro-1H-isoquinolin-2-yl)-1-(3-fluorobenzyl)-2,3-dimethyl-1H-pyrrolo[2,3-c]pyridin-5-carbaldehyde hydrochloride Step 1: 7-(3,4-dihydro-1H-isoquinolin-2-yl)-1-(3-fluorobenzyl)-2,3-dimethyl-1H-pyrrolo[2,3-c]pyridin-5-carbaldehyde In accordance with the same procedures as in Example 862, except for using 7-(3,4-dihydro-1H-isoquinolin-2-yl)-1-(3-fluorobenzyl)-2,3-dimethyl-1H-pyrrolo[2,3-c]pyridin-5-carbonitrile prepared in Example 695, the titled compound was obtained as a pale yellow solid. (Yield: 15%)

Step 2: 7-(3,4-dihydro-1H-isoquinolin-2-yl)-1-(3-fluorobenzyl)-2,3-dimethyl-1H-pyrrolo[2,3-c]pyridin-5-carbaldehyde hydrochloride A solution of 7-(3,4-dihydro-1H-isoquinolin-2-yl)-1-(3-fluorobenzyl)-2,3-dimethyl-1H-pyrrolo[2,3-c]pyridin-5-carbaldehyde prepared in Step 1 in ethyl acetate was saturated with hydrochloric acid gas and then filtered to give 20 mg of the titled compound as a white solid.

1H-NMR(400 MHz, CDCl$_3$) δ 11.18 (s, 1H), 8.25 (s, 1H), 7.22-7.17 (m, 2H), 7.13-7.07 (m, 2H), 6.95 (t, 1H), 6.67 (d, 1H), 6.24 (d, 1H), 6.18 (d, 1H), 5.70 (s, 2H), 5.00-3.00 (brs, 4H), 2.83 (brs, 2H), 2.41 (s, 3H), 2.38 (s, 3H)

EXAMPLE 865

N-[7-(3,4-dihydro-1H-isoquinolin-2-yl)-1-(3-fluorobenzyl)-2,3-dimethyl-1H-pyrrolo[2,3-c]pyridin-5-ylmethyl]-3-chlorobenzylamine hydrochloride Step 1: N-[7-(3,4-dihydro-1H-isoquinolin-2-yl)-1-(3-fluorobenzyl)-2,3-dimethyl-1H-pyrrolo[2,3-c]pyridin-5-ylmethyl]-3-chlorobenzylamine A solution of 7-(3,4-dihydro-1H-isoquinolin-2-yl)-1-(3-fluorobenzyl)-2,3-dimethyl-1H-pyrrolo[2,3-c]pyridin-5-carbaldehyde (30 mg, 0.07 mmol) prepared in Step 1 of Example 864 and 3-chlorobenzylamine (9.75 µl, 0.08 mmol) in methanol (3 ml) was refluxed for 3 hours. Titanium(IV) isopropoxide (40 µl) and sodium borohydride (5.49 mg, 0.15 mmol) were added at room temperature to the reaction mixture, which was then stirred overnight. Water was added to the reaction mixture, which was extracted with ethyl acetate. The organic layer was dried on anhydrous magnesium sulfate and then concentrated under reduced pressure. The resulting residue was purified with silica gel column chromatography (ethyl acetate/n-hexane=1/5, v/v) to give 21.7 mg of the titled compound as a white solid.

Step 2: N-[7-(3,4-dihydro-1H-isoquinolin-2-yl)-1-(3-fluorobenzyl)-2,3-dimethyl-1H-pyrrolo[2,3-c]pyridin-5-ylmethyl]-3-chlorobenzylamine hydrochloride A solution of (3-chlorobenzyl)-[7-(3,4-dihydro-1H-isoquinolin-2-yl)-1-(3-fluorobenzyl)-2,3-dimethyl-1H-pyrrolo[2,3-c]pyridin-5-ylmethyl]-amine prepared in Step 1 in ethyl acetate was saturated with hydrochloric acid gas and then filtered to give 15.2 mg of the titled compound as a white solid.

1H-NMR(400 MHz, CDCl$_3$) δ 7.84 (m, 2H), 7.36 (m, 2H), 7.22-7.19 (m, 4H), 7.13-7.07 (m, 1H), 6.96 (m, 1H), 6.28-

6.20 (m, 2H), 5.60 (s, 2H), 4.61 (s, 2H), 4.37 (s, 2H), 4.00-3.00 (brs, 4H), 2.85 (s, 2H), 2.34 (s, 6H)

EXAMPLES 866 TO 873

The titled compounds of Examples 866 to 873 were prepared, in accordance with the same procedures as in Example 865, using 7-(3,4-dihydro-1H-isoquinolin-2-yl)-1-(3-fluorobenzyl)-2,3-dimethyl-1H-pyrrolo[2,3-c]pyridin-5-carbaldehyde prepared in Step 1 of Example 864; and, 4-fluoroaniline, 4-methylbenzylamine, ethylamine, tert-butylamine, cyclobutylamine, cyclopropylamine, morpholine, or 1-methylpiperazine.

EXAMPLE 866

N-[7-(3,4-dihydro-1H-isoquinolin-2-yl)-1-(3-fluorobenzyl)-2,3-dimethyl-1H-pyrrolo[2,3-c]pyridin-5-ylmethyl]-4-fluorophenylamine hydrochloride 1H-NMR(400 MHz, CDCl$_3$) δ 8.12 (m, 2H), 7.91 (m, 1H), 7.21-7.09 (m, 6H), 6.96 (m, 1H), 6.63 (m, 1H), 6.30 (d, 1H), 6.22 (d, 1H), 5.62 (s, 2H), 4.80 (s, 2H), 4.12-3.49 (brs, 4H), 2.87 (s, 2H), 2.35 (s, 6H); (Yield: 72%)

EXAMPLE 867

N-[7-(3,4-dihydro-1H-isoquinolin-2-yl)-1-(3-fluorobenzyl)-2,3-dimethyl-1H-pyrrolo[2,3-c]pyridin-5-ylmethyl]-4-methylbenzylamine hydrochloride 1H-NMR(400 MHz, CDCl$_3$) δ 7.73 (m, 2H), 7.25-7.08 (m, 7H), 6.94 (m, 1H), 6.63 (m, 1H), 6.22 (m, 2H), 5.59 (s, 2H), 4.53 (s, 2H), 4.36 (s, 2H), 4.00-3.00 (brs, 4H), 2.83 (s, 2H), 2.34 (s, 9H); (Yield: 69%)

EXAMPLE 868

N-[7-(3,4-dihydro-1H-isoquinolin-2-yl)-1-(3-fluorobenzyl)-2,3-dimethyl-1H-pyrrolo[2,3-c]pyridin-5-ylmethyl]-ethylamine hydrochloride 1H-NMR(400 MHz, CDCl$_3$) δ 7.54 (s, 1H), 7.28 (m, 1H), 7.17 (m, 3H), 6.99 (m, 2H), 6.49 (m, 2H), 5.71 (s, 2H), 4.41 (brs, 4H), 3.46 (m, 2H), 3.04 (brs, 2H), 2.85 (brs, 2H), 2.51 (brs, 2H), 2.26 (d, 6H), 1.26 (t, 3H); (Yield: 76%)

EXAMPLE 869

N-[7-(3,4-dihydro-1H-isoquinolin-2-yl)-1-(3-fluorobenzyl)-2,3-dimethyl-1H-pyrrolo[2,3-c]pyridin-5-ylmethyl]-tert-butylamine hydrochloride 1H-NMR(400 MHz, CDCl$_3$) δ 7.90 (brs, 1H), 7.21-7.11 (m, 4H), 6.96 (m, 1H), 6.59 (m, 1H), 6.32-6.23 (m, 2H), 5.62 (s, 2H), 4.47 (brs, 2H), 4.00-3.00 (brs, 4H), 2.85 (s, 2H), 2.33 (s, 6H), 1.68 (s, 9H); (Yield: 62%)

EXAMPLE 870

N-[7-(3,4-dihydro-1H-isoquinolin-2-yl)-1-(3-fluorobenzyl)-2,3-dimethyl-1H-pyrrolo[2,3-c]pyridin-5-ylmethyl]-cyclobutylamine hydrochloride 1H-NMR(400 MHz, DMSO-d$_6$) 7.56 (s, 1H), 7.28-7.23 (m, 1H), 7.17 (m, 3H), 6.99 (m, 2H), 6.50 (m, 2H), 5.70 (s, 2H), 4.32 (brs, 2H), 4.20 (s, 2H), 3.76 (m, 3H), 2.86 (s, 2H), 2.26 (s, 3H), 2.23 (s, 3H), 2.18 (m, 4H), 1.75 (m, 2H); (Yield: 61%)

EXAMPLE 871

N-[7-(3,4-dihydro-1H-isoquinolin-2-yl)-1-(3-fluorobenzyl)-2,3-dimethyl-1H-pyrrolo[2,3-c]pyridin-5-ylmethyl]-cyclopropylamine hydrochloride 1H-NMR(400 MHz, DMSO-d$_6$) δ 7.46 (s, 1H), 7.24 (m, 1H), 7.14 (m, 3H), 7.00 (m, 2H), 6.47 (m, 2H), 5.71 (s, 2H), 4.34 (s, 4H), 3.41 (m, 3H), 2.78 (m, 2H), 2.24 (s, 3H), 2.21 (s, 3H), 0.83 (m, 2H), 0.73 (m, 2H); (Yield: 72%)

EXAMPLE 872

2-[1-(3-fluorobenzyl)-2,3-dimethyl-5-(morpholin-4-ylmethyl)-1H-pyrrolo[2,3-c]pyridin-7-yl]-1,2,3,4-tetrahydroisoquinoline hydrochloride 1H-NMR(400 MHz, CDCl$_3$) δ 8.87 (brs, 1H), 7.23-7.07 (m, 4H), 6.94 (m, 1H), 6.65 (m, 1H), 6.26 (d, 1H), 6.21 (d, 1H), 5.66 (s, 2H), 5.20 (brs, 2H), 4.23 (brs, 2H), 4.13 (brs, 2H), 3.78 (brs, 2H), 3.20 (brs, 2H), 2.84 (s, 2H), 2.44 (m, 6H); (Yield: 69%)

EXAMPLE 873

2-[1-(3-fluorobenzyl)-2,3-dimethyl-5-(4-methylpiperazin-1-ylmethyl)-1H-pyrrolo[2,3-c]pyridin-7-yl]-1,2,3,4-tetrahydroisoquinoline hydrochloride 1H-NMR(400 MHz, DMSO-d$_6$/D$_2$O) δ 7.63 (s, 1H), 7.29-7.16 (m, 4H), 7.04 (m, 1H), 6.92 (m, 1H), 6.55-6.48 (m, 2H), 5.70 (s, 2H), 4.40 (brs, 2H), 4.31 (s, 2H), 3.50 (m, 2H), 3.34-3.07 (brs, 8H), 2.83 (s, 5H), 2.00 (s, 3H), 1.96 (s, 3H); (Yield: 59%)

EXAMPLE 874

2-[2,3-dimethyl-5-(4-methylpiperazin-1-ylmethyl)-1H-pyrrolo[2,3-c]pyridin-7-yl]-1,2,3,4-tetrahydroisoquinoline hydrochloride Step 1: 2-[2,3-dimethyl-5-(4-methylpiperazin-1-ylmethyl)-1H-pyrrolo[2,3-c]pyridin-7-yl]-1,2,3,4-tetrahydroisoquinoline In accordance with the same procedures as in Step 1 of Example 865, except for using 7-(3,4-dihydro-1H-isoquinolin-2-yl)-2,3-dimethyl-1H-pyrrolo[2,3-c]pyridin-5-carbaldehyde prepared in Example 862, the titled compound was obtained as a white solid. (Yield: 61%)

Step 2: 2-[2,3-dimethyl-5-(4-methylpiperazin-1-ylmethyl)-1H-pyrrolo[2,3-c]pyridin-7-yl]-1,2,3,4-tetrahydroisoquinoline hydrochloride A solution of 2-[2,3-dimethyl-5-(4-methylpiperazin-1-ylmethyl)-1H-pyrrolo[2,3-c]pyridin-7-yl]-1,2,3,4-tetrahydroisoquinoline prepared in Step 1 in ethyl acetate was saturated with hydrochloric acid gas and filtered. The resulting solid was dried under reduced pressure to give 3,4 mg of the titled compound as a white solid.

1H-NMR(400 MHz, MeOH-d$_4$) δ 7.35 (m, 5H), 5.13 (s, 2H), 4.32 (brs, 2H), 4.13 (t, 2H), 3.46-3.18 (m, 8H), 3.20 (t, 2H), 2.97 (s, 3H), 2.56 (s, 3H), 2.25 (s, 3H)

EXAMPLE 875

2-[1-(3-chlorobenzyl)-2,3-dimethyl-5-(4-methylpiperazin-1-ylmethyl)-1H-pyrrolo[2,3-c]pyridin-7-yl]-1,2,3,4-tetrahydroisoquinoline hydrochloride Potassium tert-butoxide (15 mg, 0.12 mmol) was added to a solution of 2-[2,3-dimethyl-5-(4-methylpiperazin-1-ylmethyl)-1H-pyrrolo[2,3-c]pyridin-7-yl]-1,2,3,4-tetrahydroisoquinoline (30 mg, 0.074 mmol) prepared in Step 1 of Example 874 and 18-crown-6 (3.1 mg, 0.012 mmol) in anhydrous tetrahydrofuran (2 ml). The reaction mixture was stirred for 1 hour at room temperature and then 3-chlorobenzyl chloride (15.2 μl, 0.12 mmol) was added thereto. The reaction mixture was stirred overnight at room temperature and then concentrated under reduced pressure. The resulting residue was purified with silica gel column chromatography (ethyl acetate/n-hexane=1/5, v/v). The resulting product was dissolved in ethyl acetate, saturated with hydrochloric acid gas, and then filtered to give 21.0 mg of the titled compound as a white solid.

1H-NMR(400 MHz, MeOH-$d_4$) δ 7.83 (s, 1H), 7.25-7.14 (m, 5H), 6.82 (d, 1H), 6.61 (s, 1H), 6.50 (d, 1H) 5.70 (s, 2H), 4.45 (s, 2H), 4.22 (s, 2H), 3.73 (t, 2H), 3.63 (brs, 2H), 3.30 (brs, 4H), 2.98 (brs, 2H), 2.94 (s, 3H), 2.38 (t, 2H), 2.42 (s, 3H), 2.38 (s, 3H)

EXAMPLES 876 TO 883

The titled compounds of Examples 876 to 883 were prepared, in accordance with the same procedures as in Example 875, using 2-[2,3-dimethyl-5-(4-methylpiperazin-1-ylmethyl)-1H-pyrrolo[2,3-c]pyridin-7-yl]-1,2,3,4-tetrahydroisoquinoline prepared in Step 1 of Example 874; and, 3-methoxybenzyl bromide, 4-fluorobenzyl chloride, 3-methylbenzyl bromide, allyl iodide, (bromomethyl)cyclopropane, iodoethane, 1-bromopropane, or benzyl bromide.

EXAMPLE 876

2-[1-(3-methoxybenzyl)-2,3-dimethyl-5-(4-methylpiperazin-1-ylmethyl)-1H-pyrrolo[2,3-c]pyridin-7-yl]-1,2,3,4-tetrahydroisoquinoline hydrochloride 1H-NMR(400 MHz, MeOH-$d_4$) δ 7.87 (s, 1H), 7.23-7.11 (m, 4H), 6.78 (t, 2H), 6.18 (s, 1H), 6.11 (d, 1H), 5.69 (s, 2H), 4.88 (s, 2H), 4.37 (s, 2H), 3.75 (t, 2H), 3.61 (brs, 4H), 3.43 (brs, 4H), 2.96 (s, 3H), 2.91 (tm, 2H), 2.41 (s, 3H), 2.38 (s, 3H); (Yield: 78%)

EXAMPLE 877

2-[1-(4-fluorobenzyl)-2,3-dimethyl-5-(4-methylpiperazin-1-ylmethyl)-1H-pyrrolo[2,3-c]pyridin-7-yl]-1,2,3,4-tetrahydroisoquinoline hydrochloride 1H-NMR(400 MHz, MeOH-$d_4$) δ 7.84 (s, 1H), 7.24-7.16 (m, 3H), 6.96-6.86 (m, 3H), 6.68-6.64 (t, 2H), 5.69 (s, 2H), 4.48 (s, 2H), 4.29 (s, 2H), 3.75 (t, 2H), 3.34 (m, 6H), 3.13 (m, 2H), 2.95 (s, 3H), 2.88 (t, 2H), 2.41 (s, 3H), 2.37 (s, 3H); (Yield: 74%)

EXAMPLE 878

2-[2,3-dimethyl-1-(3-methylbenzyl)-5-(4-methylpiperazin-1-ylmethyl)-1H-pyrrolo[2,3-c]pyridin-7-yl]-1,2,3,4-tetrahydroisoquinoline hydrochloride 1H-NMR(400 MHz, MeOH-$d_4$) δ 7.72 (s, 1H), 7.25-7.16 (m, 3H), 7.05 (m, 2H), 6.79 (d, 1H), 6.48 (s, 1H), 6.29 (d, 1H), 5.68 (s, 2H), 4.40 (s, 2H), 3.94 (s, 2H), 3.66 (t, 2H), 3.34 (m, 2H), 3.09 (m, 4H), 2.94 (s, 3H), 2.91 (m, 2H), 2.62 (m, 2H), 2.41 (s, 3H), 2.37 (s, 3H), 2.16 (s, 3H); (Yield: 79%)

EXAMPLE 879

2-[1-allyl-2,3-dimethyl-5-(4-methylpiperazin-1-ylmethyl)-1H-pyrrolo[2,3-c]pyridin-7-yl]-1,2,3,4-tetrahydroisoquinoline hydrochloride 1H-NMR(400 MHz, MeOH-$d_4$) δ 7.67 (s, 1H), 7.26 (m, 3H), 7.17 (m, 1H), 5.88 (m, 1H), 5.15 (m, 3H), 4.61 (s, 2H), 4.57 (d, 1H), 3.95 (s, 2H), 3.78 (t, 2H), 3.48 (m, 2H), 3.10 (m, 6H), 3.09 (s, 3H), 2.63 (m, 2H), 2.48 (s, 3H), 2.37 (s, 3H); (Yield: 74%)

EXAMPLE 880

2-[1-cyclopropylmethyl-2,3-dimethyl-5-(4-methylpiperazin-1-ylmethyl)-1H-pyrrolo[2,3-c]pyridin-7-yl]-1,2,3,4-tetrahydroisoquinoline hydrochloride 1H-NMR(400 MHz, MeOH-$d_4$) δ 7.66 (s, 1H), 7.30-7.22 (m, 4H), 4.62 (s, 2H), 4.28 (d, 2H), 4.08 (brs, 2H), 3.87 (brs, 2H), 3.51 (brs, 2H), 3.12 (brs, 4H), 2.92 (s, 3H), 2.58 (brs, 2H), 2.58 (s, 3H), 2.33 (s, 3H), 1.23 (m, 1H), 0.34 (m, 2H), 0.11 (m, 2H); (Yield: 75%)

EXAMPLE 881

2-[1-ethyl-2,3-dimethyl-5-(4-methylpiperazin-1-ylmethyl)-1H-pyrrolo[2,3-c]pyridin-7-yl]-1,2,3,4-tetrahydroisoquinoline hydrochloride 1H-NMR(400 MHz, MeOH-$d_4$) δ 7.65 (s, 1H), 7.29-7.22 (m, 4H), 4.65 (s, 2H), 4.45 (q, 2H), 3.98 (s, 2H), 3.85 (t, 2H), 3.49 (brs, 2H), 3.13 (brs, 6H), 2.92 (s, 3H), 2.65 (brs, 2H), 2.54 (s, 3H), 2.32 (s, 3H), 1.18 (t, 3H); (Yield: 76%)

EXAMPLE 882

2-[2,3-dimethyl-5-(4-methylpiperazin-1-ylmethyl)-1-propyl-1H-pyrrolo[2,3-c]pyridin-7-yl]-1,2,3,4-tetrahydroisoquinoline hydrochloride 1H-NMR(400 MHz, MeOH-$d_4$) δ 7.67 (s, 1H), 7.28-7.18 (m, 4H), 4.63 (s, 2H), 4.27 (t, 2H), 3.88 (brs, 2H), 3.85 (t, 2H), 2.51 (brs, 2H), 3.15 (brs, 6H), 2.93 (s, 3H), 2.71 (brs, 2H), 2.53 (s, 3H), 2.35 (s, 3H), 1.56 (q, 2H), 0.58 (t, 3H); (Yield: 74%)

EXAMPLE 883

2-[1-benzyl-2,3-dimethyl-5-(4-methylpiperazin-1-ylmethyl)-1H-pyrrolo[2,3-c]pyridin-7-yl]-1,2,3,4-tetrahydroisoquinoline hydrochloride 1H-NMR(400 MHz, MeOH-$d_4$) δ 7.77 (s, 1H), 7.26-7.13 (m, 6H), 6.83 (d, 1H), 6.62 (m, 2H), 5.72 (s, 2H), 4.47 (s, 2H), 4.08 (s, 2H), 3.72 (t, 2H), 3.54 (brs, 2H), 3.21 (brs, 4H), 3.01 (s, 3H), 2.87 (t, 2H), 2.84 (brs, 2H), 2.40 (s, 3H), 2.33 (s, 3H); (Yield: 81%)

EXAMPLE 884

[7-(3,4-dihydro-1H-isoquinolin-2-yl)-1-(3-fluorobenzyl)-2,3-dimethyl-1H-pyrrolo[2,3-c]pyridin-5-yl]-acetonitrile hydrochloride

Step 1: 7-(3,4-dihydro-1H-isoquinolin-2-yl)-1-(3-fluorobenzyl)-2,3-dimethyl-1H-pyrrolo[2,3-c]pyridin-5-ylmethanesulfonic acid methyl ester Methanesulfonyl chloride (29.5 μl, 0.3 mmol) was added at 0° C. to a solution of 7-(3,4-dihydro-1H-isoquinolin-2-yl)-1-(3-fluorobenzyl)-2,3-dimethyl-1H-pyrrolo[2,3-c]pyridin-5-yl]-methanol (50 mg, 0.12 mmol) prepared in Step 1 of Example 851 and triethylamine (46 μl, 0.33 mmol) in anhydrous dichloromethane (10 ml). The reaction mixture was stirred overnight at room temperature. Water was added to the reaction mixture, which was then extracted with anhydrous dichloromethane (10 ml). The organic layer was dried on anhydrous magnesium sulfate and then concentrated under reduced pressure. The resulting residue was purified with silica gel column chromatography (ethyl acetate/n-hexane=1/5, v/v) to give 46 mg of the titled compound as pale yellow oil.

Step 2: [7-(3,4-dihydro-1H-isoquinolin-2-yl)-1-(3-fluorobenzyl)-2,3-dimethyl-1H-pyrrolo[2,3-c]pyridin-5-yl]-acetonitrile hydrochloride Sodium cyanide (6.9 mg, 0.14 mmol) was added to a solution of 7-(3,4-dihydro-1H-isoquinolin-2-yl)-1-(3-fluorobenzyl)-2,3-dimethyl-1H-pyrrolo[2,3-c]pyridin-5-ylmethanesulfonic acid methyl ester prepared in Step 1 in N,N-dimethylformamide. The reaction mixture was stirred overnight at room temperature and then concentrated under reduced pressure. The resulting residue was purified with silica gel column chromatography (ethyl acetate/n-hexane=1/3, v/v). The resulting product was dissolved in ethyl acetate, saturated with hydrochloric acid gas, and then filtered to give 16.9 mg of the titled compound as a white solid.

1H-NMR(400 MHz, DMSO-$d_6$) δ 7.43 (s, 1H), 7.26 (m, 1H), 7.14 (m, 3H), 7.00 (m, 2H), 6.53 (t, 2H), 5.72 (s, 2H), 5.43 (d, 2H), 4.19 (brs, 2H), 3.41 (brs, 2H), 3.00 (brs, 2H), 2.33 (d, 6H)

EXAMPLE 885

2-[1-(3-fluorobenzyl)-5-fluoromethyl-2,3-dimethyl-1H-pyrrolo[2,3-c]pyridin-7-yl]-1,2,3,4-tetrahydroisoquinoline hydrochloride (Diethylamino)sulfo trifluoride was added at −78° C. to a solution of 7-(3,4-dihydro-1H-isoquinolin-2-yl)-1-(3-fluorobenzyl)-2,3-dimethyl-1H-pyrrolo[2,3-c]pyridin-5-yl]-methanol (50 mg, 0.12 mmol) prepared in Step 1 of Example 851 in anhydrous dichloromethane (2 ml). The reaction mixture was stirred for 2 hours at room temperature. Water was added to the reaction mixture, which was then extracted with dichloromethane. The organic layer was dried on anhydrous magnesium sulfate and then concentrated under reduced pressure. The resulting residue was purified with silica gel column chromatography (ethyl acetate/n-hexane=1/3, v/v). The resulting product was dissolved in ethyl acetate, saturated with hydrochloric acid gas, and then filtered to give 7.7 mg of the titled compound as a white solid.

1H-NMR(400 MHz, DMSO-$d_6$) δ 7.43 (s, 1H), 7.26 (m, 1H), 7.14 (m, 3H), 7.00 (m, 2H), 6.53 (t, 2H), 5.72 (s, 2H), 5.43 (d, 2H), 4.19 (brs, 2H), 3.41 (brs, 2H), 3.00 (brs, 2H), 2.33 (d, 6H)

EXAMPLE 886

[7-(3,4-dihydro-1H-isoquinolin-2-yl)-2,3-dimethyl-1H-pyrrolo[2,3-c]pyridin-5-yl]-methylamine hydrochloride

Step 1: [7-(3,4-dihydro-1H-isoquinolin-2-yl)-2,3-dimethyl-1H-pyrrolo[2,3-c]pyridin-5-yl]-methylamine Diisobutyl aluminum hydride (1.0M in hexane solution; 13.8 ml, 13.8 mmol) was added at −78° C. to a solution of 7-(3,4-dihydro-1H-isoquinolin-2-yl)-2,3-dimethyl-1H-pyrrolo[2,3-c]pyridin-5-carbonitrile (3.8 g, 12.6 mmol) prepared in Example 682 in toluene (100 ml). The reaction mixture was stirred for 1 hour at −78° C. and then for 1 hour at 0° C. Water was added to the reaction mixture, which was then extracted with dichloromethane. The organic layer was dried on anhydrous magnesium sulfate and then concentrated under reduced pressure. The resulting residue was re-crystallized with dichloromethane to give 2.5 g of the titled compound as a pale yellow solid.

Step 2: [7-(3,4-dihydro-1H-isoquinolin-2-yl)-2,3-dimethyl-1H-pyrrolo[2,3-c]pyridin-5-yl]-methylamine hydrochloride A solution of [7-(3,4-dihydro-1H-isoquinolin-2-yl)-2,3-dimethyl-1H-pyrrolo[2,3-c]pyridin-5-yl]-methylamine (25 mg) prepared in Step 1 in ethyl acetate was saturated with hydrochloric acid gas and then filtered to give 23,4 mg of the titled compound as a white solid.

1H-NMR(400 MHz, MeOH-$d_4$) δ 7.17 (m, 4H), 6.97 (s, 1H), 4.66 (s, 2H), 3.84 (s, 2H), 3.76 (t, 2H), 3.10 (t, 2H), 2.40 (s, 3H), 2.19 (s, 3H)

EXAMPLE 887

[1-allyl-7-(3,4-dihydro-1H-isoquinolin-2-yl)-2,3-dimethyl-1H-pyrrolo[2,3-c]pyridin-5-yl]-methylamine hydrochloride

Step 1: [7-(3,4-dihydro-1H-isoquinolin-2-yl)-2,3-dimethyl-1H-pyrrolo[2,3-c]pyridin-5-ylmethyl]-carbamic acid tert-butyl ester Dimethylaminopyridine (12 mg, 0.098 mmol) was added to a solution of [7-(3,4-dihydro-1H-isoquinolin-2-yl)-2,3-dimethyl-1H-pyrrolo[2,3-c]pyridin-5-yl]-methylamine (30 mg, 0.098 mmol) prepared in Step 1 of Example 886 and di-tert-butyl dicarbonate (23.15 mg, 0.108 mmol) in anhydrous tetrahydrofuran (2 ml). The reaction mixture was stirred overnight at room temperature and then concentrated under reduced pressure. The resulting residue was purified with silica gel column chromatography (ethyl acetate/n-hexane=1/3, v/v) to give 49 mg of the titled compound as a white solid.

Step 2: [1-allyl-7-(3,4-dihydro-1H-isoquinolin-2-yl)-2,3-dimethyl-1H-pyrrolo[2,3-c]pyridin-5-yl]-methylamine hydrochloride 18-Crown-6 (3.1 mg, 0.012 mmol) and potassium tert-butoxide (16.2 mg, 0.13 mmol) were added to a solution of [7-(3,4-dihydro-1H-isoquinolin-2-yl)-2,3-dimethyl-1H-pyrrolo[2,3-c]pyridin-5-ylmethyl]-carbamic acid tert-butyl ester (49 mg, 0.12 mmol) prepared in Step 1 in anhydrous tetrahydrofuran (2 ml). The reaction mixture was stirred for 30 minutes at room temperature and then allyl bromide (11.5 µl, 0.13 mmol) was added thereto. The reaction mixture was stirred overnight and then concentrated under reduced pressure. The resulting residue was purified with silica gel column chromatography (ethyl acetate/n-hexane=1/10, v/v). The resulting product was dissolved in ethyl acetate, saturated with hydrochloric acid gas, and then filtered to give 1.0 mg of the titled compound as a white solid.

1H-NMR(400 MHz, MeOH-$d_4$) δ 7.61 (brs, 1H), 7.24 (m, 4H), 7.11 (s, 1H), 5.88 (m, 1H), 5.11 (s, 2H), 5.03 (m, 2H), 4.51 (s, 2H), 4.46 (s, 2H), 3.70 (brs, 2H), 3.14 (brs, 2H), 2.45 (s, 3H), 2.32 (s, 3H)

EXAMPLE 888

[7-(3,4-dihydro-1H-isoquinolin-2-yl)-1-(3-fluorobenzyl)-2,3-dimethyl-1H-pyrrolo[2,3-c]pyridin-5-yl]-methylamine hydrochloride In accordance with the same procedures as in Step 2 of Example 887, except for using [7-(3,4-dihydro-1H-isoquinolin-2-yl)-2,3-dimethyl-1H-pyrrolo[2,3-c]pyridin-5-ylmethyl]-carbamic acid tert-butyl ester prepared in Step 1 of Example 887 and 3-fluorobenzyl chloride, the titled compound was obtained as a white solid. (Yield: 36%)

1H-NMR(400 MHz, DMSO-$d_6$) δ 8.34 (brs, 2H), 7.49 (brs, 1H), 7.13-7.16(m, 1H), 7.10-7.03 (m, 3H), 6.95-6.87 (m, 2H), 6.40-6.38 (d, 2H), 5.67 (s, 2H), 4.18 (brs, 2H), 4.17 (s, 2H), 3.43 (brs, 2H), 2.76 (brs, 2H), 2.18 (s, 3H), 2.14 (s, 3H)

EXAMPLE 889

N-[5-chloro-1-(3-fluorobenzyl)-2,3-dimethyl-1H-pyrrolo[2,3-c]pyridin-7-yl]-(4-fluorobenzyl)-methylamine Step 1: N-(5-chloro-2,3-dimethyl-1H-pyrrolo[2,3-c]pyridin-7-yl)-(4-fluorobenzyl)-methylamine In accordance with the same procedures as in Step 3 of Example 642, except for using (6-chloro-3-nitropyridin-2-yl)-(4-fluorobenzyl)-methylamine prepared in Preparation 8, the titled compound was obtained as yellow oil. (Yield: 37%) The product was used in the subsequent step without further purification.

Step 2: N-[5-chloro-1-(3-fluorobenzyl)-2,3-dimethyl-1H-pyrrolo[2,3-c]pyridin-7-yl]-(4-fluorobenzyl)-methylamine In accordance with the same procedures as in Example 657, except for using N-(5-chloro-2,3-dimethyl-1H-pyrrolo[2,3-c]pyridin-7-yl)-(4-fluorobenzyl)-methylamine prepared in Step 1 and 3-fluorobenzyl chloride, the titled compound was obtained as a pale yellow solid. (Yield: 69%)

1H-NMR(400 MHz, CDCl$_3$) δ 7.20 (m, 2H), 7.01 (m, 2H), 6.95 (m, 1H), 6.82 (m, 2H), 6.42 (d, 1H), 6.30 (d, 1H), 5.74 (s, 2H), 4.25 (brs, 2H), 2.60 (s, 3H), 2.18 (s, 6H)

EXAMPLES 890 TO 892

The titled compounds of Examples 890 to 892 were prepared, in accordance with the same procedures as in Example 657, using N-(5-chloro-2,3-dimethyl-1H-pyrrolo[2,3-c]pyridin-7-yl)-(4-fluorobenzyl)-methylamine prepared in Step 1 of Example 889; and, allyl bromide, (bromomethyl)cyclopropane, or 3-chlorobenzyl chloride.

EXAMPLE 890

N-(1-allyl-5-chloro-2,3-dimethyl-1H-pyrrolo[2,3-c]pyridin-7-yl)-(4-fluorobenzyl)-methylamine 1H-NMR(400 MHz, CDCl$_3$) δ 7.32 (m, 2H), 7.13 (s, 1H), 6.97 (t, 2H), 5.83 (m, 1H), 5.10 (s, 2H), 5.02 (d, 1H), 4.55 (d, 1H), 4.32 (s, 2H), 2.65 (s, 3H), 2.29 (s, 3H), 2.16 (s, 3H); (Yield: 59%)

EXAMPLE 891

N-(5-chloro-1-cyclopropylmethyl-2,3-dimethyl-1H-pyrrolo[2,3-c]pyridin-7-yl)-(4-fluorobenzyl)-methylamine 1H-NMR(400 MHz, CDCl$_3$) δ 7.36 (m, 2H), 7.11 (s, 1H), 7.02 (t, 2H), 4.35 (s 2H), 4.24 (d, 2H), 2.62 (s, 3H), 2.38 (s, 3H), 2.17 (s, 3H), 0.94 (m, 1H), 0.38 (m, 2H), 0.25 (m, 2H); (Yield: 63%)

EXAMPLE 892

N-[5-chloro-1-(3-chlorobenzyl)-2,3-dimethyl-1H-pyrrolo[2,3-c]pyridin-7-yl]-(4-fluorobenzyl)-methylamine 1H-NMR(400 MHz, CDCl$_3$) δ 7.23 (m, 2H), 7.14 (t, 1H), 7.01 (m, 2H), 6.83 (t, 2H), 6.77 (s, 1H), 6.38 (d, 1H), 5.72 (s, 2H), 4.24 (s, 2H), 2.61 (s, 3H), 2.18 (s, 3H), 2.16 (s, 3H); (Yield: 59%)

EXAMPLE 893

7-[(4-fluorobenzyl)-methylamino]-2,3-dimethyl-1H-pyrrolo[2,3-c]pyridin-5-carbonitrile In accordance with the same procedures as in Example 682, except for using N-(5-chloro-2,3-dimethyl-1H-pyrrolo[2,3-c]pyridin-7-yl)-(4-fluorobenzyl)-methylamine prepared in Step 1 of Example 889, the titled compound was obtained as a white solid. (Yield: 20%)

1H-NMR(400 MHz, CDCl$_3$) δ 7.94 (s, 1H), 7.38 (s, 1H), 7.36 (m, 2H), 7.07 (m, 2H), 4.72 (s, 2H), 3.19 (s, 3H), 2.29 (s, 3H), 2.16 (s, 3H)

EXAMPLES 894 TO 900

The titled compounds of Examples 894 to 900 were prepared, in accordance with the same procedures as in Example 657, using 7-[(4-fluorobenzyl)-methylamino]-2,3-dimethyl-1H-pyrrolo[2,3-c]pyridin-5-carbonitrile prepared in Example 893; and, 3-fluorobenzyl chloride, (bromomethyl)cyclopropane, 2-bromoethyl methyl ether, 3-chlorobenzyl chloride, allyl bromide, 1-iodo-2-methylpropane, or iodomethane.

EXAMPLE 894

1-(3-fluorobenzyl)-7-[(4-fluorobenzyl)-methylamino]-2,3-dimethyl-1H-pyrrolo[2,3-c]pyridin-5-carbonitrile 1H-NMR(400 MHz, CDCl$_3$) δ 7.67 (s, 1H), 7.21 (m, 1H), 7.01 (m, 2H), 6.93 (m, 1H), 6.80 (m, 2H), 6.41 (d, 1H), 6.32 (d, 1H), 5.83 (s, 2H), 4.23 (s, 2H), 2.64 (s, 3H), 2.23 (s, 3H), 2.21 (s, 3H); (Yield: 66%)

EXAMPLE 895

1-cyclopropylmethyl-7-[(4-fluorobenzyl)-methylamino]-2,3-dimethyl-1H-pyrrolo[2,3-c]pyridin-5-carbonitrile 1H-NMR(400 MHz, CDCl$_3$) δ 7.61 (s, 1H), 7.31 (m, 2H), 7.02 (t, 2H), 4.33 (m, 2+2H), 2.63 (s, 3H), 2.42 (s, 3H), 2.22 (s, 3H), 0.99 (m, 1H), 0.42 (m, 2H), 0.26 (d, 2H); (Yield: 74%)

EXAMPLE 896

7-[(4-fluorobenzyl)-methylamino]-1-(2-methoxyethyl)-2,3-dimethyl-1H-pyrrolo[2,3-c]pyridin-5-carbonitrile 1H-NMR(400 MHz, CDCl$_3$) δ 7.61 (s, 1H), 7.32 (m, 2H), 7.00 (m, 2H), 4.58 (s, 2H), 4.35 (s, 2H), 3.41 (t, 2H), 3.17 (s, 3H), 2.64 (s, 3H), 2.40 (s, 3H), 2.20 (s, 3H); (Yield: 69%)

EXAMPLE 897

1-(3-chlorobenzyl)-7-[(4-fluorobenzyl)-methylamino]-2,3-dimethyl-1H-pyrrolo[2,3-c]pyridin-5-carbonitrile 1H-NMR(400 MHz, CDCl$_3$) δ 7.67 (s, 1H), 7.16 (m, 2H), 7.02 (m, 2H), 6.83 (m, 3H), 6.39 (d, 1H), 5.80 (s, 2H), 4.26 (s, 2H), 2.61 (s, 3H), 2.23 (s, 3H), 2.18 (s, 3H); (Yield: 71%)

EXAMPLE 898

1-allyl-7-[(4-fluorobenzyl)-methylamino]-2,3-dimethyl-1H-pyrrolo[2,3-c]pyridin-5-carbonitrile 1H-NMR(400 MHz, CDCl$_3$) δ 7.61 (s, 1H), 7.28 (m, 2H), 6.98 (t, 2H), 5.83 (m, 1H), 5.20 (d, 2H), 5.18 (d, 1H), 4.54 (d, 1H), 4.33 (s, 2H), 2.67 (s, 3H), 2.33 (s, 3H), 2.21 (s, 3H); (Yield: 68%)

EXAMPLE 899

7-[(4-fluorobenzyl)-methylamino]-1-isobutyl-2,3-dimethyl-1H-pyrrolo[2,3-c]pyridin-5-carbonitrile 1H-NMR(400 MHz, CDCl$_3$) δ 7.60 (s, 1H), 7.33 (m, 2H), 7.02 (m, 2H), 4.31 (s, 2H), 4.16 (s, 2H), 2.64 (s, 3H), 2.37 (s, 3H), 2.21 (s, 3H), 1.95 (m, 1H), 0.66 (s, 3H), 0.64 (s, 3H); (Yield: 65%)

EXAMPLE 900

7-[(4-fluorobenzyl)-methylamino]-1,2,3-trimethyl-1H-pyrrolo[2,3-c]pyridin-5-carbonitrile 1H-NMR(400 MHz, CDCl$_3$) δ 7.58 (s, 1H), 7.31 (m, 2H), 6.99 (m, 2H), 4.40 (s, 2H), 4.03 (s, 3H), 2.73 (s, 3H), 2.36 (s, 3H), 2.21 (s, 3H); (Yield: 85%)

EXAMPLE 901

1-(3-fluorobenzyl)-7-[(4-fluorobenzyl)-methylamino]-2,3-dimethyl-1H-pyrrolo[2,3-c]pyridin-5-carboxamide In accordance with the same procedures as in Example 745, except for using 1-(3-fluorobenzyl)-7-[(4-fluorobenzyl)-methylamino]-2,3-dimethyl-1H-pyrrolo[2,3-c]pyridin-5-carbonitrile prepared in Example 894, the titled compound was obtained as a white solid. (Yield: 90%)

1H-NMR(400 MHz, CDCl$_3$) δ 8.22 (s, 1H), 7.78 (s, 1H), 7.20 (m, 1H), 6.97 (m, 2H), 6.92 (m, 1H), 6.82 (m, 2H), 6.42 (d, 1H), 6.38 (d, 1H), 5.83 (s, 2H), 5.46 (s, 1H), 4.28 (s, 2H), 2.66 (s, 3H), 2.27 (s, 3H), 2.21 (s, 3H)

EXAMPLE 902

N-(1-benzyl-5-chloro-2,3-dimethyl-1H-pyrrolo[2,3-c]pyridin-7-yl)-4-fluorobenzylamine hydrochloride Step 1: (6-chloro-3-nitropyridin-2-yl)-(4-fluorobenzyl)-carbamic acid tert-butyl ester In accordance with the same procedures as in Step 2 of Preparation 5, except for using (6-chloro-3-nitropyridin-2-yl)-(4-fluorobenzyl)-methylamine prepared in Preparation 8, the titled compound was obtained as yellow oil. (Yield: 83%)

1H-NMR(400 MHz, CDCl$_3$) δ 8.16 (d, 1H), 7.46 (m, 2H), 7.20 (d, 1H), 6.99 (m, 2H), 5.17 (s, 2H), 1.38 (s, 9H)

Step 2: (5-chloro-2,3-dimethyl-1H-pyrrolo[2,3-c]pyridin-7-yl)-(4-fluorobenzyl)-carbamic acid tert-butyl ester In accordance with the same procedures as in Step 3 of Example 642, except for using (6-chloro-3-nitropyridin-2-yl)-(4-fluorobenzyl)-carbamic acid tert-butyl ester prepared in Step 1, the titled compound was obtained as yellow oil. (Yield: 50%)

1H-NMR(400 MHz, CDCl$_3$) δ 8.49 (brs, 1H), 7.27 (m, 2H), 6.92 (m, 2H), 5.15 (s, 2H), 2.35 (s, 3H), 2.13 (s, 3H), 1.45 (s, 9H)

Step 3: (1-benzyl-5-chloro-2,3-dimethyl-1H-pyrrolo[2,3-c]pyridin-7-yl)-(4-fluorobenzyl)-carbamic acid tert-butyl ester In accordance with the same procedures as in Example 657, except for using (5-chloro-2,3-dimethyl-1H-pyrrolo[2,3-c]pyridin-7-yl)-(4-fluorobenzyl)-carbamic acid tert-butyl ester prepared in Step 2 and benzyl bromide, the titled compound was obtained as yellow oil. (Yield: 70%)

Step 4: N-(1-benzyl-5-chloro-2,3-dimethyl-1H-pyrrolo[2,3-c]pyridin-7-yl)-4-fluorobenzylamine hydrochloride A solution of (1-benzyl-5-chloro-2,3-dimethyl-1H-pyrrolo[2,3-c]pyridin-7-yl)-(4-fluorobenzyl)-carbamic acid tert-butyl ester prepared in Step 3 in ethyl acetate was saturated with hydrochloric acid gas and then filtered. The resulting solid was dried under reduced pressure to give 23.5 mg of the titled compound as a white solid.

1H-NMR(400 MHz, CDCl$_3$) δ 7.29 (m, 4H), 6.78 (brs, 2H), 6.71 (m, 2H), 6.52 (s, 1H), 6.07 (brs, 2H), 5.17 (brs, 2H), 2.38 (s, 3H), 2.15 (s, 3H)

EXAMPLE 903

1-benzyl-7-(4-fluorobenzylamino)-2,3-dimethyl-1H-pyrrolo[2,3-c]pyridin-5-carbonitrile hydrochloride

Step 1: 1-benzyl-7-(4-fluorobenzylamino)-2,3-dimethyl-1H-pyrrolo[2,3-c]pyridin-5-carbonitrile In accordance with the same procedures as in Example 682, except for using (1-benzyl-5-chloro-2,3-dimethyl-1H-pyrrolo[2,3-c]pyridin-7-yl)-(4-fluorobenzyl)-carbamic acid tert-butyl ester prepared in Step 3 of Example 902, the titled compound was obtained as a white solid. (Yield: 24%)

Step 2: 1-benzyl-7-(4-fluorobenzylamino)-2,3-dimethyl-1H-pyrrolo[2,3-c]pyridin-5-carbonitrile hydrochloride A solution of 1-benzyl-7-(4-fluorobenzylamino)-2,3-dimethyl-1H-pyrrolo[2,3-c]pyridin-5-carbonitrile prepared in Step 1 in ethyl acetate was saturated with hydrochloric acid gas and then filtered to give 12.0 mg of the titled compound as a white solid.

1H-NMR(400 MHz, CDCl$_3$) δ 7.35 (m, 4H), 7.00 (brs, 1H), 6.77 (m, 5H), 6.04 (brs, 2H), 5.00 (brs, 2H), 2.45 (s, 3H), 2.27 (s, 3H)

EXAMPLE 904

1-benzyl-7-(4-fluorobenzylamino)-2,3-dimethyl-1H-pyrrolo[2,3-c]pyridin-5-carboxylic acid hydrochloride

Step 1: 1-benzyl-7-(4-fluorobenzylamino)-2,3-dimethyl-1H-pyrrolo[2,3-c]pyridin-5-carboxylic acid In accordance with the same procedures as in Example 731, except for using 1-benzyl-7-(4-fluorobenzylamino)-2,3-dimethyl-1H-pyrrolo[2,3-c]pyridin-5-carbonitrile prepared in Step 1 of Example 903, the titled compound was obtained as a white solid. (Yield: 58%)

Step 2: 1-benzyl-7-(4-fluorobenzylamino)-2,3-dimethyl-1H-pyrrolo[2,3-c]pyridin-5-carboxylic acid hydrochloride A solution of 1-benzyl-7-(4-fluorobenzylamino)-2,3-dimethyl-1H-pyrrolo[2,3-c]pyridin-5-carboxylic acid prepared in Step 1 in ethyl acetate was saturated with hydrochloric acid gas and then filtered to give 10.5 mg of the titled compound as a white solid.

1H-NMR(400 MHz, CDCl$_3$) δ 8.53 (brs, 1H), 7.56 (brs, 1H), 7.29 (m, 4H), 6.90-6.77 (m, 5H), 6.12 (brs, 2H), 4.69 (brs, 2H), 2.44 (s, 3H), 2.25 (s, 3H)

EXAMPLE 905

1-benzyl-7-(4-fluorobenzylamino)-2,3-dimethyl-1H-pyrrolo[2,3-c]pyridin-5-carboxamide hydrochloride

Step 1: 1-benzyl-7-(4-fluorobenzylamino)-2,3-dimethyl-1H-pyrrolo[2,3-c]pyridin-5-carboxamide In accordance with the same procedures as in Example 745, except for using 1-benzyl-7-(4-fluorobenzylamino)-2,3-dimethyl-1H-pyrrolo[2,3-c]pyridin-5-carbonitrile prepared in Step 1 of Example 903, the titled compound was obtained as a white solid. (Yield: 87%)

Step 2: 1-benzyl-7-(4-fluorobenzylamino)-2,3-dimethyl-1H-pyrrolo[2,3-c]pyridin-5-carboxamide hydrochloride A solution of 1-benzyl-7-(4-fluorobenzylamino)-2,3-dimethyl-1H-pyrrolo[2,3-c]pyridin-5-carboxamide prepared in Step 1 in ethyl acetate was saturated with hydrochloric acid gas and then filtered to give 17.1 mg of the titled compound as a white solid.

1H-NMR(400 MHz, CDCl$_3$) δ 8.01 (s, 1H), 7.74 (brs, 1H), 7.26 (m, 3H), 6.96-6.89 (m, 6H), 5.49 (s, 2H), 5.35 (brs, 1H), 4.51 (brs, 1H), 4.40 (s, 2H), 2.33 (s, 3H), 2.28 (s, 3H)

EXAMPLES 906 TO 909

The titled compounds of Examples 906 to 909 were prepared, in accordance with the same procedures as in Example 756, using 1-benzyl-7-(4-fluorobenzylamino)-2,3-dimethyl-1H-pyrrolo[2,3-c]pyridin-5-carboxylic acid prepared in Step 1 of Example 904; and, 1-methylpiperazine, 1-ethylpiperazine, piperidine, or morpholine.

EXAMPLE 906

[1-benzyl-7-(4-fluorobenzylamino)-2,3-dimethyl-1H-pyrrolo[2,3-c]pyridin-5-yl]-(4-methylpiperazin-1-yl)-methanone hydrochloride 1H-NMR(400 MHz, CDCl$_3$) δ 7.31 (m, 2H), 6.91 (brs, 1H), 6.83-6.75 (m, 5H), 6.63 (brs, 2H), 5.91 (brs, 1H), 5.53 (brs, 2H), 4.88-4.72 (brs, 2H), 3.85-3.67 (brs, 5H), 3.28 (brs, 3H), 2.74 (s, 3H), 2.54 (s, 3H), 2.25 (s, 3H); (Yield: 82%)

EXAMPLE 907

[1-benzyl-7-(4-fluorobenzylamino)-2,3-dimethyl-1H-pyrrolo[2,3-c]pyridin-5-yl]-(4-ethylpiperazin-1-yl)-methanone hydrochloride 1H-NMR(400 MHz, CDCl$_3$) δ 7.27 (m, 2H), 7.08 (brs, 1H), 6.83-6.72 (m, 5H), 6.58 (brs, 2H), 5.99 (brs, 1H), 5.58 (brs, 2H), 4.89-4.73 (brs, 2H), 3.85-3.75 (brs, 3H), 3.47 (brs, 3H), 3.35 (brs, 3H), 2.55 (s, 3H), 2.24 (s, 3H), 1.23 (t, 3H); (Yield: 73%)

EXAMPLE 908

[1-benzyl-7-(4-fluorobenzylamino)-2,3-dimethyl-1H-pyrrolo[2,3-c]pyridin-5-yl]-(piperidin-1-yl)-methanone hydrochloride 1H-NMR(400 MHz, CDCl$_3$) δ 7.27 (m, 2H), 6.93 (m, 3H), 6.72 (m, 4H), 6.18 (brs, 2H), 5.13 (brs, 2H), 4.54 (brs, 2H), 3.54-3.13 (brs, 2+2H), 2.51 (s, 3H), 2.22 (s, 3H), 1.92 (brs, 2H), 1.78 (brs, 4H); (Yield: 52%)

EXAMPLE 909

[1-benzyl-7-(4-fluorobenzylamino)-2,3-dimethyl-1H-pyrrolo[2,3-c]pyridin-5-yl]-(morpholin-4-yl)-methanone hydrochloride 1H-NMR(400 MHz, CDCl$_3$) δ 8.74 (s, 1H), 7.26 (m, 2H), 6.92 (d, 2H), 6.77 (s, 1H), 6.70 (m, 2H), 6.58 (m, 2H), 6.11 (brs, 2H), 5.20 (brs, 2H), 3.50 (m, 6H), 3.22 (m, 2H), 2.54 (s, 3H), 2.21 (s, 3H); (Yield: 48%)

EXAMPLE 910

7-(4-fluorobenzylamino)-2,3-dimethyl-1H-pyrrolo[2,3-c]pyridin-5-carbonitrile hydrochloride Step 1: 7-(4-fluorobenzylamino)-2,3-dimethyl-1H-pyrrolo[2,3-c]pyridin-5-carbonitrile In accordance with the same procedures as in Example 682, except for using (5-chloro-2,3-dimethyl-1H-pyrrolo[2,3-c]pyridin-7-yl)-(4-fluorobenzyl)-carbamic acid tert-butyl ester prepared in Step 2 of Example 902, the titled compound was obtained as a white solid. (Yield: 24%)

Step 2: 7-(4-fluorobenzylamino)-2,3-dimethyl-1H-pyrrolo[2,3-c]pyridin-5-carbonitrile hydrochloride A solution of 7-(4-fluorobenzylamino)-2,3-dimethyl-1H-pyrrolo[2,3-c]pyridin-5-carbonitrile prepared in Step 1 in ethyl acetate was saturated with hydrochloric acid gas and then filtered to give 3.2 mg of the titled compound as a white solid.

1H-NMR(400 MHz, CDCl$_3$) δ 12.27 (brs, 1H), 7.68 (s, 1H), 7.47 (m, 2H), 7.20 (m, 2H), 4.72 (s, 2H), 2.36 (s, 3H), 2.15 (s, 3H)

EXAMPLE 911

1-benzyl-7-(3,4-dihydro-1H-isoquinolin-2-yl)-2,3-dimethyl-1H-pyrrolo[2,3-c]pyridin-5-thiol A solution of 2-(1-benzyl-5-chloro-2,3-dimethyl-1H-pyrrolo[2,3-c]pyridin-7-yl)-1,2,3,4-tetrahydroisoquinoline (100 mg, 0.24 mmol) prepared in Example 658 and sodium hydrosulfide (26.7 mg, 0.48 mmol) in methanol (2 ml) was refluxed for 2 hours. Water was added to the reaction mixture, which was then extracted with ethyl acetate. The organic layer was dried on anhydrous magnesium sulfate and then concentrated under reduced pressure. Water was added to the resulting solid. The reaction mixture was stirred for 30 minutes and then filtered. The resulting solid washed with water 3 times and then dried to give 68 mg of the titled compound as a pale yellow solid.

1H-NMR(400 MHz, CDCl$_3$) δ 7.24 (s, 1H), 7.20 (m, 4H), 7.08 (m, 2H), 6.72 (d, 1H), 6.47 (d, 2H), 5.63 (s, 2H), 4.34 (brs, 2H), 3.81 (brs, 2H), 2.62 (brs, 2H), 2.35 (brs, 1H), 2.35 (s, 3H), 2.29 (s, 3H)

EXAMPLE 912

1-benzyl-7-(3,4-dihydro-1H-isoquinolin-2-yl)-2,3-dimethyl-1H-pyrrolo[2,3-c]pyridin-5-thiol hydrochloride A solution of 1-benzyl-7-(3,4-dihydro-1H-isoquinolin-2-yl)-2,3-dimethyl-1H-pyrrolo[2,3-c]pyridin-5-thiol prepared in Example 911 in ethyl acetate was saturated with hydrochloric acid gas and then filtered to give 15.2 mg of the titled compound as a white solid.

1H-NMR(400 MHz, CDCl$_3$) δ 7.22 (s, 1H), 7.19 (m, 4H), 7.09 (m, 2H), 6.70 (d, 1H), 6.48 (d, 2H), 5.63 (s, 2H), 4.50 (brs, 2H), 3.80 (brs, 2H), 2.80 (brs, 2H), 2.30 (brs, 1H), 2.34 (s, 3H), 2.31 (s, 3H)

EXAMPLE 913

1-benzyl-7-(3,4-dihydro-1H-isoquinolin-2-yl)-2,3-dimethyl-1H-pyrrolo[2,3-c]pyridin-5-sulfonamide hydrochloride Step 1: 5-(aminosulfanyl)-2,3-dimethyl-7-(1,2,3,4-tetrahydroisoquinolin-2-yl-1H-pyrrolo[2,3-c]pyridine 1-benzyl-7-(3,4-dihydro-1H-isoquinolin-2-yl)-2,3-dimethyl-1H-pyrrolo[2,3-c]pyridin-5-thiol (500 mg, 0.24 mmol) prepared in Example 911 was added to a sodium hydroxide solution (10 ml). Excess chloramine obtained by adding sodium hyperchloride to ammonium hydroxide was slowly added at −10° C. to the reaction mixture, which was then filtered. The resulting solid was washed with water and then dried to give 150 mg of the titled compound as yellow solid.

1H-NMR(400 MHz, CDCl$_3$) δ 7.21 (s, 1H), 7.18 (m, 4H), 7.11 (m, 2H), 6.74 (d, 1H), 6.48 (d, 2H), 5.60 (s, 2H), 4.55 (brs, 2H), 3.81 (brs, 2H), 2.90 (brs, 2H), 2.34 (s, 3H), 2.31 (s, 3H), 2.15 (s, 2H)

Step 2: 1-benzyl-7-(3,4-dihydro-1H-isoquinolin-2-yl)-2,3-dimethyl-1H-pyrrolo[2,3-c]pyridin-5-sulfonamide hydrochloride 3-Chloroperbenzoic acid (249 mg, 1.44 mmol) was added to a solution of 5-(aminosulfanyl)-2,3-dimethyl-7-(1,2,3,4-tetrahydroisoquinolin-2-yl-1H-pyrrolo[2,3-c]pyridine (150 mg, 0.36 mmol) prepared in Step 1 in dichloromethane (10 ml). The reaction mixture was stirred for 6 hours at room temperature and then concentrated under reduced pressure. The resulting residue was purified with silica gel column chromatography (ethyl acetate/n-hexane=1/5, v/v). The resulting product was dissolved in ethyl acetate, saturated with hydrochloric acid gas, and then filtered to give 54 mg of the titled compound as a white solid.

1H-NMR(400 MHz, CDCl$_3$) δ 7.34 (s, 1H), 7.20 (m, 4H), 7.11 (m, 2H), 6.74 (d, 1H), 6.49 (d, 2H), 5.69 (brs, 2H), 4.34 (brs, 2H), 3.94 (brs, 2H), 3.73 (s, 3H), 2.84 (s, 2H), 2.34 (s, 3H), 2.31 (s, 3H), 1.98 (brs, 2H)

EXAMPLE 914

7-(3,4-dihydro-1H-isoquinolin-2-yl)-1-(3-fluorobenzyl)-2,3-dimethyl-1H-pyrrolo[2,3-c]pyridin-5-ol The compound prepared in Example 847 was treated with a saturated sodium bicarbonate solution to obtain 7-(3,4-dihydro-1H-isoquinolin-2-yl)-1-(3-fluorobenzyl)-2,3-dimethyl-1H-pyrrolo[2,3-c]pyridin-5-amine. Concentrated sulfuric acid (1 ml) and water (5 ml) were added to 7-(3,4-dihydro-1H-isoquinolin-2-yl)-1-(3-fluorobenzyl)-2,3-dimethyl-1H-pyrrolo[2,3-c]pyridin-5-amine (50 mg, 0.13 mmol) and then sodium nitrite (43.1 mg, 0.63 mmol) was added thereto. The reaction mixture was stirred for 5 minutes at 100° C. under heating and then excess ammonia solution was added thereto. The reaction mixture was stirred for 2 minutes under heating at the same temperature and then filtered to discard insoluble materrals. A potassium hydroxide solution was added to the reaction mixture, which was then filtered to discard insoluble materrals. The reaction mixture was extracted with ethyl acetate. The organic layer was dried on anhydrous magnesium sulfate and then concentrated under reduced pressure to give 28.4 mg of the titled compound as a pale yellow solid.

1H-NMR(400 MHz, CDCl$_3$) δ 7.25 (s, 1H), 7.20-7.15 (m, 4H), 6.90-6.88(m, 2H), 6.77 (m, 1H), 6.40 (s, 1H), 6.31 (d, 1H), 6.25 (d, 1H), 5.26 (s, 2H), 4.97 (brs, 2H), 3.42 (brs, 2H), 2.99 (brs, 2H), 2.30 (s, 3H), 2.17 (s, 3H)

EXAMPLE 915

7-(3,4-dihydro-1H-isoquinolin-2-yl)-1-(3-fluorobenzyl)-2,3-dimethyl-1H-pyrrolo[2,3-c]pyridin-5-ol hydrochloride A solution of 7-(3,4-dihydro-1H-isoquinolin-2-yl)-1-(3-fluorobenzyl)-2,3-dimethyl-1H-pyrrolo[2,3-c]pyridin-5-ol prepared in Example 914 in ethyl acetate was saturated with hydrochloric acid gas and then filtered to give 5.7 mg of the titled compound as a white solid.

1H-NMR(400 MHz, CDCl$_3$) δ 7.19-7.15 (m, 5H), 6.92-6.88 (m, 2H), 6.76 (m, 1H), 6.43 (s, 1H), 6.34 (d, 1H), 6.24 (d, 1H), 5.26 (s, 2H), 4.47-3.51 (brs, 4H), 2.80 (brs, 2H), 2.26 (s, 3H), 2.13 (s, 3H)

EXAMPLE 916

2-(1-benzyl-5-ethynyl-2,3-dimethyl-1H-pyrrolo[2,3-c]pyridin-7-yl)-1,2,3,4-tetrahydroisoquinoline hydrochloride A solution of 2-(1-benzyl-5-chloro-2,3-dimethyl-1H-pyrrolo[2,3-c]pyridin-7-yl)-1,2,3,4-tetrahydroisoquinoline (100 mg, 0.24 mmol) prepared in Example 658, bis(triphenylphosphine)palladium chloride(II) (9.4 mg, 0.013 mmol), triphenylphosphine (12.6 mg, 0.48 mmol), copper(I) iodide (2.5 mg, 0.013 mmol), trimethylsilane acetylene (42 μl, 0.3 mmol), and triethylamine (1 ml) in anhydrous N,N-dimethylformamide (2 ml) was refluxed for 8 hours at 120° C. The reaction mixture was cooled to room temperature and then concentrated under reduced pressure. The resulting residue was purified with silica gel column chromatography (ethyl acetate/n-hexane=1/5, v/v). The resulting product was dissolved in ethyl acetate, saturated with hydrochloric acid gas, and then filtered to give 32.1 mg of the titled compound as a white solid.

1H-NMR(400 MHz, CDCl$_3$) δ 7.71 (s, 1H), 7.17 (m, 7H), 6.84 (d, 1H), 6.71 (m, 2H), 5.74 (brs, 2H), 4.27 (brs, 2H), 2.87 (s, 2H), 2.39 (s, 1H), 2.30 (s, 3H), 2.24 (s, 3H)

EXAMPLE 917

[1-allyl-7-(3,4-dihydro-1H-isoquinolin-2-yl)-3-hydroxymethyl-2-methyl-1H-pyrrolo[2,3-c]pyridin-5-yl]-(4-methylpiperazin-1-yl)-methanone hydrochloride Step 1: 2-(5-chloro-2-methyl-1H-pyrrolo[2,3-c]pyridin-7-yl)-1,2,3,4-tetrahydro-isoquinoline In accordance with the same procedures as in Step 3 of Example 642, except for using 2-(6-chloro-3-nitropyridin-2-yl)-1,2,3,4-tetrahydroisoquinoline prepared in Preparation 7 and isopropenylmagnesium bromide, the titled compound was obtained as yellow oil. (Yield: 35%) The product was used in the subsequent step without further purification.

Step 2: 7-(3,4-dihydro-1H-isoquinolin-2-yl)-2-methyl-1H-pyrrolo[2,3-c]pyridin-5-carbonitrile In accordance with the same procedures as in Example 682, except for using 2-(5-chloro-2-methyl-1H-pyrrolo[2,3-c]pyridin-7-yl)-1,2,3,4-tetrahydro-isoquinoline prepared in Step 1, the titled compound was obtained as a white solid. (Yield: 26%)

1H-NMR(400 MHz, CDCl$_3$) δ 8.40 (brs, 1H), 7.52 (s, 1H), 7.21 (m, 4H), 6.30 (s, 1H), 4.67 (s, 2H), 3.79 (brs, 2H), 3.11 (brs, 2H), 2.52 (s, 3H)

Step 3: 1-allyl-7-(3,4-dihydro-1H-isoquinolin-2-yl)-2-methyl-1H-pyrrolo[2,3-c]pyridin-5-carbonitrile In accordance with the same procedures as in Example 657, except for using 7-(3,4-dihydro-1H-isoquinolin-2-yl)-2-methyl-1H-pyrrolo[2,3-c]pyridin-5-carbonitrile prepared in Step 2 and allyl bromide, the titled compound was obtained as a white solid. (Yield: 79%)

1H-NMR (400 MHz, CDCl$_3$) δ 7.64 (s, 1H), 7.20 (m, 4H), 6.30 (s, 1H), 5.84 (m, 1H), 5.10 (m, 1+2H), 4.67 (brs, 2H), 4.63 (d, 1H), 3.84 (brs, 2H), 3.11 (brs, 2H), 2.51 (s, 3H)

Step 4: 1-allyl-7-(3,4-dihydro-1H-isoquinolin-2-yl)-3-formyl-2-methyl-1H-pyrrolo[2,3-c]pyridin-5-carbonitrile Phosphorus oxychloride (425 μl, 4.56 mmol) was added at room temperature to a solution of 1-allyl-7-(3,4-dihydro-1H-isoquinolin-2-yl)-2-methyl-1H-pyrrolo[2,3-c]pyridin-5-carbonitrile (1 g, 3.04 mmol) prepared in Step 3 in a mixture of anhydrous dichloromethane (20 ml) and N,N-dimethylformamide (353 μl, 4.56 mmol). The reaction mixture was refluxed for 3 hours, cooled to room temperature, and then filtered. The resulting solid washed with water and 1M sodium acetate (30 ml) was added thereto. The reaction mixture was stirred for 1 hour at room temperature and then filtered. The resulting solid washed with water and then dried to give 350 mg of the titled compound as a white solid.

1H-NMR(400 MHz, CDCl$_3$) δ 10.31 (s, 1H), 7.69 (s, 1H), 7.21 (m, 4H), 5.86 (m, 1H), 5.11 (m, 1+2H), 4.67 (brs, 2H), 4.61 (d, 1H), 3.85 (brs, 2H), 3.10 (brs, 2H), 2.50 (s, 3H)

Step 5: 1-allyl-7-(3,4-dihydro-1H-isoquinolin-2-yl)-3-hydroxymethyl-2-methyl-1H-pyrrolo[2,3-c]pyridin-5-carbonitrile Sodium borohydride (111.2 mg, 2.94 mmol) was added to a solution of 1-allyl-7-(3,4-dihydro-1H-isoquinolin-2-yl)-3- formyl-2-methyl-1H-pyrrolo[2,3-c]pyridin-5-carbonitrile (350 mg, 0.98 mmol) prepared in Step 4 in methanol (10 ml). The reaction mixture was stirred for 1 hour. Water was added to the reaction mixture, which was then extracted with ethyl acetate. The organic layer was dried on anhydrous magnesium sulfate and then concentrated under reduced pressure. The resulting residue was purified with silica gel column chromatography (ethyl acetate/n-hexane=1/1, v/v) to give 100 mg of the titled compound as a white solid.

1H-NMR(400 MHz, CDCl$_3$) δ 7.69 (s, 1H), 7.20 (m, 4H), 5.86 (m, 1H), 5.11 (m, 1+2H), 5.02 (s, 2H), 4.66 (brs, 2H), 4.61 (d, 1H), 3.87 (brs, 2H), 3.11 (brs, 2H), 2.71 (s, 3H)

Step 6: 1-allyl-7-(3,4-dihydro-1H-isoquinolin-2-yl)-3-hydroxymethyl-2-methyl-1H-pyrrolo[2,3-c]pyridin-5-carboxylic acid In accordance with the same procedures as in Example 731, except for using 1-allyl-7-(3,4-dihydro-1H-isoquinolin-2-yl)-3-hydroxymethyl-2-methyl-1H-pyrrolo[2,3-c]pyridin-5-carbonitrile prepared in Step 5, the titled compound was obtained as a white solid. (Yield: 86%)

1H-NMR(400 MHz, CDCl$_3$) δ 8.12 (s, 1H), 7.25 (m, 4H), 5.87 (m, 1H), 5.10 (m, 1+2H), 5.03 (s, 2H), 4.68 (brs, 2H), 4.60 (d, 1H), 3.87 (brs, 2H), 3.10 (brs, 2H), 2.59 (s, 3H)

Step 7: [1-allyl-7-(3,4-dihydro-1H-isoquinolin-2-yl)-3-hydroxymethyl-2-methyl-1H-pyrrolo[2,3-c]pyridin-5-yl]-(4-methylpiperazin-1-yl)-methanone hydrochloride In accordance with the same procedures as in Example 756, except for using 1-allyl-7-(3,4-dihydro-1H-isoquinolin-2-yl)-3-hydroxymethyl-2-methyl-1H-pyrrolo[2,3-c]pyridin-5-carboxylic acid prepared in Step 6 and 1-methylpiperazine, the titled compound was obtained as a white solid. (Yield: 64%)

1H-NMR(400 MHz, CDCl$_3$) δ 7.45 (s, 1H), 7.25 (m, 3H), 7.02 (m, 1H), 5.85 (m, 1H), 5.21-5.00 (brs, 2H), 5.01 (brs, 2H), 4.88 (d, 2H), 4.57 (brs, 1H), 4.30-4.00 (m, 3H), 3.88 (m, 4H), 3.30 (brs, 1H), 3.15 (brs, 1H), 3.10 (brs, 2H), 2.88 (s, 3H), 2.59 (s, 3H)

EXAMPLES 918 AND 919

The titled compounds of Examples 918 and 919 were prepared, in accordance with the same procedures as in Example 756, using 1-allyl-7-(3,4-dihydro-1H-isoquinolin-2-yl)-3-hydroxymethyl-2-methyl-1H-pyrrolo[2,3-c]pyridin-5-carboxylic acid prepared in Step 6 of Example 917; and, 1-ethylpiperazine or 1-piperazin-1-carboxylic acid tert-butyl ester.

EXAMPLE 918

[1-allyl-7-(3,4-dihydro-1H-isoquinolin-2-yl)-3-hydroxymethyl-2-methyl-1H-pyrrolo[2,3-c]pyridin-5-yl]-(4-ethylpiperazin-1-yl)-methanone hydrochloride 1H-NMR(400 MHz, CDCl$_3$) δ 7.46 (s, 1H), 7.26-7.23 (m, 3H), 7.01 (m, 1H), 5.96 (m, 1H), 5.21-5.00 (brs, 2H), 5.02 (brs, 2H), 4.89 (m, 2+2H), 4.57 (brs, 1H), 4.30-3.94 (m, 3H), 3.88 (m, 4H), 3.30 (brs, 1H), 3.15 (brs, 1H), 3.11 (brs, 2H), 2.48 (s, 3H), 1.57 (t, 3H); (Yield: 54%)

EXAMPLE 919

[1-allyl-7-(3,4-dihydro-1H-isoquinolin-2-yl)-3-hydroxymethyl-2-methyl-1H-pyrrolo[2,3-c]pyridin-5-yl]-(piperazin-1-yl)-methanone hydrochloride 1H-NMR(400 MHz, CDCl$_3$) δ 7.45 (s, 1H), 7.23 (m, 3H), 7.02 (m, 1H), 5.77 (m, 1H), 5.20 (d, 1H), 4.99 (m, 2+2H), 4.70 (m, 1H), 4.59 (d, 1H), 4.22 (brs, 2H), 4.12 (brs, 2H), 3.96 (brs, 2H), 3.58 (brs, 2H), 3.43 (s, 2H), 3.14 (s, 2H), 2.46 (s, 3H); (Yield: 52%)

EXAMPLE 920

[1-benzyl-7-(3,4-dihydro-1H-isoquinolin-2-yl)-3-hydroxymethyl-2-methyl-1H-pyrrolo[2,3-c]pyridin-5-yl]-(4-methylpiperazin-1-yl)-methanone hydrochloride Step 1: 1-benzyl-7-(3,4-dihydro-1H-isoquinolin-2-yl)-2-methyl-1H-pyrrolo[2,3-c]pyridin-5-carbonitrile In accordance with the same procedures as in Example 657, except for using 7-(3,4-dihydro-1H-isoquinolin-2-yl)-2-methyl-1H-pyrrolo[2,3-c]pyridin-5-carbonitrile prepared in Step 2 of Example 917 and benzyl bromide, the titled compound was obtained as a white solid. (Yield: 87%)

1H-NMR(400 MHz, CDCl$_3$) δ 7.71 (s, 1H), 7.19 (m, 6H), 6.87 (d, 1H), 6.71 (d, 2H), 6.25 (s, 1H), 5.72 (brs, 2H), 4.30 (brs, 2H), 3.45 (brs, 2H), 2.85 (brs, 2H), 2.32 (s, 3H)

Step 2: 1-benzyl-7-(3,4-dihydro-1H-isoquinolin-2-yl)-3-formyl-2-methyl-1H-pyrrolo[2,3-c]pyridin-5-carbonitrile In accordance with the same procedures as in Step 4 of Example 917, except for using 1-benzyl-7-(3,4-dihydro-1H-isoquinolin-2-yl)-2-methyl-1H-pyrrolo[2,3-c]pyridin-5-carbonitrile prepared in Step 1, the titled compound was obtained as a white solid. (Yield: 25%)

1H-NMR(400 MHz, CDCl$_3$) δ 9.98 (s, 1H), 7.91 (s, 1H), 7.25-7.19 (m, 6H), 6.85 (d, 1H), 6.72 (d, 2H), 5.72 (brs, 2H), 4.30 (brs, 2H), 3.45 (brs, 2H), 2.82 (brs, 2H), 2.39 (s, 3H)

Step 3: 1-benzyl-7-(3,4-dihydro-1H-isoquinolin-2-yl)-3-hydroxymethyl-2-methyl-1H-pyrrolo[2,3-c]pyridin-5-carbonitrile In accordance with the same procedures as in Step 5 of Example 917, except for using 1-benzyl-7-(3,4-dihydro-1H-isoquinolin-2-yl)-3-formyl-2-methyl-1H-pyrrolo[2,3-c]pyridin-5-carbonitrile prepared in Step 2, the titled compound was obtained as a white solid. (Yield: 95%) The product was used in the subsequent step without further purification.

Step 4: 1-benzyl-7-(3,4-dihydro-1H-isoquinolin-2-yl)-3-hydroxymethyl-2-methyl-1H-pyrrolo[2,3-c]pyridin-5-carboxylic acid In accordance with the same procedures as in Example 731, except for using 1-benzyl-7-(3,4-dihydro-1H-isoquinolin-2-yl)-3-hydroxymethyl-2-methyl-1H-pyrrolo[2,3-c]pyridin-5-carbonitrile prepared in Step 3, the titled compound was obtained as a white solid. (Yield: 85%)

1H-NMR(400 MHz, CDCl$_3$) δ 8.21 (s, 1H), 7.21 (m, 3H), 7.15 (m, 3H), 6.87 (d, 1H), 6.69 (m, 2H) 5.76 (brs, 2H), 5.01 (brs, 2H), 4.24 (brs, 2H), 3.49 (brs, 2H), 2.91 (brs, 2H), 2.34 (s, 3H)

Step 5: [1-benzyl-7-(3,4-dihydro-1H-isoquinolin-2-yl)-3-hydroxymethyl-2-methyl-1H-pyrrolo[2,3-c]pyridin-5-yl]-(4-methylpiperazin-1-yl)-methanone hydrochloride In accordance with the same procedures as in Example 756, except for using 1-benzyl-7-(3,4-dihydro-1H-isoquinolin-2-yl)-3-hydroxymethyl-2-methyl-1H-pyrrolo[2,3-c]pyridin-5-carboxylic acid prepared in Step 4 and 1-methylpiperazine, the titled compound was obtained as a white solid. (Yield: 62%)

1H-NMR(400 MHz, CDCl$_3$) δ 7.53 (brs, 1H), 7.20 (m, 5H), 7.10 (m, 2H), 6.56 (m, 2H), 5.71 (brs, 2H), 4.95 (brs, 2H), 4.86 (brs, 1H), 4.50-4.36 (brs, 3H), 3.82 (brs, 3H), 3.39 (brs, 2H), 2.83 (brs, 5H), 2.58 (s, 3H)

EXAMPLE 921

[1-benzyl-7-(3,4-dihydro-1H-isoquinolin-2-yl)-3-hydroxymethyl-2-methyl-1H-pyrrolo[2,3-c]pyridin-5-yl]-(piperazin-1-yl)-methanone hydrochloride In accordance with the same procedures as in Example 756, except for using 1-benzyl-7-(3,4-dihydro-1H-isoquinolin-2-yl)-3-hydroxymethyl-2-methyl-1H-pyrrolo[2,3-c]pyridin-5-carboxylic acid prepared in Step 4 of Example 920 and 1-piperazin-1-carboxylic acid tert-butyl ester, the titled compound was obtained as a white solid. (Yield: 58%)

1H-NMR(400 MHz, CDCl$_3$) δ 7.76 (brs, 1H), 7.43 (s, 2H), 7.18 (m, 3H), 6.63 (brs, 2H), 5.80 (brs, 2H), 4.22 (brs, 2+2H), 3.65 (brs, 2H), 3.30 (brs, 3H), 3.09 (brs, 2H), 2.90 (brs, 2H), 2.83 (brs, 2H), 2.52-2.18 (brs, 5H), 2.43 (s, 3H)

EXAMPLE 922

[1-allyl-7-(3,4-dihydro-1H-isoquinolin-2-yl)-2-methyl-5-(4-methylpiperazin-1-carbonyl)-1H-pyrrolo[2,3-c]pyridin-3-yl]-acetonitrile hydrochloride Step 1: 1-allyl-7-(3,4-dihydro-1H-isoquinolin-2-yl)-2-methyl-1H-pyrrolo[2,3-c]pyridin-5-carboxylic acid In accordance with the same procedures as in Example 731, except for using 1-allyl-7-(3,4-dihydro-1H-isoquinolin-2-yl)-2-methyl-1H-pyrrolo[2,3-c]pyridin-5-carbonitrile prepared in Step 3 of Example 917, the titled compound was obtained as a white solid. (Yield: 87%)

1H-NMR(400 MHz, CDCl$_3$) δ 8.21 (s, 1H), 7.21 (m, 3H), 7.09 (m, 1H), 6.42 (s, 1H), 5.86 (m, 1H), 5.12 (brs, 2H), 5.09 (d, 1H), 4.65 (d, 1H), 4.36 (brs, 2H), 3.50 (brs, 2H), 3.0 (brs, 2H), 2.51 (s, 3H)

Step 2: 1-allyl-7-(3,4-dihydro-1H-isoquinolin-2-yl)-2-methyl-1H-pyrrolo[2,3-c]pyridin-5-yl]-(4-methylpiperazin-1-yl)-methanone In accordance with the same procedures as in Step 1 of Example 756, except for using 1-allyl-7-(3,4-dihydro-1H-isoquinolin-2-yl)-2-methyl-1H-pyrrolo[2,3-c]pyridin-5-carboxylic acid prepared in Step 1 and 1-methylpiperazine, the titled compound was obtained as a white solid. (Yield: 57%)

1H-NMR(400 MHz, CDCl$_3$) δ 7.45 (s, 1H), 7.25 (m, 3H), 7.05 (m, 1H), 5.97 (brs, 1H), 5.87 (m, 1H), 5.21-5.00 (brs, 2H), 4.89 (d, 2H), 4.57 (brs, 1H), 4.30-4.01 (m, 3H), 3.91 (m, 4H), 3.35 (brs, 1H), 3.16 (brs, 1H), 3.11 (brs, 2H), 2.87 (s, 3H), 2.49 (s, 3H)

Step 3: [1-allyl-7-(3,4-dihydro-1H-isoquinolin-2-yl)-2-methyl-5-(4-methylpiperazin-1-carbonyl)-1H-pyrrolo[2,3-c]pyridin-3-ylmethyl]-trimethylammonium iodide Dimethylamine (1.05 ml, 2.1 mmol), acetic acid (0.81 ml), and formaldehyde (442 µl) were added to a solution of 1-allyl-7-(3,4-dihydro-1H-isoquinolin-2-yl)-2-methyl-1H-pyrrolo[2,3-c]pyridin-5-yl]-(4-methylpiperazin-1-yl)-methanone (600 mg, 1.40 mmol) prepared in Step 2 in ethanol (5 ml). The reaction mixture was refluxed overnight and then concentrated under reduced pressure. The resulting residue was purified with silica gel column chromatography (methanol/dichloromethane=1/10, v/v). The resulting white solid (300 mg, 0.62 mmol) was dissolved in ethanol (2 ml) and then iodomethane (77.2 µl, 1.24 mmol) was added thereto. The reaction mixture was stirred overnight at room temperature and then filtered. The resulting residue was dried to give 100 mg of the titled compound as a white solid. The product was used in the subsequent step without further purification.

Step 4: [1'-allyl-7-(3,4-dihydro-1H-isoquinolin-2-yl)-2-methyl-5-(4-methylpiperazin-1-carbonyl)-1H-pyrrolo[2,3-c]pyridin-3-yl]-acetonitrile hydrochloride Sodium cyanide (31.4 mg, 0.64 mmol) was added to a solution of [1-allyl-7-(3,4-dihydro-1H-isoquinolin-2-yl)-2-methyl-5-(4-methylpiperazin-1-carbonyl)-1H-pyrrolo[2,3-c]pyridin-3-ylmethyl]-trimethylammonium iodide (100 mg, 0.16 mmol) prepared in Step 3 in anhydrous N,N-dimethylformamide (3 ml). The reaction mixture was stirred for 5 hours at 100° C. Water was added to the reaction mixture, which was then extracted with ethyl acetate. The organic layer was dried on anhydrous magnesium sulfate and then concentrated under reduced pressure. The resulting residue was purified with silica gel column chromatography (methanol/dichloromethane=1/10, v/v). The resulting product was dissolved in ethyl acetate, saturated with hydrochloric acid gas, and then filtered to give 16 mg of the titled compound as a white solid.

1H-NMR(400 MHz, CDCl$_3$) δ 7.46 (s, 1H), 7.26-7.22 (m, 3H), 7.04 (m, 1H), 5.87-5.61 (m, 2+1H), 5.21-5.00 (brs, 2H), 4.89 (d, 2H), 4.58 (brs, 1H), 4.30-4.06 (m, 3H), 3.88 (m, 4H), 3.36 (brs, 1H), 3.16 (brs, 1H), 3.10 (brs, 2H), 2.89 (s, 3H), 2.34 (s, 3H)

EXAMPLE 923

[1-allyl-7-(3,4-dihydro-1H-isoquinolin-2-yl)-2-methyl-5-(piperazin-1-carbonyl)-1H-pyrrolo[2,3-c]pyridin-3-yl]-acetonitrile hydrochloride Step 1: [1-allyl-7-(3,4-dihydro-1H-isoquinolin-2-yl)-2-methyl-1H-pyrrolo[2,3-c]pyridin-5-yl]-(piperazin-1-yl)-methanone In accordance with the same procedures as in Step 1 of Example 756, except for using 1-allyl-7-(3,4-dihydro-1H-isoquinolin-2-yl)-2-methyl-1H-pyrrolo[2,3-c]pyridin-5-carboxylic acid prepared in Step 1 of Example 922 and 1-piperazin-1-carboxylic acid tert-butyl ester, the titled compound was obtained as a white solid. (Yield: 54%) The product was used in the subsequent step without further purification.

1H-NMR(400 MHz, CDCl$_3$) δ 7.45 (s, 1H), 7.25 (m, 3H), 7.07 (m, 1H), 6.01 (s, 1H), 5.75 (m, 1H), 5.20 (d, 1H), 4.97 (s,

2H), 4.70 (m, 1H), 4.62 (d, 1H), 4.27 (brs, 2H), 4.15 (brs, 2H), 3.92 (brs, 2H), 3.59 (brs, 2H), 3.42 (s, 2H), 3.15 (s, 2H), 2.49 (s, 3H)

Step 2: [1-allyl-7-(3,4-dihydro-1H-isoquinolin-2-yl)-2-methyl-5-(piperazin-1-carbonyl)-1H-pyrrolo[2,3-c]pyridin-3-yl]-acetonitrile hydrochloride In accordance with the same procedures as in Steps 3 and 4 of Example 922, except for using [1-allyl-7-(3,4-dihydro-1H-isoquinolin-2-yl)-2-methyl-1H-pyrrolo[2,3-c]pyridin-5-yl]-(piperazin-1-yl)-methanone prepared in Step 1, the titled compound was obtained as a white solid. (Yield: 13%)
1H-NMR(400 MHz, CDCl$_3$) δ 7.45 (s, 1H), 7.26-7.22 (m, 3H), 7.04 (m, 1H), 5.61 (m, 1H), 5.60 (brs, 2H), 5.21-4.98 (brs, 2H), 4.75 (d, 2H), 4.54 (brs, 1+1H), 4.30-4.05 (m, 3H), 3.89 (m, 4H), 3.37 (brs, 1H), 3.14 (brs, 1H), 3.10 (brs, 2H), 2.39 (s, 3H)

EXAMPLE 924

[1-allyl-7-(3,4-dihydro-1H-isoquinolin-2-yl)-2-methyl-5-(4-ethylpiperazin-1-carbonyl)-1H-pyrrolo[2,3-c]pyridin-3-yl]-acetonitrile hydrochloride Step 1: [1-allyl-7-(3,4-dihydro-1H-isoquinolin-2-yl)-2-methyl-1H-pyrrolo[2,3-c]pyridin-5-yl]-(4-ethylpiperazin-1-yl)-methanone In accordance with the same procedures as in Step 1 of Example 756, except for using 1-allyl-7-(3,4-dihydro-1H-isoquinolin-2-yl)-2-methyl-1H-pyrrolo[2,3-c]pyridin-5-carboxylic acid prepared in Step 1 of Example 922 and 1-ethylpiperazine, the titled compound was obtained as a white solid. (Yield: 49%)

Step 2: [1-allyl-7-(3,4-dihydro-1H-isoquinolin-2-yl)-2-methyl-5-(4-ethylpiperazin-1-carbonyl)-1H-pyrrolo[2,3-c]pyridin-3-yl]-acetonitrile hydrochloride In accordance with the same procedures as in Steps 3 and 4 of Example 922, except for using [1-allyl-7-(3,4-dihydro-1H-isoquinolin-2-yl)-2-methyl-1H-pyrrolo[2,3-c]pyridin-5-yl]-(4-ethylpiperazin-1-yl)-methanone prepared in Step 1, the titled compound was obtained as a white solid. (Yield: 13%)
1H-NMR(400 MHz, CDCl$_3$) δ 7.46 (s, 1H), 7.26-7.22 (m, 3H), 7.04 (m, 1H), 5.83 (brs, 2H), 5.61 (m, 2+1H), 5.21-5.00 (brs, 2H), 4.89-4.74 (m, 2+2H), 4.50 (brs, 1H), 4.30-4.06 (m, 3H), 3.92 (m, 4H), 3.37 (brs, 1H), 3.20 (brs, 1H), 3.10 (brs, 2H), 2.37 (s, 3H), 1.57 (t, 3H)

EXAMPLE 925

[1-benzyl-7-(3,4-dihydro-1H-isoquinolin-2-yl)-2-methyl-5-(4-methylpiperazin-1-carbonyl)-1H-pyrrolo[2,3-c]pyridin-3-yl]-acetonitrile hydrochloride Step 1: 1-benzyl-7-(3,4-dihydro-1H-isoquinolin-2-yl)-2-methyl-1H-pyrrolo[2,3-c]pyridin-5-carboxylic acid In accordance with the same procedures as in Example 731, except for using 1-benzyl-7-(3,4-dihydro-1H-isoquinolin-2-yl)-2-methyl-1H-pyrrolo[2,3-c]pyridin-5-carbonitrile prepared in Step 1 of Example 920, the titled compound was obtained as a white solid. (Yield: 84%)
1H-NMR(400 MHz, CDCl$_3$) δ 8.21 (s, 1H), 7.25 (m, 3H), 7.11 (m, 3H), 6.87 (d, 1H), 6.71 (m, 2H), 6.32 (s, 1H), 5.75 (brs, 2H), 4.25 (brs, 2H), 3.47 (brs, 2H), 2.83 (brs, 2H), 2.29 (s, 3H)

Step 2: [1-benzyl-7-(3,4-dihydro-1H-isoquinolin-2-yl)-2-methyl-1H-pyrrolo[2,3-c]pyridin-5-yl]-(4-methylpiperazin-1-yl)-methanone In accordance with the same procedures as in Step 1 of Example 756, except for using 1-benzyl-7-(3,4-dihydro-1H-isoquinolin-2-yl)-2-methyl-1H-pyrrolo[2,3-c]pyridin-5-carboxylic acid prepared in Step 1 and 1-methylpiperazine, the titled compound was obtained as a white solid. (Yield: 57%)
1H-NMR(400 MHz, CDCl$_3$) δ 7.57 (brs, 1H), 7.20 (m, 5H), 7.10 (m, 2H), 6.56 (m, 2H), 6.12 (brs, 1H), 5.71 (brs, 2H), 4.86 (brs, 1H), 4.50-4.36 (brs, 3H), 3.82 (brs, 3H), 3.39 (brs, 2H), 2.83 (brs, 5H), 2.51 (s, 3H)

Step 3: [1-benzyl-7-(3,4-dihydro-1H-isoquinolin-2-yl)-2-methyl-5-(4-methylpiperazin-1-carbonyl)-1H-pyrrolo[2,3-c]pyridin-3-yl]-acetonitrile hydrochloride In accordance with the same procedures as in Steps 3 and 4 of Example 922, except for using [1-benzyl-7-(3,4-dihydro-1H-isoquinolin-2-yl)-2-methyl-1H-pyrrolo[2,3-c]pyridin-5-yl]-(4-methylpiperazin-1-yl)-methanone prepared in Step 2, the titled compound was obtained as a white solid. (Yield: 15%)
1H-NMR(400 MHz, CDCl$_3$) δ 7.53 (brs, 1H), 7.20 (m, 5H), 7.10 (m, 2H), 6.56 (m, 2H), 5.71 (brs, 2H), 4.86-4.61 (brs, 2+1H), 4.50-4.36 (brs, 3H), 3.82 (brs, 3H), 3.39 (brs, 2H), 2.83 (brs, 5H), 2.46 (s, 3H)

EXAMPLE 926

[1-benzyl-7-(3,4-dihydro-1H-isoquinolin-2-yl)-2-methyl-5-(piperazin-1-carbonyl)-1H-pyrrolo[2,3-c]pyridin-3-yl]-acetonitrile hydrochloride Step 1: [1-benzyl-7-(3,4-dihydro-1H-isoquinolin-2-yl)-2-methyl-1H-pyrrolo[2,3-c]pyridin-5-yl]-(piperazin-1-yl)-methanone In accordance with the same procedures as in Step 1 of Example 756, except for using 1-benzyl-7-(3,4-dihydro-1H-isoquinolin-2-yl)-2-methyl-1H-pyrrolo[2,3-c]pyridin-5-carboxylic acid prepared in Step 1 of Example 925 and 1-piperazin-1-carboxylic acid tert-butyl ester, the titled compound was obtained as a white solid. (Yield: 63%)
1H-NMR(400 MHz, CDCl$_3$) δ 7.75 (brs, 1H), 7.43 (s, 2H), 7.15 (m, 3H), 6.63 (brs, 2H), 6.01 (brs, 1H), 5.84 (brs, 2H), 4.20 (brs, 2H), 3.66 (brs, 2H), 3.28 (brs, 3H), 3.07 (brs, 2H), 2.95 (brs, 2H), 2.83 (brs, 2H), 2.52-2.18 (brs, 5H), 1.43 (s, 3H)

Step 2: [1-benzyl-7-(3,4-dihydro-1H-isoquinolin-2-yl)-2-methyl-5-(piperazin-1-carbonyl)-1H-pyrrolo[2,3-c]pyridin-3-yl]-acetonitrile hydrochloride In accordance with the same procedures as in Steps 3 and 4 of Example 922, except for using [1-benzyl-7-(3,4-dihydro-1H-isoquinolin-2-yl)-2-methyl-1H-pyrrolo[2,3-c]pyridin-5-yl]-(piperazin-1-yl)-methanone prepared in Step 1, the titled compound was obtained as a white solid. (Yield: 16%)

1H-NMR(400 MHz, CDCl$_3$) δ 7.74 (brs, 1H), 7.40 (s, 2H), 7.15 (m, 3H), 6.63 (brs, 2H), 5.81 (brs, 2H), 4.58-4.21 (brs, 2+2H), 3.65 (brs, 2H), 3.31 (brs, 3H), 3.05 (brs, 2H), 2.91 (brs, 2H), 2.81 (brs, 2H), 2.51-2.18 (brs, 3+2H), 1.43 (s, 3H)

EXAMPLE 927

[1-benzyl-7-(3,4-dihydro-1H-isoquinolin-2-yl)-2-methyl-5-(4-ethylpiperazin-1-carbonyl)-1H-pyrrolo[2,3-c]pyridin-3-yl]-acetonitrile hydrochloride Step 1: [1-benzyl-7-(3,4-dihydro-1H-isoquinolin-2-yl)-2-methyl-1H-pyrrolo[2,3-c]pyridin-5-yl]-(4-ethylpiperazin-1-yl)-methanone In accordance with the same procedures as in Step 1 of Example 756, except for using 1-benzyl-7-(3,4-dihydro-1H-isoquinolin-2-yl)-2-methyl-1H-pyrrolo[2,3-c]pyridin-5-carboxylic acid prepared in Step 1 of Example 925 and 1-ethylpiperazine, the titled compound was obtained as a white solid. (Yield: 63%) The product was used in the subsequent step without further purification.

Step 2: [1-benzyl-7-(3,4-dihydro-1H-isoquinolin-2-yl)-2-methyl-5-(4-ethylpiperazin-1-carbonyl)-1H-pyrrolo[2,3-c]pyridin-3-yl]-acetonitrile hydrochloride In accordance with the same procedures as in Steps 3 and 4 of Example 922, except for using [1-benzyl-7-(3,4-dihydro-1H-isoquinolin-2-yl)-2-methyl-1H-pyrrolo[2,3-c]pyridin-5-yl]-(4-ethylpiperazin-1-yl)-methanone prepared in Step 1, the titled compound was obtained as a white solid. (Yield: 19%)

1H-NMR(400 MHz, CDCl$_3$) δ 7.71 (brs, 1H), 7.40 (m, 2H), 7.15 (m, 3H), 6.63 (brs, 2H), 5.81 (brs, 2H), 5.12 (d, 2H), 4.58-4.21 (brs, 2+2H), 3.65 (brs, 2H), 3.31 (brs, 3H), 3.05 (brs, 2H), 2.91-2.85 (brs, 2H), 2.79 (brs, 2H), 2.50 (s, 3H), 1.54 (t, 3H)

TEST EXAMPLE 1

Inhibitory Effects on Proton Pump (H$^+$/K$^+$-ATPase) Activity 1-1. Preparation of Gastric Proton Pump Vesicles The hog fundic regions containing parietal and peptic cells were scraped with slide-glass. The collected cells were suspended in 10 ml of 0.25M sucrose buffer and homogenized using a tight-fitting Teflon-glass homogenizer. The homogenate was centrifuged for 35 min at 8,000 rpm and the pellet was discarded. The supernatant was further centrifuged for 75 min at 25,000 rpm. The resulting pellets were re-suspended in the sucrose buffer (10 ml), and then the suspension was laid onto discontinuous density gradients consisting of 0.25M sucrose buffer and isolation medium containing 9% Ficoll (w/w). After being centrifuged for 3 hours and 15 minutes at 100,000×g, the materтal at the interface of sucrose buffer and Ficoll solution was collected and then centrifuged for 40 minutes at 100,000×g. The resulting pellets were re-suspended in 1 ml of 5 mM Hepes/Tris buffer (pH 6.1). This materтal was lyophilized and stored at –70° C. and used as an enzyme source of the in vitro enzyme reaction assay of proton pump.

1-2. Measurement of Inhibitory Effects on Proton Pump (H$^+$/K$^+$-ATPase) Activity The inhibitory effects of the compounds of the present invention against proton pump activity were evaluated in 96-well plate. In this assay, the K$^+$ specific H$^+$/K$^+$-ATPase activity was calculated based on the difference between the activity of H$^+$/K$^+$-ATPase activity with K$^+$ and without K$^+$ ion. In 96-well plate, 1% dimethylsulfoxide (DMSO) in buffer was added to negative and positive control groups and the diluted compounds of the present invention in buffer were added to test group. All assays were performed in 100 μl reaction volume at room temperature, and the hog gastric vesicle was kept in ice before use. At the beginning of the reaction, 10 μl of reaction buffer containing 1% DMSO was added to the negative and positive control groups and to each concentration of compounds in the test group. Then lyophilized vesicle in 5 mM Pipes/Tris buffer (pH 6.1) was pre-incubated in the presence of various concentrations of test compounds. After 5 minutes incubation, negative and positive buffers were respectively added to the previous reaction mixture. As the substrate, ATP was added to the reaction buffer, and incubated for 30 minutes at 37° C. Enzymatic activity was stopped by the addition of calorimetric reagent (2× malachite green, 1× ammonium molybdate, 1× polyvinyl alcohol, 2× H$_2$O) and the amount of mono phosphate (Pi) in the reaction was measured at 620 nm using the micro plate reader (Genios Pro, TECAN). The difference between the Pi production with K$^+$ and without K$^+$ is taken as K$^+$ stimulated H$^+$/K$^+$-ATPase activity. The IC$_{50}$s of test compounds were calculated from each % inhibition value of compounds using the method of Litchfield-Wilcoxon (*J. Pharmacol. Exp. Ther.* (1949) 96, 99). The results are shown in Table 1.

TABLE 1

| Example | IC$_{50}$ (uM) | Example | IC$_{50}$ (uM) |
|---|---|---|---|
| 2 | 0.41 | 3 | 0.058 |
| 4 | 0.15 | 5 | 0.45 |
| 7 | 0.38 | 15 | 0.14 |
| 16 | 0.18 | 17 | 0.43 |
| 34 | 1.459 | 35 | 0.846 |
| 43 | 0.13 | 45 | 0.071 |
| 68 | 0.212 | 89 | 0.321 |
| 91 | 0.209 | 108 | 0.424 |
| 111 | 0.025 | 112 | 0.151 |
| 113 | 0.327 | 114 | 0.027 |
| 115 | 0.142 | 116 | 0.048 |
| 117 | 0.046 | 118 | 0.332 |
| 119 | 0.405 | 120 | 0.444 |
| 126 | 0.397 | 140 | 0.24 |
| 141 | 0.064 | 143 | 0.3 |
| 144 | 0.2 | 146 | 0.11 |
| 147 | 0.2 | 149 | 0.21 |
| 150 | 0.34 | 151 | 0.34 |
| 152 | 0.17 | 155 | 0.4 |
| 156 | 0.31 | 157 | 0.38 |
| 158 | 0.27 | 159 | 0.09 |
| 175 | 0.08 | 176 | 0.26 |
| 181 | 0.36 | 183 | 0.22 |
| 184 | 0.24 | 185 | 0.32 |
| 198 | 0.064 | 204 | 0.21 |
| 205 | 0.33 | 208 | 0.094 |
| 209 | 0.066 | 210 | 0.054 |
| 213 | 0.31 | 214 | 0.29 |
| 215 | 0.42 | 216 | 0.26 |
| 219 | 1.24 | 220 | 0.43 |
| 221 | 0.63 | 223 | 0.44 |
| 225 | 0.35 | 226 | 0.07 |
| 227 | 0.073 | 228 | 0.133 |
| 229 | 0.24 | 230 | 0.092 |
| 231 | 0.138 | 242 | 0.1 |
| 243 | 0.09 | 244 | 0.09 |
| 245 | 0.1 | 246 | 0.11 |

TABLE 1-continued

| Example | IC$_{50}$ (uM) | Example | IC$_{50}$ (uM) |
|---|---|---|---|
| 247 | 0.09 | 249 | 0.05 |
| 251 | 0.46 | 253 | 0.17 |
| 256 | 0.31 | 257 | 0.27 |
| 258 | 0.33 | 262 | 0.22 |
| 263 | 0.075 | 264 | 0.49 |
| 266 | 0.14 | 267 | 0.11 |
| 268 | 0.13 | 270 | 0.45 |
| 272 | 0.22 | 274 | 0.42 |
| 275 | 0.36 | 277 | 0.129 |
| 278 | 0.39 | 279 | 0.231 |
| 280 | 0.345 | 281 | 0.292 |
| 283 | 1.743 | 284 | 0.267 |
| 289 | 1.339 | 296 | 5.076 |
| 299 | 0.35 | 300 | 0.173 |
| 301 | 0.384 | 304 | 0.915 |
| 325 | 1.98 | 326 | 0.306 |
| 350 | 0.21 | 353 | 0.49 |
| 354 | 0.15 | 360 | 0.278 |
| 402 | 0.063 | 403 | 0.07 |
| 404 | 0.095 | 405 | 0.073 |
| 406 | 0.189 | 407 | 0.113 |
| 408 | 0.089 | 409 | 0.093 |
| 410 | 0.099 | 411 | 0.284 |
| 416 | 0.12 | 417 | 0.37 |
| 418 | 0.29 | 442 | 0.1 |
| 444 | 0.122 | 445 | 0.46 |
| 446 | 0.39 | 447 | 0.46 |
| 448 | 0.23 | 449 | 0.087 |
| 450 | 0.27 | 453 | 0.34 |
| 455 | 0.4 | 468 | 0.19 |
| 469 | 0.052 | 470 | 0.32 |
| 471 | 0.23 | 473 | 0.47 |
| 474 | 0.11 | 475 | 0.3 |
| 477 | 0.3 | 479 | 1.14 |
| 480 | 0.032 | 481 | 0.059 |
| 482 | 0.36 | 483 | 0.33 |
| 484 | 0.0037 | 485 | 0.006 |
| 486 | 0.008 | 487 | 0.004 |
| 488 | 0.003 | 489 | 0.003 |
| 490 | 0.003 | 491 | 0.002 |
| 492 | 0.007 | 493 | 0.004 |
| 494 | 0.004 | 496 | 0.23 |
| 497 | 0.32 | 499 | 0.065 |
| 500 | 0.27 | 502 | 0.3 |
| 503 | 0.16 | 506 | 0.069 |
| 508 | 0.32 | 510 | 0.056 |
| 511 | 0.42 | 512 | 0.13 |
| 513 | 0.074 | 514 | 0.2 |
| 515 | 0.2 | 516 | 0.124 |
| 517 | 0.02 | 518 | 0.179 |
| 526 | 0.179 | 531 | 0.19 |
| 534 | 0.4 | 538 | 0.244 |
| 539 | 0.25 | 541 | 0.35 |
| 542 | 0.15 | 543 | 0.11 |
| 544 | 0.022 | 545 | 0.19 |
| 546 | 0.25 | 547 | 0.13 |
| 548 | 0.41 | 551 | 0.32 |
| 552 | 0.036 | 553 | 0.026 |
| 554 | 0.059 | 555 | 0.23 |
| 556 | 0.13 | 557 | 0.146 |
| 558 | 0.43 | 559 | 0.159 |
| 560 | 0.017 | 561 | 0.065 |
| 562 | 0.058 | 563 | 0.049 |
| 564 | 0.082 | 565 | 0.33 |
| 566 | 0.3 | 569 | 0.5 |
| 570 | 0.12 | 571 | 0.47 |
| 574 | 0.42 | 575 | 0.47 |
| 576 | 0.22 | 577 | 0.14 |
| 578 | 0.29 | 583 | 0.38 |
| 584 | 0.33 | 585 | 0.37 |
| 586 | 0.33 | 591 | 0.499 |
| 609 | 0.379 | 613 | 0.375 |
| 617 | 0.065 | 624 | 0.01 |
| 657 | 0.24 | 659 | 0.439 |
| 683 | 1.561 | 684 | 0.49 |
| 689 | 0.331 | 695 | 0.481 |
| 697 | 3.2 | 723 | 0.458 |
| 732 | 0.022 | 733 | 0.117 |
| 734 | 0.366 | 735 | 0.054 |
| 736 | 0.107 | 737 | 0.025 |
| 738 | 0.331 | 740 | 0.267 |
| 743 | 0.231 | 744 | 0.13 |
| 745 | 0.112 | 749 | 0.0015 |
| 750 | 0.298 | 754 | 4.049 |
| 757 | 0.03 | 758 | 0.316 |
| 760 | 0.373 | 761 | 0.125 |
| 762 | 0.35 | 764 | 0.044 |
| 765 | 0.356 | 769 | 0.103 |
| 771 | 0.036 | 772 | 0.546 |
| 776 | 0.085 | 777 | 0.0016 |
| 778 | 0.039 | 779 | 0.062 |
| 780 | 0.125 | 781 | 0.039 |
| 782 | 0.001 | 783 | 0.003 |
| 784 | 0.202 | 785 | 0.0007 |
| 786 | 0.015 | 787 | 0.0011 |
| 788 | 0.052 | 789 | 0.065 |
| 790 | 0.128 | 791 | 0.122 |
| 792 | 0.059 | 793 | 0.117 |
| 796 | 0.305 | 797 | 0.287 |
| 798 | 0.22 | 799 | 0.164 |
| 800 | 0.091 | 801 | 0.158 |
| 802 | 0.08 | 803 | 0.035 |
| 804 | 0.036 | 805 | 0.031 |
| 806 | 0.013 | 807 | 0.023 |
| 808 | 0.055 | 809 | 0.059 |
| 810 | 0.436 | 811 | 0.003 |
| 812 | 0.021 | 813 | 0.011 |
| 814 | 0.031 | 815 | 0.029 |
| 816 | 0.009 | 817 | 0.024 |
| 818 | 0.034 | 819 | 0.012 |
| 820 | 0.037 | 821 | 0.026 |
| 822 | 0.023 | 823 | 0.216 |
| 824 | 0.033 | 825 | 0.024 |
| 826 | 0.016 | 827 | 0.077 |
| 828 | 0.094 | 829 | 0.079 |
| 830 | 0.044 | 831 | 0.039 |
| 832 | 0.031 | 833 | 0.043 |
| 834 | 0.037 | 835 | 0.134 |
| 836 | 0.129 | 837 | 0.029 |
| 839 | 0.257 | 840 | 0.169 |
| 841 | 0.242 | 842 | 0.48 |
| 845 | 0.287 | 846 | 0.139 |
| 847 | 0.062 | 848 | 0.029 |
| 849 | 0.129 | 850 | 0.053 |
| 851 | 0.032 | 852 | 0.427 |
| 853 | 0.036 | 854 | 0.282 |
| 860 | 0.313 | 862 | 0.403 |
| 863 | 0.109 | 864 | 0.213 |
| 866 | 1.031 | 867 | 0.412 |
| 868 | 0.039 | 869 | 0.04 |
| 870 | 0.043 | 871 | 0.037 |
| 872 | 0.043 | 873 | 0.026 |
| 875 | 0.258 | 876 | 0.099 |
| 878 | 0.152 | 879 | 0.05 |
| 883 | 0.087 | 884 | 0.216 |
| 885 | 0.217 | 887 | 0.009 |
| 888 | 0.02 | 906 | 0.031 |
| 907 | 0.032 | 908 | 0.384 |
| 909 | 0.09 | 910 | 0.393 |

As shown in Table 1, the compounds of the present invention have excellent inhibitory effects on gastric $H^+/K^+$-ATPase.

TEST EXAMPLE 2

Inhibitory Effects on Basal Gastric Acid Secretion in Pylorus-Ligated Rats

Inhibitory effects of the compounds of the present invention on basal gastric acid secretion were performed according to Shay's rat model (Shay, H., et al., 1945, gastroenterology, 5, 43-61). Male Sprague Dawley (SD) rats (200±10 g body weight) were divided into 3 groups (n=5) and fasted for 24 hours with free access to water. Control group was orally administered with 0.5% methylcellulose alone and the other groups were orally administered with test compounds suspended in 0.5% methylcellulose solution at doses of 1, 3 and 10 mg/kg/5 ml one hour before pylorus ligation.

Under ether anesthesia, the abdomens of the rats were incised and then the pylorus was ligated. 5 hours after ligation, the animals were sacrificed, and the gastric contents were collected. The collected contents were centrifuged at 1,000×g for 10 minutes to obtain the gastric juice. Total acid output was measured by 0.01N NaOH volume (ueq/ml) for automatic titration of the gastric juice to pH 7.0 and the $ED_{50}$s of test compounds were calculated using the Litchfield-Wilcoxon method. % inhibitory activity was calculated from the following equation and the results are shown in Table 2.

% inhibitory activity of test compound=(total acid output of control group–total acid output of the group treated with test compounds)/total acid output of control group×100

TABLE 2

| Example | $ED_{50}$(mg/kg) | Example | $ED_{50}$(mg/kg) |
| --- | --- | --- | --- |
| 141 | 2.3 | 207 | 8.3 |
| 208 | 1.3 | 210 | 1.9 |
| 218 | 4.1 | 229 | 2.2 |
| 402 | 11.2 | 468 | 5.2 |
| 469 | 1.4 | 470 | 4.4 |
| 473 | 2.8 | 474 | 11.9 |
| 477 | 2 | 480 | 1.8 |
| 482 | 2.4 | 484 | 1.4 |
| 507 | 3.1 | 511 | 2.1 |
| 553 | 2.1 | 557 | 4.1 |
| 563 | 3.5 | | |

As shown in Table 2, the compounds of the present invention have potent inhibition activities against basal gastric acid secretion in pylorus-ligated rats.

TEST EXAMPLE 3

Reversible Inhibition of Hog Gastric $H^+/K^+$-ATPase 3-1. Preparation of Gastric Vesicles Gastric vesicles were prepared from hog fundic mucosa using the method of Saccomani et al. (Saccomani G, Stewart H B, Shqw D, Lewin M and Sachs G, Charactertzation of gastric mucosal membranes. IX. Fraction and purification of K-ATPase-containing vesicles by zonal centrifugation and free-flow electrophoresis techinque. Biochem. Biophy. Acta. (BBA)-Biomembranes 465, 311-330, 1977). This matertal was lyophilized and stored at −70° C. The protein content of gastric vesicles was determined by the Bradford method using bovine serum albumin as a standard (Bradford M M, A rapid and sensitive method for the quantitation of microgram quantities of protein utilizing the principle of protein-dye binding. Anal Biochem. 72, 248-254, 1976).

3-2. Determination of Reversible Inhibition of Hog Gastric $H^+/K^+$-ATPase

Activity of $H^+/K^+$-ATPase in hog microsome (lyophilized vesicle) was measured by the inorganic phosphate released from ATP using an one-step calorimetric detection method at the concentration at which the test compounds have 50% inhibition of the proton pump (Chan K M, Delfert D, and Junger K D, A direct calorimetric assay for $Ca^{2+}$-stimulated ATPase activity. Anal Biochem, 157, 375-380, 1986). The mode of action of test compounds on $H^+/K^+$-ATPase was investigated according to the Washout method (Beil W, Staar U, and Sewing K F, Substituted thieno[3,4-d]imidazoles, a novel group of $H^+/K$+-ATPase inhibitors. Differentiation of their inhibition charactertstics from those of omeprazole. Eur. J. Pharmacol., 187, 455-67, 1990).

Lyophilized vesicle in the solution of 5 mM Pipes/Tris buffer was pre-incubated in the presence of the test compound (the compound of Example 480) at the concentration at which it has 50% inhibition of the proton pump. The previous reaction buffer was added with 2 mM $MgCl_2$, 50 mM KCl, 5 uM Valinomycin, and 0.5 mM ATP and then incubated for 30 minutes at 37° C. The $H^+/K^+$-ATPase activity was measured using the calorimetric detection method and then the test sample was centrifuged at 100,000×g for 1 hr. The vesicles are present in the form of pellets in the test sample. The supernatant thereof was replaced with the same buffer not having the test compound. The test sample was pre-incubated for 5 minutes at room temperature and then incubated further for 30 minutes at 37° C. The $H^+/K^+$-ATPase activity was also measured using the colorimetric detection method. The $H^+/K^+$-ATPase activity before washout and after washout in the test sample was analyzed, in comparison with those in the non-treated group.

As a result, the compound of Example 480 inhibited $H^+/K^+$-ATPase activity by 50% before washout and did not inhibit $H^+/K^+$-ATPase activity after washout; the gastric $H^+/K^+$-ATPase activity by the compound of Example 480 was completely recovered to non-treated group level after washout. These results confirm that the compounds of formula (I) exhibited reversible inhibition of the gastric $H^+/K^+$-ATPase.

The invention claimed is:

1. A compound of the formula (I) or a pharmaceutically acceptable salt thereof:

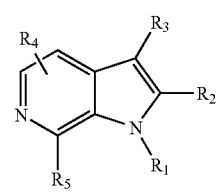

(I)

wherein:

$R_1$ is hydrogen; a straight or branched $C_1$-$C_7$ alkyl group, optionally substituted with one or more substiwents selected from the group consisting of hydroxy, halogen, cyano, $C_3$-$C_7$ cycloalkyl. $C_1$-$C_5$ alkoxy, $C_1$-$C_5$ alkoxycarbonyl, a straight or branched $C_1$-$C_5$ alkylcarbonyloxy, $C_1$-$C_3$ alkoxy-$C_1$-$C_3$ alkoxy, $C_1$-$C_3$ alkylsulfanyl, $C_2$-$C_5$ alkenyloxy, formyl, pyridyl, naphthyl, thiazolyl (the thizole ring is optionally substituted with one or more $C_1$-$C_3$ alkyl), thiophenyl (the thiophene ring is optionally substituted with one or more halogen), isoxazolyl (the isoxazole ring is optionally substituted with one or more $C_1$-$C_3$ alkyl), 1,3-dioxolanyl (the 1,3-dioxolane ring is optionally substituted with one or more $C_1$-$C_3$ alkyl), 1,3-dioxanyl, oxiranyl, and tetrahydropyranyl; a straight or branched $C_2$-$C_6$ alkenyl group optionally substituted with phenyl; a straight or branched $C_2$-$C_6$ alkynyl group; a $C_3$-$C_6$ dienyl group; or a —$(CH_2)_p$-phenyl group (p is 0, 1, 2, or 3 and the phenyl ring is optionally substituted with one or more substituents selected from the group consisting of halogen, cyano, a straight or branched $C_1$-$C_5$ alkyl, $C_1$-$C_3$ alkoxy, $C_1$-$C_3$ alkoxycarbonyl, trifluoro-$C_1$-$C_3$ alkyl, trifluoro-$C_1$-$C_3$ alkoxy, and $C_1$-$C_3$ alkylsulfonyl), $R_2$ is a straight or branched $C_1$-$C_6$ alkyl group, $R_3$ is hydrogen; a straight or branched $C_1$-$C_6$ alkyl group, optionally substituted with one or more substituents selected from the group consisting of hydroxy, $C_1$-$C_5$ alkoxy, $C_1$-$C_3$ alkylcarbonyloxy, cyano, morpholinyl, and mono-, di-, or tri-$C_1$-$C_3$ alkylamino; a halogen group; a cyano group; a formyl group; a $C_1$-$C_3$ alkylsulfanyl group; a $C_1$-$C_3$ alkylsulfonyl group; or a $C_1$-$C_3$ alkylsulfinyl group, $R_4$ is hydrogen; a straight or branched $C_1$-$C_6$ alkyl group, optionally substituted with one or more substituents selected from the group consisting of halogen, hydroxy, cyano, amino, $C_1$-$C_5$ alkylamino, $C_3$-$C_6$ cycloalkylamino, phenylamino (the phenyl ring is optionally substituted with one or more halogen), benzylamino (the benzyl ring is optionally substituted with one or more substituents selected from the group consisting of halogen and $C_1$-$C_3$ alkyl), morpholinyl, and piperazinyl (the piperazinyl ring is optionally substituted with $C_1$-$C_3$ alkyl); a straight or branched $C_2$-$C_6$ alkynyl group; a halogen group; a cyano group; a hydroxy group; an amino group; a morpholinyl group; a mercapto group; an aminosulfonyl group; a tetrazolyl group optionally substituted with one or more $C_1$-$C_3$ alkyl; a group of the formula (A)

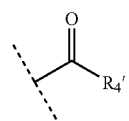

(A)

wherein, $R_4'$ is hydrogen, a hydroxy group, a $C_1$-$C_5$ alkyl group, a $C_1$-$C_3$ alkoxy group, a $C_3$-$C_6$ cycloalkyl group, an imidazolyl group, a morpholinyl group, a thiomorpholinyl group, a pyrrolidyl group, a tetrahydropyridyl group, a piperazinyl group (the piperazinyl ring is optionally substituted with $C_1$-$C_3$ alkyl or phenyl), or a piperidinyl group (the piperidinyl ring is optionally substituted with $C_1$-$C_3$ alkyl, hydroxy, or hydroxy-$C_1$-$C_3$ alkyl); or a group of formula (B)

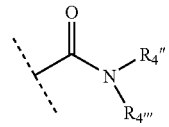

(B)

wherein, $R_4''$ is hydrogen or a $C_1$-$C_3$ alkyl group and $R_4'''$ is hydrogen, a straight or branched $C_1$-$C_5$ alkyl group, a $C_2$-$C_5$ alkenyl group, a $C_3$-$C_6$ cycloalkyl group, a hydroxy-$C_1$-$C_3$ alkyl group, a trifluoro-$C_1$-$C_3$ alkyl group, a benzyl group (the benzyl ring is optionally one or more substituted with $C_1$-$C_3$ alkyl or halogen), or a piperonyl group, and $R_5$ is a 1,2,3,4-tetrahydroisoquinolinyl group, optionally substituted with one or more substituents selected from the group consisting of $C_1$-$C_5$ alkyl, $C_1$-$C_3$ alkoxy, halogen, and $C_3$-$C_6$ cycloalkyl; a naphthyl group; a phenyl-$C_2$-$C_5$ alkenyl group; an oxo-1,2,3,4-tetrahydroisoquinolinyl group; a phenoxymethyl group (the phenyl ring is optionally substituted with one or more substituents selected from the group consisting of halogen and $C_1$-$C_3$ alkyl); a —$(CH_2)_q$-phenyl group (q is 0, 1, 2, or 3 and the phenyl ring is optionally substituted with one or more substituents selected from the group consisting of halogen, $C_1$-$C_3$ alkyl, $C_1$-$C_3$ alkoxy, $C_2$-$C_5$ alkenyl, and $C_1$-$C_5$ alkylsulfanyl); or a group of formula (C)

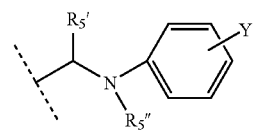

(C)

wherein, Y is hydrogen or a halogen group, $R_5'$ is hydrogen, a $C_1$-$C_3$ alkyl group, a benzyl group, or a cyano group, and $R_5''$ is hydrogen, or $C_1$-$C_5$ alkyl group.

2. The compound or a pharmaceutically acceptable salt thereof according to claim 1, wherein $R_1$ is hydrogen; a straight or branched $C_1$-$C_7$ alkyl group; a $C_1$-$C_3$ alkyl group substituted with one or more substituents selected from the group consisting of hydroxy, halogen, cyano, cyclopropyl, cyclobutyl, cyclohexyl, methoxy, ethoxy, methoxycarbonyl, methylcarbonyloxy, tert-butylcarbonyloxy, methoxyethoxy, methylsulfanyl, allyloxy, formyl, pyridyl, naphthyl, methylthiazolyl, chlorothiophenyl, dimethylisoxazolyl, 1,3-dioxolanyl, 1,3-dioxanyl, oxiranyl, and tetrahydropyranyl; a chlorobutyl group; a (methyl-1,3-dioxolanyl)propyl group; a straight or branched $C_2$-$C_6$ alkenyl group; a phenylallyl group; a straight or branched $C_2$-$C_6$ alkynyl group; a propa-1,2-dienyl group; or a —$(CH_2)_n$-phenyl group (n is 1, 2, or 3 and the phenyl ring is optionally substituted with one or more substituents selected from the group consisting of halogen, cyano, $C_1$-$C_5$ alkyl, $C_1$-$C_3$ alkoxy, $C_1$-$C_3$ alkoxycarbonyl, trifluoromethyl, trifluoromethoxy, and methylsulfonyl), $R_2$ is a methyl group, $R_3$ is hydrogen; a straight or branched $C_1$-$C_6$ alkyl group; a $C_1$-$C_3$ alkyl group substituted with one or more substituents selected from the group consisting of hydroxy, ethoxy, methylcarbonyloxy, cyano, morpholinyl, dimethylamino, and trimethylamino; a bromo group; a cyano group; a formyl group; a methylsulfanyl group; a methylsulfonyl group; or a methylsulfinyl group, $R_4$ is hydrogen; a $C_1$-$C_3$ alkyl group substituted with one or more substituents selected from the group consisting of halogen, hydroxy, cyano, amino, $C_1$-$C_5$ alkylamino, cyclopropylamino, cyclobutylamino, fluorophenylamino, chlorobenzylamino, methylbenzylamino, morpholinyl, and methylpiperazinyl; a ethynyl group; a halogen group; a cyano group; a hydroxy group; an amino group; a morpholinyl group; a mercapto group; an aminosulfonyl group; a tetrazolyl group; a methyltetrazolyl group; an ethyltetrazolyl group; a group of the formula (A)

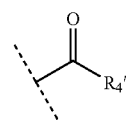

(A)

wherein, $R_4'$ is hydrogen, a hydroxy group, a $C_1$-$C_5$ alkyl group, a $C_1$-$C_3$ alkoxy group, a cyclohexyl group, an imidazolyl group, a morpholinyl group, a thiomorpholinyl group, a pyrrolidyl group, a dihydropyridyl group, a piperazinyl group, a methylpiperazinyl group, an ethylpiperazinyl group, a phenylpiperazinyl group, or a piperidinyl group (the piperidinyl ring is optionally substituted with $C_1$-$C_3$ alkyl, hydroxy, or hydroxy-$C_1$-$C_3$ alkyl); or a group of formula (B)

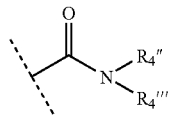
(B)

wherein, $R_4''$ is hydrogen or a $C_1$-$C_3$ alkyl group and $R_4'''$ is hydrogen, a $C_1$-$C_5$ alkyl group, a $C_2$-$C_5$ alkenyl group, a $C_3$-$C_6$ cycloalkyl group, a hydroxyethyl group, a trifluoro-$C_1$-$C_3$ alkyl group, a chlorobenzyl group, a methylbenzyl group, or a piperonyl group, and $R_5$ is a 1,2,3,4-tetrahydroisoquinolinyl group, optionally substituted with one or more substituents selected from the group consisting of $C_1$-$C_3$ alkyl, $C_1$-$C_3$ alkoxy, halogen, and $C_3$-$C_6$ cycloalkyl; a naphthyl group; a phenylethenyl group; a 3,4-dihydro-2H-isoquinolin-1-one-2-yl group; a phenoxymethyl group substituted with one or more substituents selected from the group consisting of halogen and $C_1$-$C_3$ alkyl; a —$(CH_2)_m$-phenyl group (m is 0, 1, 2, or 3 and the phenyl ring is optionally substituted with one or more substituents selected from the group consisting of halogen, $C_1$-$C_3$ alkyl, $C_1$-$C_3$ alkoxy, $C_2$-$C_5$ alkenyl, and methylsulfanyl); or a group of formula (C)

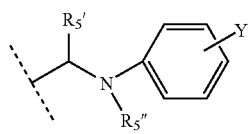
(C)

wherein, Y is hydrogen or a halogen group, $R_5'$ is hydrogen, a $C_1$-$C_3$ alkyl group, a benzyl group, or a cyano group, and $R_5''$ is hydrogen, or $C_1$-$C_5$ alkyl group.

3. The compound or a pharmaceutically acceptable salt thereof according to claim 1, which is selected from the group consisting of:
    7-(4-fluorophenoxymethyl)-2,3-dimethyl-1H-pyrrolo[2,3-c]pyridine;
    1-allyl-7-(4-fluorophenoxymethyl)-2,3-dimethyl-1H-pyrrolo[2,3-c]pyridine hydrochloride;
    1-benzyl-7-(4-fluorophenoxymethyl)-2,3-dimethyl-1H-pyrrolo[2,3-c]pyridine hydrochloride;
    7-(4-fluorophenoxymethyl)-1-(3-methoxybenzyl)-2,3-dimethyl-1H-pyrrolo[2,3-c]pyridine hydrochloride;
    7-(4-fluorophenoxymethyl)-2,3-dimethyl-1-(4-methylbenzyl)-1H-pyrrolo[2,3-c]pyridine hydrochloride;
    7-(4-fluorophenoxymethyl)-1-(2-methoxyethyl)-2,3-dimethyl-1H-pyrrolo[2,3-c]pyridine hydrochloride;
    1-cyclopropylmethyl-7-(4-fluorophenoxymethyl)-2,3-dimethyl-1H-pyrrolo[2,3-c]pyridine hydrochloride;
    7-(4-fluorophenoxymethyl)-2,3-dimethyl-1-propyl-1H-pyrrobo[2,3-c]pyridine hydrochloride;
    1-(2-fluorobenzyl)-7-(4-fluorophenoxymethyl)-2,3-dimethyl-1H-pyrrolo[2,3-c]pyridine hydrochloride;
    1-ethyl-7-(4-fluorophenoxymethyl)-2,3-dimethyl-1H-pyrrolo[2,3-c]pyridine hydrochloride;
    1-(4-fluorobenzyl)-7-(4-fluorophenoxymethyl)-2,3-dimethyl-1H-pyrrolo[2,3-c]pyridine hydrochloride;
    7-(4-fluorophenoxymethyl)-2,3-dimethyl-1-(3-methylbut-2-enyl)-1H-pyrrolo[2,3-c]pyridine hydrochloride;
    7-(4-fluorophenoxymethyl)-2,3-dimethyl-1-(prop-2-ynyl)-1H-pyrrolo[2,3-c]pyridine hydrochloride;
    2,3-dimethyl-7-(4-methylphenoxymethyl)-1H-pyrrolo[2,3-c]pyridine;
    1-benzyl-2,3-dimethyl-7-(p-tolyloxymethyl)-1H-pyrrolo[2,3-c]pyridine hydrochloride;
    1-(3-methoxybenzyl)-2,3-dimethyl-7-(p-tolyloxymethyl)-1H-pyrrolo[2,3-c]pyridine hydrochloride;
    2,3-dimethyl-1-(4-methylbenzyl)-7-(p-tolyloxymethyl)-1H-pyrrolo[2,3-c]pyridine hydrochloride;
    1-cyclopropylmethyl-2,3-dimethyl-7-(p-tolyloxymethyl)-1H-pyrrolo[2,3-c]pyridine hydrochloride;
    1-(4-fluorobenzyl)-2,3-dimethyl-7-(p-tolyloxymethyl)-1H-pyrrolo[2,3-c]pyridine hydrochloride;
    1-(4-chlorobenzyl)-2,3-dimethyl-7-(p-tolyloxymethyl)-1H-pyrrolo[2,3-c]pyridine hydrochloride;
    1-(3,4-dichlorobenzyl)-2,3-dimethyl-7-(p-tolyloxymethyl)-1H-pyrrolo[2,3-c]pyridine hydrochloride;
    2,3-dimethyl-1-(3-methylbenzyl)-7-(p-tolyloxymethyl)-1H-pyrrolo[2,3-c]pyridine hydrochloride;
    2,3-dimethyl-1-(2-methylthiazol-4-ylmethyl)-7-(p-tolyloxymethyl)-1H-pyrrolo[2,3-c]pyridine hydrochloride;
    2,3-dimethyl-1-(3-methylbut-2-enyl)-7-(p-tolyloxymethyl)-1H-pyrrolo[2,3-c]pyridine hydrochloride;
    1-(2-methoxyethyl)-2,3-dimethyl-7-(p-tolyloxymethyl)-1H-pyrrolo[2,3-c]pyridine hydrochloride;
    2,3-dimethyl-1-propyl-7-(p-tolyloxymethyl)-1H-pyrrolo[2,3-c]pyridine hydrochloride;
    1-ethyl-2,3-dimethyl-7-(p-tolyloxymethyl)-1H-pyrrolo[2,3-c]pyridine hydrochloride;
    2,3-dimethyl-1-(2-methylbenzyl)-7-(p-tolyloxymethyl)-1H-pyrrolo[2,3-c]pyridine hydrochloride;
    1-(4-tert-butylbenzyl)-2,3-dimethyl-7-(p-tolyloxymethyl)-1H-pyrrolo[2,3-c]pyridine hydrochloride;
    2,3-dimethyl-1-(2,5-dimethylbenzyl)-7-(p-tolyloxymethyl)-1H-pyrrolo[2,3-c]pyridine hydrochloride;
    2,3-dimethyl-7-(p-tolyloxymethyl)-1-(4-trifluoromethylbenzyl)-1H-pyrrolo[2,3-c]pyridine hydrochloride;
    7-(2,4-difluorophenoxymethyl)-2,3-dimethyl-1H-pyrrolo[2,3-c]pyridine;
    7-(2,4-difluorophenoxymethyl)-2,3-dimethyl-1-propyl-1H-pyrrolo[2,3-c]pyridine hydrochloride;
    7-(2,4-difluorophenoxymethyl)-1-(2-methoxyethyl)-2,3-dimethyl-1H-pyrrolo[2,3-c]pyridine hydrochloride;
    1-cyclopropylmethyl-7-(2,4-difluorophenoxymethyl)-2,3-dimethyl-1H-pyrrolo[2,3-c]pyridine hydrochloride;
    1-ethyl-7-(2,4-difluorophenoxymethyl)-2,3-dimethyl-1H-pyrrolo[2,3-c]pyridine hydrochloride;
    1-allyl-7-(2,4-difluorophenoxymethyl)-2,3-dimethyl-1H-pyrrolo[2,3-c]pyridine hydrochloride;
    7-(2,4-difluorophenoxymethyl)-2,3-dimethyl-1-(3-methylbut-2-enyl)-1H-pyrrolo[2,3-c]pyridine hydrochloride;
    7-(2,4-difluorophenoxymethyl)-1,2,3-trimethyl-1H-pyrrolo[2,3-c]pyridine hydrochloride;
    1-(4-fluorobenzyl)-7-(2,4-difluorophenoxymethyl)-2,3-dimethyl-1H-pyrrolo[2,3-c]pyridine hydrochloride;
    7-(4-chlorophenoxymethyl)-2,3-dimethyl-1H-pyrrolo[2,3-c]pyridine;
    7-(4-chlorophenoxymethyl)-2,3-dimethyl-1H-pyrrolo[2,3-c]pyridine hydrochloride;

1-benzyl-7-(4-chlorophenoxymethyl)-2,3-dimethyl-1H-pyrrolo[2,3-c]pyridine hydrochloride;
7-(4-chlorophenoxymethyl)-1-cyclopropylmethyl-2,3-dimethyl-1H-pyrrolo[2,3-c]pyridine hydrochloride;
7-(4-chlorophenoxymethyl)-1-(3-methoxybenzyl)-2,3-dimethyl-1H-pyrrolo[2,3-c]pyridine hydrochloride;
7-(4-chlorophenoxymethyl)-2,3-dimethyl-1-propyl-1H-pyrrolo[2,3-c]pyridine hydrochloride;
7-(4-chlorophenoxymethyl)-1-ethyl-2,3-dimethyl-1H-pyrrolo[2,3-c]pyridine hydrochloride;
7-(4-chlorophenoxymethyl)-2,3-dimethyl-1-(3-methylbut-2-enyl)-1H-pyrrolo[2,3-c]pyridine hydrochloride;
7-(4-chlorophenoxymethyl)-1-(2-fluorobenzyl )-2,3-dimethyl-1H-pyrrolo[2,3-c]pyridine hydrochloride;
7-(4-chlorophenoxymethyl)-1,2,3-trimethyl-1H-pyrrolo[2,3-c]pyridine hydrochloride;
7-(4-chlorophenoxymethyl)-2,3-dimethyl-1-(4-methylbenzyl)-1H-pyrrolo[2,3-c]pyridine hydrochloride;
7-(4-chlorophenoxymethyl)-1-(4-fluorobenzyl)-2,3-dimethyl-1H-pyrrolo[2,3-c]pyridine hydrochloride;
7-(2-chlorophenoxymethyl)-2,3-dimethyl-1H-pyrrolo[2,3-c]pyridine;
1-allyl-7-(2-chlorophenoxymethyl)-2,3-dimethyl-1H-pyrrolo[2,3-c]pyridine hydrochloride;
7-(2-chlorophenoxymethyl)-1-(2-methoxyethyl)-2,3-dimethyl-1H-pyrrolo[2,3-c]pyridine hydrochloride;
7-(2-chlorophenoxymethyl)-1-cyclopropvlmethyl-2,3-dimethyl-1H-pyrrolo[2,3-c]pyridine hydrochloride;
7-(2-chlorophenoxymethyl)-2,3-dimethyl-1-(4-methylbenzyl)-1H-pyrrolo[2,3-c]pyridine hydrochloride;
7-(2-chlorophenoxymethyl)-1-(4-fluorobenzyl)-2,3-dimethyl-1H-pyrrolo[2,3-c]pyridine hydrochloride;
1-benzyl-7-(2-chlorophenoxymethyl)-2,3-dimethyl-1H-pyrrolo[2,3-c]pyridine hydrochloride;
7-(2-chlorophenoxymethyl)-2,3-dimethyl-1-(3-methylbut-2-enyl)-1H-pyrrolo[2,3-c]pyridine hydrochloride;
7-(2-chlorophenoxymethyl)-2,3-dimethyl-1-propyl-1H-pyrrolo[2,3-c]pyridine hydrochloride;
7-(2-chlorophenoxymethyl)-1,2,3-trimethyl-1H-pyrrolo[2,3-c]pyridine hydrochloride;
7-(2-chlorophenoxymethyl)-1-ethyl-2,3-dimethyl-1H-pyrrolo[2,3-c]pyridine hydrochloride;
7-(2-chlorophenoxymethyl)-1-(3-methoxybenzyl)-2,3-dimethyl-1H-pyrrolo[2,3-c]pyridine hydrochloride;
2,3-dimethyl-7-(2,4-dimethylphenoxymethyl)-1H-pyrrolo[2,3-c]pyridine;
1-allyl-2,3-dimethyl-7-(2,4-dimethylphenoxymethyl)-1H-pyrrolo[2,3-c]pyridine hydrochloride;
1-benzyl-2,3-dimethyl-7-(2,4-dimethylphenoxymethyl)-1H-pyrrolo[2,3-c]pyridine hydrochloride;
1-(3-methoxybenzyl)-2,3-dimethyl-7-(2,4-dimethylphenoxymethyl)-1H-pyrrolo[2,3-c]pyridine hydrochloride;
1-cyclopropylmethyl-2,3-dimethyl-7-(2,4-dimethylphenoxymethyl)-1H-pyrrolo[2,3-c]pyridine hydrochloride;
2,3-dimethyl-1-(3-methylbut-2-enyl)-7-(2,4-dimethylphenoxymethyl)-1H-pyrrolo[2,3-c]pyridine hydrochloride;
1-(2-methoxyethyl)-2,3-dimethyl-7-(2,4-dimethylphenoxymethyl)-1H-pyrrolo[2,3-c]pyridine hydrochloride;
2,3-dimethyl-7-(2,4-dimethylphenoxymethyl)-1-propyl-1H-pyrrolo[2,3-c]pyridine hydrochloride;
1-(2-fluorobenzyl)-2,3-dimethyl-7-(2,4-dimethylphenoxymethyl)-1H-pyrrolo[2,3-c]pyridine hydrochloride;
7-(2,4-dimethylphenoxymethyl)-1,2,3-trimethyl-1H-pyrrolo[2,3-c]pyridine hydrochloride;
1-ethyl-2,3-dimethyl-7-(2,4-dimethylphenoxymethyl)-1H-pyrrolo[2,3-c]pyridine hydrochloride
2,3-dimethyl-1-(4-methylbenzyl)-7-(2,4-dimethylphenoxymethyl)-1H-pyrrolo[2,3-c]pyridine hydrochloride;
1-(4-fluorobenzyl)-2,3-dimethyl-7-(2,4-dimethylphenoxymethyl)-1H-pyrrolo[2,3-c]pyridine hydrochloride;
7-(3,4-dichlorophenoxymethyl)-1-(2-methoxyethyl )-2,3-dimethyl-1H-pyrrolo[2,3-c]pyridine hydrochloride;
7-(3,4-dichlorophenoxymethyl)-1-ethyl-2,3-dimethyl-1H-pyrrolo[2,3-c]pyridine hydrochloride;
1-allyl-7-(3,4-dichlorophenoxymethyl)-2,3-dimethyl-1H-pyrrolo[2,3-c]pyridine hydrochloride;
7-(3,4-dichlorophenoxymethyl)-2,3-dimethyl-1-(4-methylbenzyl)-1H-pyrrolo[2,3-c]pyridine hydrochloride;
7-(3,4-dichlorophenoxymethyl)-1-(4-fluorobenzyl)-2,3-dimethyl-1H-pyrrolo[2,3-c]pyridine hydrochloride;
1-benzyl-7-(3,4-dichlorophenoxymethyl)-2,3-dimethyl-1H-pyrrolo[2,3-c]pyridine hydrochloride;
7-(3,4-dichlorophenoxymethyl)-2,3-dimethyl-1-(3-methylbut-2-enyl)-1H-pyrrolo[2,3-c]pyridine hydrochloride;
1-cyclopropylmethyl-7-(3,4-dichlorophenoxymethyl)-2,3-dimethyl-1H-pyrrolo[2,3-c]pyridine hydrochloride;
7-(3,4-dichlorophenoxymethyl)-2,3-dimethyl-1-propyl-1H-pyrrolo[2,3-c]pyridine hydrochloride;
7-(3,4-dichlorophenoxymethyl)-1,2,3-trimethyl-1H-pyrrolo[2,3-c]pyridine hydrochloride;
N-(1-allyl-2,3-dimethyl-1H-pyrrolo[2,3-c]pyridin-7-ylmethyl)-4-fluorophenylamine hydrochloride;
N-(1-benzyl-2,3-dimethyl-1H-pyrrolo[2,3-c]pyridin-7-ylmethyl)-4-fluorophenylamine hydrochloride;
N-(1-cyclopropylmethyl-2,3-dimethyl-1H-pyrrolo[2,3-c]pyridin-7-ylmethyl)-4-fluorophenylamine hydrochloride;
N-[1-(3-fluorobenzyl)-2,3-dimethyl-1H-pyrrolo[2,3-c]pyridin-7-ylmethyl]-4-fluorophenylamine hydrochloride;
N-[1-(3-methoxybenzyl)-2,3-dimethyl-1H-pyrrolo[2,3-c]pyridin-7-ylmethyl]-4-fluorophenylamine hydrochloride;
N-[1-(4-chlorobenzyl)-2,3-dimethyl-1H-pyrrolo[2,3-c]pyridin-7-ylmethyl]-4-fluorophenylamine hydrochloride;
N-[1-(2-methoxyethyl)-2,3-dimethyl-1H-pyrrolo[2,3-c]pyridin-7-ylmethyl]-4-fluorophenylamine hydrochloride;
N-[2,3-dimethyl-1-(2-methylbenzyl)-1H-pyrrolo[2,3-c]pyridin-7-ylmethyl]-4-fluorophenylamine hydrochloride;
N-[1-(4-tert-butylbenzyl)-2,3-dimethyl-1H-pyrrolo[2,3-c]pyridin-7-ylmethyl]-4-fluorophenylamine hydrochloride;
N-[1-(2-chlorobenzyl)-2,3-dimethyl-1H-pyrrolo[2,3-c]pyridin-7-ylmethyl]-4-fluorophenylamine hydrochloride;
N-[1-(3,4-dichlorobenzyl)-2,3-dimethyl-1H-pyrrolo[2,3-c]pyridin-7-ylmethyl]-4-fluorophenylamine hydrochloride;
N-[1-(2,5-dimethylbenzyl)-2,3-dimethyl-1H-pyrrolo[2,3-c]pyridin-7-ylmethyl]-4-fluorophenylamine hydrochloride;
N-(1-ethyl-2,3-dimethyl-1H-pyrrolo[2,3-c]pyridin-7-ylmethyl)-4-fluorophenylamine hydrochloride;
N-(2,3-dimethyl-1-propyl-1H-pyrrolo[2,3-c]pyridin-7-ylmethyl)-4-fluorophenylamine hydrochloride;
N-[2,3-dimethyl-1-(3-methylbenzyl)-1H-pyrrolo[2,3-c]pyridin-7-ylmethyl-4-fluorophenylamine hydrochloride;

N-[2,3-dimethyl-1(propa-1,2-dienyl)-1H-pyrrolo[2,3-c]pyridin-7-ylmethyl]-4-fluorophenylamine hydrochloride;
N-[2,3-dimethyl-1-(4-trifluoromethylbenzyl)-1H-pyrrolo[2,3-c]pyridin-7-ylmethyl]-4-fluorophenylamine hydrochloride;
N-(1,2,3-trimethyl-1H-pyrrolo[2,3-c]pyridin-7-ylmethyl)-4-fluorophenylamine hydrochloride;
N-[1-(2-ethoxyethyl)-2,3-dimethyl-1H-pyrrolo[2,3-c]pyridin-7-ylmethyl]-4-fluorophenylamine hydrochloride;
N-[2,3-dimethyl-1-(4-methylbenzyl)-1H-pyrrolo[2,3-c]pyridin-7-ylmethyl]-4-fluorophenylamine hydrochloride;
N-(2,3-dimethyl-1-propenyl-1H-pyrrolo[2,3-c]pyridin-7-ylmethyl)-4-fluorophenylamine hydrochloride;
N-(2,3-dimethyl-1H-pyrrolo[2,3-c]pyridin-7-ylmethyl)-4-fluorophenylamine hydrochloride;
N-(2,3-dimethyl-1H-pyrrolo[2,3-c]pyridin-7-ylmethyl)-N-(4-fluorophenyl)-methylamine
N-(1-benzyl-2,3-dimethyl-1H-pyrrolo[2,3-c]pyridin-7-ylmethyl)-N-(4-fluorophenyl)-methylamine hydrochloride;
N-(1-cyclopropylmethyl-2,3-dimethyl-1H-pyrrolo[2,3-c]pyridin-7-ylmethyl)-N-(4-fluorophenyl)-methylamine hydrochloride;
N-[1-(4-chlorobenzyl)-2,3-dimethyl-1H-pyrrolo[2,3-c]pyridin-7-ylmethyl]-N-(4-fluorophenyl)-methylamine hydrochloride;
N-[1-(3-fluorobenzyl)-2,3-dimethyl-1H-pyrrolo[2,3-c]pyridin-7-ylmethyl]-N-(4-fluorophenyl)-methylamine hydrochloride;
N-[1-(2-fluorobenzyl)-2,3-dimethyl-1H-pyrrolo[2,3-c]pyridin-7-ylmethyl]-N-(4-fluorophenyl)-methylamine hydrochloride;
N-(4-fluorophenyl)-N-[1-(3-methoxybenzyl)-2,3-dimethyl-1H-pyrrolo[2,3-c]pyridin-7-ylmethyl]-methylamine hydrochloride;
N-[2,3-dimethyl-1-(4-methylbenzyl)-1H-pyrrolo[2,3-c]pyridin-7-ylmethyl]-N-(4-fluorophenyl)-methylamine hydrochloride;
N-[1-(4-fluorobenzyl)-2,3-dimethyl-1H-pyrrolo[2,3-c]pyridin-7-ylmethyl]-N-(4-fluorophenyl)-methylamine hydrochloride;
N-[2,3-dimethyl-1-(3-methylbut-2-enyl)-1H-pyrrolo[2,3-c]pyridin-7-ylmethyl]-N-(4-fluorophenyl)-methylamine hydrochloride;
N-(4-fluorophenyl)-N-[1-(2-methoxyethyl)-2,3-dimethyl-1H-pyrrolo[2,3-c]pyridin-7-ylmethyl]-methylamine hydrochloride;
N-[1-(2-chlorobenzyl)-2,3-dimethyl-1H-pyrrolo[2,3-c]pyridin-7-ylmethyl]-N-(4-fluorophenyl)-methylamine hydrochloride;
N-[1-(3,4-dichlorobenzyl)-2,3-dimethyl-1H-pyrrolo[2,3-c]pyridin-7-ylmethyl]-N-(4-fluorophenyl)-methylamine hydrochloride;
N-(1-ethyl-2,3-dimethyl-1H-pyrrolo[2,3-c]pyridin-7-ylmethyl)-N-(4-fluorophenyl)-methylamine hydrochloride;
N-(2,3-dimethyl-1-propyl-1H-pyrrolo[2,3-c]pyridin-7-ylmethyl)-N-(4-fluorophenyl)-methylamine hydrochloride;
N-(4-fluorophenyl)-N-[1-(4-methoxybenzyl)-2,3-dimethyl-1H-pyrrolo[2,3-c]pyridin-7-ylmethyl]-methylamine hydrochloride;
N-[2,3-dimethyl-1-(3-methylbenzyl)-1H-pyrrolo[2,3-c]pyridin-7-yl methyl]-N-(4-fluorophenyl)-methylamine hydrochloride;
N-[2,3-dimethyl-1-(propa-1,2-dienyl)-1H-pyrrolo[2,3-c]pyridin-7-ylmethyl]-N-(4-fluorophenyl)-methylamine hydrochloride;
N-(11-allyl-2,3-dimethyl-1H-pyrrolo[2,3-c]pyridin-7-ylmethyl)-N-(4-fluorophenyl)-methylamine hydrochloride;
N-[2,3-dimethyl-1-(3,4-dimethylbenzyl)-1H-pyrrolo[2,3-c]pyridin-7-ylmethyl]-N-(4-fluorophenyl)-methylamine hydrochloride;
N-[2,3-dimethyl-1-(2-methylbenzyl)-1H-pyrrolo[2,3-c]pyridin-7-ylmethyl]-N-(4-fluorophenyl)-methylamine hydrochloride;
N-[1-(4-tert-butylbenzyl)-2,3-dimethyl-1H-pyrrolo[2,3-c]pyridin-7-ylmethyl]-N-(4-fluorophenyl)-methylamine hydrochloride;
N-[1-(2,5-dimethylbenzyl)-2,3-dimethyl-1H-pyrrolo[2,3-c]pyridin-7-ylmethyl]-N-(4-fluorophenyl)-methylamine hydrochloride:
N-(4-fluorophenyl)-N-(1,2,3-trimethyl-1H-pyrrolo[2,3-c]pyridin-7-ylmethyl)-methylamine hydrochloride;
N-[1-(2-ethoxyethyl)-2,3-dimethyl-1H-pyrrolo[2,3-c]pyridin-7-ylmethyl]-N-(4-fluorophenyl)-methylamine hydrochloride;
N-[1-(1-allyl-2,3-dimethyl-1H-pyrrolo[2,3-c]pyridin-7-yl)-ethyl]-4-fluorophenylamine hydrochloride;
N-[1-(1-allyl-2,3-dimethyl-1H-pyrrolo[2,3-c]pyridin-7-yl)-2-phenylethyl]-4-fluorophenylamine hydrochloride;
(1-allyl-2,3-dimethyl-1H-pyrrolo[2,3-c]pyridin-7-yl)-(4-fluorophenylamino)-acetonitrile hydrochloride;
2,3-dimethyl-7-(4-vinylphenyl)-1H-pyrrolo[2,3-c]pyridine;
1-(3-fluorobenzyl)-2,3-dimethyl-7-(4-vinylphenyl)-1H-pyrrolo[2,3-c]pyridine hydrochloride;
2,3-dimethyl-1-(4-methylbenzyl)-7-(4-vinylphenyl)-1H-pyrrolo[2,3-c]pyridine hydrochloride;
1-allyl-2,3-dimethyl-7-(4-vinylphenyl)-1H-pyrrolo[2,3-c]pyridine hydrochloride;
1-benzyl-2,3-dimethyl-7-(4-vinylphenyl)-1H-pyrrolo[2,3-c]pyridine hydrochloride;
1-(2-methoxyethyl)-2,3-dimethyl-7-(4-vinylphenyl)-1H-pyrrolo[2,3-c]pyridine hydrochloride;
1-cyclopropylmethyl-2,3-dimethyl-7-(4-vinylphenyl)-1H-pyrrolo[2,3-c]pyridine hydrochloride;
2,3-dimethyl-1-(prop-2-ynyl)-7-(4-vinylphenyl)-1H-pyrrolo[2,3-c]pyridine hydrochloride;
2,3-dimethyl-1-(2,5-dimethylbenzyl)-7-(4-vinylphenyl)-1H-pyrrolo[2,3-c]pyridine hydrochloride;
1-ethyl-2,3-dimethyl-7-(4-vinylphenyl)-1H-pyrrolo[2,3-c]pyridine hydrochloride;
2,3-dimethyl-1-propyl-7-(4-vinylphenyl)-1H-pyrrolo[2,3-c]pyridine hydrochloride;
2,3-dimethyl-1-(3-methoxybenzyl)-7-(4-vinylphenyl)-1H-pyrrolo[2,3-c]pyridine hydrochloride;
2,3-dimethyl-1-(4-methoxybenzyl)-7-(4-vinylphenyl)-1H-pyrrolo[2,3-c]pyridine hydrochloride;
2,3-dimethyl-1-(3-methylbenzyl)-7-(4-vinylphenyl)-1H-pyrrolo[2,3-c]pyridine hydrochloride;
2,3-dimethyl-1-(3-methylbutyl)-7-(4-vinylphenyl)-1H-pyrrolo[2,3-c]pyridine hydrochloride;
2,3-dimethyl-1-(naphthalen-2-ylmethyl)-7-(4-vinylphenyl)-1H-pyrrolo[2,3-c]pyridine hydrochloride;
2,3-dimethyl-1-(4-fluorobenzyl)-7-(4-vinylphenyl)-1H-pyrrolo[2,3-c]pyridine hydrochloride;
2,3-dimethyl-1-(2-fluorobenzyl)-7-(4-vinylphenyl)-1H-pyrrolo[2,3-c]pyridine hydrochloride;

1-(4-tert-butylbenzyl)-2,3-dimethyl-7-(4-vinylphenyl)-1H-pyrrolo[2,3-c]pyridine hydrochloride;
2,3-dimethyl-1-(3-methylbut-2-enyl)-7-(4-vinylphenyl)-1H-pyrrolo[2,3-c]pyridine hydrochloride;
2,3-dimethyl-7-(4-methylsulfanylphenyl)-1H-pyrrolo[2,3-c]pyridine
1-allyl-2,3-dimethyl-7-(4-methylsulfanylphenyl)-1H-pyrrolo[2,3-c]pyridine hydrochloride;
1-(2-methoxyethyl)-2,3-dimethyl-7-(4-methylsulfanylphenyl)-1H-pyrrolo[2,3-c]pyridine hydrochloride;
1-ethyl-2,3-dimethyl-7-(4-methylsulfanylphenyl)-1H-pyrrolo[2,3-c]pyridine hydrochloride;
1-(3-methoxybenzyl)-2,3-dimethyl-7-(4-methylsulfanylphenyl)-1H-pyrrolo[2,3-c]pyridine hydrochloride;
2,3-dimethyl-1-(4-methylbenzyl)-7-(4-methylsulfanylphenyl)-1H-pyrrolo[2,3-c]pyridine hydrochloride;
1-benzyl-2,3-dimethyl-7-(4-methylsulfanylphenyl)-1H-pyrrolo[2,3-c]pyridine hydrochloride;
2,3-dimethyl-1-(3-methylbut-2-enyl)-7-(4-methylsulfanylphenyl)-1H-pyrrolo[2,3-c]pyridine hydrochloride;
1-cyclopropylmethyl-2,3-dimethyl-7-(4-methylsulfanylphenyl)-1H-pyrrolo[2,3-c]pyridine hydrochloride;
1-(4-chlorobenzyl)-2,3-dimethyl-7-(4-methylsulfanylphenyl)-1H-pyrrolo[2,3-c]pyridine hydrochloride;
2,3-dimethyl-1-(3-fluorobenzyl)-7-(4-methylsulfanylphenyl)-1H-pyrrolo[2,3-c]pyridine hydrochloride;
2,3-dimethyl-1-(3-methylbenzyl)-7-(4-methylsulfanylphenyl)-1H-pynolo[2,3-c]pyridine hydrochloride;
2,3-dimethyl-1-(4-fluorobenzyl)-7-(4-methylsulfanylphenyl)-1H-pyrrolo[2,3-c]pyridine hydrochloride;
2,3-dimethyl-1-(2-fluorobenzyl)-7-(4-methylsulfanylphenyl)-1H-pyrrolo[2,3-c]pyridine hydrochloride;
2,3-dimethyl-7-(p-tolyl)-1H-pyrrolo[2,3-c]pyridine;
1-allyl-2,3-dimethyl-7-(p-tolyl)-1H-pyrrolo[2,3-c]pyridine hydrochloride;
1-(3-methoxybenzyl)-2,3-dimethyl-7-(p-tolyl)-1H-pyrrolo[2,3-c]pyridine hydrochloride;
2,3-dimethyl-1-(4-methylbenzyl)-7-(p-tolyl)-1H-pyrrolo[2,3-c]pyridine hydrochloride;
2,3-dimethyl-1-(prop-2-ynyl)-7-(p-tolyl)-1H-pyrrolo[2,3-c]pyridine hydrochloride;
1-benzyl-2,3-dimethyl-7-(p-tolyl)-1-pyrrolo[2,3-c]pyridine hydrochloride;
2,3-dimethyl-1-(2-methoxyethyl)-7-(p-tolyl)-1H-pyrrolo[2,3-c]pyridine hydrochloride;
1-(4-chlorobenzyl)-2,3-dimethyl-7-(p-tolyl)-1H-pyrrolo[2,3-c]pyridine hydrochloride;
2,3-dimethyl-1-(3-fluorobenzyl)-7-(p-tolyl)-1H-pyrrolo[2,3-c]pyridine hydrochloride;
1-isobutyl-2,3-dimethyl-7-(p-tolyl)-1H-pyrrolo[2,3-c]pyridine hydrochloride;
2,3-dimethyl-1-propyl-7-(p-tolyl)-1H-pyrrolo[2,3-c]pyridine hydrochloride;
2,3-dimethyl-1-(4-methoxybenzyl)-7-(p-tolyl)-1H-pyrrolo[2,3-c]pyridine hydrochloride;
2,3-dimethyl-1-(4-fluorobenzyl)-7-(p-tolyl)-1H-pyrrolo[2,3-c]pyridine hydrochloride;
1-cyclobutylmethyl-2,3-dimethyl-7-(p-tolyl)-1H-pyrrolo[2,3-c]pyridine hydrochloride;
2,3-dimethyl-1-(2-fluorobenzyl)-7-(p-tolyl)-1H-pyrrolo[2,3-c]pyridine hydrochloride;
2,3-dimethyl-1-(3-methylbut-2-enyl)-7-(p-tolyl)-1H-pyrrolo[2,3-c]pyridine hydrochloride;
2,3-dimethyl-1-(3-methylbutyl)-7-(p-tolyl)-1H-pyrrolo[2,3-c]pyridine hydrochloride;
1-cyclopropylmethyl-2,3-dimethyl-7-(p-tolyl)-1H-pyrrolo[2,3-c]pyridine hydrochloride;
1-(2,5-dimethylbenzyl)-2,3-dimethyl-7-(p-tolyl)-1H-pyrrolo[2,3-c]pyridine hydrochloride;
1-(2-chlorobenzyl)-2,3-dimethyl-7-(p-tolyl)-1H-pyrrolo[2,3-c]pyridine hydrochloride;
1-(3,4-dichlorobenzyl)-2,3-dimethyl-7-(p-tolyl)-1H-pyrrolo[2,3-c]pyridine hydrochloride;
1-ethyl-2,3-dimethyl-7-(p-tolyl)-1H-pyrrolo[2,3-c]pyridine hydrochloride;
2,3-dimethyl-1-(3-methylbenzyl)-7-(p-tolyl)-1H-pyrrolo[2,3-c]pyridine hydrochloride;
7-(4-chlorophenyl)-2,3-dimethyl-1H-pyrrolo[2,3-c]pyridine hydrochloride;
1-allyl-7-(4-chlorophenyl)-2,3-dimethyl-1H-pyrrolo[2,3-c]pyridine hydrochloride;
1-benzyl-7-(4-chlorophenyl)-2,3-dimethyl-1H-pyrrolo[2,3-c]pyridine hydrochloride;
7-(4-chlorophenyl)-1-(2-methoxyethyl)-2,3-dimethyl-1H-pyrrolo[2,3-c]pyridine hydrochloride;
7-(4-chlorophenyl)-1-(3-fluorobenzyl)-2,3-dimethyl-1H-pyrrolo[2,3-c]pyridine hydrochloride;
7-(4-chlorophenyl)-1-isobutyl-2,3-dimethyl-1H-pyrrolo[2,3-c]pyridine hydrochloride;
7-(4-chlorophenyl)-2,3-dimethyl-1-(4-methylbenzyl)-1H-pyrrolo[2,3-c]pyridine hydrochloride;
7-(4-chlorophenyl)-2,3-dimethyl-1-(3-methoxybenzyl)-1H-pyrrolo[2,3-c]pyridine hydrochloride;
7-(4-chlorophenyl)-2,3-dimethyl-1-(4-methoxybenzyl)-1H-pyrrolo[2,3-c]pyridine hydrochloride;
7-(4-chlorophenyl)-2,3-dimethyl-1-(prop-2-ynyl)-1H-pyrrolo[2,3-c]pyridine hydrochloride;
7-(4-chlorophenyl)-1-methoxymethyl-2,3-dimethyl-1H-pyrrolo[2,3-c]pyridine hydrochloride;
7-(4-chlorophenyl)-2,3-dimethyl-1-(3-methylbut-2-enyl)-1H-pyrrolo[2,3-c]pyridine hydrochloride;
7-(4-chlorophenyl)-2,3-dimethyl-1-(3-methylbutyl)-1H-pyrrolo[2,3-c]pyridine hydrochloride;
7-(4-chlorophenyl)-1-cyclopropylmethyl-2,3-dimethyl-1H-pyrrolo[2,3-c]pyridine hydrochloride;
7-(4-chlorophenyl)-2,3-dimethyl-1-(naphthalen-2-ylmethyl-1H-pyrrobo[2,3-c]pyridine hydrochloride;
1-(4-tert-butylbenzyl)-7-(4-chlorophenyl)-2,3-dimethyl-1H-pyrrobo[2,3-c]pyridine hydrochloride;
1-(4-chlorobenzyl)-7-(4-chlorophenyl)-2,3-dimethyl-1H-pyrrolo[2,3-c]pyridine hydrochloride;
7-(4-chlorophenyl)-2,3-dimethyl-1-oxiranylmethyl-1H-pyrrolo[2,3-c]pyridine hydrochloride;
7-(4-chlorophenyl)-1-(2,5-dimethylbenzyl)-2,3-dimethyl-1H-pyrrolo[2,3-c]pyridine hydrochloride;
7-(4-chlorophenyl)-1-ethyl-2,3-dimethyl-1H-pyrrolo[2,3-c]pyridine hydrochloride;
7-(4-chlorophenyl)-2,3-dimethyl-1-propyl-1H-pyrrolo[2,3-c]pyridine hydrochloride; 7-(4-chlorophenyl)-2,3-dimethyl-1-(3-methylbenzyl)-1H-pyrrolo[2,3-c]pyridine hydrochloride;
3-[7-(4-chlorophenyl)-2,3-dimethylpyrrolo[2,3-c]pyridin-1-ylmethyl]-benzonitrile hydrochloride;
7-(4-chlorophenyl)-1-(4-fluorobenzyl)-2,3-dimethyl-1H-pyrrolo[2,3-c]pyridine hydrochloride;
7-(4-chlorophenyl)-1-(3-chlorobenzyl)-2,3-dimethyl-1H-pyrrolo[2,3-c]pyridine hydrochloride;
7-(4-chlorophenyl)-1-cyclobutylmethyl-2,3-dimethyl-1H-pyrrolo[2,3-c]pyridine hydrochloride;
7-(4-fluorophenyl)-2,3-dimethyl-1H-pyrrolo[2,3-c]pyridine hydrochloride;
1-allyl-7-(4-fluorophenyl)-2,3-dimethyl-1H-pyrrolo[2,3-c]pyridine hydrochloride;

7-(4-fluorophenyl)-1-(2-methoxyethyl)-2,3-dimethyl-1H-pyrrolo[2,3-c]pyridine hydrochloride;
1-(3-fluorobenzyl)-7-(4-fluorophenyl)-2,3-dimethyl-1H-pyrrobo[2,3-c]pyridine hydrochloride;
1-benzyl-7-(4-fluorophenyl)-2,3-dimethyl-1H-pyrrolo[2,3-c]pyridine hydrochloride;
7-(4-fluorophenyl)-1-methoxymethyl-2,3-dimethyl-1H-pyrrolo[2,3-c]pyridine hydrochloride;
7-(4-fluorophenyl)-2,3-dimethyl-1-(3-methylbut-2-enyl)-1H-pyrrolo[2,3-c]pyridine hydrochloride;
7-(4-fluorophenyl)-2,3-dimethyl-1-(3-methyl butyl)-1H-pyrrolo[2,3-c]pyridine hydrochloride;
1-cyclopropylmethyl-7-(4-fluorophenyl)-2,3-dimethyl-1H-pyrrolo[2,3-c]pyridine hydrochloride; 7-(4-fluorophenyl)-2,3-dimethyl-1-(naphthalen-2-ylmethyl)-1H-pyrrolo[2,3-c]pyridine hydrochloride;
1-(4-tert-butylbenzyl)-7-(4-fluorophenyl)-2,3-dimethyl-1H-pyrrolo[2,3-c]pyridine hydrochloride;
1-(4-chlorobenzyl)-7-(4-fluorophenyl)-2,3-dimethyl-1H-pyrrolo[2,3-C]pyridine hydrochloride;
1-(2,5-dimethylbenzyl)-7-(4-fluorophenyl)-2,3-dimethyl-1H-pyrrolo[2,3-c]pyridine hydrochloride;
7-(4-fluorophenyl)-2,3-dimethyl-1-oxiranylmethyl-1H-pyrrolo[2,3-c]pyridine hydrochloride;
1-ethyl-7-(4-fluorophenyl)-2,3-dimethyl-1H-pyrrolo[2,3-c]pyridine hydrochloride;
7-(4-fluorophenyl)-1-isobutyl-2,3-dimethyl-1H-pyrrolo[2,3-c]pyridine hydrochloride;
7-(4-fluorophenyl)-2,3-dimethyl-1-propyl-1H-pyrrolo[2,3-c]pyridine hydrochloride;
7-(4-fluorophenyl)-1-(3-methoxybenzyl)-2,3-dimethyl-1H-pyrrolo[2,3-c]pyridine hydrochloride;
7-(4-fluorophenyl)-1-(4-methoxybenzyl)-2,3-dimethyl-1H-pyrrolo[2,3-c]pyridine hydrochloride;
7-(4-fluorophenyl)-1-(3-methylbenzyl)-2,3-dimethyl-1H-pyrrolo[2,3-c]pyridine hydrochloride;
7-(4-fluorophenyl)-1-(4-methylbenzyl)-2,3-dimethyl-1H-pyrrolo[2,3-c]pyridine hydrochloride;
3-[7-(4-fluorophenyl)-2,3-dimethylpyrrolo[2,3-c]pyridin-1-ylmethyl]-benzonitrile hydrochloride;
1-(4-fluorobenzyl)-7-(4-fluorophenyl)-2,3-dimethyl-1H-pyrrolo[2,3-c]pyridine hydrochloride;
7-(4-fluorophenyl)-2,3-dimethyl-1-(prop-2-ynyl)-1H-pyrrolo[2,3-c]pyridine hydrochloride;
7-(4-methoxyphenyl)-2,3-dimethyl-1H-pyrrolo[2,3-c]pyridine;
1-benzyl-7-(4-methoxyphenyl)-2,3-dimethyl-1H-pyrrolo[2,3-c]pyridine hydrochloride;
1-cyclopropylmethyl-7-(4-methoxyphenyl)-2,3-dimethyl-1H-pyrrolo[2,3-c]pyridine hydrochloride;
1-(3-fluorobenzyl)-7-(4-methoxyphenyl)-2,3-dimethyl-1H-pyrrolo[2,3-c]pyridine hydrochloride;
1-(2-fluorobenzyl)-7-(4-methoxyphenyl)-2,3-dimethyl-1H-pyrrolo[2,3-c]pyridine hydrochloride;
7-(4-methoxyphenyl)-2,3-dimethyl-1-(prop-2-ynyl)-1H-pyrrolo[2,3-c]pyridine hydrochloride;
7-(4-methoxyphenyl)-2,3-dimethyl-1-(2-methoxyethyl)-1H-pyrrolo[2,3-c]pyridine hydrochloride;
7-(4-methoxyphenyl)-2,3-dimethyl-1-(naphthalen-2-ylmethyl)-1H-pyrrolo[2,3-c]pyridine hydrochloride;
1-(4-chlorobenzyl)-7-(4-methoxyphenyl)-2,3-dimethyl-1H-pyrrolo[2,3-c]pyridine hydrochloride;
1-isobutyl-7-(4-methoxyphenyl)-2,3-dimethyl-1H-pyrrolo[2,3-c]pyridine hydrochloride;
1-cyclobutylmethyl-7-(4-methoxyphenyl)-2,3-dimethyl-1H-pyrrolo[2,3-c]pyridine hydrochloride;
1allyl-7-(4-methoxyphenyl)-2,3-dimethyl-1H-pyrrolo[2,3-c]pyridine hydrochloride;
7-(4-methoxyphenyl)-2,3-dimethyl-1-(3-methylbut-2-enyl)-1H-pyrrobo[2,3-c]pyridine hydrochloride;
7-(4-methoxyphenyl)-2,3-dimethyl-1-(3-methylbutyl)-1H-pyrrobo[2,3-c]pyridine hydrochloride;
1-(4-tert-butylbenzyl)-7-(4-methoxyphenyl)-2,3-dimethyl-1H-pyrrolo[2,3-c]pyridine hydrochloride;
1-(2,5-dimethylbenzyl)-7-(4-methoxyphenyl)-2,3-dimethyl-1H-pyrrolo[2,3-c]pyridine hydrochloride;
7-(4-methoxyphenyl)-2,3-dimethyl-1-oxiranylmethyl-1H-pyrrolo[2,3-c]pyridine hydrochloride;
1-ethyl-7-(4-methoxyphenyl)-2,3-dimethyl-1H-pyrrolo[2,3-c]pyridine hydrochloride;
7-(4-methoxyphenyl)-2,3-dimethyl-1-propyl-1H-pyrrolo[2,3-c]pyridine hydrochloride;
1-(3-methoxybenzyl)-7-(4-methoxyphenyl)-2,3-dimethyl-1H-pyrrolo[2,3-c]pyridine hydrochloride;
1-(4-methoxybenzyl)-7-(4-methoxyphenyl)-2,3-dimethyl-1H-pyrrolo[2,3-c]pyridine hydrochloride;
1-(4-fluorobenzyl)-7-(4-methoxyphenyl)-2,3-dimethyl-1H-pyrrolo[2,3-c]pyridine hydrochloride;
2,3-dimethyl-7-phenyl-1H-pyrrolo[2,3-c]pyridine hydrochloride;
1-allyl-2,3-dimethyl-7-phenyl-1H-pyrrolo[2,3-c]pyridine hydrochloride;
2,3-dimethyl-1-(4-methylbenzyl)-7-phenyl-1H-pyrrolo[2,3-c]pyridine hydrochloride;
1-ethyl-2,3-dimethyl-7-phenyl-1H-pyrrolo[2,3-c]pyridine hydrochloride;
2,3-dimethyl-1-(3-fluorobenzyl)-7-phenyl-1H-pyrrolo[2,3-c]pyridine hydrochloride;
1-benzyl-2,3-dimethyl-7-phenyl-1H-pyrrolo[2,3-c]pyridine hydrochloride;
1-isobutyl-2,3-dimethyl-7-phenyl-1H-pyrrolo[2,3-c]pyridine hydrochloride;
1-methoxymethyl-2,3-dimethyl-7-phenyl-1H-pyrrolo[2,3-c]pyridine hydrochloride;
1-(2-methoxyethyl)-2,3-dimethyl-7-phenyl-1H-pyrrolo[2,3-c]pyridine hydrochloride;
1-(4-methoxybenzyl)-2,3-dimethyl-7-phenyl-1H-pyrrolo[2,3-c]pyridine hydrochloride;
1-(4-chlorobenzyl)-2,3-dimethyl-7-phenyl-1H-pyrrolo[2,3-c]pyridine hydrochloride;
1-(2-chlorobenzyl)-2,3-dimethyl-7-phenyl-1H-pyrrolo[2,3-c]pyridine hydrochloride;
2,3-dimethyl-1-(3-methylbut-2-enyl)-7-phenyl-1H-pyrrolo[2,3-c]pyridine hydrochloride;
1-cyclopropylmethyl-2,3-dimethyl-7-phenyl-1H-pyrrolo[2,3-c]pyridine hydrochloride;
1-cyclohexylmethyl-2,3-dimethyl-7-phenyl-1H-pyrrolo[2,3-c]pyridine hydrochloride;
2,3-dimethyl-1-pentyl-7-phenyl-1H-pyrrolo[2,3-c]pyridine hydrochloride;
1-(2,5-dimethylbenzyl)-2,3-dimethyl-7-phenyl-1H-pyrrolo[2,3-c]pyridine hydrochloride;
1-(3,4-dichlorobenzyl)-2,3-dimethyl-7-phenyl-1H-pyrrolo[2,3-c]pyridine hydrochloride;
2,3-dimethyl-7-phenyl-1-propyl-1H-pyrrolo[2,3-c]pyridine hydrochloride;
1-(3-methoxybenzyl)-2,3-dimethyl-7-phenyl-1H-pyrrolo[2,3-c]pyridine hydrochloride;
1-(3-methylbenzyl)-2,3-dimethyl-7-phenyl-1H-pyrrolo[2,3-c]pyridine hydrochloride;
1-(4-fluorobenzyl)-2,3-dimethyl-7-phenyl-1H-pyrrolo[2,3-c]pyridine hydrochloride;

1-cyclobutylmethyl-2,3-dimethyl-7-phenyl-1H-pyrrolo[2,3-c]pyridine hydrochloride;
1-(2-fluorobenzyl)-2,3-dimethyl-7-phenyl-1H-pyrrolo[2,3-c]pyridine hydrochloride;
(1-benzyl-2-methyl-7-phenyl-1H-pyrrolo[2,3-c]pyridin-3-yl)-methanol hydrochloride;
1-benzyl-2-methyl-7-phenyl-1H-pyrrolo[2,3-c]pyridin-3-yl acetic acid methyl ester;
2,3-dimethyl-7-(naphthalen-1-yl)-1H-pyrrolo[2,3-c]pyridine;
1-benzyl-2,3-dimethyl-7-(naphthalen-1-yl)-1H-pyrrolo[2,3-c]pyridine hydrochloride;
1-isobutyl-2,3-dimethyl-7-(naphthalen-1-yl)-1H-pyrrolo[2,3-c]pyridine hydrochloride;
2,3-dimethyl-7-(naphthalen-1-yl)-1-propyl-1H-pyrrolo[2,3-c]pyridine hydrochloride;
1-(3-methoxybenzyl)-2,3-dimethyl-7-(naphthalen-1-yl)-1H-pyrrolo[2,3-c]pyridine hydrochloride;
2,3-dimethyl-7-(naphthalen-2-yl)-1H-pyrrolo[2,3-c]pyridine hydrochloride;
1-cyclopropylmethyl-2,3-dimethyl-7-(naphthalen-2-yl)-1H-pyrrolo[2,3-c]pyridine hydrochloride;
1-ethyl-2,3-dimethyl-7-(naphthalen-2-yl)-1H-pyrrolo[2,3-c]pyridine hydrochloride;
1-(3-fluorobenzyl)-2,3-dimethyl-7-(naphthalen-2-yl)-1H-pyrrolo[2,3-c]pyridine hydrochloride;
1-(4-tert-butylbenzyl)-2,3-dimethyl-7-(naphthalen-2-yl)-1H-pyrrolo[2,3-c]pyridine hydrochloride;
2,3-dimethyl-7-(naphthalen-2-yl)-1-propyl-1H-pyrrolo[2,3-c]pyridine hydrochloride;
2,3-dimethyl-7-(naphthalen-2-yl)-1-(prop-2-ynyl)-1H-pyrrolo[2,3-c]pyridine hydrochloride;
1-(2-fluorobenzyl)-2,3-dimethyl-7-(naphthalen-2-yl)-1H-pyrrolo[2,3-c]pyridine hydrochloride;
2,3-dimethyl-7-(naphthalen-2-yl)-1H-pyrrolo[2,3-c]pyridine sodium;
1-(3-fluorobenzyl)-3-hydroxymethyl-2-methyl-7-(naphthalen-2-yl)-1H-pyrrolo[2,3-c]pyridine hydrochloride;
1-benzyl-3-hydroxymethyl-2-methyl-7-(4-methylsulfanylphenyl)-1H-pyrrolo[2,3-c]pyridine hydrochloride;
1-benzyl-3-ethoxymethyl-2-methyl-7-(4-methylsulfanylphenyl)-1H-pyrrolo[2,3-c]pyridine hydrochloride;
2,3-dimethyl-7-styryl-1H-pyrrolo[2,3-c]pyridine hydrochloride;
1-ethyl-2,3-dimethyl-7-styryl-1H-pyrrolo[2,3-c]pyridine hydrochloride;
1-allyl-2,3-dimethyl-7-styryl-1H-pyrrolo[2,3-c]pyridine hydrochloride;
2,3-dimethyl-1-(4-methylbenzyl)-7-styryl-1H-pyrrolo[2,3-c]pyridine hydrochloride;
1-benzyl-2,3-dimethyl-7-styryl-1H-pyrrolo[2,3-c]pyridine hydrochloride;
1-(3-fluorobenzyl)-2,3-dimethyl-7-styryl-1H-pyrrolo[2,3-c]pyridine hydrochloride;
1-(2-methoxyethyl)-2,3-dimethyl-7-styryl-1H-pyrrolo[2,3-c]pyridine hydrochloride;
1-isobutyl-2,3-dimethyl-7-styryl-1H-pyrrolo[2,3-c]pyridine hydrochloride;
1-(3-methoxybenzyl)-2,3-dimethyl-7-styryl-1H-pyrrolo[2,3-c]pyridine hydrochloride;
1-cyclopropylmethyl-2,3-dimethyl-7-styryl-1H-pyrrolo[2,3-c]pyridine hydrochloride;
1,2,3-trimethyl-7-styryl-1H-pyrrolo[2,3-c]pyridine hydrochloride;
1-methoxymethyl-2,3-dimethyl-7-styryl-1H-pyrrolo[2,3-c]pyridine hydrochloride;
1-(4-methoxybenzyl)-2,3-dimethyl-7-styryl-1H-pyrrolo[2,3-c]pyridine hydrochloride;
1-(4-chlorobenzyl)-2,3-dimethyl-7-styryl-1H-pyrrolo[2,3-c]pyridine hydrochloride;
7-benzyl-2,3-dimethyl-1H-pyrrolo[2,3-c]pyridine hydrochloride;
1,7-dibenzyl-2,3-dimethyl-1H-pyrrolo[2,3-c]pyridine hydrochloride;
7-benzyl-1-cyclopropylmethyl-2,3-dimethyl-1H-pyrrolo[2,3-c]pyridine hydrochloride;
7-benzyl-1-(4-chlorobenzyl)-2,3-dimethyl-1H-pyrrolo[2,3-c]pyridine hydrochloride;
7-benzyl-1-(3-fluorobenzyl)-2,3-dimethyl-1H-pyrrolo[2,3-c]pyridine hydrochloride;
7-benzyl-1-ethyl-2,3-dimethyl-1H-pyrrolo[2,3-c]pyridine hydrochloride;
7-benzyl-2,3-dimethyl-1-(3-methylbenzyl)-1H-pyrrolo[2,3-c]pyridine hydrochloride;
7-benzyl-2,3-dimethyl-1-(4-methylbenzyl)-1H-pyrrolo[2,3-c]pyridine hydrochloride;
7-benzyl-1-(4-fluorobenzyl)-2,3-dimethyl-1H-pyrrolo[2,3-c]pyridine hydrochloride;
1-allyl-7-benzyl-2,3-dimethyl-1H-pyrrolo[2,3-c]pyridine hydrochloride;
7-benzyl-1-(3-chlorobenzyl)-2,3-dimethyl-1H-pyrrolo[2,3-c]pyridine hydrochloride;
7-benzyl-1-(4-methoxybenzyl)-2,3-dimethyl-1H-pyrrolo[2,3-c]pyridine hydrochloride;
2,3-dimethyl-7-phenethyl-1H-pyrrolo[2,3-c]pyridine hydrochloride;
1-ethyl-2,3-dimethyl-7-phenethyl-1H-pyrrolo[2,3-c]pyridine hydrochloride;
1-benzyl-2,3-dimethyl-7-phenethyl-1H-pyrrolo[2,3-c]pyridine hydrochloride;
1-(2-methoxyethyl)-2,3-dimethyl-7-phenethyl-1H-pyrrolo[2,3-c]pyridine hydrochloride;
2,3-dimethyl-1-(4-methylbenzyl)-7-phenethyl-1H-pyrrolo[2,3-c]pyridine hydrochloride;
1-(4-methoxybenzyl)-2,3-dimethyl-7-phenethyl-1H-pyrrolo[2,3-c]pyridine hydrochloride;
1-(4-chlorobenzyl)-2,3-dimethyl-7-phenethyl-1H-pyrrolo[2,3-c]pyridine hydrochloride;
1-isobutyl-2,3-dimethyl-7-phenethyl-1H-pyrrolo[2,3-c]pyridine hydrochloride;
1-allyl-2,3-dimethyl-7-phenethyl-1H-pyrrolo[2,3-c]pyridine hydrochloride;
1-(3-fluorobenzyl)-2,3-dimethyl-7-phenethyl-1H-pyrrolo[2,3-c]pyridine hydrochloride;
1-(2-fluorobenzyl)-2,3-dimethyl-7-phenethyl-1H-pyrrolo[2,3-c]pyridine hydrochloride;
1-(3,4-dichlorobenzyl)-2,3-dimethyl-7-phenethyl-1H-pyrrolo[2,3-c]pyridine hydrochloride;
2,3-dimethyl-1-(2-methylthiazol-4-ylmethyl)-7-phenethyl-1H-pyrrolo[2,3-c]pyridine hydrochloride;
1-cyclopropylmethyl-2,3-dimethyl-7-phenethyl-1H-pyrrolo[2,3-c]pyridine hydrochloride;
2,3-dimethyl-7-phenethyl-1-(3-phenylallyl)-1H-pyrrolo[2,3-c]pyridine hydrochloride;
1-(4-fluorobenzyl)-2,3-dimethyl-7-phenethyl-1H-pyrrolo[2,3-c]pyridine hydrochloride;
1-(3,5-dimethylisoxazol-4-ylmethyl)-2,3-dimethyl-7-phenethyl-1H-pyrrolo[2,3-c]pyridine hydrochloride;
1-(3-methylbut-2-enyl)-2,3-dimethyl-7-phenethyl-1H-pyrrolo[2,3-c]pyridine hydrochloride;
2,3-dimethyl-7-phenethyl-1-(prop-2-ynyl)-1H-pyrrolo[2,3-c]pyridine hydrochloride;

2,3-dimethyl-7-phenethyl-1-(prop-1-ynyl)-1H-pyrrolo[2,3-c]pyridine hydrochloride;
1,2,3-trimethyl-7-phenethyl-1H-pyrrolo[2,3-c]pyridine hydrochloride;
1-(2-chlorobenzyl)-2,3-dimethyl-7-phenethyl-1H-pyrrolo[2,3-c]pyridine hydrochloride;
2,3-dimethyl-1-oxiranylmethyl-7-phenethyl-1H-pyrrolo[2,3-c]pyridine hydrochloride;
7-(4-chlorophenyl)-2-methyl-1H-pyrrolo[2,3-c]pyridine;
1-benzyl-2-methyl-7-phenyl-1H-pyrrolo[2,3-c]pyridine hydrochloride;
1-allyl-7-(4-fluorophenyl)-2-methyl-1H-pyrrolo[2,3-c]pyridine hydrochloride;
7-(4-chlorophenyl)-3-ethoxymethyl-2-methyl-1H-pyrrolo[2,3-c]pyridine;
1-benzyl-7-(4-chlorophenyl)-3-ethoxymethyl-2-methyl-1H-pyrrolo[2,3-c]pyridine hydrochloride;
7-(1,2,3,4-tetrahydroisoquinolin-2-yl)-2,3-dimethyl-1H-pyrrolo[2,3-c]pyridine hydrochloride;
1-benzyl-7-(1,2,3,4-tetrahydroisoquinolin-2-yl)-2,3-dimethyl-1H-pyrrolo[2,3-c]pyridine hydrochloride;
7-(1,2,3,4-tetrahydroisoquinolin-2-yl)-1,2,3-trimethyl-1H-pyrrolo[2,3-c]pyridine hydrochloride;
1-(4-fluorobenzyl)-7-(1,2,3,4-tetrahydroisoquinolin-2-yl)-2,3-dimethyl-1H-pyrrolo[2,3-c]pyridine hydrochloride;
1-(2-chlorobenzyl)-7-(1,2,3,4-tetrahydroisoquinolin-2-yl)-2,3-dimethyl-1H-pyrrolo[2,3-c]pyridine hydrochloride;
1-propyl-7-(1,2,3,4-tetrahydroisoquinolin-2-yl)-2,3-dimethyl-1H-pyrrolo[2,3-c]pyridine hydrochloride;
1-(2-methylthiazol-4-ylmethyl)-7-(1,2,3,4-tetrahydroisoquinolin-2-yl)-2,3-dimethyl-1H-pyrrolo[2,3-c]pyridine hydrochloride;
1-(3-methylbut-2-enyl)-7-(1,2,3,4-tetrahydroisoquinolin-2-yl)-2,3-dimethyl-1H-pyrrolo[2,3-c]pyridine hydrochloride;
1-isobutyl-7-(1,2,3,4-tetrahydroisoquinolin-2-yl)-2,3-dimethyl-1H-pyrrolo[2,3-c]pyridine hydrochloride;
1-(4-methylbenzyl)-7-(1,2,3,4-tetrahydroisoquinolin-2-yl)-2,3-dimethyl-1H-pyrrolo[2,3-c]pyridine hydrochloride;
1-(4-chlorobenzyl)-7-(1,2,3,4-tetrahydroisoquinolin-2-yl)-2,3-dimethyl-1H-pyrrolo[2,3-c]pyridine hydrochloride;
1-(4-trifluoromethoxybenzyl)-7-(1,2,3,4-tetrahydroisoquinolin-2-yl)-2,3-dimethyl-1H-pyrrolo[2,3-c]pyridine hydrochloride;
1-(3-fluorobenzyl)-7-(1,2,3,4-tetrahydroisoquinolin-2-yl)-2,3-dimethyl-1H-pyrrolo[2,3-c]pyridine hydrochloride;
1-ethyl-7-(1,2,3,4-tetrahydroisoquinolin-2-yl)-2,3-dimethyl-1H-pyrrolo[2,3-c]pyridine hydrochloride;
1-(4-methoxybenzyl)-7-(1,2,3,4-tetrahydroisoquinolin-2-yl)-2,3-dimethyl-1H-pyrrolo[2,3-c]pyridine hydrochloride;
1-(2-fluorobenzyl)-7-(1,2,3,4-tetrahydroisoquinolin-2-yl)-2,3-dimethyl-1H-pyrrolo[2,3-c]pyridine hydrochloride;
1-allyl-7-(1,2,3,4-tetrahydroisoquinolin-2-yl)-2,3-dimethyl-1H-pyrrolo[2,3-c]pyridine hydrochloride;
1-allyl-7-(1,2,3,4-tetrahydroisoquinolin-2-yl)-2,3-dimethyl-1H-pyrrolo[2,3-c]pyridine citrate;
1-allyl-7-(1,2,3,4-tetrahydroisoquinolin-2-yl)-2,3-dimethyl-1H-pyrrolo[2,3-c]pyridine tartrate;
1-allyl-7-(1,2,3,4-tetrahydroisoquinolin-2-yl)-2,3-dimethyl-1H-pyrrolo[2,3-c]pyridine methanesulfonate;
1-allyl-7-(1,2,3,4-tetrahydroisoquinolin-2-yl)-2,3-dimethyl-1H-pyrrolo[2,3-c]pyridine sulfate;
1-allyl-7-(1,2,3,4-tetrahydroisoquinolin-2-yl)-2,3-dimethyl-1H-pyrrolo[2,3-c]pyridine p-toluenesulfonate;
1-allyl-7-(,1,2,3,4-tetrahydroisoquinolin-2-yl)-2,3-dimethyl-1H-pyrrolo[2,3-c]pyridine nitrate;
1-allyl-7-(1,2,3,4-tetrahydroisoquinolin-2-yl)-2,3-dimethyl-1H-pyrrolo[2,3-c]pyridine maleate;
1-allyl-7-(1,2,3,4-terahydroisoquinolin-2-yl)-2,3-dimethyl-1H-pyrrolo[2,3-c]pyridine phosphate;
1-allyl-7-(1,2,3,4-tetrahydroisoquinolin-2-yl)-2,3-dimethyl-1H-pyrrolo[2,3-c]pyridine benzenesulfonate;
1-allyl-7-(1,2,3,4-tetrahydroisoquinolin-2-yl)-2,3-dimethyl-1H-pyrrolo[2,3-c]pyridine hydrobromide;
1-(3,4-dichlorobenzyl)-7-(1,2,3,4-tetrahydroisoquinolin-2-yl)-2,3-dimethyl-1H-pyrrolo[2,3-c]pyridine hydrochloride;
1-methoxymethyl-7-(1,2,3,4-tetrahydroisoquinolin-2-yl)-2,3-dimethyl-1H-pyrrolo[2,3-c]pyridine hydrochloride;
1-cyclopropylmethyl-7-(1,2,3,4-tetrahydroisoquinolin-2-yl)-2,3-dimethyl-1H-pyrrolo[2,3-c]pyridine hydrochloride;
1-cyanomethyl-7-(1,2,3,4-tetrahydroisoquinolin-2-yl)-2,3-dimethyl-1H-pyrrolo[2,3-c]pyridine hydrochloride;
1-(2-methoxyethyl)-7-(1,2,3,4-tetrahydroisoquinolin-2-yl)-2,3-dimethyl-1H-pyrrolo[2,3-c]pyridine hydrochloride;
7-(1,2,3,4-tetrahydroisoquinolin-2-yl)-1-(4-trifluoromethylbenzyl)-2,3-dimethyl-1H-pyrrolo[2,3-c]pyridine hydrochloride;
1-methoxycarbonylmethyl-7-(1,2,3,4-tetrahydroisoquinolin-2-yl)-2,3-dimethyl-1H-pyrrolo[2,3-c]pyridine hydrochloride;
1-(naphthalen-2-ylmethyl)-7-(1,2,3,4-tetrahydroisoquinolin-2-yl)-2,3-dimethyl-1H-pyrrolo[2,3-c]pyridine hydrochloride;
1-(2-ethoxyethyl)-7-(1,2,3,4-tetrahydroisoquinolin-2-yl)-2,3-dimethyl-1H-pyrrolo[2,3-c]pyridine hydrochloride;
1-methylsulfanylmethyl-7-(1,2,3,4-tetrahydroisoquinolin-2-yl)-2,3-dimethyl-1H-pyrrolo[2,3-c]pyridine hydrochloride;
1-cyclobutylmethyl-7-(1,2,3,4-tetrahydroisoquinolin-2-yl)-2,3-dimethyl-1H-pyrrolo[2,3-c]pyridine hydrochloride;
1-(prop-2-ynyl)-7-(1,2,3,4-tetrahydroisoquinolin-2-yl)-2,3-dimethyl-1H-pyrrolo[2,3-c]pyridine hydrochloride;
1-(4-tert-butylbenzyl)-7-(1,2,3,4-tetrahydroisoquinolin-2-yl)-2,3-dimethyl-1H-pyrrolo[2,3-c]pyridine hydrochloride;
1-(but-3-enyl)-7-(1,2,3,4-tetrahydroisoquinolin-2-yl)-2,3-dimethyl-1H-pyrrolo[2,3-c]pyridine hydrochloride;
1-pentyl-7-(1,2,3,4-tetrahydroisoquinolin-2-yl)-2,3-dimethyl-1H-pyrrolo[2,3-c]pyridine hydrochloride;
1-(3-methoxybenzyl)-7-(1,2,3,4-tetrahydroisoquinolin-2-yl)-2,3-dimethyl-1H-pyrrolo[2,3-c]pyridine hydrochloride;
1-(2-vinyloxyethyl)-7-(1,2,3,4-tetrahydroisoquinolin-2-yl)-2,3-dimethyl-1H-pyrrolo[2,3-c]pyridine hydrochloride;
1-[2-(4-methylsulfonylphenyl)ethyl]-7-(1,2,3,4-tetrahydroisoquinolin-2-yl) -2,3-dimethyl-1H-pyrrolo[2,3-c]pyridine hydrochloride;
1-(3-chlorobutyl)-7-(1,2,3,4-tetrahydroisoquinolin-2-yl)-2,3-dimethyl-1H-pyrrolo[2,3-c]pyridine hydrochloride;
1-(5-chlorothiophene-2-ylmethyl)-7-(1,2,34-tetrahydroisoquinolin-2-yl)-2,3-dimethyl-1H-pyrrolo[2,3-c]pyridine hydrochloride;

1-(3-methylbenzyl)-7-(1,2,3,4-tetrahydroisoquinolin-2-yl)-2,3-dimethyl-1H-pyrrolo[2,3-c]pyridine hydrochloride;
1-(pyridin-3-ylmethyl)-7-(1,2,3,4-tetrahydroisoquinolin-2-yl)-2,3-dimethyl-1H-pyrrolo[2,3-c]pyridine hydrochloride;
1-(pyridin-2-ylmethyl)-7-(1,2,3,4-tetrahydroisoquinolin-2-yl)-2,3-dimethyl-1H-pyrrolo[2,3-c]pyridine hydrochloride;
1-(pyridin-4-ylmethyl)-7-(1,2,3,4-tetrahydroisoquinolin-2-yl)-2,3-dimethyl-1H-pyrrolo[2,3-c]pyridine hydrochloride;
1-(2,3-dichlorobenzyl)-7-(1,2,3,4-tetrahydroisoquinolin-2-yl)-2,3-dimethyl-1H-pyrrolo[2,3-c]pyridine hydrochloride;
1-(3-methylbutyl)-7-(1,2,3,4-tetrahydroisoquinolin-2-yl)-2,3-dimethyl-1H-pyrrolo[2,3-c]pyridine hydrochloride;
1-(2,4,6-trimethylbenzyl)-7-(1,2,3,4-tetrahydroisoquinolin-2-yl)-2,3-dimethyl-1H-pyrrolo[2,3-c]pyridine hydrochloride;
1-(2,5-dimethylbenzyl)-7-(1,2,3,4-tetrahydroisoquinolin-2-yl)-2,3-dimethyl-1H-pyrrolo[2,3-c]pyridine hydrochloride;
1-(pent-4-ynyl)-7-(1,2,3,4-tetrahydroisoquinolin-2-yl)-2,3-dimethyl-1H-pyrrolo[2,3-c]pyridine hydrochloride;
1-(3,5-dimethylisoxazol-4-ylmethyl)-7-(1,2,3,4-tetrahydroisoquinolin-2-yl)-2,3-dimethyl-1H-pyrrolo[2,3-c]pyridine hydrochloride;
1-butyl-7-(1,2,3,4-tetrahydroisoquinolin-2-yl)-2,3-dimethyl-1H-pyrrolo[2,3-c]pyridine hydrochloride;
1-(propa-1,2-dienyl)-7-(1,2,3A-tetrahydroisoquinolin-2-yl)-2,3-dimethyl-1H-pyrrolo[2,3-c]pyridine hydrochloride;
2-(2,3-dimethyl-1H-pyrrolo[2,3-c]pyridin-7-yl)-7-methoxy-1-methyl-1,2,3,4-tetrahydroisoquinoline hydrochloride;
2-(1-allyl-2,3-dimethyl-1H-pyrrolo[2,3-c]pyridin-7-yl)-7-methoxy-1methyl-1,2,3,4-tetrahydroisoquinoline hydrochloride;
2-[1-(3-fluorobenzyl)-2,3-dimethyl-1H-pyrrolo[2,3-c]pyridin-7-yl]-7-methoxy-1-methyl-1,2,3,4-tetrahydroisoquinoline hydrochloride;
7-chloro-2-(2,3-dimethyl-1H-pyrrolo[2,3-c]pyridin-7-yl)-1-methyl-1,2,3,4-tetrahydroisoquinoline hydrochloride;
7-chloro-2-(1-allyl-2,3-dimethyl-1H-pyrrolo[2,3-c]pyridin-7-yl)-1-methyl-1,2,3,4-tetrahydroisoquinoline hydrochloride;
7-chloro-2-(1-ethyl-2,3-dimethyl-1H-pyrrolo[2,3-c]pyridin-7-yl)-1-methyl-1,2,3,4-tetrahydroisoquinoline hydrochloride;
7-chloro-1-methyl-2-(1,2,3-trimethyl-1H-pyrrolo[2,3-c]pyridin-7-yl)-1,2,3,4-tetrahydroisoquinoline hydrochloride;
7-chloro-2-[2,3-dimethyl-1-(3-methylbut-2-enyl)-1H-pyrrolo[2,3-c]pyridin-7-yl]-1-methyl-1,2,3,4-tetrahydroisoquinoline hydrochloride;
7-chloro-2-(1-benzyl-2,3-dimethyl-1H-pyrrolo[2,3-c]pyridin-7-yl)-1-methyl-1,2,3,4-tetrahydroisoquinoline hydrochloride;
7-chloro-2-[2,3-dimethyl-1-(4-methylbenzyl)-1H-pyrrolo[2,3-c]pyridin-7-yl]-1-methyl-1,2,3,4-tetrahydroisoquinoline hydrochloride;
7-chloro-2-(1-methoxymethyl-2,3-dimethyl-1H-pyrrolo[2,3-c]pyridin-7-yl)-1-methyl-1,2,3,4-tetrahydroisoquinoline hydrochloride;
7-chloro-2-[2,3-dimethyl-1-(2-methylthiazol-4-ylmethyl)-1H-pyrrolo[2,3-c]pyridin-7-yl]-1-methyl-1,2,3,4-tetrahydroisoquinoline hydrochloride;
7-chloro-2-[1-(3-fluorobenzyl)-2,3-dimethyl-1H-pyrrolo[2,3-c]pyridin-7-yl]-1-methyl-1,2,3,4-tetrahydroisoquinoline hydrochloride;
7-chloro-2-[1-(4-fluorobenzyl)-2,3-dimethyl-1H-pyrrolo[2,3-c]pyridin-7-yl]-1-methyl-1,2,3,4-tetrahydroisoquinoline hydrochloride;
7-fluoro-2-(2,3-dimethyl-1H-pyrrolo[2,3-c]pyridin-7-yl)-1-methyl-1,2,3,4-tetrahydroisoquinoline hydrochloride;
7-fluoro-2-[1-(3-fluorobenzyl)-2,3-dimethyl-1H-pyrrolo[2,3-c]pyridin-7-yl ]-1-methyl-1,2,3,4-tetrahydroisoquinoline hydrochloride;
2-(1-ethyl-2,3-dimethyl-1H-pyrrolo[2,3-c]pyridin-7-yl)-7-fluoro-1-methyl-1,2,3,4-tetrahydroisoquinoline hydrochloride;
2-(1-allyl-2,3-dimethyl-1H-pyrrolo[2,3-c]pyridin-7-yl)-7-fluoro-1-methyl-1,2,3,4-tetrahydroisoquinoline hydrochloride;
2-[2,3-dimethyl-1-(3-methylbut-2-enyl)-1H-pyrrolo[2,3-c]pyridin-7-yl]-7-fluoro-1-methyl-1,2,3,4-tetrahydroisoquinoline hydrochloride;
7-fluoro-2-[1-(2-methoxyethyl)-2,3-dimethyl-1H-pyrrolo[2,3-c]pyridin-7-yl]-1-methyl-1,2,3,4-tetrahydroisoquinoline hydrochloride;
2-(1-benzyl-2,3-dimethyl-1H-pyrrolo[2,3-c]pyridin-7-yl)-7-fluoro-1-methyl-1,2,3,4-tetrahydroisoquinoline hydrochloride;
2-[2,3-dimethyl-1-(4-methylbenzyl)-1H-pyrrolo[2,3-c]pyridin-7-yl]-7-fluoro-1-methyl-1,2,3,4-tetrahydroisoquinoline hydrochloride;
7-fluoro-2-[1-(4-fluorobenzyl)-2,3-dimethyl-1H-pyrrolo[2,3-c]pyridin-7-yl]-1 -methyl-1,2,3,4-tetrahydroisoquinoline hydrochloride;
7-fluoro-2-(1-methoxymethyl-2,3-dimethyl-1H-pyrrolo[2,3-c]pyridin-7-yl)-1-methyl-1,2,3,4-tetrahydroisoquinoline hydrochloride;
2-[2,3-dimethyl-1-(2-methylthiazol-4-ylmethyl)-1H-pyrrolo[2,3-c]pyridin-7-yl]-7-fluoro-1-methyl-1,2,3,4-tetrahydroisoquinoline hydrochloride;
2-(2,3-dimethyl-1H-pyrrolo[2,3-c]pyridin-7-yl)-1-methyl-1,2,3,4-tetrahydroisoquinoline hydrochloride;
2-(1-allyl-2,3-dimethyl-1H-pyrrolo[2,3-c]pyridin-7-yl)-1-methyl-1,2,3,4-tetrahydroisoquinoline hydrochloride;
2-(1-ethyl-2,3-dimethyl-1H-pyrrolo[2,3-c]pyridin-7-yl)-1-methyl-1,2,3,4-tetrahydroisoquinoline hydrochloride;
2-[1-(2-methoxyethyl)-2,3-dimethyl-1H-pyrrolo[2,3-c]pyridin-7-yl]-1-methyl-1,2,3,4-tetrahydroisoquinoline hydrochloride;
2-(1-benzyl-2,3-dimethyl-1H-pyrrolo[2,3-c]pyridin-7-yl)-1-methyl-1,2,3,4-tetrahydroisoquinoline hydrochloride;
2-[1-(3-fluorobenzyl)-2,3-dimethyl-1H-pyrrolo[2,3-c]pyridin-7-yl]-1-methyl-1,2,3,4-tetrahydroisoquinoline hydrochloride;
2-[l-(4-methoxybenzyl)-2,3-dimethyl-1H-pyrrolo[2,3-c]pyridin-7-yl]-1-methyl-1,2,3,4-tetrahydroisoquinoline hydrochloride;
2-[2,3-dimethyl-1-(2-methylthiazol-4-ylmethyl)-1H-pyrrolo[2,3-c]pyridin-7-yl]-1-methyl-1,2,3,4-tetrahydroisoquinoline hydrochloride;
2-(2,3-dimethyl-1H-pyrrolo[2,3-c]pyridin-7-yl)-1-methyl-1,2,3,4-tetrahydroisoquinoline sodium;

6-fluoro-2-(2,3-dimethyl-1H-pyrrolo[2,3-c]pyridin-7-yl)-1-methyl-1,2,3,4-tetrahydroisoquinoline hydrochloride;
2-(1-ethyl-2,3-dimethyl-1H-pyrrolo[2,3-c]pyridin-7-yl)-6-fluoro-1-methyl-1,2,3,4-tetrahydroisoquinoline hydrochloride;
2-(1-allyl-2,3-dimethyl-1H-pyrrolo[2,3-c]pyridin-7-yl)-6-fluoro-1-methyl-1,2,3,4-tetrahydroisoquinoline hydrochloride;
6-fluoro-2-[1-(2-methoxyethyl)-2,3-dimethyl-1H-pyrrolo[2,3-c]pyridin-7-yl]-1-methyl-1,2,3,4-tetrahydroisoquinoline hydrochloride;
6-fluoro-2-[1-(3fluorobenzyl)-2,3-dimethyl-1H-pyrrolo[2,3-c]pyridin-7-yl]-1-methyl-1,2,3,4-tetrahydroisoquinoline hydrochloride;
6-fluoro-2-[1-(4-methoxybenzyl)-2,3-dimethyl-1H-pyrrolo[2,3-c]pyridin-7-yl]-1-methyl-1,2,3,4-tetrahydroisoquinoline hydrochloride;
6-fluoro-2-(2,3-dimethyl-1H-pyrrolo[2,3-c]pyridin-7-yl]-1-methyl-1,2,3,4-tetrahydroisoquinoline sodium;
1-cyclopropyl-2-(2,3-dimethyl-1H-pyrrolo[2,3-c]pyridin-7-yl)-1,2,3,4-tetrahydroisoquinoline hydrochloride;
1-cyclopropyl-2-(1-ethyl-2,3-dimethyl-1H-pyrrolo[2,3-c]pyridin-7-yl)-1,2,3,4-tetrahydroisoquinoline hydrochloride;
2-(1-allyl-2,3-dimethyl-1H-pyrrolo[2,3-c]pyridin-7-yl)-1-cyclopropyl-1,2,3,4-tetrahydroisoquinoline hydrochloride;
1-cyclopropyl-2-[1-(2-methoxyethyl)-2,3-dimethyl-1H-pyrrolo[2,3-c]pyridin-7-yl]-1,2,3,4-tetrahydroisoquinoline hydrochloride;
1-cyclopropyl-2-[1-(3-fluorobenzyl)-2,3-dimethyl-1H-pyrrolo[2,3-c]pyridin-7-yl]-1,2,3,4-tetrahydroisoquinoline hydrochloride;
1-cyclopropyl-2-[1-(4-methoxybenzyl)-2,3-dimethyl-1H-pyrrolo[2,3-c]pyridin-7-yl]-1,2,3,4-tetrahydroisoquinoline hydrochloride;
2-(2,3-dimethyl-1H-pyrrolo[2,3-c]pyridin-7-yl)-1-ethyl-1,2,3,4-tetrahydroisoquinoline hydrochloride;
1-ethyl-2-(1,2,3-trimethyl-1H-pyrrolo[2,3-c]pyridin-7-yl)-1,2,3,4-tetrahydroisoquinoline hydrochloride;
1-ethyl-2-(1-ethyl-2,3-dimethyl-1H-pyrrolo[2,3-c]pyridin-7-yl)-1,2,3,4-tetrahydroisoquinoline hydrochloride;
2-(1-allyl-2,3-dimethyl-1H-pyrrolo[2,3-c]pyridin-7-yl)-1-ethyl-1,2,3,4-tetrahydroisoquinoline hydrochloride;
2-[2,3-dimethyl-1-(3-methylbut-2-enyl)-1H-pyrrolo[2,3-c]pyridin-7-yl]-1-ethyl-1,2,3,4-tetrahydroisoquinoline hydrochloride;
2-(1-benzyl-2,3-dimethyl-1H-pyrrolo[2,3-c]pyridin-7-yl)-1-ethyl-1,2,3,4-tetrahydroisoquinoline hydrochloride;
2-[2,3-dimethyl-1-(4-methylbenzyl)-1H-pyrrolo[2,3-c]pyridin-7-yl]-1-ethyl-1,2,3,4-tetrahydroisoquinoline hydrochloride;
1-ethyl-2-[1-(4-fluorobenzyl)-2,3-dimethyl-1H-pyrrolo[2,3-c]pyridin-7-yl]-1,2,3,4-tetrahydroisoquinoline hydrochloride;
1-ethyl-2-[1-(3-fluorobenzyl)-2,3-dimethyl-1H-pyrrolo[2,3-c]pyridin-7-yl]-1,2,3,4-tetrahydroisoquinoline hydrochloride;
1-ethyl-2-[1-(4-methoxybenzyl)-2,3-dimethyl-1H-pyrrolo[2,3-c]pyridin-7-yl]-1,2,3,4-tetrahydroisoquinoline hydrochloride;
1-ethyl-2-(1-methoxymethyl-2,3-dimethyl-1H-pyrrolo[2,3-c]pyridin-7-yl)-1,2,3,4-tetrahydroisoquinoline hydrochloride;
1-ethyl-2-[1-(2-methoxyethyl)-2,3-dimethyl-1H-pyrrolo[2,3-c]pyridin-7-yl]1,2,3,4-tetrahydroisoquinoline hydrochloride;
1-ethyl-2-[2,3-dimethyl-1-(2-methylthiazol-4-ylmethyl)-1H-pyrrolo[2,3-c]pyridin-7-yl]-1,2,3,4-tetrahydroisoquinoline hydrochloride;
1-ethyl-2-[1-(2-methoxyethoxymethyl)-2,3-dimethyl-1H-pyrrolo[2,3-c]pyridin-7-yl]-1,2,3,4-tetrahydroisoquinoline hydrochloride;
2-[1-(but-3-enyl)-2,3-dimethyl-1H-pyrrolo[2,3-c]pyridin-7-yl]-1-ethyl-1,2,3,4-tetrahydroisoquinoline hydrochloride;
2-[1-(2-allyloxyethyl)-2,3-dimethyl-1H-pyrrolo[2,3-c]pyridin-7-yl]-1-ethyl-1,2,3,4-tetrahydroisoquinoline hydrochloride;
1-ethyl-2-[1-(2-fluorobenzyl)-2,3-dimethyl-1H-pyrrolo[2,3-c]pyridin-7-yl]-1,2,3,4-tetrahydroisoquinoline hydrochloride;
2-ethyl-3-methyl-7-(1,2,3,4-tetrahydroisoquinolin-2-yl)-1H-pyrrolo[2,3-c]pyridine;
1-benzyl-2-ethyl-3-methyl-7-(1,2,3,4-tetrahydroisoquinolin-2-yl)-1H-pyrrolo[2,3-c]pyridine hydrochloride;
2-ethyl-1-(3-fluorobenzyl)-3-methyl-7-(1,2,3,4-tetrahydroisoquinolin-2-yl)-1H-pyrrolo[2,3-c]pyridine hydrochloride;
2-ethyl-1-(3-methoxybenzyl)-3-methyl-7-(1,2,3,4-tetrahydroisoquinolin-2-yl)-1H-pyrrolo[2,3-c]pyridine hydrochloride;
1-allyl-2-ethyl-3-methyl-7-(1,2,3,4-tetrahydroisoquinolin-2-yl)-1H-pyrrolo[2,3-c]pyridine hydrochloride;
2-ethyl-3-methyl-1-(3-methylbut-2-enyl)-7-(1,2,3,4-tetrahydroisoquinolin-2-yl)-1H-pyrrolo[2,3-c]pyridine hydrochloride;
2-ethyl-1-(2-methoxyethyl)-3-methyl-7-(1,2,3,4-tetrahydroisoquinolin-2-yl)-1H-pyrrolo[2,3-c]pyridine hydrochloride;
1-cyclopropylmethyl-2-ethyl-3-methyl-7-(1,2,3,4-tetrahydroisoquinolin-2-yl)-1H-pyrrolo[2,3-c]pyridine hydrochloride;
1-(4-chlorobenzyl)-2-ethyl-3-methyl-7-(1,2,3,4-tetrahydroisoquinolin-2-yl)-1H-pyrrolo[2,3-c]pyridine hydrochloride;
1-(3,4-dichlorobenzyl)-2-ethyl-3-methyl-7-(1,2,3,4-tetrahydroisoquinolin-2-yl)-1H-pyrrolo[2,3-c]pyridine hydrochloride;
1,2-diethyl-3-methyl-7-(1,2,3,4-tetrahydroisoquinolin-2-yl)-1H-pyrrolo[2,3-c]pyridine hydrochloride;
2-ethyl-1-(4-methoxybenzyl)-3-methyl-7-(1,2,3,4-tetrahydroisoquinolin-2-yl)-1H-pyrrolo[2,3-c]pyridine hydrochloride;
2-ethyl-3-methyl-1-(3-methylbenzyl)-7-(1,2,3,4-tetrahydroisoquinolin-2-yl)-1H-pyrrolo[2,3-c]pyridine hydrochloride;
2-ethyl-3-methyl-1-(4-methylbenzyl)-7-(1,2,3,4-tetrahydroisoquinolin-2-yl)-1H-pyrrolo[2,3-c]pyridine hydrochloride;
2-ethyl-3-methyl-1-(prop-2-ynyl)-7-(1,2,3,4-tetrahydroisoquinolin-2-yl)-1H-pyrrolo[2,3-c]pyridine hydrochloride;
2-ethyl-1-(4-fluorobenzyl)-3-methyl-7-(1,2,3,4-tetrahydroisoquinolin-2-yl)-1H-pyrrolo[2,3-c]pyridine hydrochloride;
2-ethyl-1-(4-trifluoromethylbenzyl)-3-methyl-7-(1,2,3,4-tetrahydroisoquinolin-2-yl)-1H-pyrrolo[2,3-c]pyridine hydrochloride;

2-ethyl-1-(2-fluorobenzyl)-3-methyl-7-(1,2,3,4-tetrahydroisoquinolin-2-yl)-1H-pyrrolo[2,3-c]pyridine hydrochloride;

2-ethyl-1,3-dimethyl-7-(1,2,3,4-tetrahydroisoquinolin-2-yl)-1H-pyrrolo[2,3-c]pyridine hydrochloride;

1-(3-chlorobenzyl)-2-ethyl-3-methyl-7-(1,2,3,4-tetrahydroisoquinolin-2-yl)-1H-pyrrolo[2,3-c]pyridine hydrochloride;

2-(2-ethyl-3-methyl-1-propyl-1H-pyrrolo[2,3-c]pyridin-7-yl)-1,2,3,4-tetrahydroisoquinoline hydrochloride;

2-[1-(3-fluorobenzyl)-2-methyl-1H-pyrrolo[2,3-c]pyridin-7-yl]-1,2,3,4-tetrahydroisoquinoline hydrochloride;

2-(1-benzyl-2-methyl-1H-pyrrolo[2,3-c]pyridin-7-yl)-1,2,3,4-tetrahydroisoquinoline hydrochloride;

2-[3-bromo-1-(3-fluorobenzyl)-2-methyl-1H-pyrrolo[2,3-c]pyridin-7-yl]-1,2,3,4-tetrahydroisoquinoline hydrochloride;

7-(3,4-dihydro-1H-isoquinolin-2-yl)-1-(3-fluorobenzyl)-2-methyl-1H-pyrrolo[2,3-c]pyridin-3-carbaldehyde hydrochloride;

[7-(3,4-dihydro-1H-isoquinolin-2-yl)-1-(3-fluorobenzyl)-2-methyl-1H-pyrrolo[2,3-c]pyridin-3-yl]-methanol hydrochloride;

2-[1-(3-fluorobenzyl)-2-methyl-3-(morpholin-4-ylmethyl)-1H-pyrrolo[2,3-c]pyridin-7-yl]-1,2,3,4-tetrahydroisoquinoline hydrochloride;

[7-(3,4-dihydro-1H-isoquinolin-2-yl)-1-(3-fluorobenzyl)-2-methyl-1H-pyrrolo[2,3-c]pyridin-3-ylmethyl]-dimethylamine hydrochloride;

[7-(3,4-dihydro-1H-isoquinolin-2-yl)-1-(3-fluorobenzyl)-2-methyl-1H-pyrrolo[2,3-c]pyridin-3-ylmethyl]-trimethylammonium iodide;

[7-(3,4-dihydro-1H-isoquinolin-2-yl)-1-(3-fluorobenzyl)-2-methyl-1H-pyrrolo[2,3-c]pyridin-3-yl]-acetonitrile hydrochloride;

[1-benzyl-7-(3,4-dihydro-1H-isoquinolin-2-yl)-2-methyl-1H-pyrrolo[2,3-c]pyridin-3-ylmethyl]-dimethylamine hydrochloride;

[1-benzyl-7-(3,4-dihydro-1H-isoquinolin-2-yl)-2-methyl-1H-pyrrolo[2,3-c]pyridin-3-ylmethyl]-trimethylammonium iodide;

[1-benzyl-7-(3,4-dihydro-1H-isoquinolin-2-yl)-2-methyl-1H-pyrrolo[2,3-c]pyridin-3-yl]-acetonitrile hydrochloride;

2-(2-methyl-3-methylsulfanyl-1H-pyrrolo[2,3-c]pyridin-7-yl)-1,2,3,4-tetrahydroisoquinoline hydrochloride;

2-(1-benzyl-2-methyl-3-methylsulfanyl-1H-pyrrolo[2,3-c]pyridin-7-yl)-1,2,3,4-tetrahydroisoquinoline hydrochloride;

2[1-(3-fluorobenzyl)-2-methyl-3-methylsulfanyl-1H-pyrrolo[2,3-c]pyridin-7-yl]-1,2,3,4-tetrahydroisoquinoline hydrochloride;

2-(1-cyclopropylmethyl-2-methyl-3-methylsulfanyl-1H-pyrrolo[2,3-c]pyridin-7-yl)-1,2,3,4-tetrahydroisoquinoline hydrochloride;

2-(2-methyl-3-methylsulfanyl-1-propyl-1H-pyrrolo[2,3-c]pyridin-7-yl)-1,2,3,4-tetrahydroisoquinoline hydrochloride;

2-[1-(2-methoxyethyl)-2-methyl-3-methylsulfanyl-1H-pyrrolo[2,3-c]pyridin-7-yl]-1,2,3,4-tetrahydroisoquinoline hydrochloride;

2-(1-allyl-2-methyl-3-methylsulfanyl-1H-pyrrolo[2,3-c]pyridin-7-yl)-1,2,3,4-tetrahydroisoquinoline hydrochloride;

2-(1-allyl-3-methylsulfinyl-2-methyl-1H-pyrrolo[2,3-c]pyridin-7-yl)-1,2,3,4-tetrahydroisoquinoline hydrochloride;

2-[1-(3-fluorobenzyl)-3-methylsulfinyl-2-methyl-1H-pyrrolo[2,3-c]pyridin-7-yl]-1,2,3,4-tetrahydroisoquinoline hydrochloride;

2-(1-cyclopropylmethyl-3-methylsulfinyl-2-methyl-1H-pyrrolo[2,3-c]pyridin-7-yl)-1,2,3,4-tetrahydroisoquinoline hydrochloride;

2-(3-methylsulfinyl-2-methyl-1-propyl-1H-pyrrolo[2,3-c]pyridin-7-yl)-1,2,3,4-tetrahydroisoquinoline hydrochloride;

2-[1-(2-methoxyethyl)-3-methylsulfinyl-2-methyl-1H-pyrrolo[2,3-c]pyridin-7-yl]-1,2,3,4-tetrahydroisoquinoline hydrochloride;

2-(1-allyl-3-methylsulfonyl-2-methyl-1H-pyrrolo[2,3-c]pyridin-7-yl)-1,2,3,4-tetrahydroisoquinoline hydrochloride;

2-(1-cyclopropylmethyl-3-methylsulfonyl-2-methyl-1H-pyrrolo[2,3-c]pyridin-7-yl)-1,2,3,4-tetrahydroisoquinoline hydrochloride;

2-(3-methylsulfonyl-2-methyl-1-propyl-1H-pyrrolo[2,3-c]pyridin-7-yl)-1,2,3,4-tetrahydroisoquinoline hydrochloride;

2-[3-methylsulfonyl-1-(2-methoxyethyl)-2-methyl-1H-pyrrolo[2,3-c]pyridin-7-yl]-1,2,3,4-tetrahydroisoquinoline hydrochloride;

2-[1-(3-fluorobenzyl)-3-methylsulfonyl-2-methyl-1H-pyrrolo[2,3-c]pyridin-7-yl]-1,2,3,4-tetrahydroisoquinoline hydrochloride;

2-(1-benzyl-5-fluoro-2,3-dimethyl-1H-pyrrolo[2,3-c]pyridin-7-yl)-1,2,3,4-tetrahydroisoquinoline hydrochloride;

2-(1-cyclopropylmethyl-5-fluoro-2,3-dimethyl-1H-pyrrolo[2,3-c]pyridin-7-yl)-1,2,3,4-tetrahydroisoquinoline hydrochloride;

2-[1-(3-chlorobenzyl)-5-fluoro-2,3-dimethyl-1H-pyrrolo[2,3-c]pyridin-7-yl]-1,2,3,4-tetrahydroisoquinoline hydrochloride;

2-[5-fluoro-1-(3-fluorobenzyl)-2,3-dimethyl-1H-pyrrolo[2,3-c]pyridin-7-yl]-1,2,3,4-tetrahydroisoquinoline hydrochloride;

2-(1-allyl-5-fluoro-2,3-dimethyl-1H-pyrrolo[2,3-c]pyridin-7-yl)-1,2,3,4-tetrahydroisoquinoline hydrochloride;

4-fluoro-2,3-dimethyl-7-(1,2,3,4-tetrahydroisoquinolin-2-yl)-1H-pyrrolo[2,3-c]pyridine;

1-allyl-4-fluoro-2,3-dimethyl-7-(1,2,3,4-tetrahydroisoquinolin-2-yl)-1H-pyrrolo[2,3-c]pyridine hydrochloride;

2,3-dimethyl-4-fluoro-1-propyl-7-(1,2,3,4-tetrahydroisoquinolin-2-yl)-1H-pyrrolo[2,3-c]pyridine hydrochloride;

2,3-dimethyl-4-fluoro-1-(2-methoxyethyl)-7-(1,2,3,4-tetrahydroisoquinolin-2-yl)-1H-pyrrolo[2,3-c]pyridine hydrochloride;

1-benzyl-2,3-dimethyl-4-fluoro-7-(1,2,3,4-tetrahydroisoquinolin-2-yl)-1H-pyrrolo[2,3-c]pyridine hydrochloride;

2-(5-chloro-2,3-dimethyl-1H-pyrrolo[2,3-c]pyridin-7-yl)-1,2,3,4-tetrahydroisoquinoline 5-chloro-[1-(3-fluorobenzyl)-7-(1,2,3,4-tetrahydroisoquinolin-2-yl)]-2,3-dimethyl-1H-pyrrolo[2,3-c]pyridine hydrochloride;

2-(1-benzyl-5-chloro-2,3-dimethyl-1H-pyrrolo[2,3-c]pyridin-7-yl)-1,2,3,4-tetrahydroisoquinoline;

2-[5-chloro-2,3-dimethyl-1-(prop-2-ynyl)-1H-pyrrolo[2,3-c]pyridin-7-yl]-1,2,3,4-tetrahydroisoquinoline;
2-[5-chloro-1-(2-methoxyethyl)-2,3-dimethyl-1H-pyrrolo[2,3-c]pyridin-7-yl]-1,2,3,4-tetrahydroisoquinoline;
2-(1-allyl-5-chloro-2,3-dimethyl-1H-pyrrolo[2,3-c]pyridin-7-yl)-1,2,3,4-tetrahydroisoquinoline;
2-[5-chloro-1-(3-fluorobenzyl)-2,3-dimethyl-1H-pyrrolo[2,3-c]pyridin-7-yl]-1,2,3,4-tetrahydroisoquinoline;
2-[1-(but-3-enyl)-5-chloro-2,3-dimethyl-1H-pyrrolo[2,3-c]pyridin-7-yl]-1,2,3,4-tetrahydroisoquinoline;
2-[5-chloro-2,3-dimethyl-1-(3-methylbut-2-enyl)-1H-pyrrolo[2,3-c]pyridin-7-yl]-1,2,3,4-tetrahydroisoquinoline;
2-[5-chloro-2,3-dimethyl-1-(3-methylbutyl)-1H-pyrrolo[2,3-c]pyridin-7-yl]-1,2,3,4-tetrahydroisoquinoline;
2-(5-chloro-1-cyclopropylmethyl-2,3-dimethyl-1H-pyrrolo[2,3-c]pyridin-7-yl)-1,2,3,4-tetrahydroisoquinoline;
2-[5-chloro-2,3-dimethyl-1-(naphthalen-2-ylmethyl)-1H-pyrrolo[2,3-c]pyridin-7-yl]-1,2,3,4-tetrahydroisoquinoline;
2-[1-(4-tert-butylbenzyl)-5-chloro-2,3-dimethyl-1H-pyrrolo[2,3-c]pyridin-7-yl]-1,2,3,4-tetrahydroisoquinoline;
2-[5-chloro-1-(4-chlorobenzyl)-2,3-dimethyl-1H-pyrrolo[2,3-c]pyridin-7-yl]-1,2,3,4-tetrahydroisoquinoline;
2-[5-chloro-1-(2,5-dimethylbenzyl)-2,3-dimethyl-1H-pyrrolo[2,3-c]pyridin-7-yl]-1,2,3,4-tetrahydroisoquinoline;
2-(5-chloro-1-ethyl-2,3-dimethyl-1H-pyrrolo[2,3-c]pyridin-7-yl)-1,2,3,4-tetrahydroisoquinoline;
2-(5-chloro-1-isobutyl-2,3-dimethyl-1H-pyrrolo[2,3-c]pyridin-7-yl)-1,2,3,4-tetrahydroisoquinoline;
2-(5-chloro-2,3-dimethyl-1-propyl-1H-pyrrolo[2,3-c]pyridin-7-yl)-1,2,3,4-tetrahydroisoquinoline;
2-[5-chloro-1-(3-methoxybenzyl)-2,3-dimethyl-1H-pyrrolo[2,3-c]pyridin-7-yl]-1,2,3,4-tetrahydroisoquinoline;
2-[5-chloro-1-(4-methoxybenzyl)-2,3-dimethyl-1H-pyrrolo[2,3-c]pyridin-7-yl]-1,2,3,4-tetrahydroisoquinoline;
2-[5-chloro-2,3-dimethyl-1-(3-methylbenzyl)-1H-pyrrolo[2,3-c]pyridin-7-yl]-1,2,3,4-tetrahydroisoquinoline;
2-[5-chloro-2,3-dimethyl-1-(4-methylbenzyl)-1H-pyrrolo[2,3-c]pyridin-7-yl]-1,2,3,4-tetrahydroisoquinoline;
2-[5-chloro-1-(4-fluorobenzyl)-2,3-dimethyl-1H-pyrrolo[2,3-c]pyridin-7-yl]-1,2,3,4-tetrahydroisoquinoline;
2-(5-chloro-1-cyclobutylmethyl-2,3-dimethyl-1H-pyrrolo[2,3-c]pyridin-7-yl)-1,2,3,4-tetrahydroisoquinoline;
2-[5-chloro-1-(2-fluorobenzyl)-2,3-dimethyl-1H-pyrrolo[2,3-c]pyridin-7-yl]-1,2,3,4-tetrahydroisoquinoline;
2-(5-chloro-1,2,3-trimethyl-1H-pyrrolo[2,3-c]pyridin-7-yl)-1,2,3,4-tetrahydroisoquinoline;
7-(3,4-dihydro-1H-isoquinolin-2-yl)-2,3-dimethyl-1H-pyrrolo[2,3-c]pyridin-5-carbonitrile;
1-(but-3-enyl)-7-(3,4-dihydro-1H-isoquinolin-2-yl)-2,3-dimethyl-1H-pyrrolo[2,3-c]pyridin-5-carbonitrile;
1-allyl-7-(3,4-dihydro-1H-isoquinolin-2-yl)-2,3-dimethyl-1H-pyrrolo[2,3-c]pyridin-5-carbonitrile;
7-(3,4-dihydro-1H-isoquinolin-2-yl)-2,3-dimethyl-1-(2-vinyloxyethyl)-1H-pyrrolo[2,3-c]pyridin-5-carbonitrile;
1-benzyl-7-(3,4-dihydro-1H-isoquinolin-2-yl)-2,3-dimethyl-1H-pyrrolo[2,3-c]pyridin-5-carbonitrile;
7-(3,4-dihydro-1H-isoquinolin-2-yl)-1-(2-methoxyethyl)-2,3-dimethyl-1H-pyrrolo[2,3-c]pyridin-5-carbonitrile;
7-(3,4-dihydro-1H-isoquinolin-2-yl)-2,3-dimethyl-1-(prop-2-ynyl)-1H-pyrrolo[2,3-c]pyridin-5-carbonitrile;
1-(3-chlorobenzyl)-7-(3,4-dihydro-1H-isoquinolin-2-yl)-2,3-dimethyl-1H-pyrrolo[2,3-c]pyridin-5-carbonitrile;
7-(3,4-dihydro-1H-isoquinolin-2-yl)-1-(4-fluorobenzyl)-2,3-dimethyl-1H-pyrrolo[2,3-c]pyridin-5-carbonitrile;
7-(3,4-dihydro-1H-isoquinolin-2-yl)-1-(3-methoxybenzyl)-2,3-dimethyl-1H-pyrrolo[2,3-c]pyridin-5-carbonitrile;
7-(3,4-dihydro-1H-isoquinolin-2-yl)-1-(4-methoxybenzyl)-2,3-dimethyl-1H-pyrrolo[2,3-c]pyridin-5-carbonitrile;
7-(3,4-dihydro-1H-isoquinolin-2-yl)-2,3-dimethyl-1-(4-methylbenzyl)-1H-pyrrolo[2,3-c]pyridin-5-carbonitrile;
7-(3,4-dihydro-1H-isoquinolin-2-yl)-2,3-dimethyl-1-(3-methylbut-2-enyl)-1H-pyrrolo[2,3-c]pyridin-5-carbonitrile;
7-(3,4-dihydro-1H-isoquinolin-2-yl)-1-(3-fluorobenzyl)-2,3-dimethyl-1H-pyrrolo[2,3-c]pyridin-5-carbonitrile;
7-(3,4-dihydro-1H-isoquinolin-2-yl)-1-ethyl-2,3-dimethyl-1H-pyrrolo[2,3-c]pyridin-5-carbonitrile;
7-(3,4-dihydro-1H-isoquinolin-2-yl)-2,3-dimethyl-1-propyl-1H-pyrrolo[2,3-c]pyridin-5-carbonitrile;
1-butyl-7-(3,4-dihydro-1H-isoquinolin-2-yl)-2,3-dimethyl-1H-pyrrolo[2,3-c]pyridin-5-carbonitrile;
7-(3,4-dihydro-1H-isoquinolin-2-yl)-1-methoxymethyl-2,3-dimethyl-1H-pyrrolo[2,3-c]pyridin-5-carbonitrile;
1-cyclopropylmethyl-7-(3,4-dihydro-1H-isoquinolin-2-yl)-2,3-dimethyl-1H-pyrrolo[2,3-c]pyridin-5-carbonitrile;
1-(4-tert-butylbenzyl)-7-(3,4-dihydro-1H-isoquinolin-2-yl)-2,3-dimethyl-1H-pyrrolo[2,3-c]pyridin-5-carbonitrile;
1-(4-chlorobenzyl)-7-(3,4-dihydro-1H-isoquinolin-2-yl)-2,3-dimethyl-1H-pyrrolo[2,3-c]pyridin-5-carbonitrile;
1-(2-chlorobenzyl)-7-(3,4-dihydro-1H-isoquinolin-2-yl)-2,3-dimethyl-1H-pyrrolo[2,3-c]pyridin-5-carbonitrile;
1-(3,4-dichlorobenzyl)-7-(3,4-dihydro-1H-isoquinolin-2-yl)-2,3-dimethyl-1H-pyrrolo[2,3-c]pyridin-5-carbonitrile;
7-(3,4-dihydro-1H-isoquinolin-2-yl)-1-(2,5-dimethylbenzyl)-2,3-dimethyl-1H-pyrrolo[2,3-c]pyridin-5-carbonitrile;
7-(3,4-dihydro-1H-isoquinolin-2-yl)-2,3-dimethyl-1-(3-methylbenzyl)-1H-pyrrolo[2,3-c]pyridin-5-carbonitrile;
7-(3,4-dihydro-1H-isoquinolin-2-yl)-1,2,3-trimethyl-1H-pyrrolo[2,3-c]pyridin-5-carbonitrile;
7-(3,4-dihydro-1H-isoquinolin-2-yl)-1-isobutyl-2,3-dimethyl-1H-pyrrolo[2,3-c]pyridin-5-carbonitrile;
7-(3,4-dihydro-1H-isoquinolin-2-yl)-1-(3-methylbutyl)-2,3-dimethyl-1H-pyrrolo[2,3-c]pyridin-5-carbonitrile;
7-(3,4-dihydro-1H-isoquinolin-2-yl)-2,3-dimethyl-1-(3-phenylpropyl)-1H-pyrrolo[2,3-c]pyridin-5-carbonitrile;
2-[5-cyano-7-(3,4-dihydro-1H-isoquinolin-2-yl)-2,3-dimethyl-pyrrolo[2,3-c]pyridin-1-yl]-acetic aicd ethyl ester;
7-(3,4-dihydro-1H-isoquinolin-2-yl)-1-[2-[1,3]dioxan-2-ylethyl]-2,3-dimethyl-1H-pyrroio[2,3-c]pyridin-5-carbonitrile;
7-(3,4-dihydro-1H-isoquinolin-2-yl)-2,3-dimethyl-1-phenethyl-1H-pyrrolo[2,3-c]pyridin-5-carbonitrile;
1-cyclobutylmethyl-7-(3,4-dihydro-1H-isoquinolin-2-yl)-2,3-dimethyl-1H-pyrrolo[2,3-c]pyridin-5-carbonitrile;

1-cyclohexylmethyl-7-(3,4-dihydro-1H-isoquinolin-2-yl)-2,3-dimethyl-1H-pyrrolo[2,3-c]pyridin-5-carbonitrile;

7-(3,4-dihydro-1H-isoquinolin-2-yl)-2,3-dimethyl-1-(naphthalen-2-ylmethyl)-1H-pyrrolo[2,3-c]pyridin-5-carbonitrile;

7-(3,4-dihydro-1H-isoquinolin-2-yl)-2,3-dimethyl-1-(2-methylbenzyl)-1H-pyrrolo[2,3-c]pyridin-5-carbonitrile;

7-(3,4-dihydro-1H-isoquinolin-2-yl)-2,3-dimethyl-1-(pent-4-ynyl)-1H-pyrrolo[2,3-c]pyridin-5-carbonitrile;

7-(3,4-dihydro-1H-isoquinolin-2-yl)-2,3-dimethyl-1-[3-(2-methyl-[1,3]dioxolan-2-yl)-propyl]-1H-pyrrolo[2,3-c]pyridin-5-carbonitrile;

7-(3,4-dihydro-1H-isoquinolin-2-yl)-1-heptyl-2,3-dimethyl-1H-pyrrolo[2,3-c]pyridin-5-carbonitrile;

[5-cyano-7-(3,4-dihydro-1H-isoquinolin-2-yl)-2,3-dimethyl-1H-pyrrolo[2,3-c]pyridin-1-yl]methyl-2,2-dimethylpropanate;

7-(3,4-dihydro-1H-isoquinolin-2-yl)-1-(2-ethylbutyl)-2,3-dimethyl-1H-pyrrolo[2,3-c]pyridin-5-carbonitrile;

1-(but-2-ynyl)-7-(3,4-dihydro-1H-isoquinolin-2-yl)-2,3-dimethyl-1H-pyrrolo[2,3-c]pyridin-5-carbonitrile;

7-(3,4-dihydro-1H-isoquinolin-2-yl)-1-(2-fluorobenzyl)-2,3-dimethyl-1H-pyrrolo[2,3-c]pyridin-5-carbonitrile;

7-(3,4-dihydro-1H-isoquinolin-2-yl)-1-(2-methoxyethoxymethyl)-2,3-dimethyl-1H-pyrrolo[2,3-c]pyridin-5-carbonitrile;

[5-cyano-7-(3,4-dihydro-1H-isoquinolin-2-yl)-2,3-dimethyl-pyrrolo[2,3-c]pyridin-1-yl]-acetic aicd methyl ester;

4-[5-cyano-7-(3,4-dihydro-1H-isoquinolin-2-yl)-2,3-dimethyl-pyrrolo[2,3-c]pyridin-1-ylmethyl]-benzoic acid methyl ester;

7-(3,4-dihydro-1H-isoquinolin-2-yl)-2,3-dimethyl-1-(4-trifluoromethylbenzyl)-1H-pyrrolo[2,3-c]pyridin-5-carbonitrile;

7-(3,4-dihydro-1H-isoquinolin-2-yl)-1-(2-methoxybenzyl)-2,3-dimethyl-1H-pyrrolo[2,3-c]pyridin-5-carbonitrile;

7-(3,4-dihydro-1H-isoquinolin-2-yl)-1-(3-fluorobenzyl)-2-methyl-1H-pyrrolo[2,3-c]pyridin-3,5-dicarbonitrile;

7-(3,4-dihydro-1H-isoquinolin-2-yl)-1-(4-fluorobenzyl)-2,3-dimethyl-1H-pyrrolo[2,3-c]pyridin-5-carboxylic acid;

1-allyl-7-(3,4-dihydro-1H-isoquinolin-2-yl)-2,3-dimethyl-1H-pyrrolo[2,3-c]pyridin-5-carboxylic acid;

1-benzyl-7-(3,4-dihydro-1H-isoquinolin-2-yl)-2,3-dimethyl-1H-pyrrolo[2,3-c]pyridin-5-carboxylic acid;

7-(3,4-dihydro-1H-isoquinolin-2-yl)-1-(2-melhoxyethyl)-2,3-dimethyl-1H-pyrrolo[2,3-c]pyridin-5-carboxylic acid;

1-(3-chlorobenzyl)-7-(3,4-dihydro-1H-isoquinolin-2-yl)-2,3-dimethyl-1H-pyrrolo[2,3-c]pyridin-5-carboxylic acid;

7-(3,4-dihydro-1H-isoquinolin-2-yl)-1-(3-methoxybenzyl)-2,3-dimethyl-1H-pyrrolo[2,3-c]pyridin-5-carboxylic acid;

7-(3,4-dihydro-1H-isoquinolin-2-yl)-1-(3-fluorobenzyl)-2,3-dimethyl-1H-pyrrolo[2,3-c]pyridin-5-carboxylic acid;

7-(3,4-dihydro-1H-isoquinol in-2-yl)-1-ethyl-2,3-dimethyl-1H-pyrrolo[2,3-c]pyridin-5-carboxylic acid;

7-(3,4-dihydro-1H-isoquinolin-2-yl)-2,3-dimethyl-1-propyl-1H-pyrrolo[2,3-c]pyridin-5-carboxylic acid;

1-cyclopropylmethyl-7-(3,4-dihydro-1H-isoquinolin-2-yl)-2,3-dimethyl-1H-pyrrolo[2,3-c]pyridin-5-carboxylic acid;

7-(3,4-dihydro-1H-isoquinolin-2-yl)-2,3-dimethyl-1-(3-methylbenzyl)-1H-pyrrolo[2,3-c]pyridin-5-carboxylic acid;

7-(3,4-dihydro-1H-isoquinolin-2-yl)-1-isobutyl-2,3-dimethyl-1H-pyrrolo[2,3-c]pyridin-5-carboxylic acid;

1-benzyl-7-(3,4-dihydro-1H-isoquinol in-2-yl)-2,3-dimethyl-1H-pyrrolo[2,3-c]pyridin-5-carboxylic acid methyl ester;

1-benzyl-7-(3,4-dihydro-1H-isoquinolin-2-yl)-2,3-dimethyl-1H-pyrrolol[2,3-c]pyridin-5-carboxylate sodium;

1-benzyl-7-(3,4-dihydro-1H-isoquinolin-2-yl)-2,3-dimethyl-1H-pyrrolo[2,3-c]pyridin-5-carboxamide;

7-(3,4-dihydro-1H-isoquinol in-2-yl)-2,3-dimethyl-1H-pyrrolo[2,3-c]pyridin-5-carboxamide;

1H -allyl-7-(3,4-dihydro-1H-isoquinolin-2-yl)-2,3-dimethyl-1H-pyrrolo[2,3-c]pyridin-5-carboxamide;

7-(3,4-dihydro-1H-isoquinolin-2-yl)-1-(2-methoxyethyl)-2,3-dimethyl-1H-pyrrolo[2,3-c]pyridin-5-carboxamide;

7-(3,4-dihydro-1H-isoquinolin-2-yl)-2,3-dimethyl-1-(prop-2-ynyl)-1H-pyrrolo[2,3-c]pyridin-5-carboxamide;

1-(3-chlorobenzyl)-7-(3,4-dihydro-1H-isoquinolin-2-yl)-2,3-dimethyl-1H-pyrrolo[2,3-c]pyridin-5-carboxamide;

7-(3,4-dihydro-1H-isoquinol in-2-yl)-1-(3-methoxybenzyl)-2,3-dimethyl-1H-pyrrolo[2,3-c]pyridin-5-carboxamide;

7-(3,4-dihydro-1H-isoquinolin-2-yl)-1-(3-fluorobenzyl)-2,3-dimethyl-1H-pyrrolo[2,3-c]pyridin-5-carboxamide;

7-(3,4-dihydro-1H-isoquinolin-2-yl)-2,3-dimethyl-1-propyl-1H-pyrrolo[2,3-c]pyridin-5-carboxamide;

1-cyclopropylmethyl-7-(3,4-dihydro-1H-isoquinolin-2-yl)-2,3-dimethyl-1H-pyrrolo[2,3-c]pyridin-5-carboxamide;

7-(3,4-dihydro-1H-isoquinolin-2-yl)-1-isobutyl-2,3-dimethyl-1H-pyrrolo[2,3-c]pyridin-5-carboxamide;

1-allyl-7-(3,4-dihydro-1H-isoquinolin-2-yl)-2,3-dimethyl-N-(4-methylbenzyl)-1H-pyrrolo[2,3-c]pyridin-5-carboxamide hydrochloride;

1-allyl-7-(3,4-dihydro-1H-isoquinolin-2-yl)-2,3-dimethyl-N-methyl-1H-pyrrolo[2,3-c]pyridin-5-carboxamide hydrochloride;

1-allyl-7-(3,4-dihydro-1H-isoquinolin-2-yl)-2,3-dimethyl-N-(3-chlorobenzyl)-1H-pyrrolo[2,3-c]pyridin-5-carboxamide hydrochloride;

1-allyl-7-(3,4-dihydro-1H-isoquinolin-2-yl)-2,3-dimethyl-N-(2,2,2-trifluoroethyl)-1H-pyrrolo[2,3-c]pyridin-5-carboxamide hydrochloride;

1-allyl-7-(3,4-dihydro-1H-isoquinolin-2-yl)-2,3-dimethyl-N-(benzo[1,3]dioxol-5-ylmethyl)-1H-pyrrolo[2,3-c]pyridin-5-carboxamide hydrochloride;

1-allyl-7-(3,4-dihydro-1H-isoquinolin-2-yl)-2,3-dimethyl-N-cyclopropyl-1H-pyrrolo[2,3-c]pyridin-5-carboxamide;

1-allyl-7-(3,4-dihydro-1H-isoquinolin-2-yl)-2,3-dimethyl-N-(2,2,2-trifluoroethyl)-1H-pyrrolo[2,3-c]pyridin-5-carboxamide;

1-allyl-7-(3,4-dihydro-1H-isoquinolin-2-yl)-2,3-dimethyl-N-tert-butyl-1H-pyrrolo[2,3-c]pyridin-5-carboxamide;

[1-benzyl-7-(3,4-dihydro-1H-isoquinolin-2-yl)-2,3-dimethyl-1H-pyrrolo[2,3-c]pyridin-5-yl]-(morpholin-4-yl)-methanone;

1-benzyl-7-(3,4-dihydro-1H-isoquinolin-2-yl)-2,3-dimethyl-N-ethyl-1H-pyrrolo[2,3-c]pyridin-5-carboxamide;

1-benzyl-7-(3,4-dihydro-1H-isoquinolin-2-yl)-2,3-dimethyl-N-tert-butyl-1H-pyrrolo[2,3-c]pyridin-5-carboxamide;

1-benzyl-7-(3,4-dihydro-1H-isoquinol in-2-yl)-2,3-dimethyl-N-(2,2,2,-trifluoroethyl)-1H-pyrrolo[2,3-c]pyridin-5-carboxamide;

1-benzyl-7-(3,4-dihydro-1H-isoquinolin-2-yl)-2,3-dimethyl-N-(4-methylbenzyl-1H-pyrrolo[2,3-c]pyridin-5-carboxamide;

[1-benzyl-7-(3,4-dihydro-1H-isoquinolin-2-yl)-2,3-dimethyl-1H-pyrrolo[2,3-c]pyridin-5-yl]-(morpholin-4-yl)-methanone hydrochloride;

1-benzyl-7-(3,4-dihydro-1H-isoquinolin-2-yl)-2,3-dimethyl-N-diethyl-1H-pyrrolo[2,3-c]pyridin-5-carboxamide hydrochloride;

1-benzyl-7-(3A-dihydro-1H-isoquinolin-2-yl)-2,3-dimethyl-N-dimethyl-1H-pyrrolo[2,3-c]pyridin-5-carboxamide hydrochloride;

1-benzyl-7-(3,4-dihydro-1H-isoquinolin-2-yl)-2,3-dimethyl-N-methyl-1H-pyrrolo[2,3-c]pyridin-5-carboxamide hydrochloride;

1-benzyl-7-(3,4-dihydro-1H-isoquinol in-2-yl)-2,3-dimethyl-N-(3-chlorobenzyl)-1H-pyrrolo[2,3-c]pyridin-5-carboxamide hydrochloride;

1-benzyl-7-(3,4-dihydro-1H-isoquinolin-2-yl)-2,3-dimethyl-N-(1,3-benzodioxol-5-yl methyl)-1H-pyrrolo[2,3-c]pyridin-5-carboxamide hydrochloride;

1-benzyl-7-(3,4-dihydro-1H-isoquinolin-2-yl)-2,3-dimethyl-N-ethyl-1H-pyrrolo[2,3-c]pyridin-5-carboxamide hydrochloride;

[7-(3,4-dihydro-1H-isoquinolin-2-yl)-2,3-dimethyl-1H-pyrrolo[2,3-c]pyridin-5-yl]-(morpholin-4-yl)-methanone;

[1-allyl-7-(3,4-dihydro-1H-isoquinolin-2-yl)-2,3-dimethyl-1H-pyrrolo[2,3-c]pyridin-5-yl]-(morpholin-4-yl)-methanone hydrochloride;

[1-cyclopropylmethyl-7-(3,4-dihydro-1H-isoquinolin-2-yl)-2,3-dimethyl-1H-pyrrolo[2,3-c]pyridin-5-yl]-(morpholin-4-yl)-methanone hydrochloride;

[7-(3,4-dihydro-1H-isoquinolin-2-yl)-1-(3-fluorobenzyl)-2,3-dimethyl-1H-pyrrolo[2,3-c]pyridin-5-yl]-(morpholin-4-yl)-methanone hydrochloride;

[7-(3,4-dihydro-1H-isoquinolin-2-yl)-1-(3-methoxybenzyl)-2,3-dimethyl-1H-pyrrolo[2,3-c]pyridin-5-yl]-(morpholin-4-yl)-methanone hydrochloride;

[7-(3,4-dihydro-1H-isoquinolin-2-yl)-2,3-dimethyl-1-propyl-1JJ-pyrrolo[2,3-c]pyridin-5-yl]-(morpholin-4-yl)-methanone hydrochloride;

[7-(3,4-dihydro-1H-isoquinolin-2-yl)-1-ethyl-2,3-dimethyl-1H-pyrrolo[2,3-c]pyridin-5-yl]-(4-methylpiperazin-1-yl)-methanone hydrochloride;

[7-(3,4-dihydro-1H-isoquinolin-2-yl)-1-(3-methoxybenzyl)-2,3-dimethyl-1H-pyrrolo[2,3-c]pyridin-5-yl]-(4-methylpiperazin-1-yl)-methanone hydrochloride;

[7-(3,4-dihydro-1H-isoquinolin-2-yl)-1-(3-methoxybenzyl)-2,3-dimethyl-1H-pyrrolo[2,3-c]pyridin-5-yl]-(thiomorpholin-1-yl)-methanone hydrochloride;

[1-allyl-7-(3,4-dihydro-1H-isoquinolin-2-yl)-2,3-dimethyl-1H-pyrrolo[2,3-c]pyridin-5-yl]-(4-methylpiperazin-1-yl)-methanone hydrochloride;

[1-allyl-7-(3,4-dihydro-1H-isoquinolin-2-yl)-2,3-dimethyl-1H-pyrrolo[2,3-c]pyridin-5-yl]-(piperidin-1-yl)-methanone hydrochloride;

[7-(3,4-dihydro-1H-isoquinolin-2-yl)-1-ethyl-2,3-dimethyl-1H-pyrrolo[2,3-c]pyridin-5-yl]-(piperidin-1-yl)-methanone hydrochloride;

[1-benzyl-7-(3,4-dihydro-1H-isoquinol in-2-yl)-2,3-dimethyl-1H-pyrrolo[2,3-c]pyridin-5-yl]-(piperidin-1-yl)-methanone hydrochloride;

[1-benzyl-7-(3,4-dihydro-1H-isoquinolin-2-yl)-2,3-dimethyl-1H-pyrrolo[2,3-c]pyridin-5-yl]-(thiomorpholin-1-yl)-methanone hydrochloride;

[1-(3-chlorobenzyl)-7-(3,4-dihydro-1H-isoquinolin-2-yl)-2,3-dimethyl-1H-pyrrolo[2,3-c]pyridin-5-yl]-(thiomorpholin-1-yl)-methanone hydrochloride;

[7-(3,4-dihydro-1H-isoquinolin-2-yl)-2,3-dimethyl-1H-pyrrolo[2,3-c]pyridin-5-yl]-(piperidin-1-yl)-methanone hydrochloride;

[7-(3,4-dihydro-1H-isoquinolin-2-yl)-1-(2-methoxyethyl)-2,3-dimethyl-1H-pyrrolo[2,3-c]pyridin-5-yl]-(piperidin-1-yl)-methanone hydrochloride;

[1-cyclopropylmethyl-7-(3,4-dihydro-1H-isoquinolin-2-yl)-2,3-dimethyl-1H-pyrrolo[2,3-c]pyridin-5-yl]-(piperidin-1-yl)-methanone hydrochloride;

[7-(3,4-dihydro-1H-isoquinolin-2-yl)-1-isobutyl-2,3-dimethyl-1H-pyrrolo[2,3-c]pyridin-5-yl]-(piperidin-1-yl)-methanone hydrochloride;

[7-(3,4-dihydro-1H-isoquinolin-2-yl)-2,3-dimethyl-1-(3-methylbut-2-enyl)-1H-pyrrolo[2,3-c]pyridin-5-yl]-(piperidin-1-yl)-methanone hydrochloride;

[7-(3,4-dihydro-1H-isoquinolin-2-yl)-1-(3-fluorobenzyl)-2,3-dimethyl-1H-pyrrolo[2,3-c]pyridin-5-yl]-(piperidin-1-yl)-methanone hydrochloride;

[7-(3,4-dihydro-1H-isoquinolin-2-yl)-1-(4-fluorobenzyl)-2,3-dimethyl-1H-pyrrolo[2,3-c]pyridin-5-yl]-(piperidin-1-yl)-methanone hydrochloride;

[7-(3,4-dihydro-1H-isoquinolin-2-yl)-2,3-dimethyl-1-(3-methylbenzyl)-1H-pyrrolo[2,3-c]pyridin-5-yl]-(piperidin-1-yl)-methanone hydrochloride;

[1-(3-chlorobenzyl)-7-(3,4-dihydro-1[-1-isoquinolin-2-yl)-2,3-dimethyl-1H-pyrrolo[2,3-c]pyridin-5-yl]-(piperidin-1-yl)-methanone hydrochloride;

[7-(3,4-dihydro-1H-isoquinolin-2-yl)-1-methoxymethyl-2,3-dimethyl-1H-pyrrolo[2,3-c]pyridin-5-yl]-(piperidin-1-yl)-methanone hydrochloride;

[7-(3,4-dihydro-1H-isoquinolin-2-yl)-2,3-dimethyl-1-propyl-1H-pyrrolo[2,3-c]pyridin-5-yl]-(piperidin-1-yl)-methanone hydrochloride;

[7-(3,4-dihydro-1H-isoquinolin-2-yl)-2,3-dimethyl-1-(prop-2-ynyl)-1H-pyrrolo[2,3-c]pyridin-5-yl]-(piperidin-1-ly)-methanone hydrochloride;

[7-(3,4-dihydro-1H-isoquinolin-2-yl)-1-ethyl-2,3-dimethyl-1H-pyrrolo[2,3-c]pyridin-5-yl]-(pyrrolidin-1-yl)-methanone hydrochloride;

[7-(3,4-dihydro-1H-isoquinolin-2-yl)-1-ethyl-2,3-dimethyl-1H-pyrrolo[2,3-c]pyridin-5-yl]-[4-(2-hydroxyethyl)-piperidin-1-yl]-methanone hydrochloride;

[7-(3,4-dihydro-1H-isoquinolin-2-yl)-1-ethyl-2,3-dimethyl-1H-pyrrolo[2,3-c]pyridin-5-yl]-(4-hydroxymethylpiperidin-1-yl)-methanone hydrochloride;

[7-(3,4-dihydro-1H-isoquinolin-2-yl)-1-ethyl-2,3-dimethyl-1H-pyrrolo[2,3-c]pyridin-5-yl]-(4-hydroxypiperidin-1-yl)-methanone hydrochloride;

[7-(3,4-dihydro-1H-isoquinolin-2-yl)-1-ethyl-2,3-dimethyl-1H-pyrrolo[2,3-c]pyridin-5-yl]-(3-hydroxypiperidin-1-yl)-methanone hydrochloride;

[7-(3,4-dihydro-1H-isoquinolin-2-yl)-1-ethyl-2,3-dimethyl-1H-pyrrolo[2,3-c]pyridin-5-yl]-(thiomorpholin-4-yl)-methanone hydrochloride;

[7-(3,4-dihydro-1H-isoquinolin-2-yl)-1-ethyl-2,3-dimethyl-1H-pyrrolo[2,3-c]pyridin-5-yl]-(3,6-dihydro-2H-pyridin-1-yl)-methanone hydrochloride;

[7-(3,4-dihydro-1H-isoquinolin-2-yl)-1-ethyl-2,3-dimethyl-1H-pyrrolo[2,3-c]pyridin-5-yl]-(4-phenylpiperazin-1-yl)-methanone hydrochloride;

[1-allyl-7-(3,4-dihydro-1H-isoquinolin-2-yl)-2,3-dimethyl-1H-pyrrolo[2,3-c]pyridin-5-yl]-(piperazin-1-yl)-methanone hydrochloride;

[1-benzyl-7-(3,4-dihydro-1H-isoquinolin-2-yl)-2,3-dimethyl-1H-pyrrolo[2,3-c]pyridin-5-yl]-(piperazin-1-yl)-methanone hydrochloride;

[7-(3,4-dihydro-1H-isoquinolin-2-yl)-2,3-dimethyl-1-propyl-1H-pyrrolo[2,3-c]pyridin-5-yl]-(piperazin-1-yl)-methanone hydrochloride;

[7-(3,4-dihydro-1H-isoquinolin-2-yl)-2,3-dimethyl-1-(3-methylbenzyl)-1H-pyrrolo[2,3-c]pyridin-5-yl]-(piperazin-1-yl)-methanone hydrochloride;

[7-(3,4-dihydro-1H-isoquinolin-2-yl)-1-isobutyl-2,3-dimethyl-1H-pyrrolo[2,3-c]pyridin-5-yl]-(piperazin-1-yl)-methanone hydrochloride;

[1-cyclopropylmethyl-7-(3,4-dihydro-1H-isoquinolin-2-yl)-2,3-dimethyl-1H-pyrrolo[2,3-c]pyridin-5-yl]-(piperazin-1-yl)-methanone hydrochloride;

[1-cyclopropylmethyl-7-(3,4-dihydro-1H-isoquinolin-2-yl)-2,3-dimethyl-1H-pyrrolo[2,3-c]pyridin-5-yl]-(4-methylpiperazin-1-yl)-methanone hydrochloride;

[1-cyclopropylmethyl-7-(3,4-dihydro-1H-isoquinolin-2-yl)-2,3-dimethyl-1H-pyrrolo[2,3-c]pyridin-5-yl]-(4-ethylpiperazin-1-yl)-methanone hydrochloride;

[1-benzyl-7-(3,4-dihydro-1H-isoquinolin-2-yl)-2,3-dimethyl-1H-pyrrolo[2,3-c]pyridin-5-yl]-(4-methylpiperazin-1-yl)-methanone hydrochloride;

[7-(3,4-dihydro-1H-isoquinolin-2-yl)-2,3-dimethyl-1-(3-methylbenzyl)-1H-pyrrolo[2,3-c]pyridin-5-yl]-(4-methylpiperazin-1-yl)-methanone hydrochloride;

[7-(3,4-dihydro-1H-isoquinolin-2-yl)-1-(2-methoxyethyl)-2,3-dimethyl-1H-pyrrolo[2,3-c]pyridin-5-yl]-(4-methylpiperazin-1-yl)-methanone hydrochloride;

[7-(3,4-dihydro-1H-isoquinolin-2-yl)-1-(3-methoxybenzyl)-2,3-dimethyl-1H-pyrrolo[2,3-c]pyridin-5-yl]-(piperazin-1-yl)-methanone hydrochloride;

[7-(3,4-dihydro-1H-isoquinolin-2-yl)-1-(3-methoxybenzyl)-2,3-dimethyl-1H-pyrrolo[2,3-c]pyridin-5-yl]-(4-methylpiperidin-1-yl)-methanone hydrochloride;

[7-(3,4-dihydro-1H-isoquinolin-2-yl)-1-(3-methoxybenzyl)-2,3-dimethyl-1H-pyrrolo[2,3-c]pyridin-5-yl]-(4-ethylpiperazin-1-yl)-methanone hydrochloride;

[7-(3,4-dihydro-1H-isoquinolin-2-yl)-2,3-dimethyl-1-propyl-1H-pyrrolo[2,3-c]pyridin-5-yl]-(4-methylpiperazin-1-yl)-methanone hydrochloride;

[7-(3,4-dihydro-1H-isoquinolin-2-yl)-1-ethyl-2,3-dimethyl-1H-pyrrolo[2,3-c]pyridin-5-yl]-(4-ethylpiperazin-1-yl)-methanone hydrochloride;

[7-(3,4-dihydro-1H-isoquinolin-2-yl)-2,3-dimethyl-1H-pyrrolo[2,3-c]pyridin-5-yl]-(4-methylpiperazin-1-yl)-methanone hydrochloride;

[7-(3,4-dihydro-1H-isoquinolin-2-yl)-1-(4-methylbenzyl)-2,3-dimethyl-1H-pyrrolo[2,3-c]pyridin-5-yl]-(4-methylpiperazin-1-yl)-methanone hydrochloride;

[7-(3,4-dihydro-1H-isoquinolin-2-yl)-1-(4-methoxybenzyl)-2,3-dimethyl-1H-pyrrolo[2,3-c]pyridin-5-yl]-(4-methylpiperazin-1-yl)-methanone hydrochloride;

[1-cyclobutylmethyl-7-(3,4-dihydro-1H-isoquinolin-2-yl)-2,3-dimethyl-1H-pyrrolo[2,3-c]pyridin-5-yl]-(4-methylpiperazin-1-yl)-methanone hydrochloride;

[7-(3,4-dihydro-1H-isoquinolin-2-yl)-1-(4-fluorobenzyl)-2,3-dimethyl-1H-pyrrolo[2,3-c]pyridin-5-yl]-(4-methylpiperazin-1-yl)-methanone hydrochloride;

[7-(3,4-dihydro-1H-isoquinolin-2-yl)-1-(3-fluorobenzyl)-2,3-dimethyl-1H-pyrrolo[2,3-c]pyridin-5-yl]-(4-methylpiperazin-1-yl)-methanone hydrochloride;

[7-(3,4-dihydro-1H-isoquinolin-2-yl)-1-isobutyl-2,3-dimethyl-1H-pyrrolo[2,3-c]pyridin-5-yl]-(4-methylpiperazin-1-yl)-methanone hydrochloride;

[7-(3,4-dihydro-1H-isoquinolin-2-yl)-2,3-dimethyl-1-(3-methylbut-2-enyl)-1H-pyrrolo[2,3-c]pyridin-5-yl]-(4-methylpiperazin-1-yl)-methanone hydrochloride;

[1-(4-tert-butylbenzyl)-7-(3,4-dihydro-1H-isoquinolin-2-yl)-2,3-dimethyl-1H-pyrrolo[2,3-c]pyridin-5-yl]-(4-methylpiperazin-1-yl)-methanone hydrochloride;

[1-(3-chlorobenzyl)-7-(3,4-dihydro-1H-isoquinolin-2-yl)-2,3-dimethyl-1H-pyrrolo[2,3-c]pyridin-5-yl]-(4-methylpiperazin-1-yl)-methanone hydrochloride;

1-allyl-7-(3,4-dihydro-1H-isoquinolin-2-yl)-2,3-dimethyl-N-(2-hydroxyethyl)-1H-pyrrolo[2,3-c]pyridin-5-carboxamide hydrochloride;

[7-(3,4-dihydro-1H-isoquinolin-2-yl)-1-ethyl-2,3-dimethyl-1H-pyrrolo[2,3-c]pyridin-5-yl]-(imidazol-1-yl)-methanone hydrochloride;

[1-benzyl-7-(3,4-dihydro-1H-isoquinolin-2-yl)-2,3-dimethyl-1H-pyrrolo[2,3-c]pyridin-5-yl]-(imidazol-1-yl)-methanone hydrochloride;

[7-(3,4-dihydro-1H-isoquinolin-2-yl)-1-(3-fluorobenzyl)-2,3-dimethyl-1H-pyrrolo[2,3-c]pyridin-5-yl]-(imidazol-1-yl)-methanone hydrochloride;

[7-(3,4-dihydro-1H-isoquinolin-2-yl)-1-(3-methoxybenzyl)-2,3-dimethyl-1H-pyrrolo[2,3-c]pyridin-5-yl]-(imidazol-1-yl)-methanone hydrochloride;

[7-(3,4-dihydro-1H-isoquinolin-2-yl)-1-(2-methoxyethyl)-2,3-dimethyl-1H-pyrrolo[2,3-c]pyridin-5-yl]-(imidazol-1-yl)-methanone hydrochloride;

[7-(3,4-dihydro-1H-isoquinolin-2-yl)-2,3-dimethyl-1-propyl-1H-pyrrolo[2,3-c]pyridin-5-yl]-(imidazol-1-yl)-methanone hydrochloride;

2-[1-(3-fluorobenzyl)-2,3-dimethyl-5-(morpholin-4-yl)-1H-pyrrolo[2,3-c]pyridin-7-yl]-1,2,3,4-tetrahydroisoquinoline hydrochloride;

1-(3-chlorobenzyl)-7-(3,4-dihydro-1H-isoquinolin-2-yl)-2,3-dimethyl-1H-pyrrolo[2,3-c]pyridin-5-amine hydrochloride;

1-allyl-7-(3,4-dihydro-1H-isoquinolin-2-yl)-2,3-dimethyl-1H-pyrrolo[2,3-c]pyridin-5-amine hydrochloride;

7-(3,4-dihydro-1H-isoquinolin-2-yl)-1-(3-fluorobenzyl)-2,3-dimethyl-1H-pyrrolo[2,3-c]pyridin-5-amine hydrochloride;

7-(3,4-dihydro-1H-isoquinolin-2-yl)-1-(3-methoxybenzyl)-2,3-dimethyl-1H-pyrrolo[2,3-c]pyridin-5-amine hydrochloride;

7-(3,4-dihydro-1H-isoquinolin-2-yl)-1-ethyl-2,3-dimethyl-1H-pyrrolo[2,3-c]pyridin-5-amine hydrochloride;

[1-benzyl-7-(3,4-dihydro-1H-isoquinolin-2-yl)-2,3-dimethyl-1H-pyrrolo[2,3-c]pyridin-5-yl]-methanol hydrochloride;

7-(3,4-dihydro-1H-isoquinolin-2-yl)-1-(3-fluorobenzyl)-2,3-dimethyl-1H-pyrrolo[2,3-c]pyridin-5-yl]-methanol hydrochloride;

2-[1-(3-chlorobenzyl)-2,3-dimethyl-5-(1H-tetrazol-5-yl)-1H-pyrrolo[2,3-c]pyridin-7-yl]-1,2,3,4-tetrahydroisoquinoline;

2-[1-(3-chlorobenzyl)-2,3-dimethyl-5-(1-methyl-1H-tetrazol-5-yl)-1H-pyrrolo[2,3-c]pyridin-7-yl]-1,2,3,4-tetrahydroisoquinoline;

2-[1-(3-chlorobenzyl)-2,3-dimethyl-5-(1-ethyl-1H-tetrazol-5-yl)-1H-pyrrolo[2,3-c]pyridin-7-yl]-1,2,3,4-tetrahydroisoquinoline;

1-[7-(3,4-dihydro-1H-isoquinolin-2-yl)-1-(3-fluorobenzyl)-2,3-dimethyl-1H-pyrrolo[2,3-c]pyridin-5-yl]-ethanone hydrochloride;

1-[1-benzyl-7-(3,4-dihydro-1H-isoquinolin-2-yl)-2,3-dimethyl-1H-pyrrolo[2,3-c]pyridin-5-yl]-propan-1-one hydrochloride;

1-[1-(3-chlorobenzyl)-7-(3,4-dihydro-1H-isoquinolin-2-yl)-2,3-dimethyl-1H-pyrrolo[2,3-c]pyridin-5-yl]-propan-1-one hydrochloride;

cyclohexyl-[7-(3,4-dihydro-1H-isoquinolin-2-yl)-1-ethyl-2,3-dimethyl-1H-pyrrolo[2,3-c]pyridin-5-yl]-methanone hydrochloride;

cyclohexyl-[7-(3,4-dihydro-1H-isoquinolin-2-yl)-1-(3-methoxybenzyl)-2,3-dimethyl-1H-pyrrolo[2,3-c]pyridin-5-yl]-methanone hydrochloride;

1-[7-(3,4-dihydro-1H-isoquinolin-2-yl)-1-(3-fluorobenzyl)-2,3-dimethyl-1H-pyrrolo[2,3-c]pyridin-5-yl]-ethanol hydrochloride;

1-[1-benzyl-7-(3,4-dihydro-1H-isoquinolin-2-yl)-2,3-dimethyl-1H-pyrrolo[2,3-c]pyridin-5-yl]-propan-1-ol hydrochloride;

7-(3,4-dihydro-1H-isoquinolin-2-yl)-2,3-dimethyl-1H-1-pyrrolo[2,3-c]pyridin-5-carbaldehyde 1-(3-chlorobenzyl)-7-(3,4-dihydro-1H-isoquinolin-2-yl)-2,3-dimethyl-1H-pyrrolo[2,3-c]pyridin-5-carbaldehyde;

7-(3,4-dihydro-1H-isoquinolin-2-yl)-1-(3-fluorobenzyl)-2,3-dimethyl-1H-pyrrolo[2,3-c]pyridin-5-carbaldehyde hydrochloride;

N-[7-(3,4-dihydro-1H-isoquinolin-2-yl)-1-(3-fluorobenzyl)-2,3-dimethyl-1H-pyrrolo[2,3-c]pyridin-5-ylmethyl]-3-chlorobenzylamine hydrochloride;

N-[7-(3,4-dihydro-1H-isoquinolin-2-yl)-1-(3-fluorobenzyl)-2,3-dimethyl-1H-pyrrolo[2,3-c]pyridin-5-ylmethyl]-4-fluorophenylamine hydrochloride;

N-[7-(3,4-dihydro-1H-isoquinolin-2-yl)-1-(3-fluorobenzyl)-2,3-dimethyl-1H-pyrrolo[2,3-c]pyridin-5-ylmethyl]-4-methylbenzylamine hydrochloride;

N-[7-(3,4-dihydro-1H-isoquinolin-2-yl)-1-(3-fluorobenzyl)-2,3-dimethyl-1H-pyrrolo[2,3-c]pyridin-5-ylmethyl]-ethylamine hydrochloride;

N-[7-(3,4-dihydro-1H-isoquinolin-2-yl)-1-(3-fluorobenzyl)-2,3-dimethyl-1H-pyrrolo[2,3-c]pyridin-5-ylmethyl]-tert-butylamine hydrochloride;

N-[7-(3,4-dihydro-1H-isoquinolin-2-yl)-1-(3-fluorobenzyl)-2,3-dimethyl-1H-pyrrolo[2,3-c]pyridin-5-ylmethyl]-cyclobutylamine hydrochloride;

N-[7-(3,4-dihydro-1H-isoquinolin-2-yl)-1-(3-fluorobenzyl)-2,3-dimethyl-1H-pyrrolo[2,3-c]pyridin-5-ylmethyl]-cyclopropylamine hydrochloride;

2-[1-(3-fluorobenzyl)-2,3-dimethyl-5-(morpholin-4-ylmethyl)-1H-pyrrolo[2,3-c]pyridin-7-yl]-1,2,3,4-tetrahydroisoquinoline hydrochloride;

2-[1-(3-fluorobenzyl)-2,3-dimethyl-5-(4-methylpiperazin-1-ylmethyl)-1H-pyrrolo[2,3-c]pyridin-7-yl]-1,2,3,4-tetrahydroisoquinoline hydrochloride;

2-[2,3-dimethyl-5-(4-methylpiperazin-1-ylmethyl)-1H-pyrrolo[2,3-c]pyridin-7-yl]-1,2,3,4-tetrahydroisoquinoline hydrochloride;

2-[1-(3-chlorobenzyl)-2,3-dimethyl-5-(4-methylpiperazin-1-ylmethyl)-1H-pyrrolo[2,3-c]pyridin-7-yl]-1,2,3,4-tetrahydroisoquinoline hydrochloride;

2-[1-(3-methoxybenzyl)-2,3-dimethyl-5-(4-methylpiperazin-1-ylmethyl)-1H-pyrrolo[2,3-c]pyridin-7-yl]-1,2,3,4-tetrahydroisoquinoline hydrochloride;

2-[1-(4-fluorobenzyl)-2,3-dimethyl-5-(4-methylpiperazin-1-ylmethyl)-1H-pyrrolo[2,3-c]pyridin-7-yl]-1,2,3,4-tetrahydroisoquinoline hydrochloride;

2-[2,3-dimethyl-1-(3-methylbenzyl)-5-(4-methylpiperazin-1-ylmethyl)-1H-pyrrolo[2,3-c]pyridin-7-yl]-1,2,3,4-tetrahydroisoquinoline hydrochloride;

2-[1-allyl-2,3-dimethyl-5-(4-methylpiperazin-1-ylmethyl)-1H-pyrrolo[2,3-c]pyridin-7-yl]-1,2,3,4-tetrahydroisoquinoline hydrochloride;

2-[1-cyclopropylmethyl-2,3-dimethyl-5-(4-methylpiperazin-1-ylmethyl)-1H-pyrrolo[2,3-c]pyridin-7-yl]-1,2,3,4-tetrahydroisoquinoline hydrochloride;

2-1-ethyl-2,3-dimethyl-5-(4-methylpiperazin-1-ylmethyl)-1H-pyrrolo[2,3-c]pyridin-7-yl]-1,2,3,4-tetrahydroisoquinoline hydrochloride;

2-[2,3-dimethyl-5-(4-methylpiperazin-1-ylmethyl)-1-propyl-1H-pyrrolo[2,3-c]pyridin-7-yl]-1,2,3,4-tetrahydroisoquinoline hydrochloride;

2-[-benzyl-2,3-dimethyl-5-(4-methylpiperazin-1-ylmethyl)-1H-pyrrolo[2,3-c]pyridin-7-yl]1,2,3,4-tetrahydroisoquinoline hydrochloride;

[7-(3,4-dihydro-1H-isoquinolin-2-yl)-1-(3-fluorobenzyl)-2,3-dimethyl-1H-pyrrolo[2,3-c]pyridin-5-yl]-acetonitrile hydrochloride;

2-[1-(3-fluorobenzyl)-5-fluoromethyl-2,3-dimethyl-1H-pyrrolo[2,3-c]pyridin-7-yl]-1,2,3,4-tetrahydroisoquinoline hydrochloride;

[7-(3,4-dihydro -1H-isoquinolin-2-yl)-2,3-dimethyl-1H-pyrrolo[2,3-c]pyridin-5-yl]-methylamine hydrochloride;

[1-allyl-7-(3,4-dihydro-1H-isoquinolin-2-yl)-2,3-dimethyl-1H-pyrrolo[2,3-c]pyridin-5-yl]-methylamine hydrochloride;

[7-(3,4-dihydro-1H-isoquinolin-2-yl)-1-(3-fluorobenzyl)-2,3-dimethyl-1H-pyrrolo[2,3-c]pyridin-5-yl]-methylamine hydrochloride;

1-benzyl-7-(3,4-dihydro-1H-isoquinolin-2-yl)-2,3-dimethyl-1H-pyrrolo[2,3-c]pyridin-5-thiol;

1-benzyl-7-(3,4-dihydro-1H-isoquinolin-2-yl)-2,3-dimethyl-1H-pyrrolo[2,3-c]pyridin-5-thiol hydrochloride;

1-benzyl-7-(3,4-dihydro-1H-isoquinolin-2-yl)-2,3-dimethyl-1H -pyrrolo[2,3-c]pyridin-5-sulfonamide hydrochloride;

7-(3,4-dihydro-1H-isoquinolin-2-yl)-1-(3-fluorobenzyl)-2,3-dimethyl-I J-J-pyrrolo[2,3-c]pyridin-5-ol;

7-(3,4-dihydro-1H-isoquinolin-2-yl)-1-(3-fluorobenzyl)-2,3-dimethyl-1H-pyrrolo[2,3-c]pyridin-5-ol hydrochloride;

2-(1-benzyl-5-ethynyl-2,3-dimethyl-1H-pyrrolo[2,3-c]pyridin-7-yl)-1,2,3,4-tetrahydroisoquinoline hydrochloride;

[1-allyl-7-(3,4-dihydro-1H-isoquinolin-2-yl)-3-hydroxymethyl-2-methyl-1H-pyrrolo[2,3-c]pyridin-5-yl]-(4-methylpiperazin-1-yl)-methanone hydrochloride;

[1-allyl-7-(3,4-dihydro-1H-isoquinolin-2-yl)-3-hydroxymethyl-2-methyl-1H-pyrrolo[2,3-c]pyridin-5-yl]-(4-ethylpiperazin-1-yl)-methanone hydrochloride;

[1-allyl-7-(3,4-dihydro-1H-isoquinolin-2-yl)-3-hydroxymethyl-2-methyl-1H-pyrrolo[2,3-c]pyridin-5-yl]-(piperazin-1-yl)-methanone hydrochloride;

[1-benzyl-7-(3,4-dihydro-1H-isoquinolin-2-yl)-3-hydroxymethyl-2-methyl-1H-pyrrolo[2,3-c]pyridin-5-yl]-(4-methylpiperazin-1-yl)-methanone hydrochloride;

[1-benzyl-7-(3,4-dihydro-1H-isoquinolin-2-yl)-3-hydroxymethyl-2-methyl-1H-pyrrolo[2,3-c]pyridin-5-yl]-(piperazin-1-yl)-methanone hydrochloride;

[1-allyl-7-(3,4-dihydro-1H-isoquinolin-2-yl)-2-methyl-5-(4-methylpiperazin-1-carbonyl)-pyrrolo-1H-pyrrolo[2,3-c]pyridin-3-yl]-acetonitrile hydrochloride;

[1-allyl-7-(3,4-dihydro-1H-isoquinolin-2-yl)-2-methyl-5-(piperazin-1-carbonyl)-1H-pyrrolo[2,3-c]pyridin-3-yl]-acetonitrile hydrochloride;

[1-allyl-7-(3,4-dihydro-1H-isoquinolin-2-yl)-2-methyl-5-(4-ethylpiperazin-1-carbonyl)-1H-pyrrolo[2,3-c]pyridin-3-yl]-acetonitrile hydrochloride;

[1-benzyl-7-(3,4-dihydro-1H-isoquinolin-2-yl)-2-methyl-5-(4-methylpiperazin-1-carbonyl)-1H-pyrrolo[2,3-c]pyridin-3-yl]-acetonitrile hydrochloride;

[1-benzyl-7-(3,4-dihydro-1H-isoquinolin-2-yl)-2-methyl-5-(piperazin-1-carbonyl)-1H-pyrrolo[2,3-c]pyridin-3-yl]-acetonitrile hydrochloride; and

[1-benzyl-7-(3,4-dihydro-1H-isoquinolin-2-yl)-2-methyl-5-(4-ethylpiperazin-1-carbonyl)-1H-pyrrolo[2,3-c]pyridin-3-yl]-acetonitrile hydrochloride.

4. A process for preparing a compound of formula (I) or a pharmaceutically acceptable salt thereof, which comprises:

reacting a compound of formula (II) with $R_5$-Q to obtain a compound of formula (III), reacting the compound of formula (III) with a compound of formula (IV) to obtain a compound of formula (Ia), and reacting the compound of formula (Ia) with $R_1$—X to obtain a compound of formula (I):

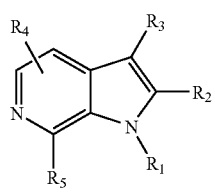  (I)

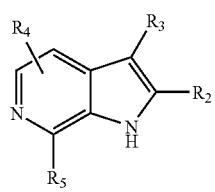  (Ia)

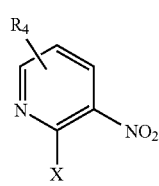  (II)

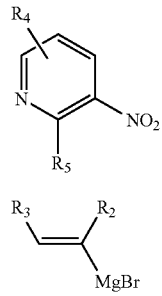  (III)

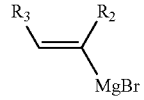  (IV)

wherein,

X is halogen;

Q is hydrogen or $B(OH)_2$;

$R_1$ is hydrogen; a straight or branched $C_1$-$C_7$ alkyl group, optionally substituted with one or more substituents selected from the group consisting of hydroxy, halogen, cyano, $C_3$-$C_7$ cycloalkyl, $C_1$-$C_5$ alkoxy, $C_1$-$C_5$ alkoxycarbonyl, a straight or branched $C_1$-$C_5$ alkylcarbonyloxy, $C_1$-$C_3$ alkoxy-$C_1$-$C_3$ alkoxy-$C_1$-$C_3$ alkylsulfanyl, $C_2$-$C_5$ alkenyloxy, formyl, pyridyl, naphthyl, thiazolyl (the thizole ring is optionally substituted with one or more $C_1$-$C_3$ alkyl, thiophenyl (the thiophene ring is optionally substituted with one or more halogen), isoxazolyl (the isoxazole ring is optionally substituted with one or more $C_1$-$C_3$ alkyl), 1,3-dioxolanyl (the 1,3-dioxolane ring is optionally substituted with one or more $C_1$-$C_3$ alkyl), 1,3-dioxanyl, oxiranyl, and tetrahydropyranyl; a straight or branched $C_2$-$C_6$ alkenyl group optionally substituted with phenyl; a straight or branched $C_2$-$C_6$ alkynyl group; a $C_3$-$C_6$ dienyl group; or a —$(CH_2)_p$-phenyl group (p is 0, 1, 2, or 3 and the phenyl ring is optionally substituted with one or more substituents selected from the group consisting of halogen, cyano, a straight or branched $C_1$-$C_5$ alkyl, $C_1$-$C_3$ alkoxy, $C_1$-$C_3$ alkoxycarbonyl, trifluoro-$C_1$-$C_3$ alkyl, trifluoro-$C_1$-$C_3$ alkoxy, and $C_1$-$C_3$ alkylsulfonyl), $R_1$ is a straight or branched $C_1$-$C_6$ alkyl group, $R_3$ is hydrogen; a straight or branched $C_1$-$C_6$ alkyl group, optionally substituted with one or more substituents selected from the group consisting of hydroxy, $C_1$-$C_5$ alkoxy, $C_1$-$C_3$ alkylcarbonyloxy, cyano, morpholinyl, and mono-, di-, or tri-$C_1$-$C_3$ alkylamino; a halogen group; a cyano group; a formyl group; a $C_1$-$C_3$ alkylsulfanyl group; a $C_1$-$C_3$ alkylsulfonyl group; or a $C_1$-$C_3$ alkylsulfinyl group, $R_4$ is hydrogen; a straight or branched $C_{1-C6}$ alkyl group, optionally substituted with one or more substituents selected from the group consisting of halogen, hydroxy, cyano, amino, $C_1$-$C_5$ alkylamino, $C_3$-$C_6$ cycloalkylamino, phenylamino (the phenyl ring is optionally substituted with one or more halogen), benzylamino (the benzyl ring is optionally substituted with one or more substituents selected from the group consisting of halogen and $C_1$-$C_3$ alkyl), morpholinyl, and piperazinyl (the piperazinyl ring is optionally substituted with $C_1$-$C_3$ alkyl); a straight or branched $C_2$-$C_6$ alkynyl group; a halogen group; a cyano group; a hydroxy group; an amino group; a morpholinyl group; a mercapto group; an aminosulfonyl group; a tetrazolyl group optionally substituted with one or more $C_1$-$C_3$ alkyl; a group of the formula (A)

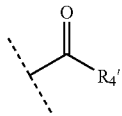

(A)

wherein, R₄' is hydrogen, a hydroxy group, a $C_1$-$C_5$ alkyl group, a $C_1$-$C_3$ alkoxy group, a $C_3$-$C_6$ cycloalkyl group, an imidazolyl group, a morpholinyl group, a thiomorpholinyl group, a pyrrolidyl group, a tetrahydropyridyl group, a piperazinyl group (the piperazinyl ring is optionally substituted with $C_1$-$C_3$ alkyl or phenyl), or a piperidinyl group (the piperidinyl ring is optionally substituted with $C_1$-$C_3$ alkyl, hydroxy, or hydroxy-$C_1$-$C_3$ alkyl); or a group of formula (B)

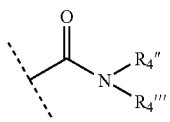

(B)

wherein, R₄" is hydrogen or a $C_1$-$C_3$ alkyl group and R₄'" is hydrogen, a straight or branched $_1$-$C_5$ alkyl group, a $C_2$-$C_5$ alkenyl group, a $_3$-$C_6$ cycloalkyl group, a hydroxy-$C_1$-$C_3$ alkyl group, a trifluoro-$C_1$-$C_3$ alkyl group, a benzyl group (the benzyl ring is optionally one or more substituted with $C_1$-$C_3$ alkyl or halogen), or a piperonyl group, and R₅ is a 1,2,3,4-tetrahydroisopuinolinyl group, optionally substituted with one or more substituents selected from the group consisting of $C_1$-$C_5$ alkyl, $C_1$-$C_3$ alkoxy, halogen, and $C_3$-$C_6$ cycloalkyl; a naphthyl group; a phenyl-$C_2$-$C_5$ alkenyl group; an oxo-1,2,3,4-tetrahydroisoquinolinyl group; a phenoxymethyl group (the phenyl ring is optionally substituted with one or more substituents selected from the group consisting of halogen and $C_1$-$C_3$ alkyl); a -(CH₂)$_q$-phenyl group (q is 0, 1, 2, or 3 and the phenyl ring is optionally substituted with one or more substituents selected from the group consisting of halogen, $C_1$-$C_3$ alkyl, $C_1$-$C_3$ alkoxy, $C_2$-$C_5$ alkenyl, and $_1$-$C_5$ alkylsulfanyl); a group of formula (C)

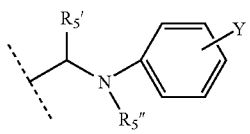

(C)

wherein, Y is hydrogen or a halogen group, R₅' is hydrogen, a $C_1$-$C_3$ alkyl group, a benzyl group, or a cyano group, and R₅" is hydrogen, or $C_1$-$C_5$ alkyl group; or a group of formula (D)

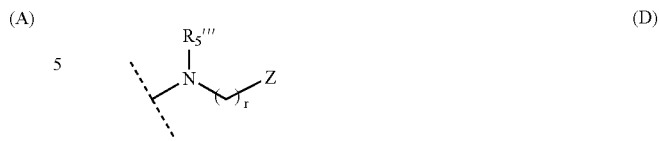

(D)

wherein, r is 0, 1, 2, or 3, R₅'" is hydrogen or a $C_1$-$C_3$ alkyl group, and Z is a 1,3-benzodioxolyl group or a phenyl group (the phenyl ring is optionally substituted with one or more substituents selected from the group consisting of halogen, $C_1$-$C_5$ alkyl, trifluoro-$C_1$-$C_3$ alkoxy, and formyl).

5. A process for preparing a compound of formula (I) or a pharmaceutically acceptable salt thereof, which comprises:
   (a) adding a sodium nitrite solution to a compound of formula (V), followed by reducing the resulting product with tin chloride, to obtain a comound of formula (VI),
   (b) reacting the compound of formula (VI) with a compound of formula (VII) to obtain a compound of formula (VIII),
   (c) cyclizing the compound of formula (VIII) to obtain a compound of formula (Ib),
   (d) reacting the compound of formula (Ib) with R₅-Q to obtain a compound of formula (Ia), and
   (e) reacting the compound of formula (Ia) with R₁-X to obtain a compound of formula (I):

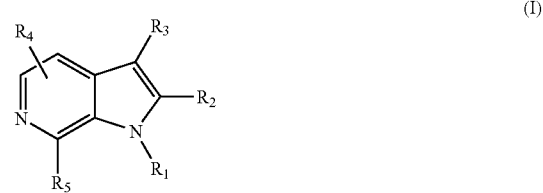

(I)

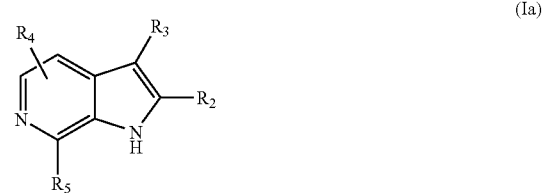

(Ia)

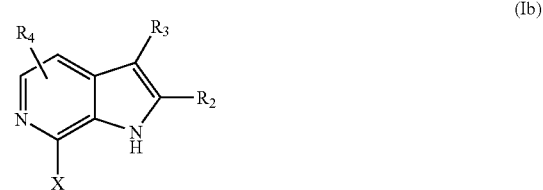

(Ib)

(V)

-continued

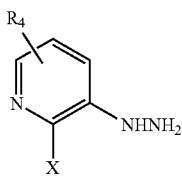
(VI)

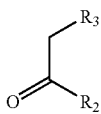
(VII)

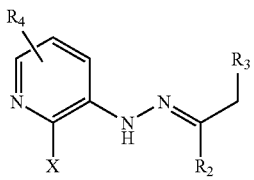
(VIII)

wherein,
X is halogen;
Q is hydrogen or B(OH)$_2$;
R$_1$ is hydrogen; a straight or branched C$_1$-C$_7$ alkyl group, optionally substituted with one or more substituents selected from the group consisting of hydroxy, halogen, cyano, C$_3$-C$_7$ cycloalkyl, C$_1$-C$_5$ alkoxy, C$_1$-C$_5$ alkoxycarbonyl, a straight or branched C$_1$-C$_5$ alkylcarbonyloxy, C$_1$-C$_3$ alkoxy-C$_1$-C$_3$ alkoxy, C$_1$-C$_3$ alkylsulfanyl, C$_2$-C$_5$ alkenyloxy, formyl, pyridyl, naphthyl, thiazolyl (the thizole ring is optionally substituted with one or more C$_1$-C$_3$ alkyl), thiophenyl (the thiophene ring is optionally substituted with one or more halogen), isoxazolyl (the isoxazole ring is optionally substituted with one or more C$_1$-C$_3$ alkyl), 1,3-dioxolanyl (the 1,3-dioxolane ring is optionally substituted with one or more C$_1$-C$_3$ alkyl), 1,3-dioxanyl, oxiranyl, and tetrahydropyranyl; a straight or branched C$_2$-C$_6$ alkynyl group optionally substituted with phenyl; a straight or branched C$_2$-C$_6$ alkynyl group; a C$_3$-C$_6$ dienyl group; or a —(CH$_2$)$_p$-phenyl group (p is 0, 1, 2, or 3 and the phenyl ring is optionally substituted with one or more substituents selected from the group consisting of halogen, cyano, a straight or branched C$_1$-C$_5$ alkyl, C$_1$-C$_3$ alkoxy, C$_1$-C$_3$ alkoxycarbonyl, trifluoro-C$_1$-C$_3$ alkyl trifluoro-C$_1$-C$_3$ alkoxy, and C$_1$-C$_3$ alkylsulfonyl),
R$_2$ is a straight or branched C$_1$-C$_6$ alkyl group,
R$_3$ is hydrogen; a straight or branched C$_1$-C$_6$ alkyl group, optionally substituted with one or more substituents selected from the group consisting of hydroxy, C$_1$-C$_5$ alkoxy, C$_1$-C$_3$ alkylcarbonyloxy, cyano, morpholinyl, and mono-, di-, or tri-C$_1$-C$_3$ alkylamino; a halogen group; a cyano group; a formyl group; a C$_1$-C$_3$ alkylsulfanyl group; a C$_1$-C$_3$ alkylsulfonyl group; or a C$_1$-C$_3$ alkylsulfinyl group,
R$_4$ is hydrogen; a straight or branched C$_1$-C$_6$ alkyl group, optionally substituted with one or more substituents selected from the group consisting of halogen, hydroxy, cyano, amino, C$_1$-C$_5$ alkylamino, C$_3$-C$_6$ cycloalkylamino, phenylamino (the phenyl ring is optionally substituted with one or more halogen), benzylamino (the benzyl ring is optionally substituted with one or more substituents selected from the group consisting of halogen and C$_1$-C$_3$ alkyl), morpholinyl, and piperazinyl (the piperazinyl ring is optionally substituted with C$_1$-C$_3$ alkyl); a straight or branched C$_2$-C$_6$ alkynyl group; a halogen group; a cyano group; a hydroxy group; an amino group; a morpholinyl group; a mercapto group; an aminosulfonyl group; a tetrazolyl group optionally substituted with one or more C$_1$-C$_3$ alkyl; a group of the formula (A)

(A)

wherein, R$_4$' is hydrogen, a hydroxy group, a C$_1$-C$_5$ alkyl group, a C$_1$-C$_3$ alkoxy group, a C$_3$-C$_6$ cycloalkyl group, an imidazolyl group, a morpholinyl group, a thiomorpholinyl group, a pyrrolidyl group, a tetrahydropyridyl group, a piperazinyl group (the piperazinyl ring is optionally substituted with C$_1$-C$_3$ alkyl or phenyl), or a piperidinyl group (the piperidinyl ring is optionally substituted with C$_1$-C$_3$ alkyl hydroxy, or hydroxy-C$_1$-C$_3$ alkyl); or a group of formula (B)

(B)

wherein, R$_4$" is hydrogen or a C$_1$-C$_3$ alkyl group and R$_4$''' is hydrogen, a straight or branched C$_1$-C$_5$ alkyl group, a C$_2$-C$_5$ alkenyl group, a C$_3$-C$_6$ cycloalkyl group, a hydroxy-C$_1$-C$_3$ alkyl group, a trifluoro-C$_1$-C$_3$ alkyl group, a benzyl group (the benzyl ring is optionally one or more substituted with C$_1$-C$_3$ alkyl or halogen), or a piperonyl group, and R$_5$ is a 1,2,3,4-tetrahydroisopuinolinyl group, optionally substituted with one or more substituents selected from the group consisting of C$_1$-C$_5$ alkyl C$_1$-C$_3$ alkoxy, halogen, and C$_3$-C$_6$ cycloalkyl; a naphthyl group; a phenyl-C$_2$-C$_5$ alkenyl group; an oxo-1,2,3,4-tetrahydroisoquinolinyl group; a phenoxymethyl group (the phenyl ring is optionally substituted with one or more substituents selected from the group consisting of halogen and C$_1$-C$_3$ alkyl); a —(CH$_2$)$_q$-phenyl group (q is 0, 1, 2, or 3 and the phenyl ring is optionally substituted with one or more substituents selected from the group consisting of halogen, C$_1$-C$_3$ alkyl, C$_1$-C$_3$ alkoxy, C$_2$-C$_5$ alkenyl, and C$_1$-C$_5$ alkylsulfanyl); a group of formula (C)

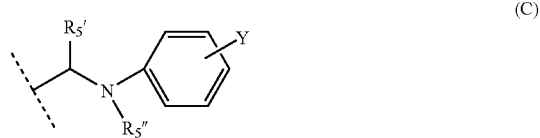
(C)

wherein Y is hydrogen or a halogen group, R$_5$' is hydrogen, a C$_1$-C$_3$ alkyl group, a benzyl group, or a cyano group, and R$_5$" is hydrogen, or C$_1$-C$_5$ alkyl group; or a group of formula (D)

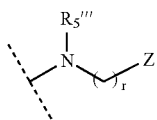 (D)

wherein, r is 0, 1, 2, or 3, $R_5'''$ is hydrogen or a $C_1$-$C_3$ alkyl group, and Z is a 1,3-benzodioxolyl group or a phenyl group (the phenyl ring is optionally substituted with one or more substituents selected from the group consisting of halogen, $C_1$-$C_5$ alkyl, trifluoro-$C_1$-$C_3$ alkoxy, and formyl).

6. A pharmaceutical composition comprising a therapeutically effective amount of any of the compound of formula (I) or a pharmaceutically acceptable salt thereof according to claim 1 and a pharmaceutically acceptable carrier.

* * * * *